(12) United States Patent
Swanson et al.

(10) Patent No.: US 12,281,968 B2
(45) Date of Patent: Apr. 22, 2025

(54) AGRICULTURAL SAMPLING SYSTEM AND RELATED METHODS

(71) Applicant: Precision Planting LLC, Tremont, IL (US)

(72) Inventors: Todd Swanson, Morton, IL (US); Dale Koch, Tremont, IL (US); Kent Levy, Morton, IL (US); Matthew O'Neall, Ellsworth, IL (US); Reid Harman, Trivoli, IL (US)

(73) Assignee: Precision Planting LLC, Tremont, IL (US)

( * ) Notice: Subject to any disclaimer, the term of this patent is extended or adjusted under 35 U.S.C. 154(b) by 0 days.

(21) Appl. No.: 18/465,309

(22) Filed: Sep. 12, 2023

(65) Prior Publication Data

US 2023/0417635 A1   Dec. 28, 2023

Related U.S. Application Data

(62) Division of application No. 17/144,099, filed on Jan. 7, 2021, now Pat. No. 11,781,948.

(51) Int. Cl.
*G01N 1/08* (2006.01)
*A01C 23/00* (2006.01)
(Continued)

(52) U.S. Cl.
CPC .............. *G01N 1/08* (2013.01); *A01C 23/007* (2013.01); *B01D 19/00* (2013.01); *B01D 21/262* (2013.01); *B01D 29/112* (2013.01); *B01F 23/53* (2022.01); *B01F 23/807* (2022.01); *B01F 23/808* (2022.01); *B01F 25/30* (2022.01); *B01F 25/54* (2022.01); *B01F 27/11253* (2022.01); *B01F 27/808* (2022.01); *B01F 27/906* (2022.01); *B01F 35/1452* (2022.01); *B01F 35/187* (2022.01); *B01F 35/2117* (2022.01); *B01F 35/453* (2022.01); *B04B 5/0421* (2013.01);
(Continued)

(58) Field of Classification Search
CPC .... G01N 1/08; G01N 33/24; G01N 2033/245; A01B 29/06; A01B 35/16; A01B 35/32; A01B 76/00; A01B 79/005
See application file for complete search history.

(56) References Cited

U.S. PATENT DOCUMENTS

| | | | | |
|---|---|---|---|---|
| 2,543,888 A | * | 3/1951 | Bunch | A01C 21/002 111/91 |
| 6,766,865 B1 | * | 7/2004 | Dagel | G01N 33/24 172/457 |
| 2010/0037712 A1 | * | 2/2010 | Burton | E21B 49/02 53/284.7 |

* cited by examiner

*Primary Examiner* — Benjamin R Schmitt

(57) ABSTRACT

A coulter assembly for collecting soil samples from an agricultural field in one embodiment comprises an annular collection blade configured for penetrating soil to capture a sample, an annular cam ring configured for stationary mounting to a frame of an agricultural vehicle and comprising a cam track, a blade hub coupled to the blade for rotatably supporting the annular collection blade from the annular cam ring, and a movable sample collector mounted to the annular collection blade. The moveable sample collector is configured and operable for extracting a soil sample as the annular collection blade is rotated through the soil. The moveable sample collector in one embodiment comprises a piston mechanism including a cylinder and rod movably disposed therein which actuated by the annular cam ring to alternatingly open and close a collection end of the cylinder as the annular collection blade rotates through the soil.

20 Claims, 274 Drawing Sheets

(51) Int. Cl.
- *B01D 19/00* (2006.01)
- *B01D 21/26* (2006.01)
- *B01D 29/11* (2006.01)
- *B01F 23/53* (2022.01)
- *B01F 23/80* (2022.01)
- *B01F 25/30* (2022.01)
- *B01F 25/54* (2022.01)
- *B01F 27/1125* (2022.01)
- *B01F 27/808* (2022.01)
- *B01F 27/906* (2022.01)
- *B01F 35/00* (2022.01)
- *B01F 35/10* (2022.01)
- *B01F 35/21* (2022.01)
- *B01F 35/45* (2022.01)
- *B04B 5/04* (2006.01)
- *F04B 43/06* (2006.01)
- *G01G 17/04* (2006.01)
- *G01N 1/38* (2006.01)
- *G01N 1/40* (2006.01)
- *G01N 21/05* (2006.01)
- *G01N 21/25* (2006.01)
- *G01N 21/78* (2006.01)
- *G01N 33/24* (2006.01)
- *G01N 35/00* (2006.01)
- *G01N 35/10* (2006.01)
- *G05B 15/02* (2006.01)
- *B01F 23/50* (2022.01)
- *B01F 101/00* (2022.01)
- *B01F 101/23* (2022.01)

(52) U.S. Cl.
CPC .............. *F04B 43/06* (2013.01); *G01G 17/04* (2013.01); *G01N 1/38* (2013.01); *G01N 1/4055* (2013.01); *G01N 1/4077* (2013.01); *G01N 21/05* (2013.01); *G01N 21/251* (2013.01); *G01N 21/78* (2013.01); *G01N 33/24* (2013.01); *G01N 35/00584* (2013.01); *G01N 35/1004* (2013.01); *G01N 35/1095* (2013.01); *G05B 15/02* (2013.01); *B01D 2201/4092* (2013.01); *B01F 23/581* (2022.01); *B01F 2101/005* (2022.01); *B01F 2101/23* (2022.01); *G01N 2001/4061* (2013.01); *G01N 2001/4083* (2013.01); *G01N 2001/4088* (2013.01); *G01N 2033/245* (2013.01); *G01N 2035/00188* (2013.01); *G01N 2035/00475* (2013.01); *G01N 2035/00495* (2013.01); *G01N 2035/00514* (2013.01)

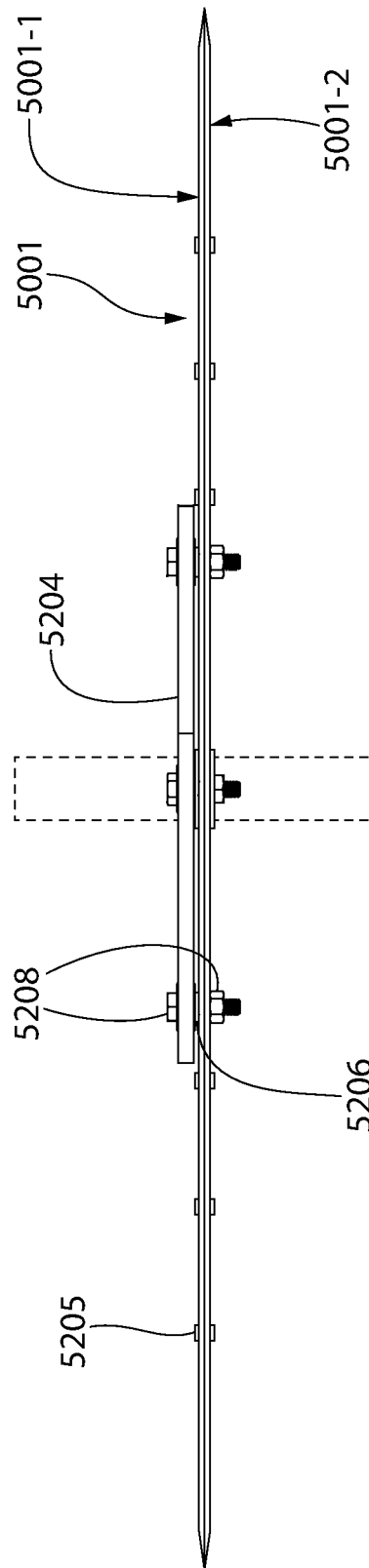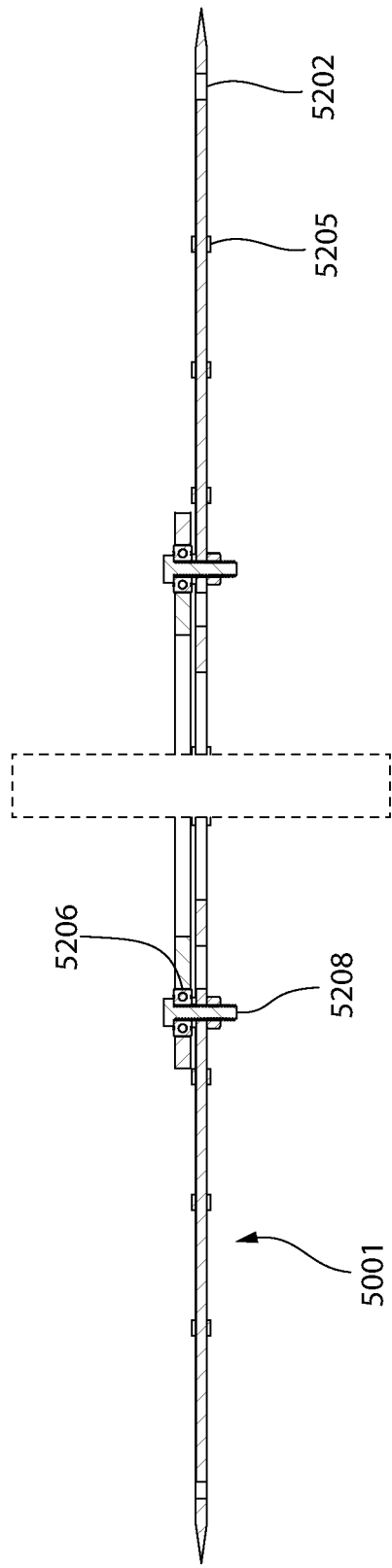

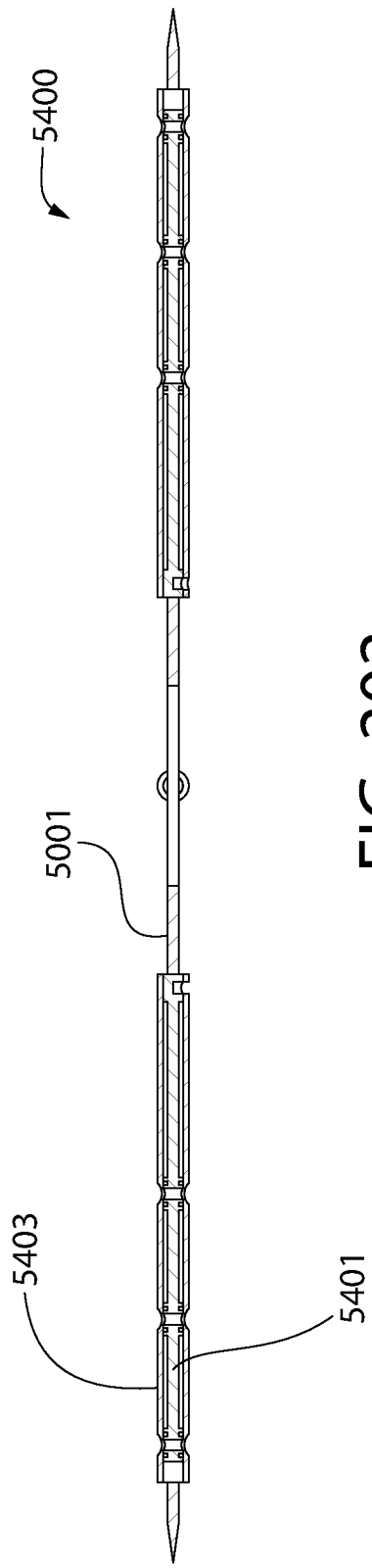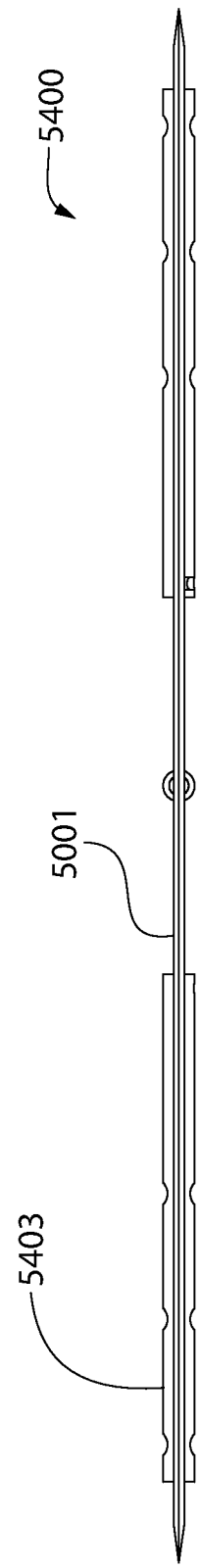

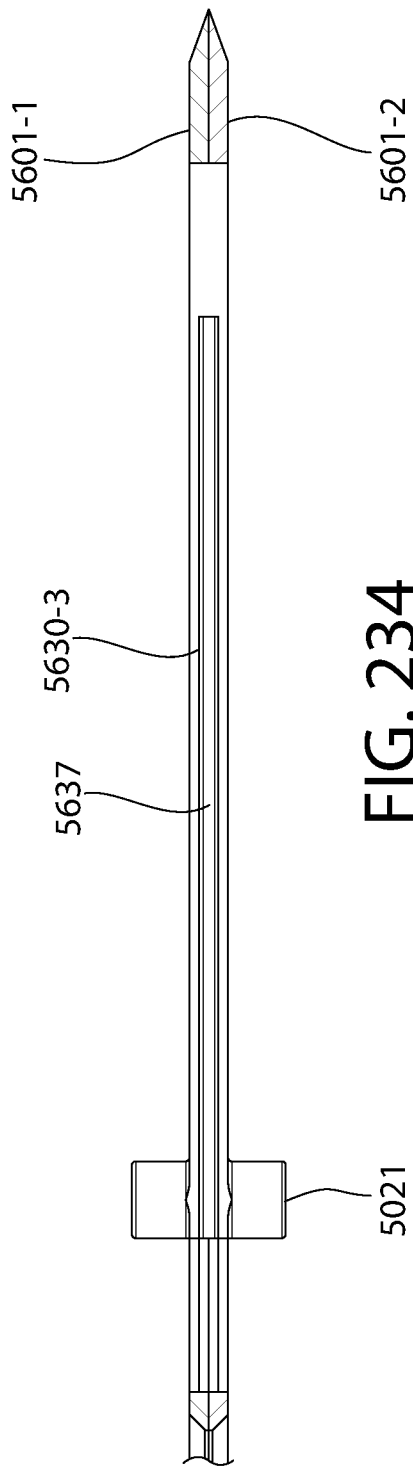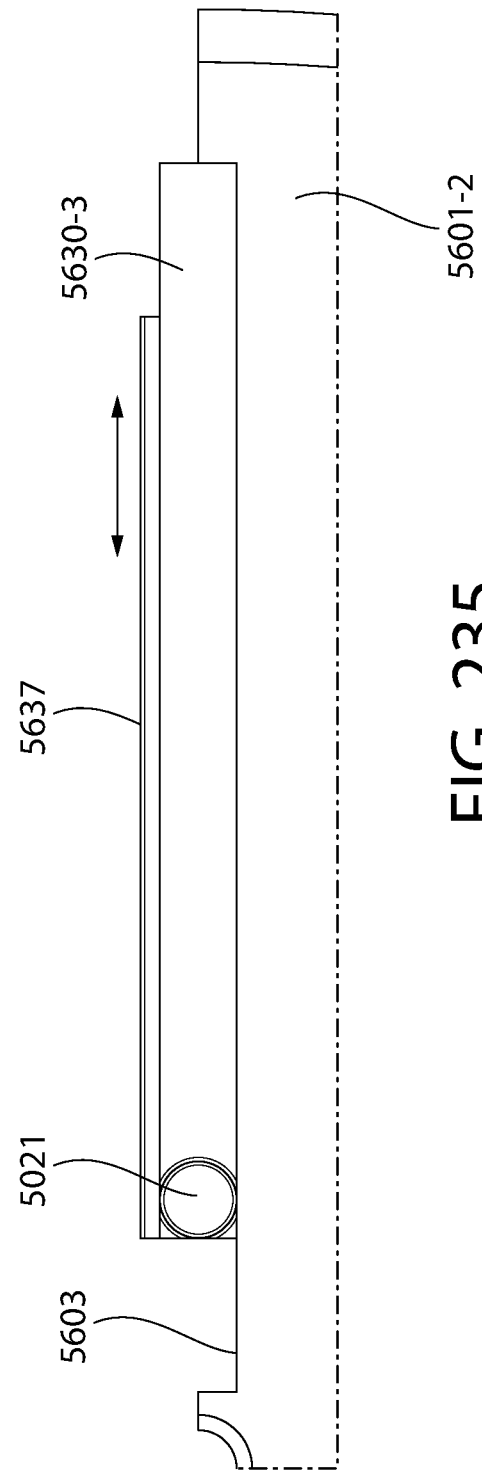
FIG. 234
FIG. 235

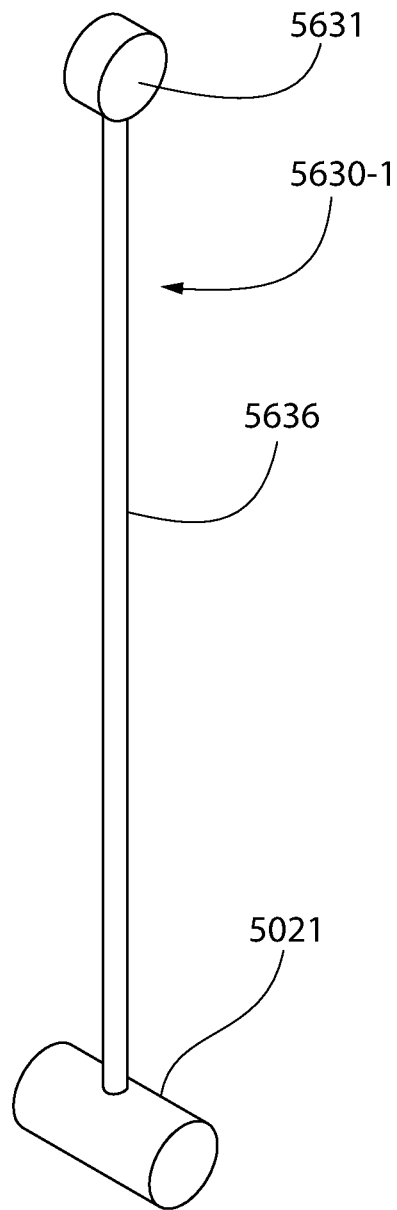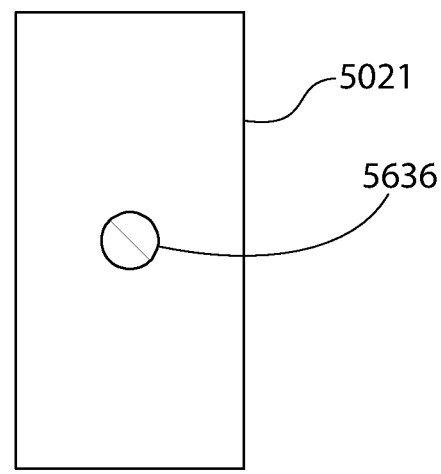
FIG. 250B
FIG. 250A

AGRICULTURAL SAMPLING SYSTEM AND RELATED METHODS

CROSS-REFERENCE TO RELATED APPLICATIONS

The present application is a divisional application of U.S. application Ser. No. 17/144,099, filed 7 Jan. 2021, which is a national stage entry of PCT Application No. PCT/IB2019/055862, filed 10 Jul. 2019, which claims the benefit of priority to U.S. Provisional Patent Application No. 62/696,271 filed Jul. 10, 2018, U.S. Provisional Patent Application No. 62/729,623 filed Sep. 11, 2018, U.S. Provisional Patent Application No. 62/745,606 filed Oct. 15, 2018, U.S. Provisional Patent Application No. 62/792,987 filed Jan. 16, 2019, U.S. Provisional Patent Application No. 62/829,807 filed Apr. 5, 2019, U.S. Provisional Patent Application No. 62/860,297 filed Jun. 12, 2019. The entireties of all the foregoing listed applications are incorporated herein by reference.

BACKGROUND

The present invention relates generally to agricultural sampling and analysis, and more particularly to a fully automated system for performing soil and other types of agricultural related sampling and chemical property analysis.

Periodic soil testing is an important aspect of the agricultural arts. Test results provide valuable information on the chemical makeup of the soil such as plant-available nutrients and other important properties (e.g. levels of nitrogen, magnesium, phosphorous, potassium, pH, etc.) so that various amendments may be added to the soil to maximize the quality and quantity of crop production.

In some existing soil sampling processes, collected samples are dried, ground, water is added, and then filtered to obtain a soil slurry suitable for analysis. Extractant is added to the slurry to pull out plant available nutrients. The slurry is then filtered to produce a clear solution or supernatant which is mixed with a chemical reagent for further analysis.

Improvements in testing soil, vegetation, and manure are desired.

BRIEF SUMMARY

The present invention provides an automated computer-controlled sampling system and related methods for collecting, processing, and analyzing soil samples for various chemical properties such as plant available nutrients (hereafter referred to as a "soil sampling system"). The sampling system allows multiple samples to be processed and analyzed for different analytes (e.g. plant-available nutrients) and/or chemical properties (e.g. pH) in a simultaneous concurrent or semi-concurrent manner, and in relatively continuous and rapid succession. Advantageously, the system can process soil samples in the "as collected" condition without the drying and grinding steps previously described.

The present system generally includes a sample preparation sub-system which receives soil samples collected by a probe collection sub-system and produces a slurry (i.e. mixture of soil, vegetation, and/or manure and water) for further processing and chemical analysis, and a chemical analysis sub-system which receives and processes the prepared slurry samples from the sample preparation sub-system for quantification of the analytes and/or chemical properties of the sample. The described chemical analysis sub-system can be used to analyze soil, vegetation, and/or manure samples.

In one embodiment, the sample preparation system generally includes a mixer-filter apparatus which mixes the collected raw soil sample in the "as sampled" condition (e.g. undried and unground) with water to form a sample slurry. The mixer-filter apparatus then filters the slurry during its extraction from the apparatus for processing in the chemical analysis sub-system. The chemical analysis sub-system processes the slurry and performs the general functions of extractant and color-changing reagent addition/mixing, centrifugating the slurry sample to yield a clear supernatant, and finally sensing or analysis for detection of the analytes and/or chemical properties such as via colorimetric analysis.

Although the sampling systems (e.g. sample collection, preparation, and processing) may be described herein with respect to processing soil samples which represents one category of use for the disclosed embodiments, it is to be understood that the same systems including the apparatuses and related processes may further be used for processing other types of agricultural related samples including without limitation vegetation/plant, forage, manure, feed, milk, or other types of samples. The embodiments of the invention disclosed herein should therefore be considered broadly as an agricultural sampling system. Accordingly, the present invention is expressly not limited to use with processing and analyzing soil samples alone for chemical properties of interest.

BRIEF DESCRIPTION OF THE DRAWINGS

The present invention will become more fully understood from the detailed description and the accompanying drawings, wherein like elements are labeled similarly and in which:

FIG. 119 is a schematic flow diagram thereof in a sixteenth operating mode configuration;

FIG. 120 is a side cross sectional view of an light emitting diode (LED) emitting diode assembly and LED receiving diode assembly associated with the flow analysis cell window shown in FIGS. 104-119 for measuring an analyte;

FIG. 121 is a top cross sectional view thereof;

FIG. 122 is a top perspective view of a standalone absorbance flow analysis cell;

FIG. 123 is a bottom perspective view thereof;

FIG. 124 is an exploded perspective view thereof;

FIG. 125 is a front view thereof;

FIG. 126 is a side view thereof;

FIG. 127 is a top plan view thereof;

FIG. 128 is a bottom plan view thereof;

FIG. 129 is a front cross-sectional view thereof;

FIG. 130 is front top perspective view of a second embodiment of a centrifuge configured for use with the microfluidic processing disk of FIG. 96;

Figure 96:
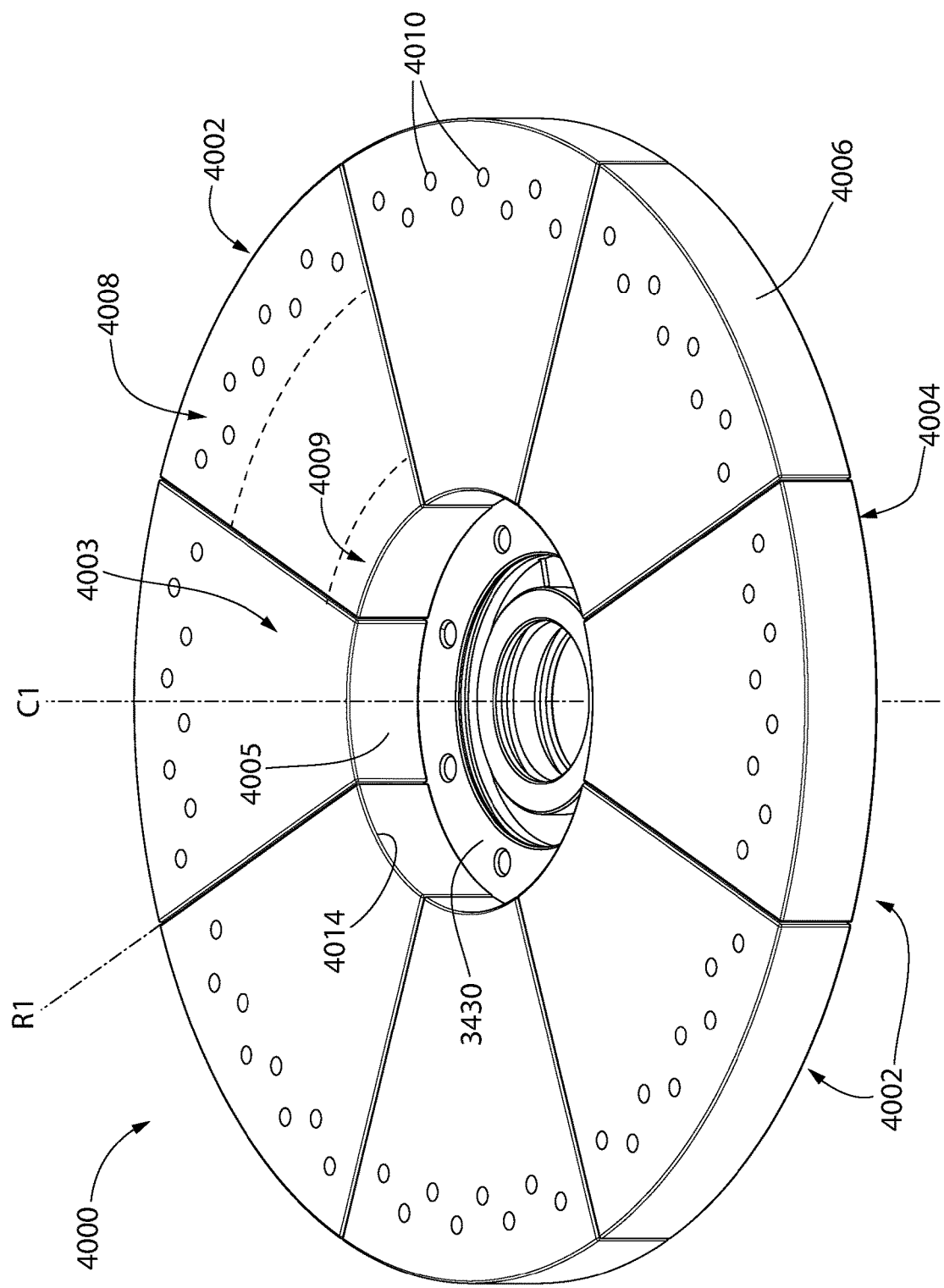
FIG. 96 is a top perspective view of a microfluidic processing disk with plurality of chemical processing wedges each configured as a stand alone processing training for performing complete soil slurry processing and chemical analysis.
Figure 97:
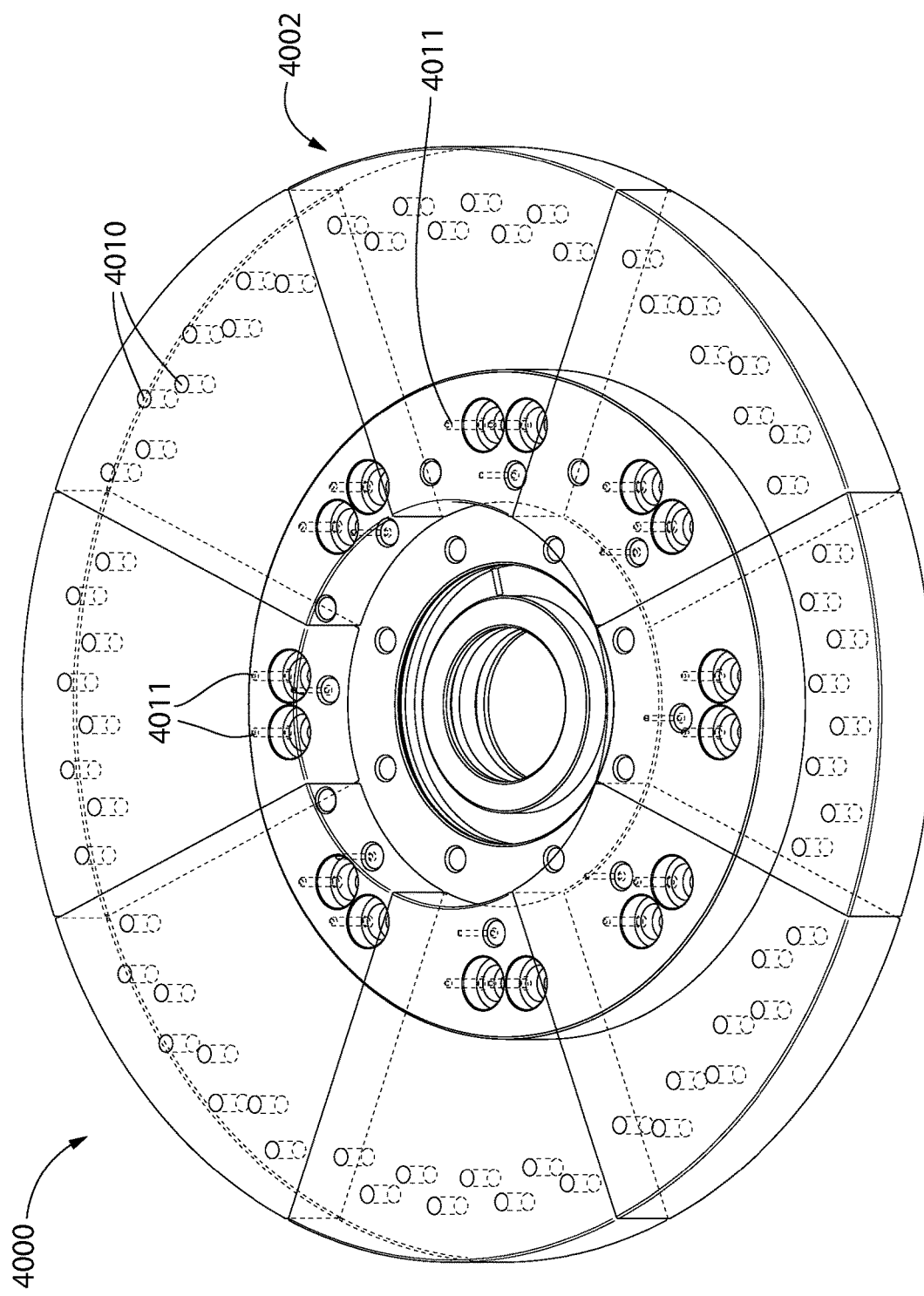
FIG. 97 is a bottom perspective view thereof.
Figure 98:
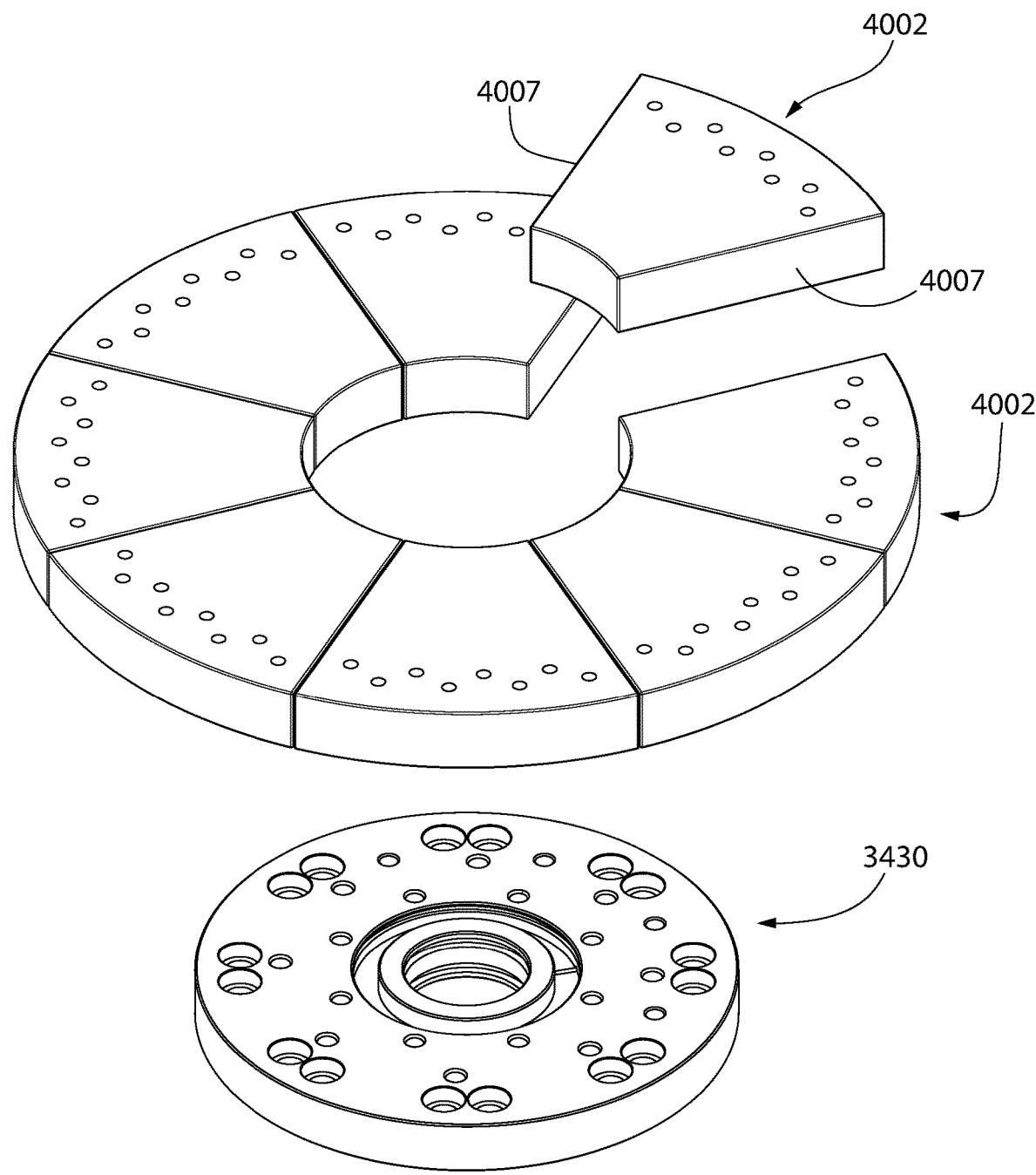
FIG. 98 is a partially exploded perspective view thereof with fluid exchange dock which fluidly couples to the microfluidic processing disk shown below.
Figure 99:
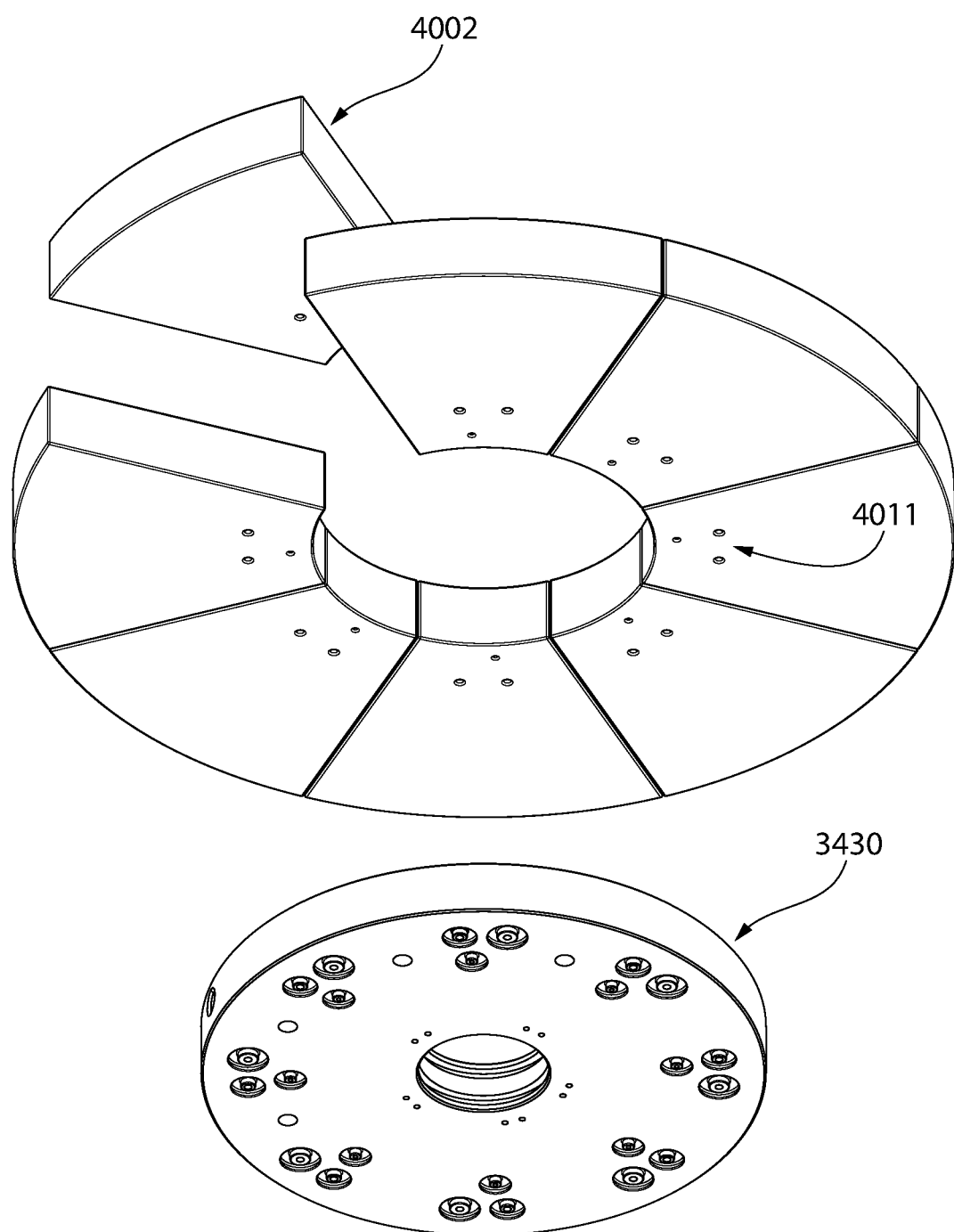
FIG. 99 is a bottom perspective view thereof.
Figure 100:
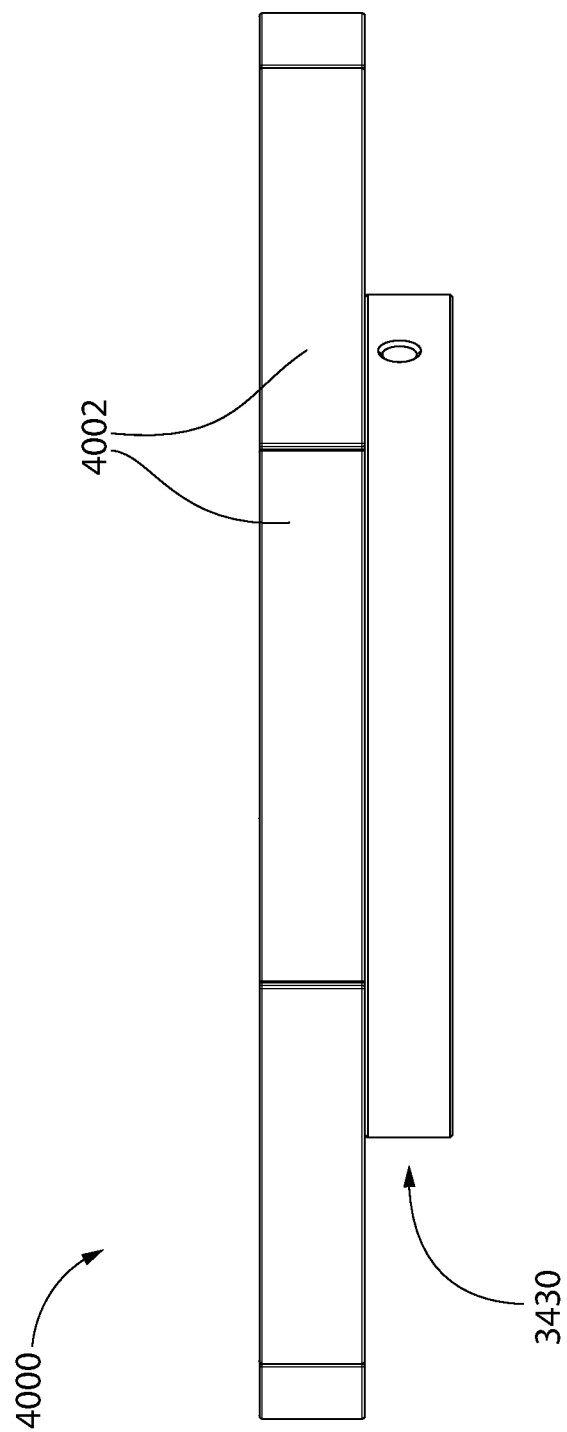
FIG. 100 is a side view of the microfluidic processing disk.
Figure 101:
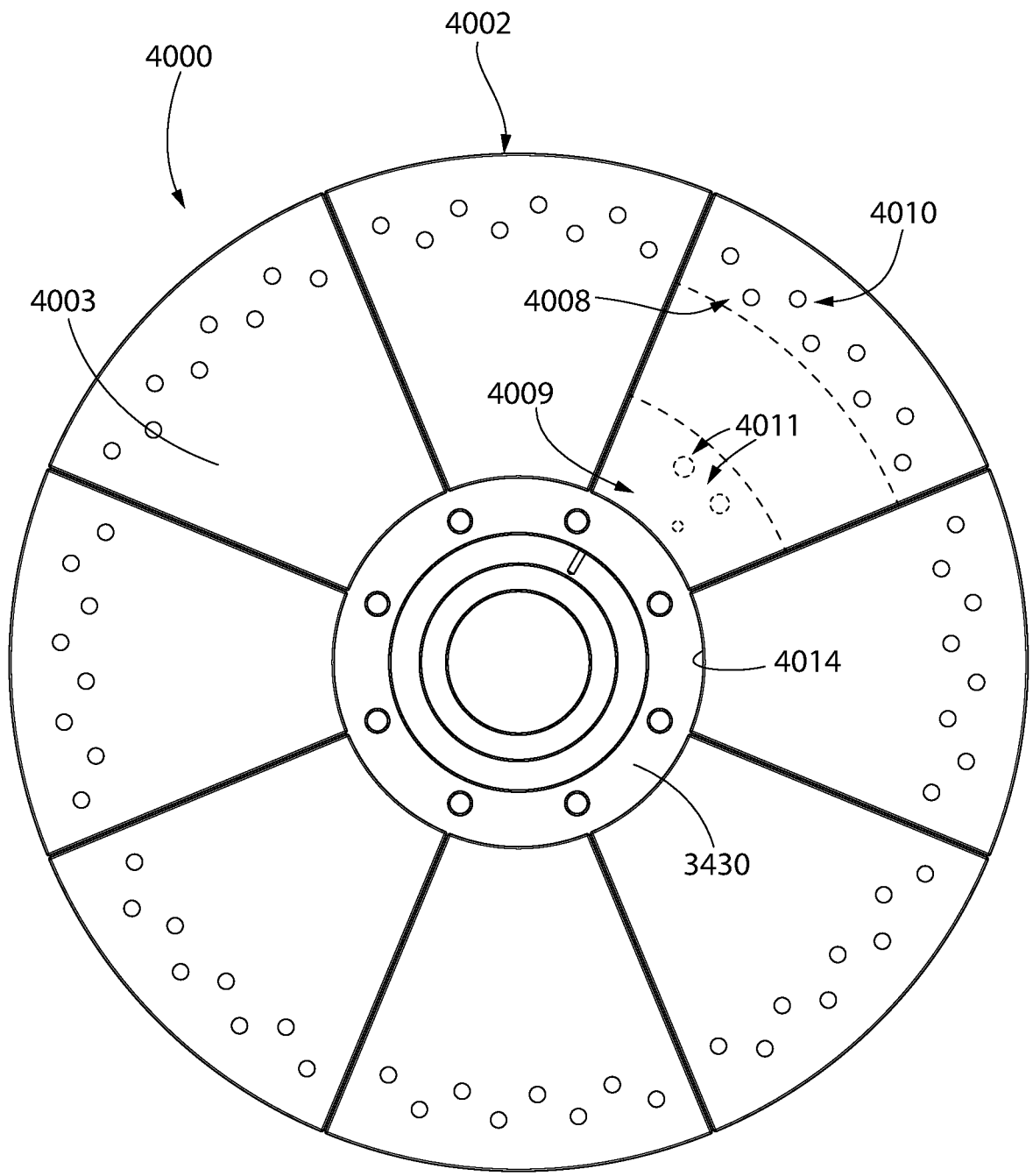
FIG. 101 is a top view thereof.
Figure 102:
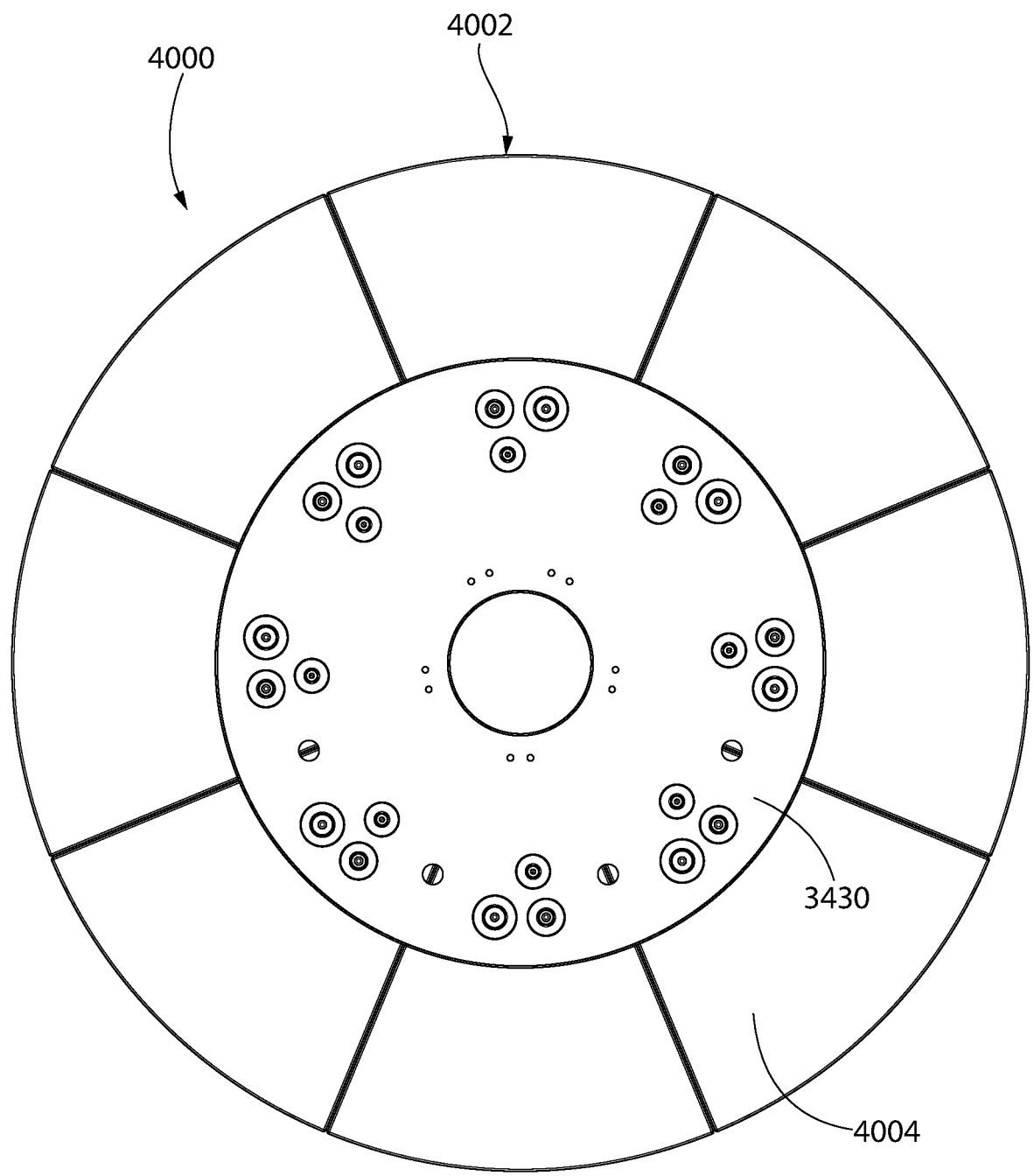
FIG. 102 is a bottom view thereof.
Figure 103:
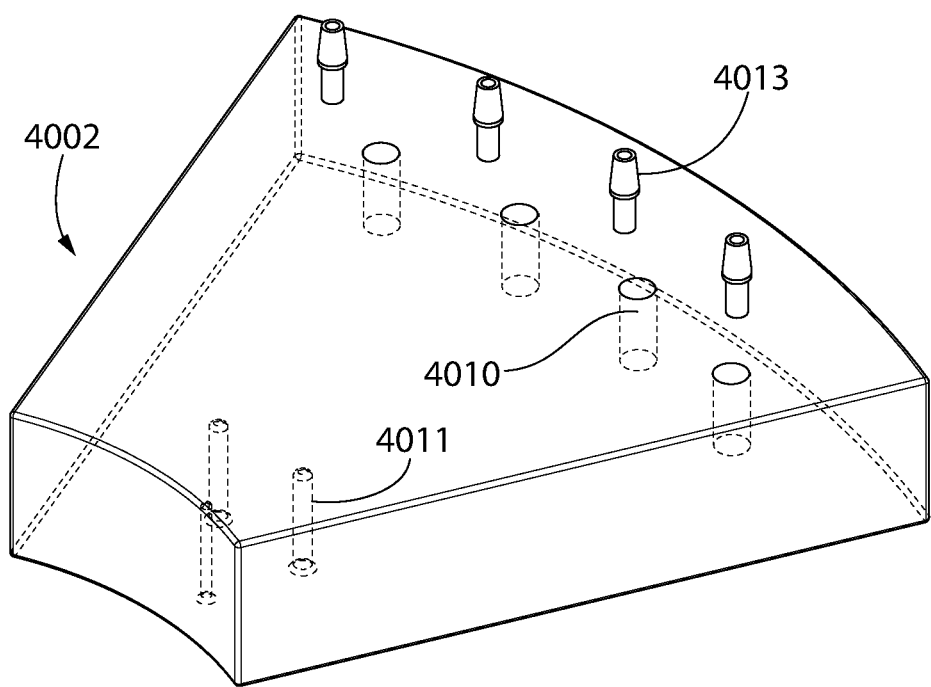
FIG. 103 is a perspective view of one processing wedge showing its flow conduits and external fluid connections.
Figure 131:
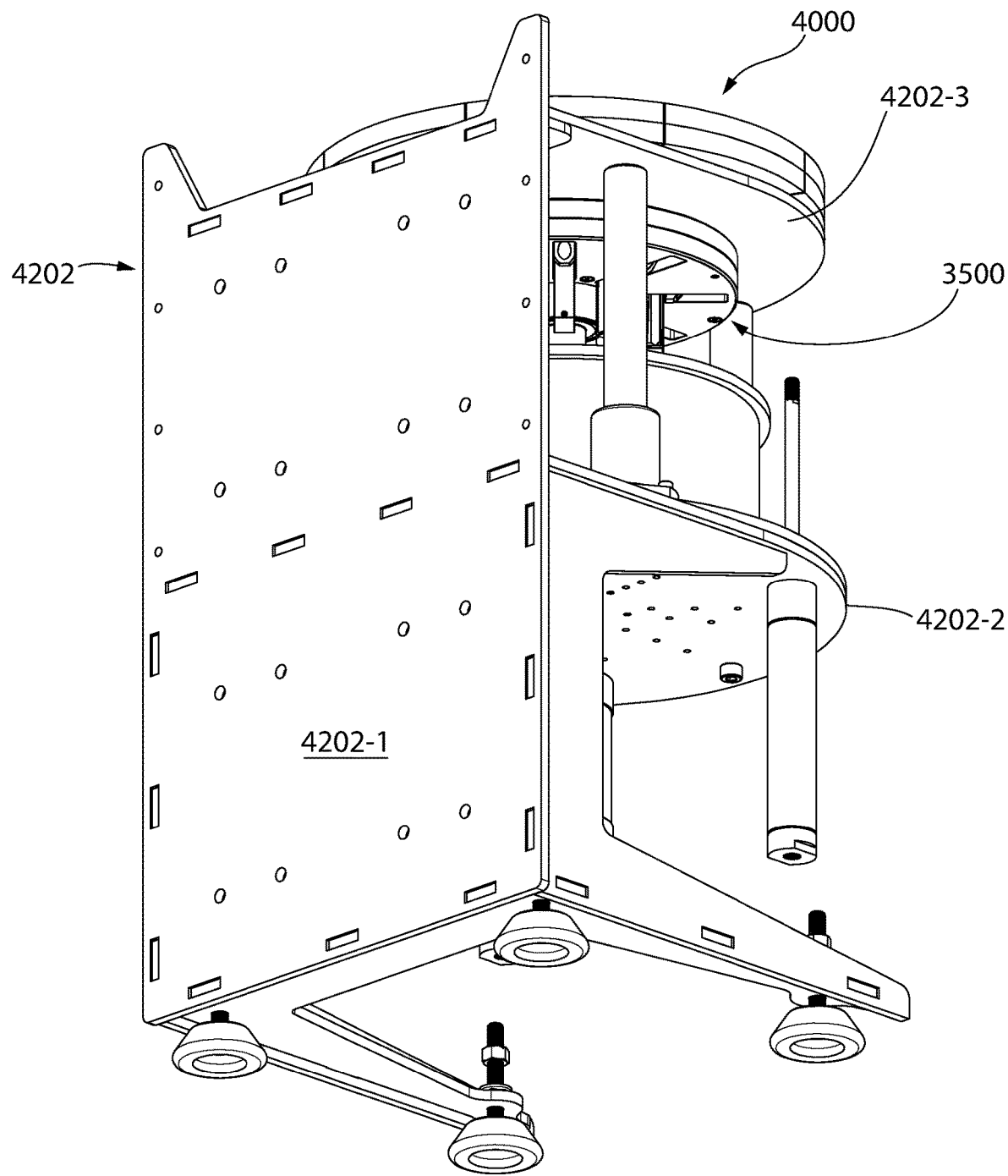
Figure 132:
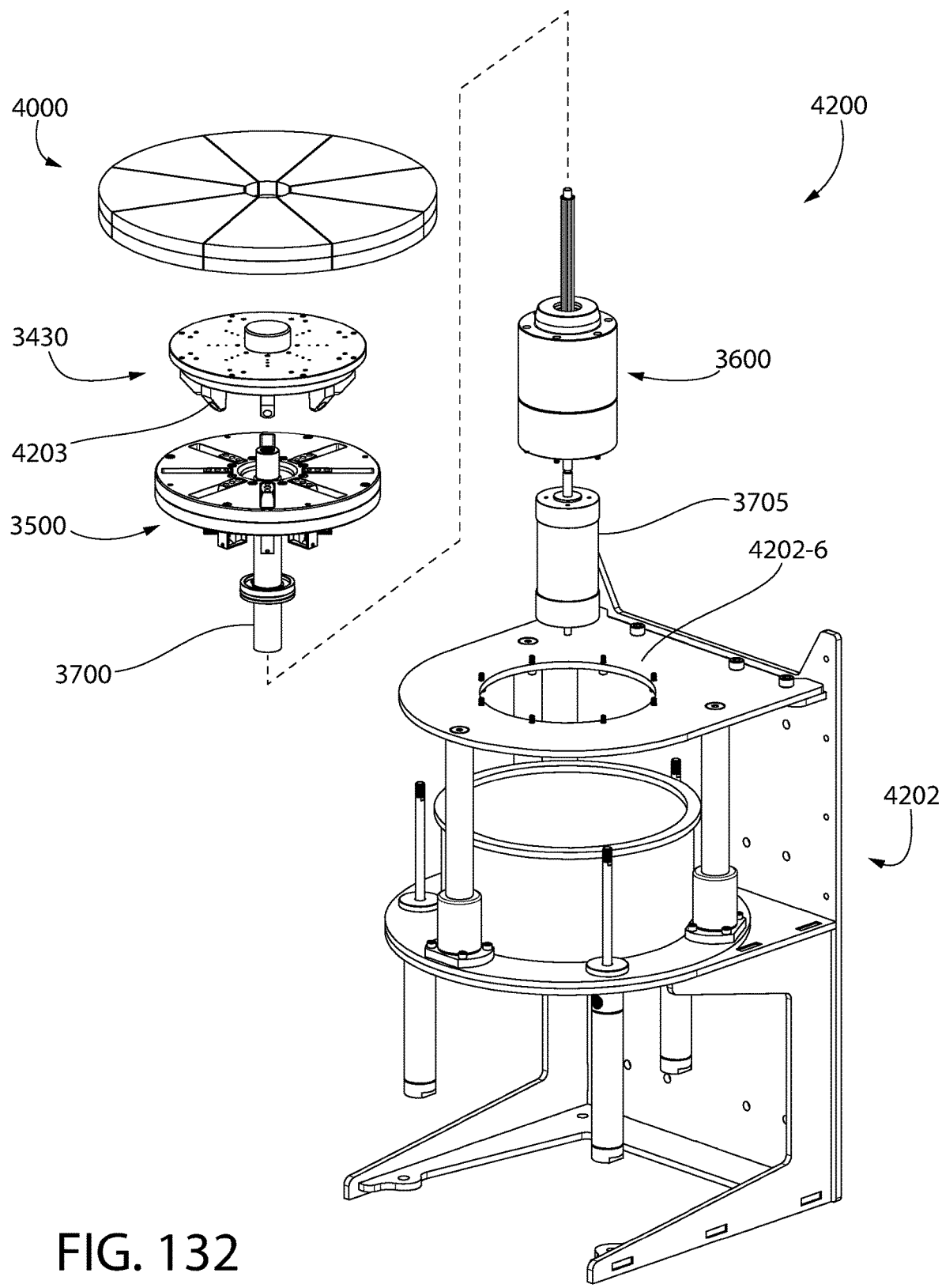
Figure 133:
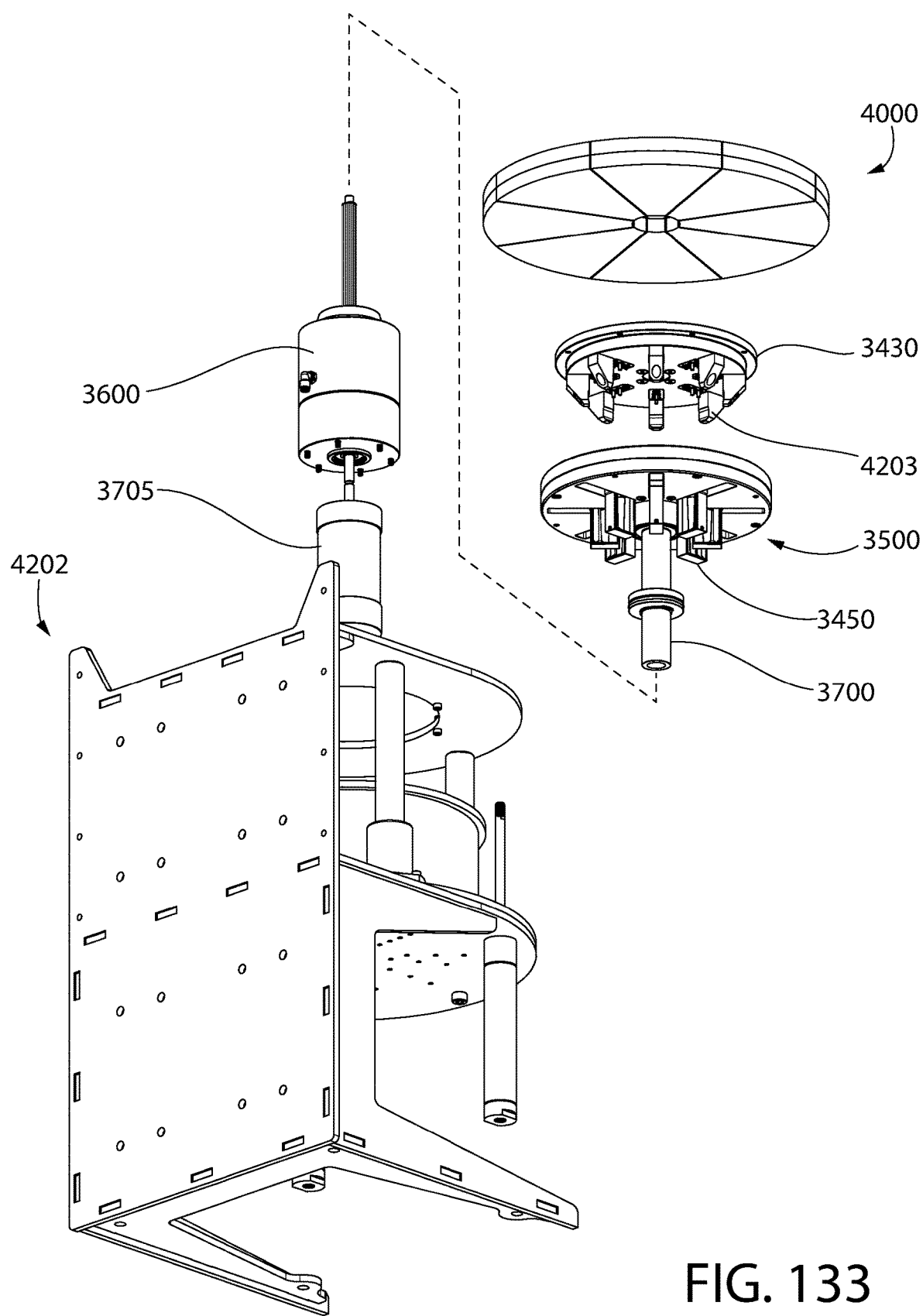
Figure 134:
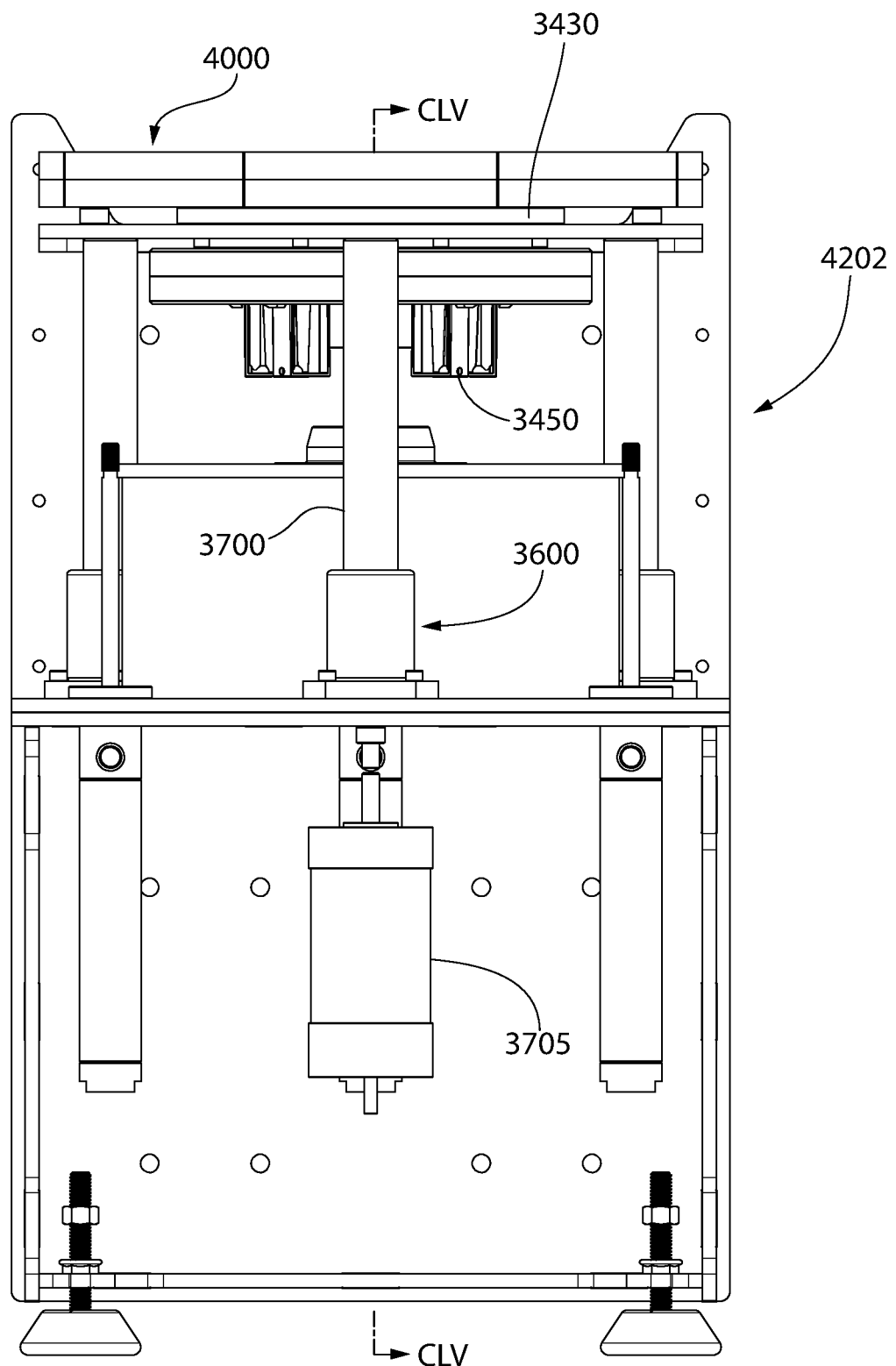
Figure 135:
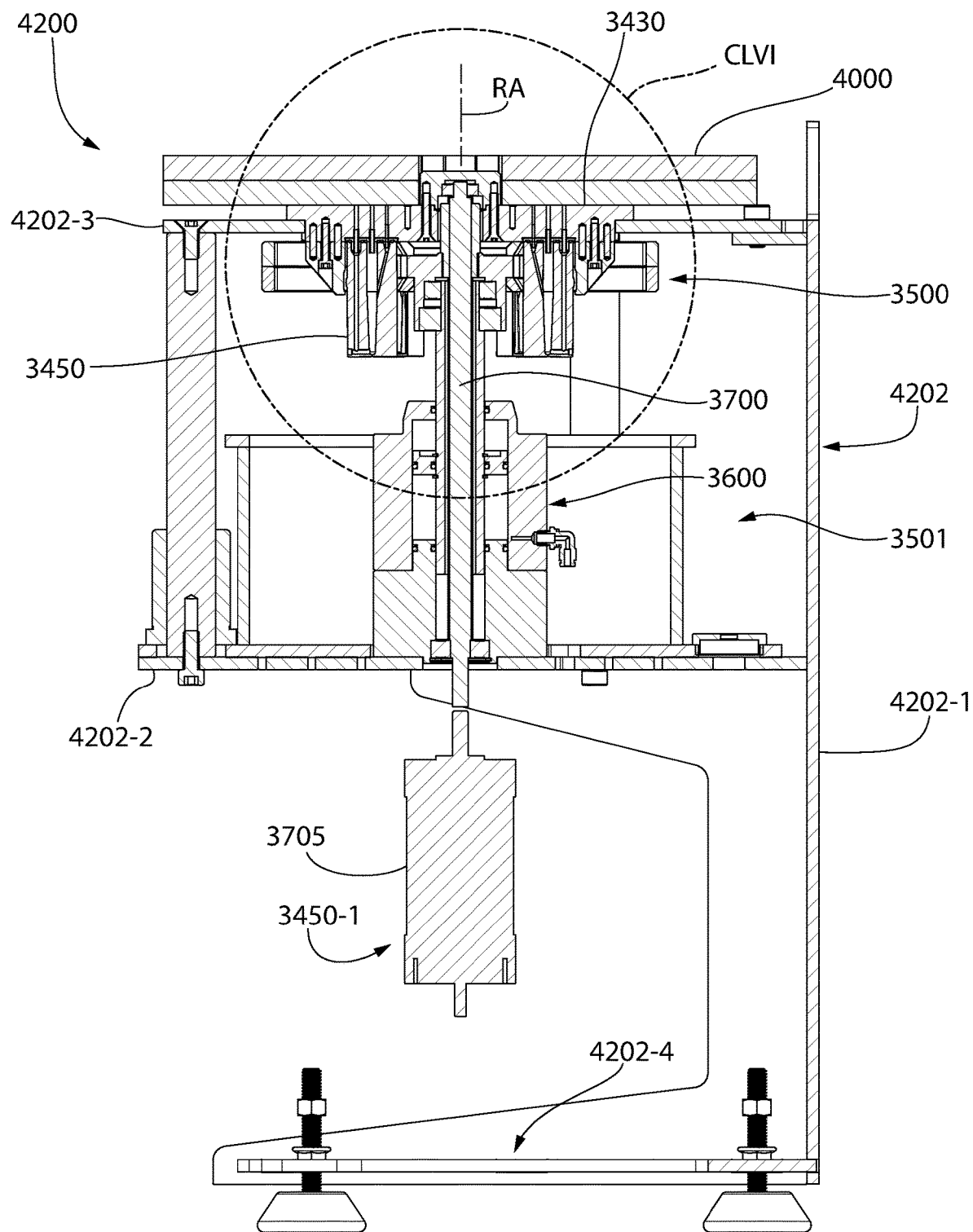
Figure 136:
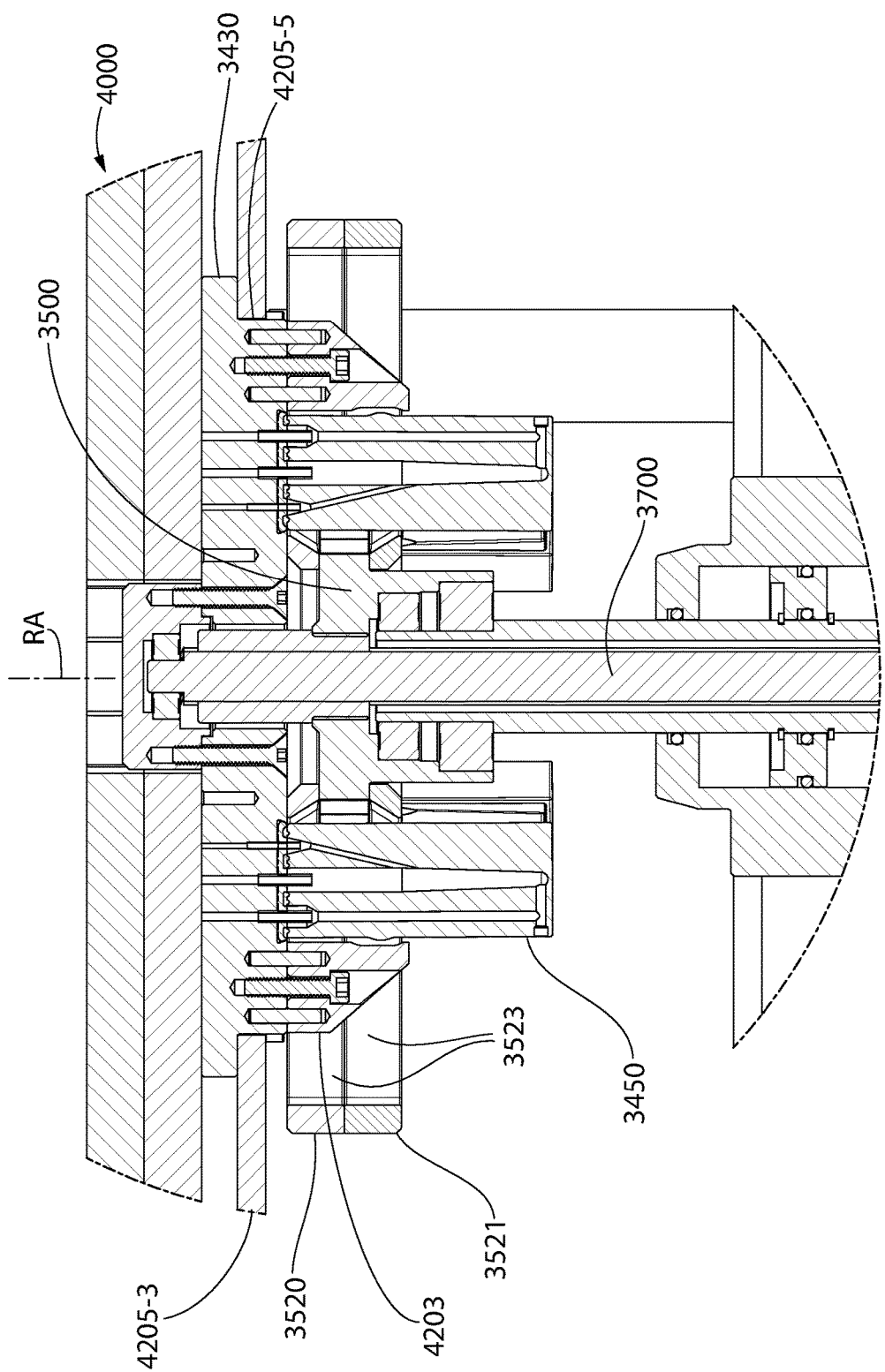
Figure 137:
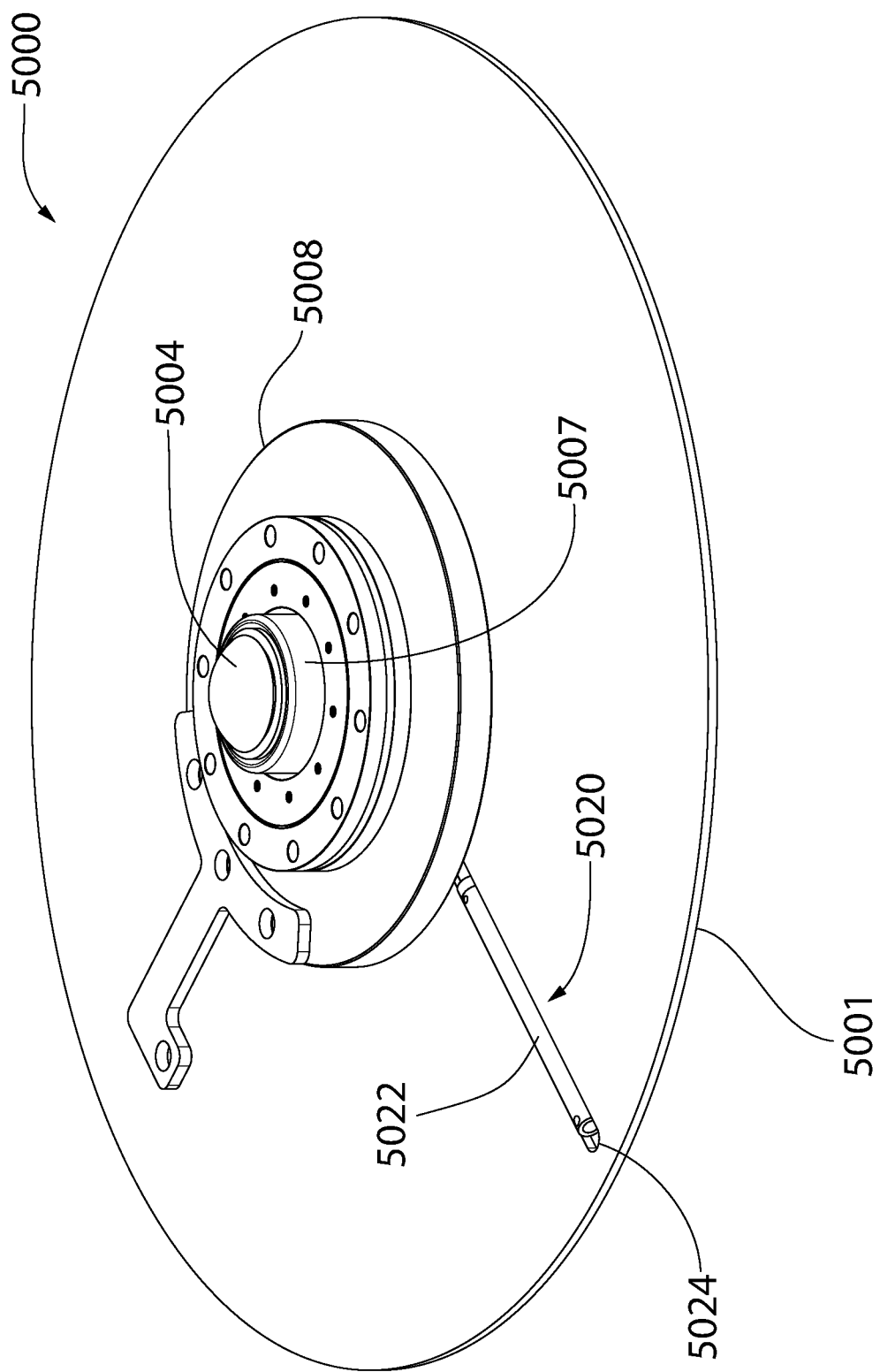
Figure 138:
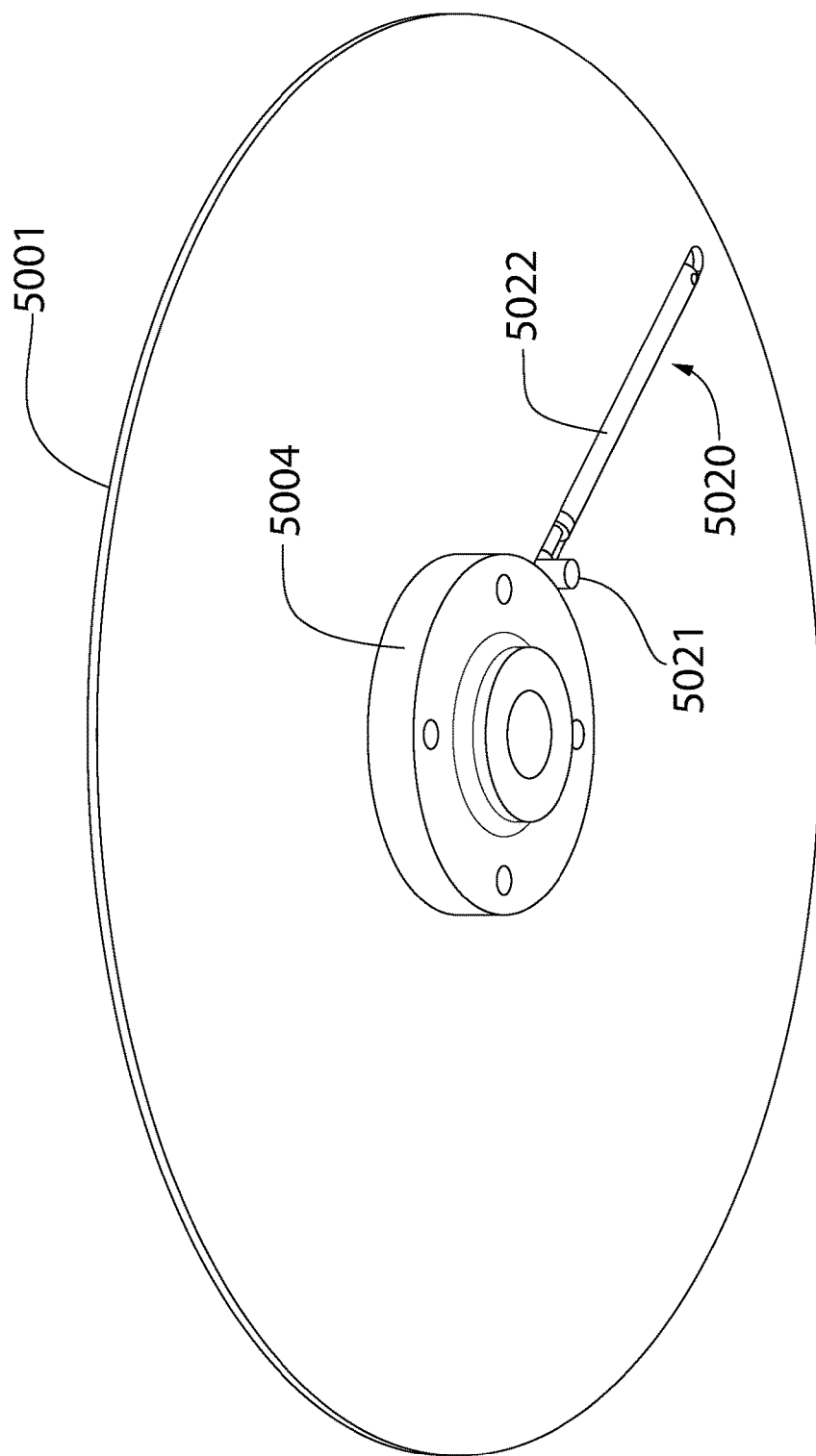
Figure 139:
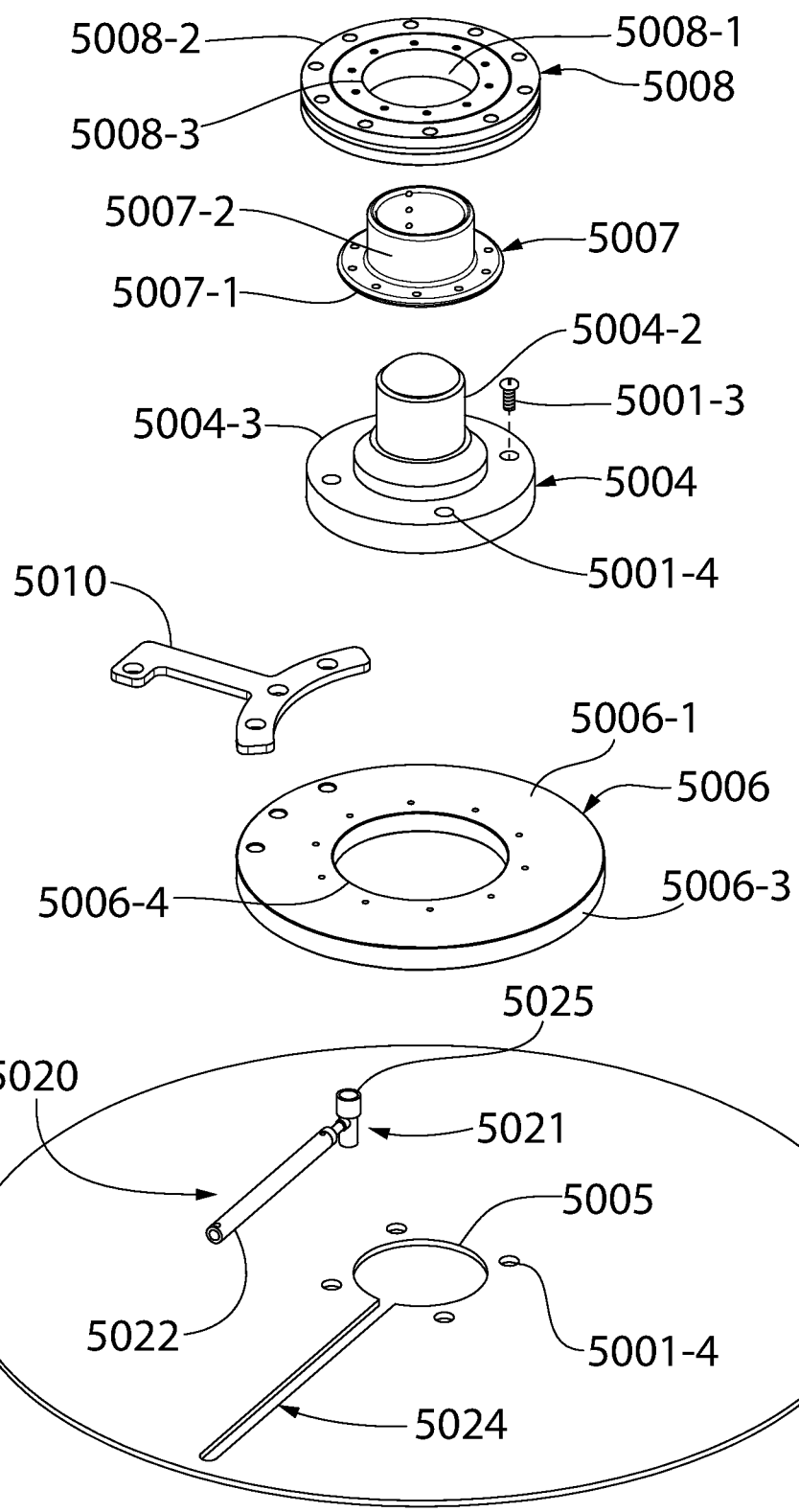
Figure 140:
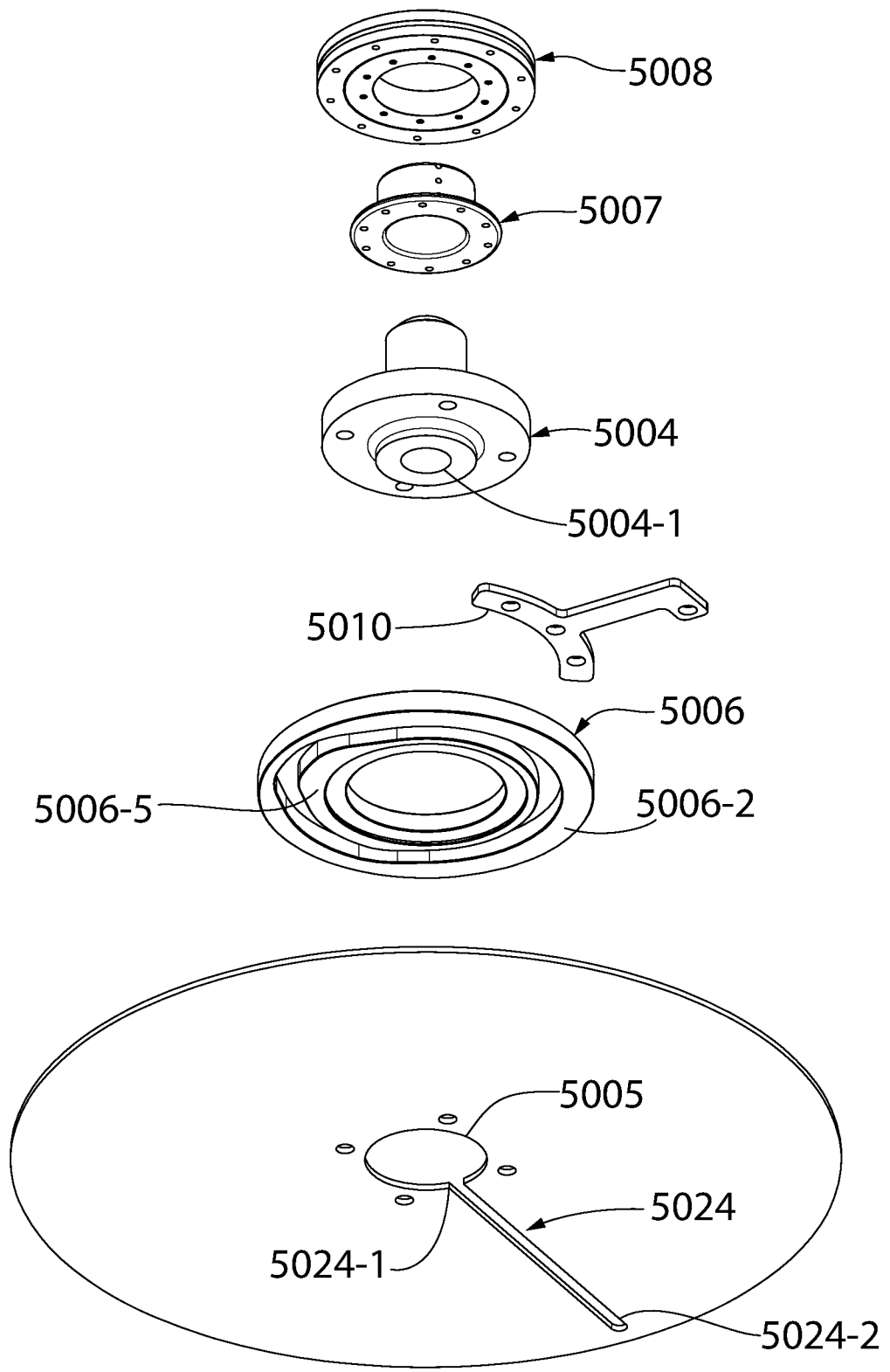
Figure 141:
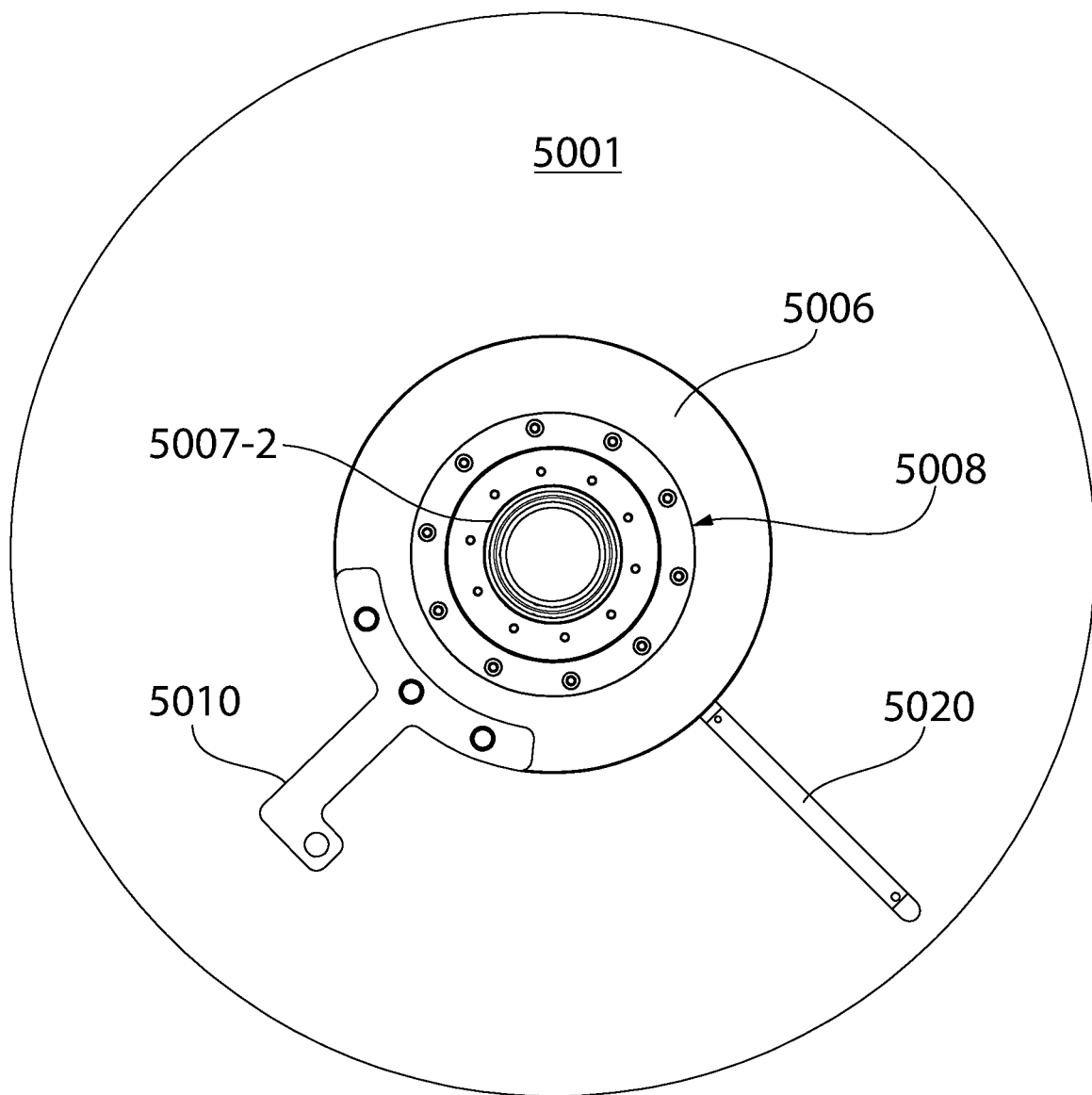
Figure 142:
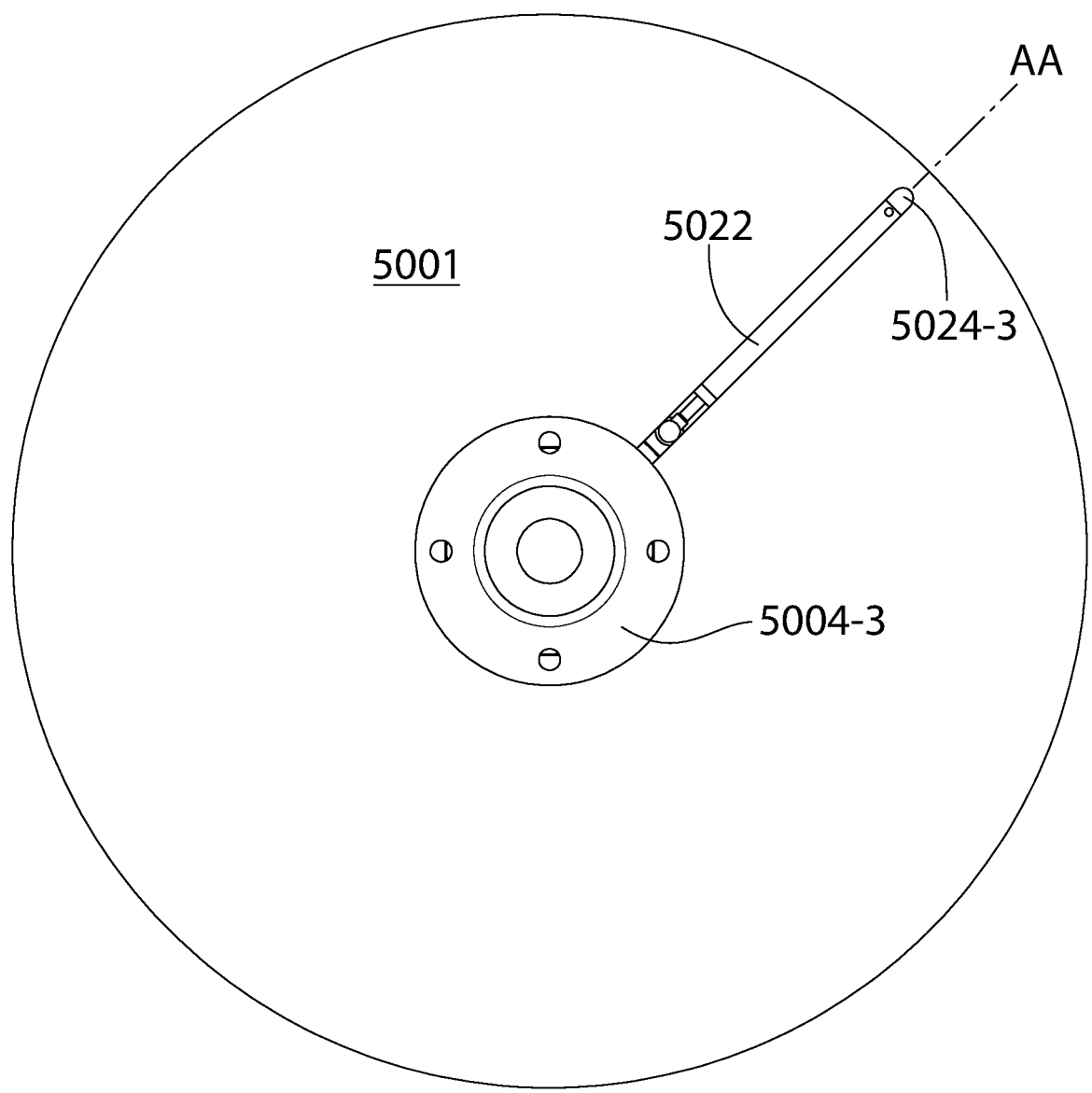
Figure 143:
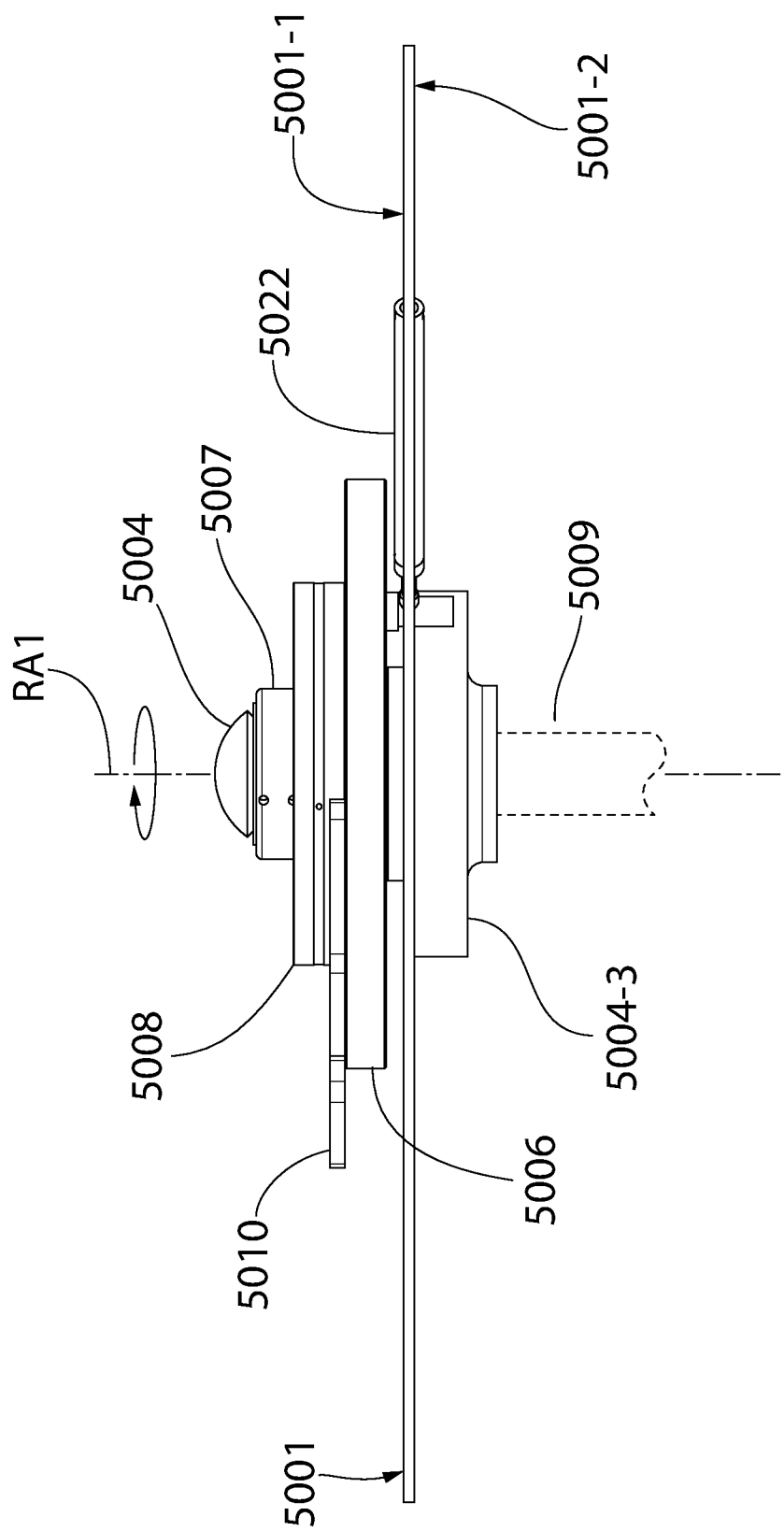
Figure 144:
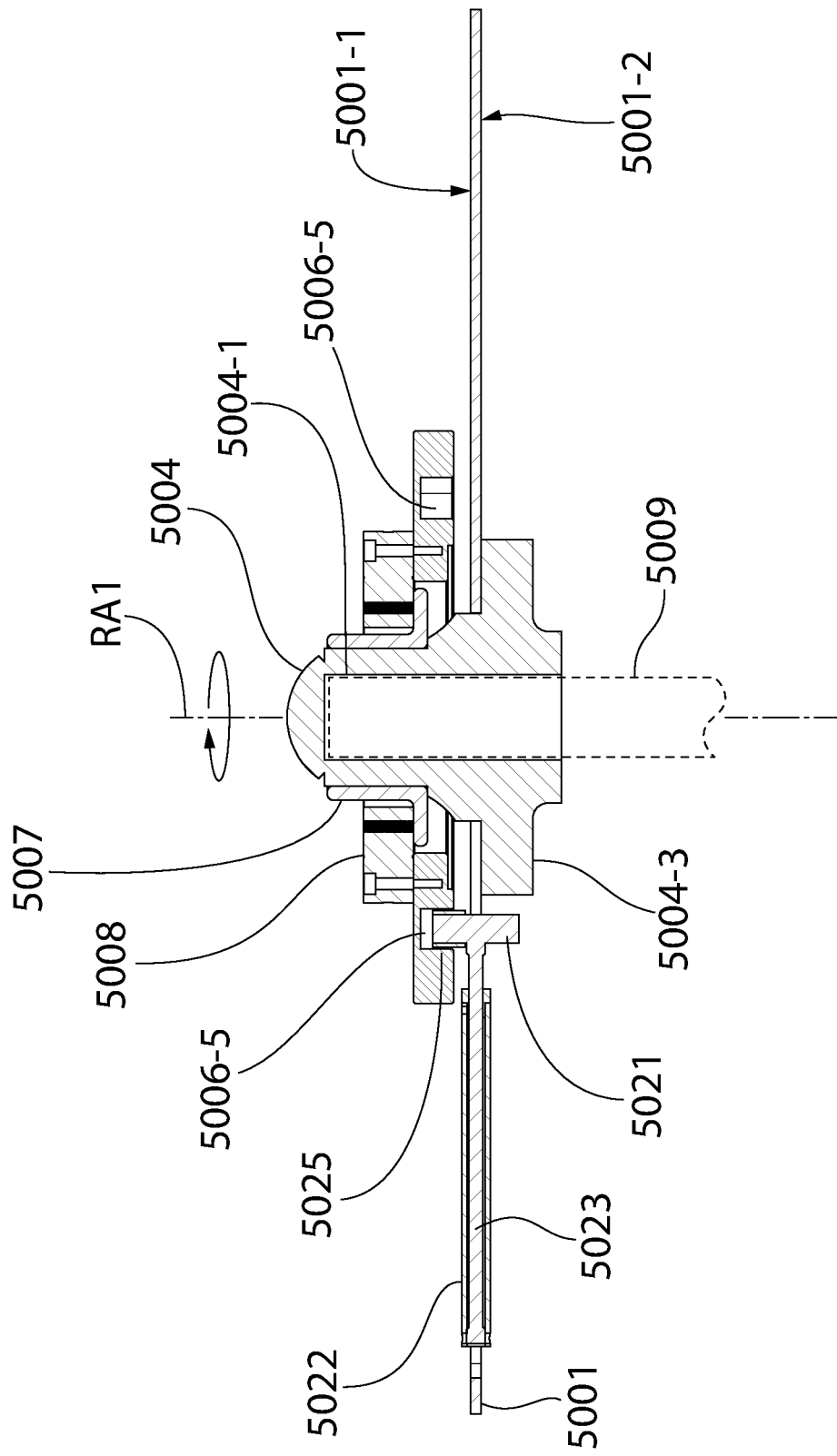
Figure 145:
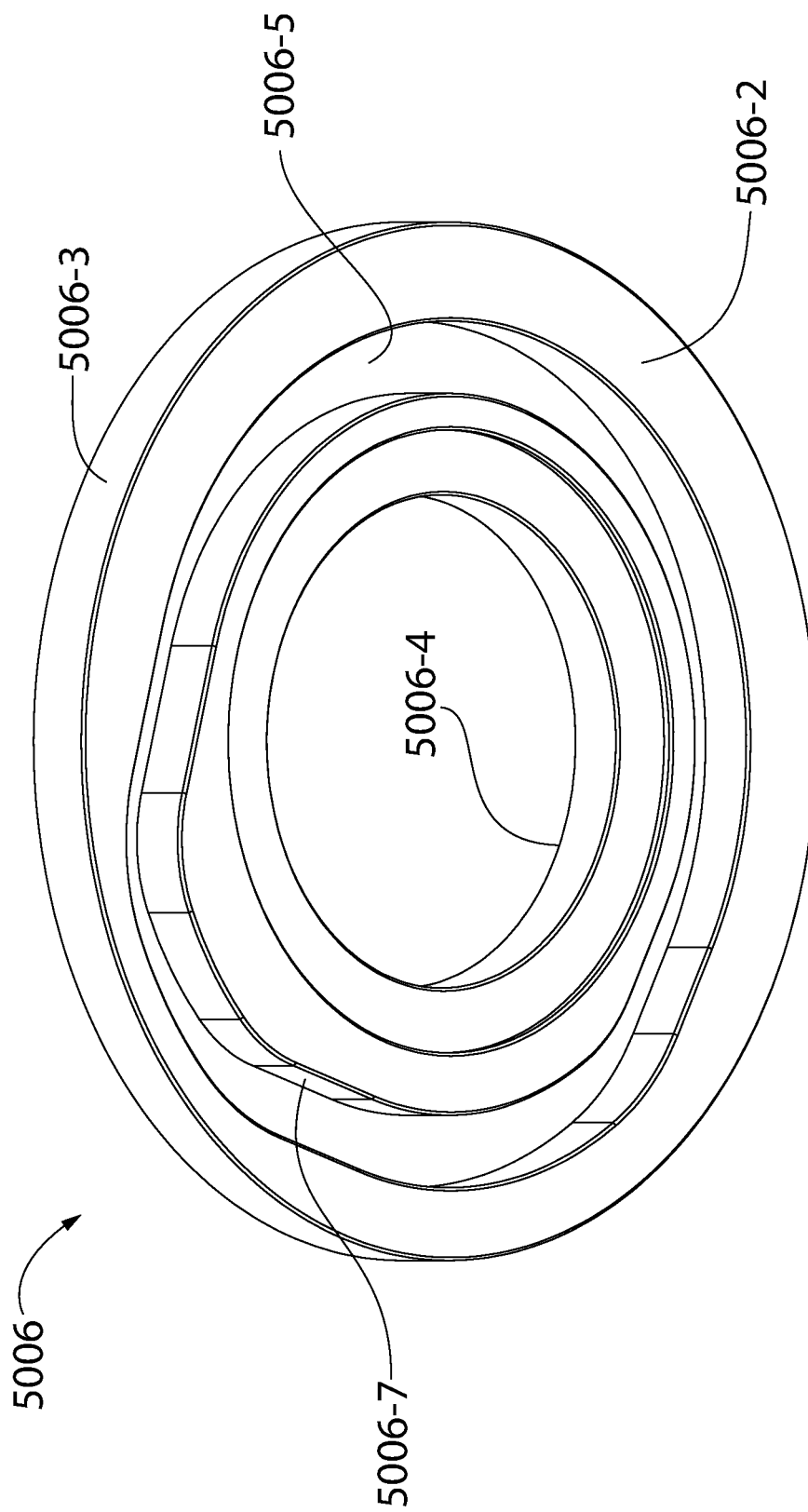
Figure 146:
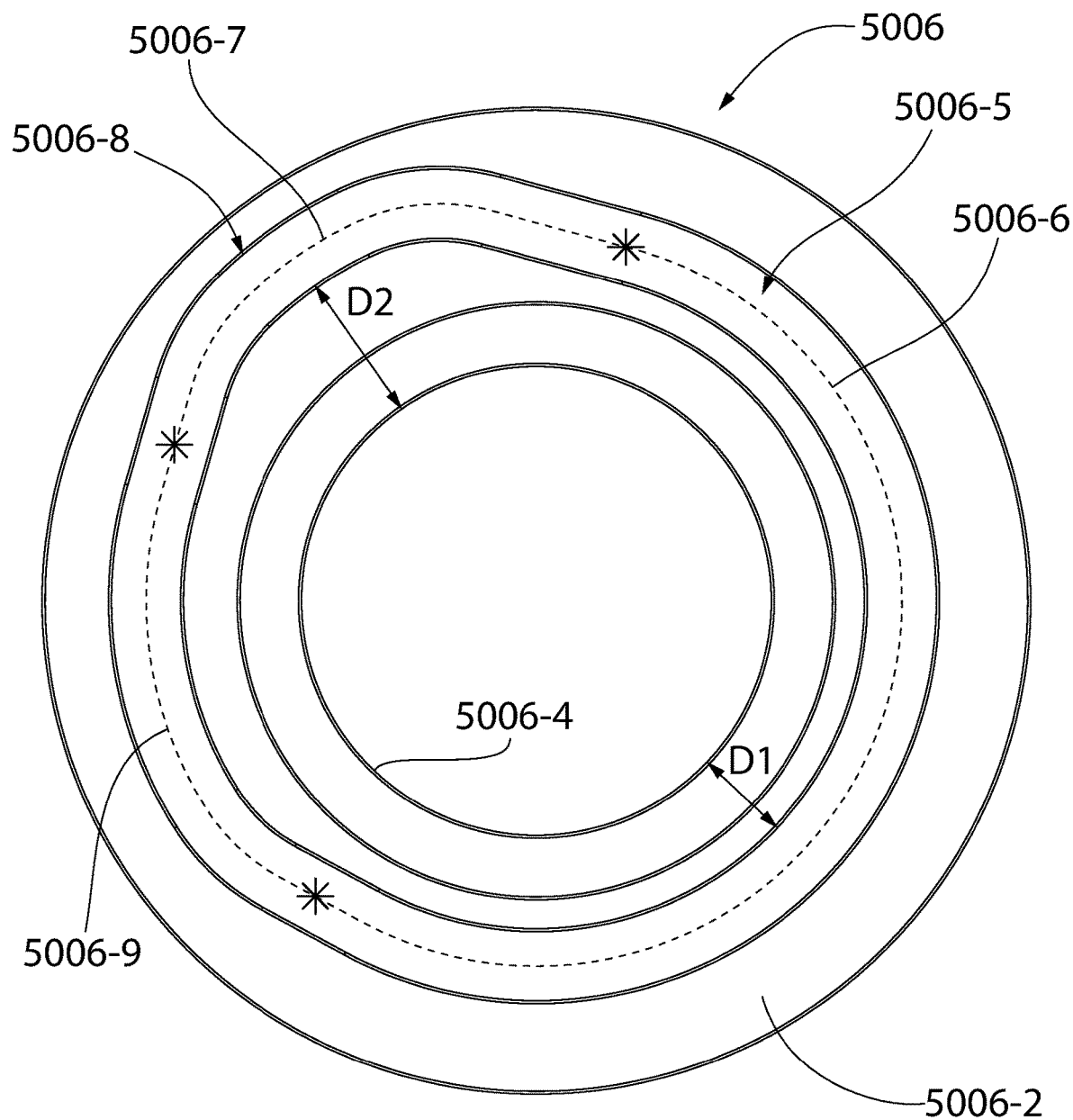
Figure 147:
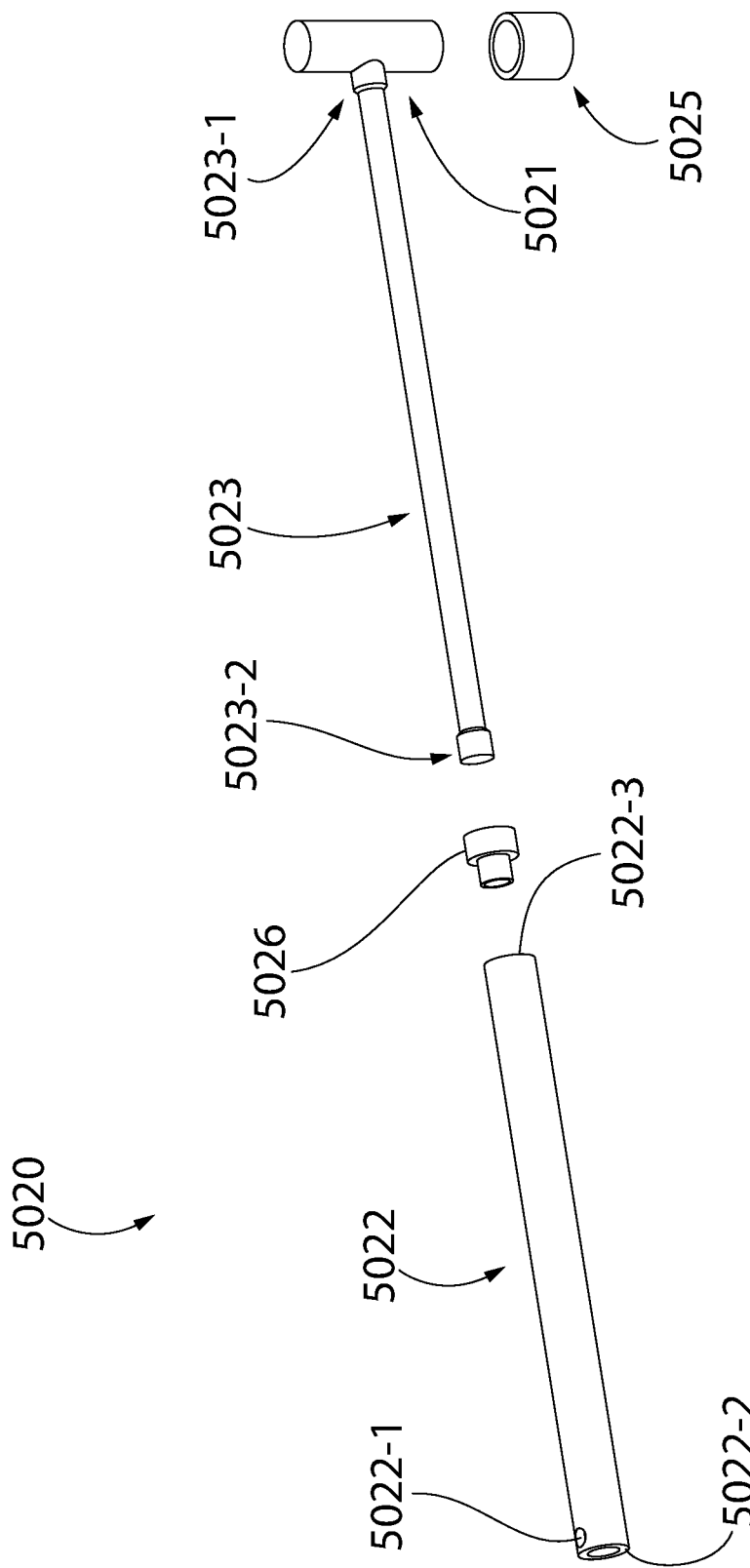
Figure 148:
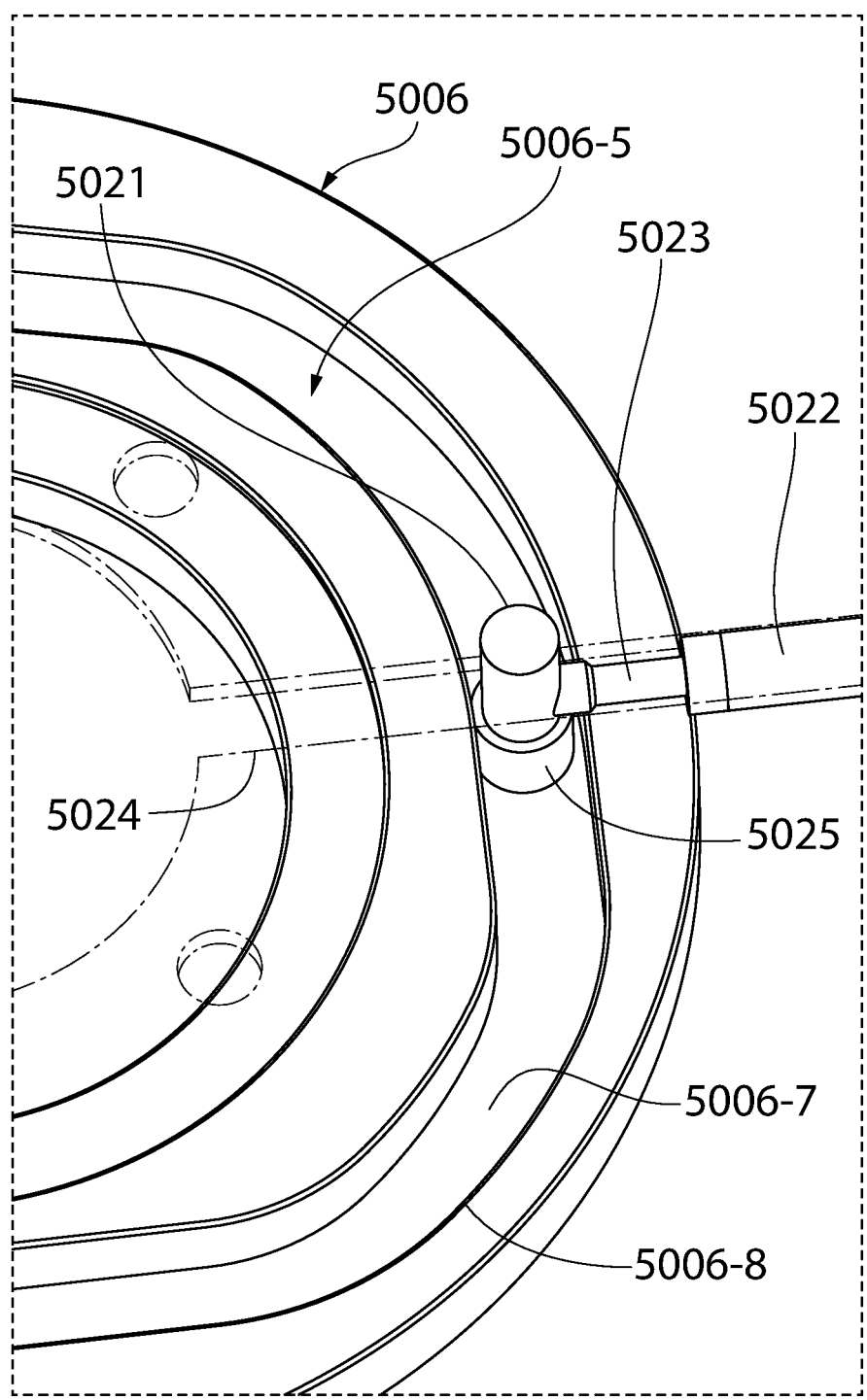
Figure 149A:
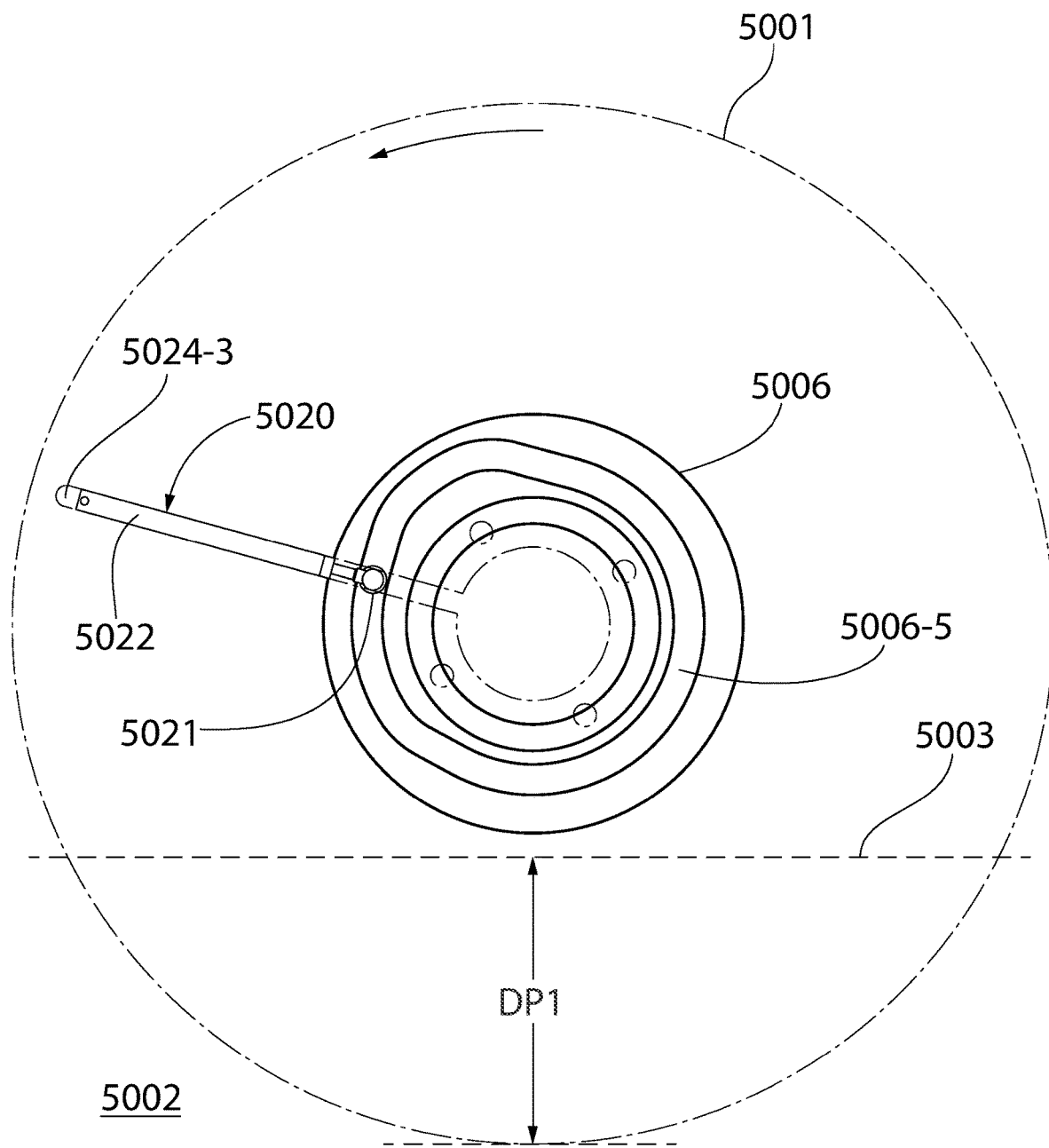
Figure 149B:
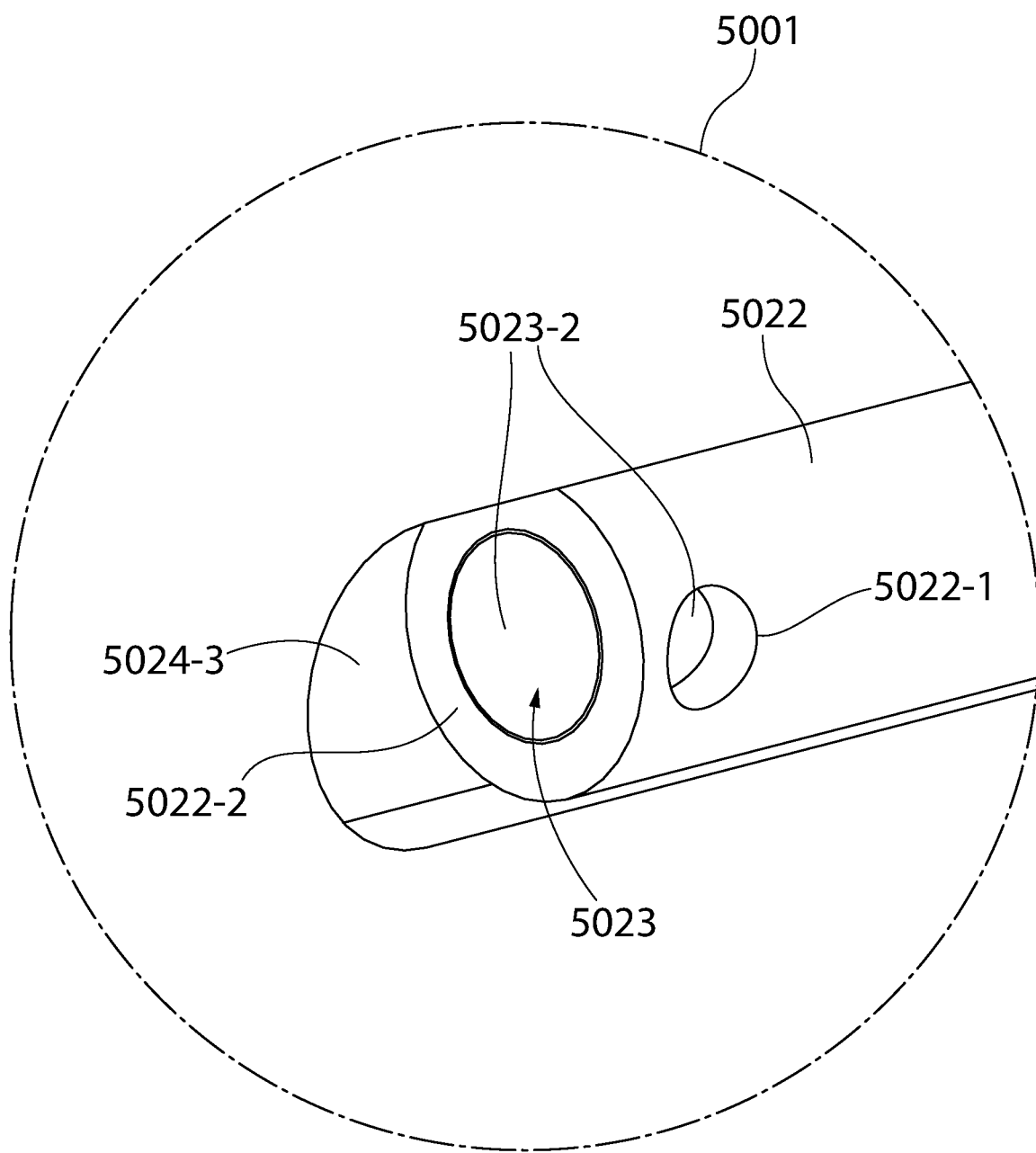
Figure 150A:
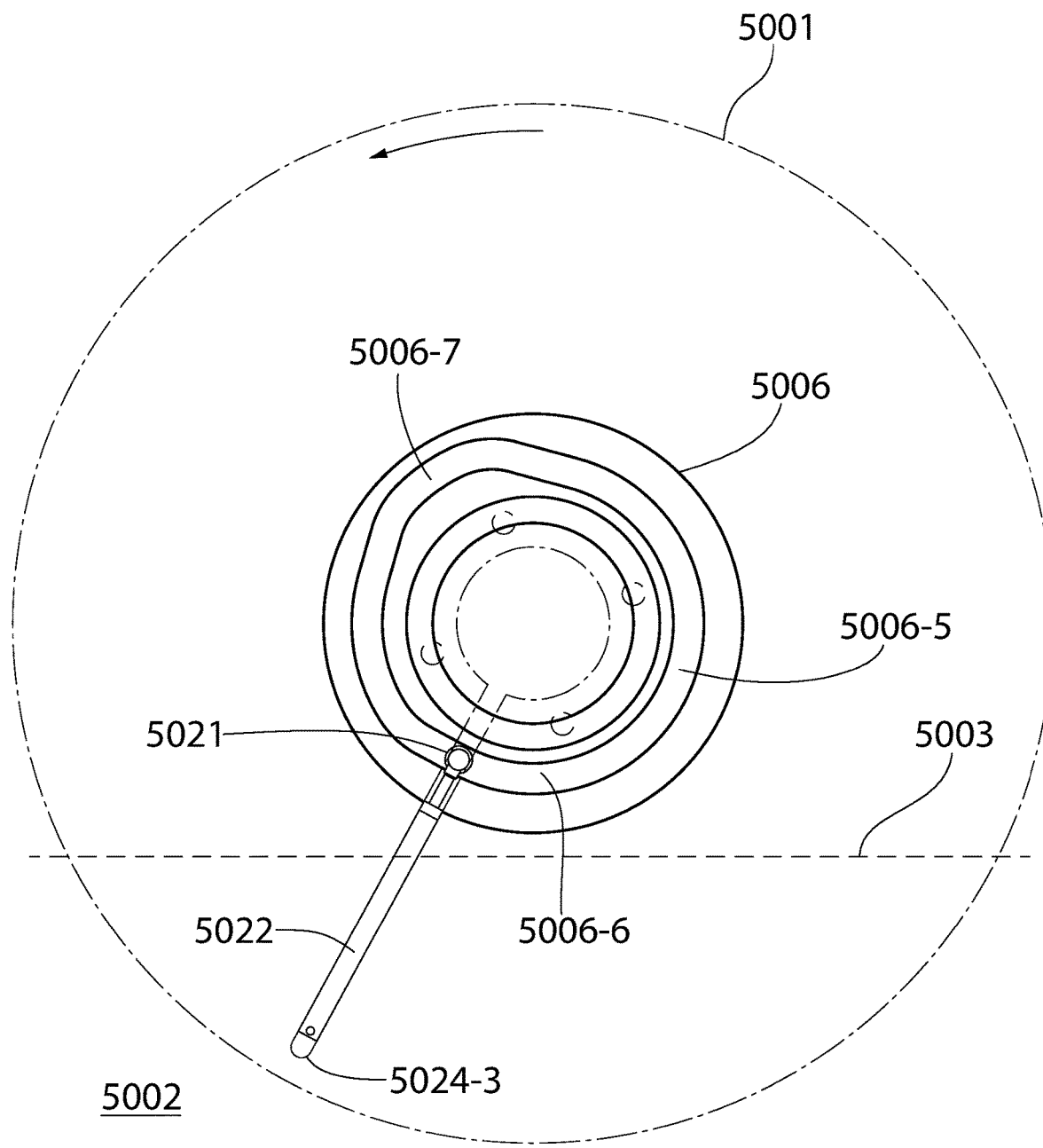
Figure 150B:
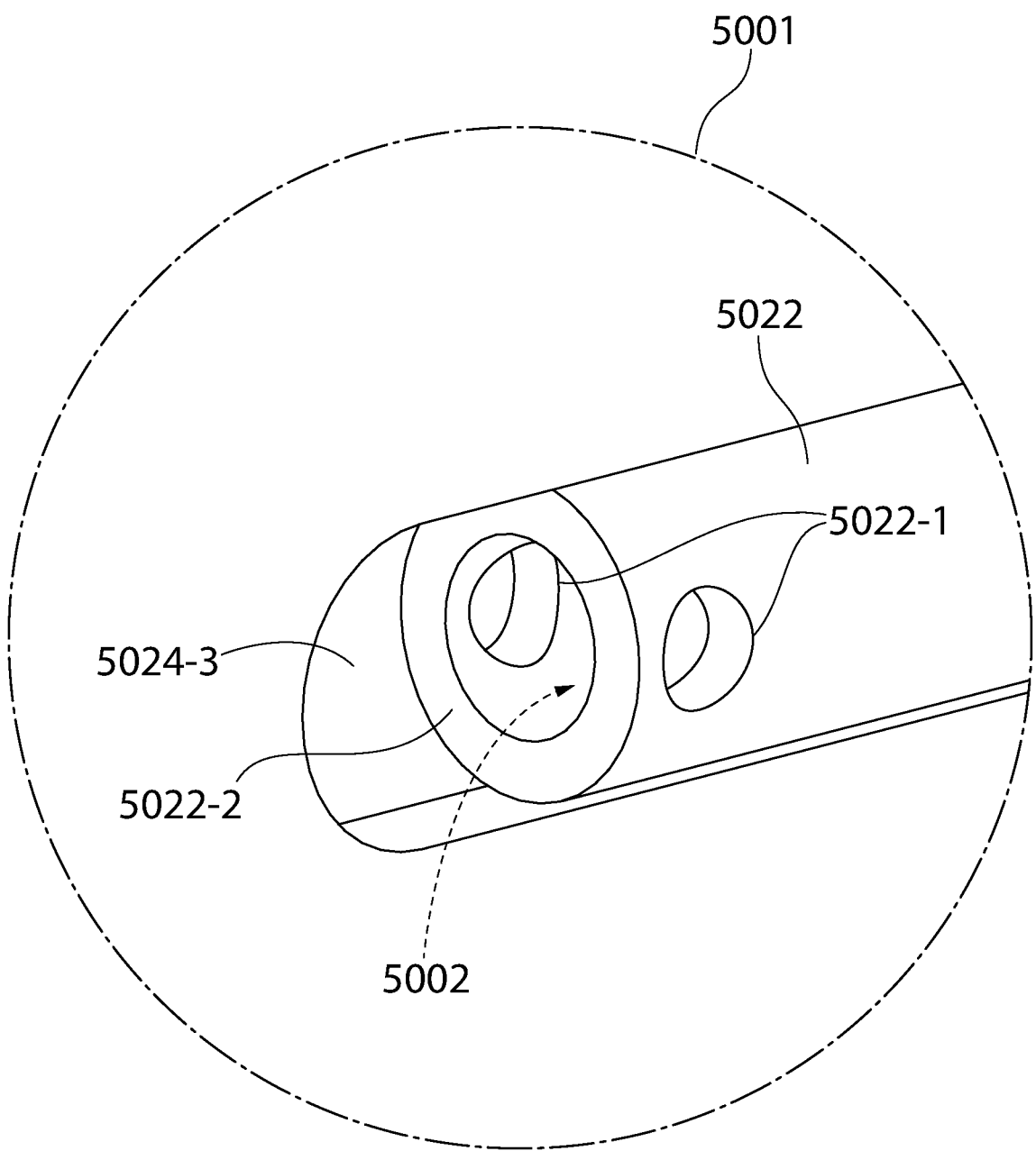
Figure 151A:
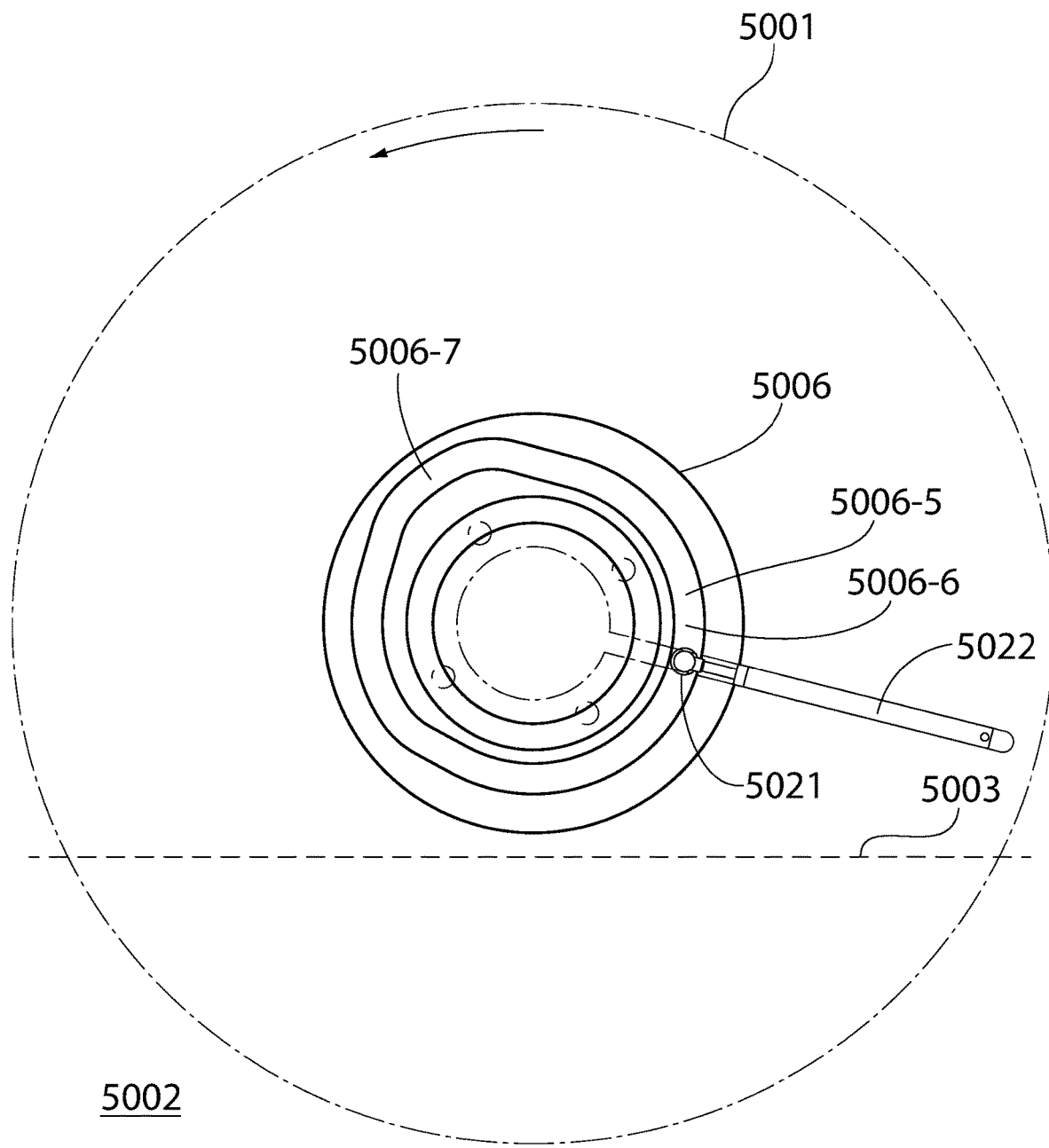
Figure 151B:
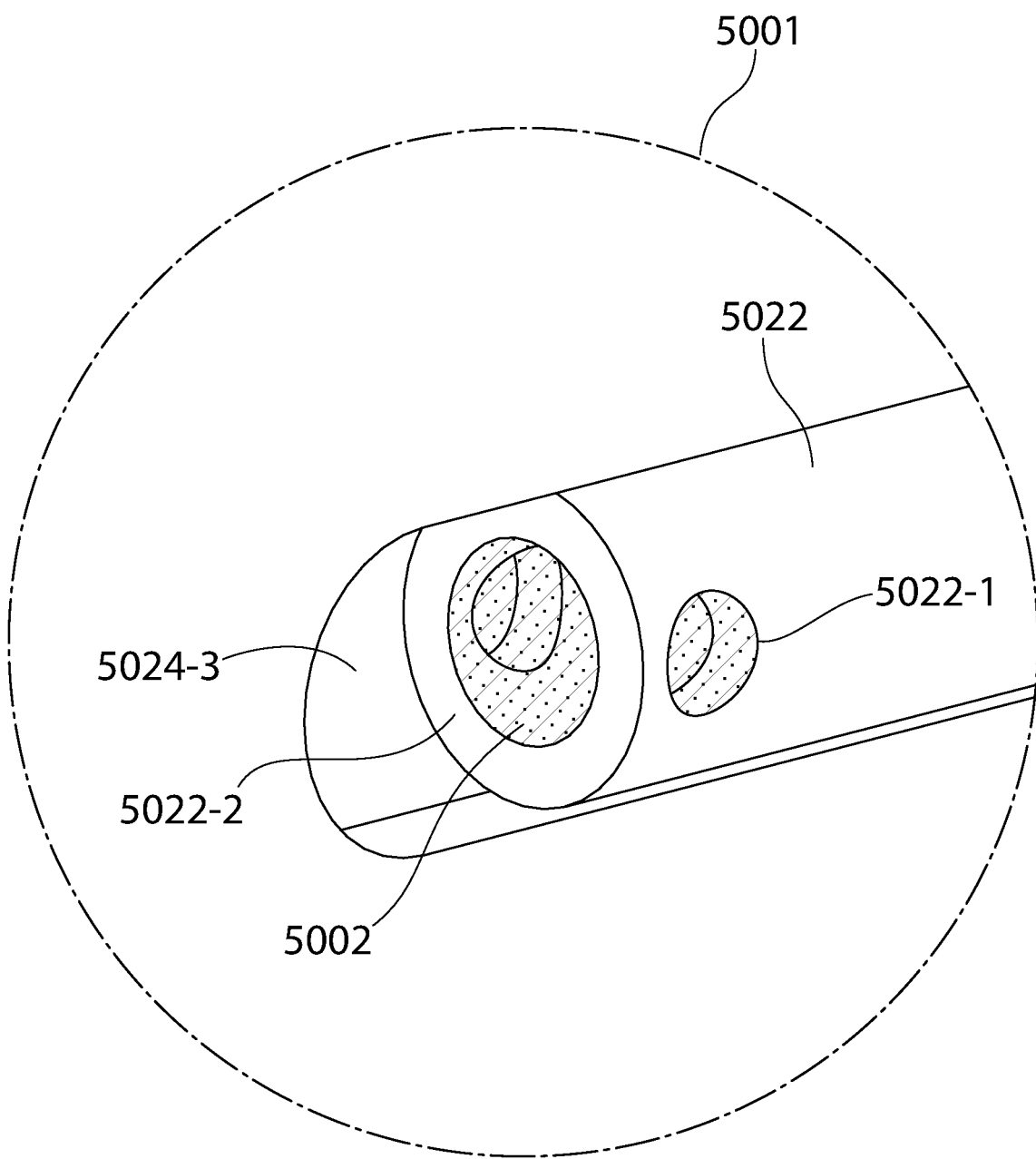
Figure 152A:
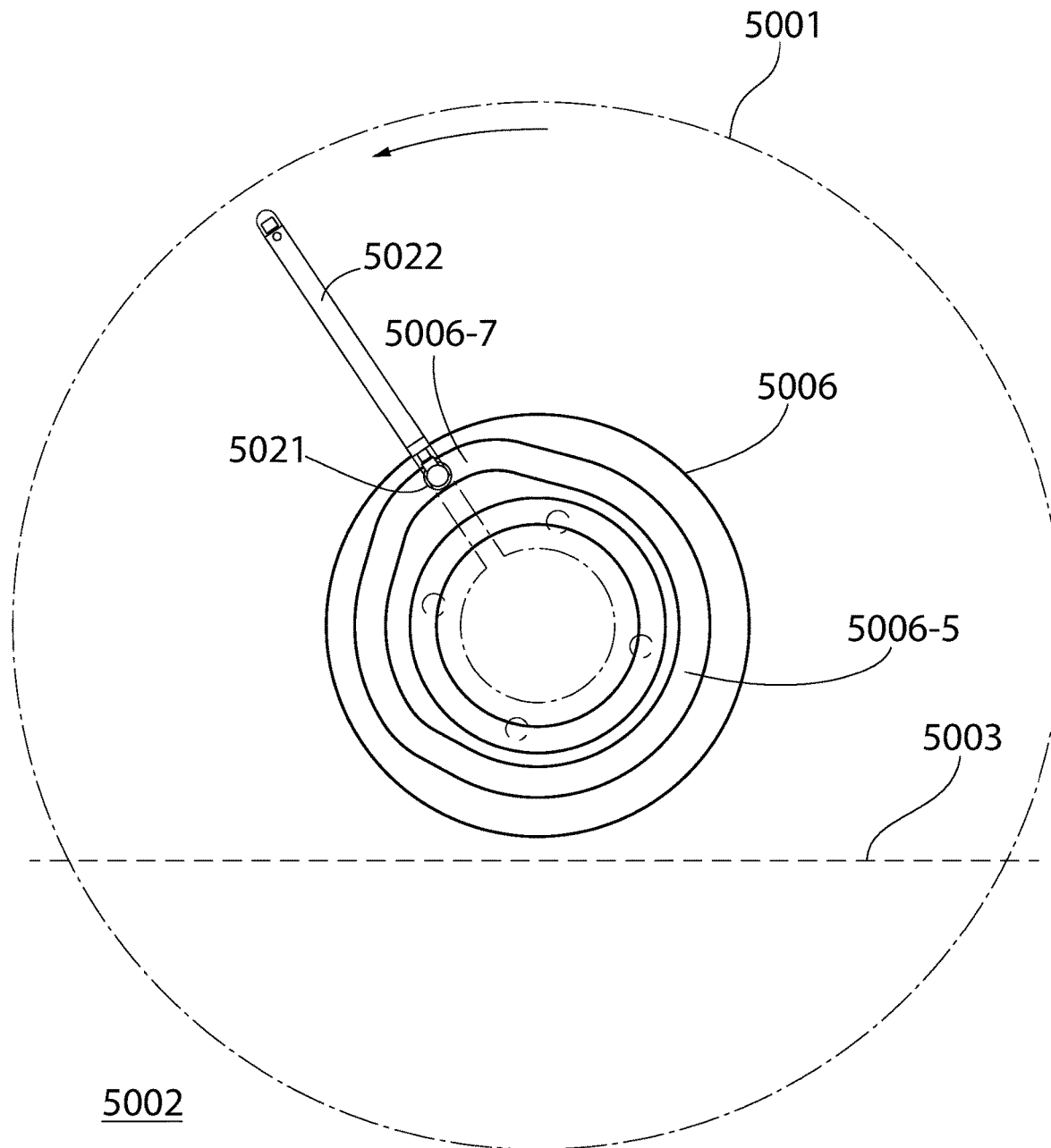
Figure 152B:
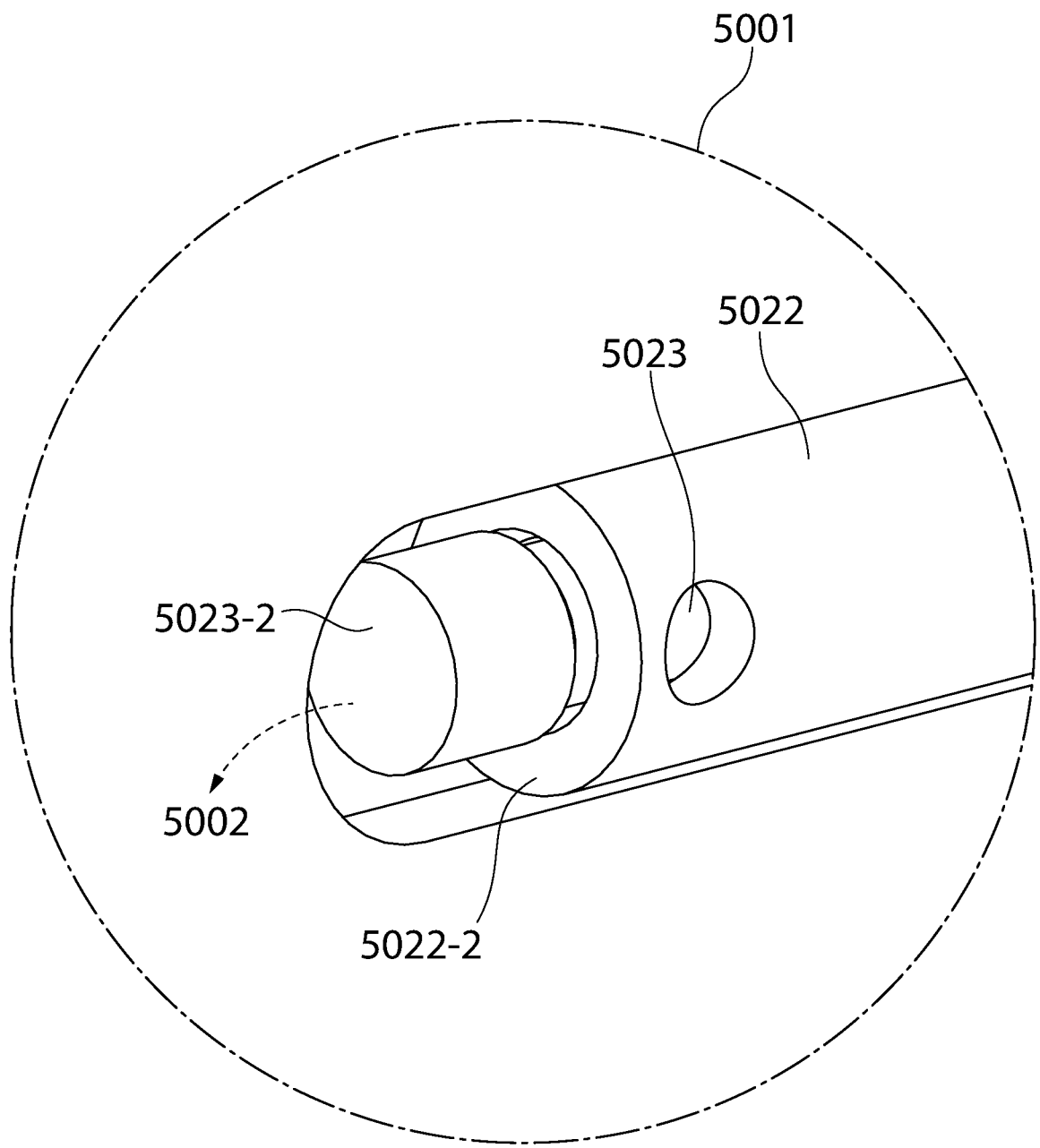
Figure 153:
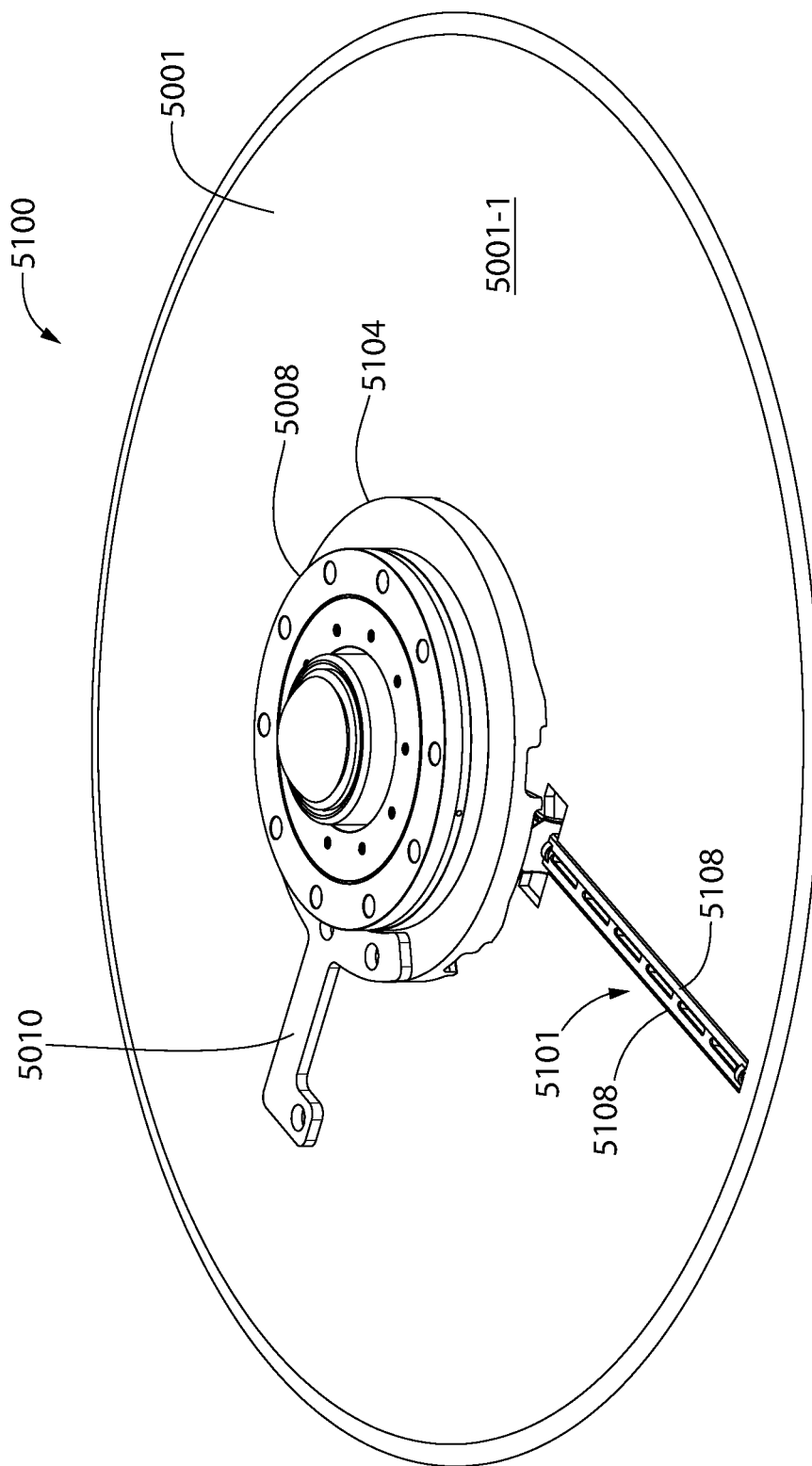
Figure 154:
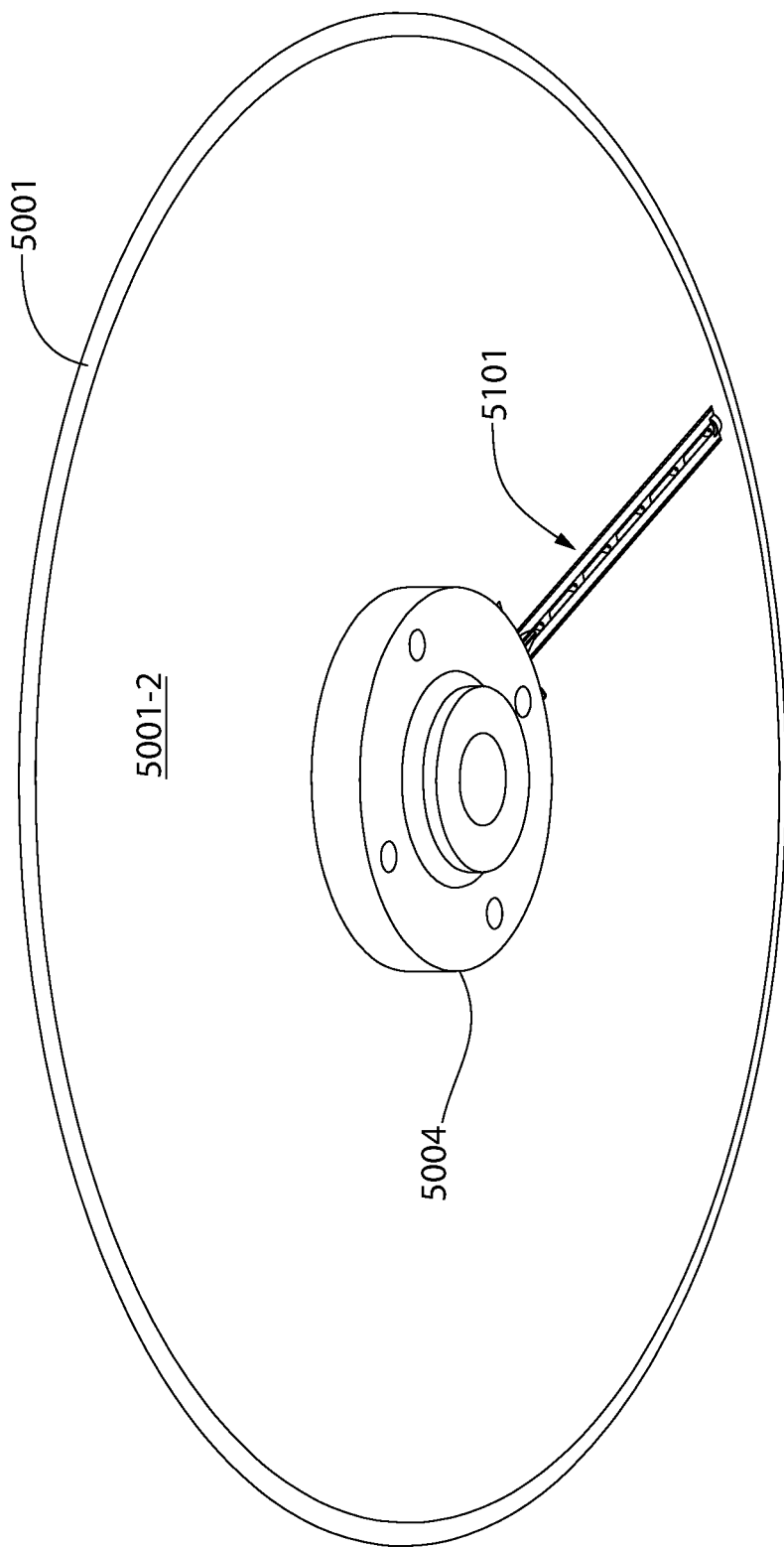
Figure 155:
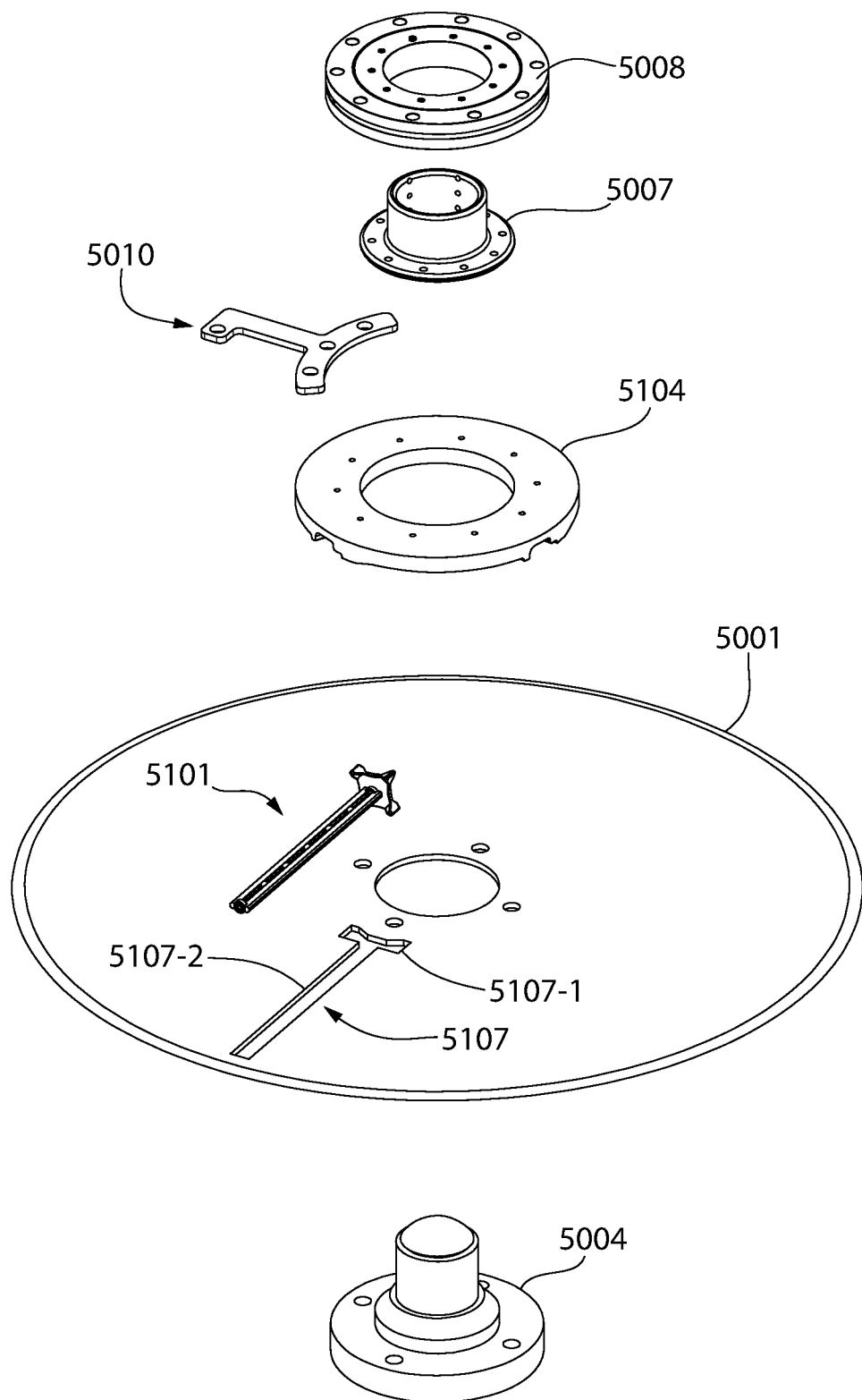
Figure 156:
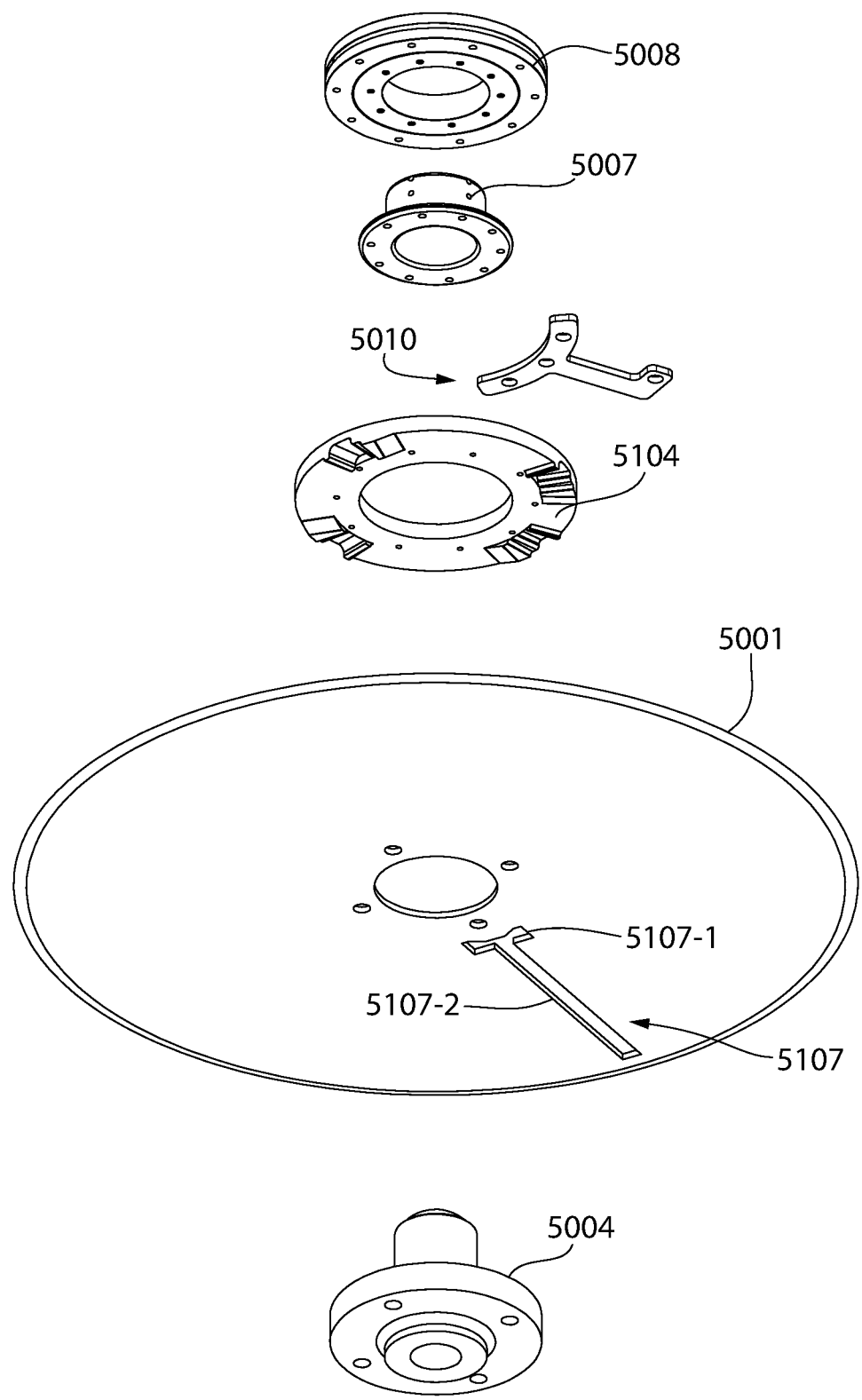
Figure 157:
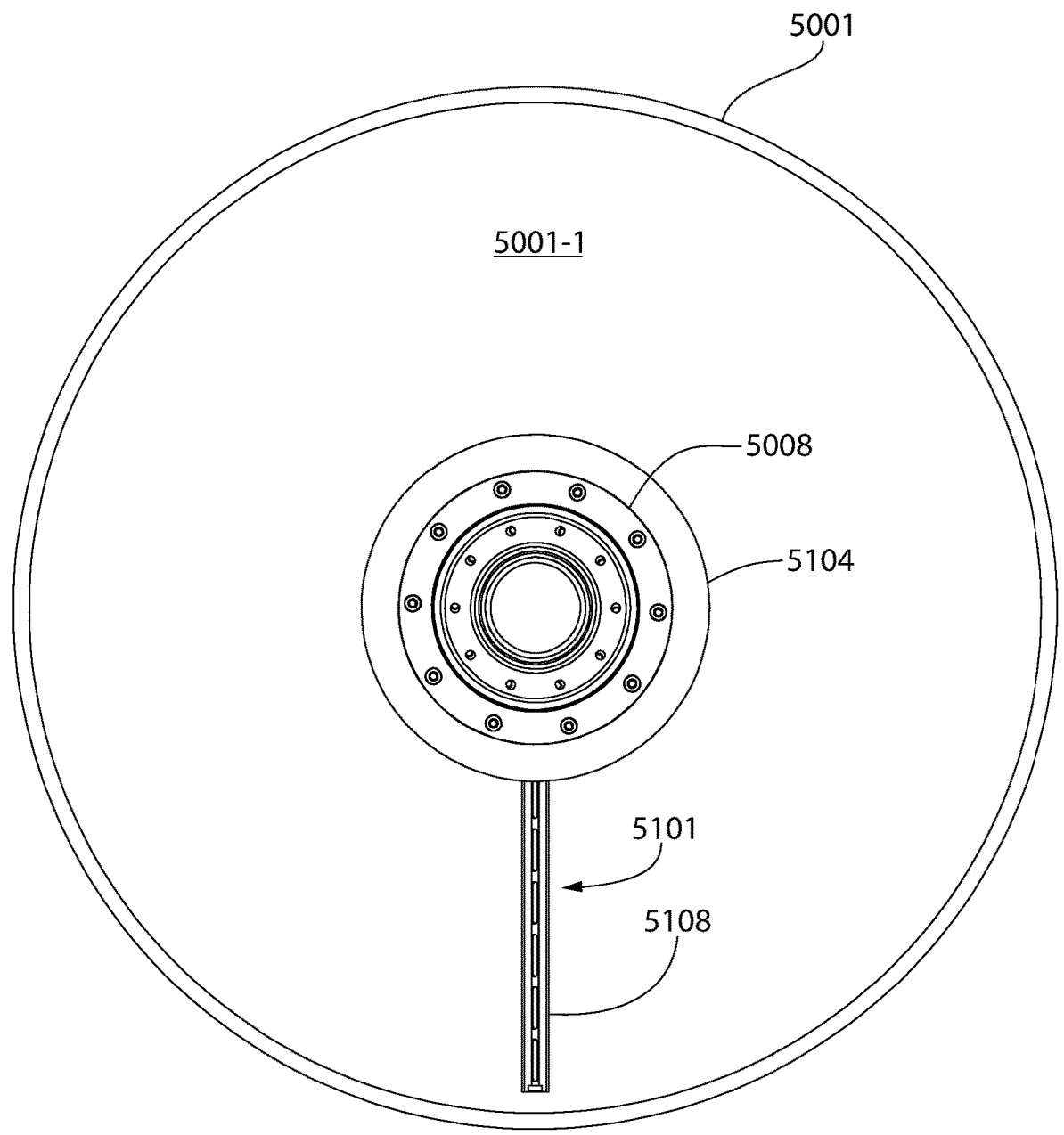
Figure 158:
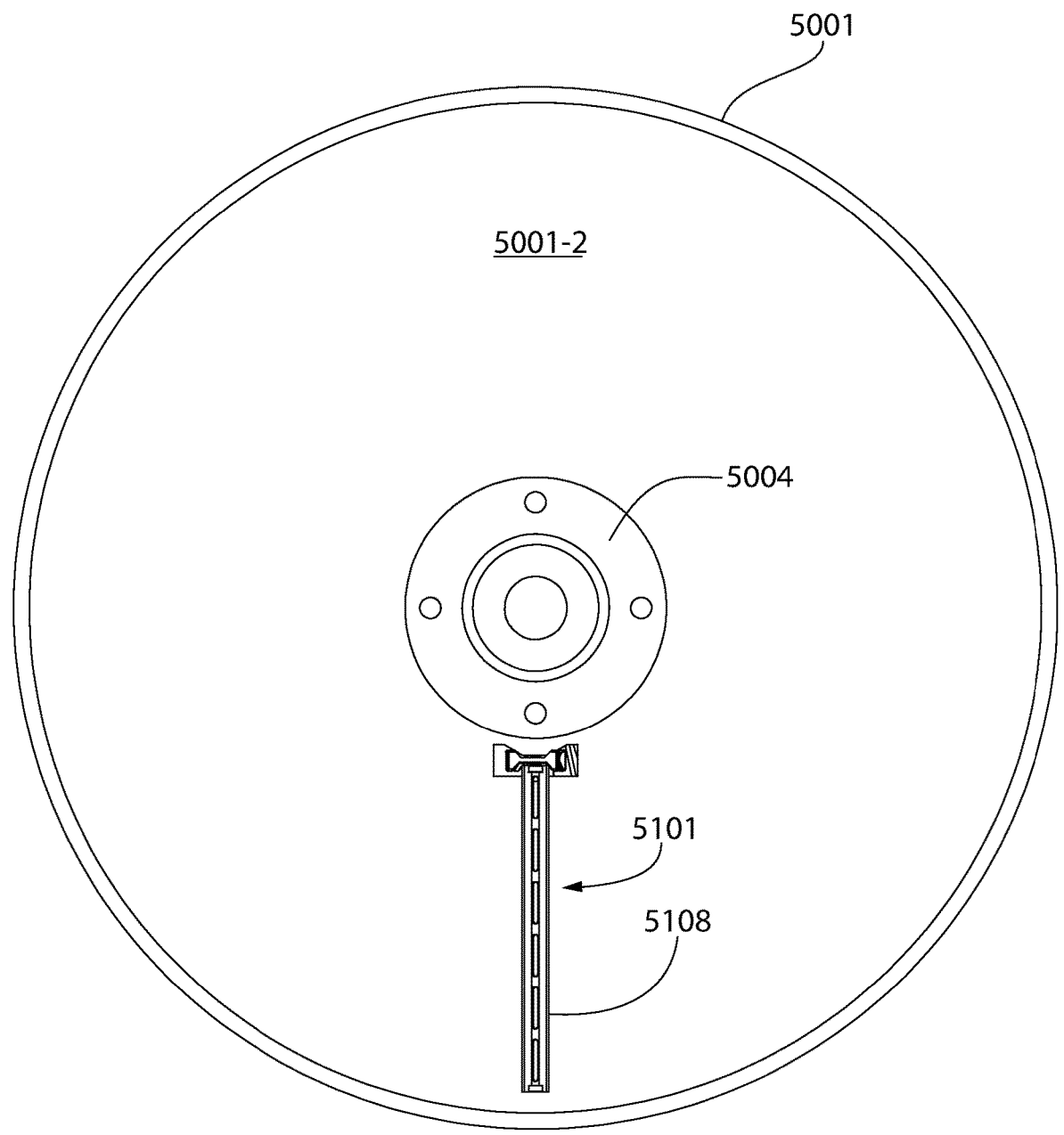
Figure 159:
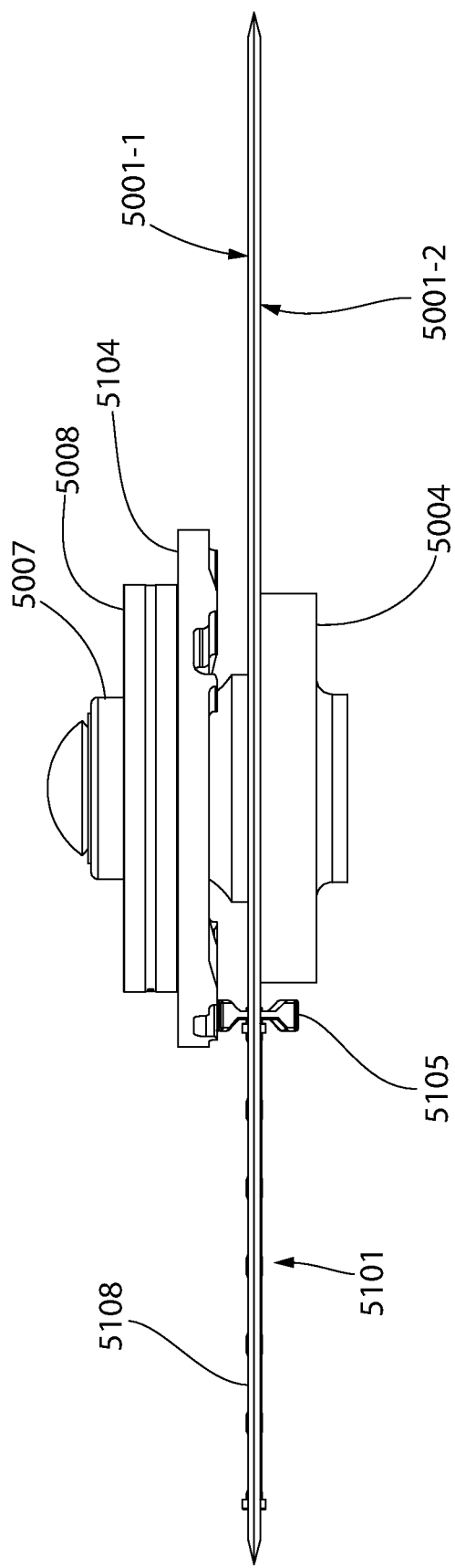
Figure 160:
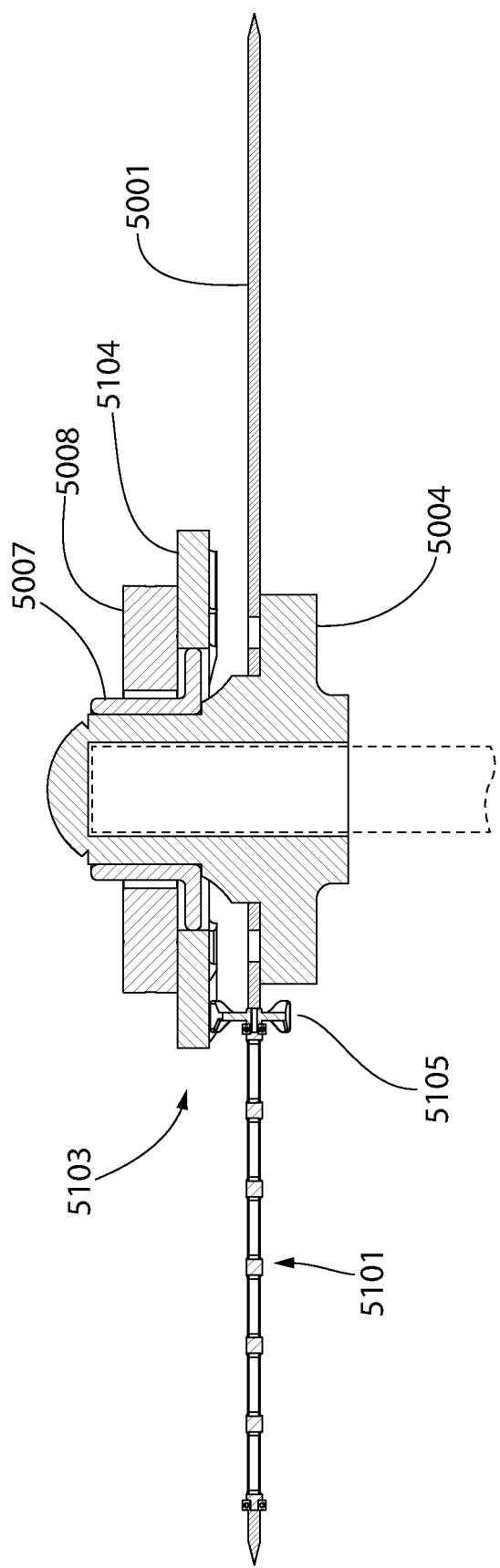
Figure 161:
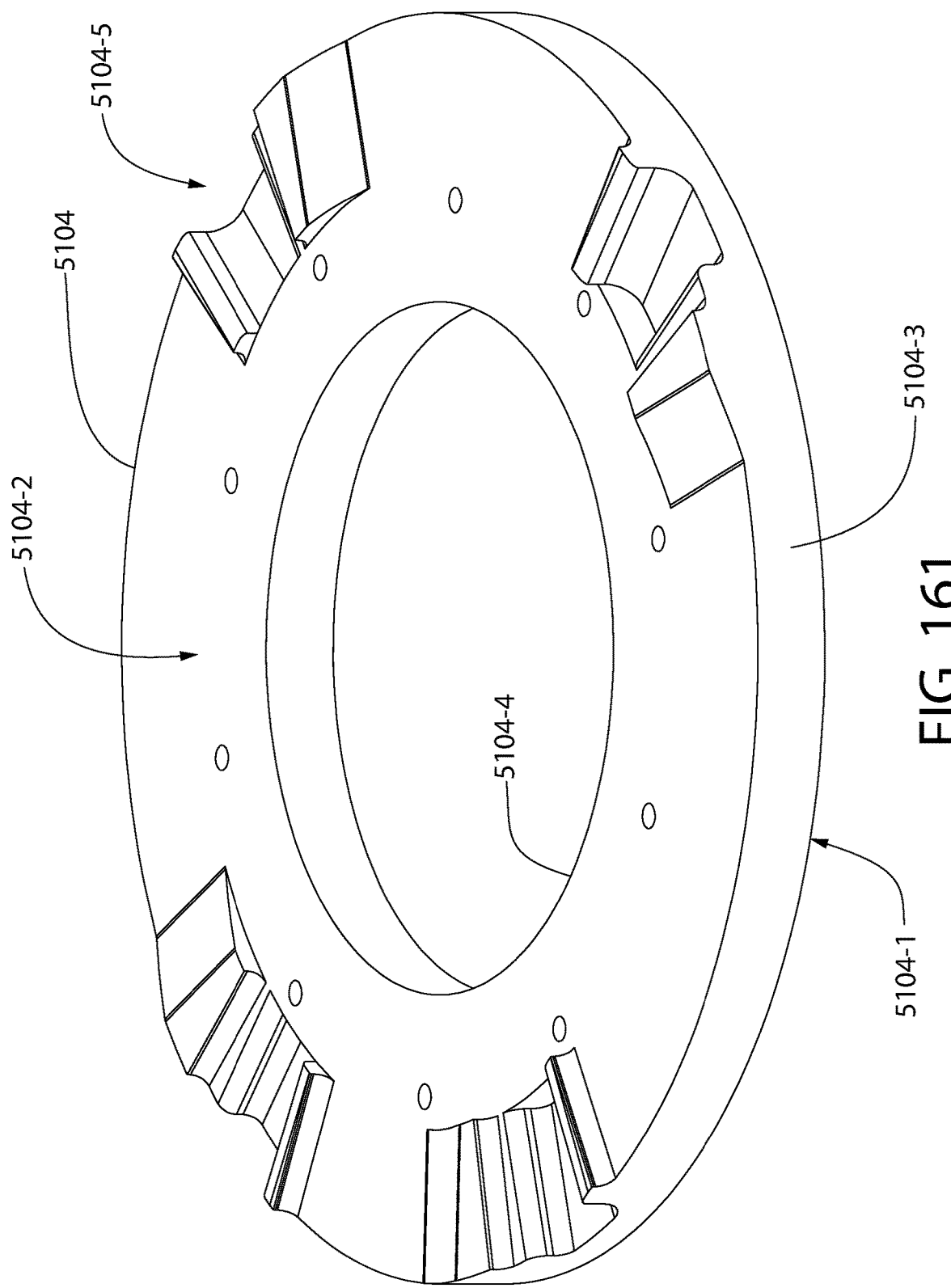
Figure 162:
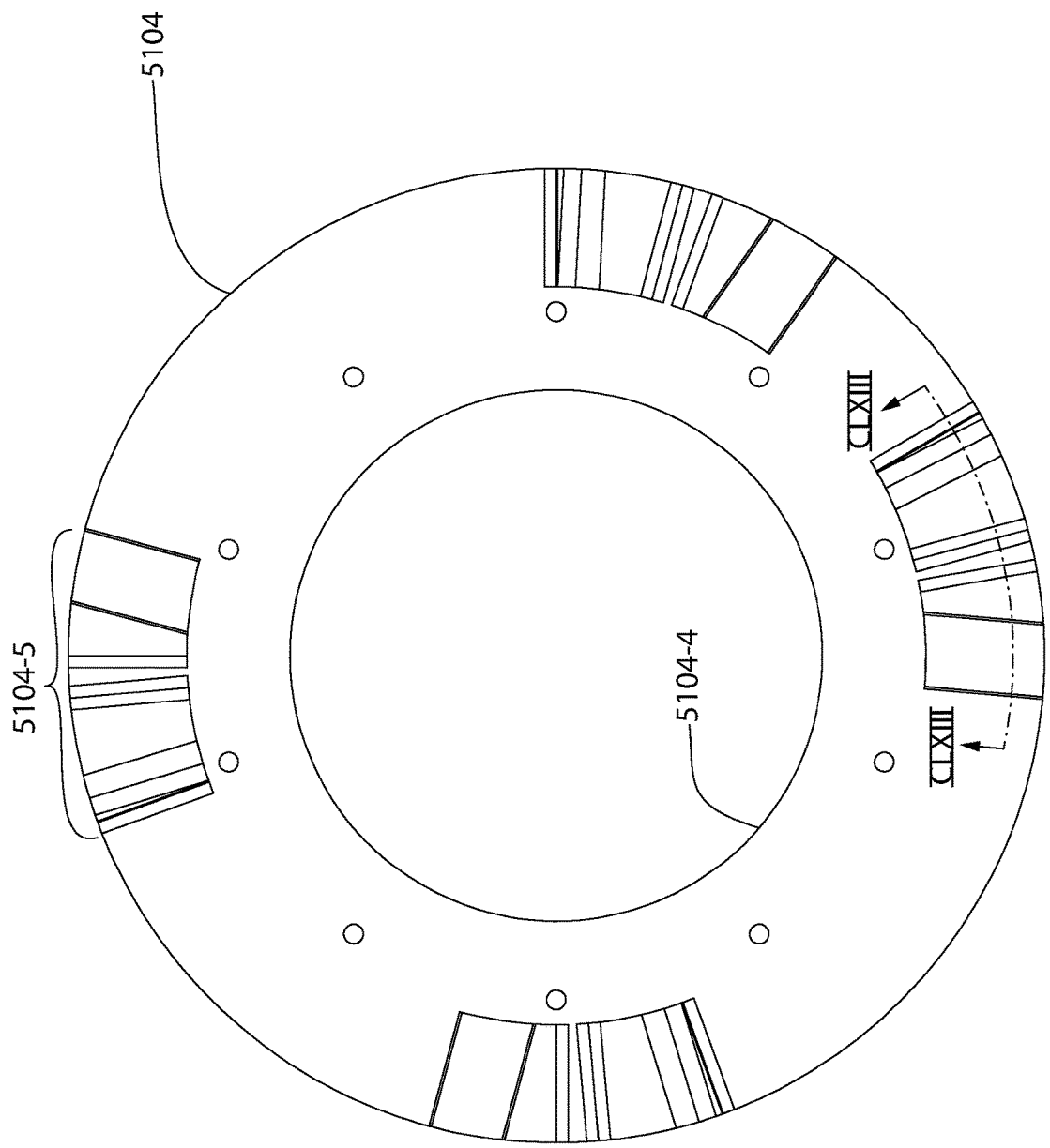
Figure 163:
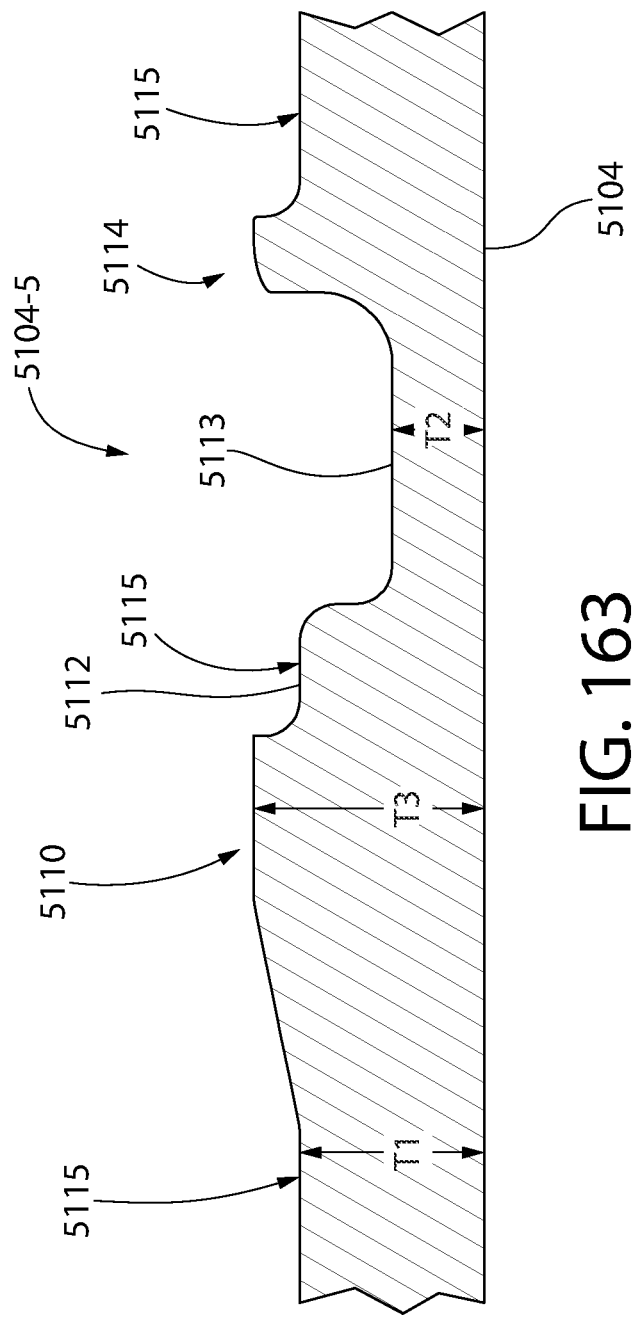
Figure 164:
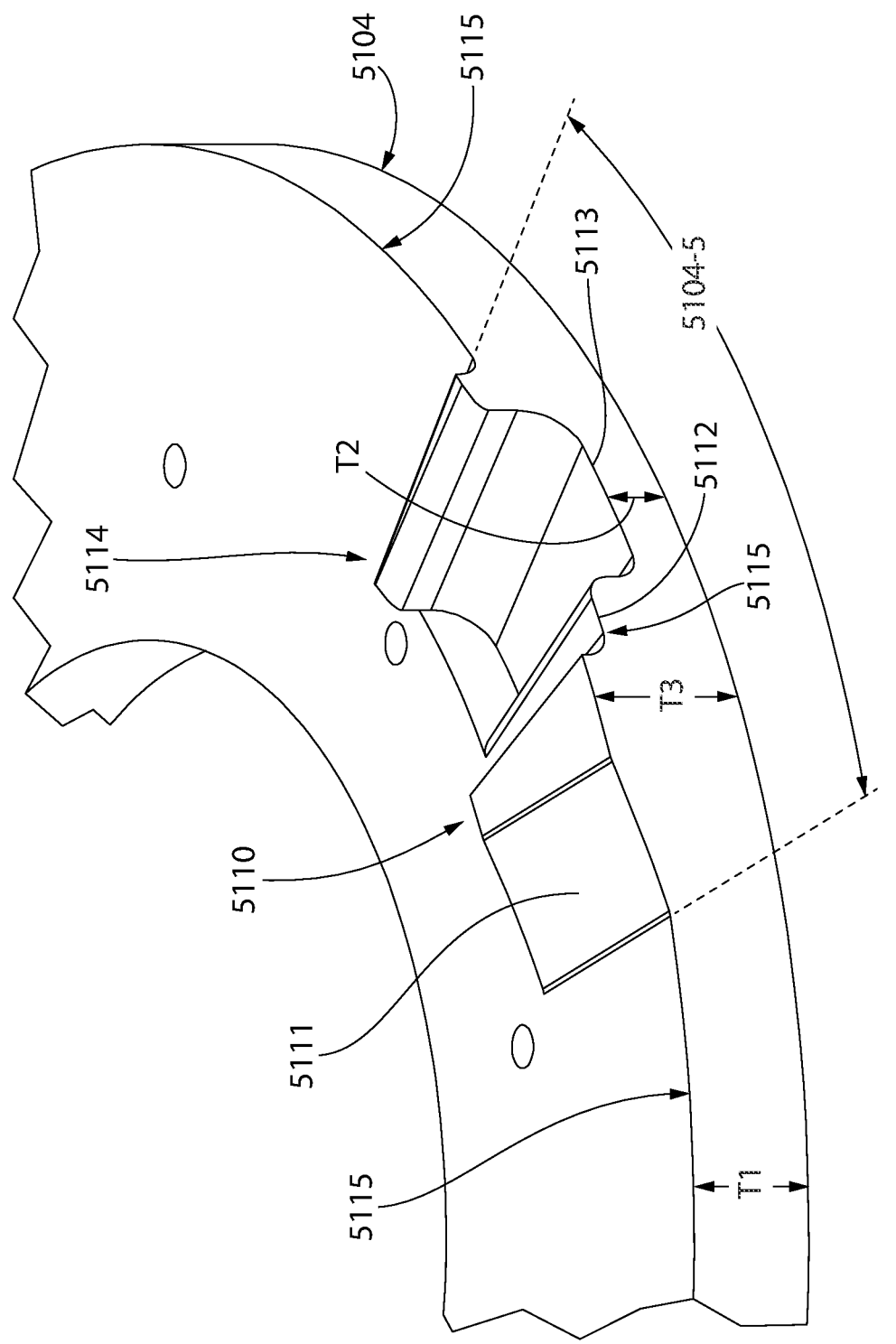
Figure 165:
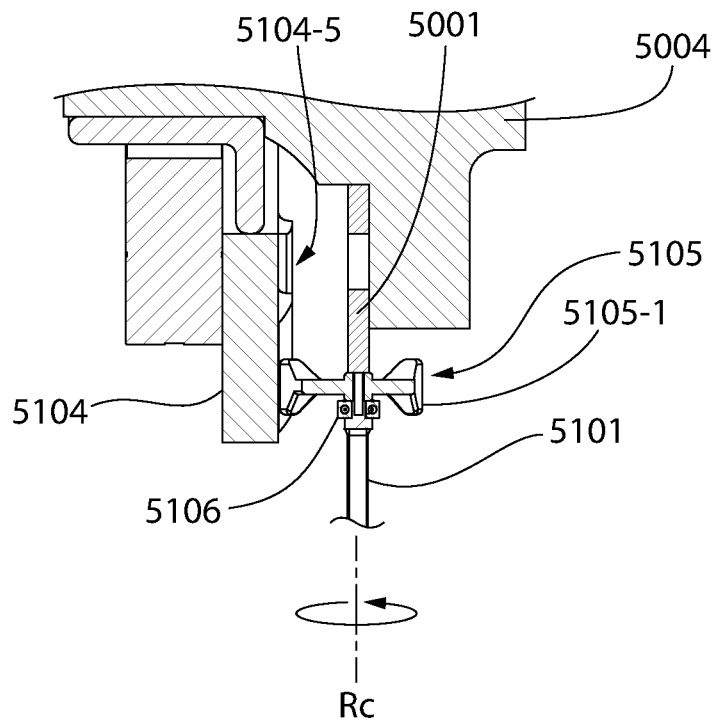
Figure 166:
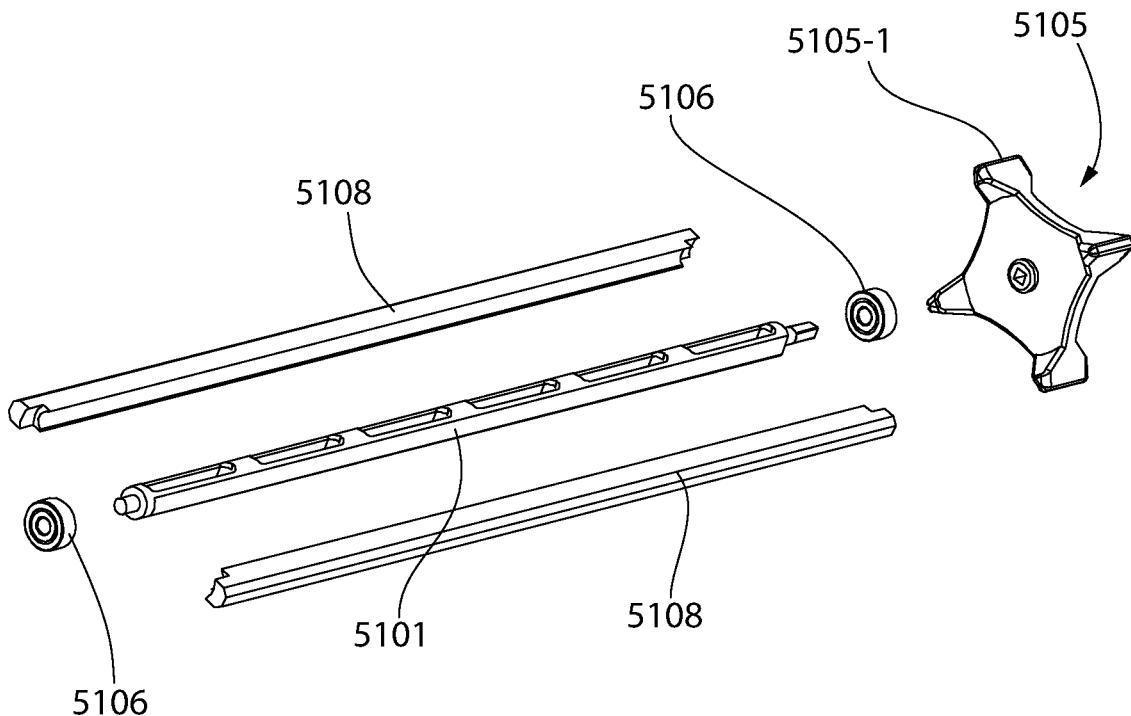
Figure 167:
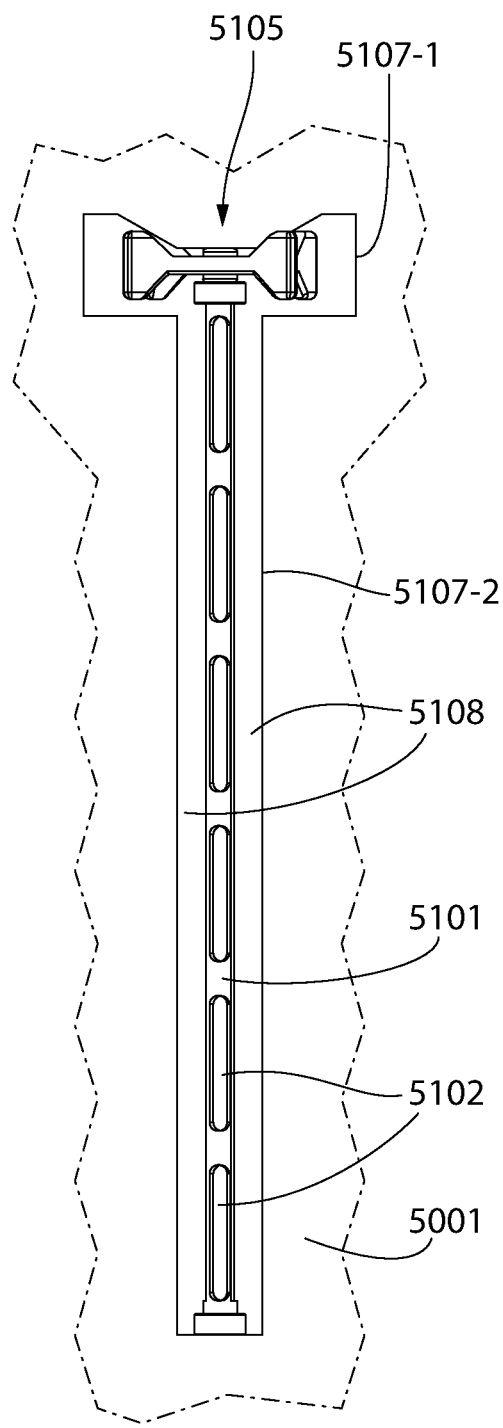
Figure 168:
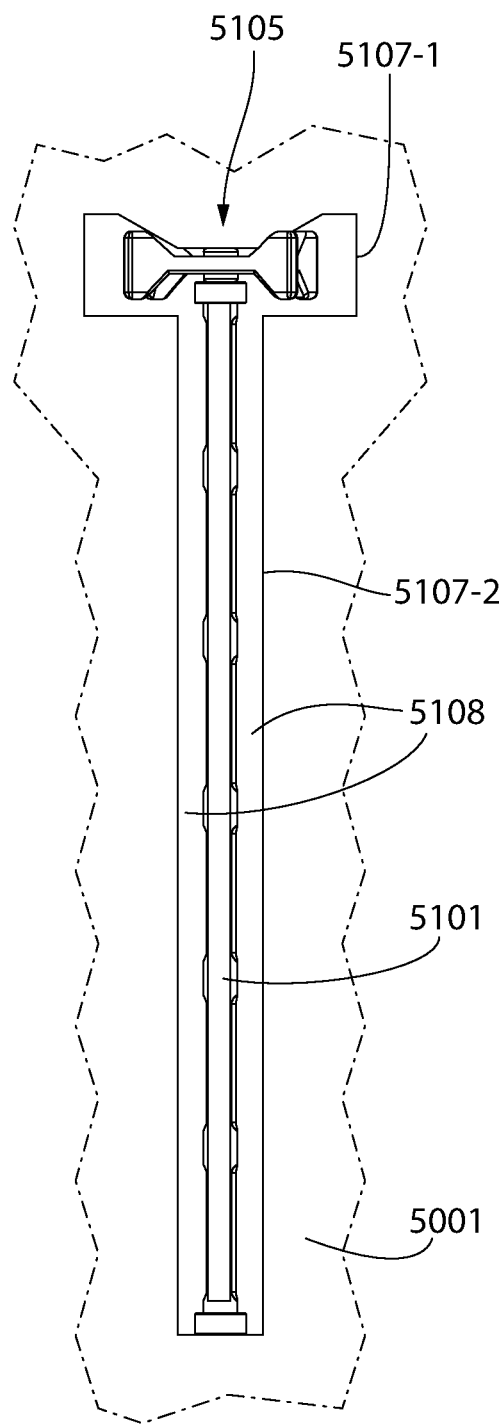
Figure 169:
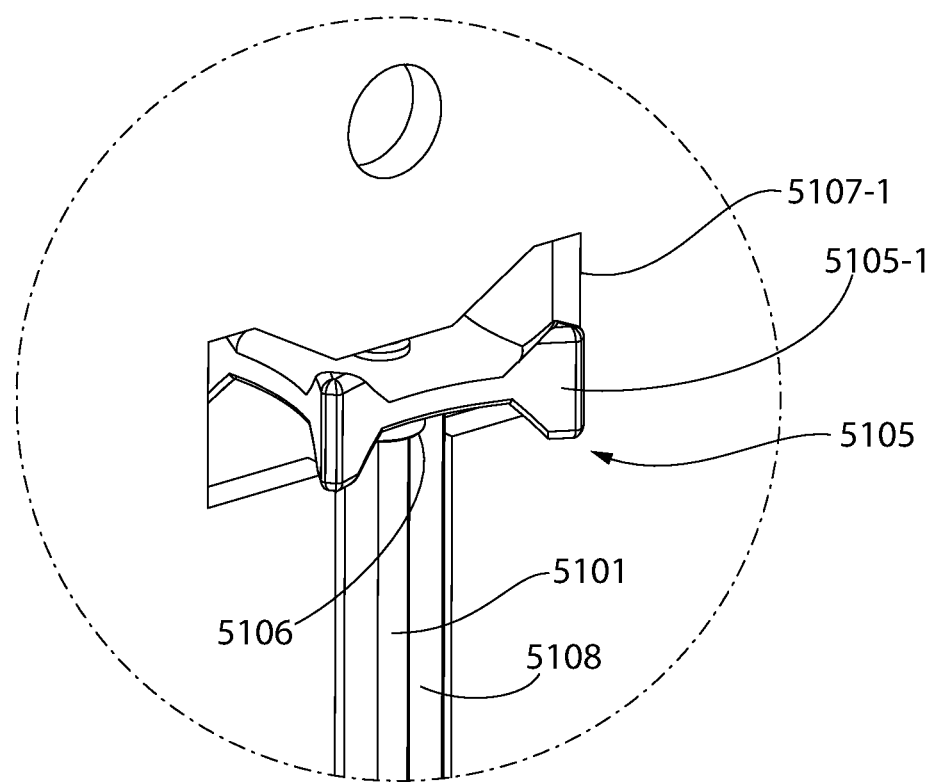
Figure 170:
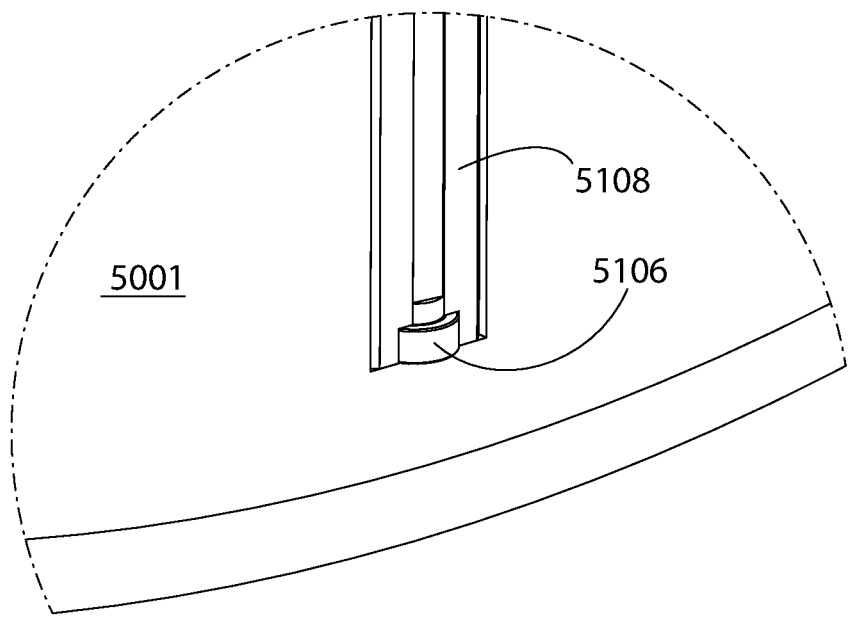
Figure 171:
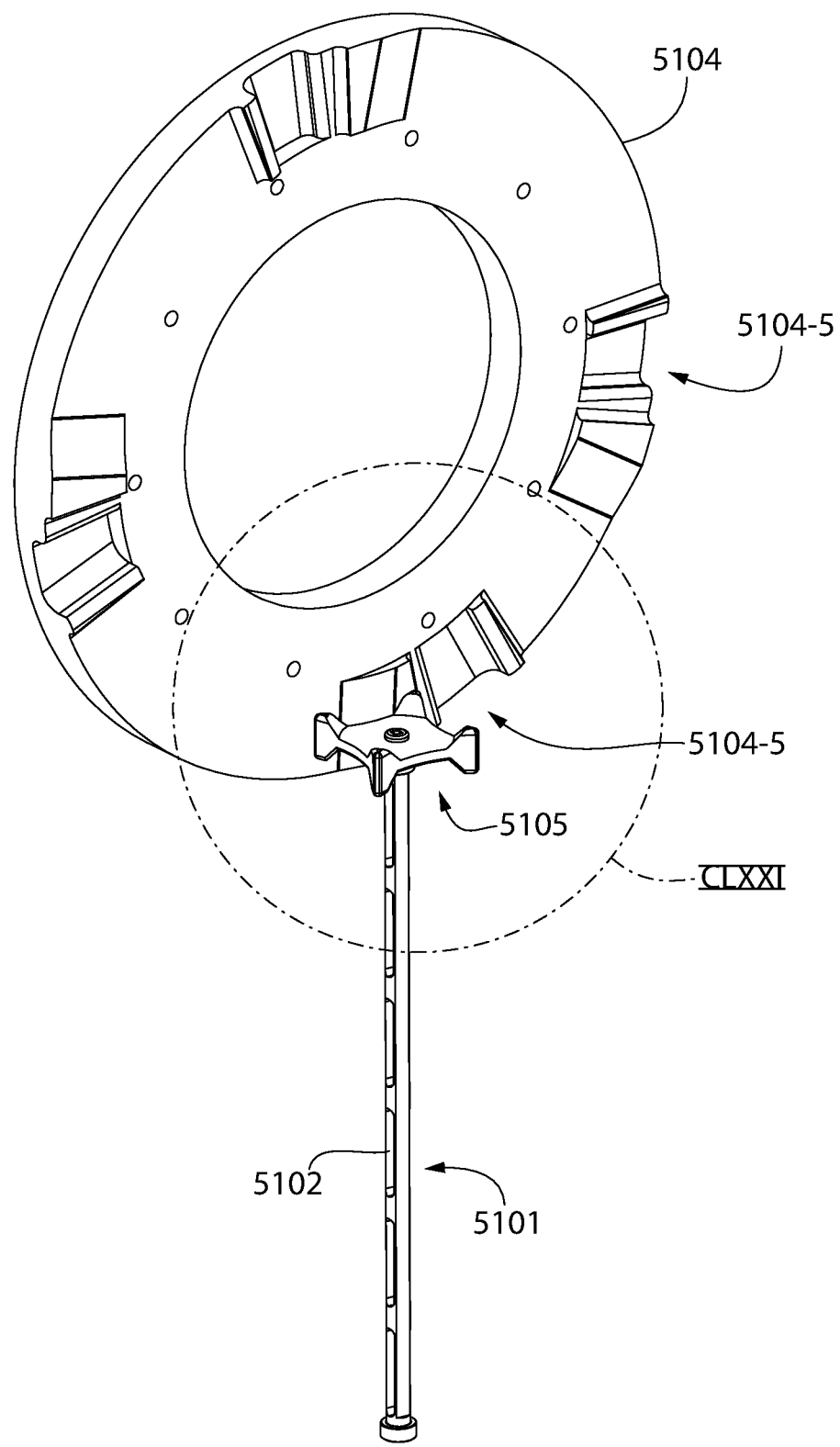
Figure 172:
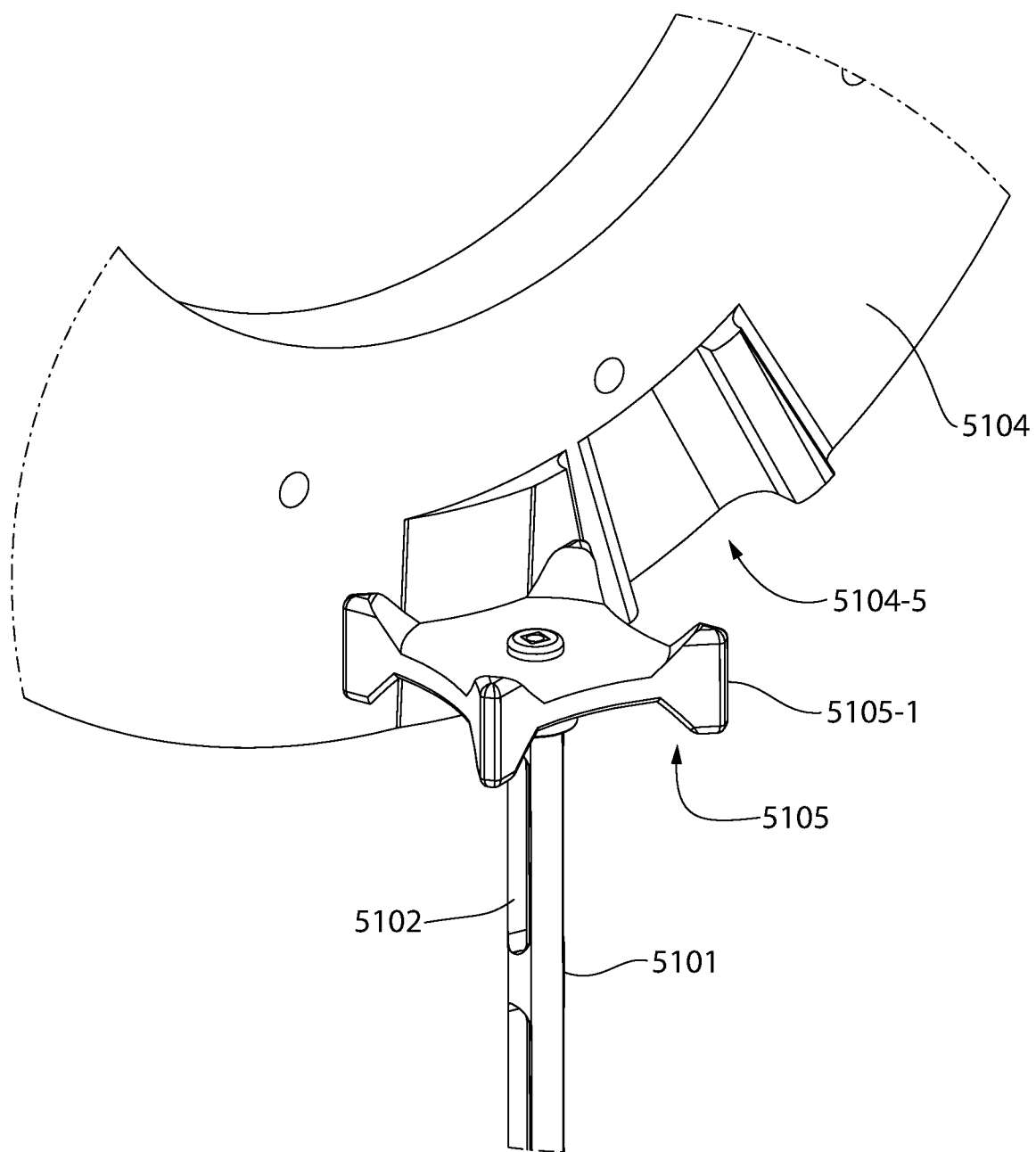
Figure 173A:
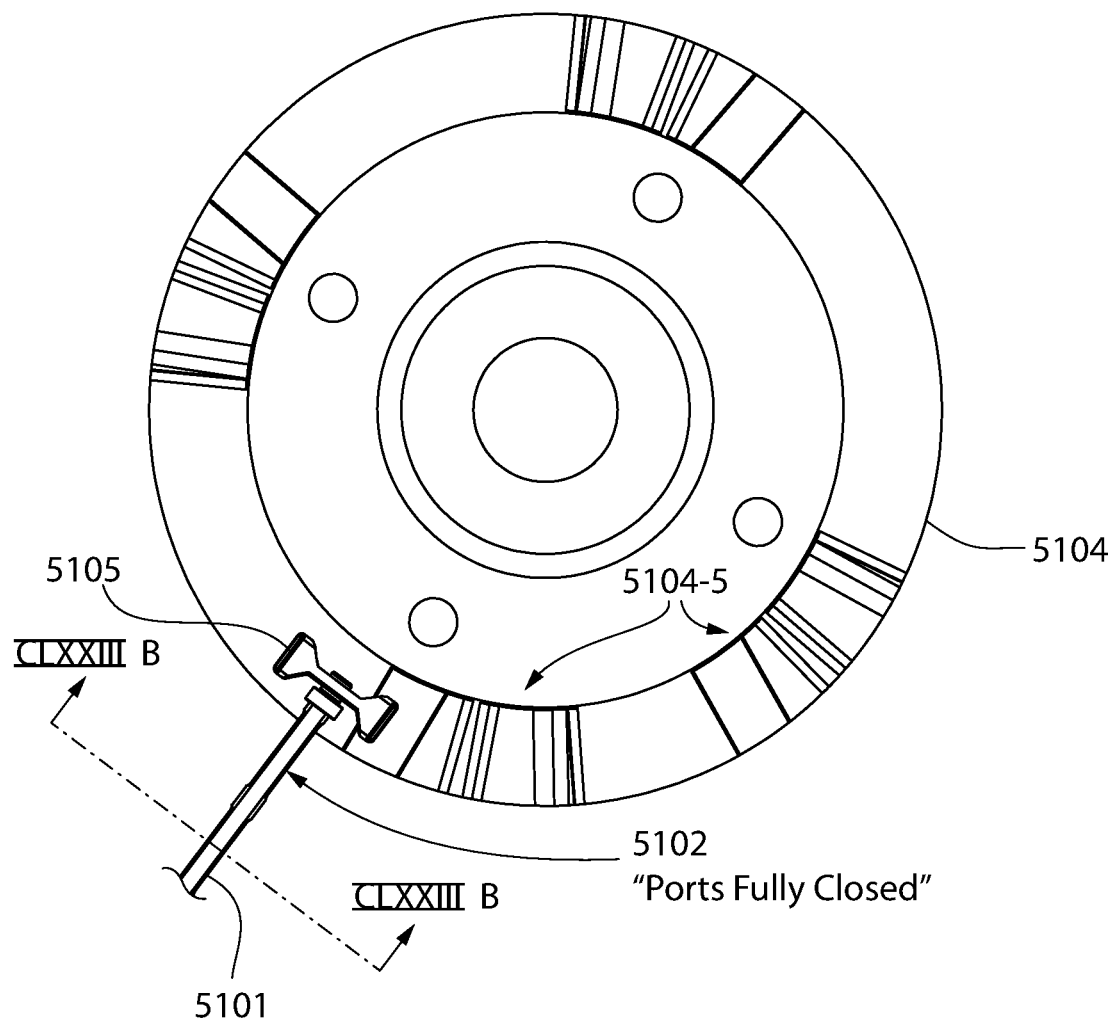
Figure 173B:
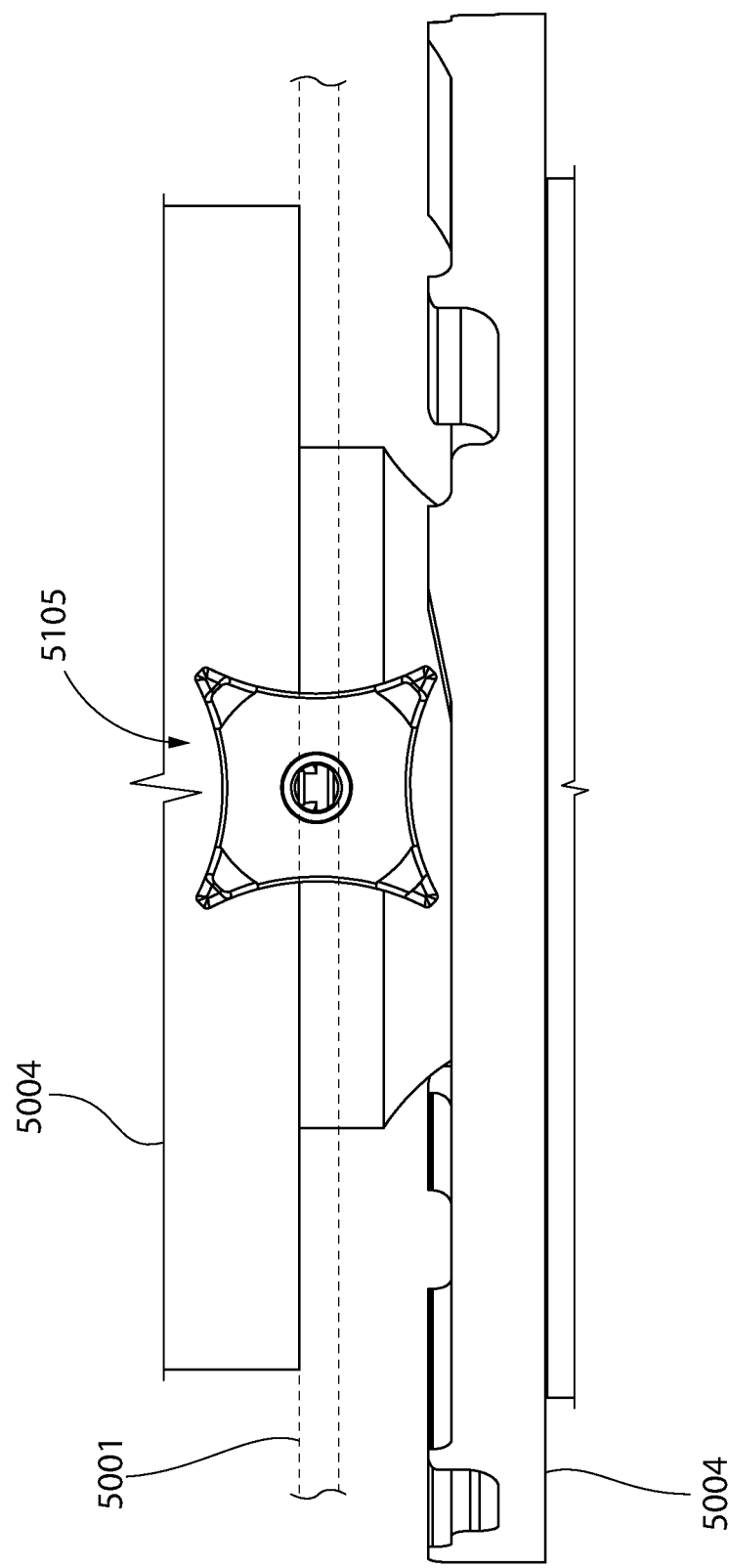
Figure 174A:
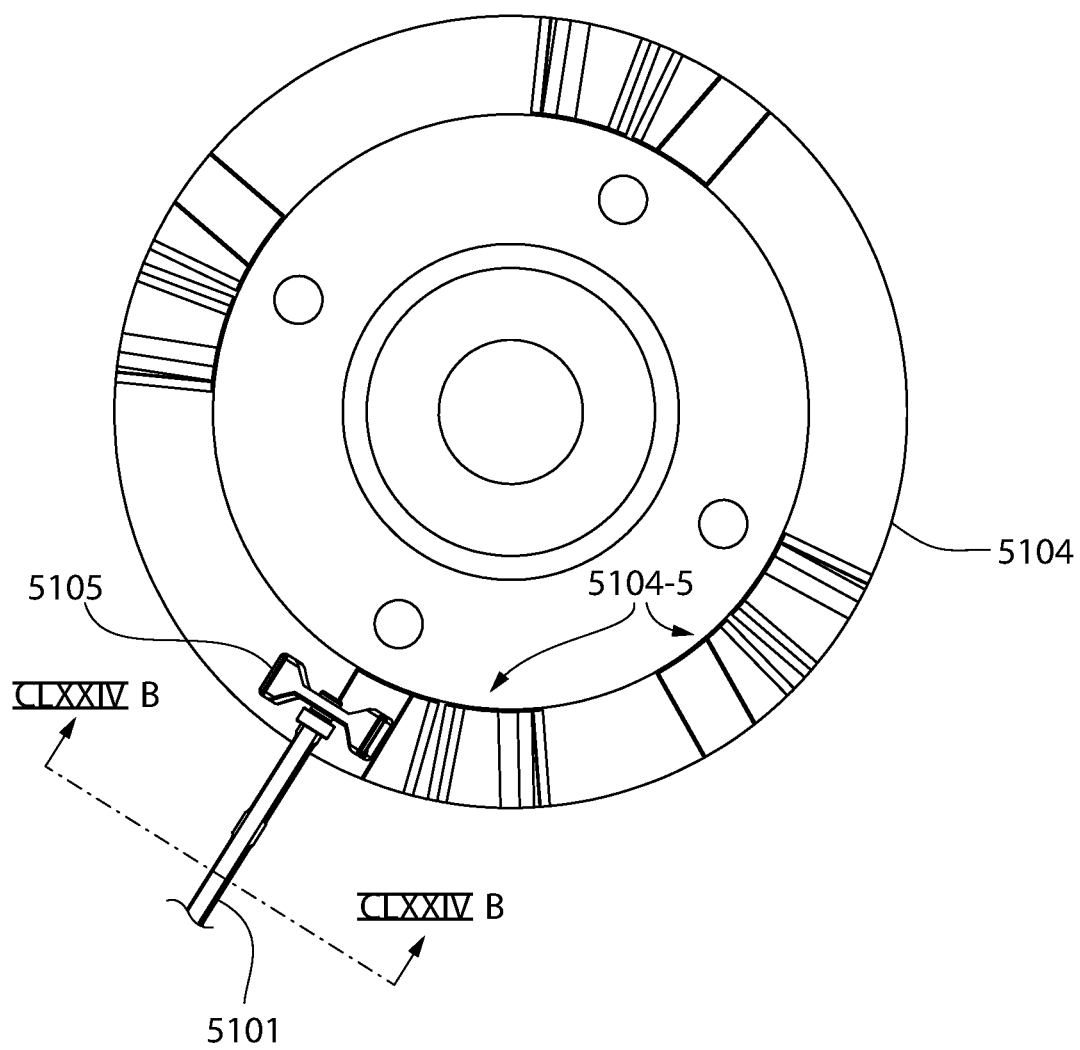
Figure 174B:
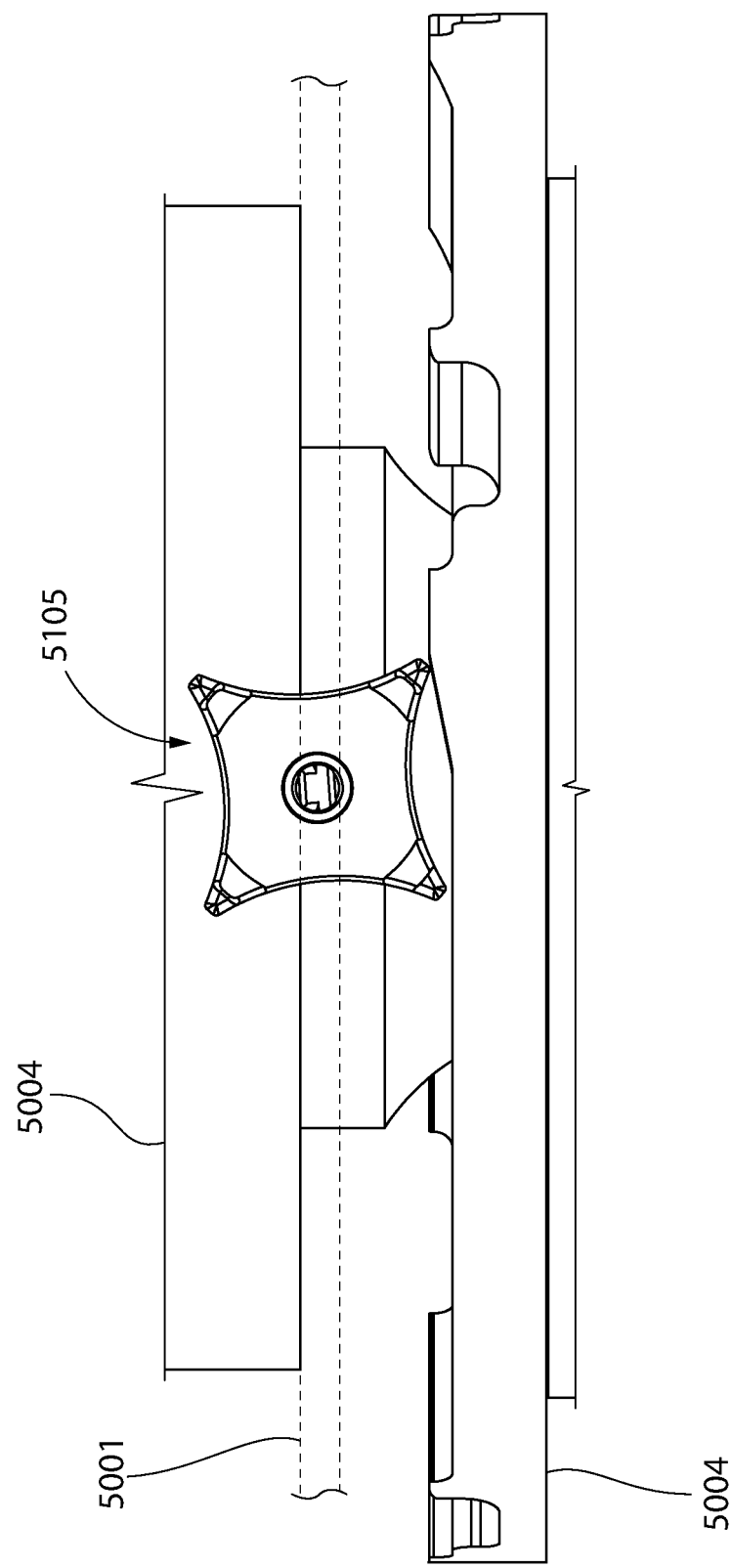
Figure 175A:
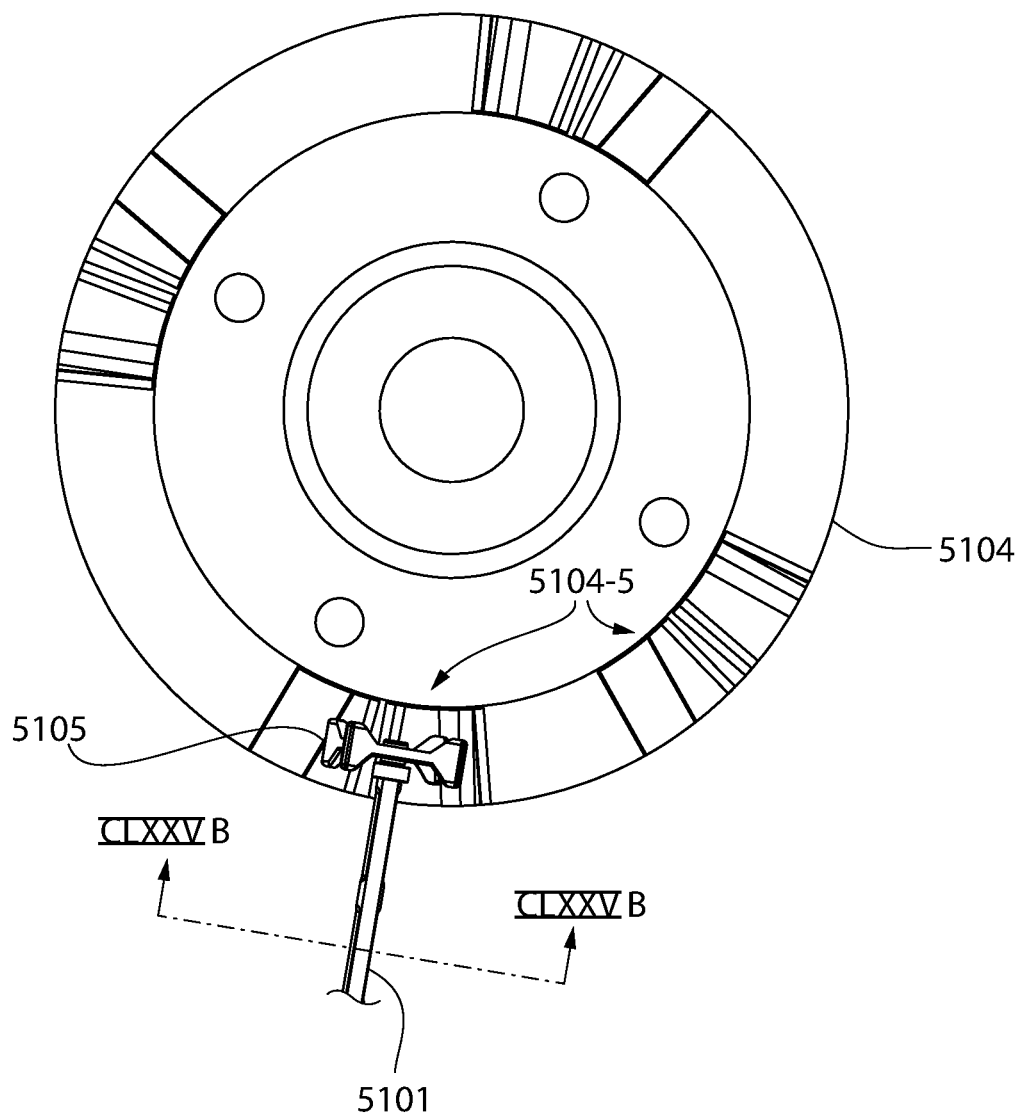
Figure 175B:
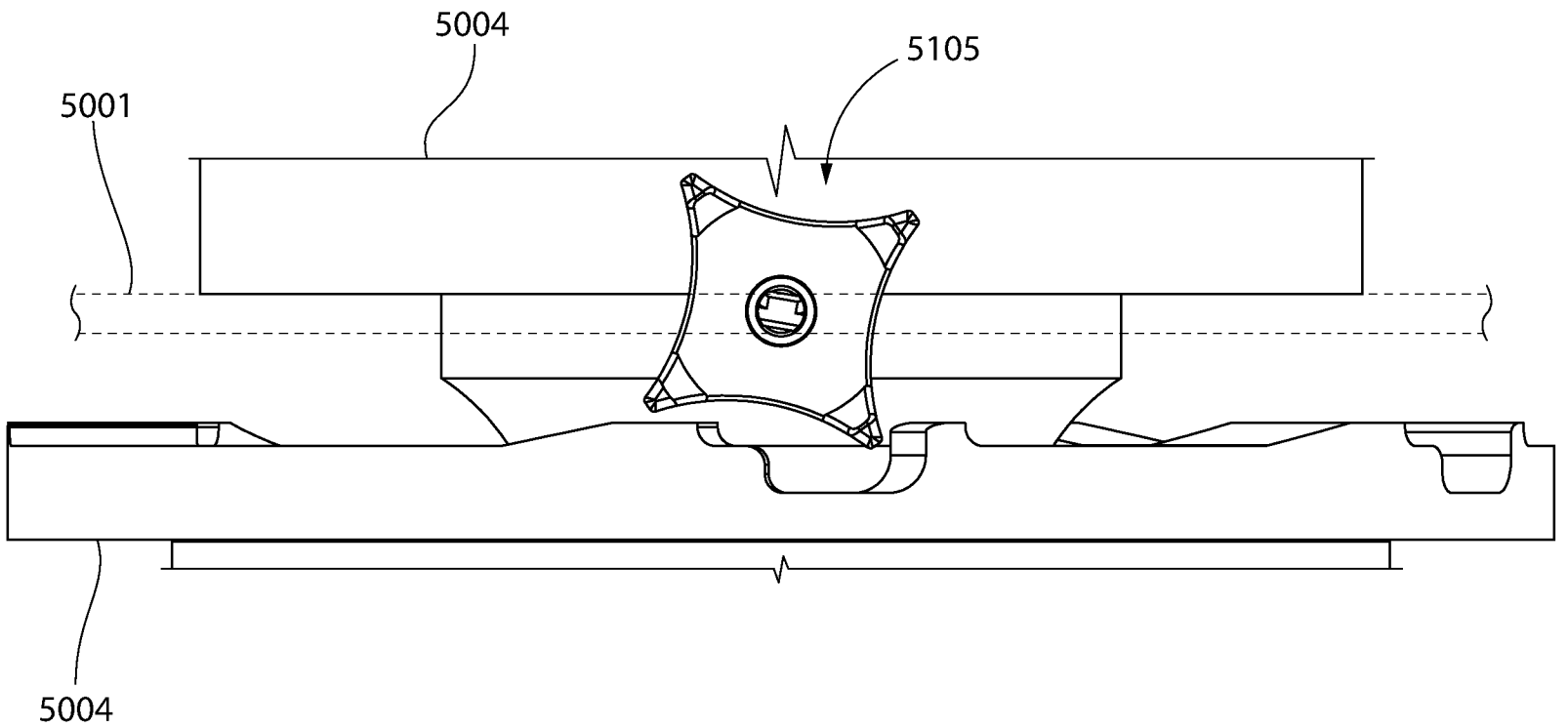
Figure 176A:
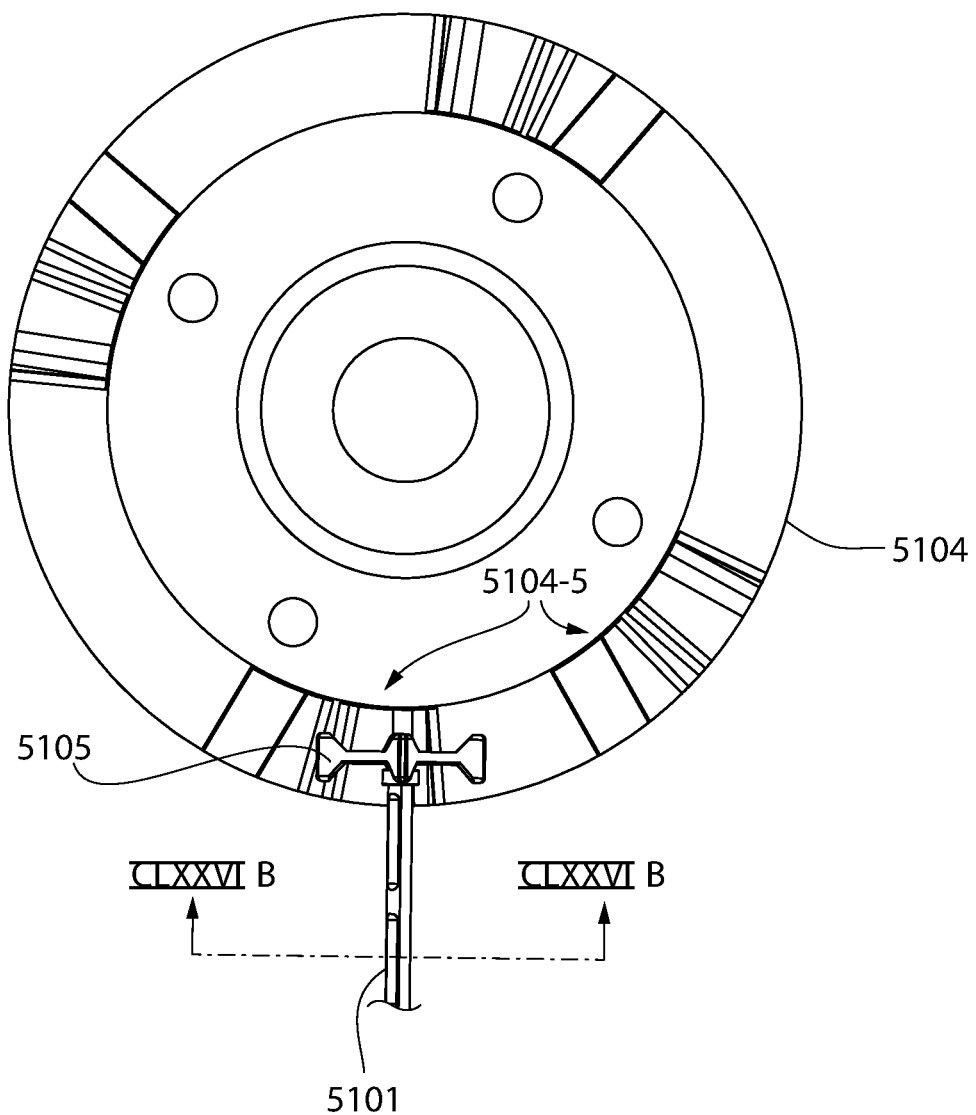
Figure 176B:
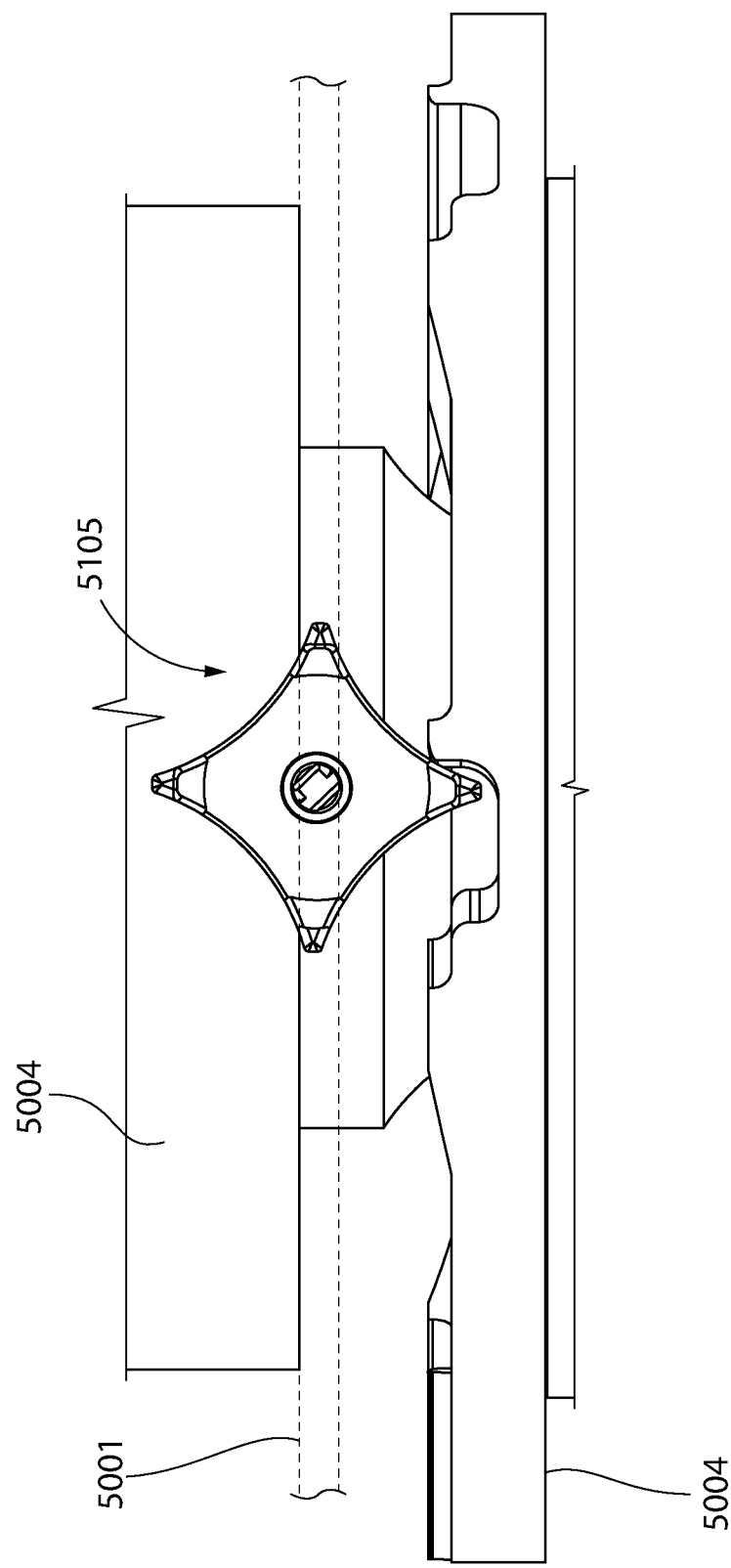
Figure 177A:
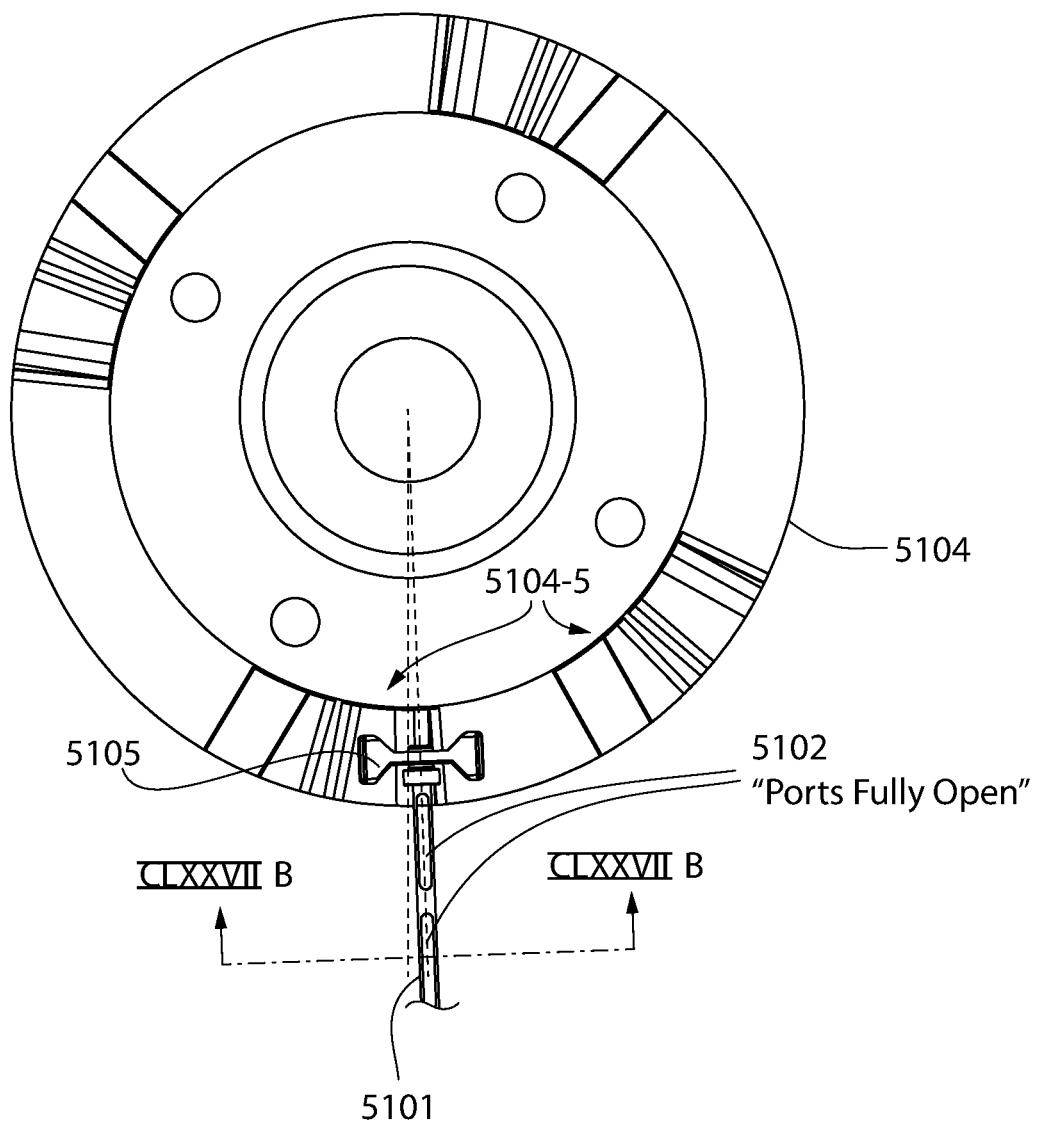
Figure 177B:
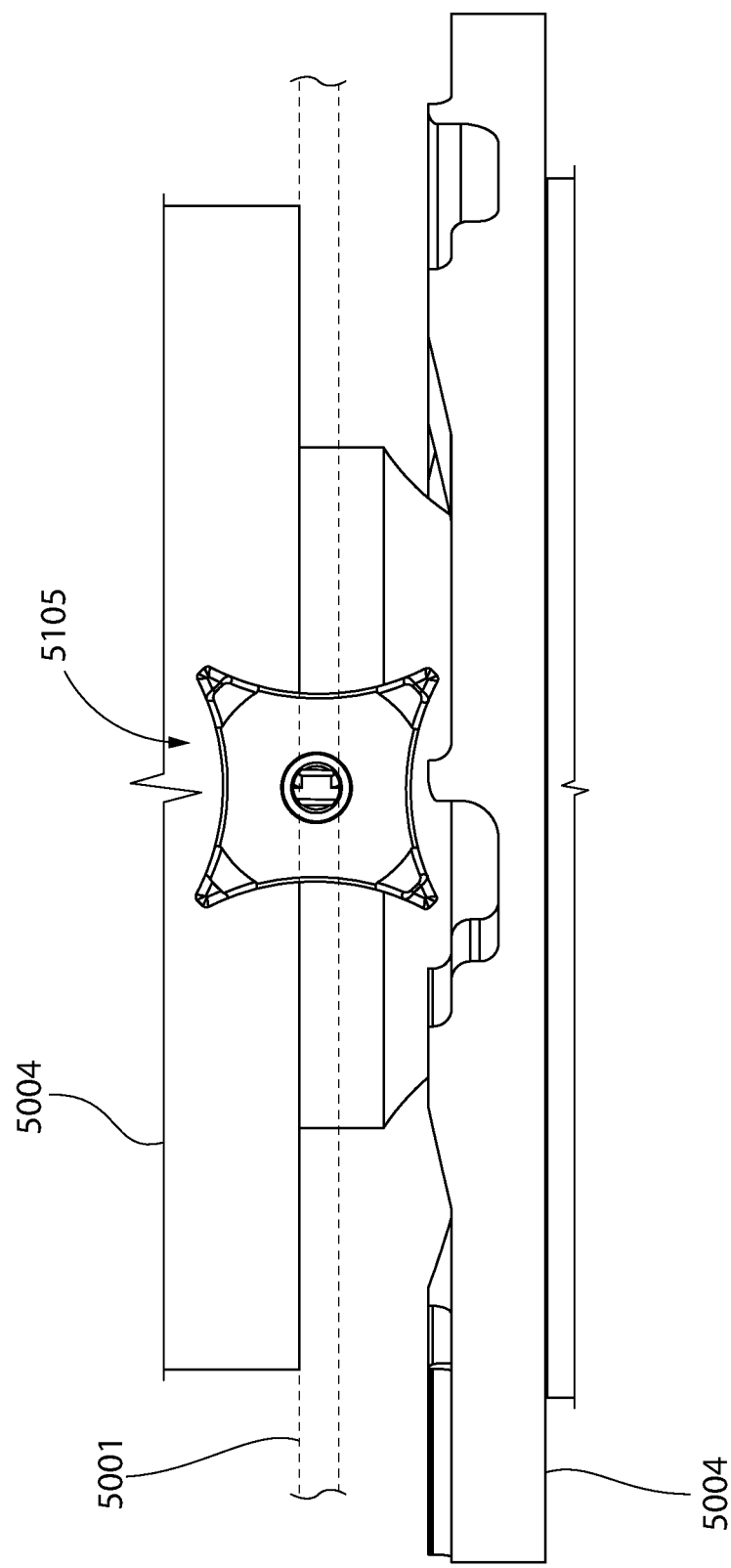
Figure 178A:
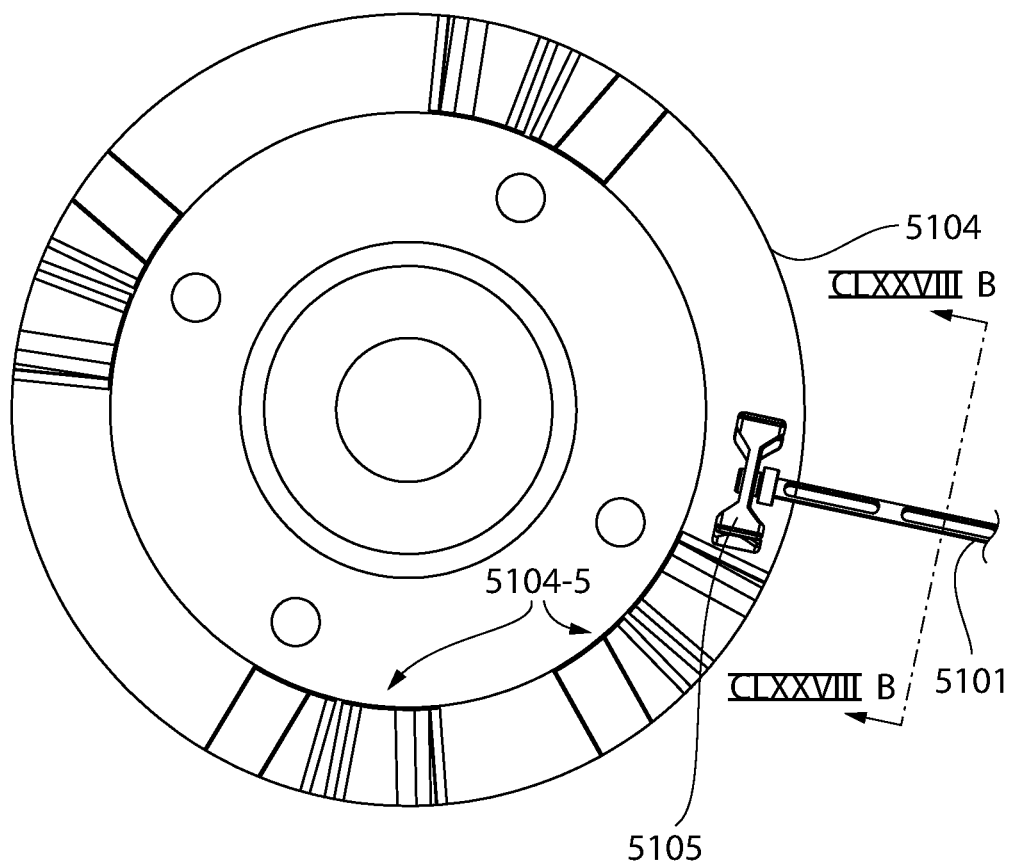
Figure 178B:
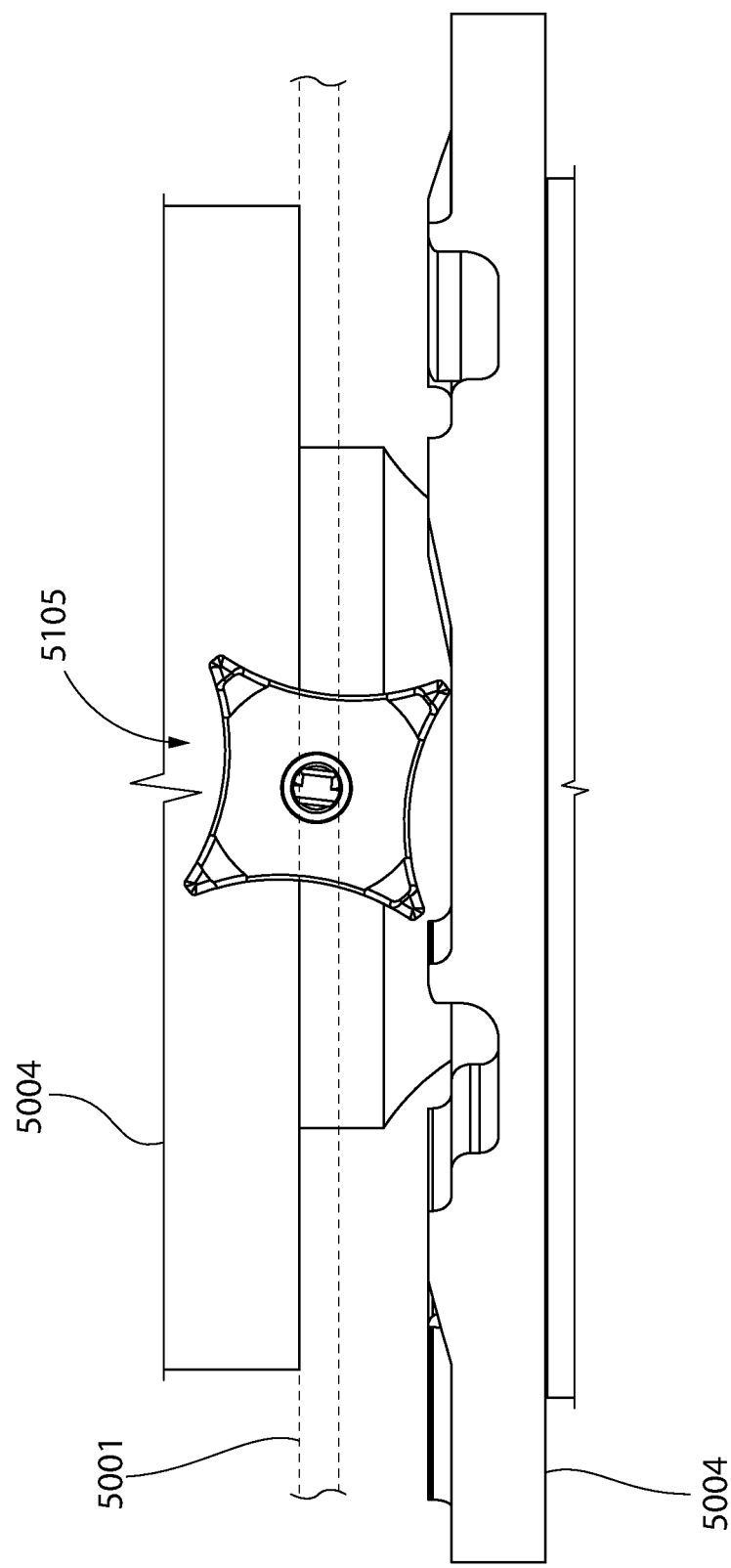
Figure 179:
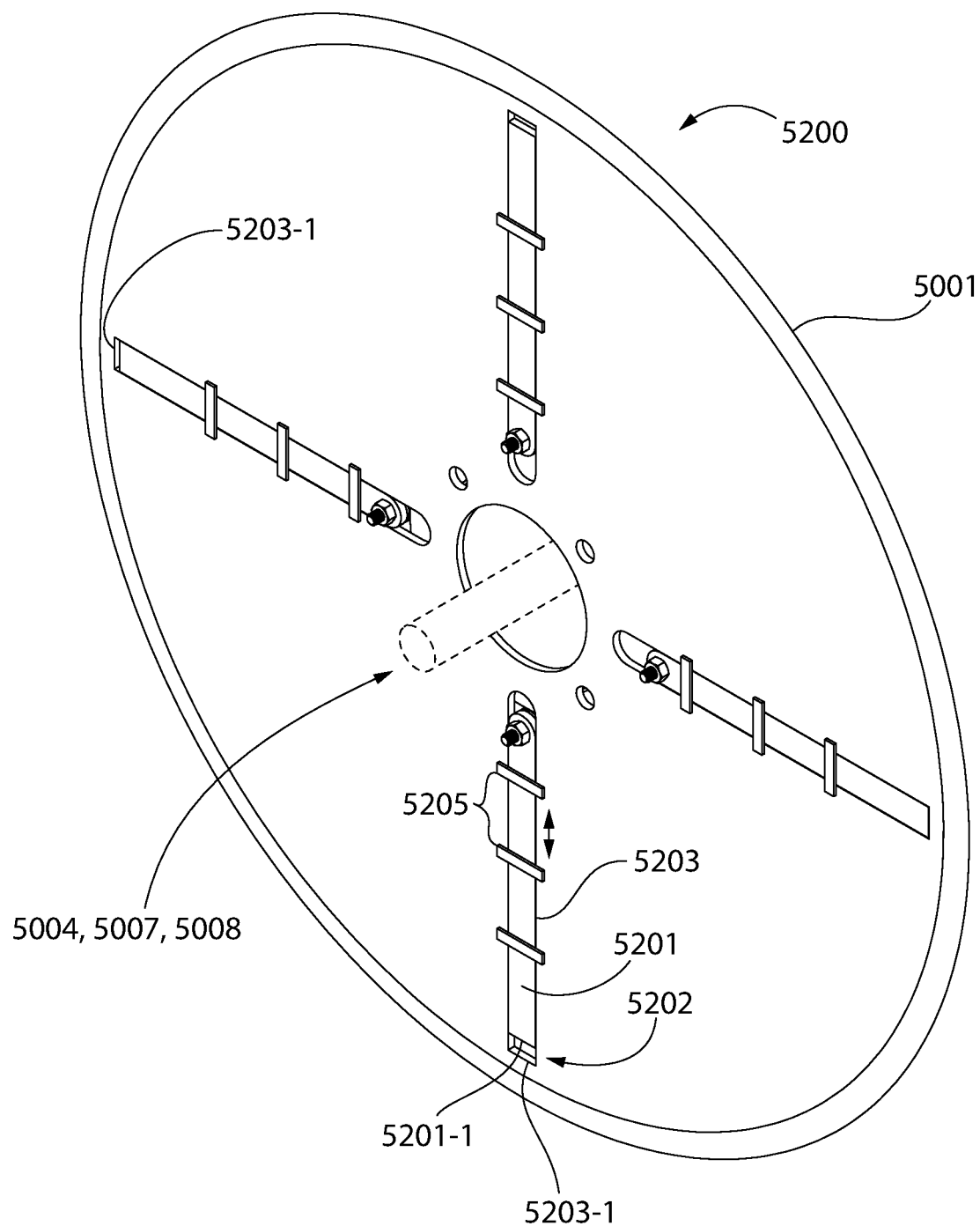
Figure 180:
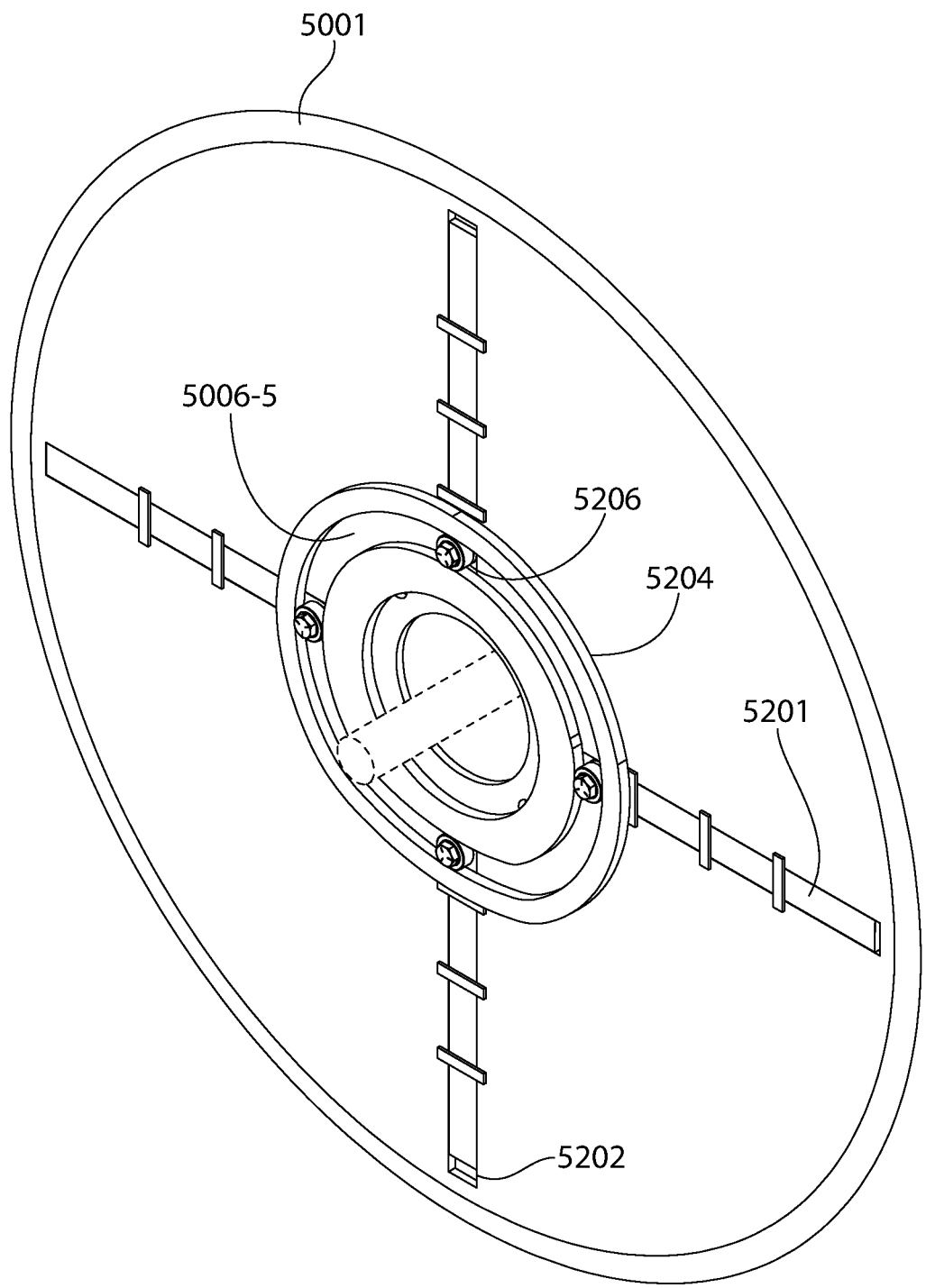
Figure 181:
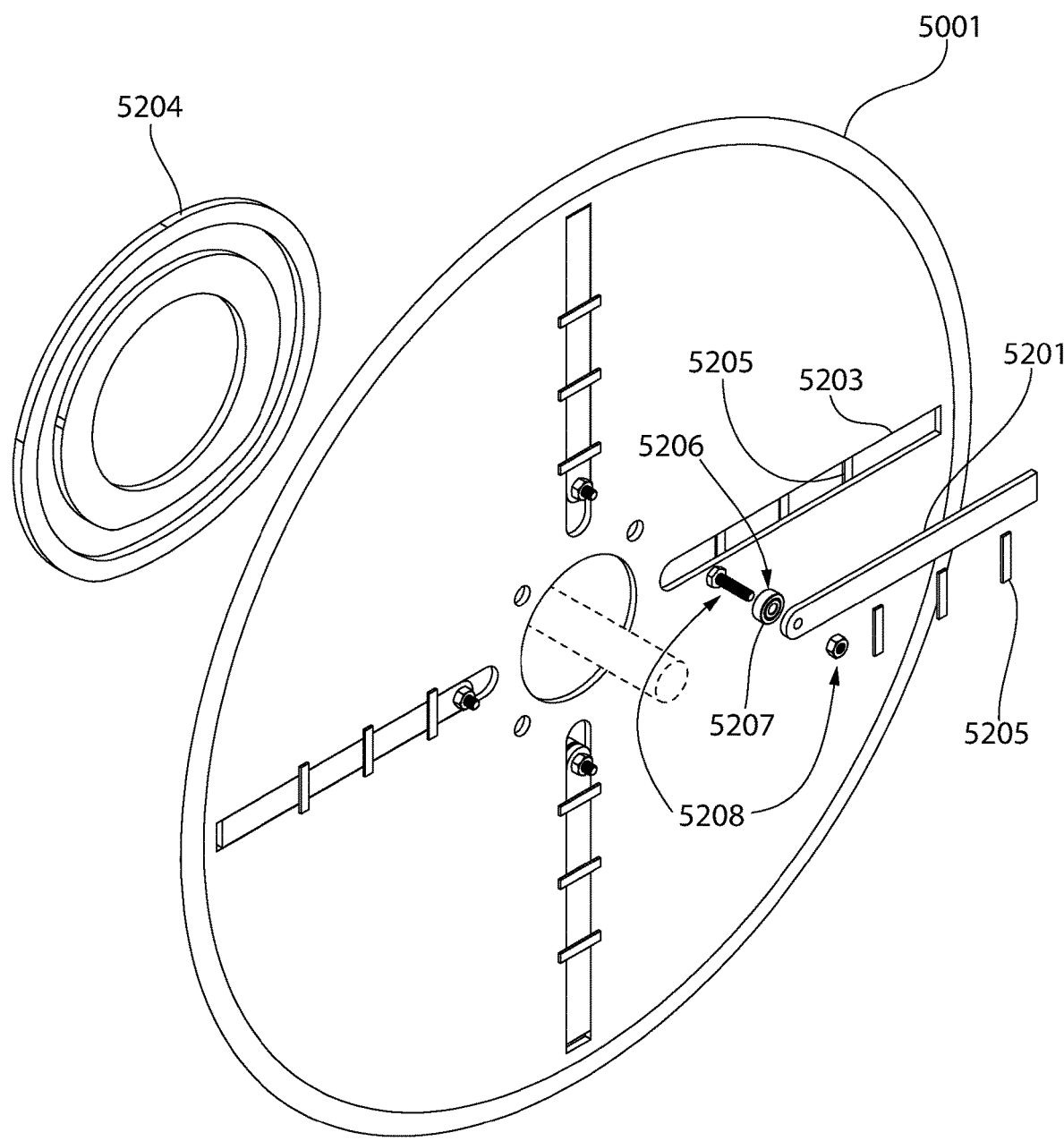
Figure 182:
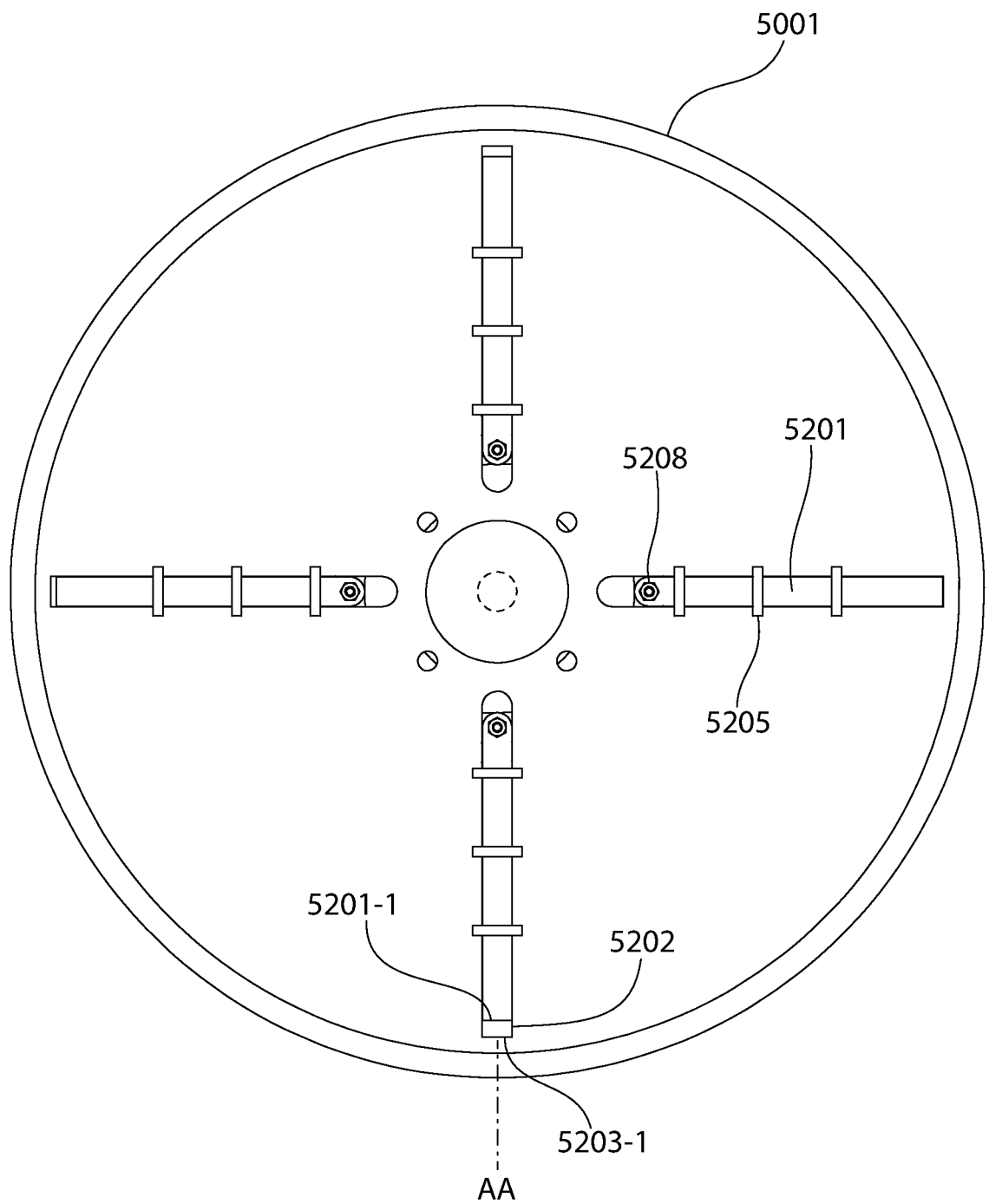
Figure 183:
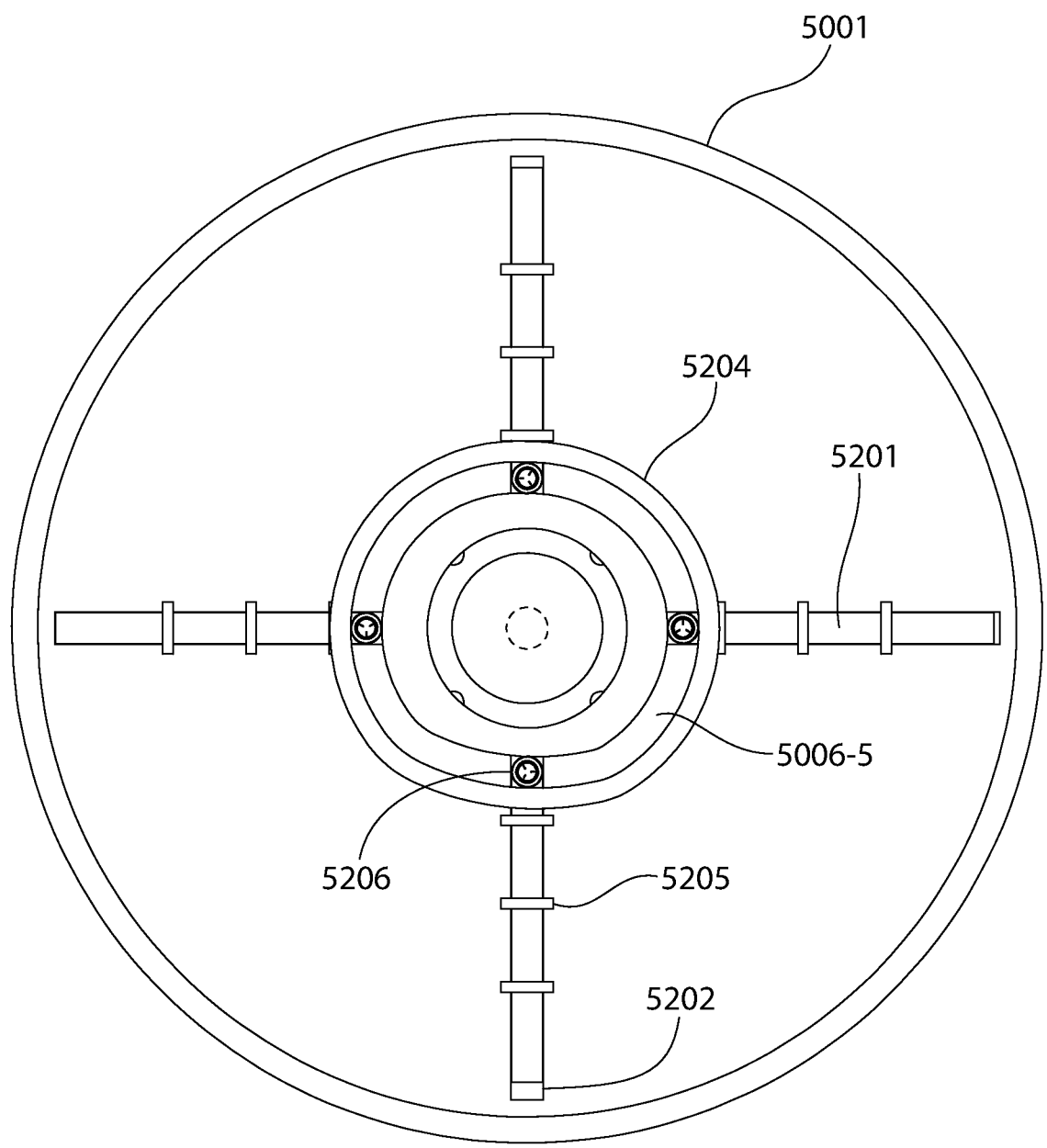
Figure 184:
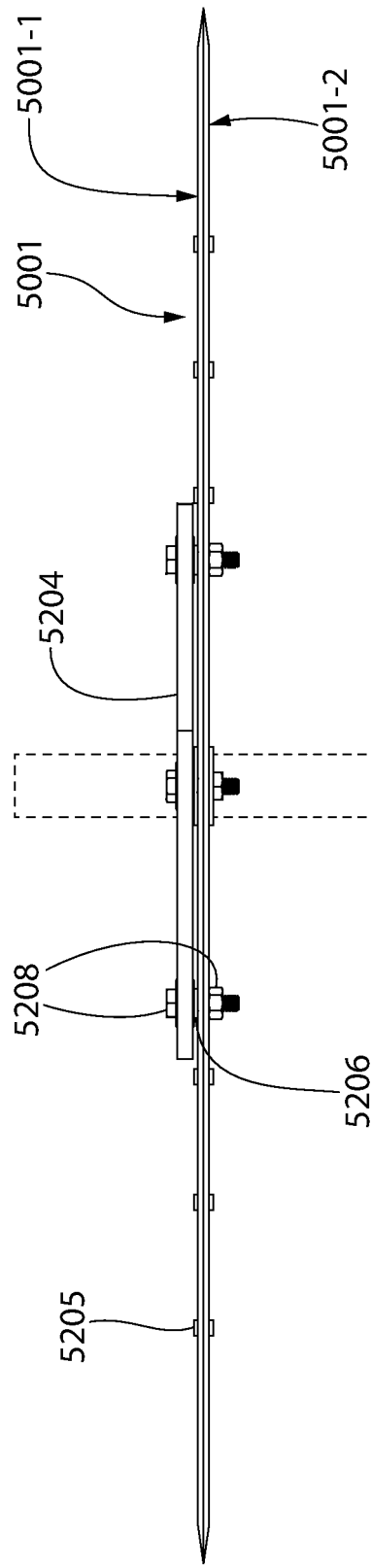
Figure 185:
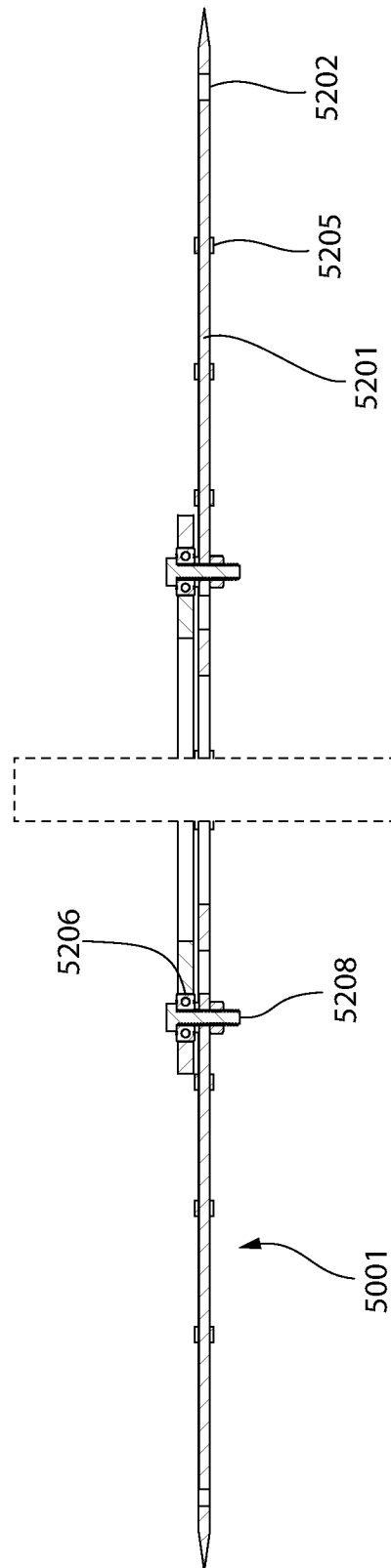
Figure 186:
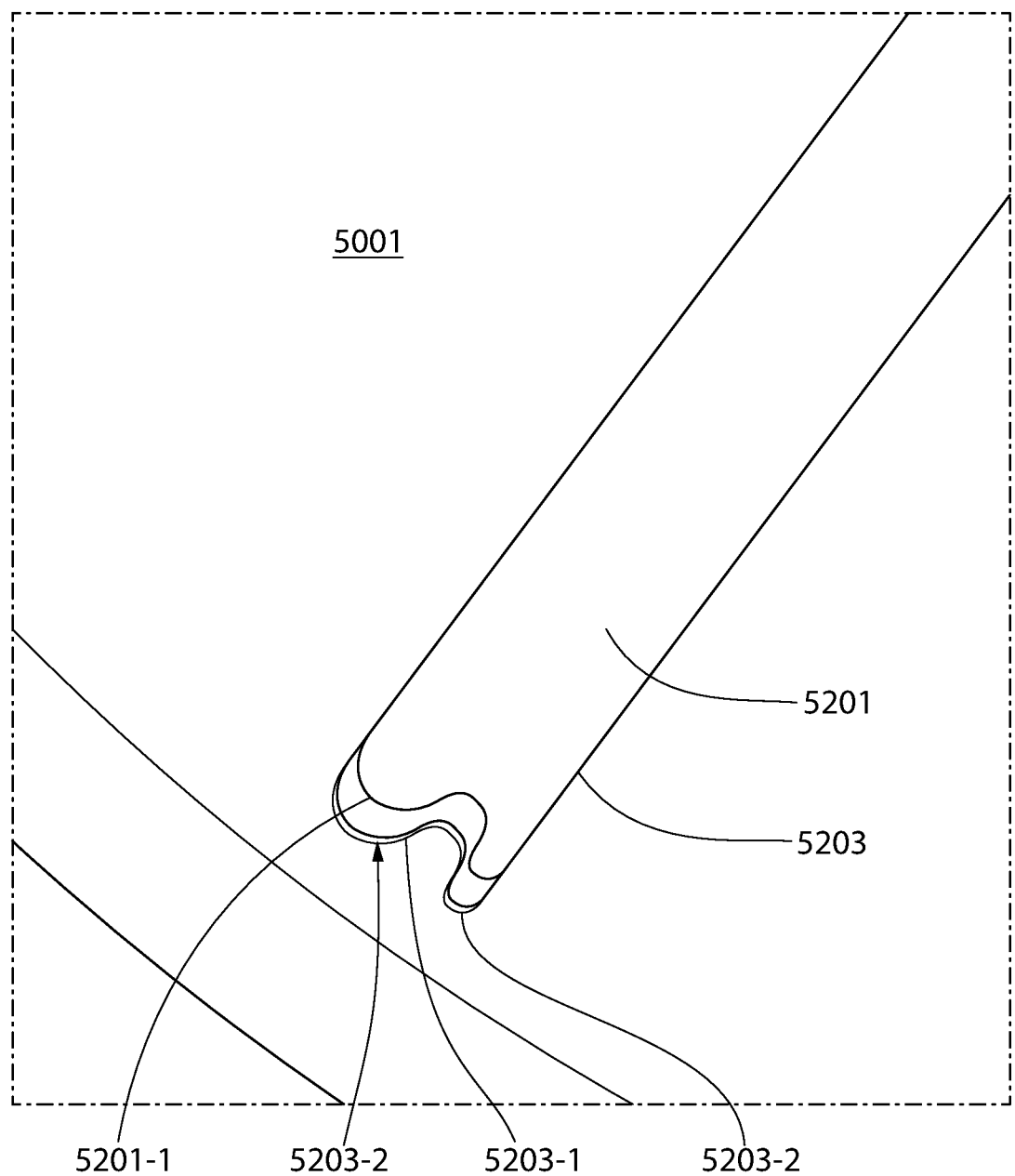
Figure 187:
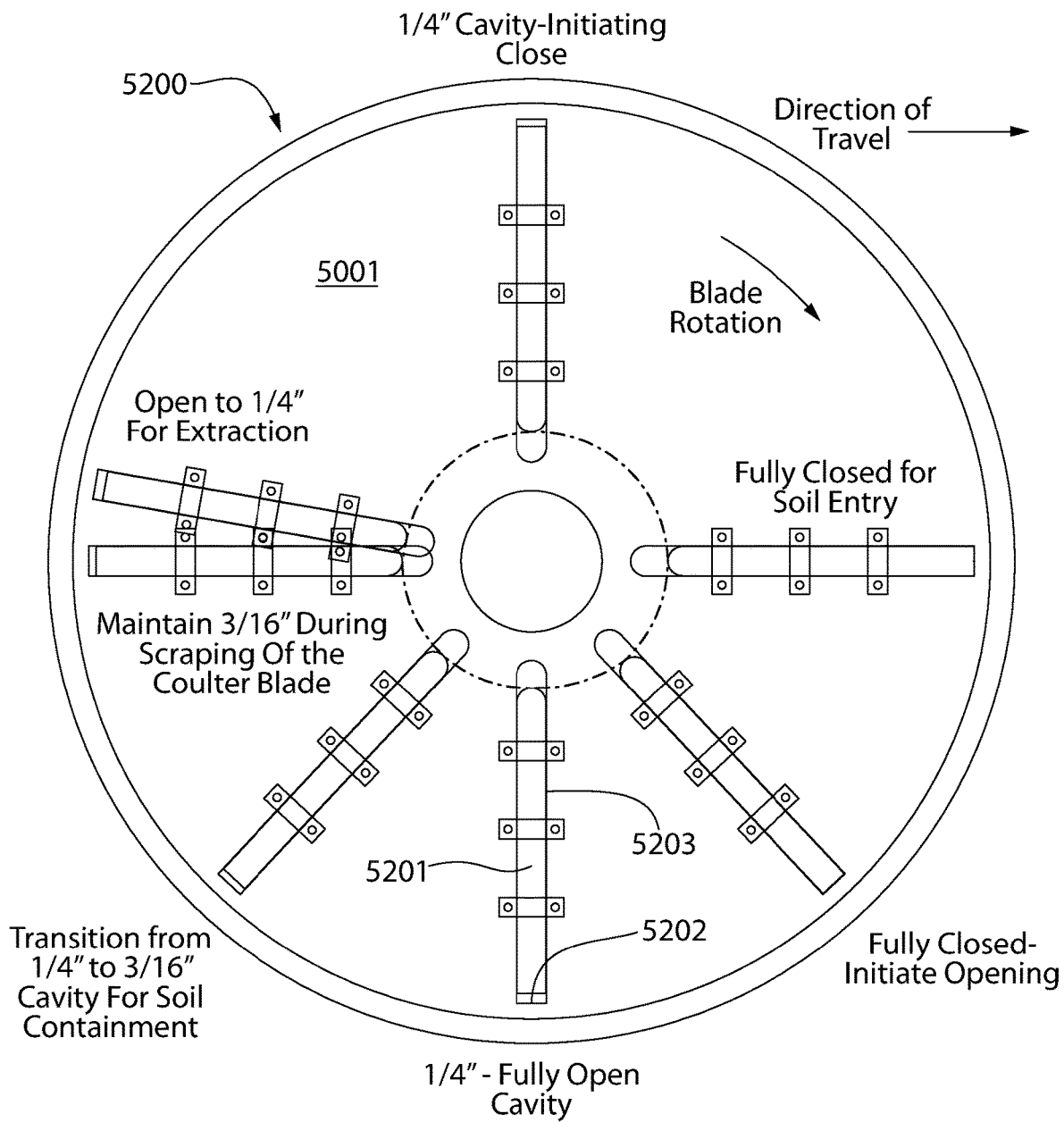
Figure 188:
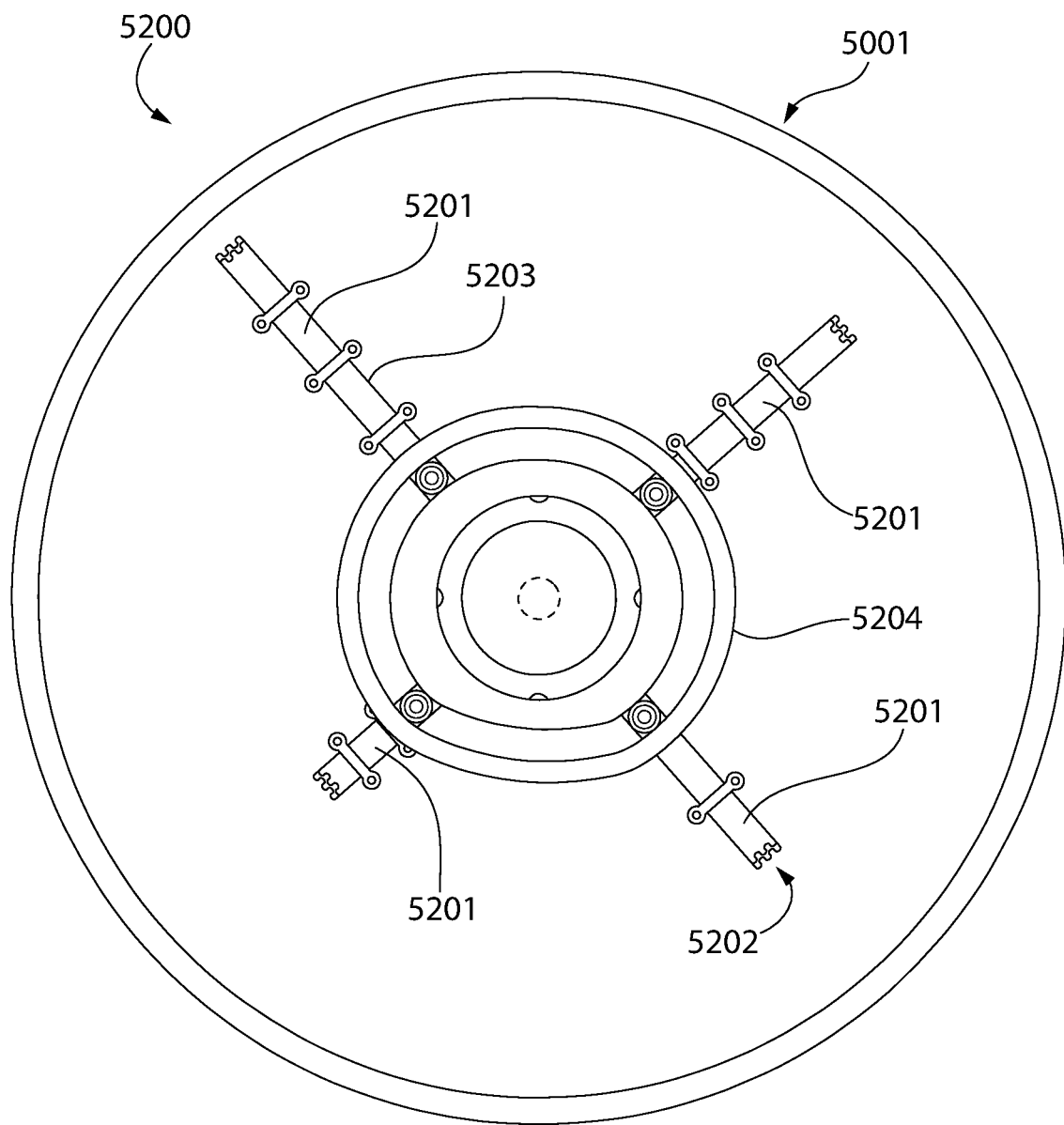
Figure 189:
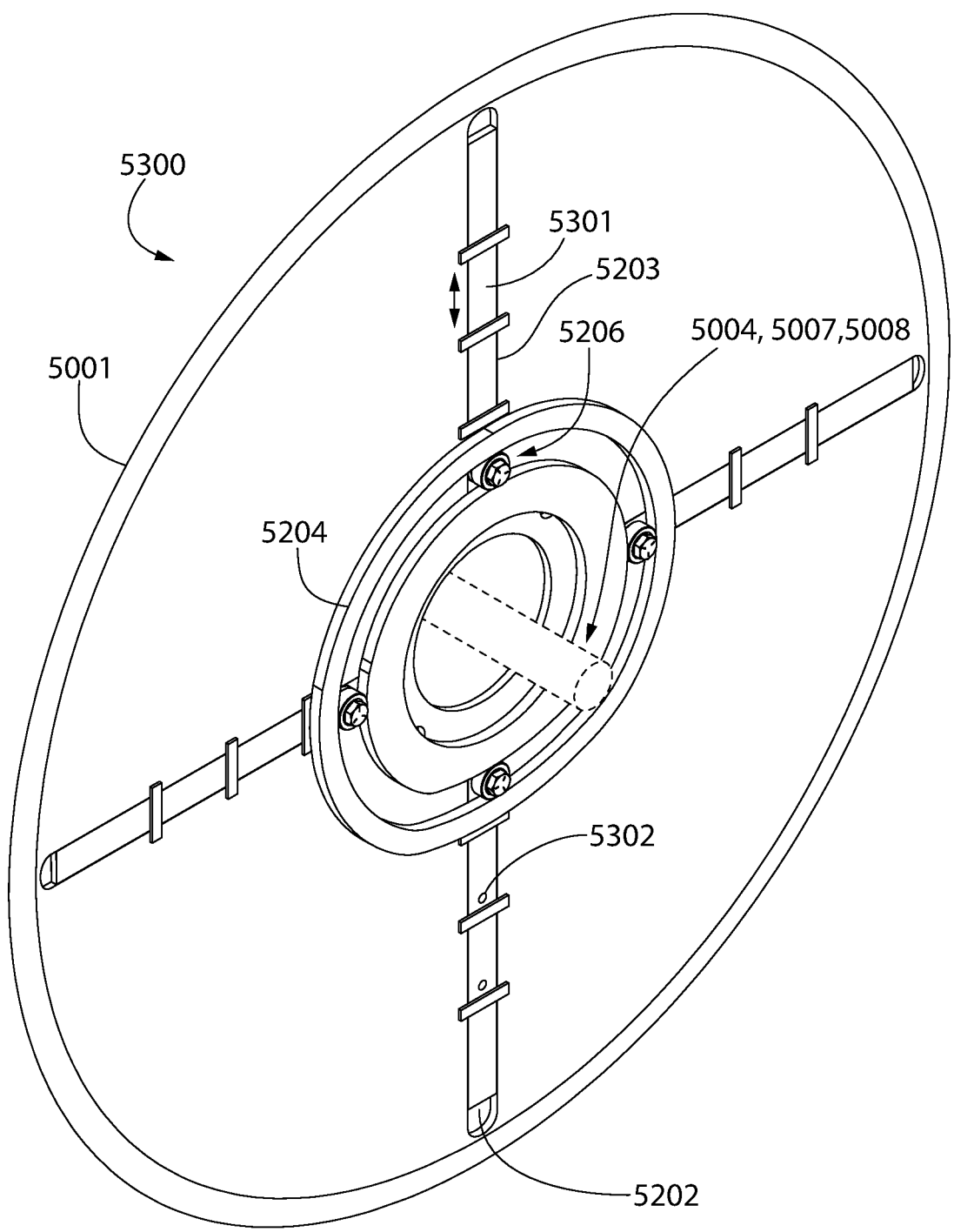
Figure 190:
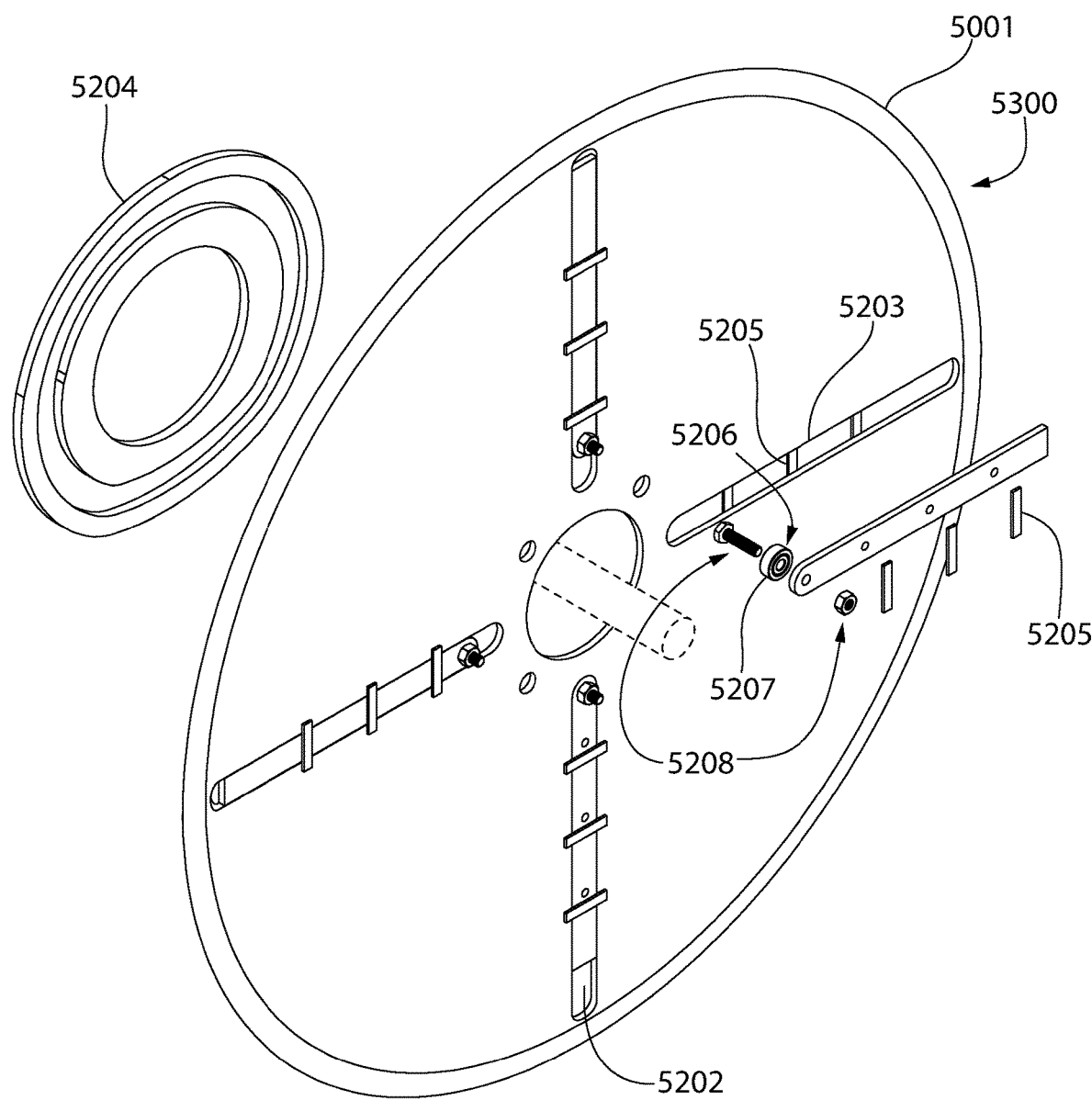
Figure 191:
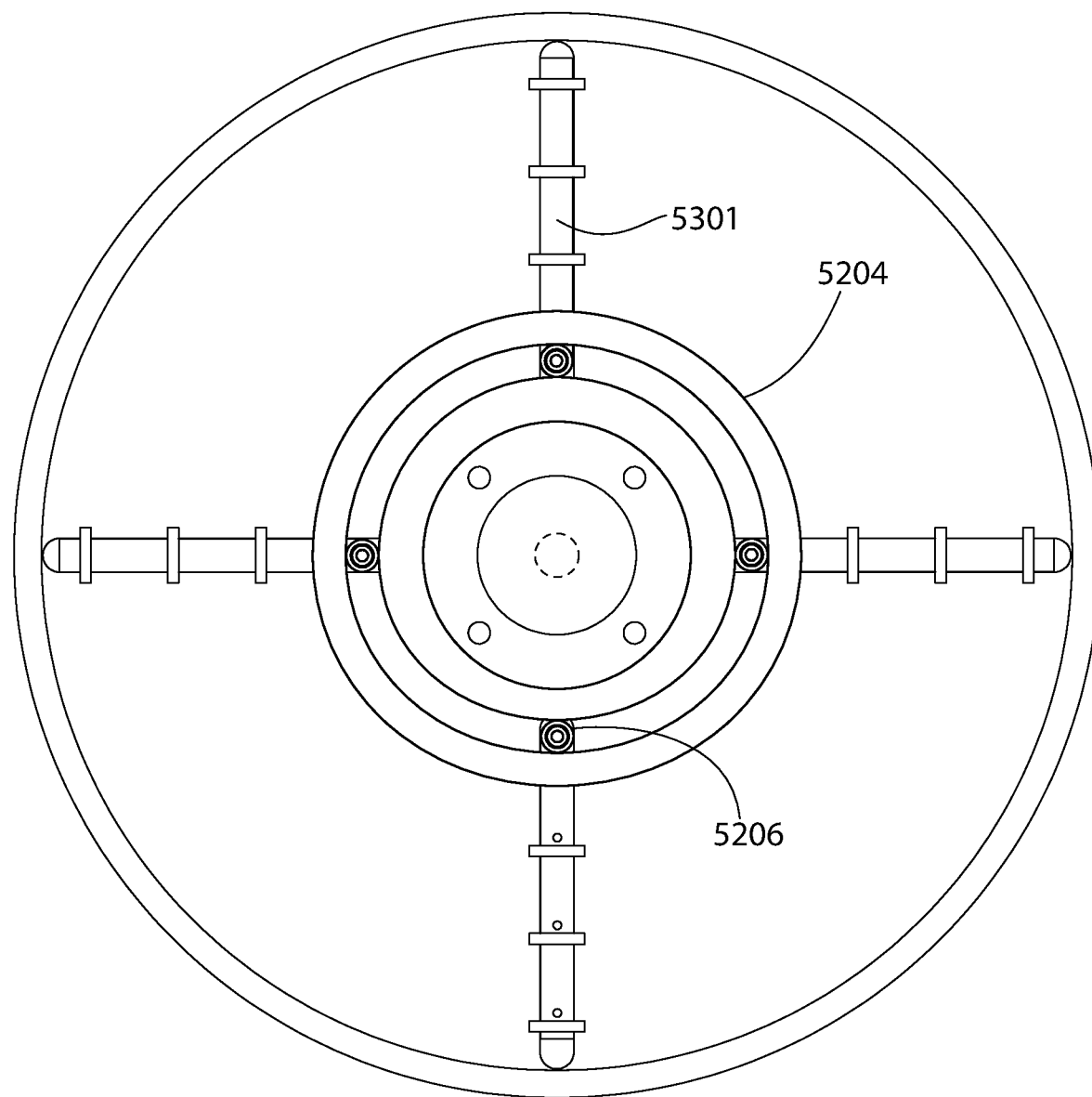
Figure 192:
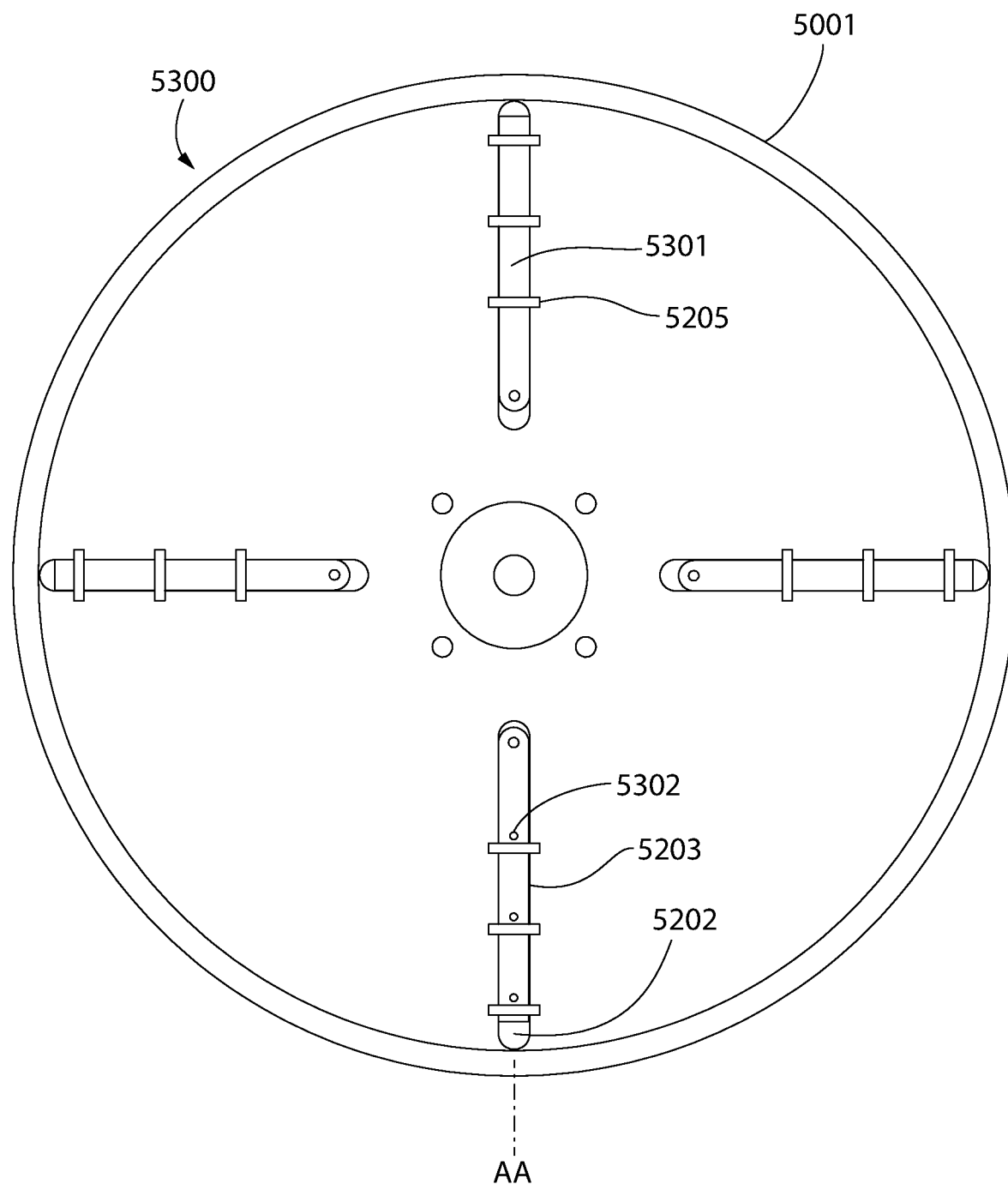
Figure 195:
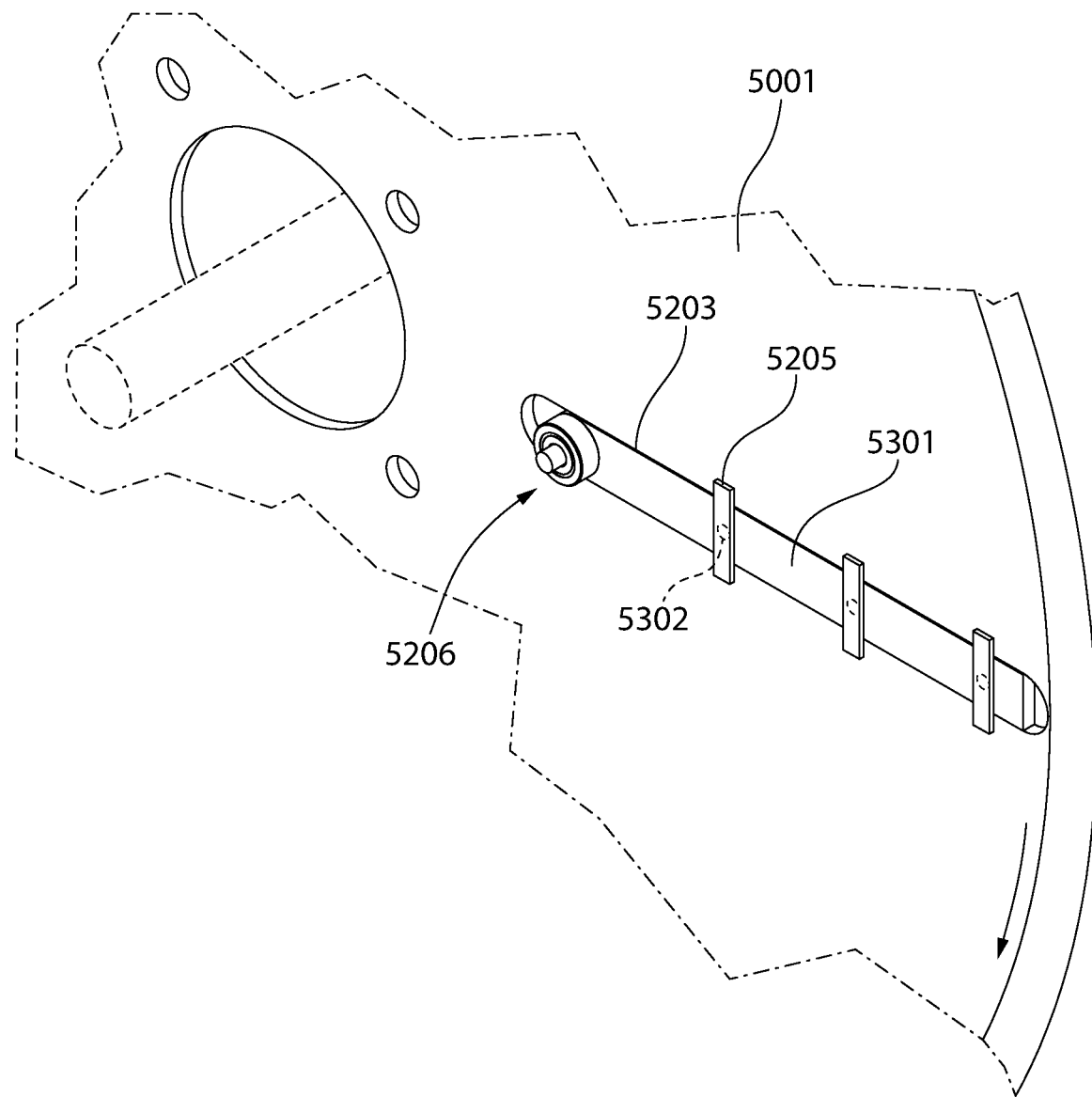
Figure 196:
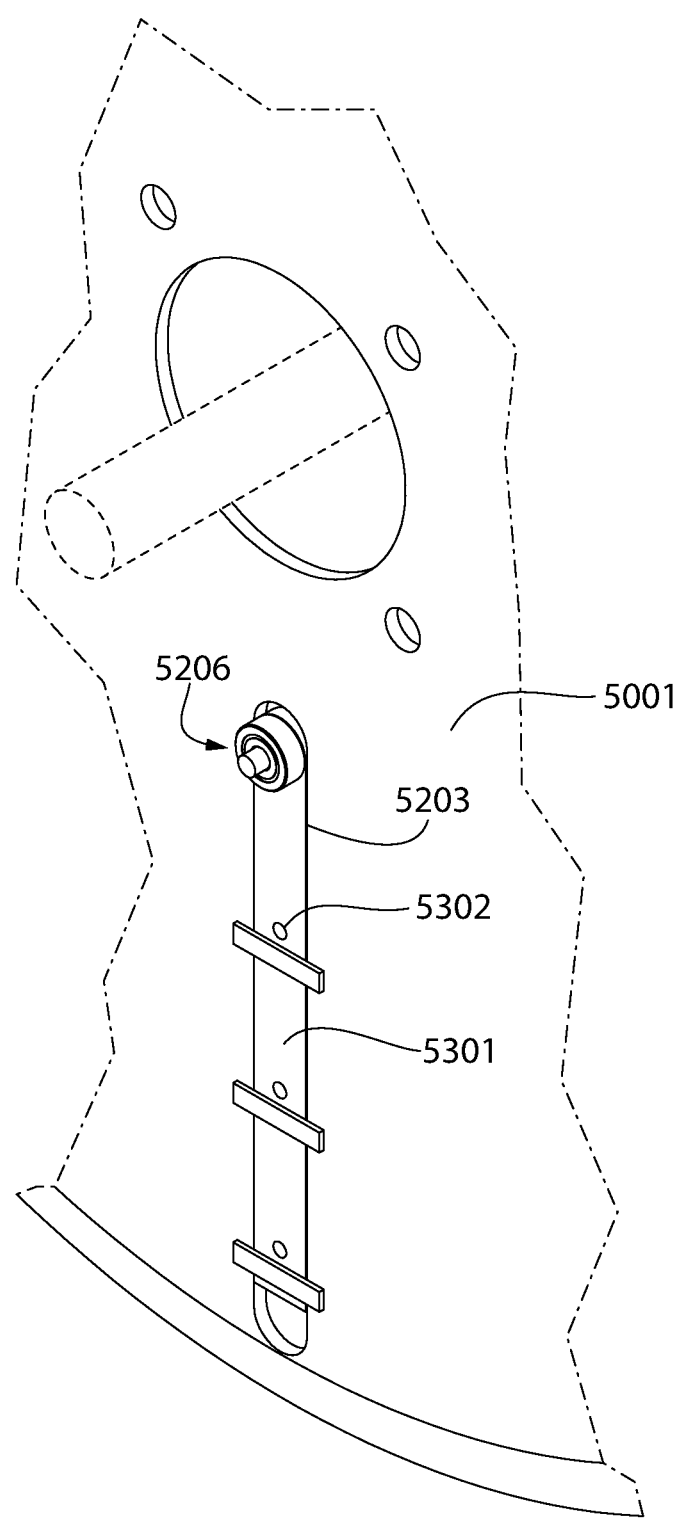
Figure 197:
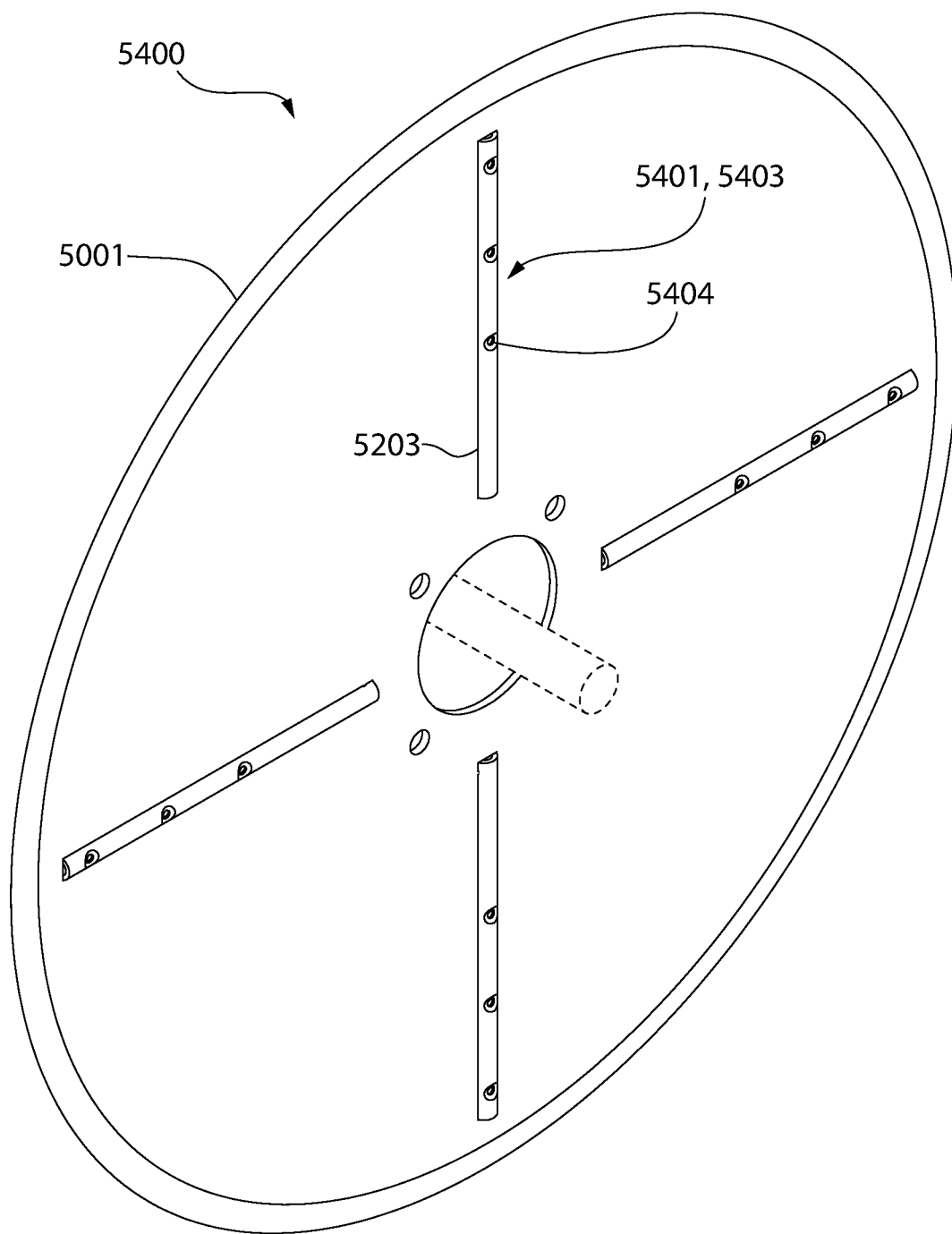
Figure 198:
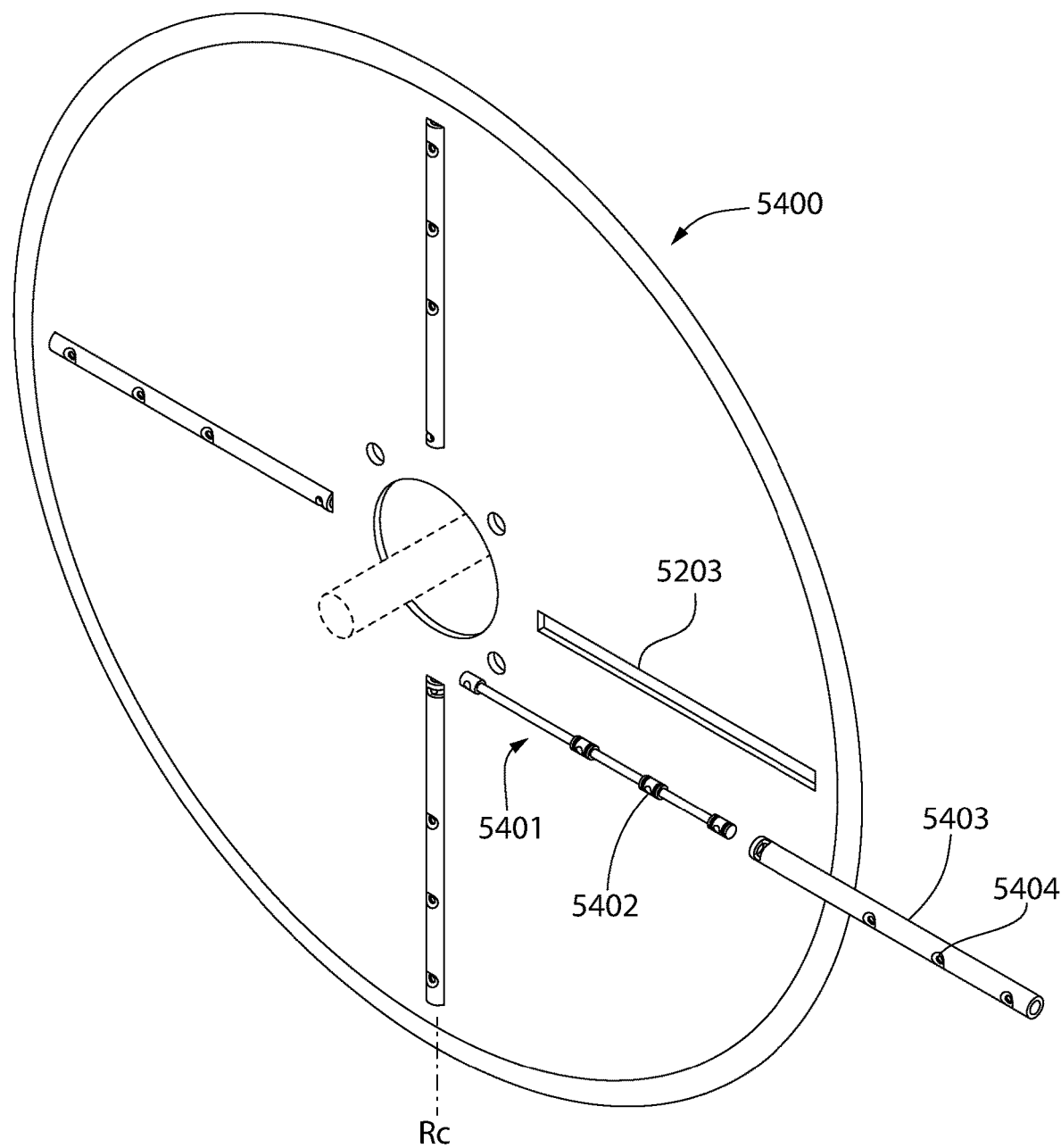
Figure 199:
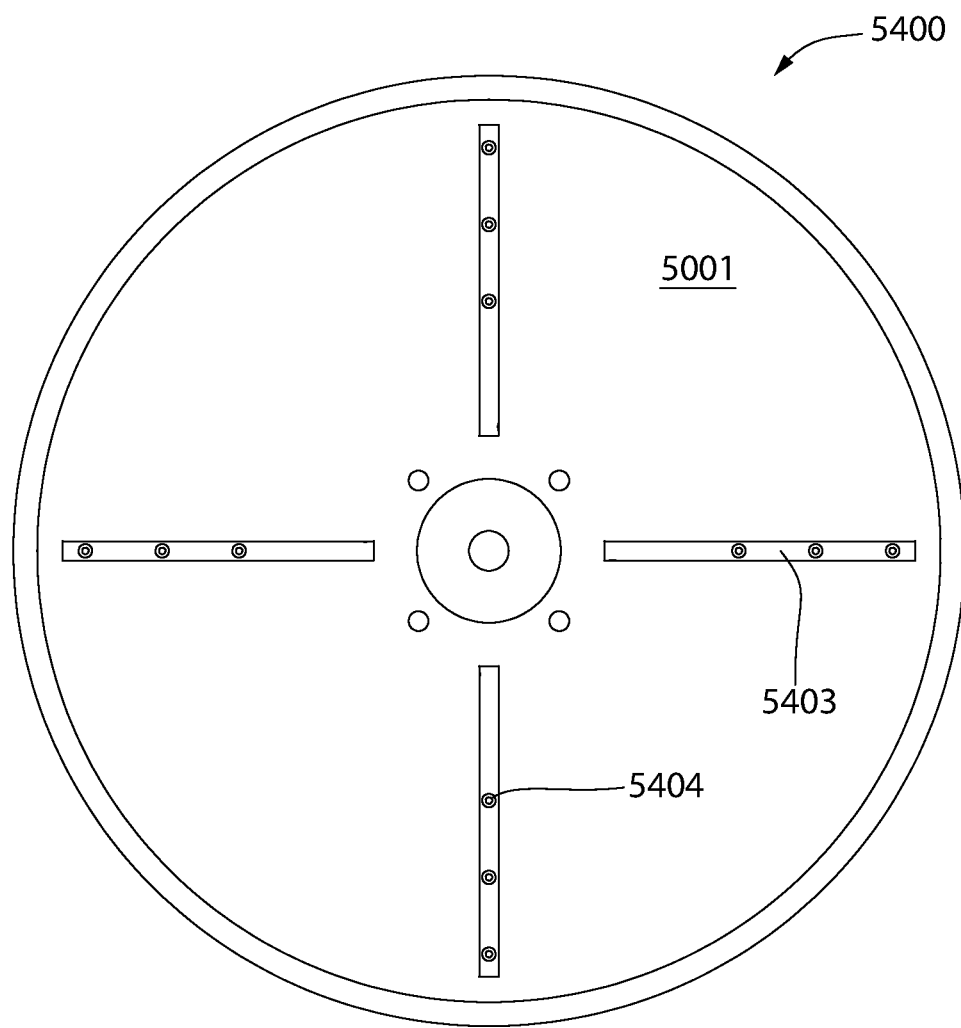
Figure 200:
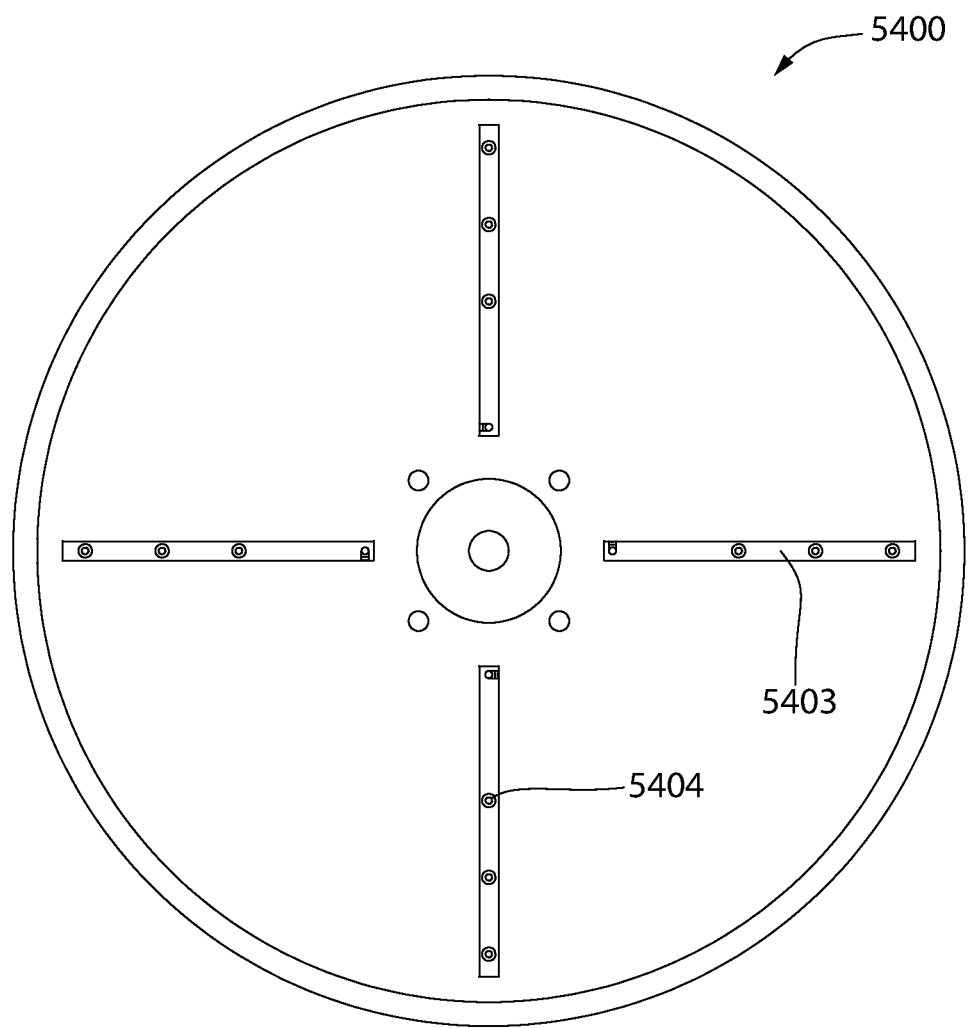
Figure 201:
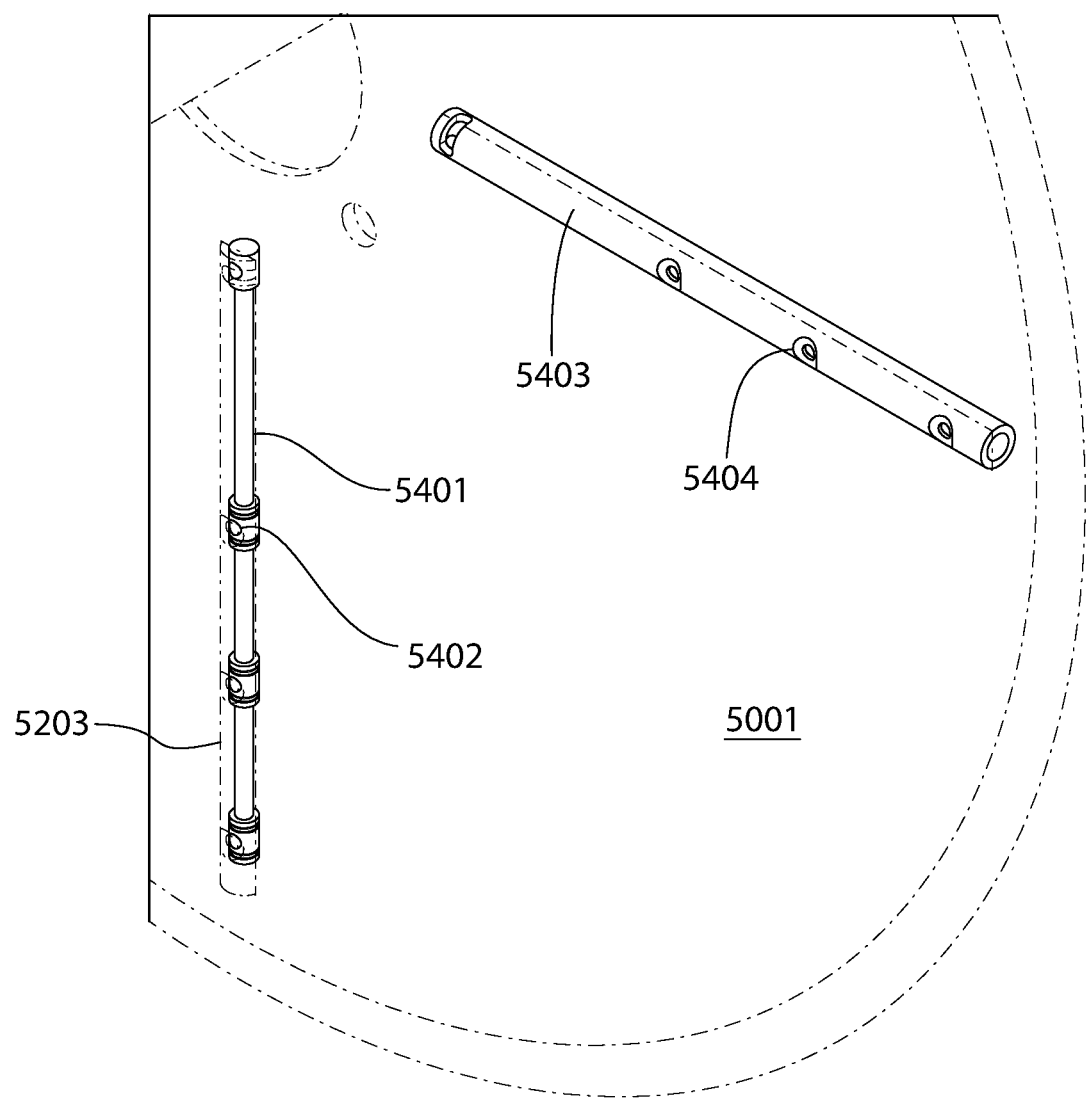
Figure 205:
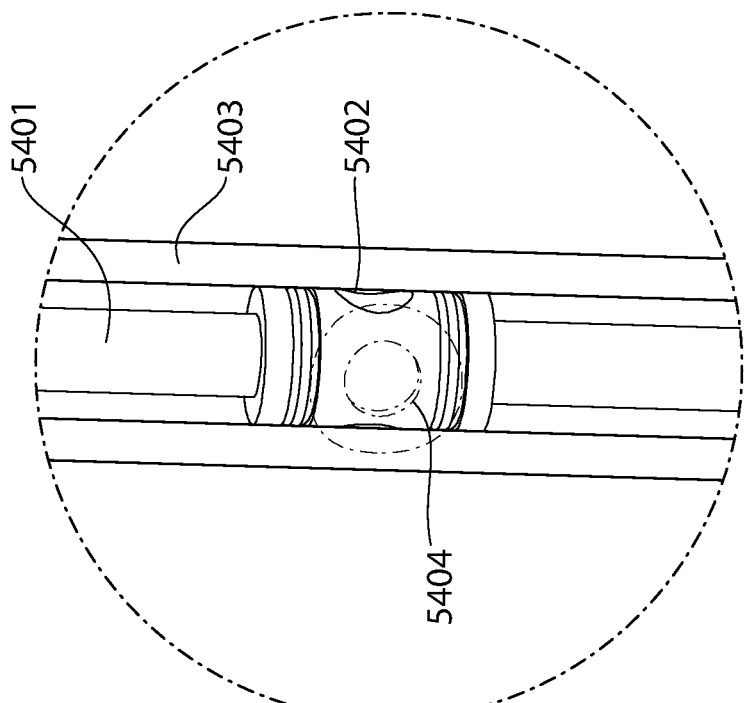
Figure 204:
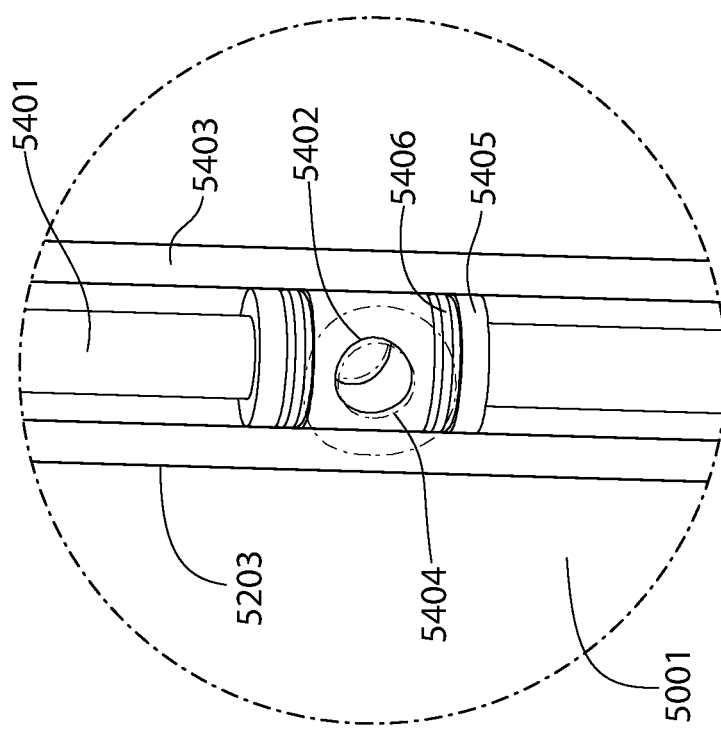
Figure 206:
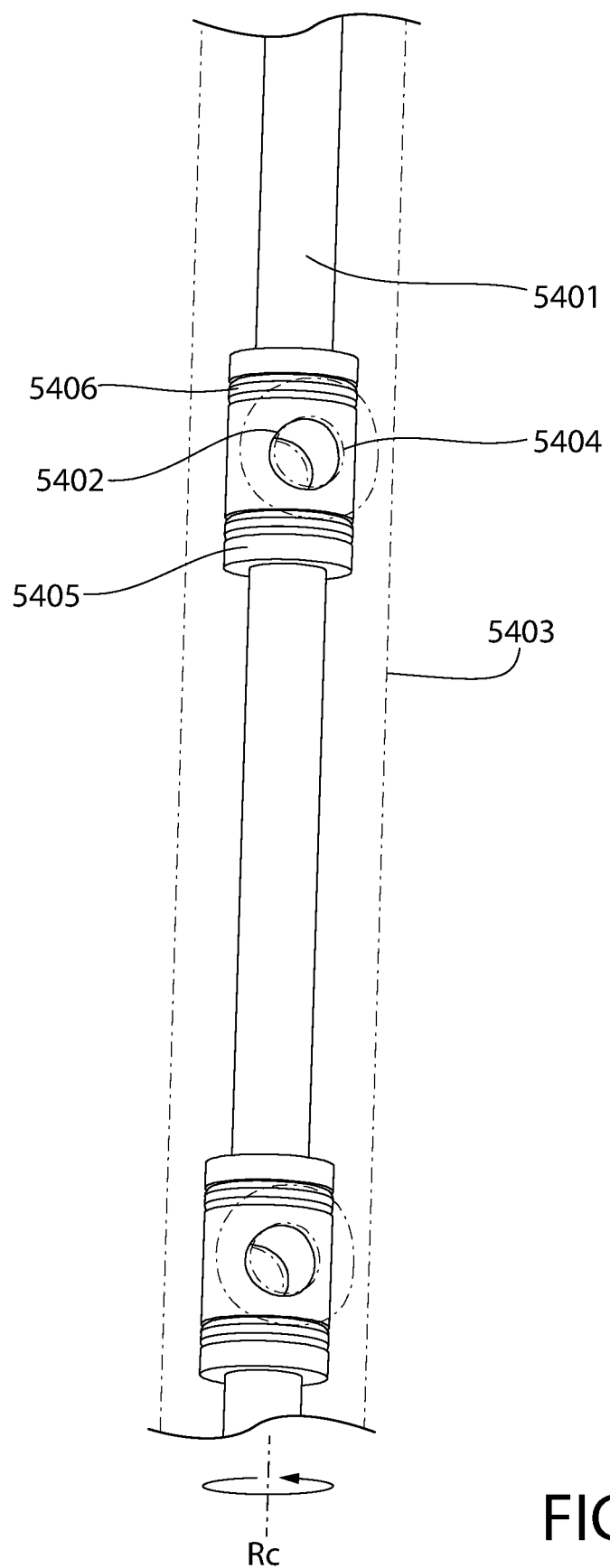
Figure 207:
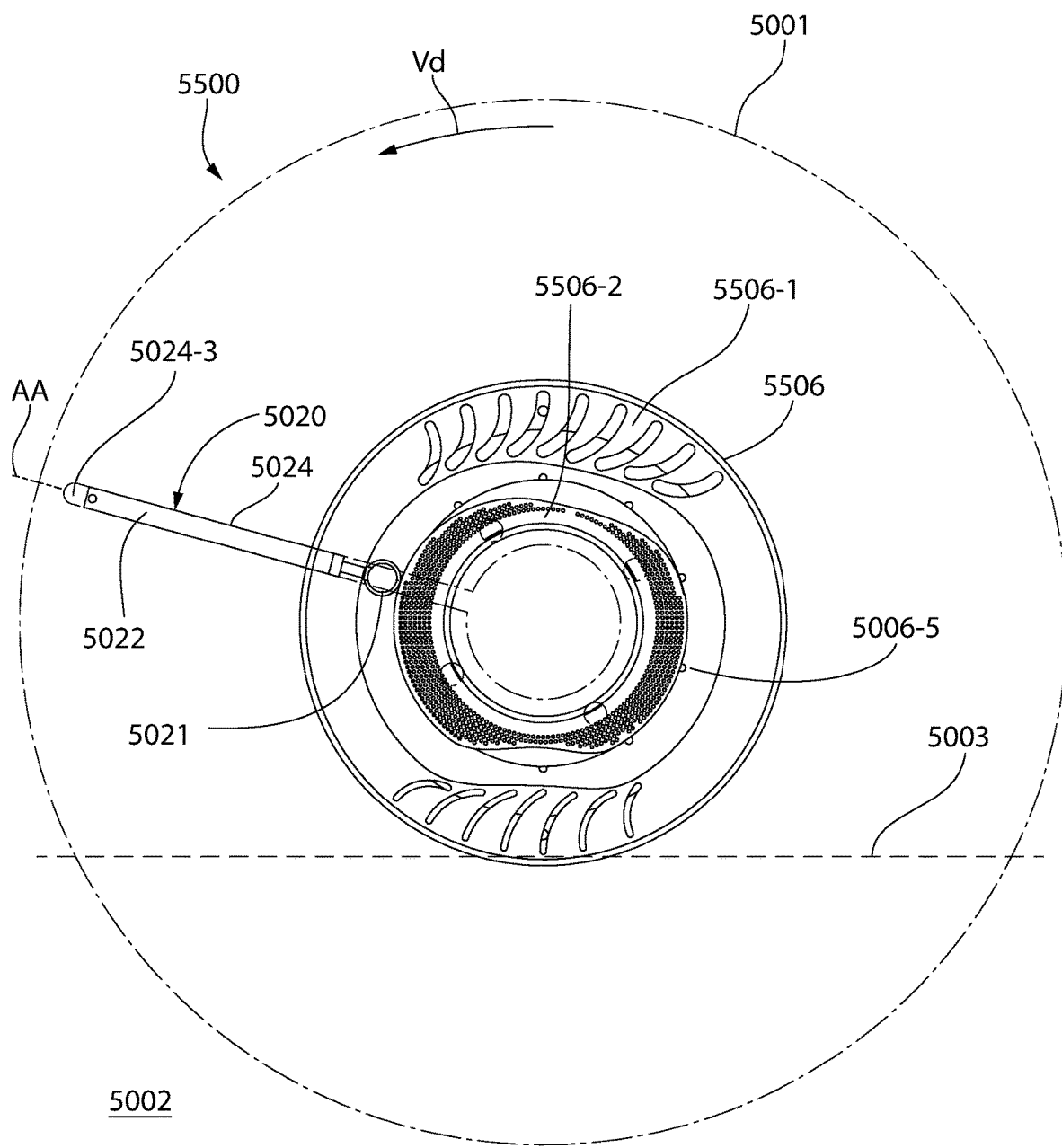
Figure 208:
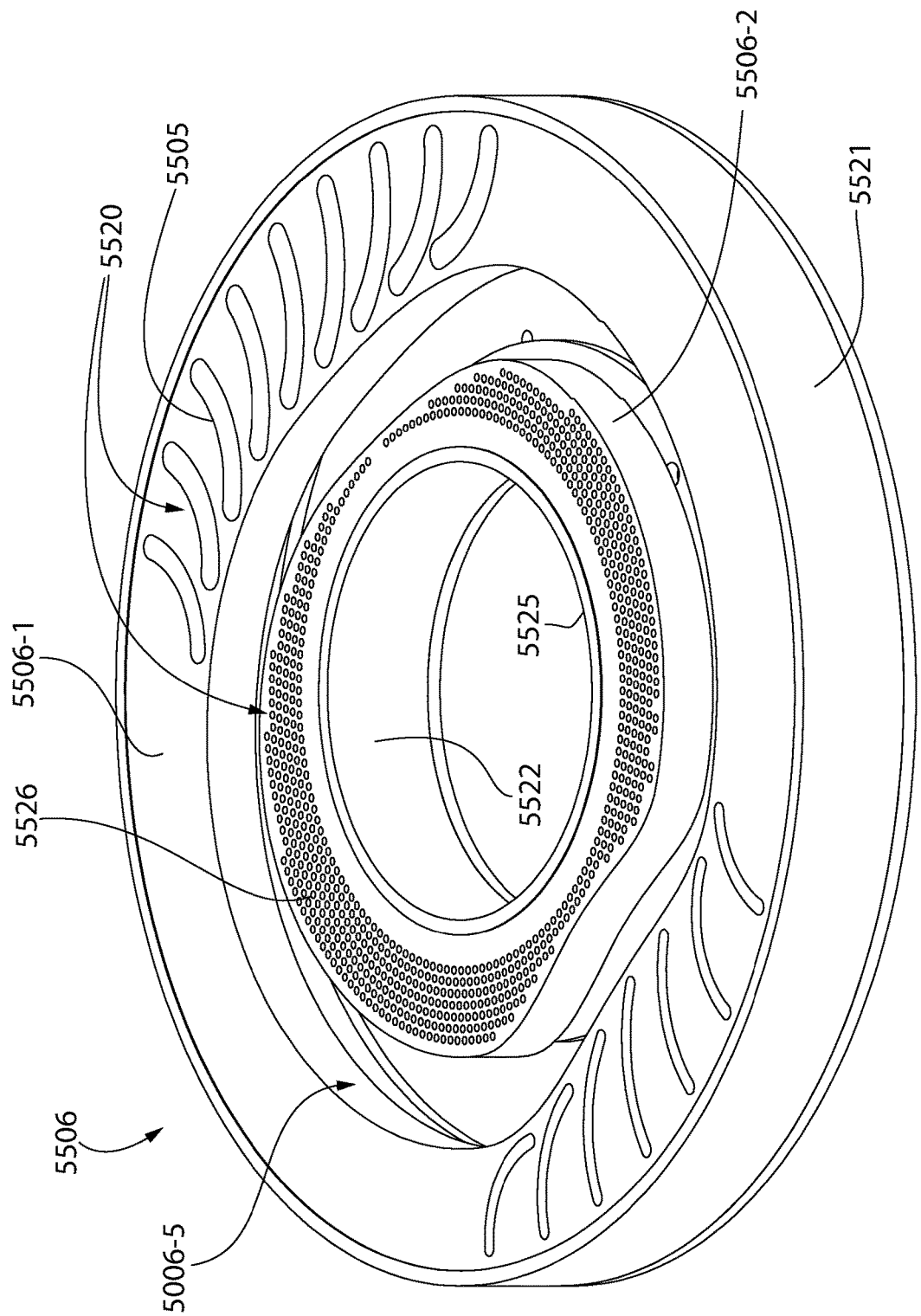
Figure 209:
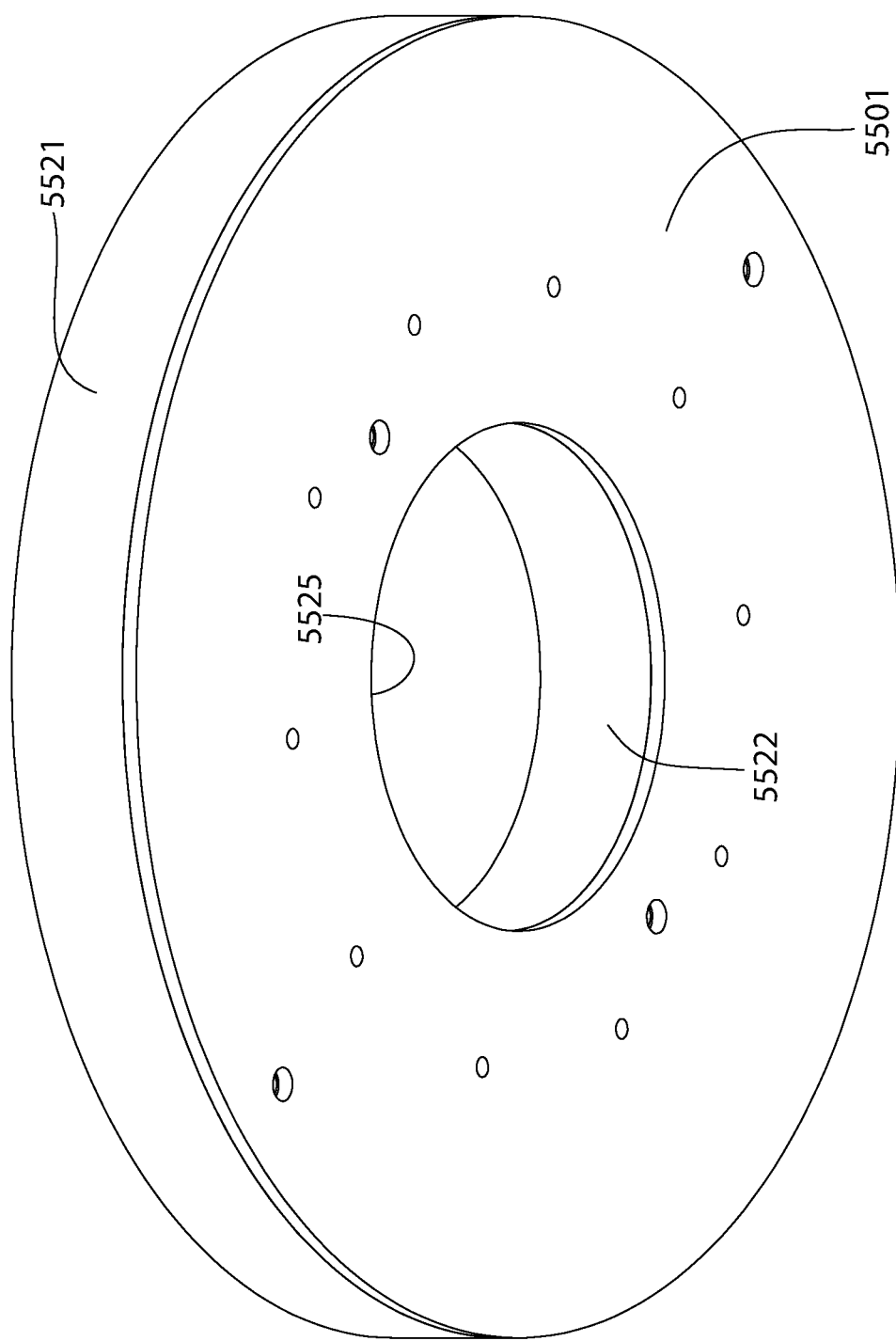
Figure 210:
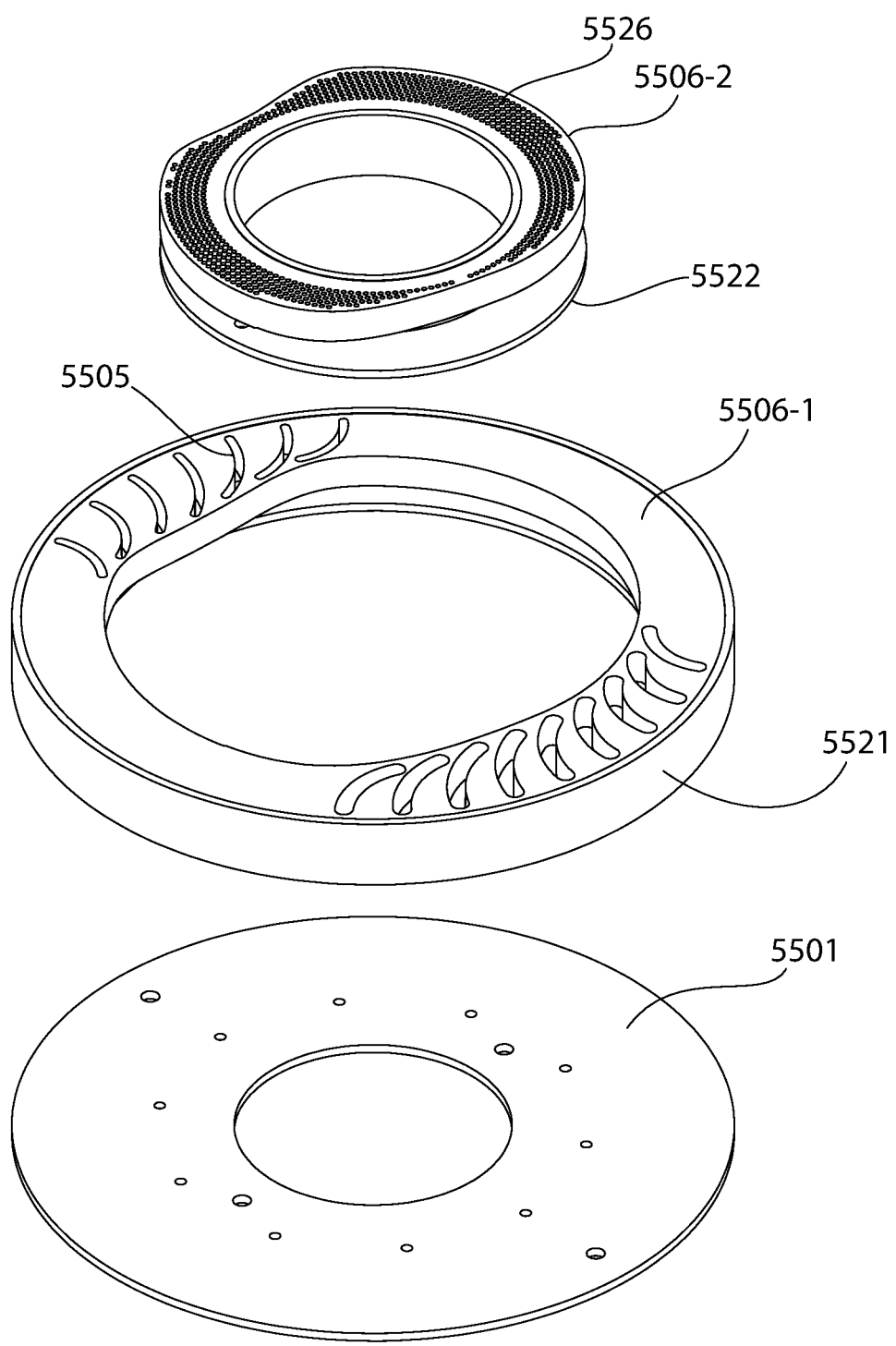
Figure 211:
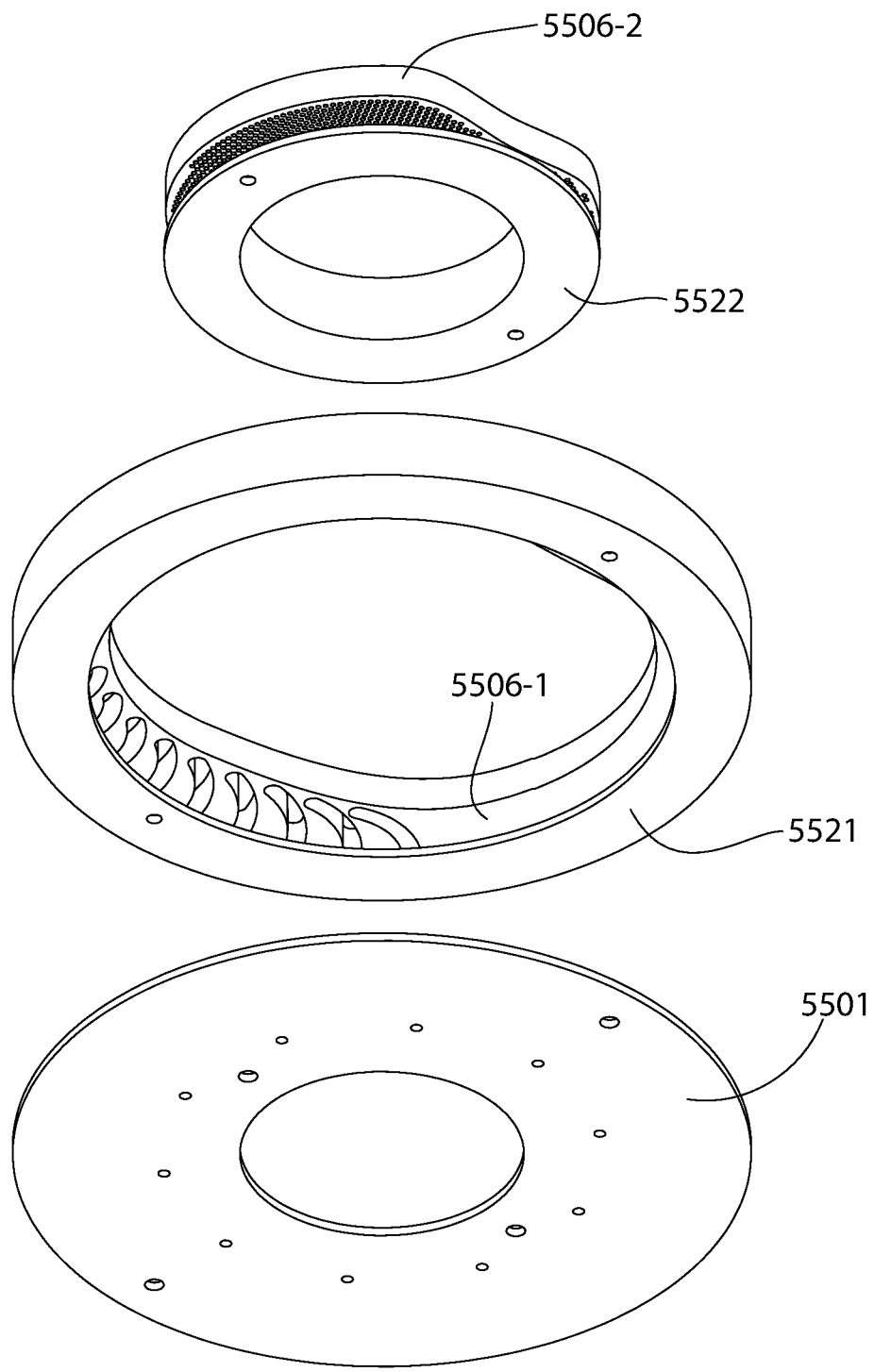
Figure 212:
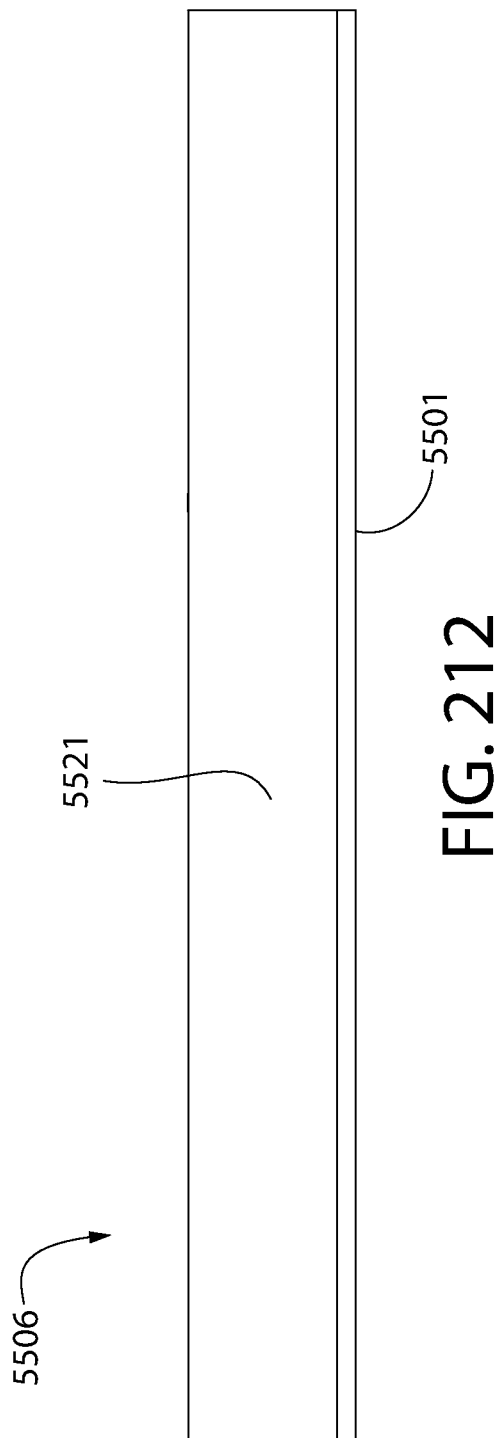
Figure 213:
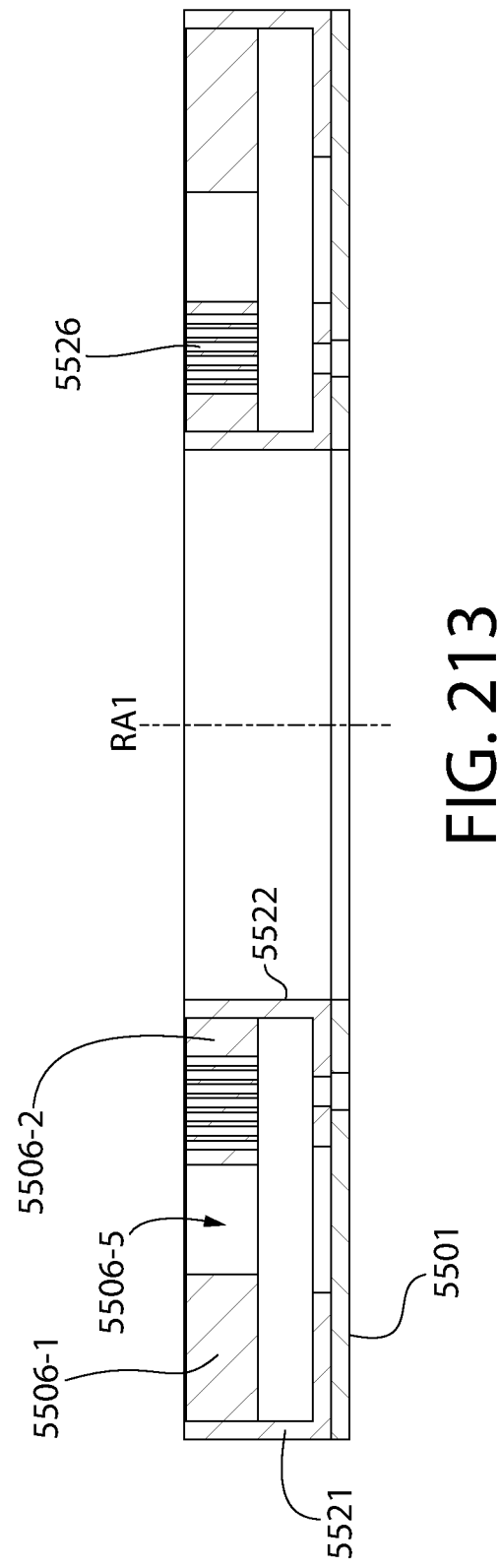
Figure 214:
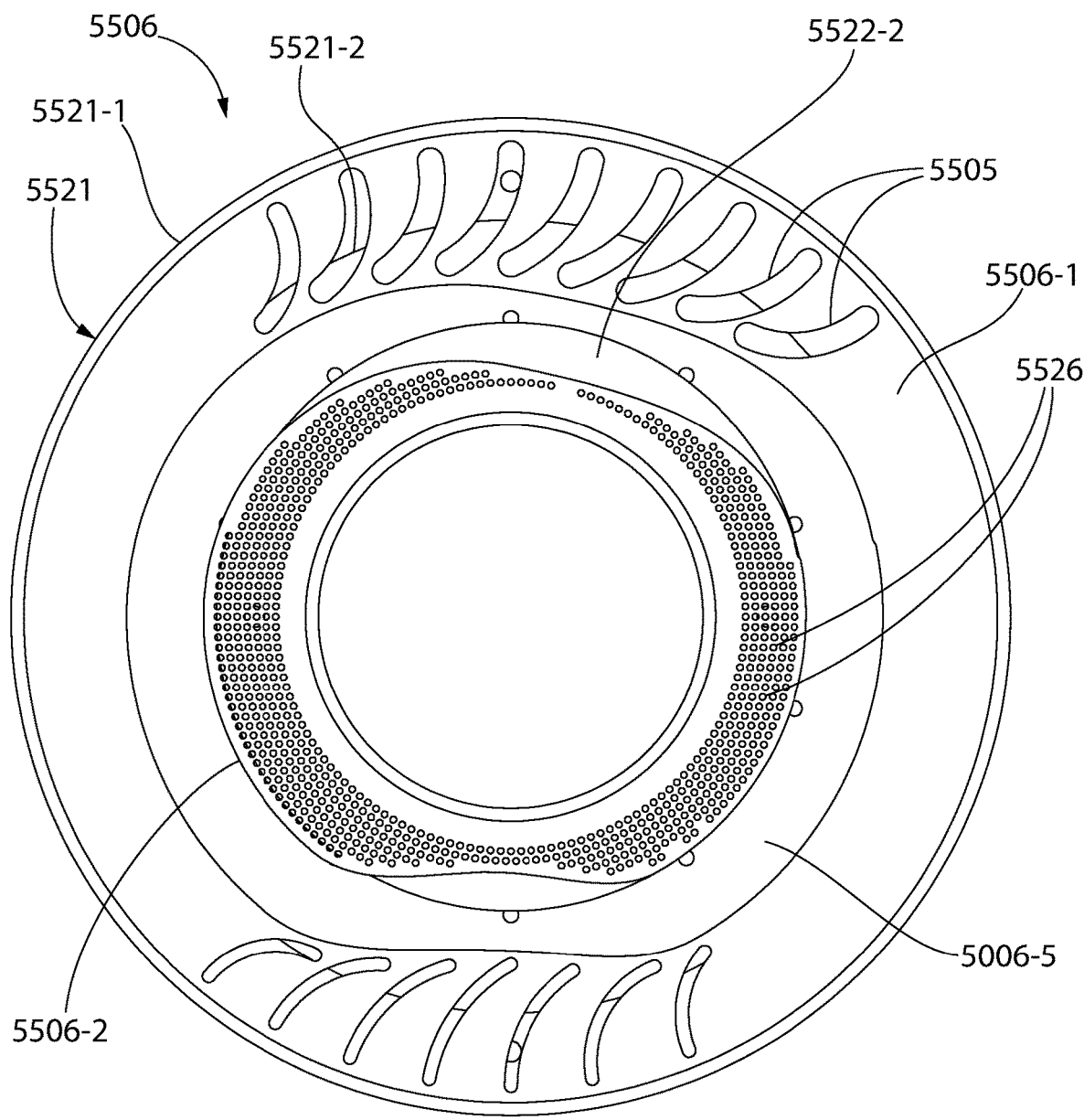
Figure 215:
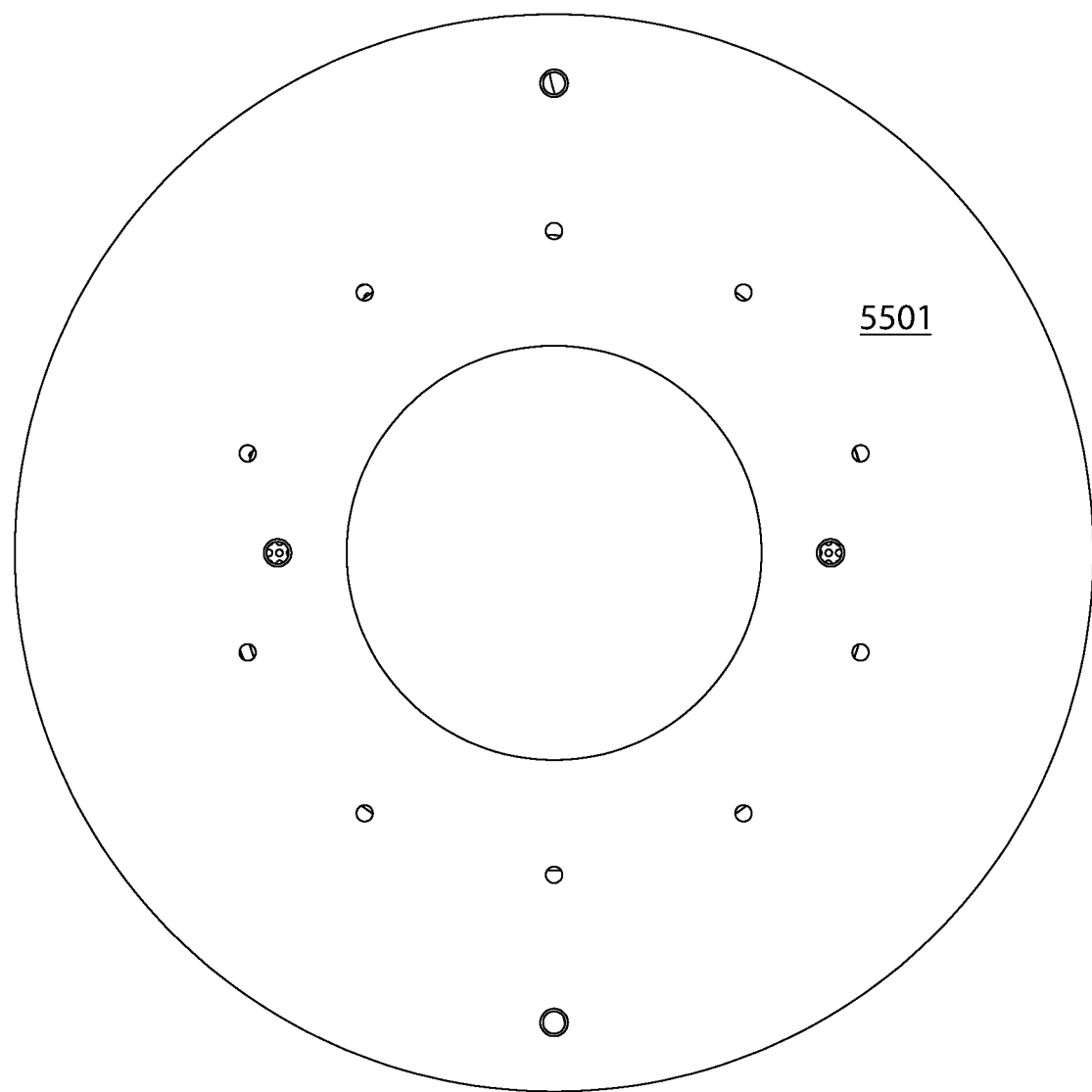
Figure 216:
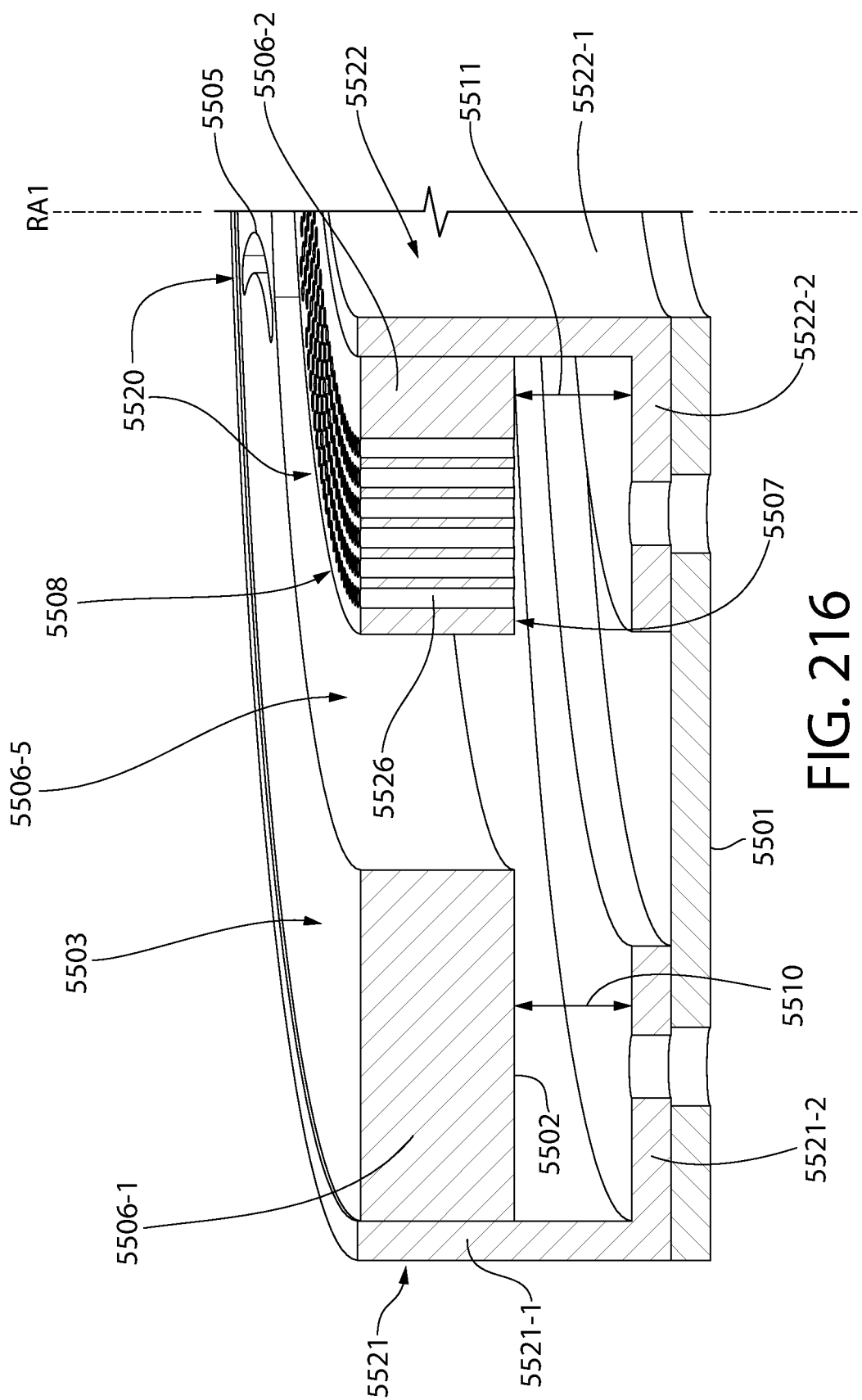
Figure 217:
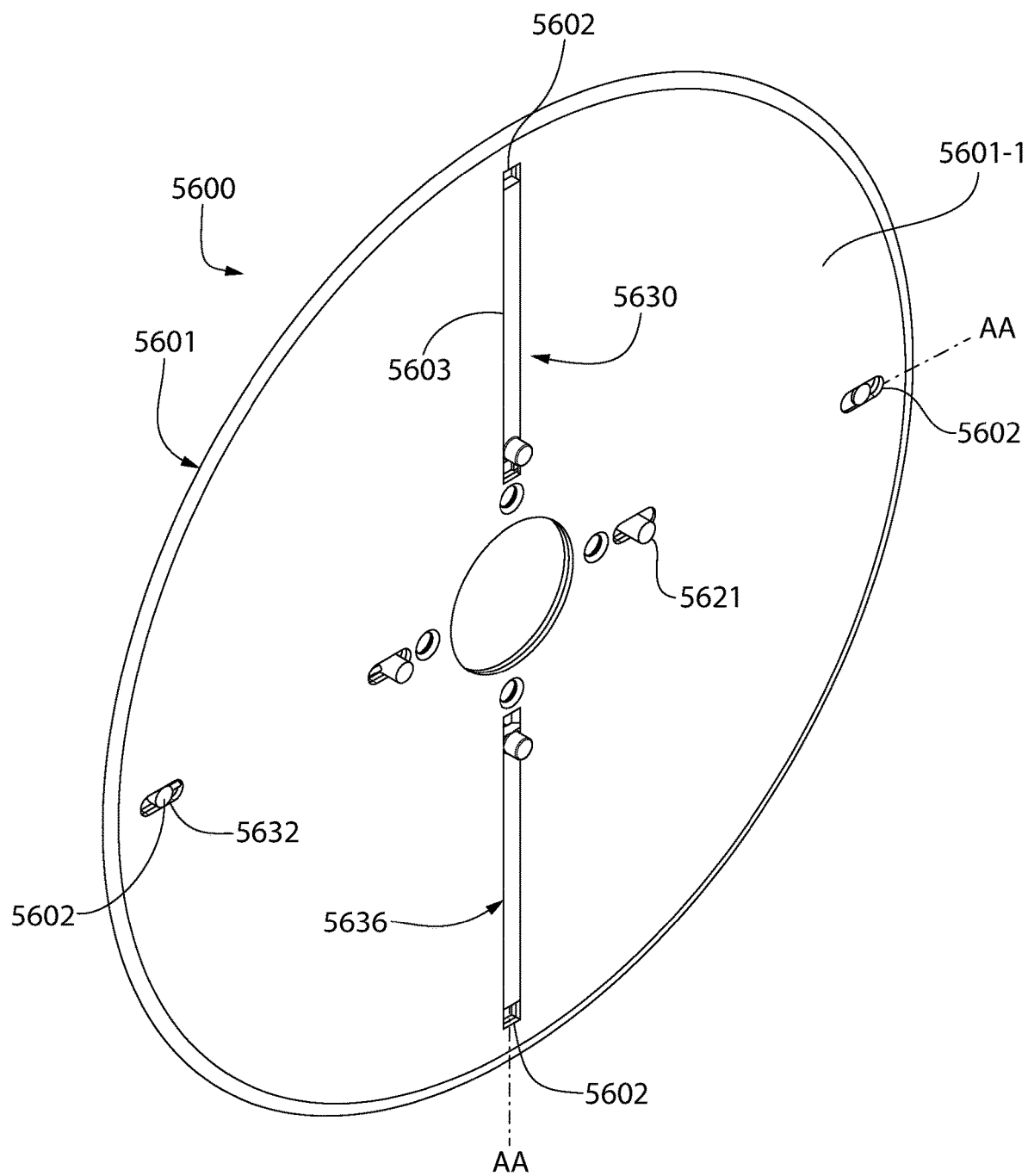
Figure 218:
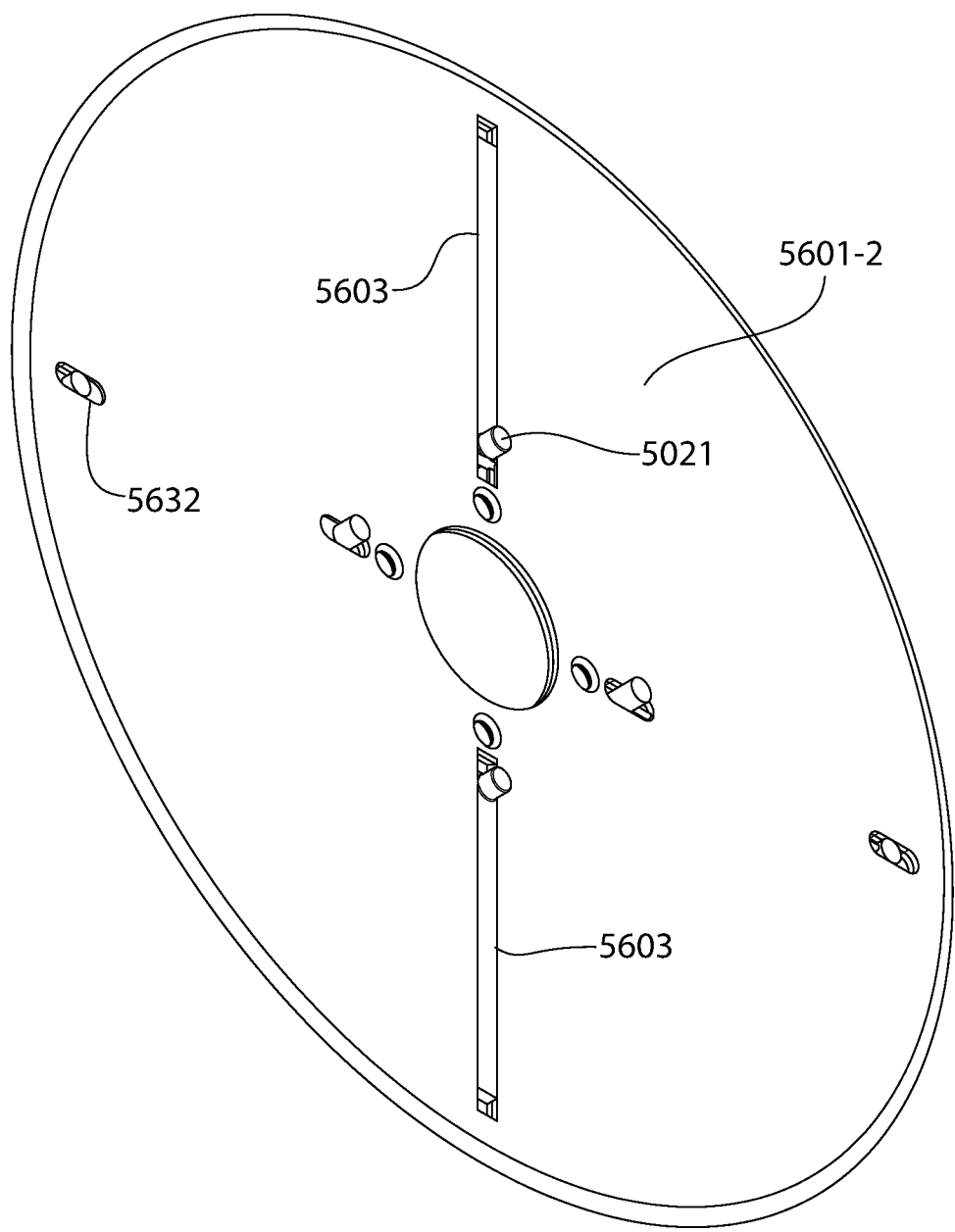
Figure 219:
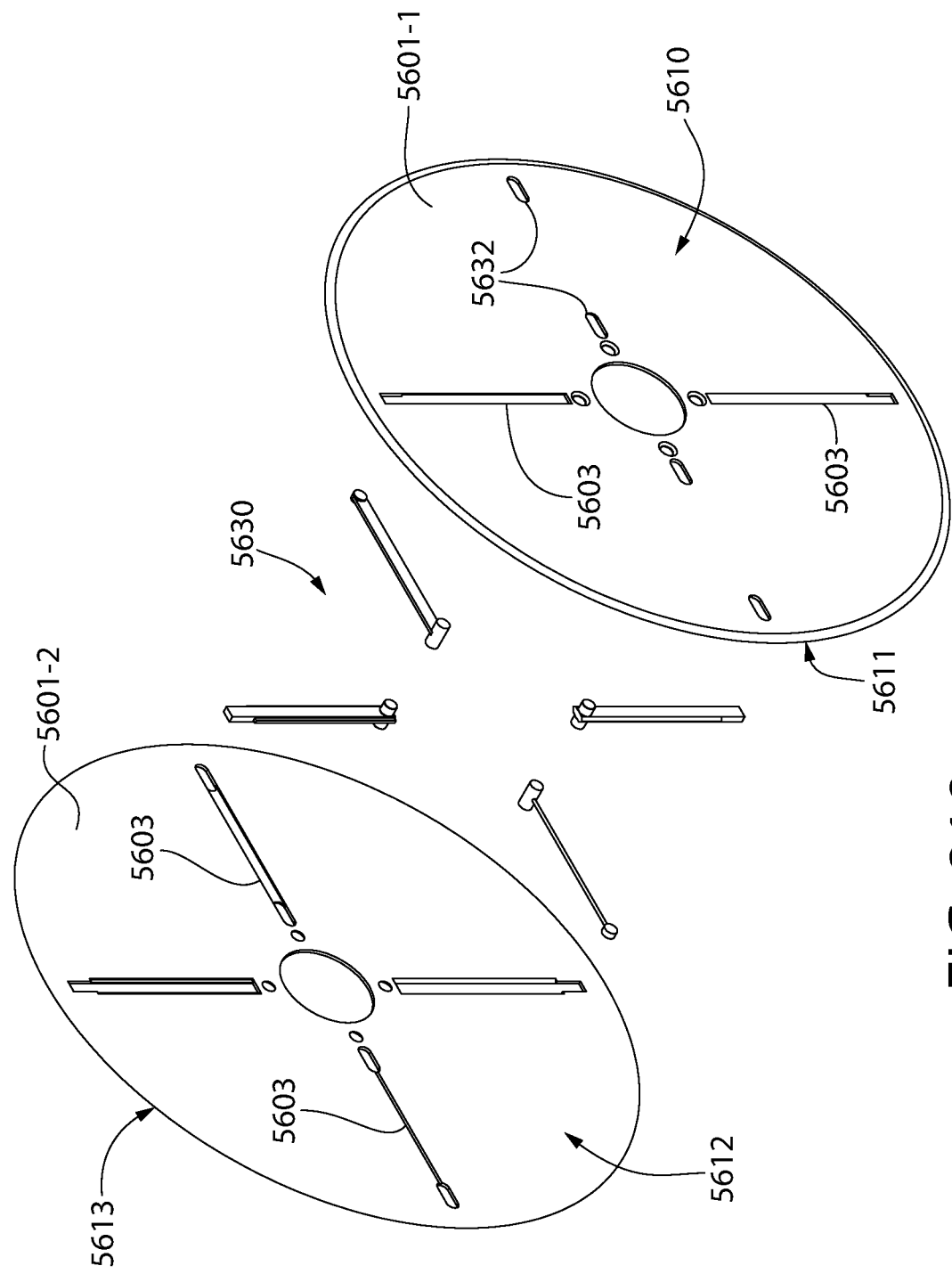
Figure 220:
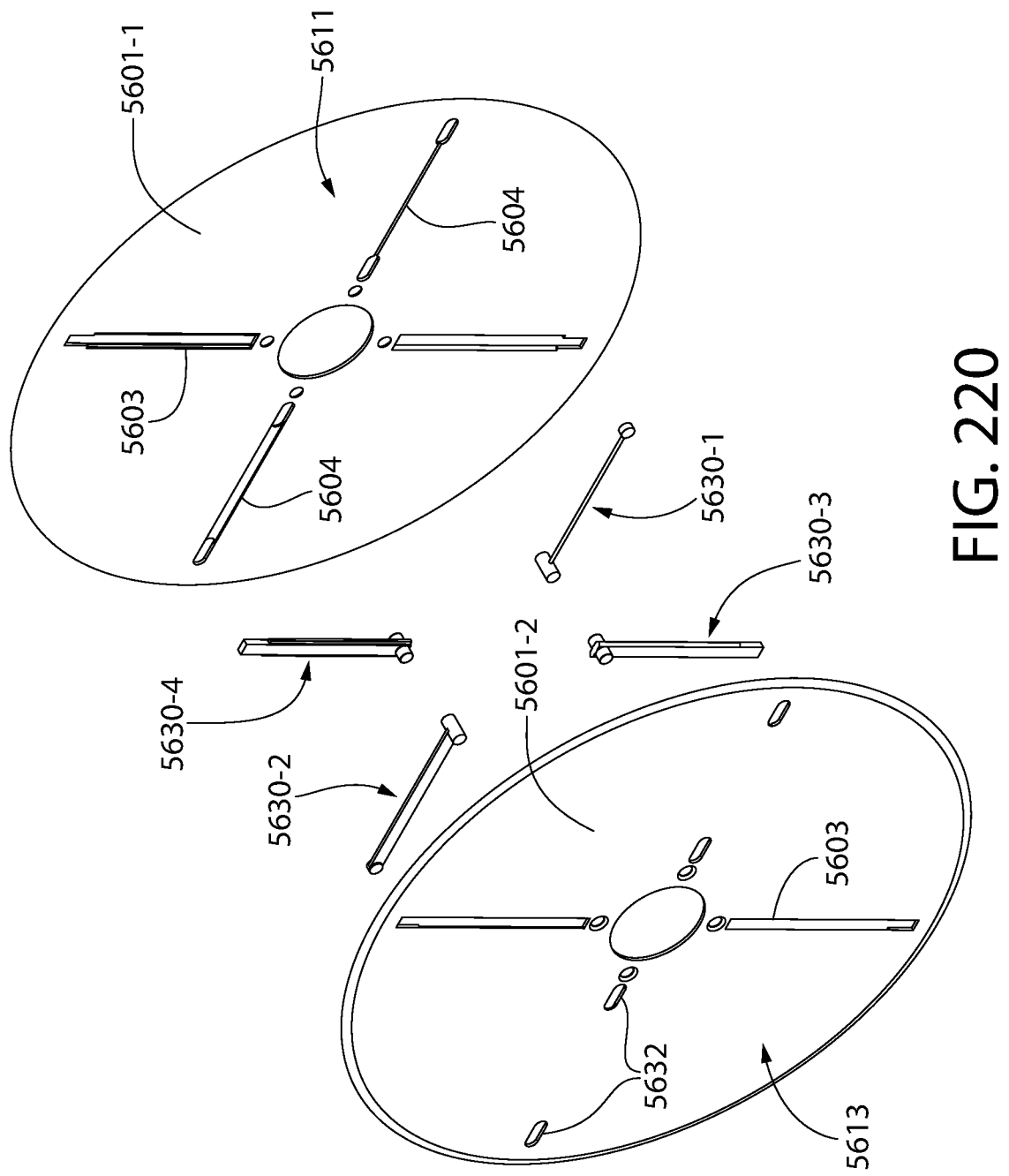
Figure 221:
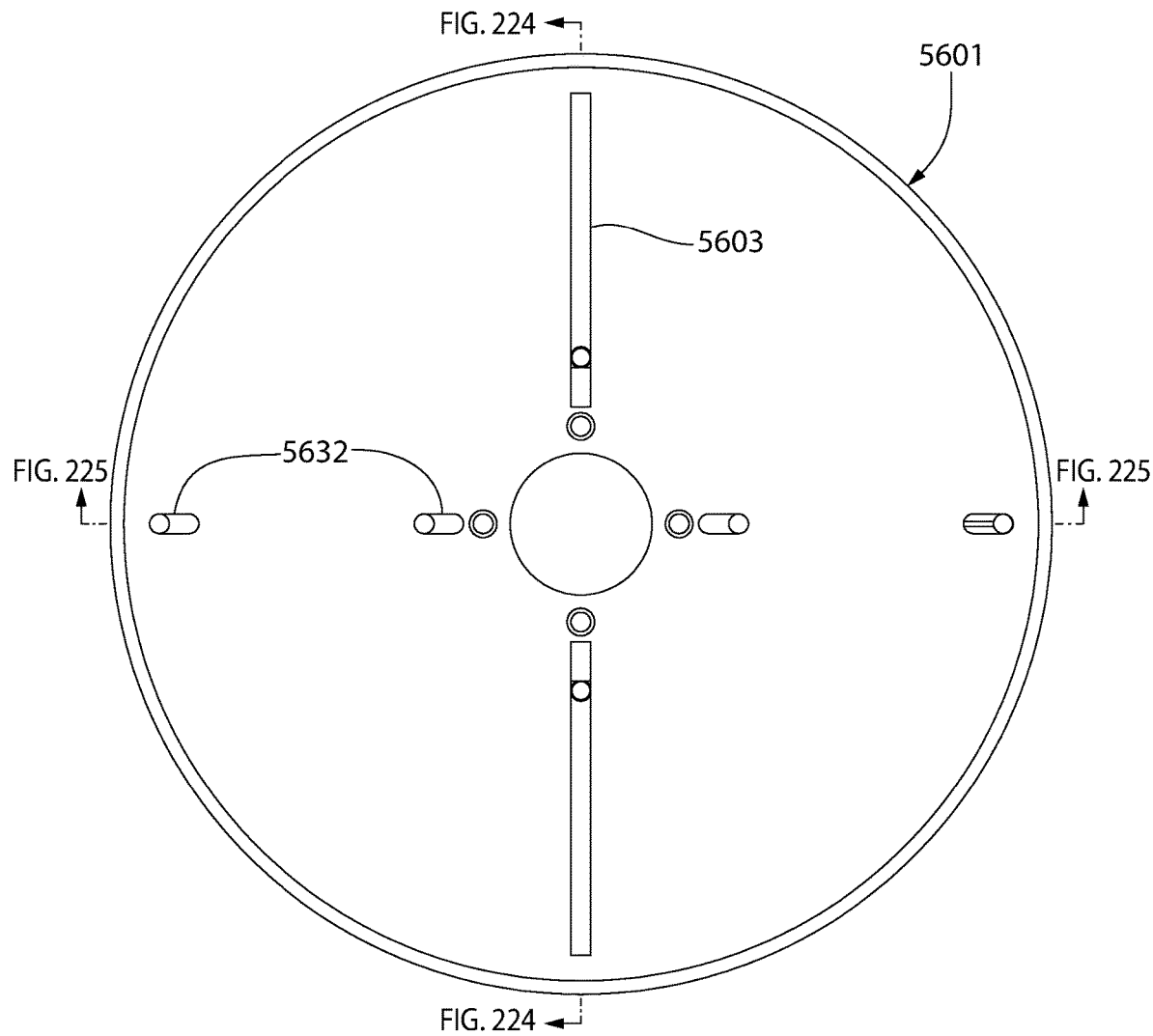
Figure 222:
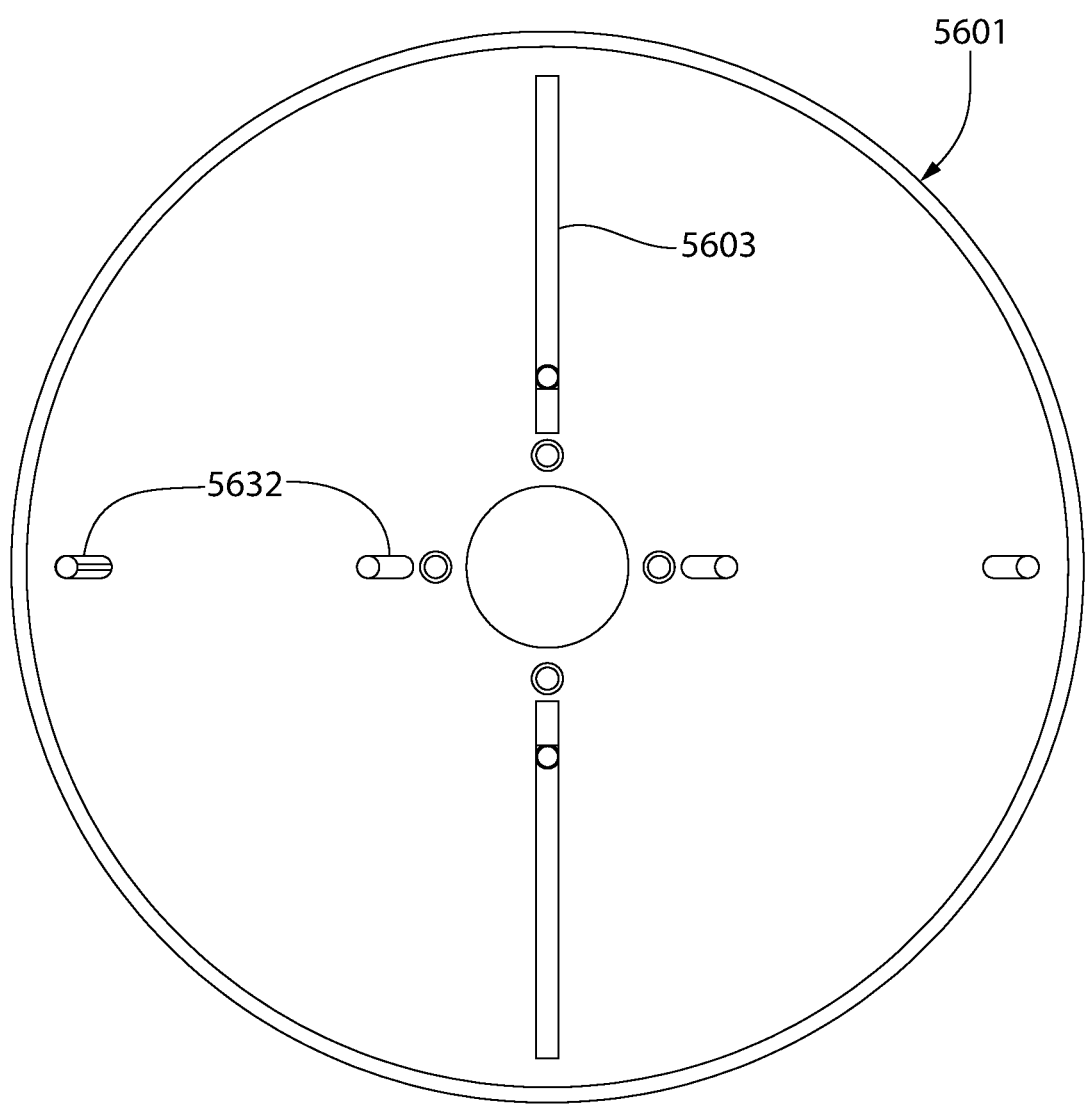
Figure 223:
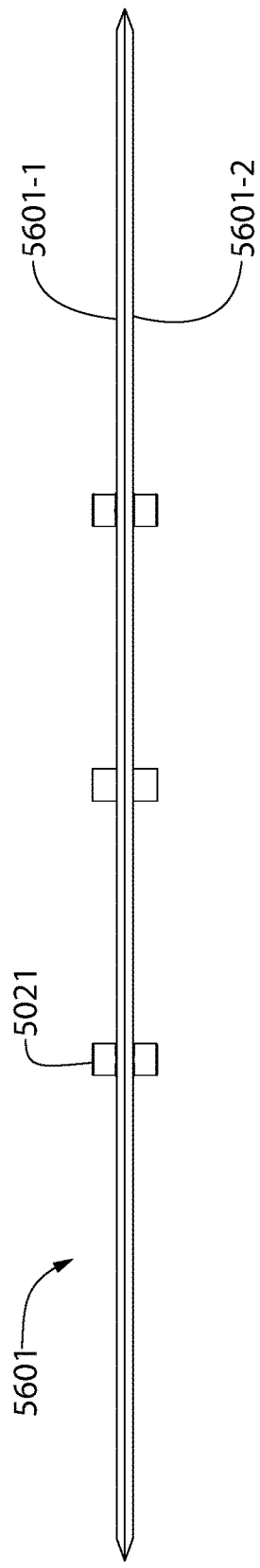
Figure 224:
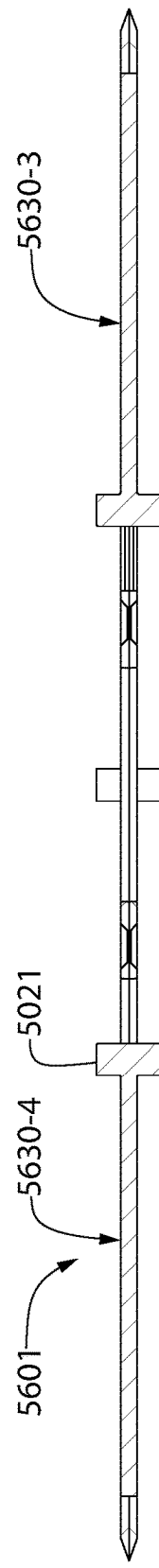
Figure 225:
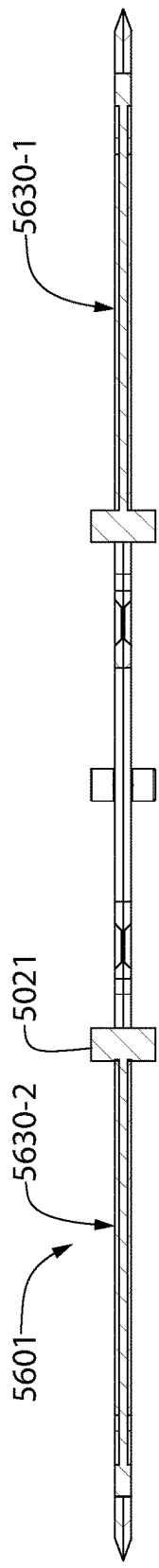
Figure 226:
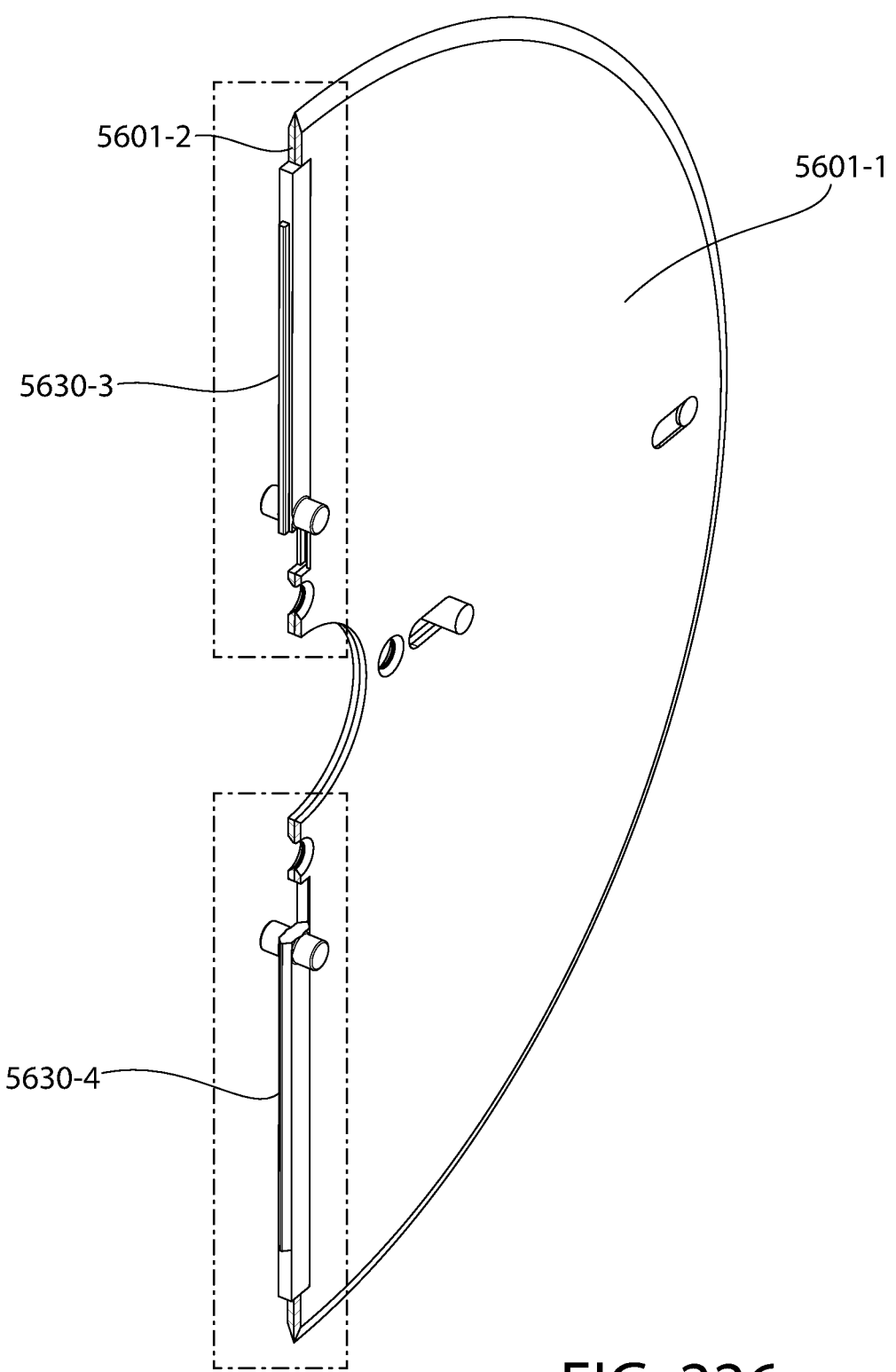
Figure 227:
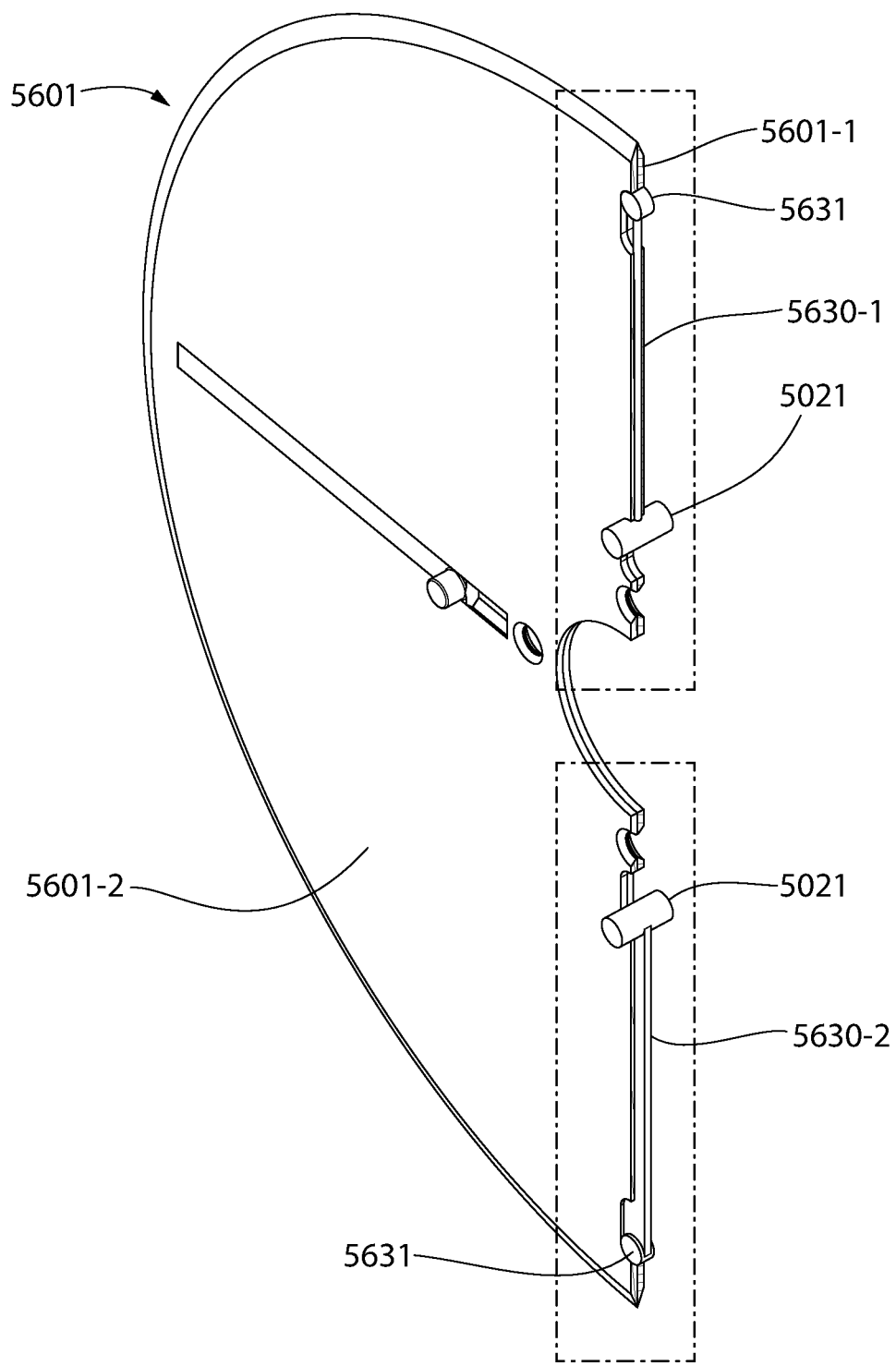
Figures 228, 229:
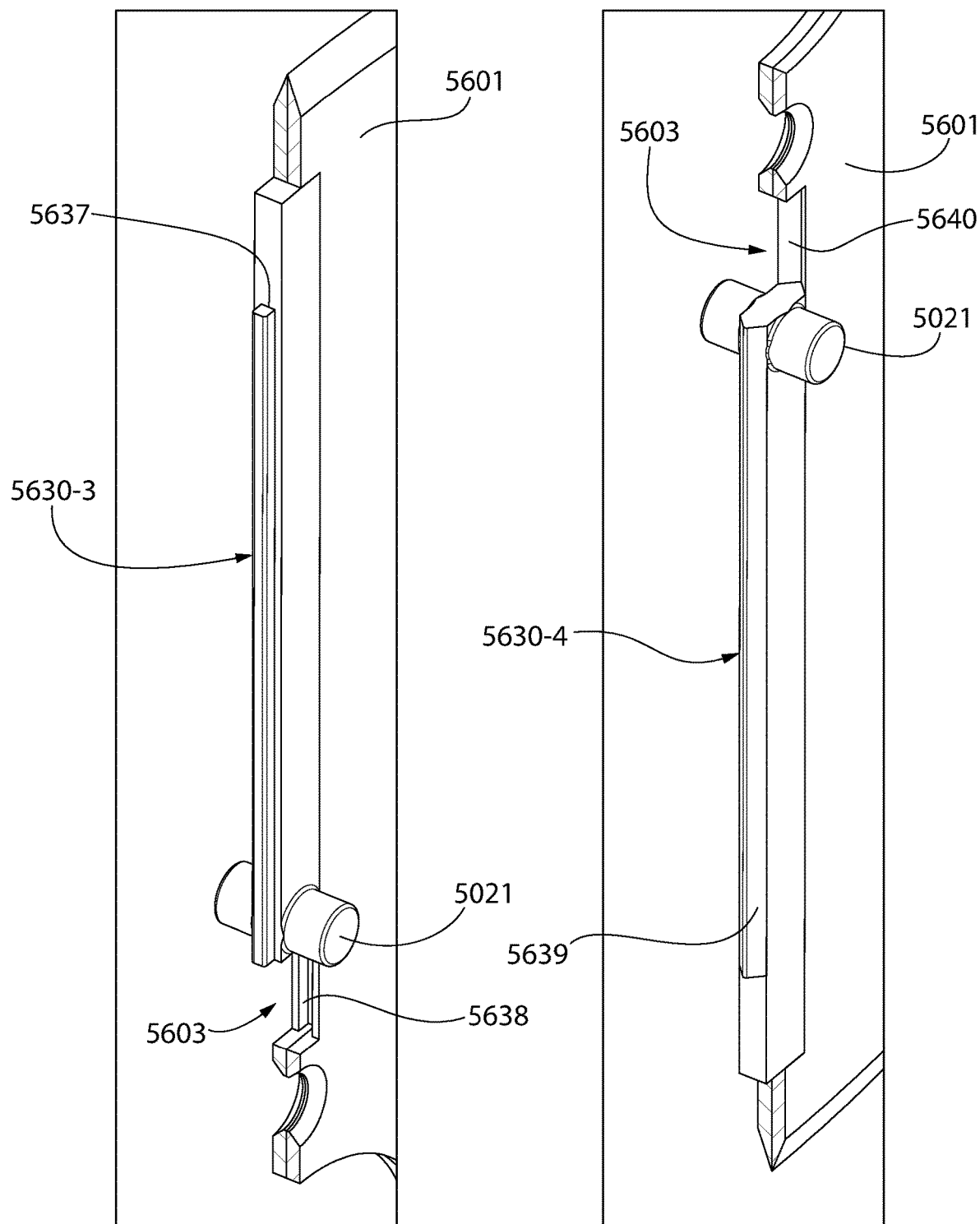
Figure 230:
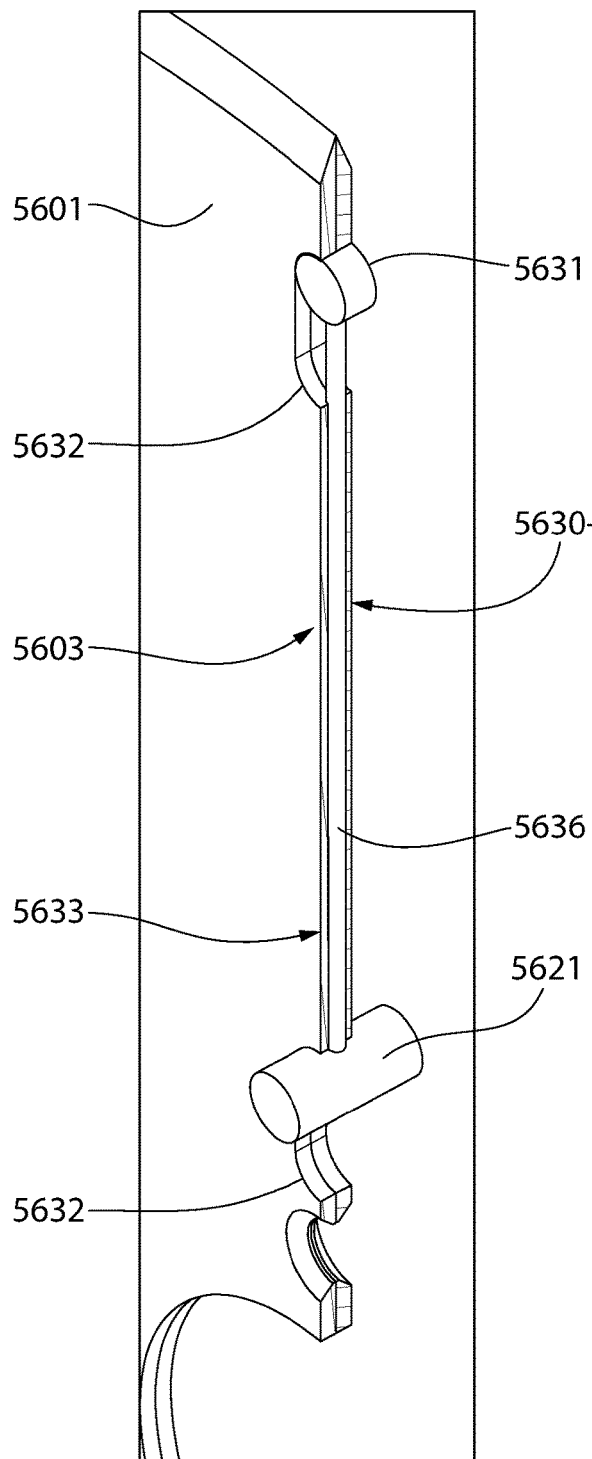
Figure 231:
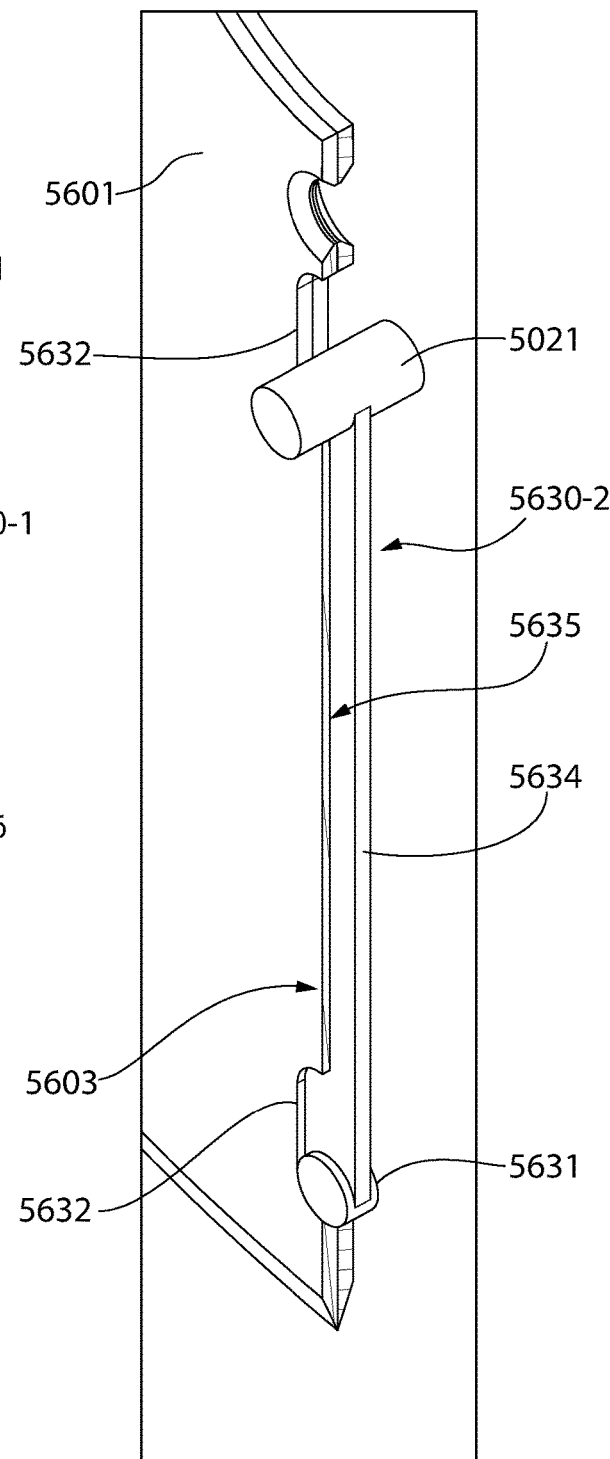
Figure 232:
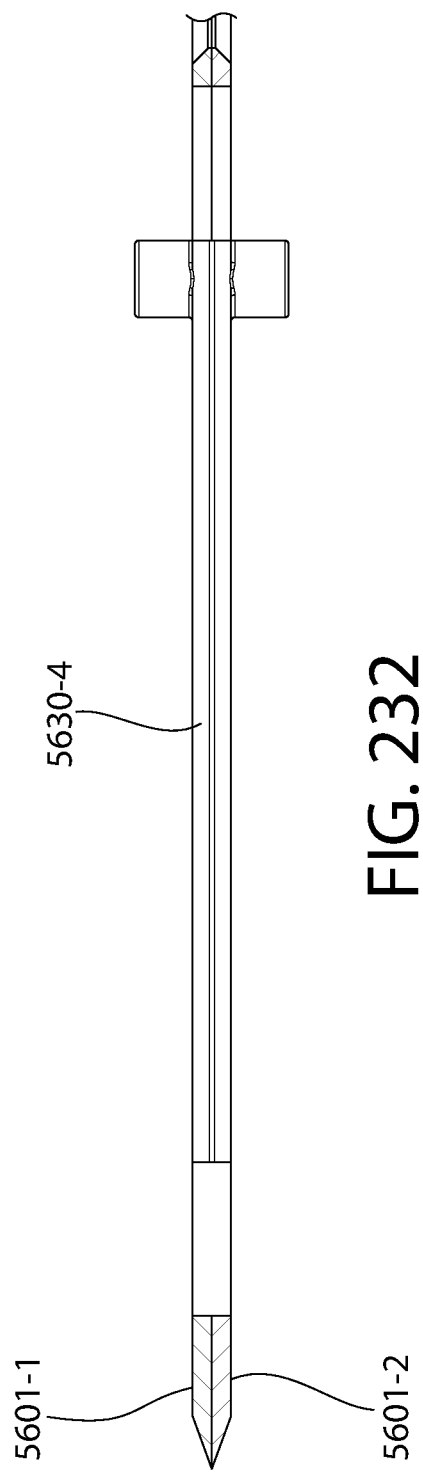
Figure 233:
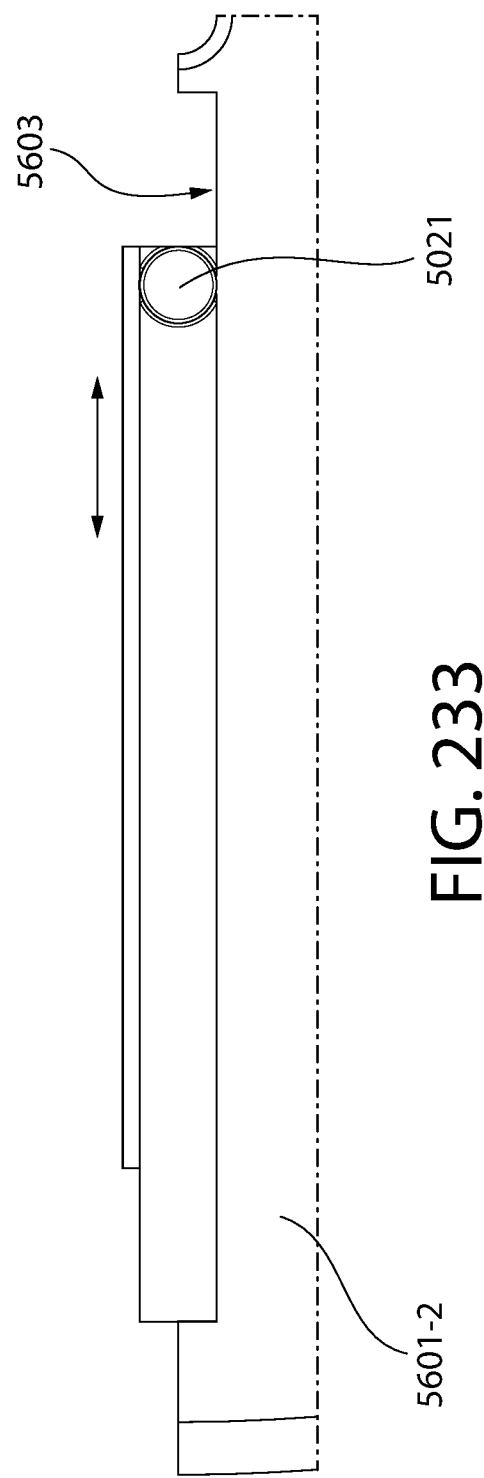
Figure 236:
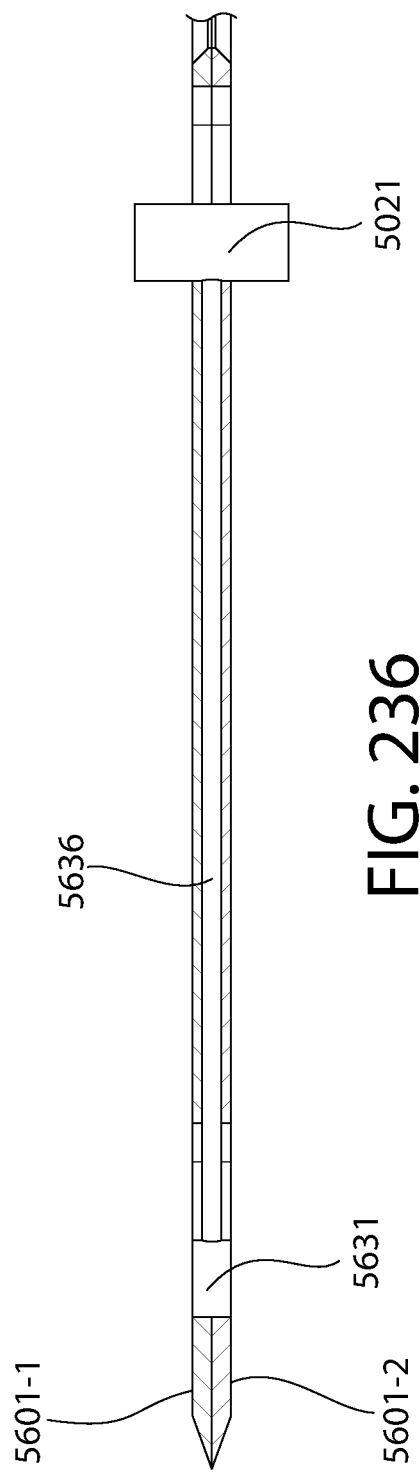
Figure 237:
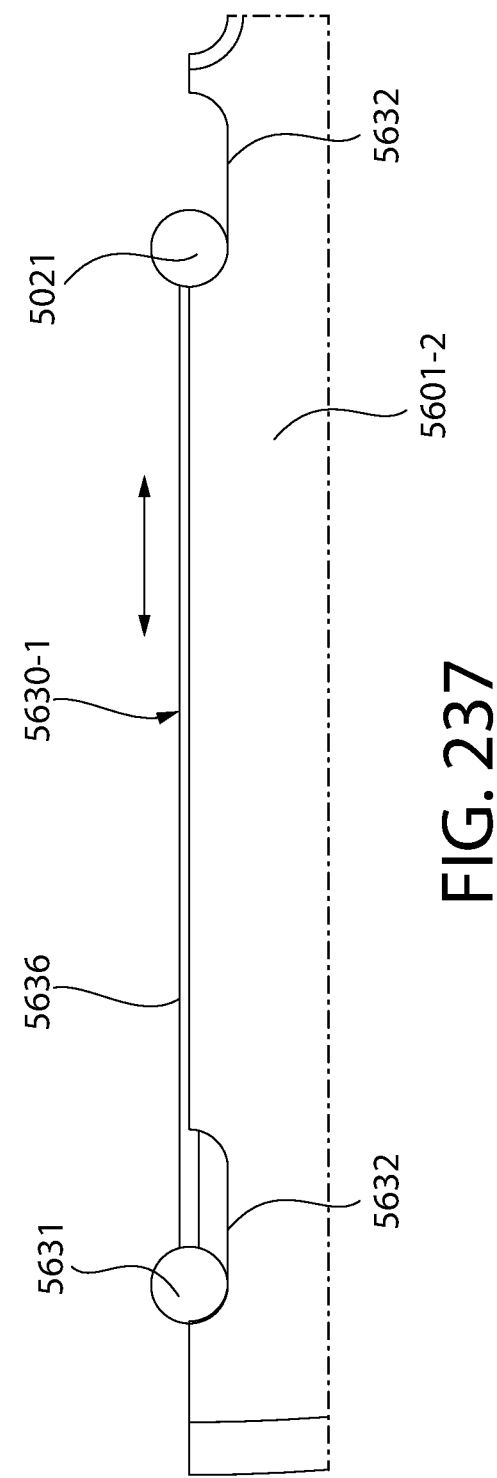
Figure 238:
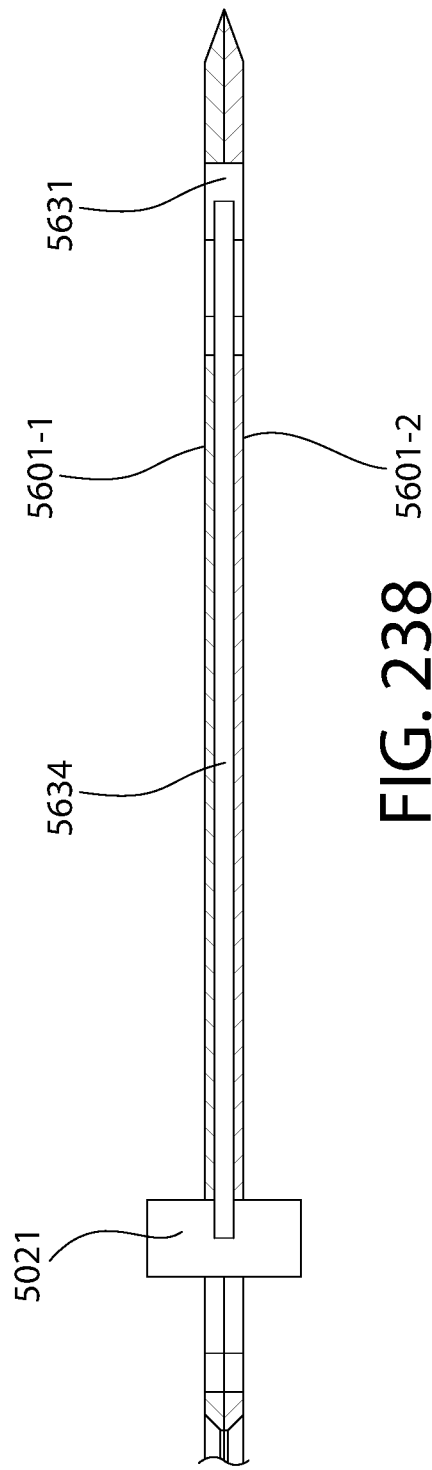
Figure 239:
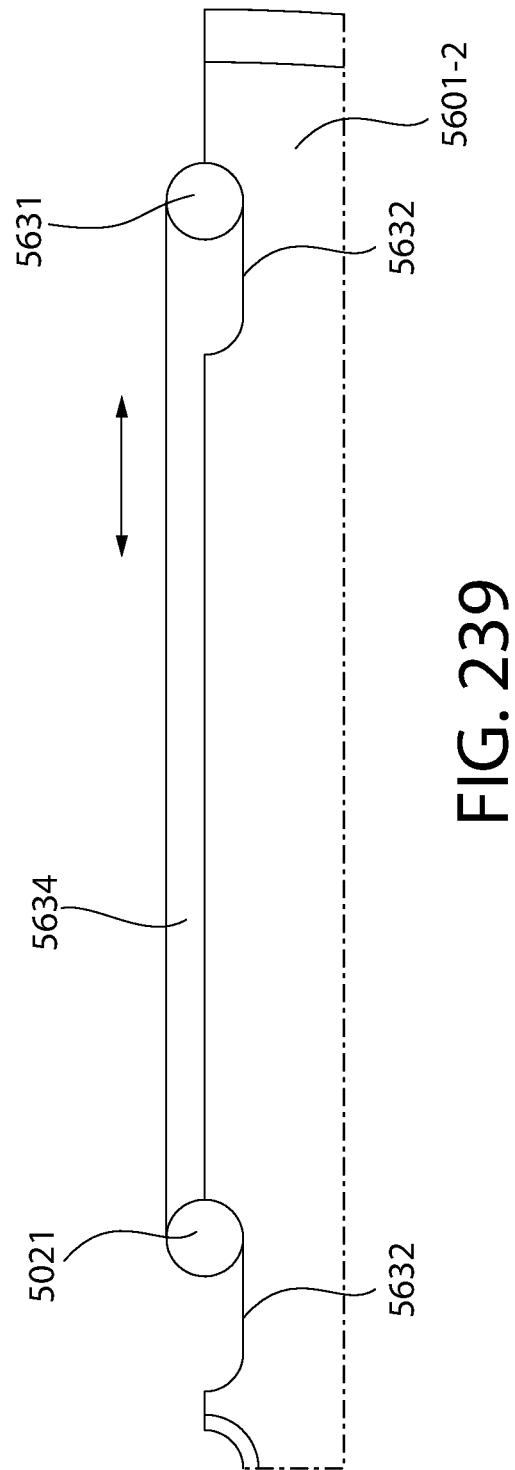
Figure 240:
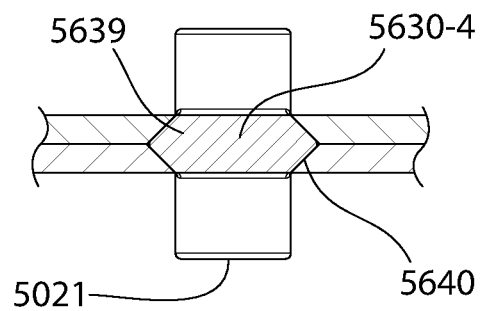
Figure 241:
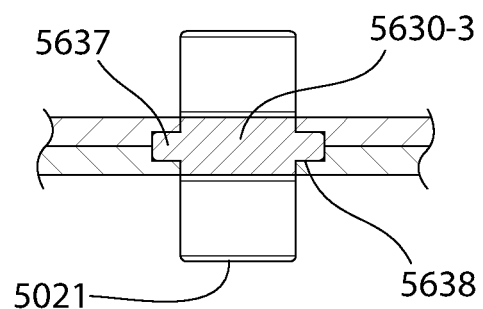
Figure 242:
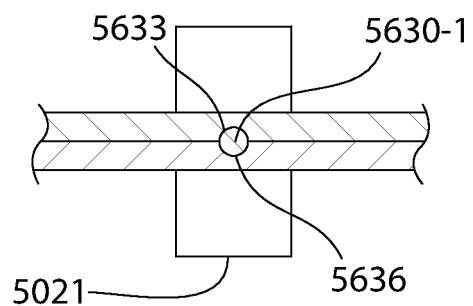
Figure 243:
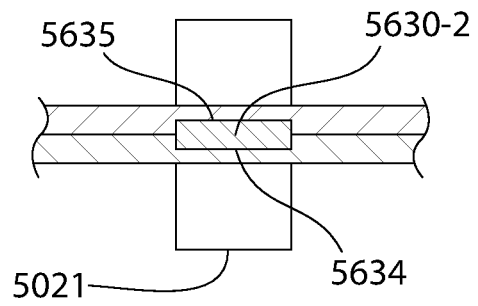
Figure 244A:
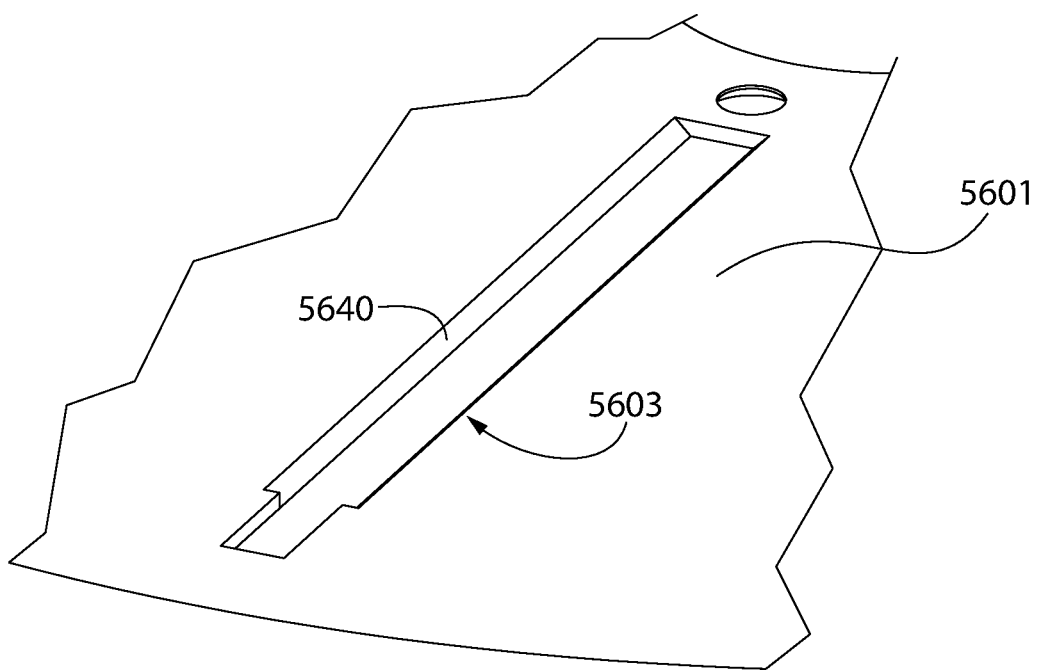
Figure 244B:
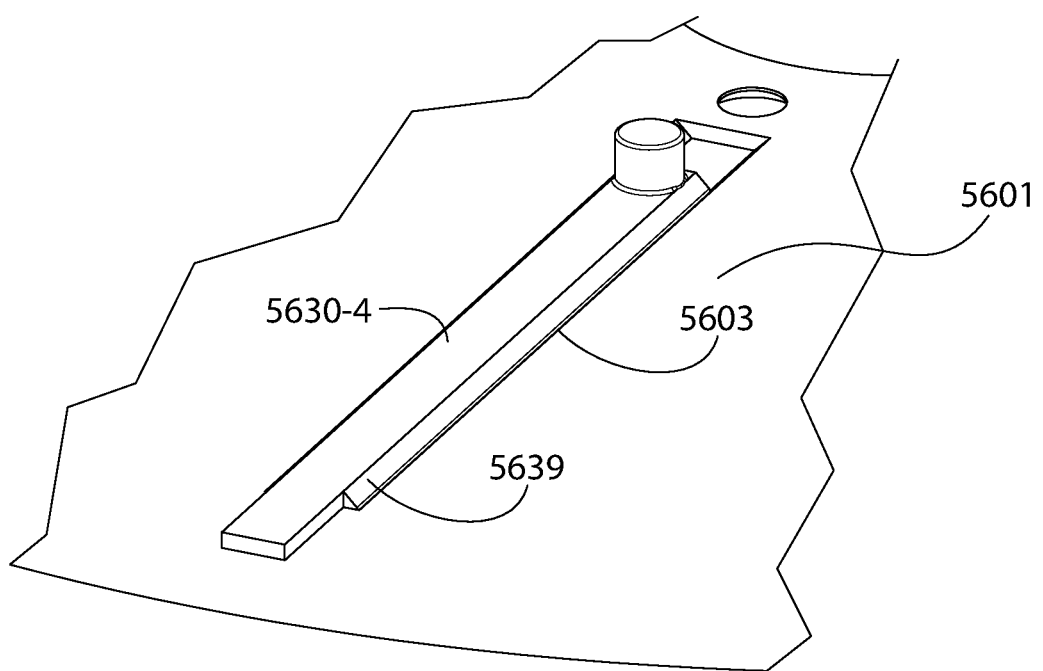
Figure 245A:
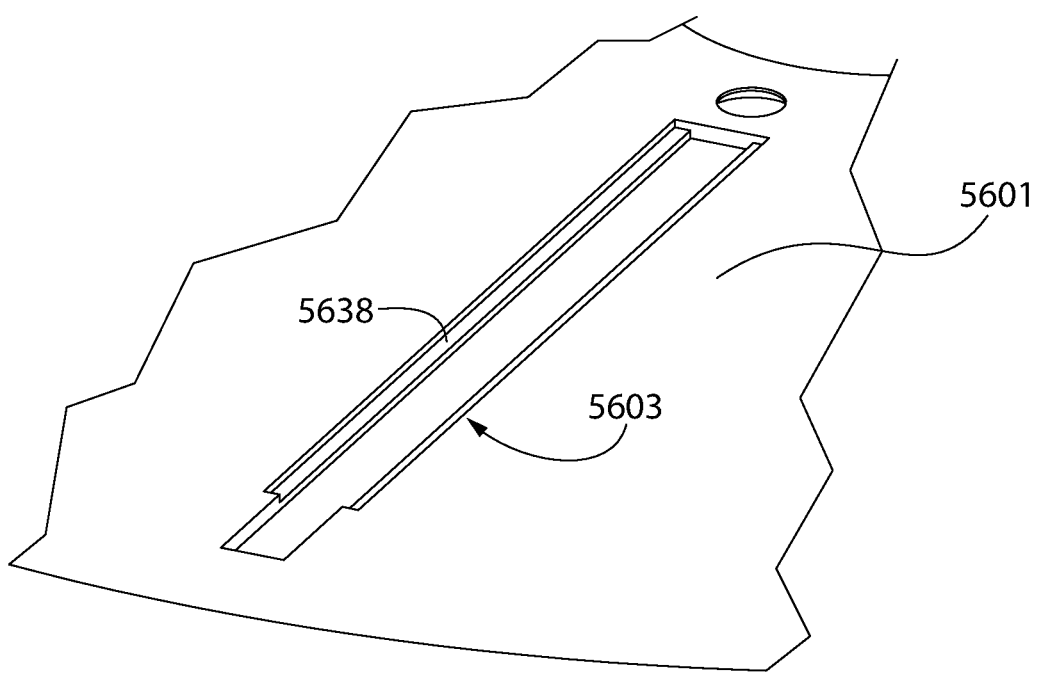
Figure 245B:
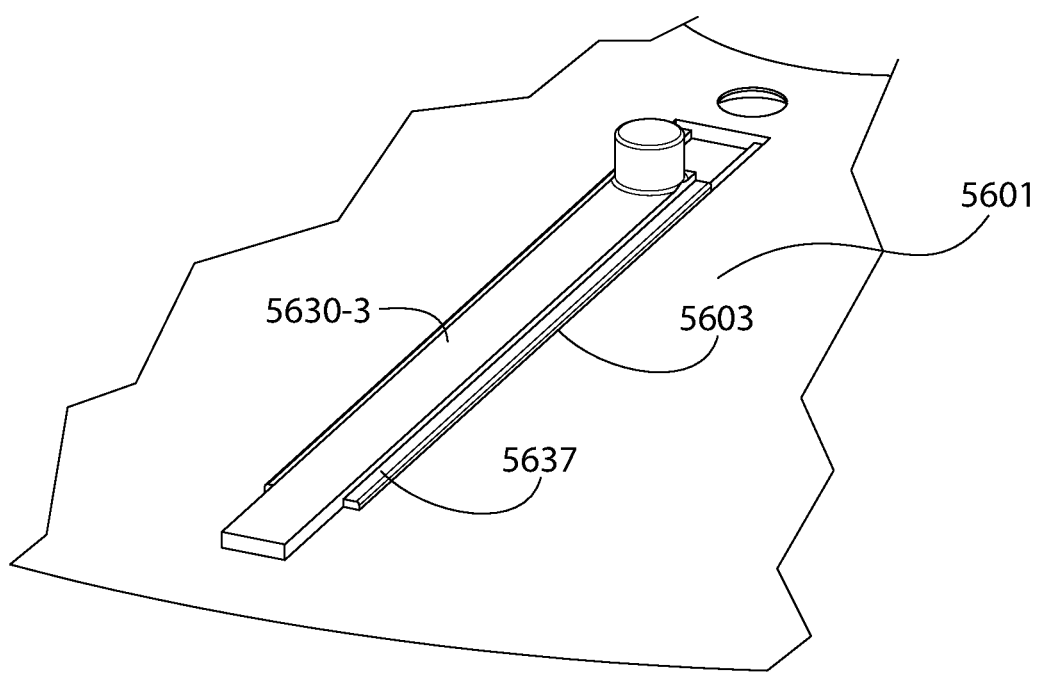
Figure 246A:
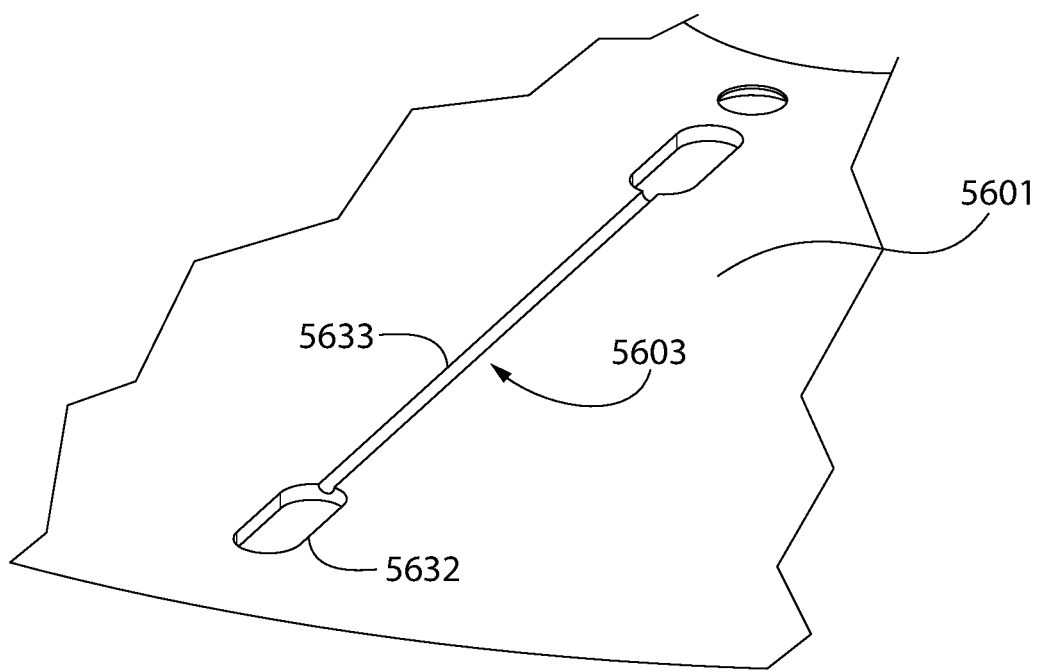
Figure 246B:
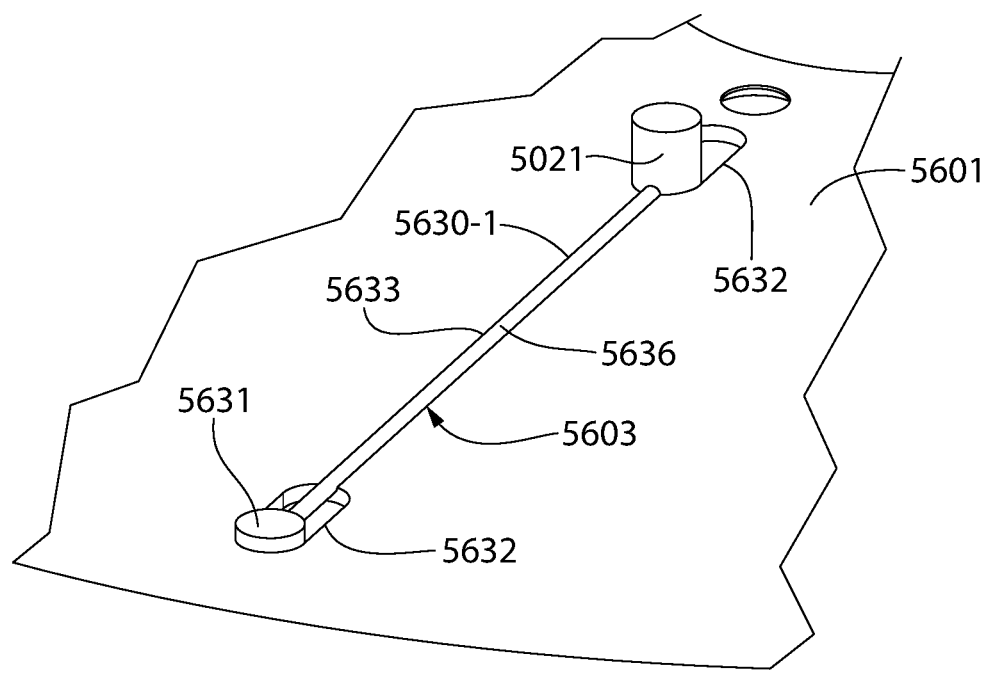
Figure 247A:
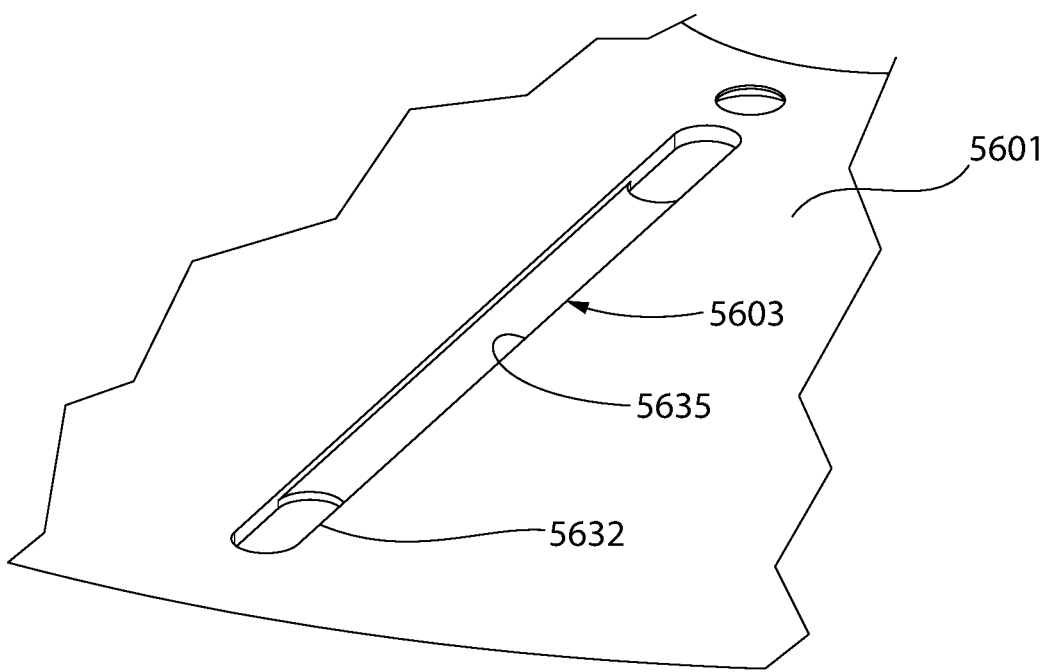
Figure 247B:
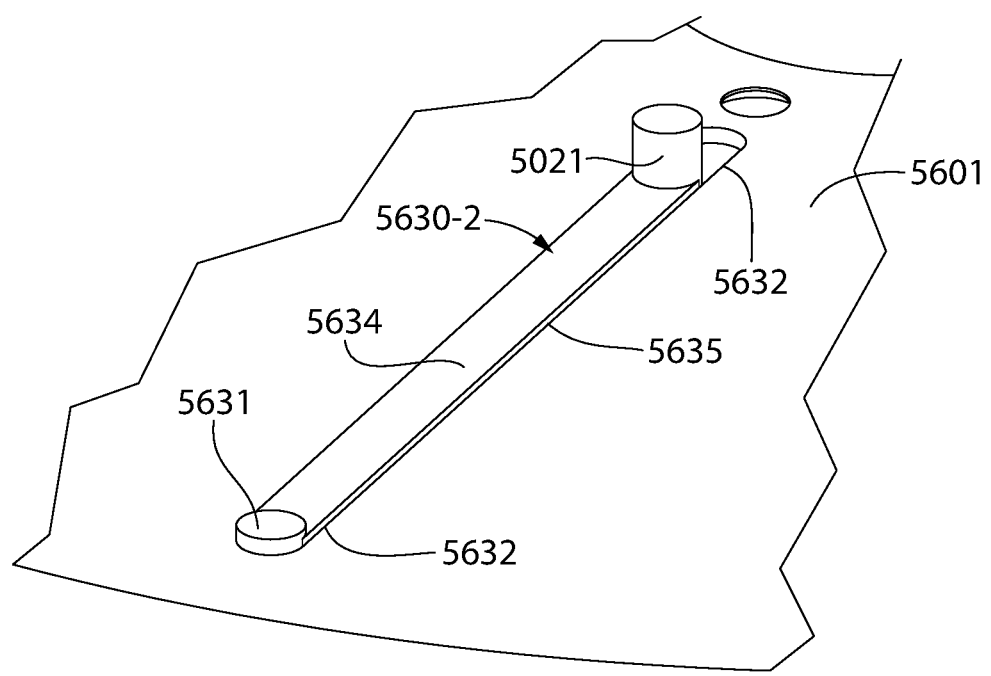
Figures 248A, 248B:
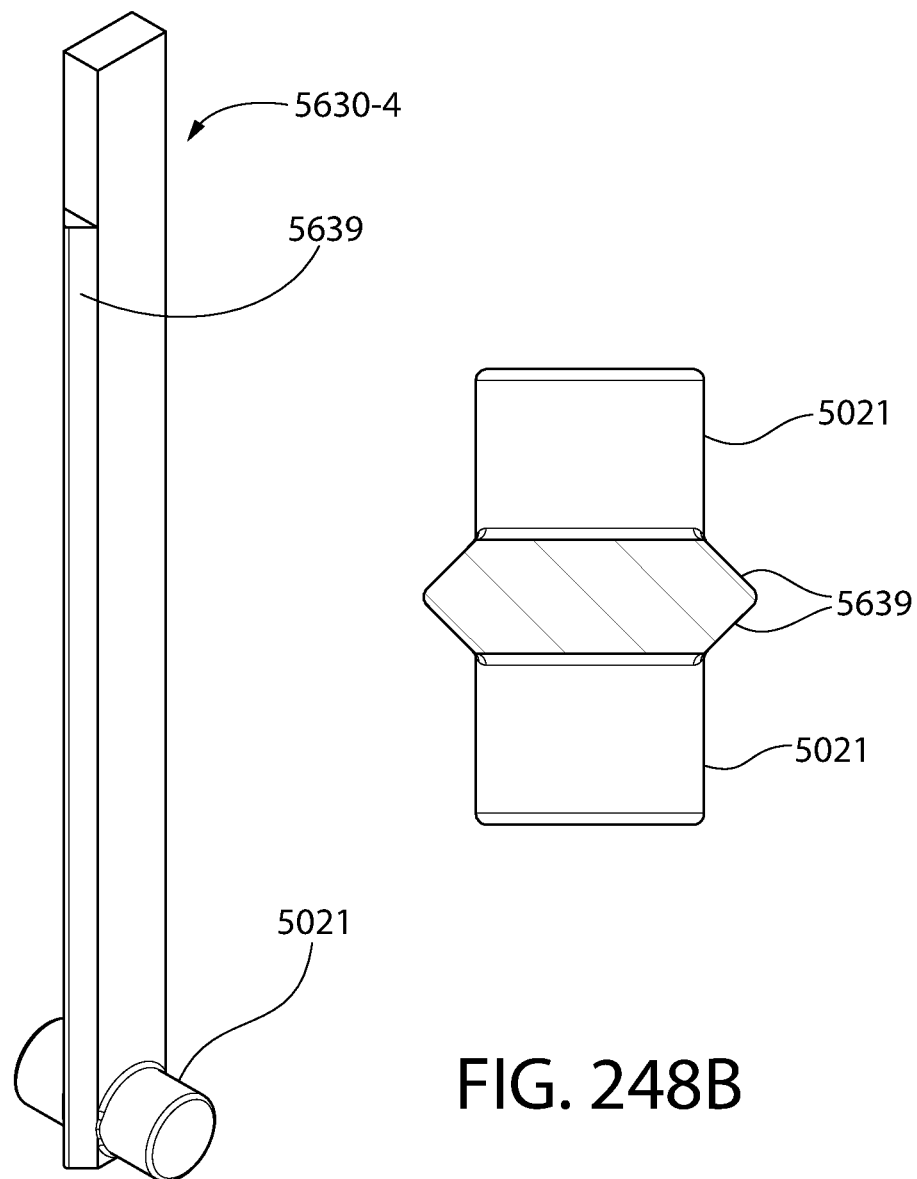
Figures 249A, 249B:
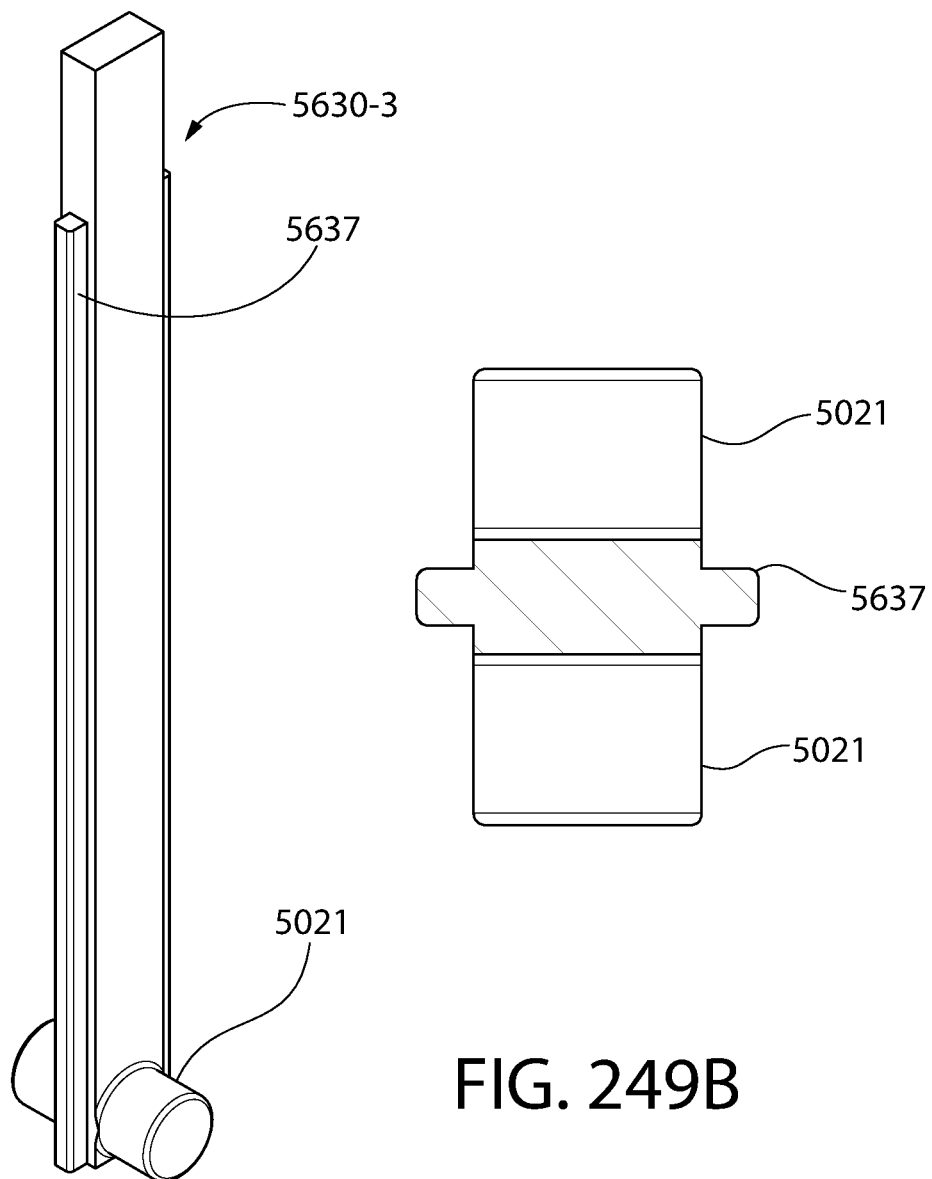
Figures 251A, 251B:
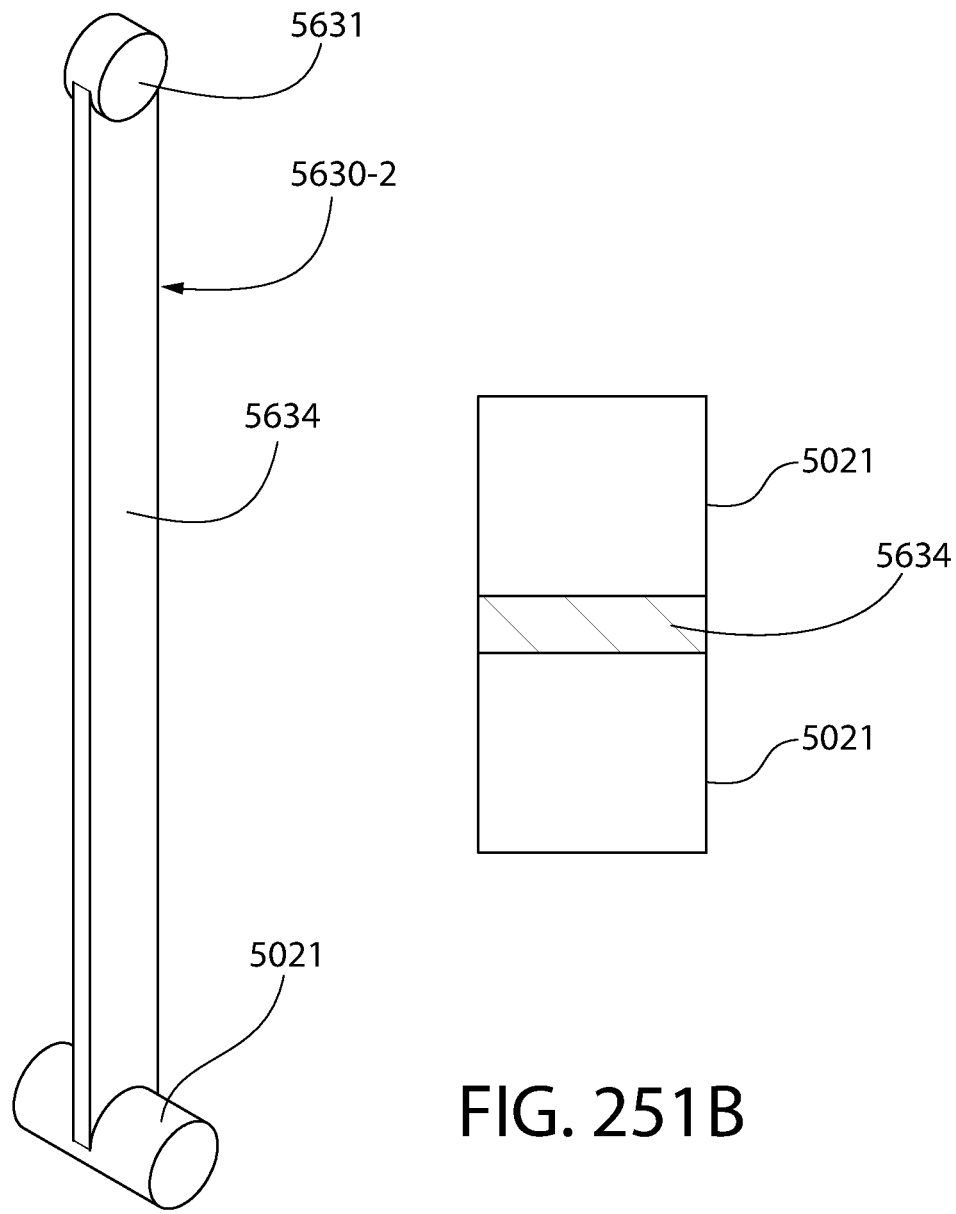
Figure 252:
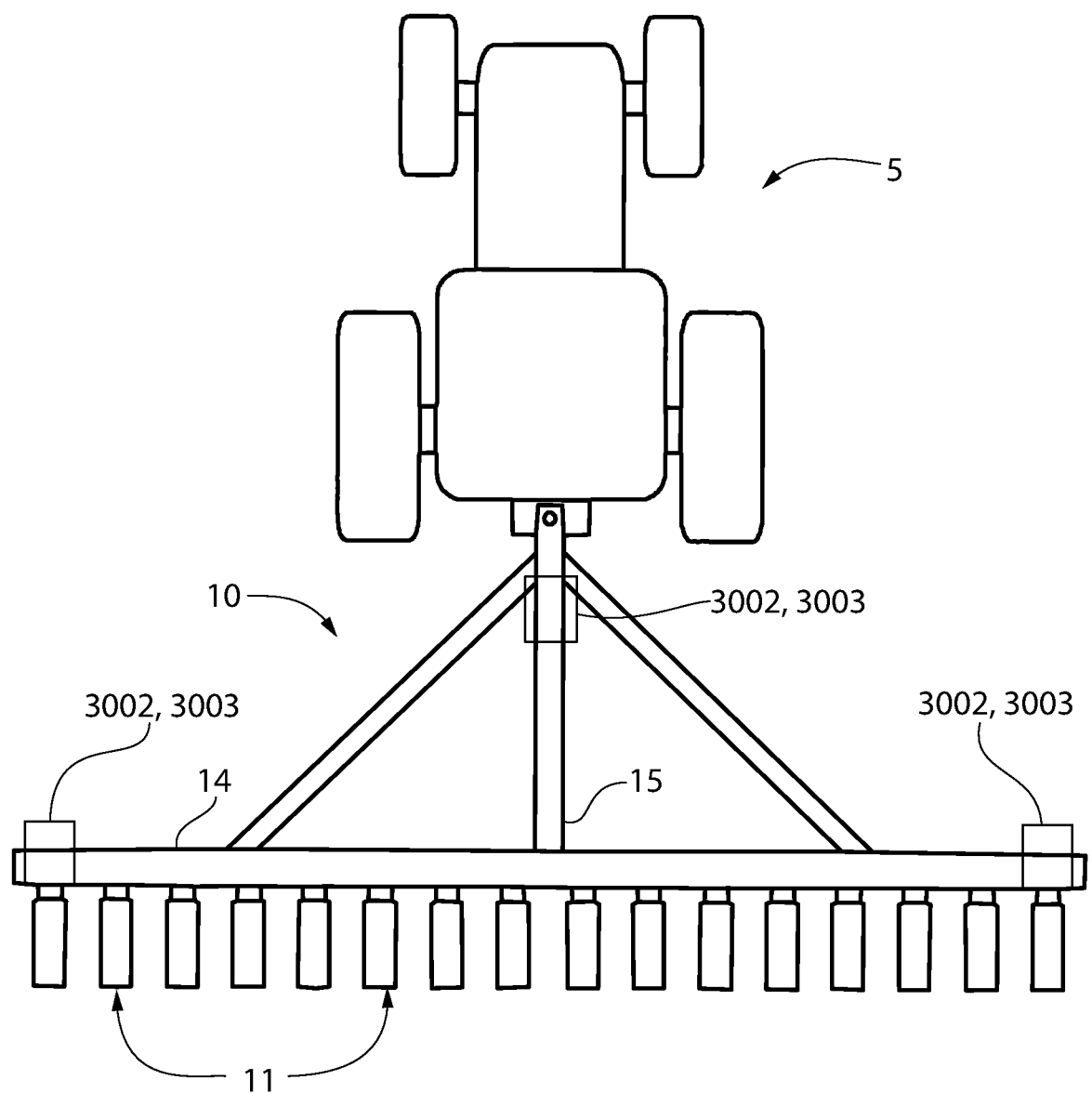
Figure 253:
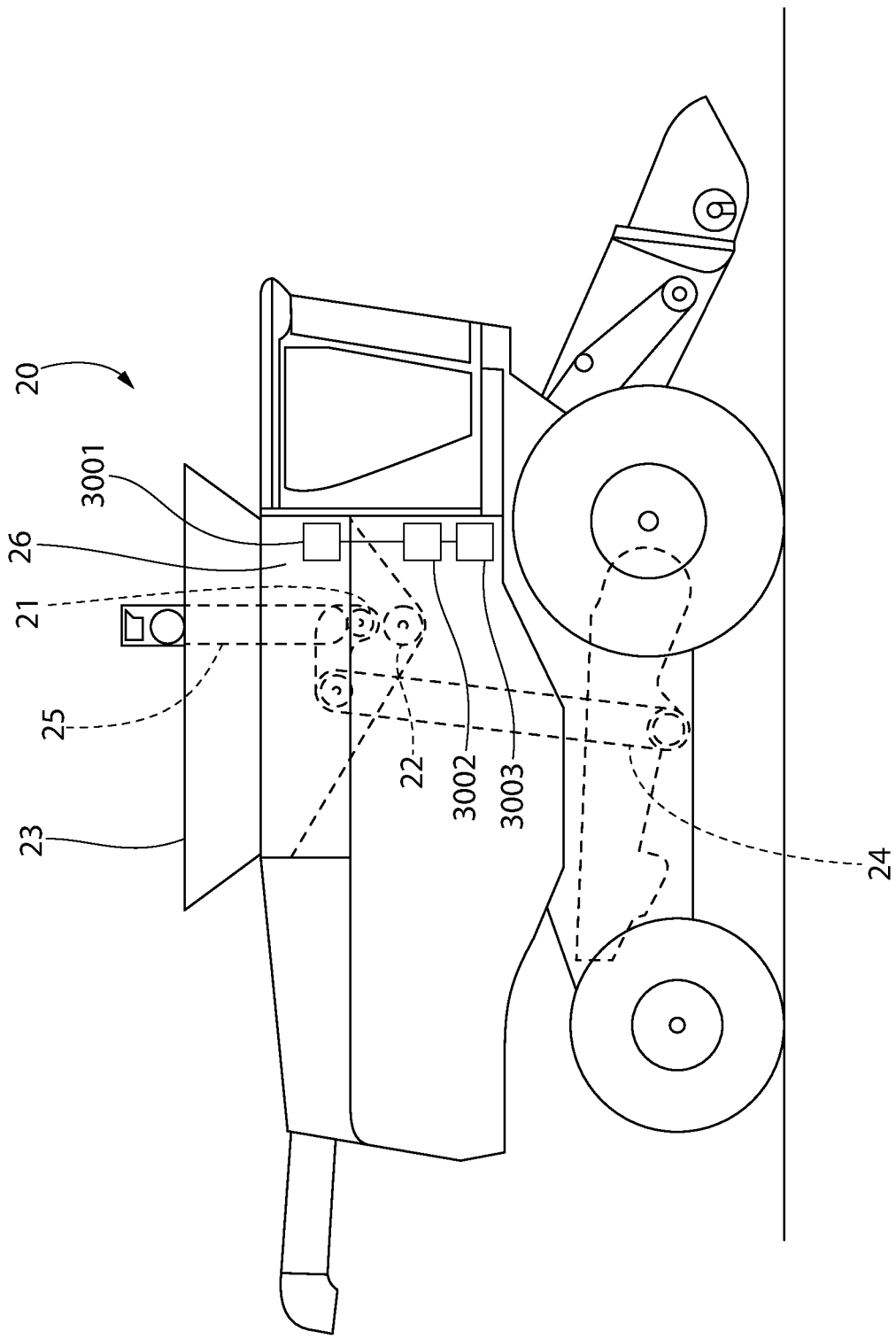
Figure 254:
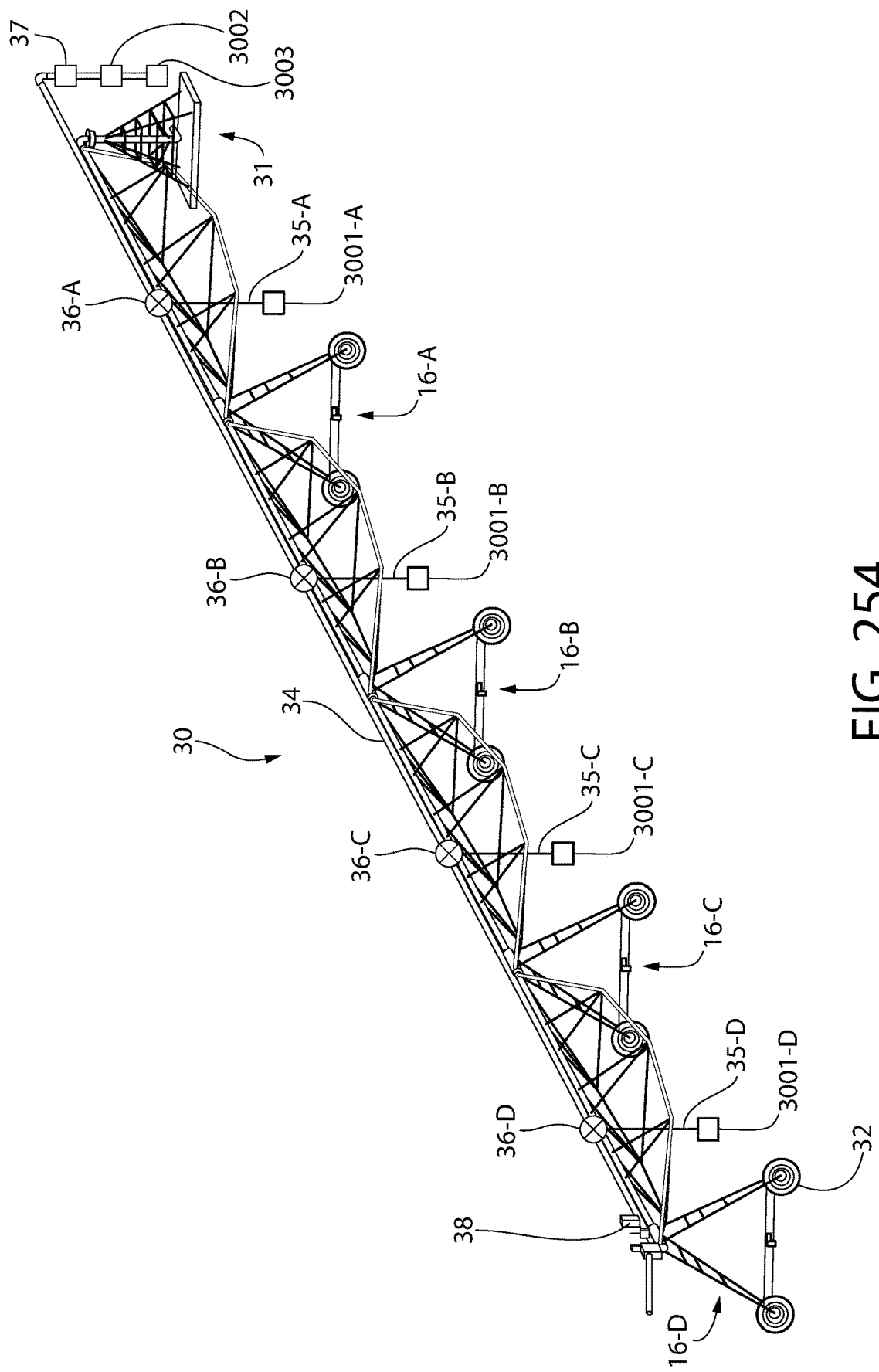
Figure 255:
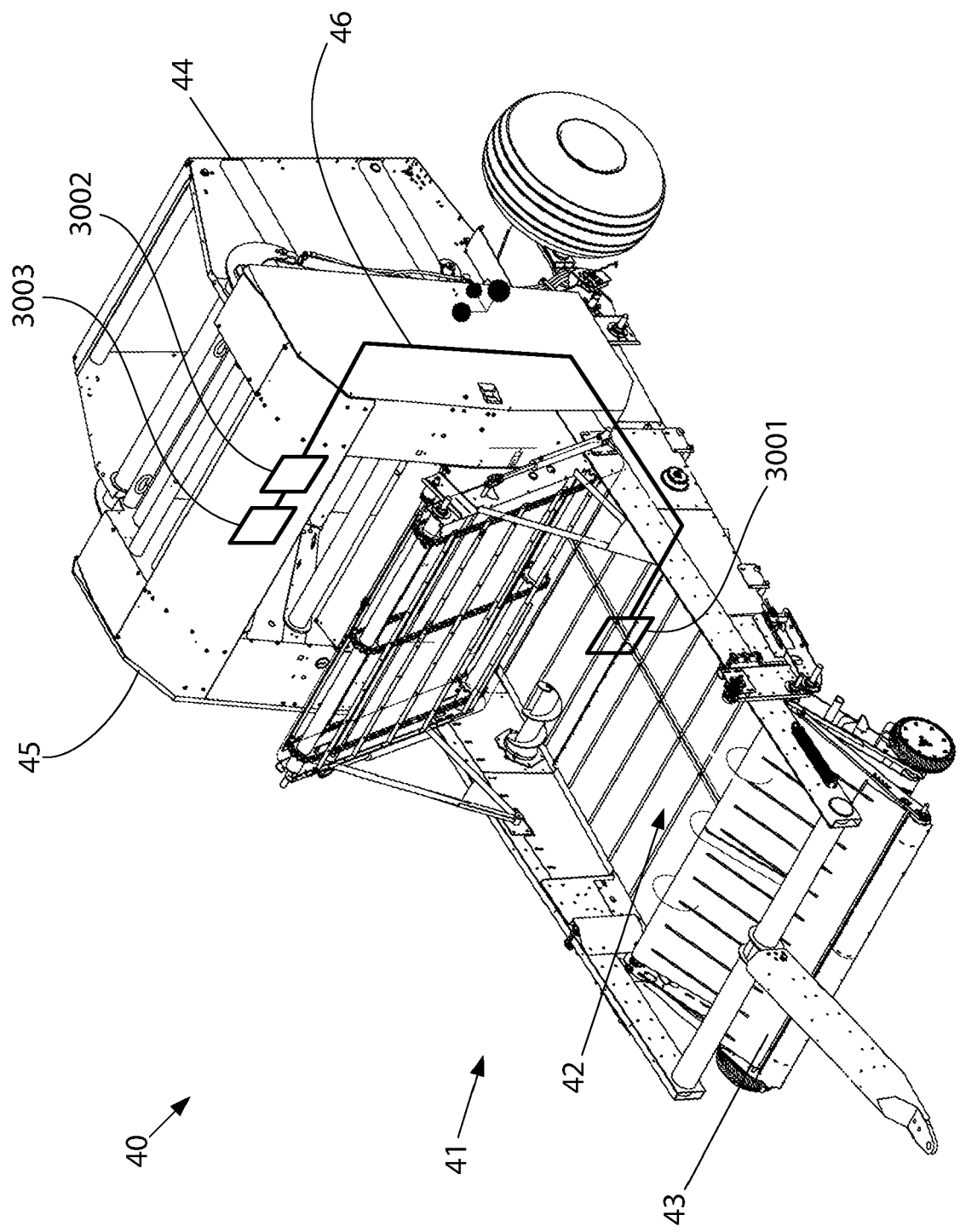
Figure 256:
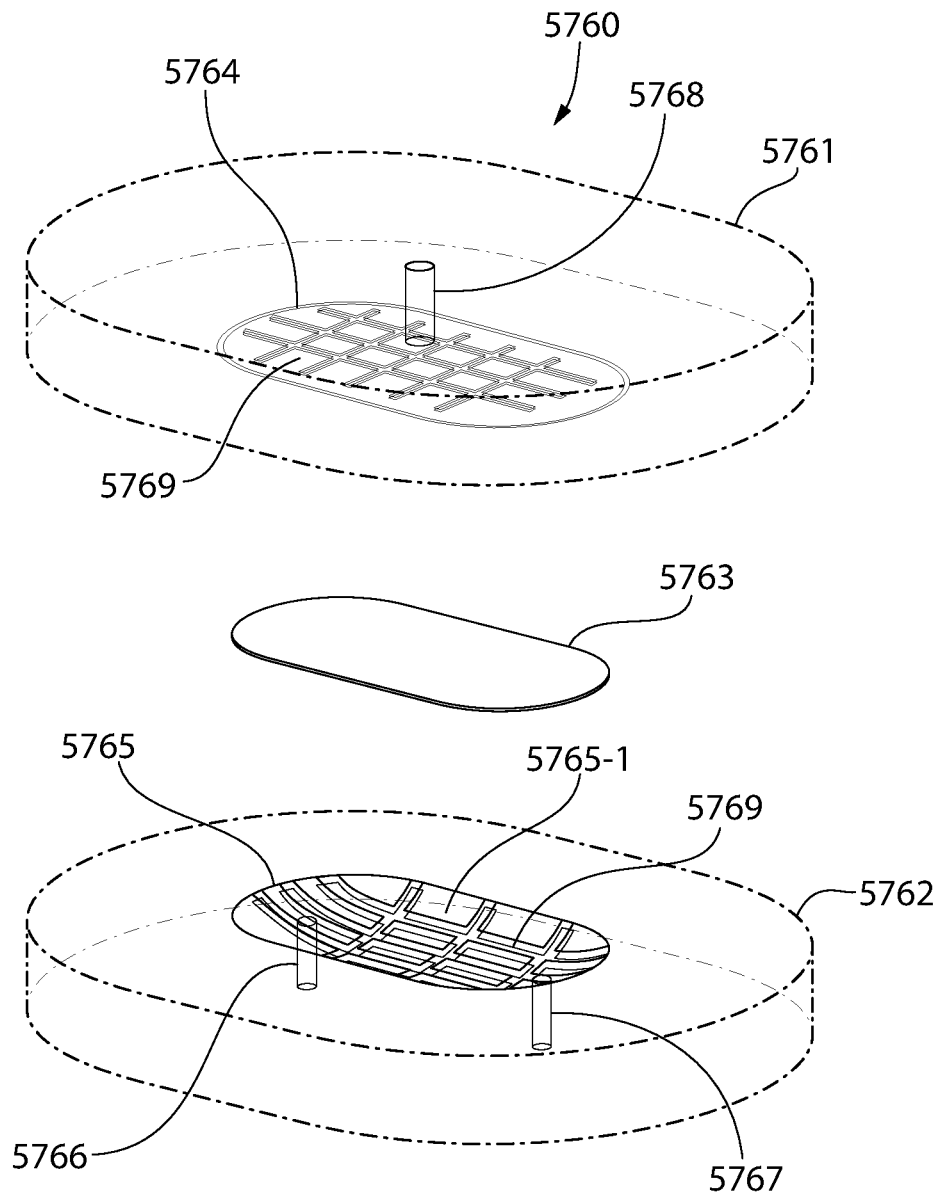
Figure 257:
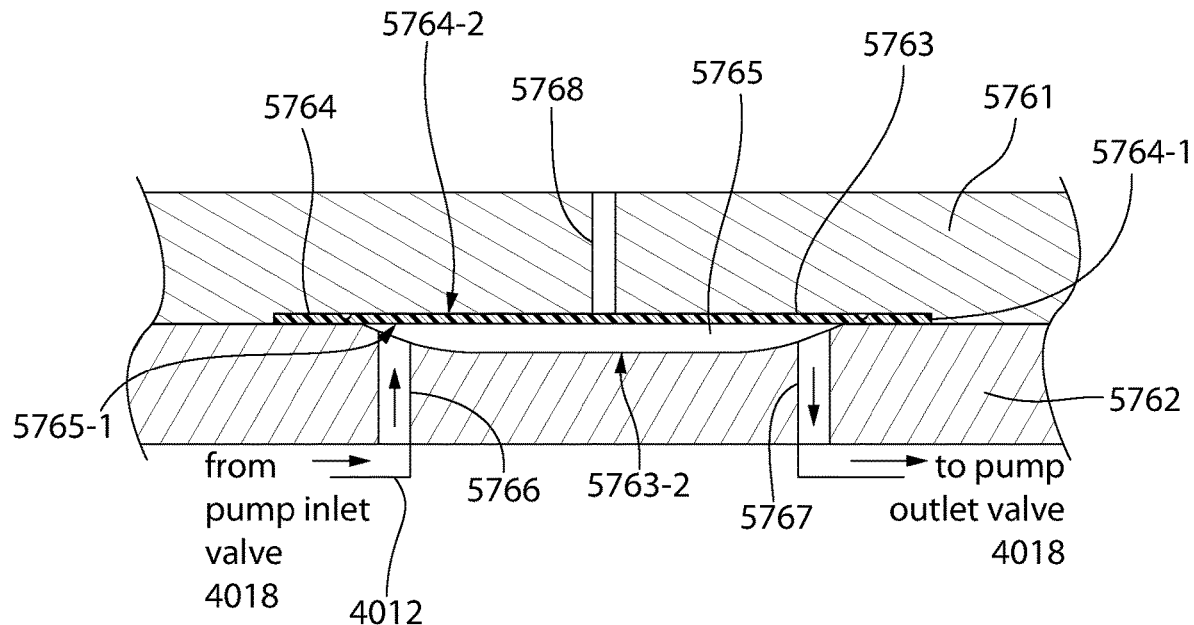
Figure 258:
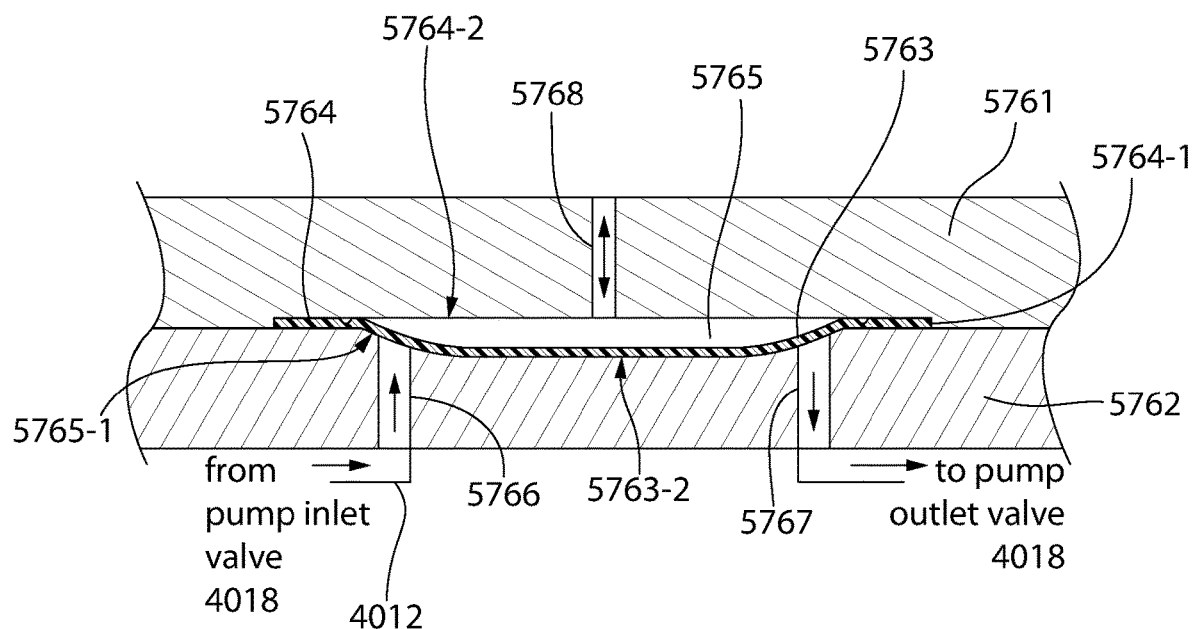
Figure 259:
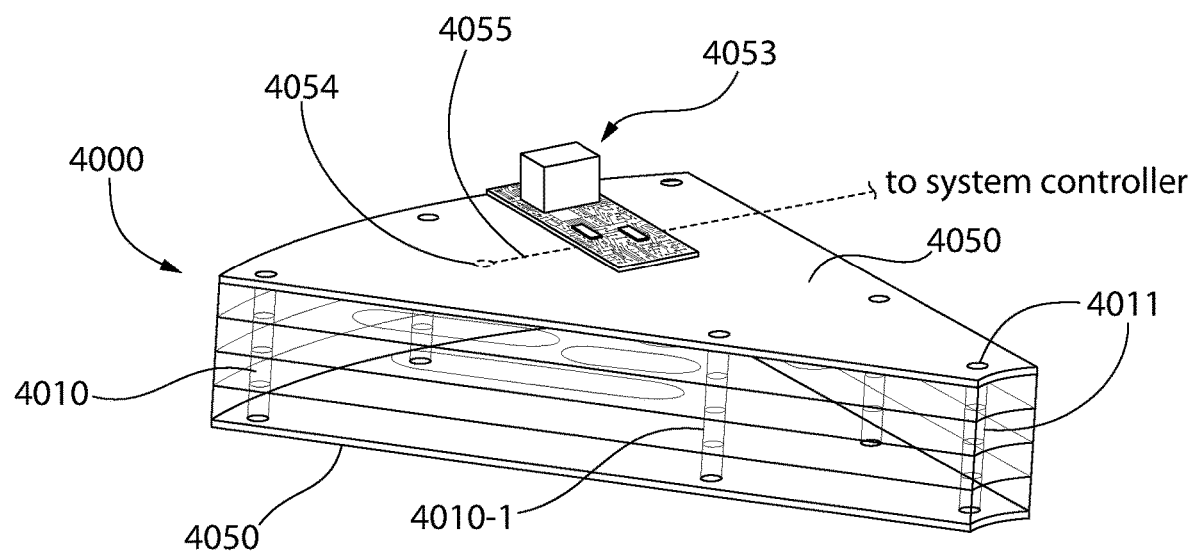
Figure 260:
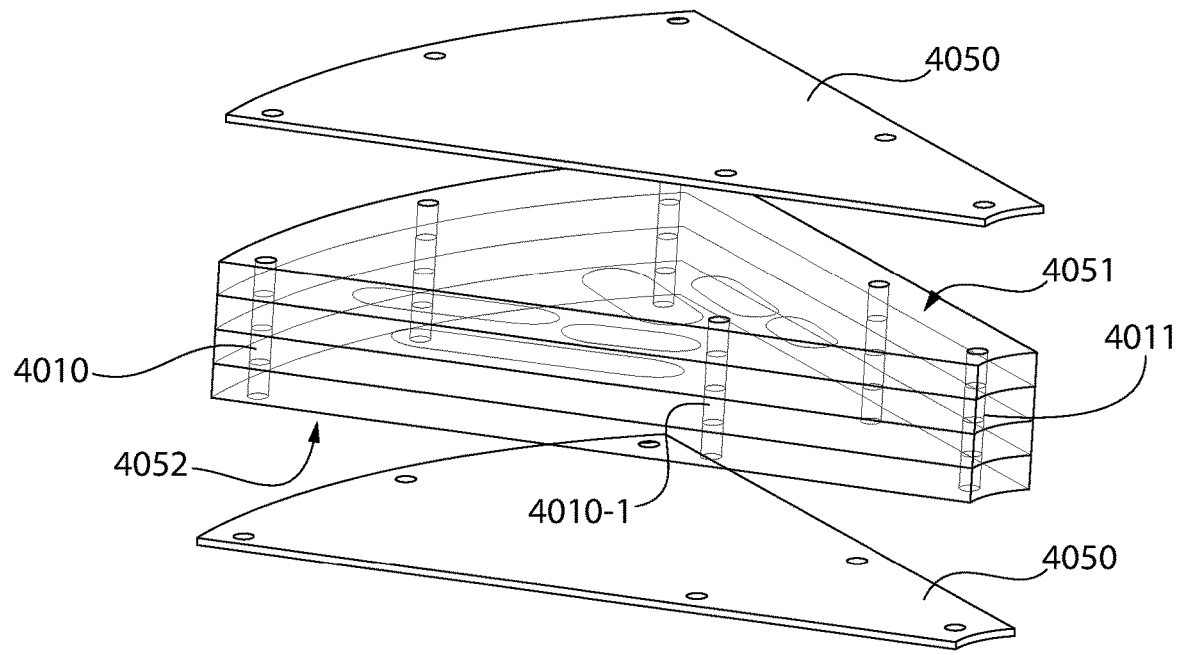
Figure 261:
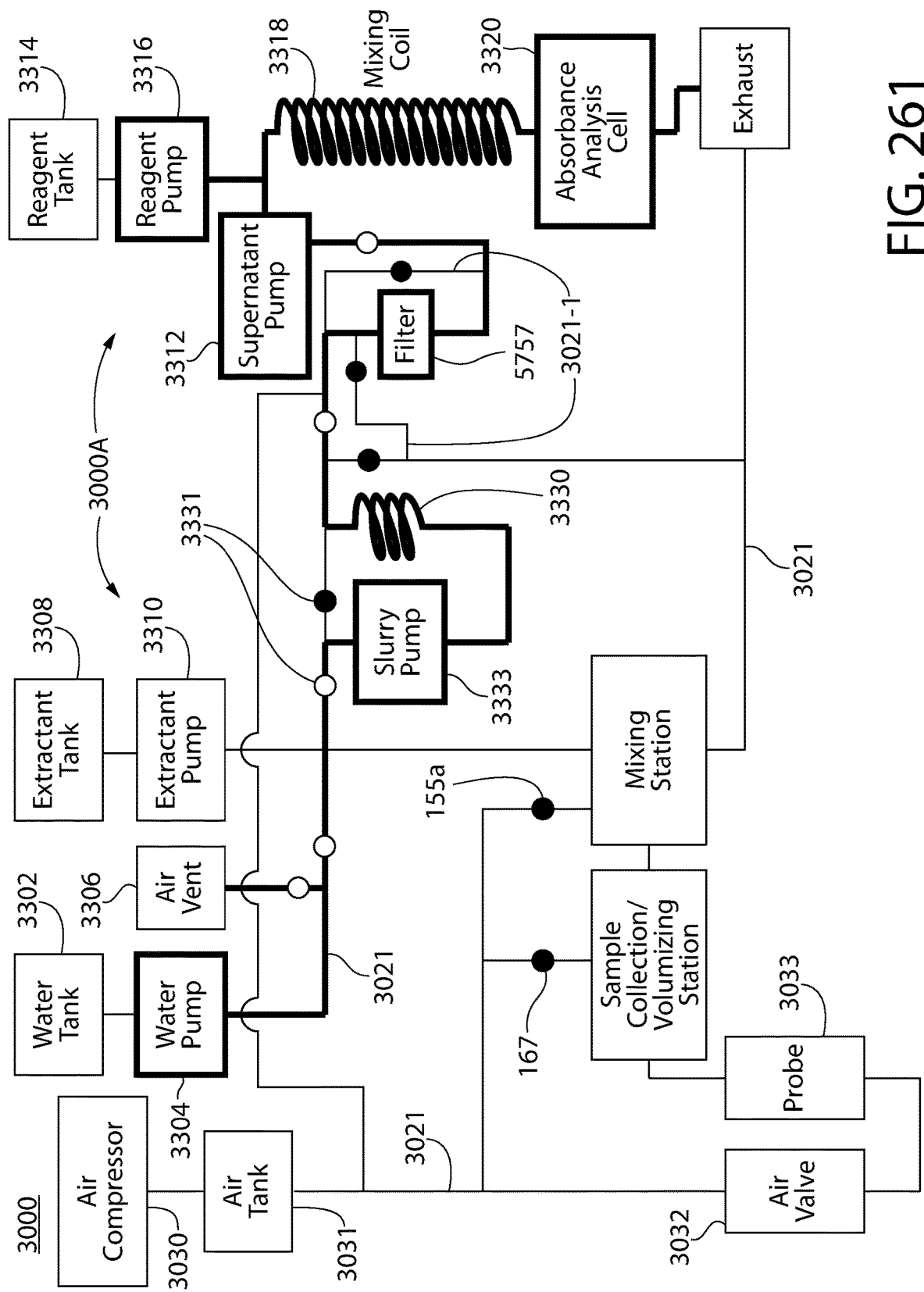
Figure 262:
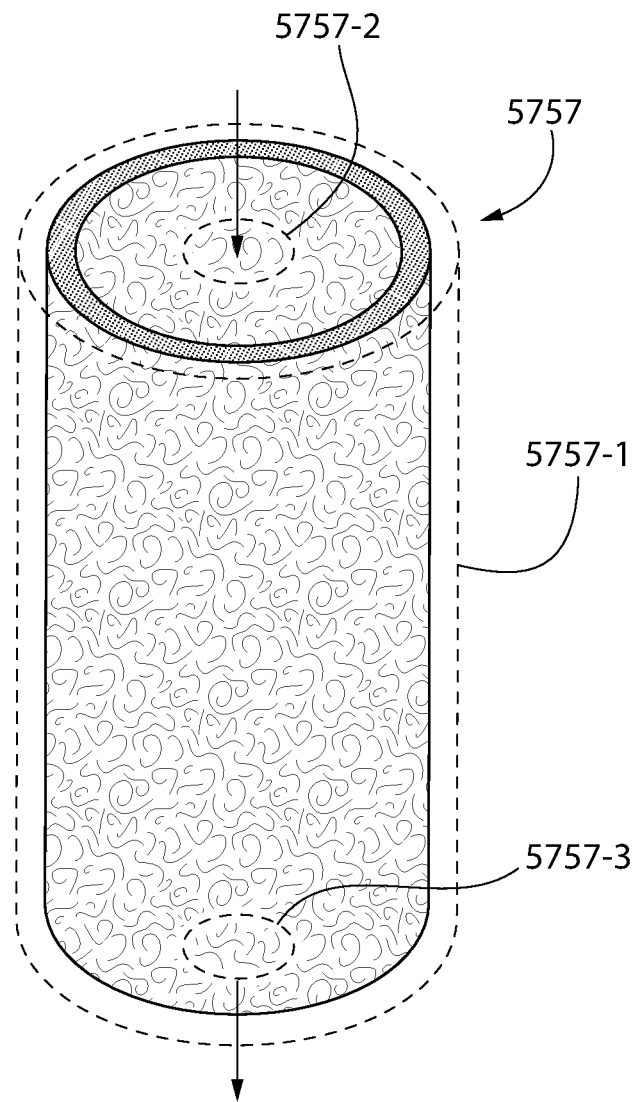
Figure 263:
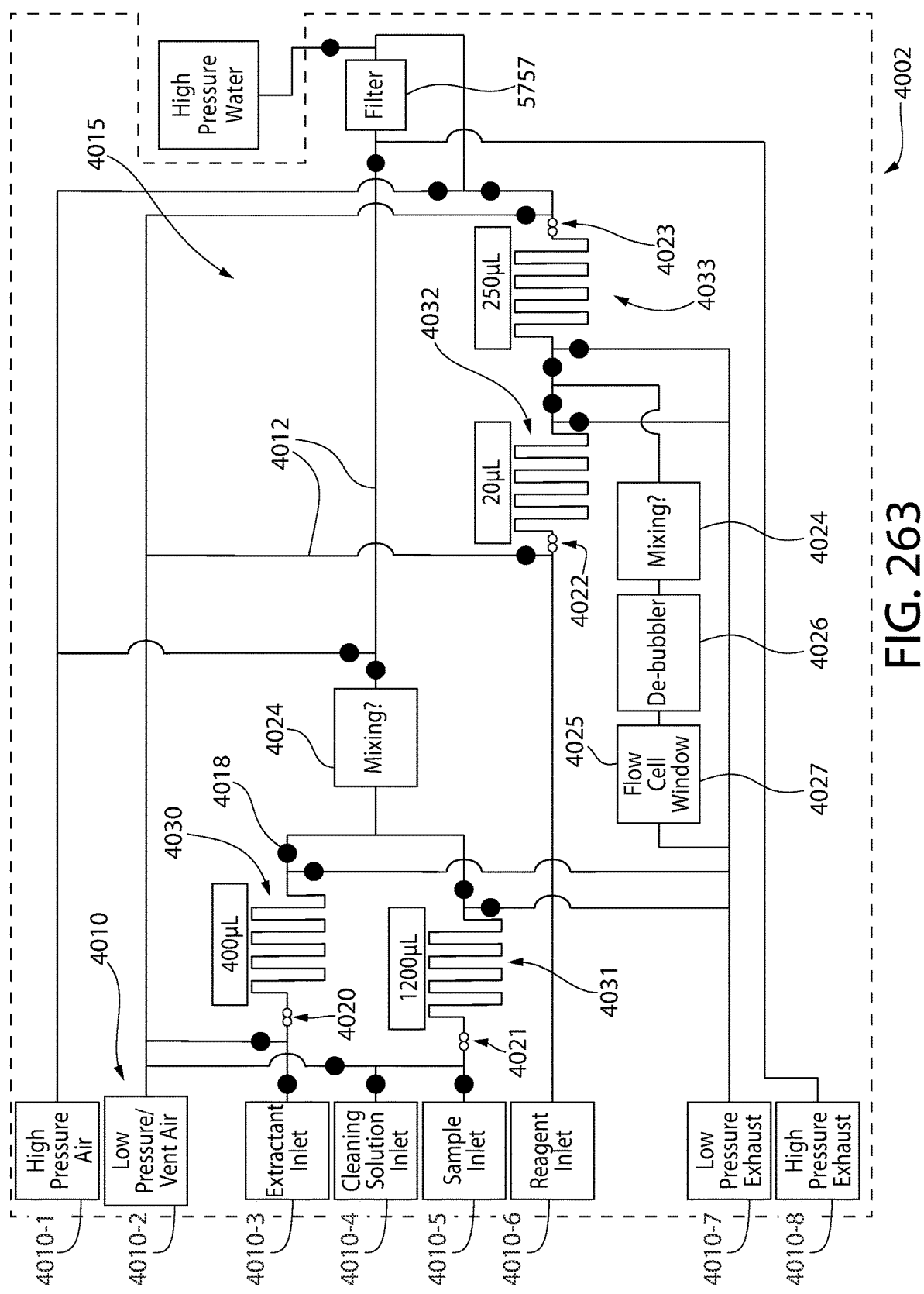
Figure 264:
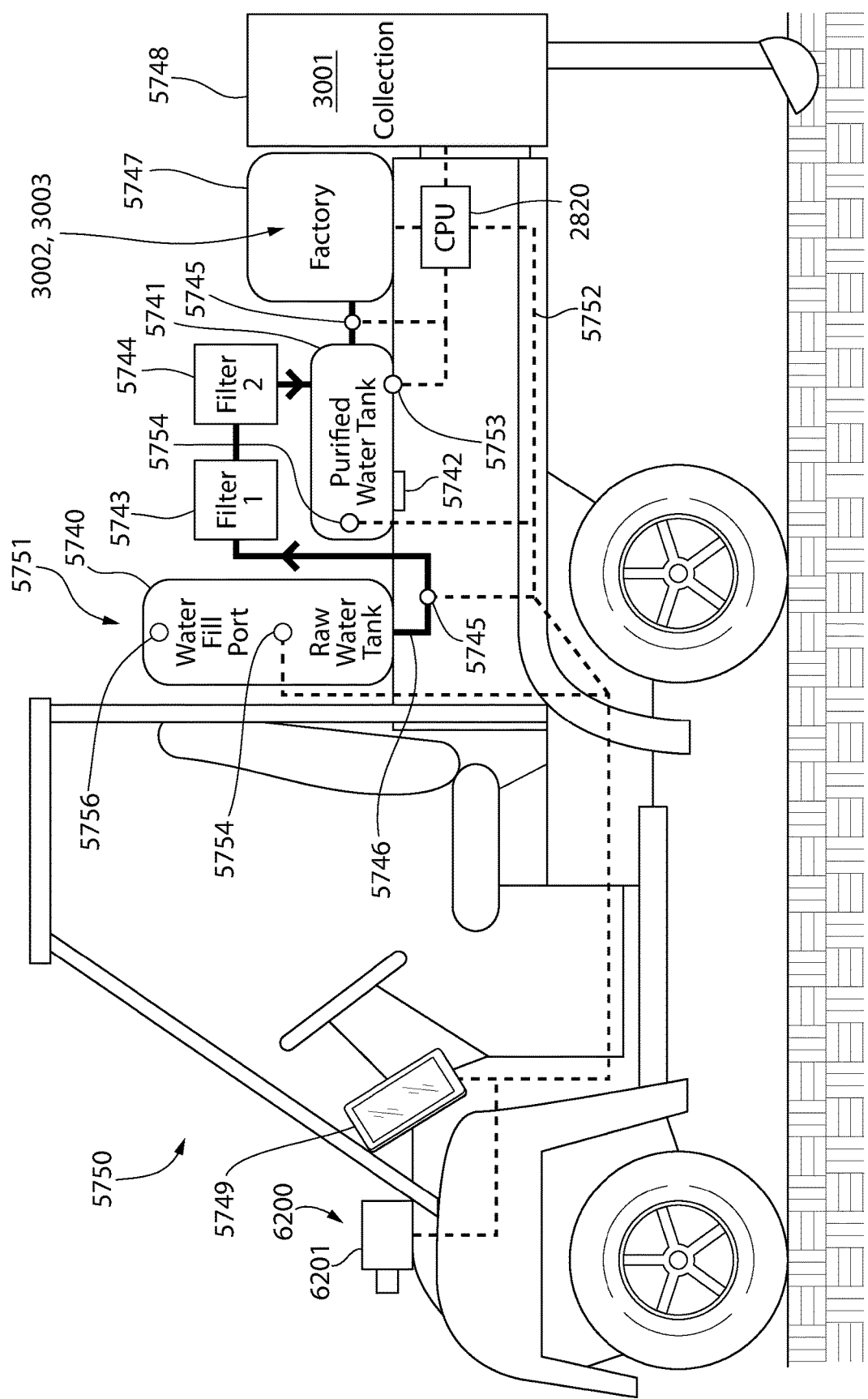
Figure 265:
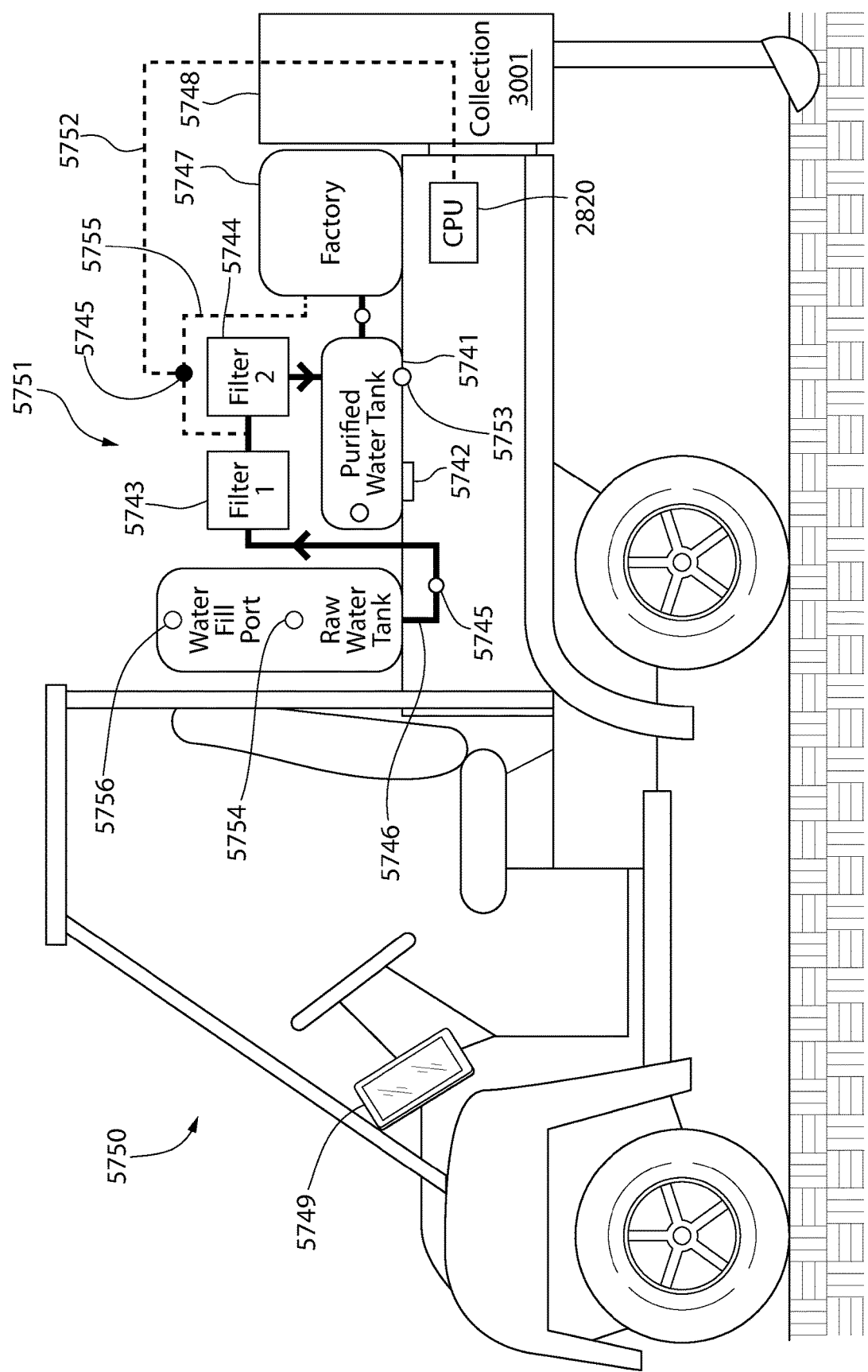
Figure 266:
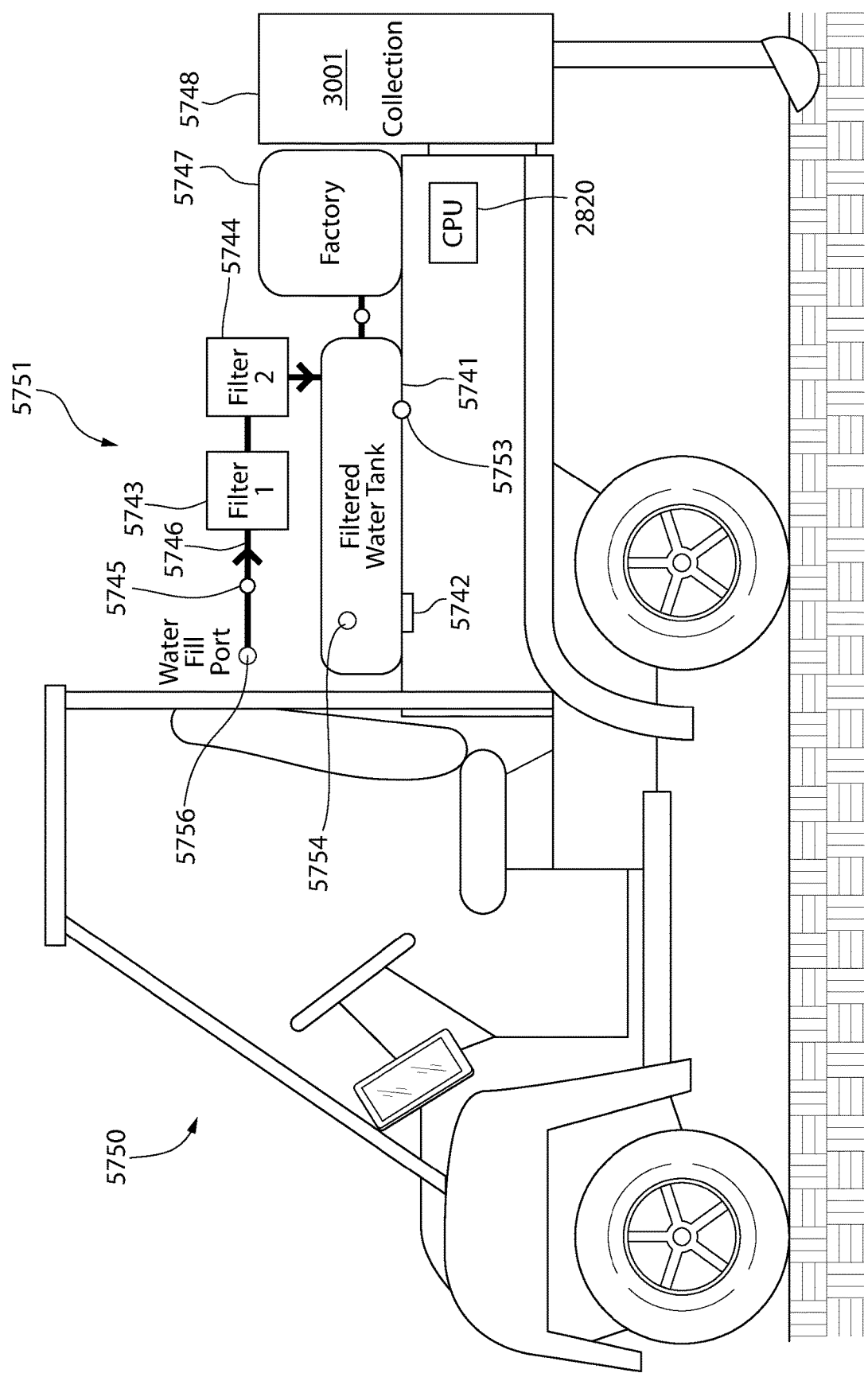
Figure 267:
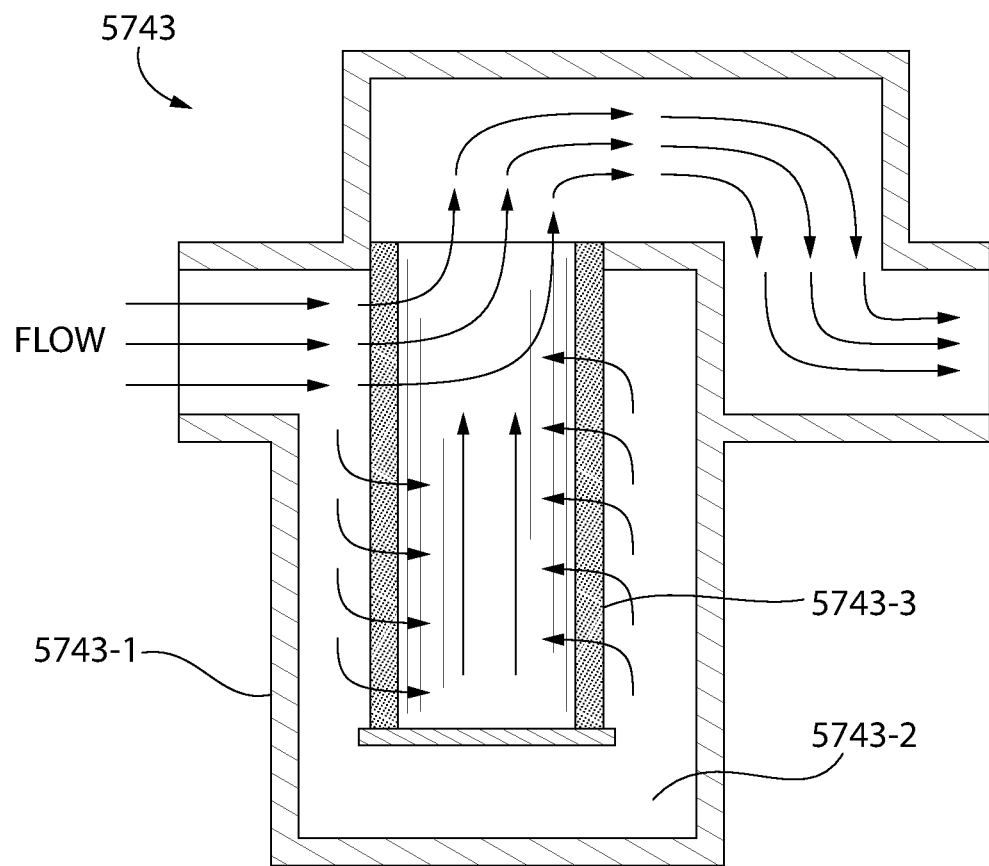
Figure 268:
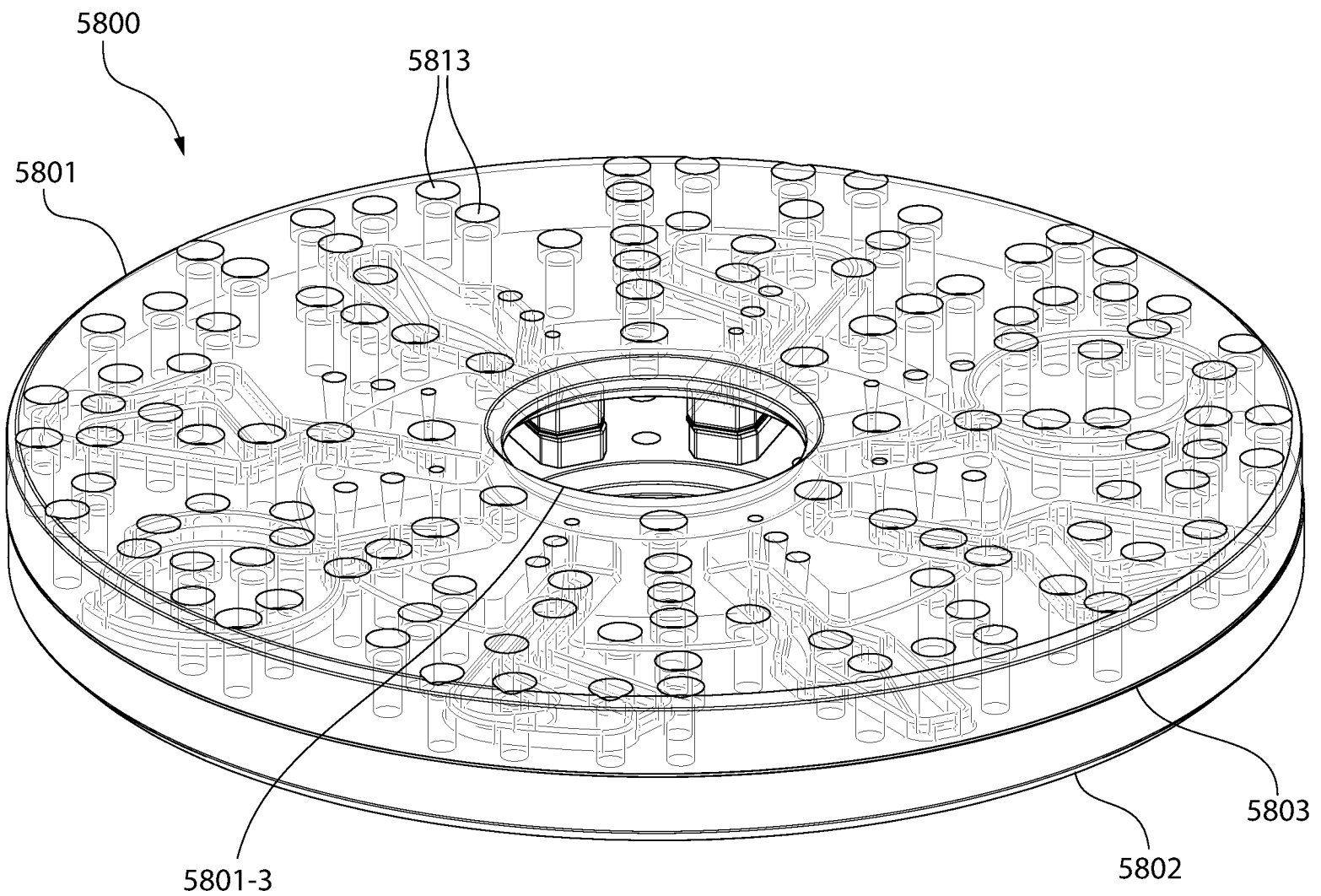
Figure 269:
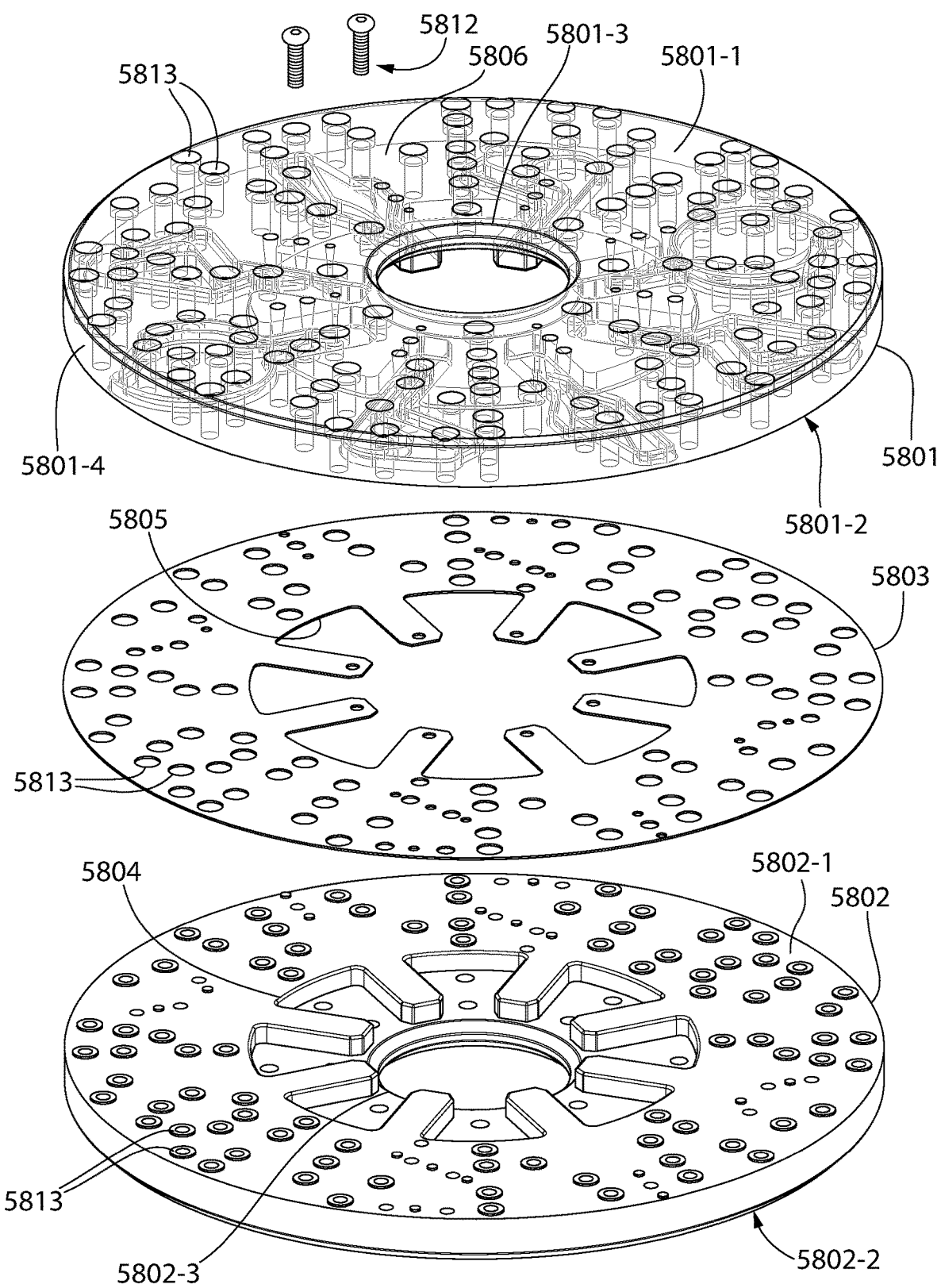
Figure 270:
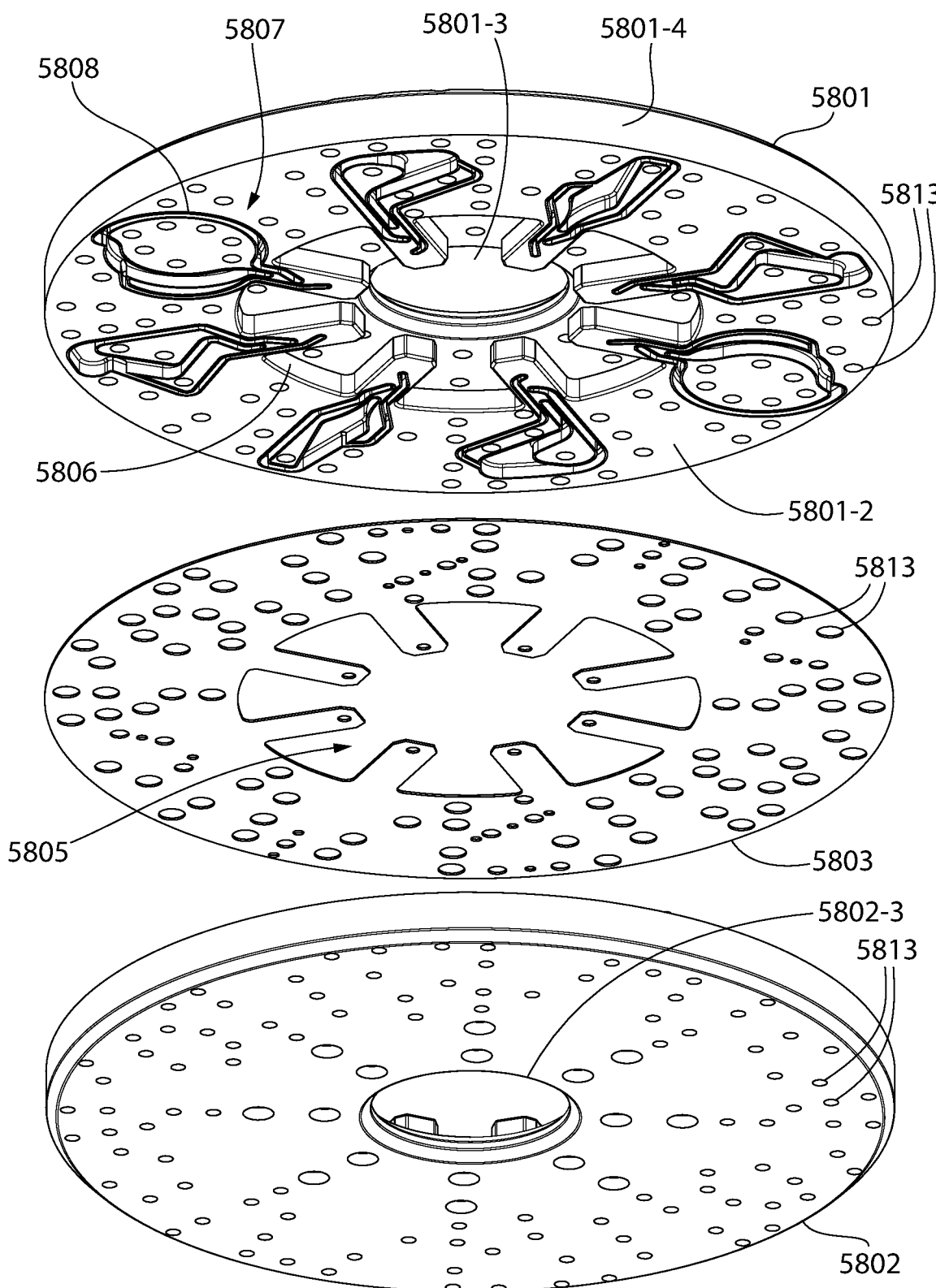
Figure 271:
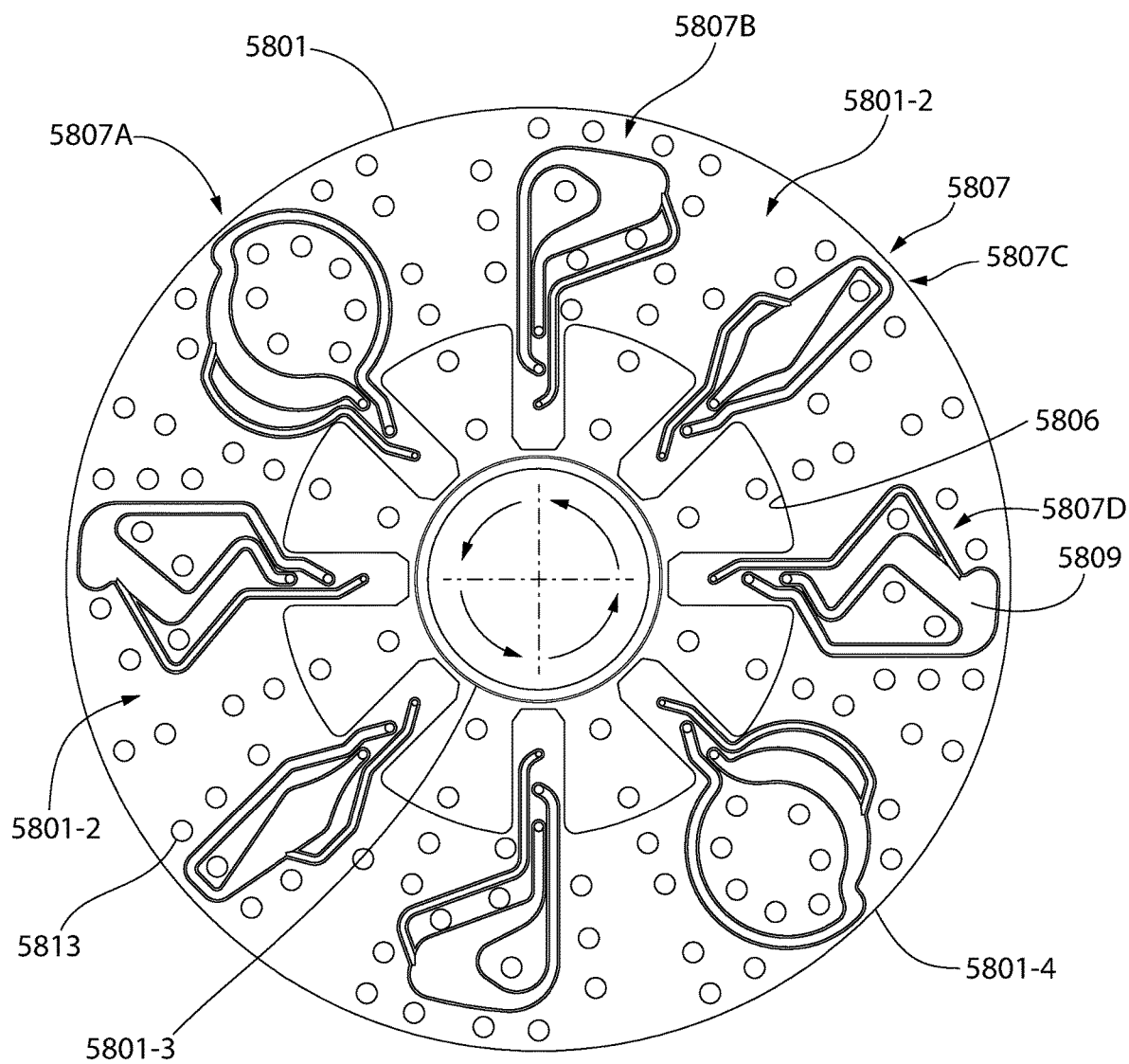
Figure 272:
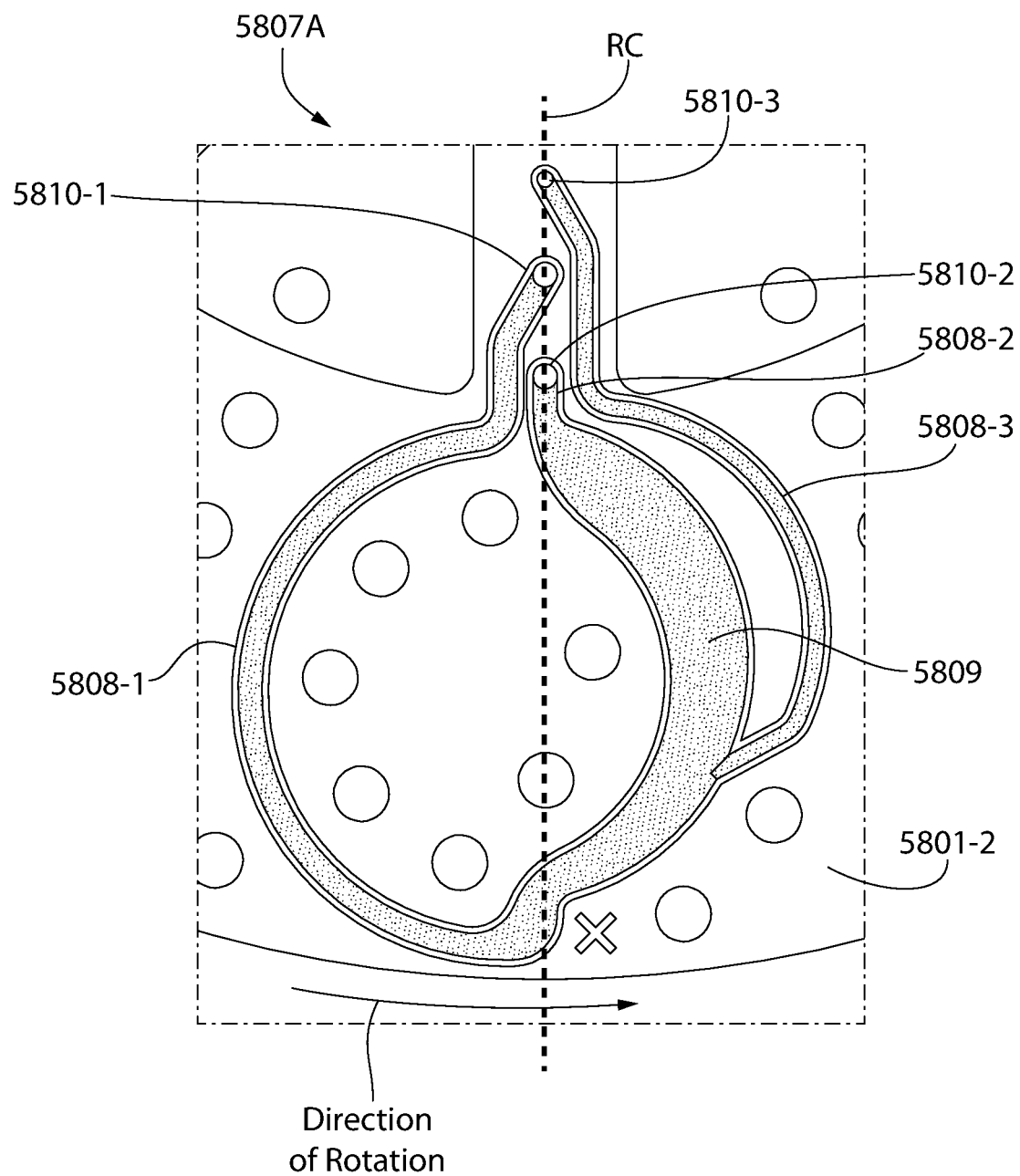
Figure 273:
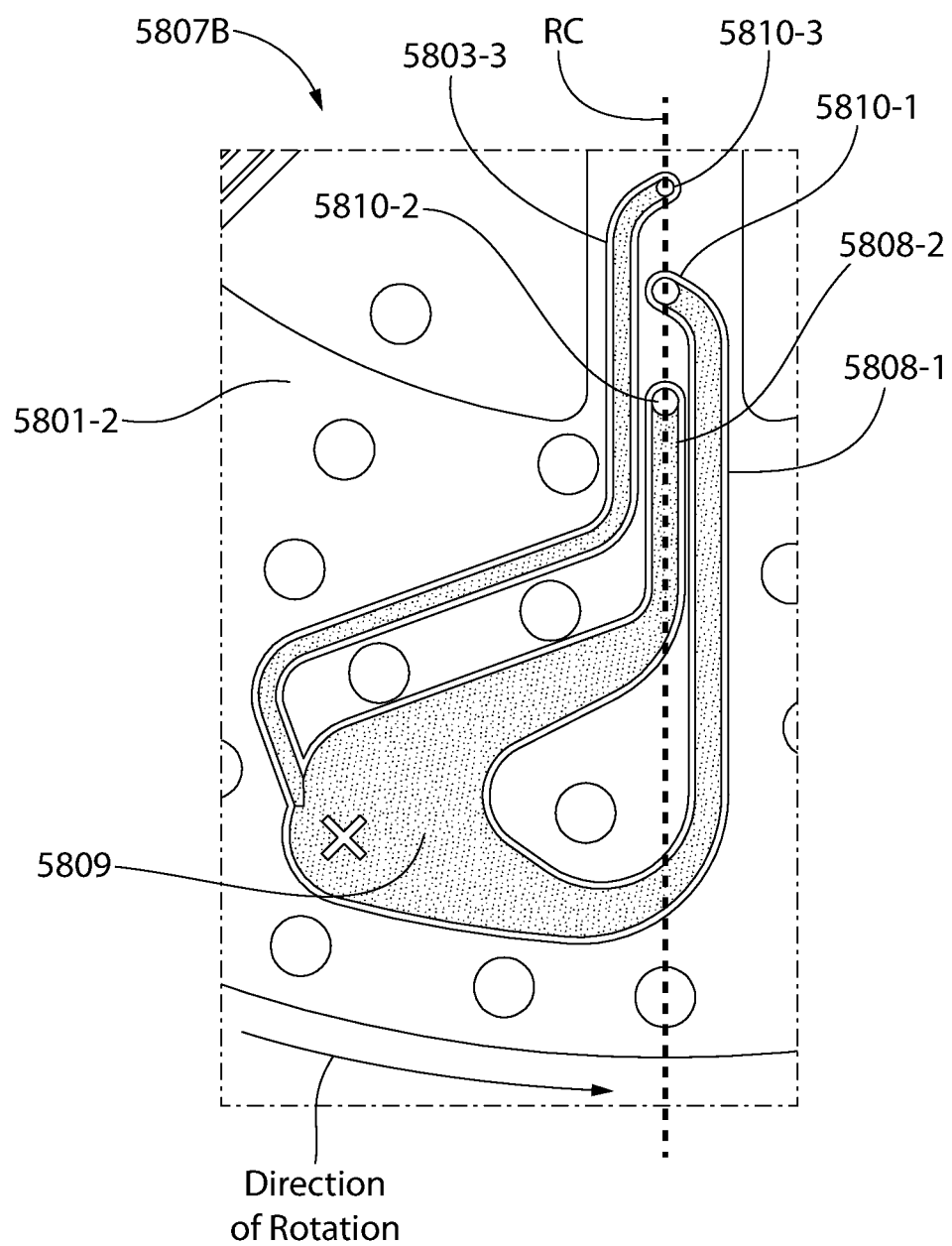
Figure 274:
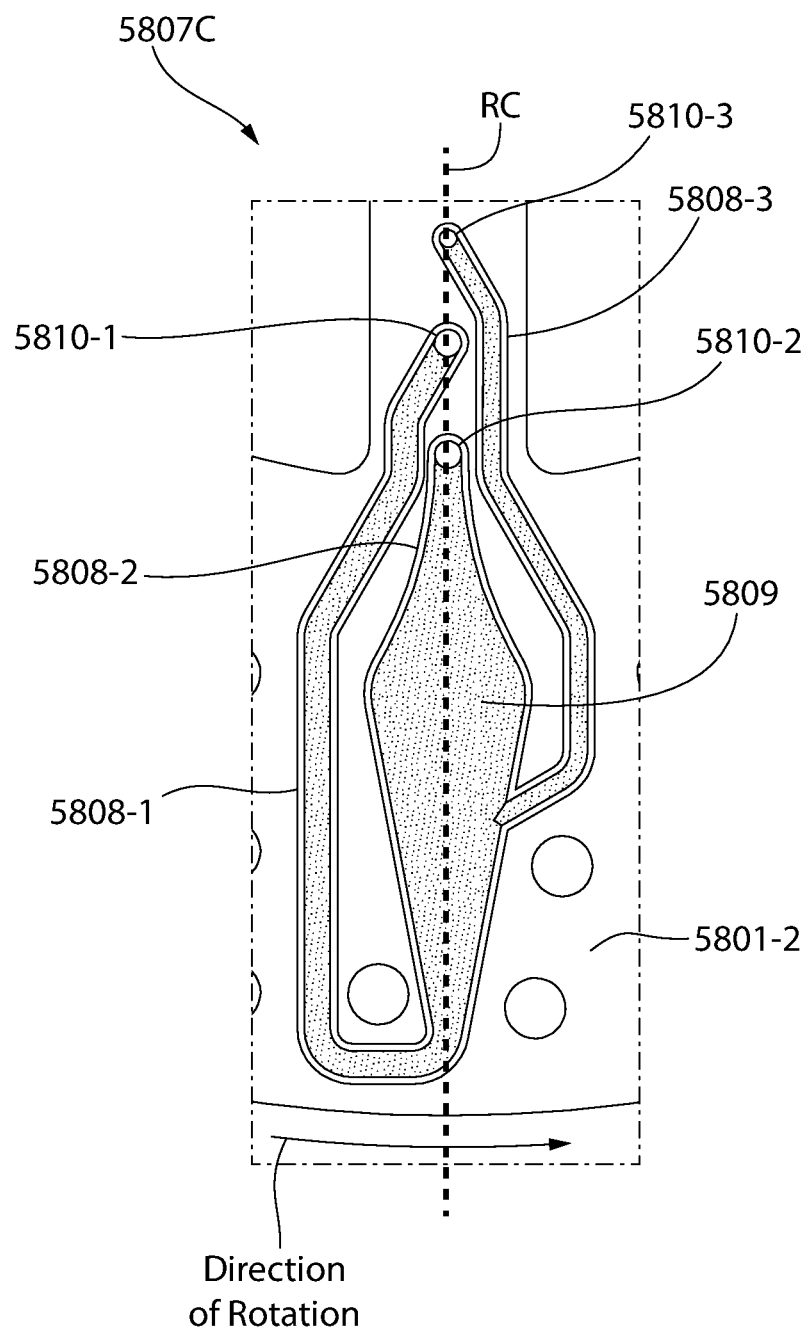
Figure 275:
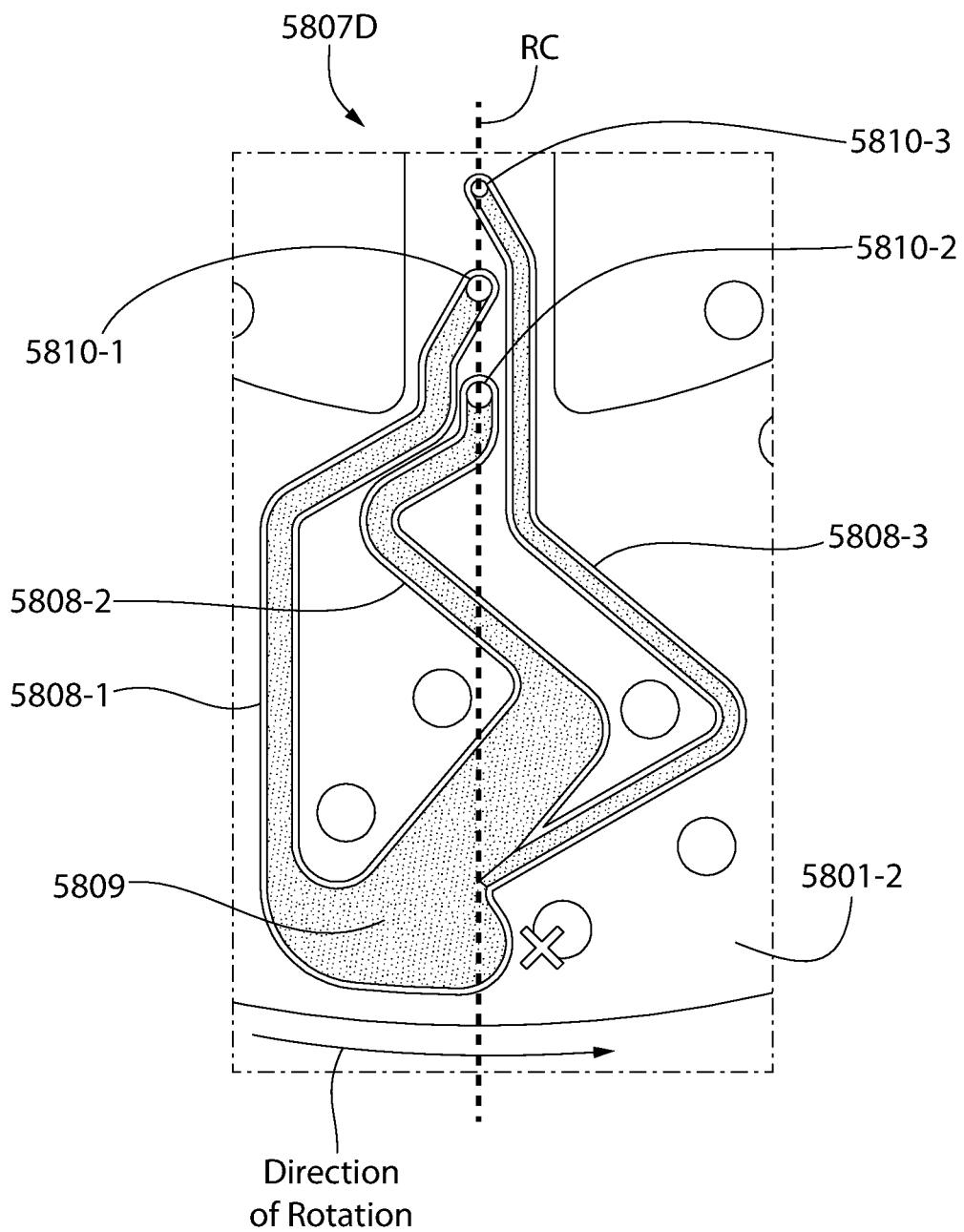
Figure 276:
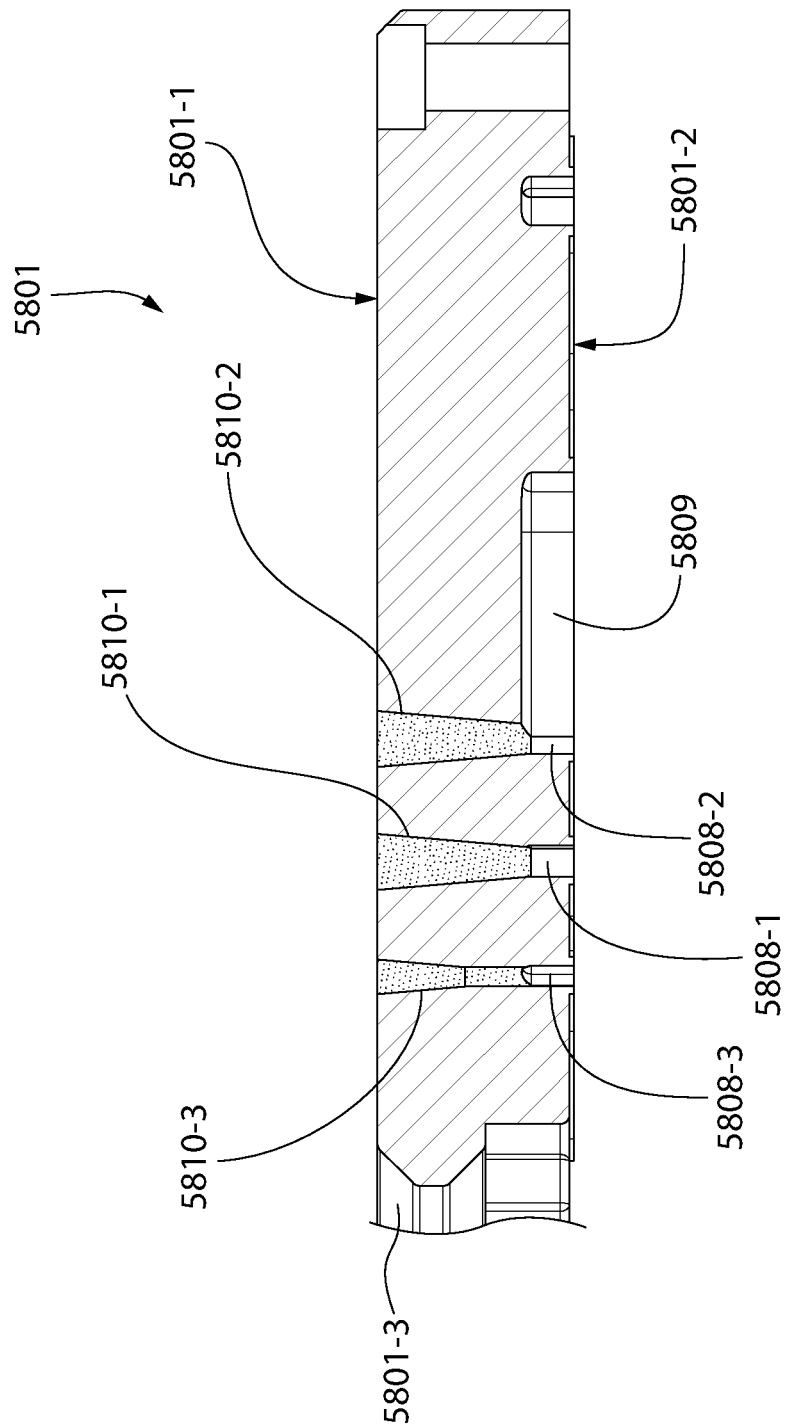
Figure 277:
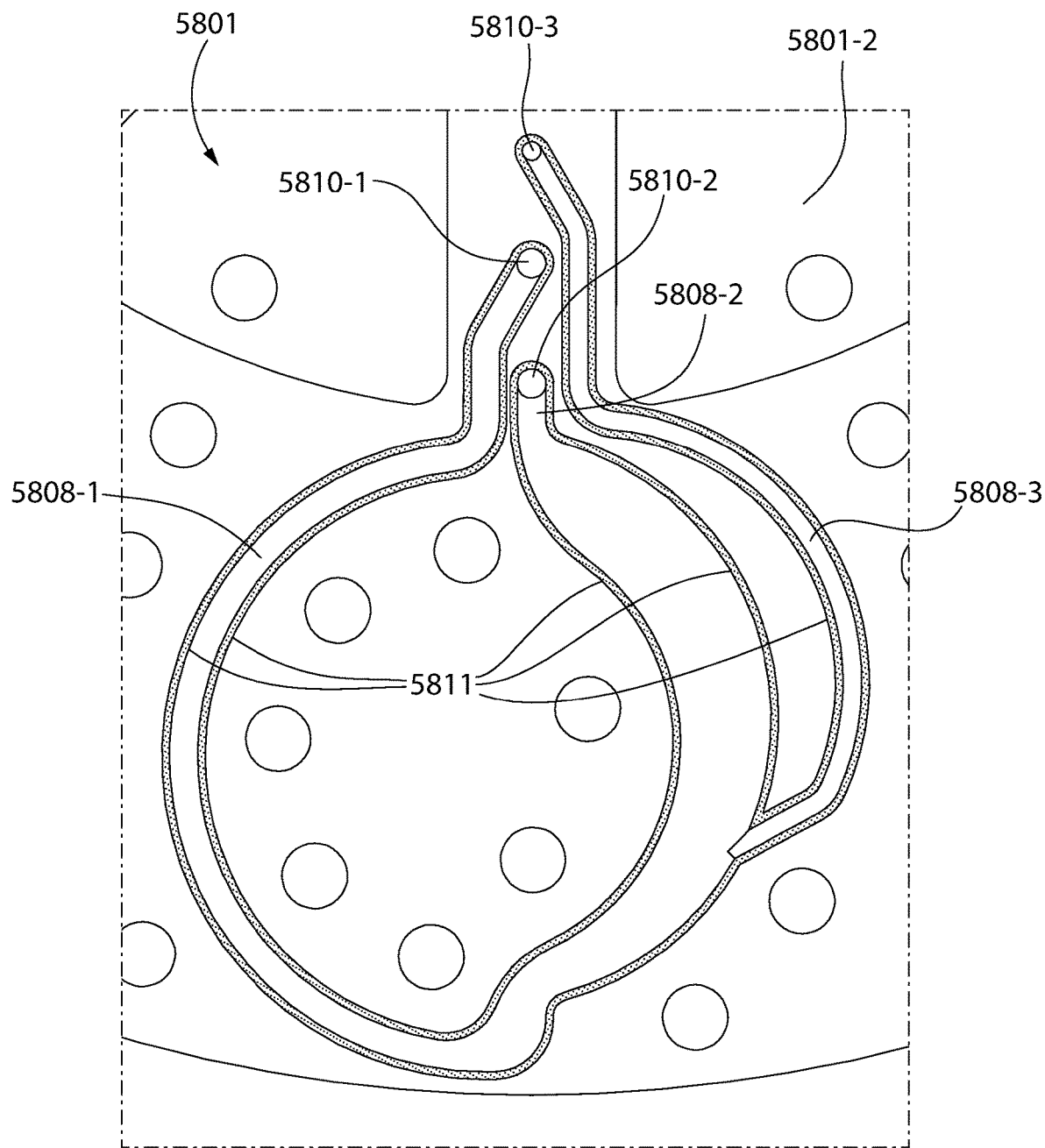
Figure 278:
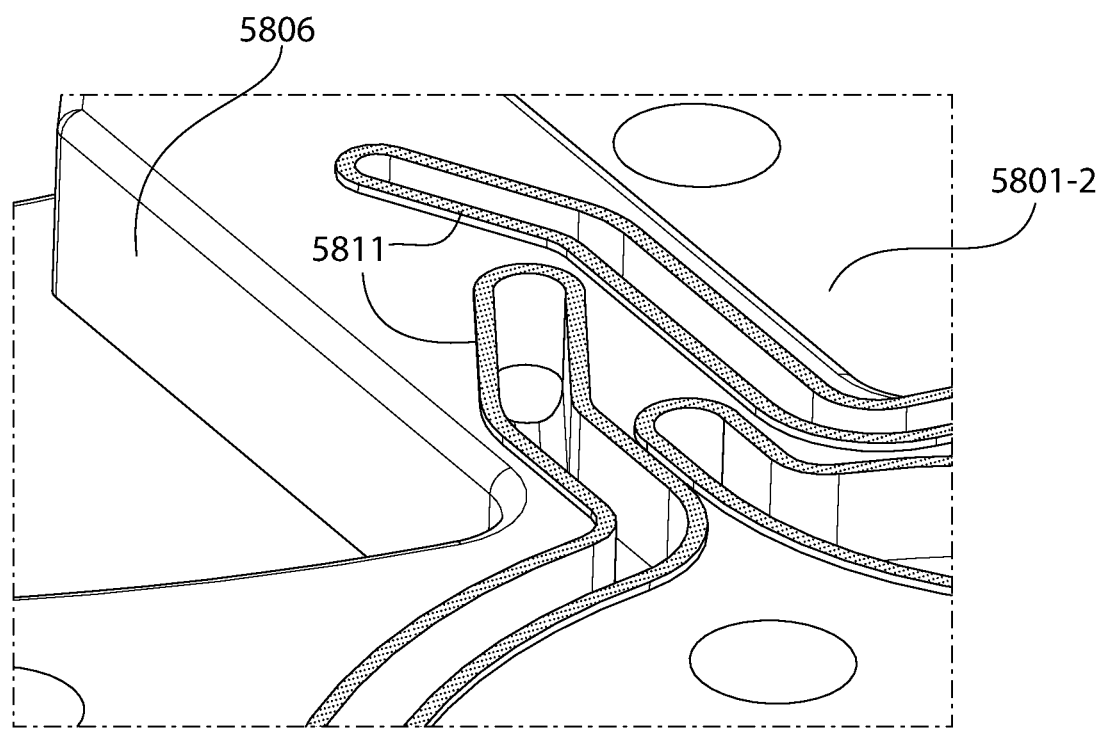
Figure 279:
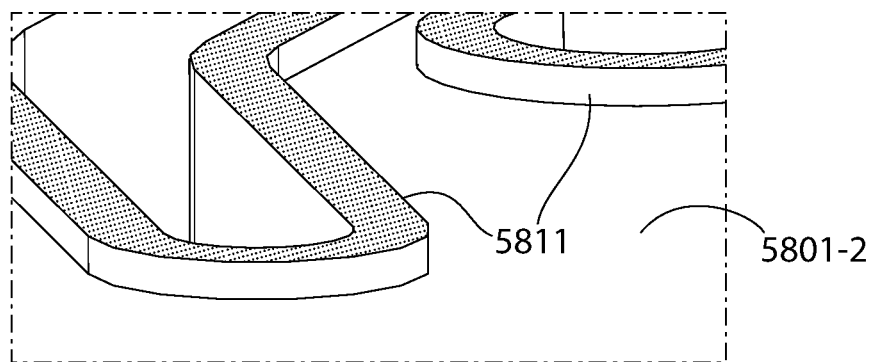
Figure 280:
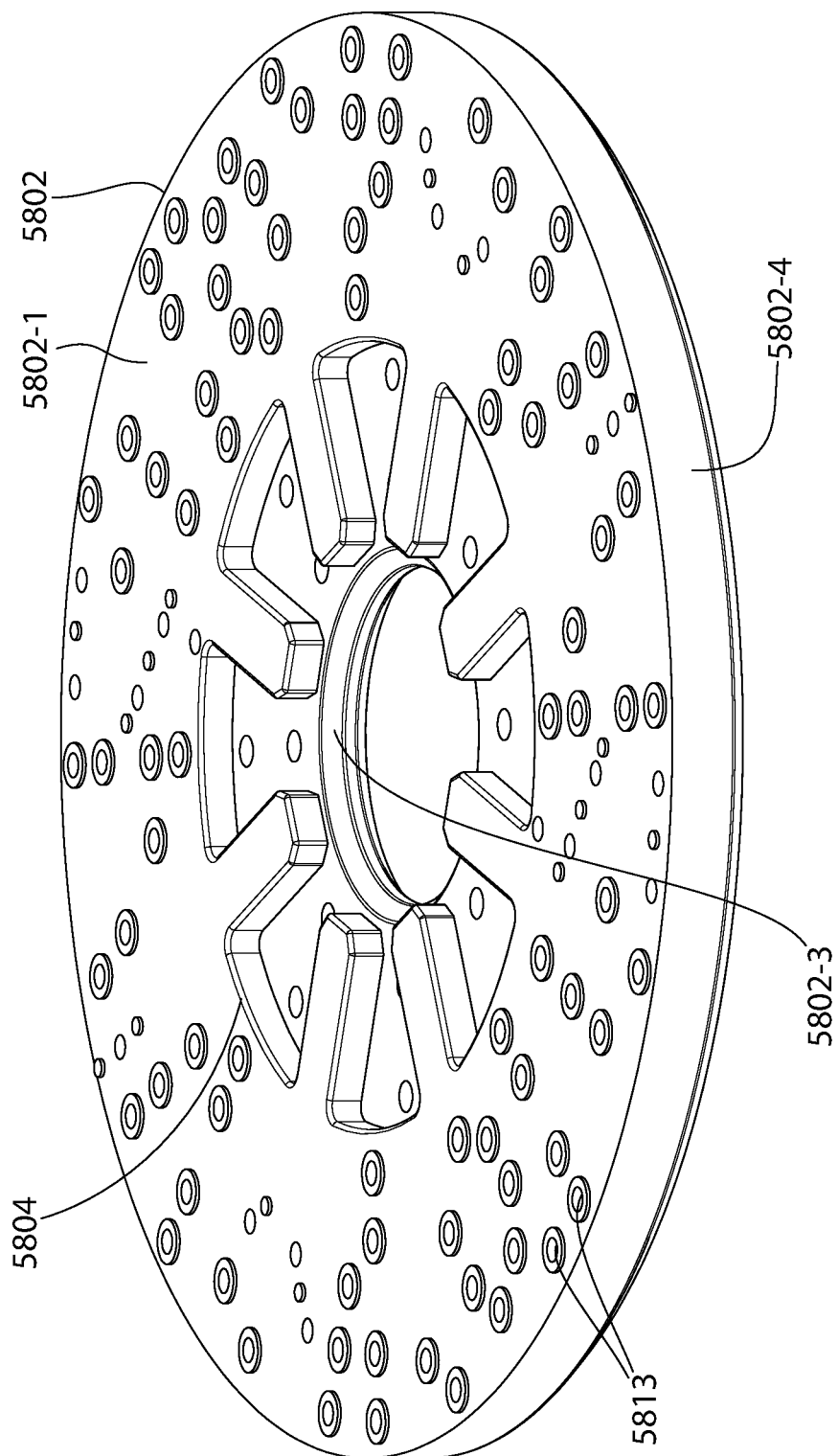
Figure 281:
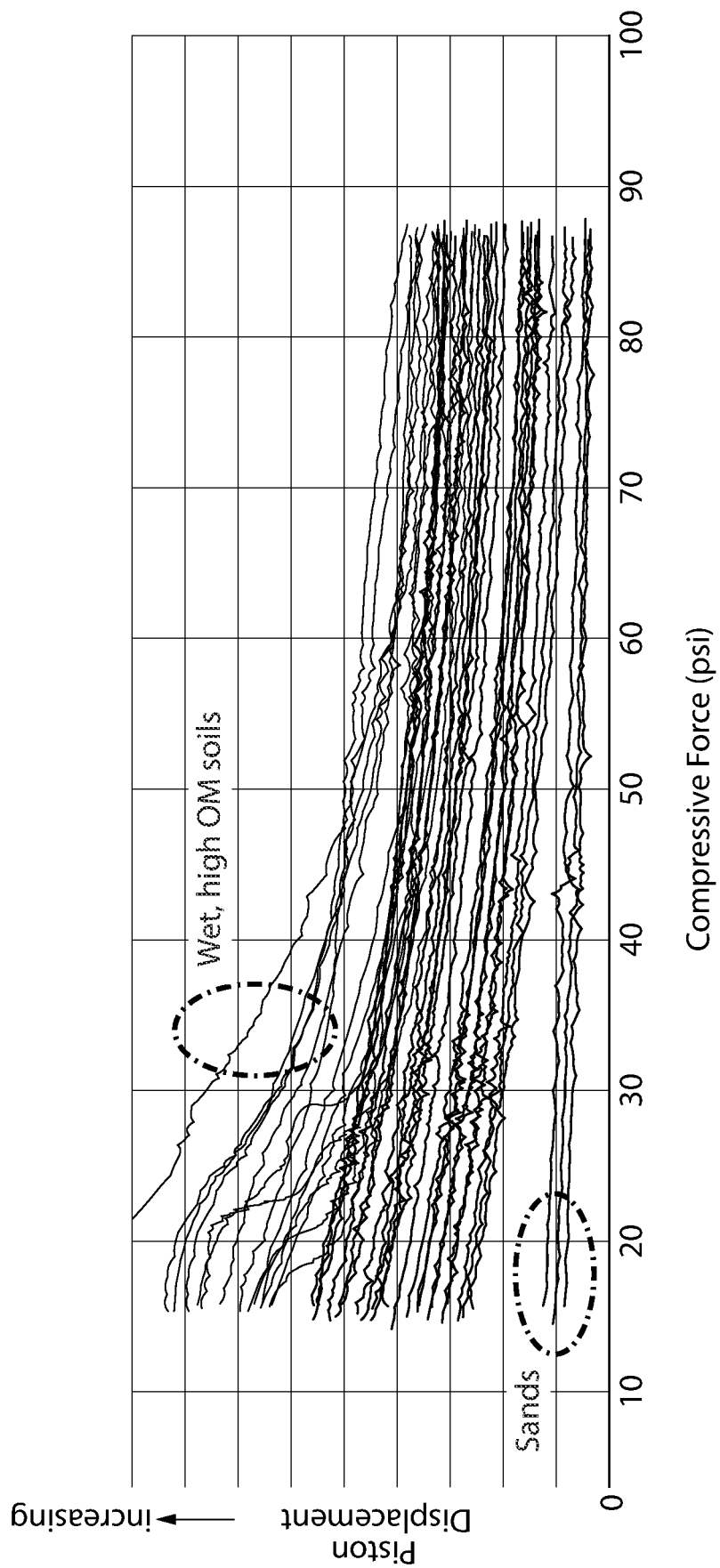
Figure 282:
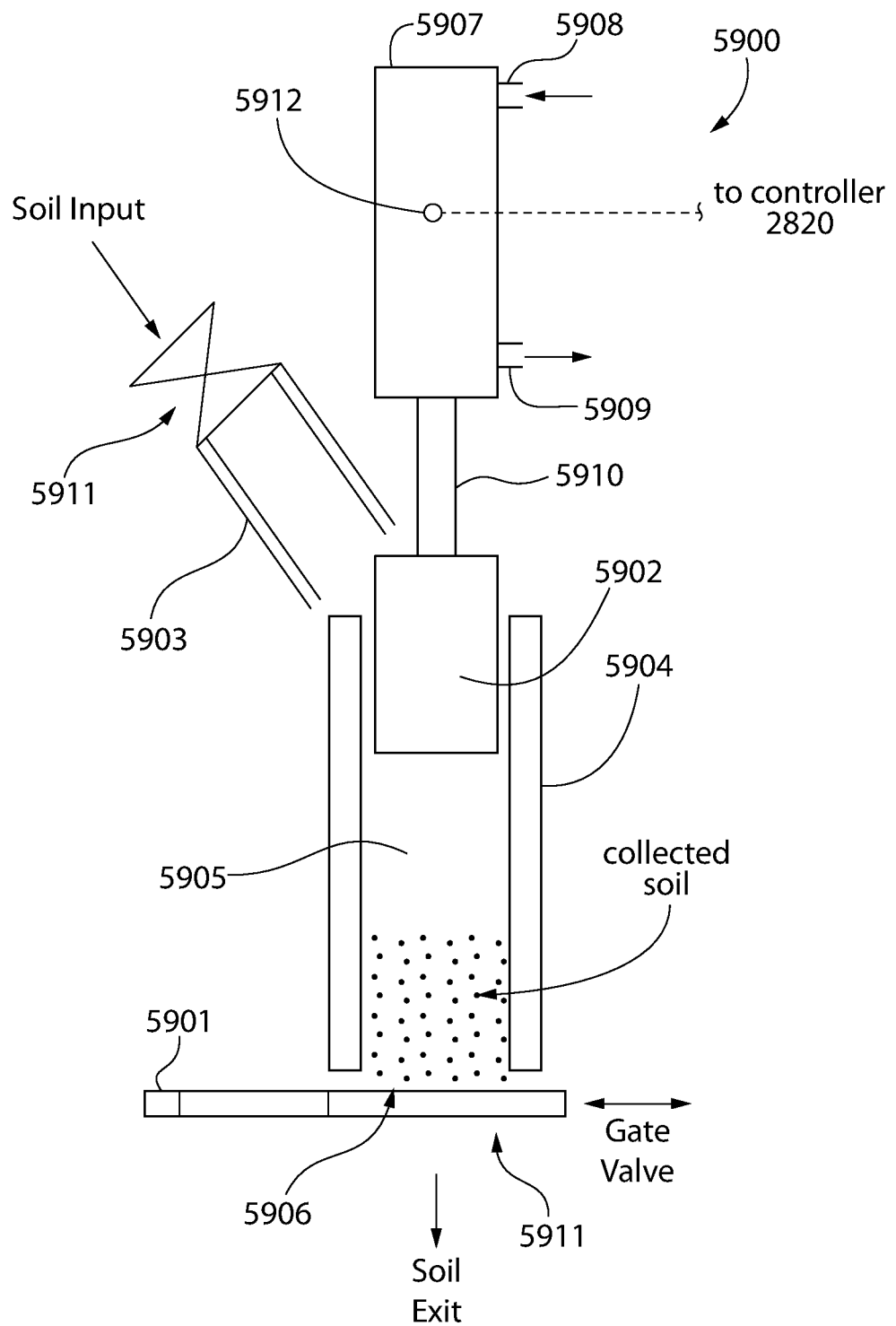
Figure 283:
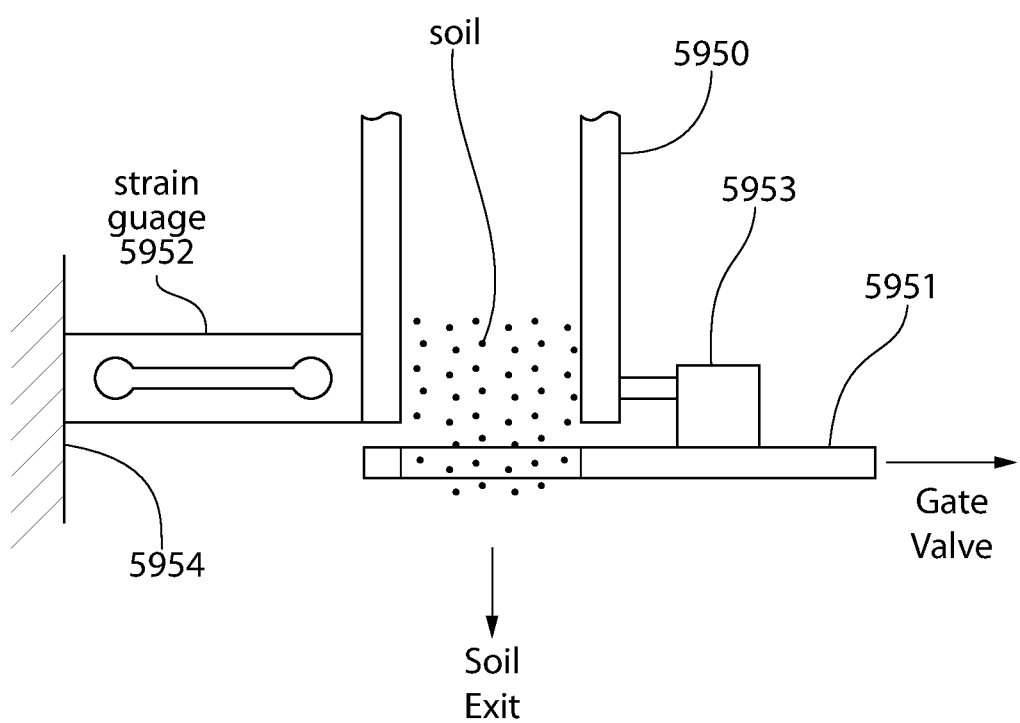
Figure 284:
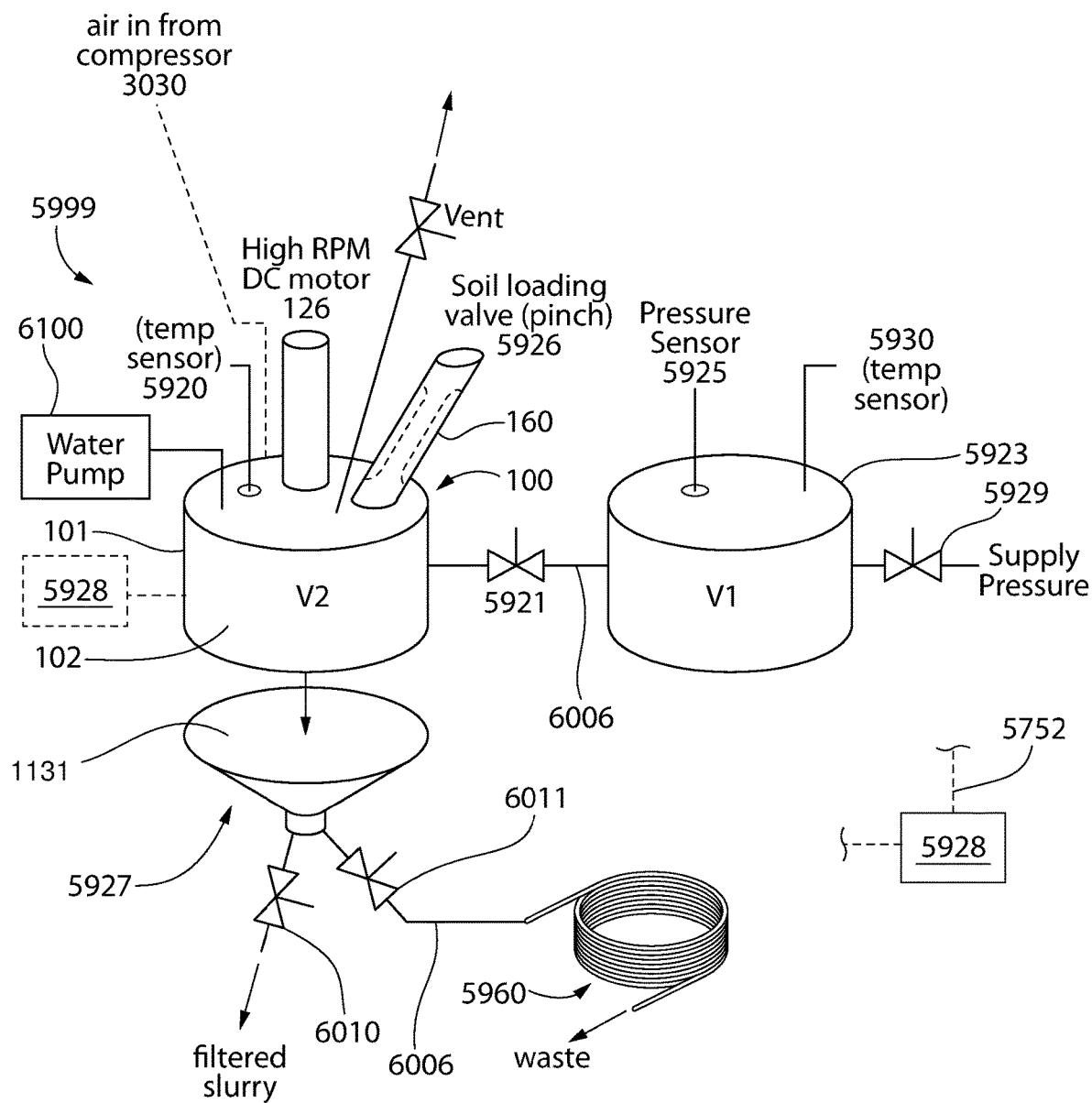
Figure 285:
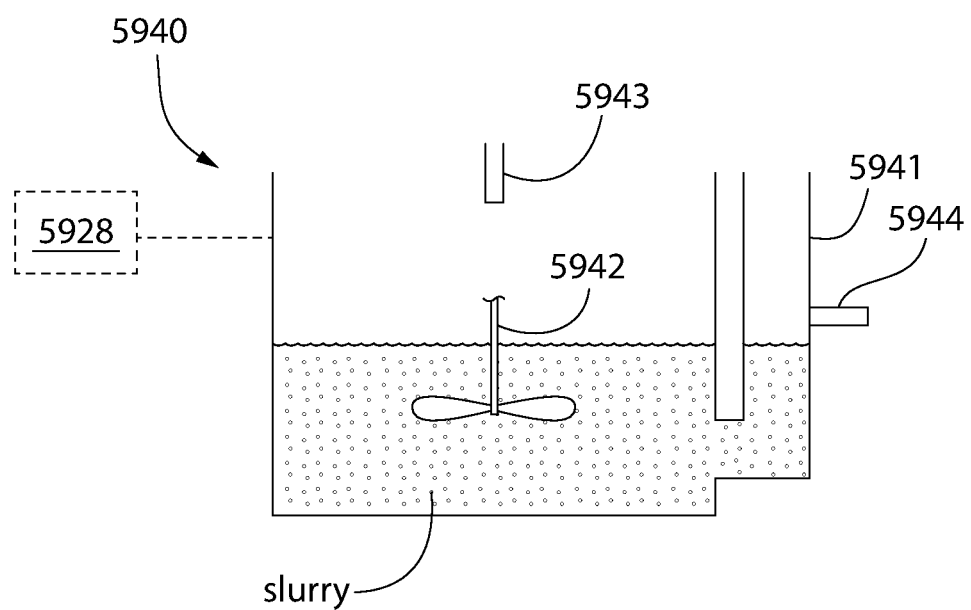
Figure 286:
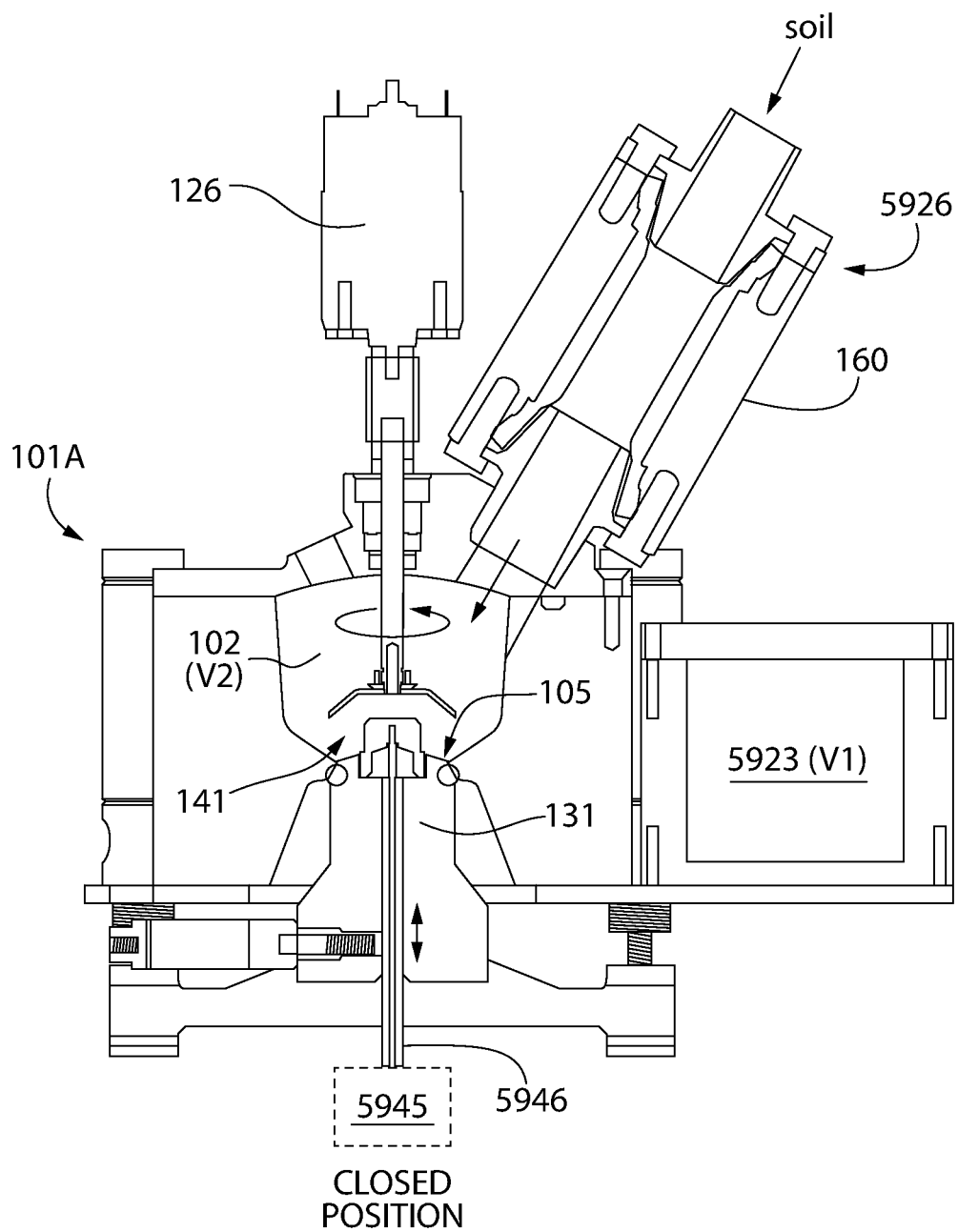
Figure 287:
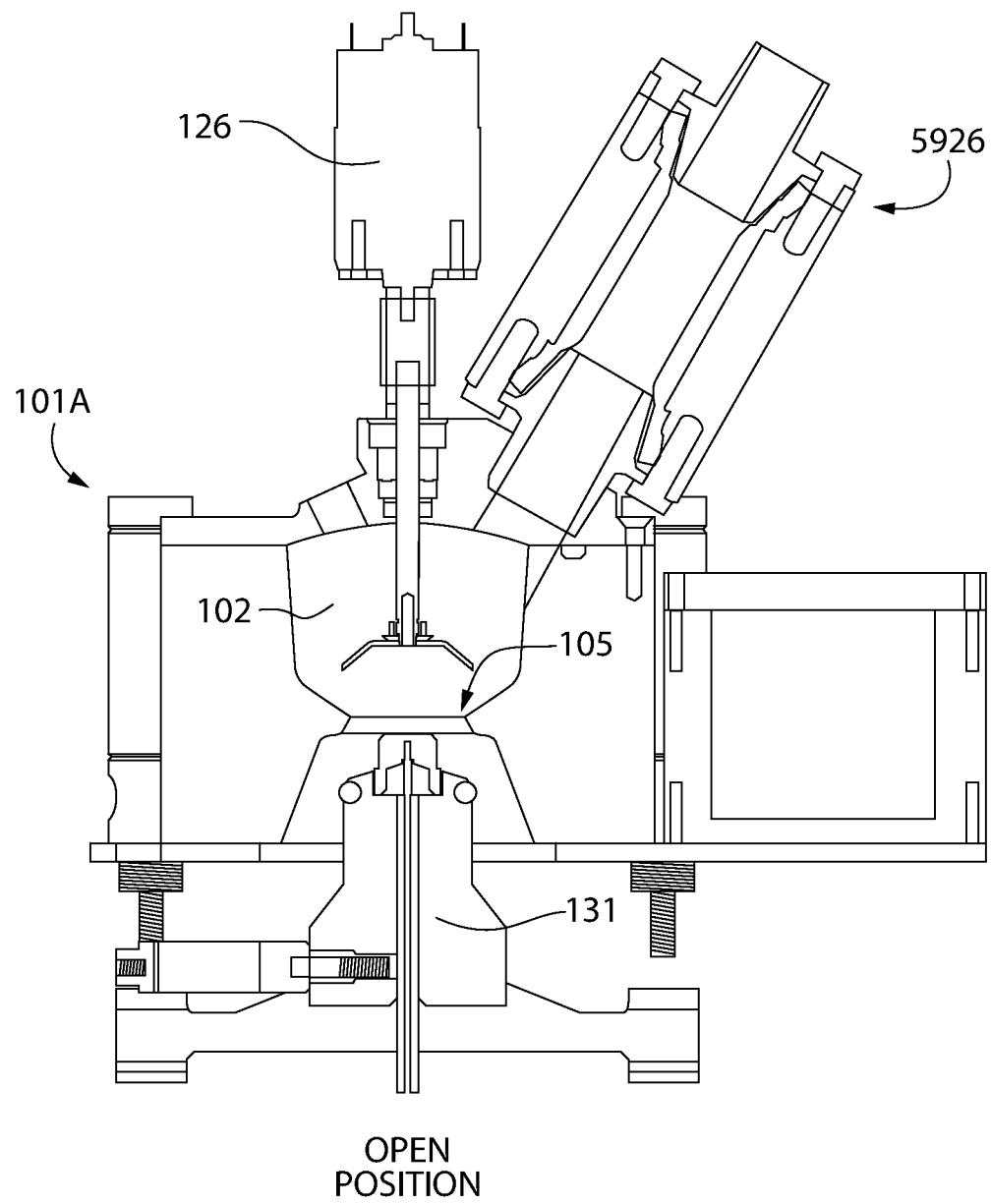
Figure 288:
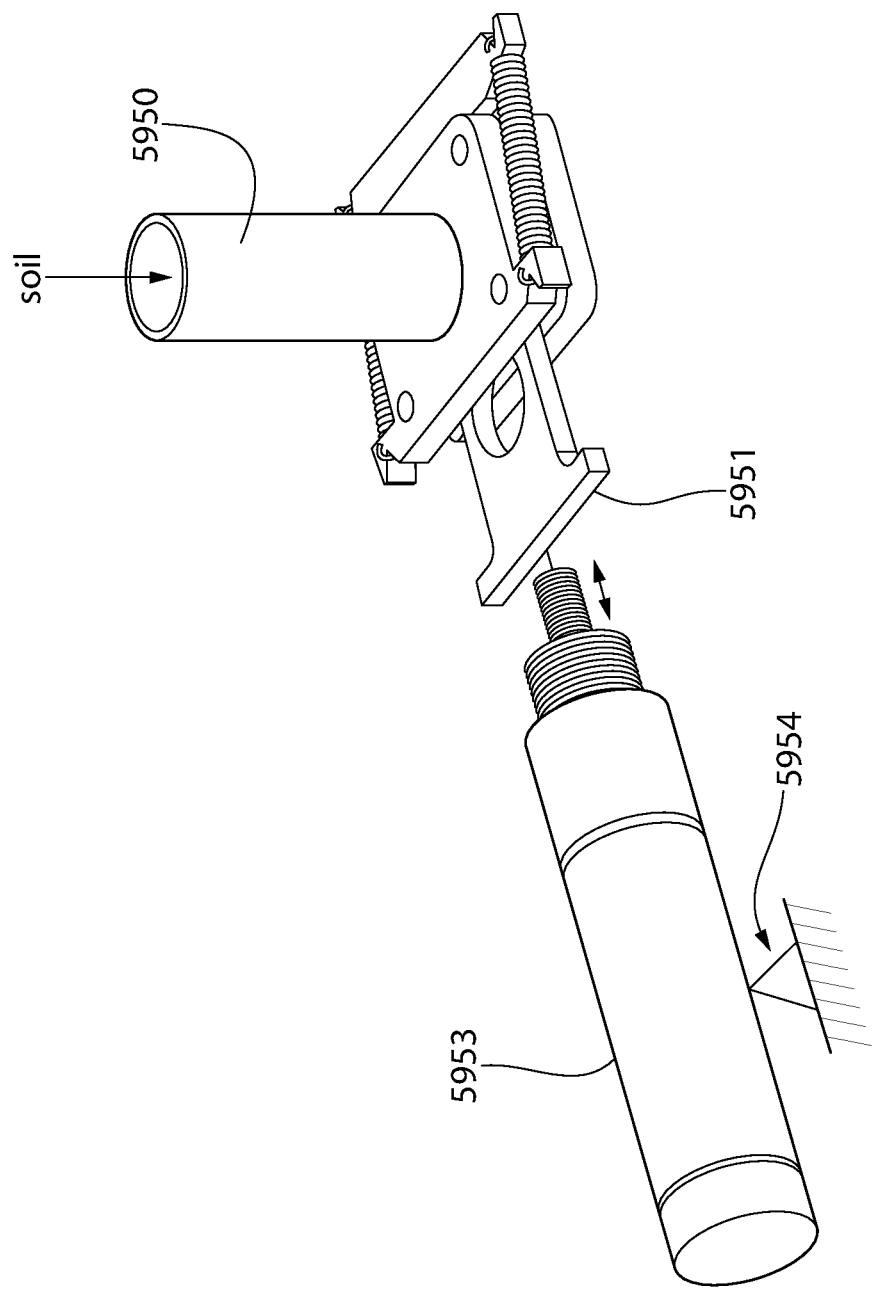
Figure 289:
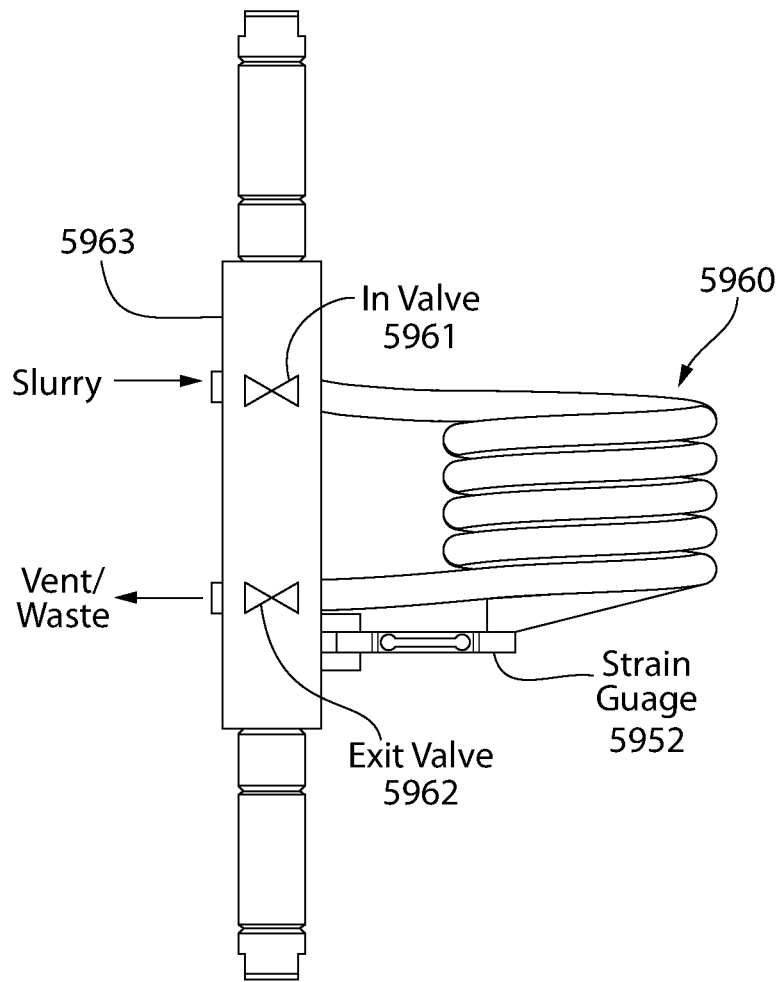
Figure 290:
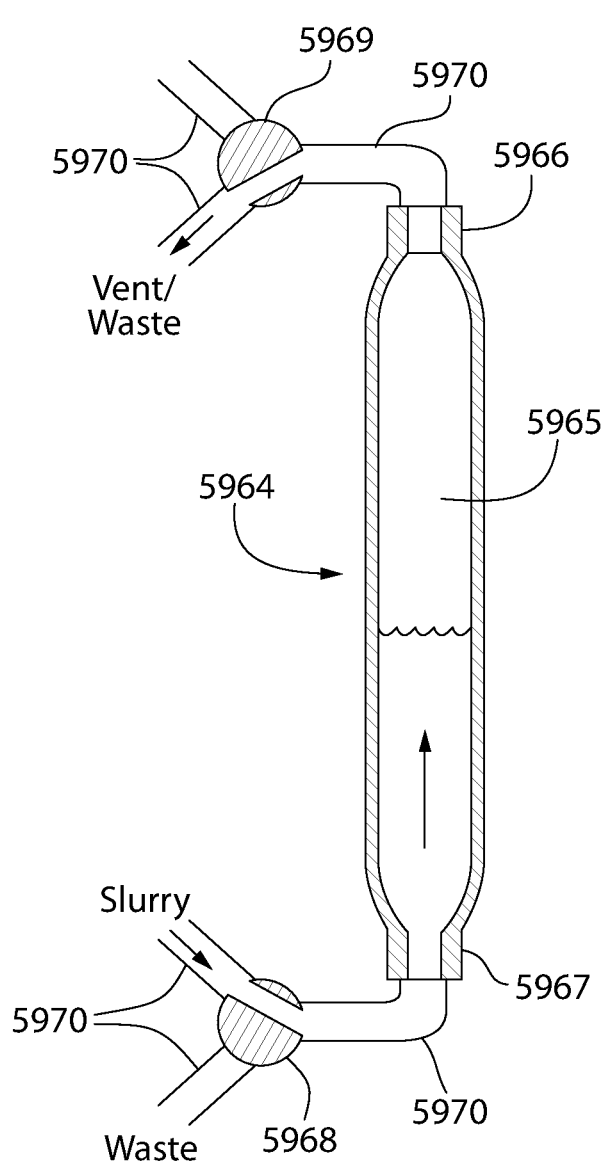
Figure 291:
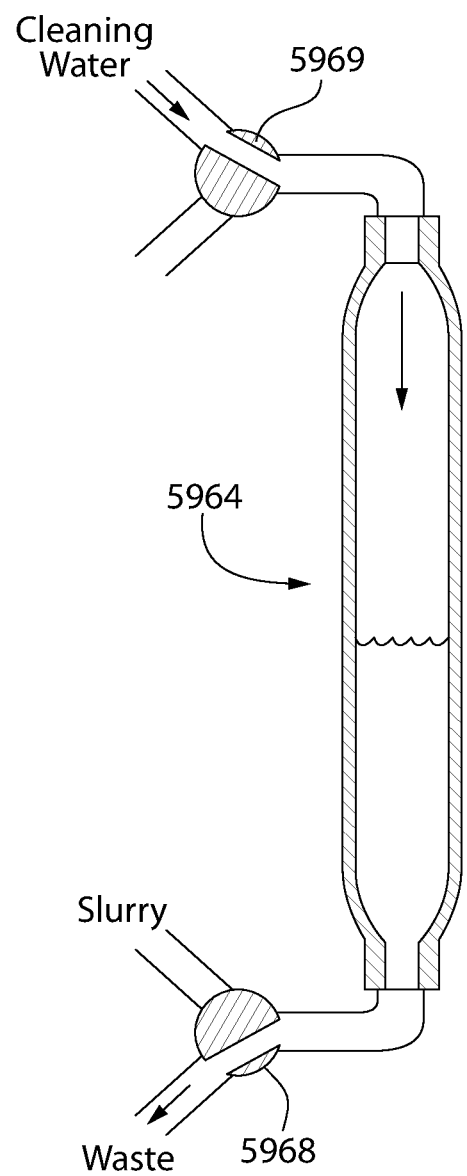
Figure 292:
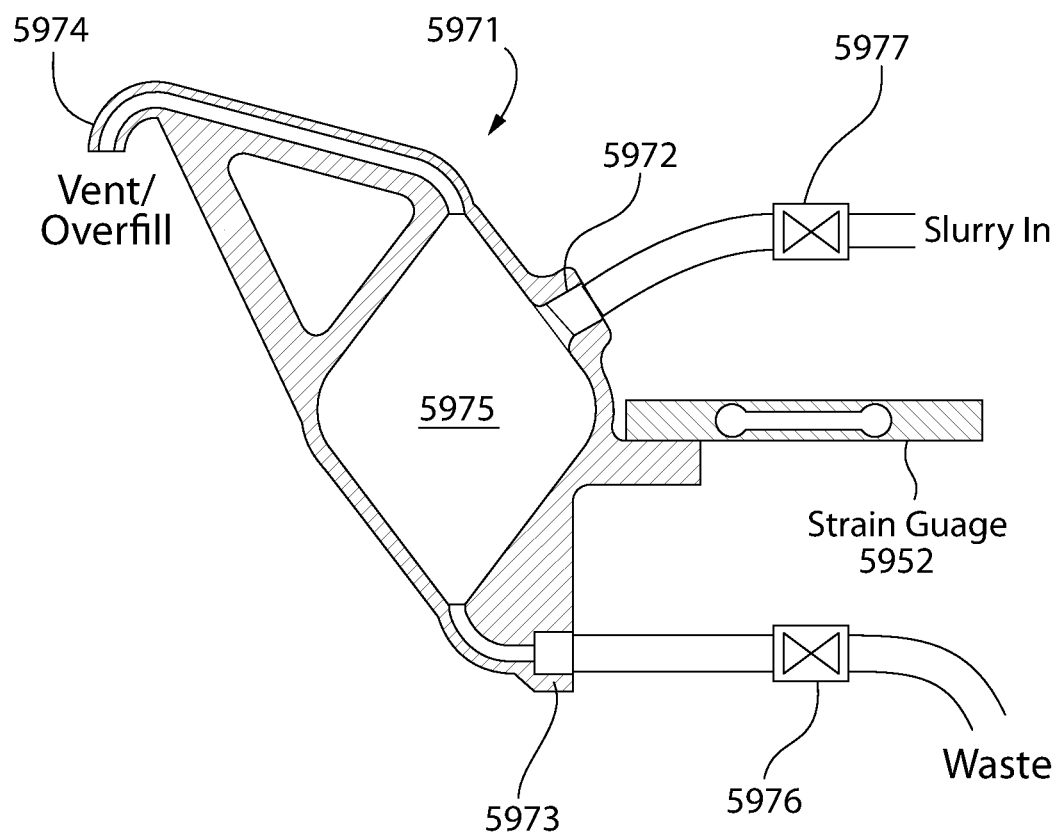
Figure 293:
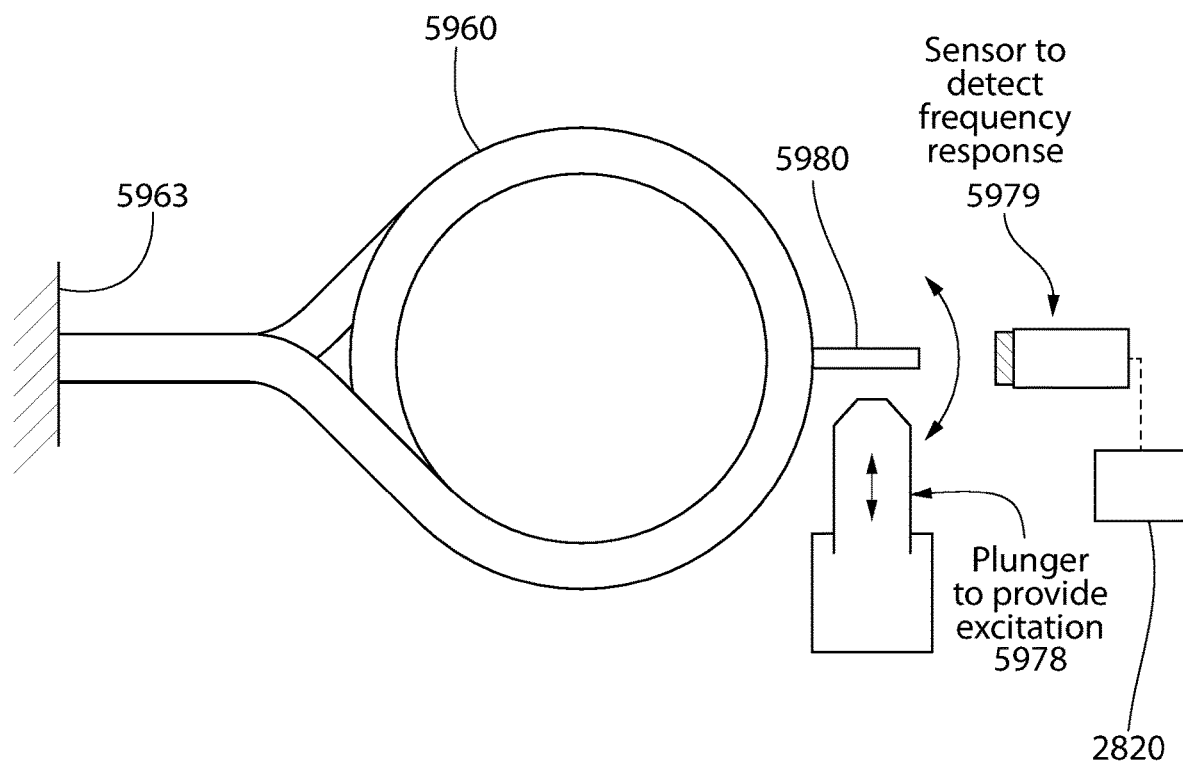
Figure 294:
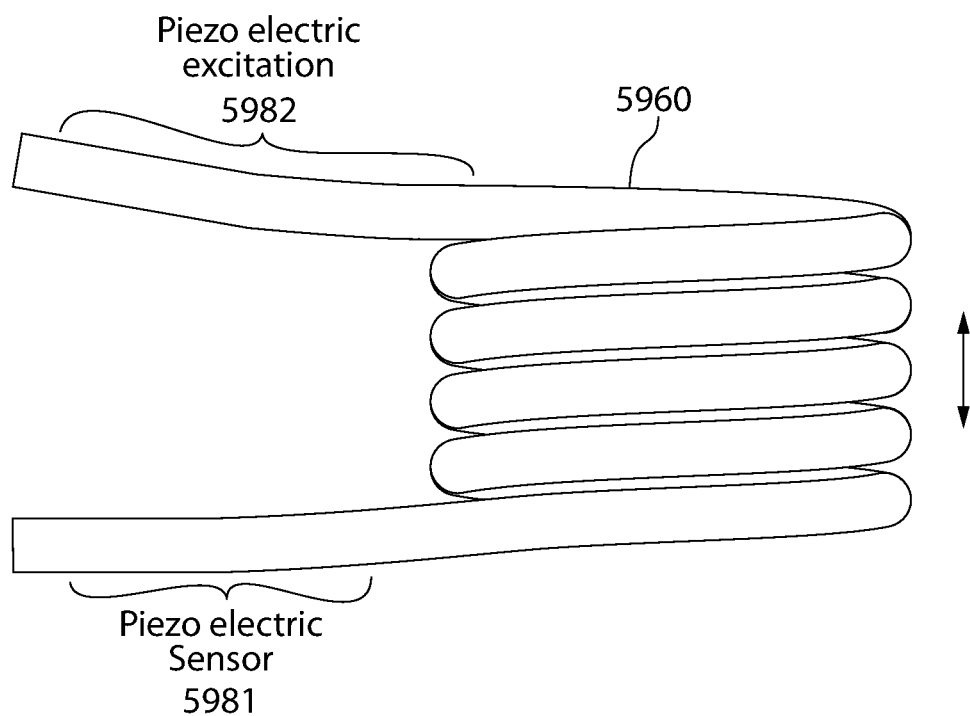
Figure 295:
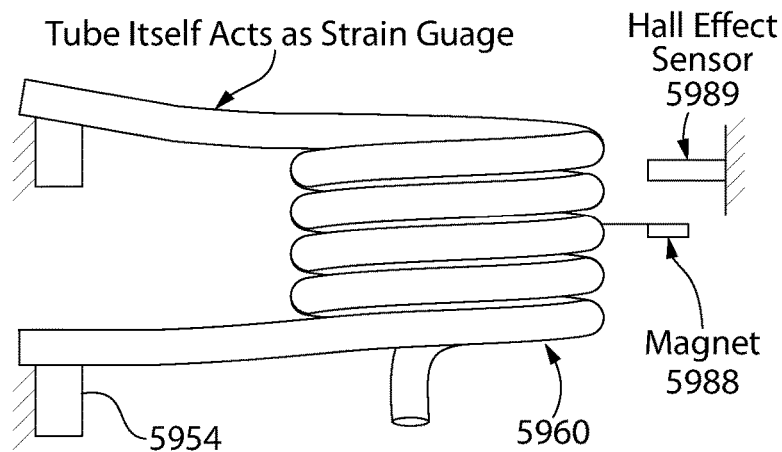
Figure 296:
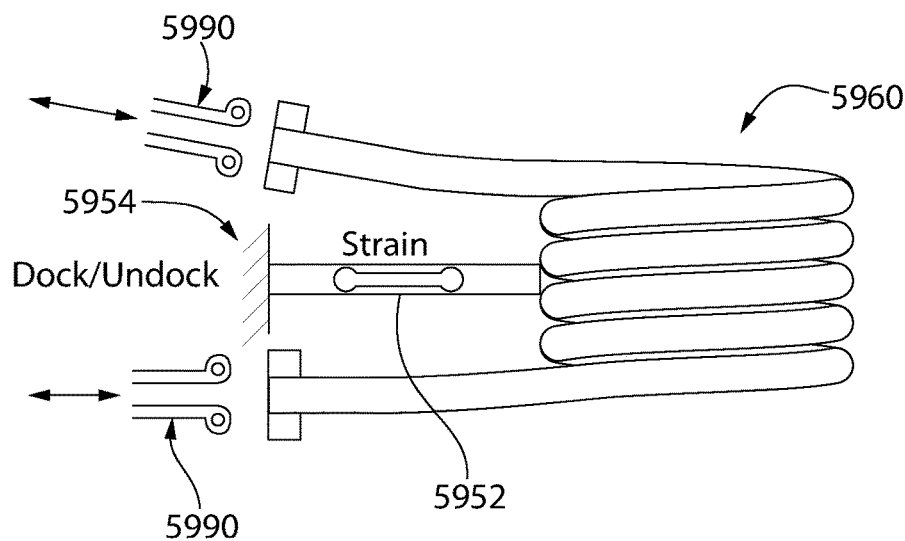
Figure 297:
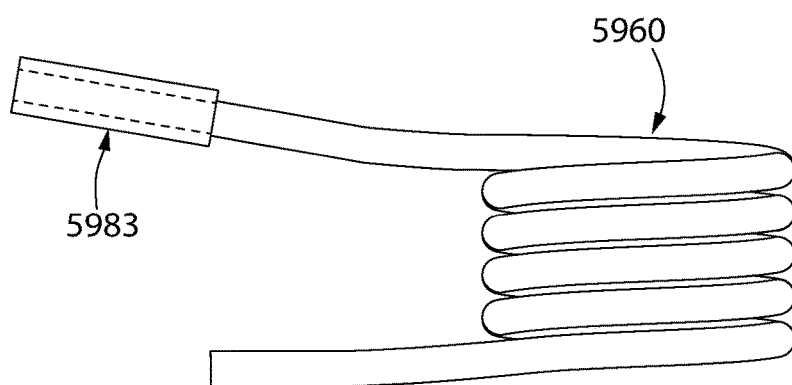
Figure 298:
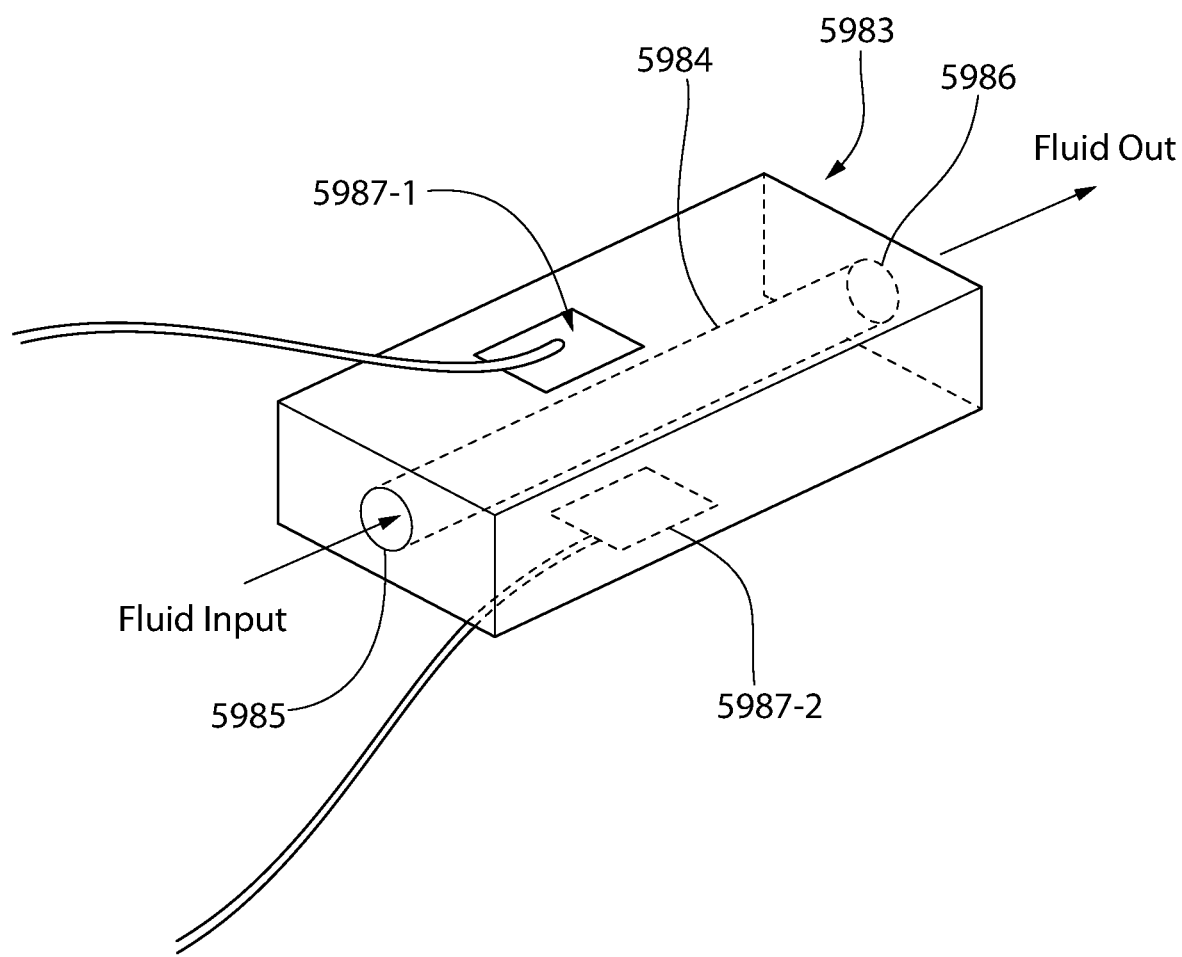
Figures 299, 300:
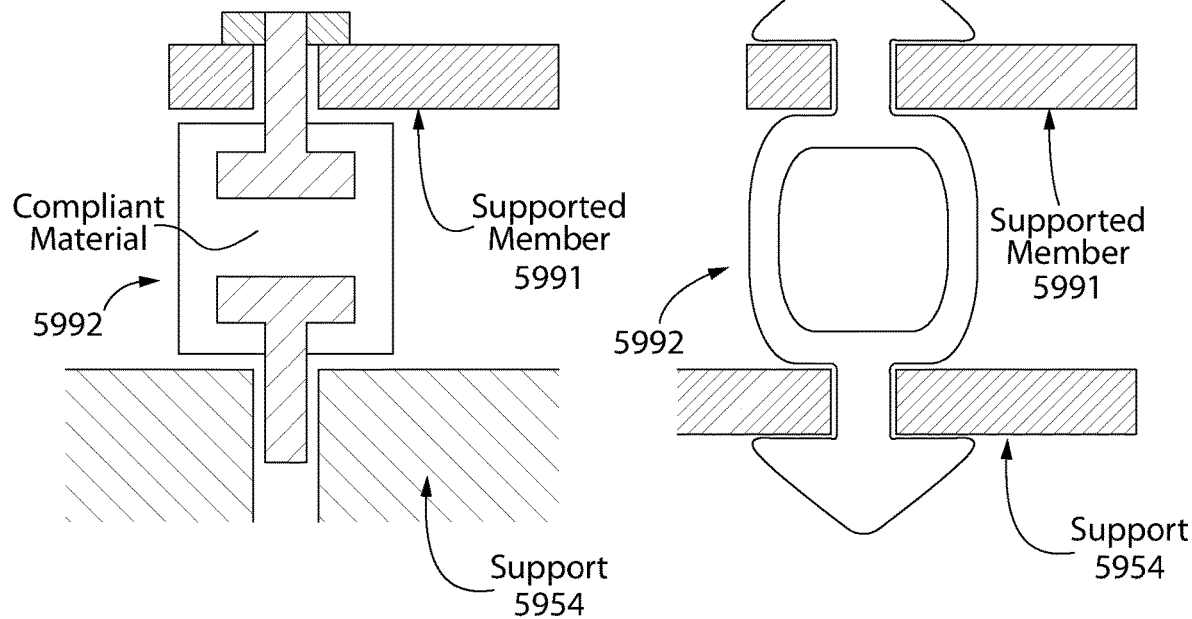
Figure 301:
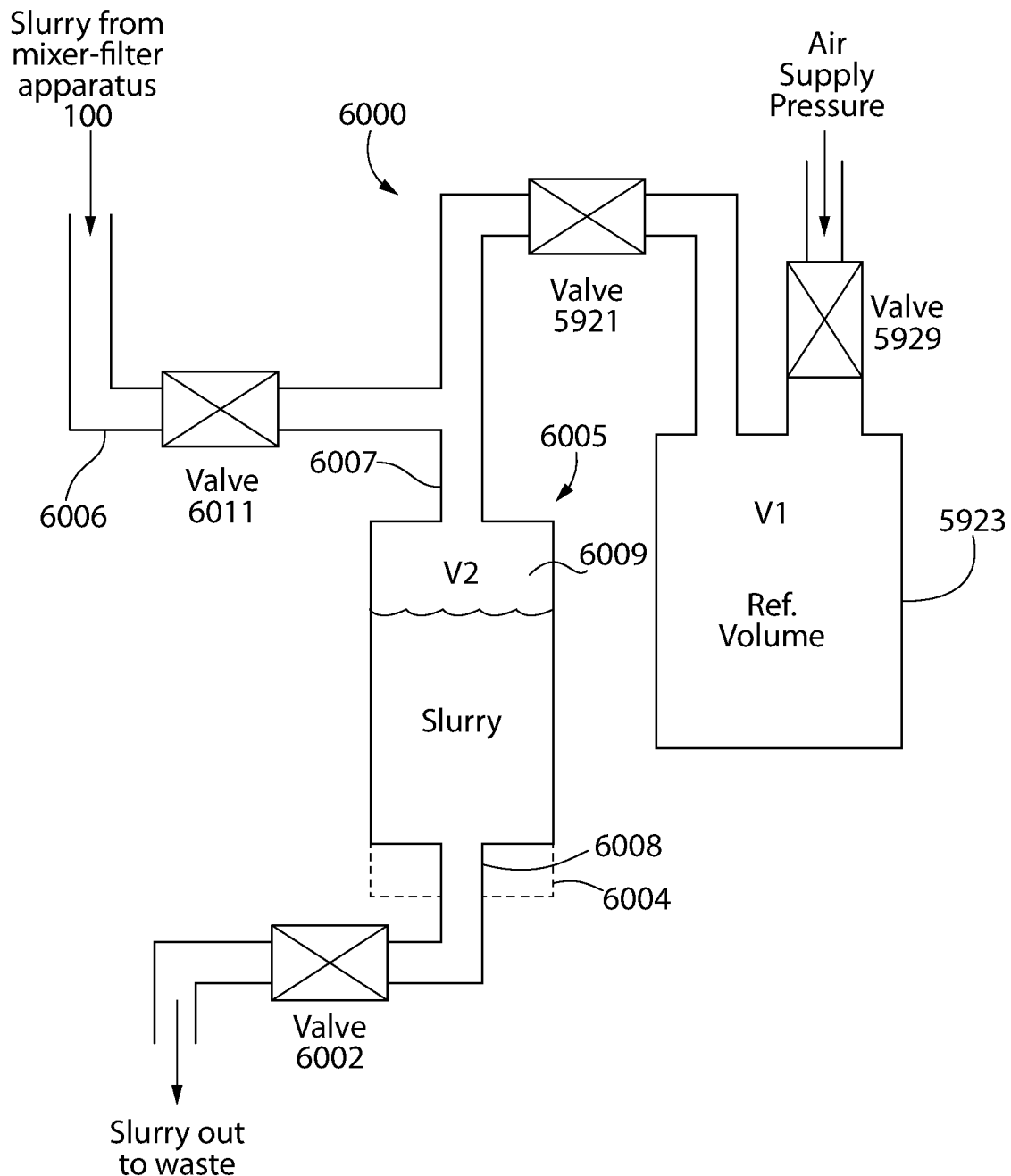

FIG. 131 is a bottom rear perspective view thereof;

FIG. 132 is a front exploded perspective view thereof;

FIG. 133 is a rear exploded perspective view thereof;

FIG. 134 is a front view thereof;

FIG. 135 is a side cross sectional view thereof;

FIG. 136 is a detailed view taken from FIG. 135;

FIG. 137 is a front perspective view of a first embodiment of a coulter assembly with sample collection apparatus or probe for collecting a soil sample from an agricultural field;

FIG. 138 is a rear perspective view thereof;

FIG. 139 is a front exploded perspective view thereof;

FIG. 140 is a rear exploded perspective view thereof;

FIG. 141 is a front view thereof;

FIG. 142 is a rear view thereof;

FIG. 143 is a side view thereof;

FIG. 144 is a side cross-sectional view thereof;

FIG. 145 is a perspective view of a cam ring of the coulter assembly of FIG. 137;

FIG. 146 is a plan view thereof;

FIG. 147 is an exploded perspective view of the sample collection probe of the coulter assembly of FIG. 137;

FIG. 148 is a perspective view thereof showing the cam track probe actuation mechanism of the cam ring;

FIG. 149A is a side view of the coulter assembly in a first rotational position showing the probe in a first open position for collecting a soil sample;

FIG. 149B is an enlarged detail thereof in perspective view;

FIG. 150A is a side view of the coulter assembly in a second rotational position showing the probe in the first open position movably embedded in the ground for capturing a soil sample;

FIG. 150B is an enlarged detail thereof in perspective view;

FIG. 151A is a side view of the coulter assembly in a third rotational position showing the probe in the first open position with captured soil sample;

FIG. 151B is an enlarged detail thereof in perspective view;

FIG. 152A is a side view of the coulter assembly in a fourth rotational position showing the probe in a second protruding position after the captured soil sample is ejected from the probe;

FIG. 152B is an enlarged detail thereof in perspective view;

FIG. 153 is a front perspective view of a second embodiment of a coulter assembly with sample collection apparatus or probe for collecting a soil sample from an agricultural field;

FIG. 154 is a rear perspective view thereof;

FIG. 155 is a front exploded perspective view thereof;

FIG. 156 is a rear exploded perspective view thereof;

FIG. 157 is a front view thereof;

FIG. 158 is a rear view thereof;

FIG. 159 is a side view thereof;

FIG. 160 is a side cross-sectional view thereof;

FIG. 161 is a perspective view of a sprocket type indexing cam ring of the coulter assembly of FIG. 153;

FIG. 162 is a plan view thereof;

FIG. 163 is a side cross sectional view of a sprocket indexing segment of the cam ring of FIG. 161;

FIG. 164 is a side perspective view thereof;

FIG. 165 is an enlarged cross sectional view of the probe blade, cam ring, and collection probe assembly;

FIG. 166 is an exploded perspective view of the probe;

FIG. 167 is a plan view showing the probe in an open position for collecting soil samples;

FIG. 168 is a plan view thereof showing the probe in a closed position for not capturing a soil sample or maintaining a captured soil sample;

FIG. 169 is a perspective view of the inner end of the probe and sprocket;

FIG. 170 is a perspective view of the outer end of the probe;

FIG. 171 is a perspective view of the sprocket engaging the indexing cam ring;

FIG. 172 is an enlarged detail taken from FIG. 171;

FIG. 173A is a top plan view of the coulter assembly of FIG. 153 with sprocket engaged with the indexing cam ring in a first operating position;

FIG. 173B is a side view thereof;

FIG. 174A is a top plan view of the coulter assembly of FIG. 153 with sprocket engaged with the indexing cam ring in a second operating position;

FIG. 174B is a side view thereof;

FIG. 175A is a top plan view of the coulter assembly of FIG. 153 with sprocket engaged with the indexing cam ring in a third operating position;

FIG. 175B is a side view thereof;

FIG. 176A is a top plan view of the coulter assembly of FIG. 153 with sprocket engaged with the indexing cam ring in a fourth operating position;

FIG. 176B is a side view thereof;

FIG. 177A is a top plan view of the coulter assembly of FIG. 153 with sprocket engaged with the indexing cam ring in a fifth operating position;

FIG. 177B is a side view thereof;

FIG. 178A is a top plan view of the coulter assembly of FIG. 153 with sprocket engaged with the indexing cam ring in a sixth operating position;

FIG. 178B is a side view thereof;

FIG. 179 is a front perspective view of a third embodiment of a coulter assembly with sample collection apparatus or probe for collecting a soil sample from an agricultural field;

FIG. 180 is a rear perspective view thereof;

FIG. 181 is an exploded perspective view thereof;

FIG. 182 is a front view thereof;

FIG. 183 is a rear view thereof;

FIG. 184 is a side view thereof;

FIG. 185 is a side cross-sectional view thereof;

FIG. 186 is an enlarged view showing the coulter blade and collection probe arrangement details;

FIG. 187 is a plan view showing the various rotational positions of the collection probe as the coulter blade rotates;

FIG. 188 is a plan view showing an alternative variation of the coulter assembly for collecting soil samples at different depths;

FIG. 189 is a rear perspective view of a fourth embodiment of a coulter assembly with sample collection apparatus or probe for collecting a soil sample from an agricultural field;

FIG. 190 is a front exploded perspective view thereof;

FIG. 191 is a rear view thereof;

FIG. 192 is a front view thereof;

FIG. 193 is a side view thereof;

FIG. 194 is a side cross-sectional view thereof;

FIG. 195 is an enlarged perspective view showing the coulter blade and collection probe arrangement details with collection ports of the probe in a closed position;

FIG. 196 is an enlarged perspective view thereof showing the collection ports in an open position for capturing a soil sample;

FIG. 197 is a front perspective view of a fifth embodiment of a coulter assembly with sample collection apparatus or probe for collecting a soil sample from an agricultural field;

FIG. 198 is a rear perspective view thereof;

FIG. 199 is a front view thereof;

FIG. 200 is a rear view thereof;

FIG. 201 is an enlarged view showing the coulter blade and collection probe arrangement details;

FIG. 202 is a side view thereof;

FIG. 203 is a side cross-sectional view thereof;

FIG. 204 is an enlarged perspective view detail showing the collection probe in an open position for capturing a soil sample;

FIG. 205 is a view thereof showing the collection probe in a closed position;

FIG. 206 is an enlarged perspective view detail showing two collection ports of the collection probe in an open position for capturing a soil sample;

FIG. 207 is a front perspective view of a sixth embodiment of a coulter assembly with sample collection apparatus or probe for collecting a soil sample from an agricultural field;

FIG. 208 is a front perspective view of the resiliently flexible cam ring of the coulter assembly of FIG. 207;

FIG. 209 is a rear perspective view thereof;

FIG. 210 is a front exploded perspective view thereof;

FIG. 211 is a rear exploded perspective view thereof;

FIG. 212 is a side view thereof;

FIG. 213 is a side cross sectional view thereof;

FIG. 214 is a front view thereof;

FIG. 215 is a rear view thereof;

FIG. 216 is a partial cross-sectional view thereof;

FIG. 217 is a front perspective view of a seventh embodiment of a coulter assembly with sample collection apparatus or probe with laminated blade assembly for collecting a soil sample from an agricultural field;

FIG. 218 is a rear perspective view thereof;

FIG. 219 is a first front exploded perspective view thereof showing four alternative types of sample collection probes usable together as shown or individually in the coulter assembly;

FIG. 220 is a second front exploded perspective view thereof;

FIG. 221 is a front view thereof;

FIG. 222 is a rear view thereof;

FIG. 223 is a side view thereof;

FIG. 224 is a first side cross-sectional view thereof taken from FIG. 221;

FIG. 225 is a second side cross sectional view thereof taken from FIG. 221;

FIG. 226 is a first cross-sectional perspective view showing a first set of two types of collection probes;

FIG. 227 is a second cross-sectional perspective view showing a second set of two other types of collection probes;

FIG. 228 is an enlarged cross-sectional perspective view showing a first type of collection probe;

FIG. 229 is an enlarged cross-sectional perspective view showing a second type of collection probe;

FIG. 230 is an enlarged cross-sectional perspective view showing a third type of collection probe;

FIG. 231 is an enlarged cross-sectional perspective view showing a fourth type of collection probe;

FIG. 232 is a side cross-sectional view of the coulter blade showing the foregoing second type of collection probe;

FIG. 233 is a front view thereof;

FIG. 234 is a side cross-sectional view of the coulter blade showing the foregoing first type of collection probe;

FIG. 235 is a front view thereof;

FIG. 236 is a side cross-sectional view of the coulter blade showing the foregoing third type of collection probe;

FIG. 237 is a front view thereof;

FIG. 238 is a side cross-sectional view of the coulter blade showing the foregoing fourth type of collection probe;

FIG. 239 is a front view thereof;

FIG. 240 is a transverse cross-sectional of a portion of the coulter blade showing the foregoing second type of collection probe;

FIG. 241 is a transverse cross-sectional of a portion of the coulter blade showing the foregoing first type of collection probe;

FIG. 242 is a transverse cross-sectional of a portion of the coulter blade showing the foregoing third type of collection probe;

FIG. 243 is a transverse cross-sectional of a portion of the coulter blade showing the foregoing fourth type of collection probe;

FIG. 244A is a perspective view of the coulter blade showing a radial slot for the foregoing second type of collection probe;

FIG. 244B is a view thereof showing the second type of collection probe mounted in the slot;

FIG. 245A is a perspective view of the coulter blade showing a radial slot for the foregoing first type of collection probe;

FIG. 245B is a view thereof showing the second type of collection probe mounted in the slot;

FIG. 246A is a perspective view of the coulter blade showing a radial slot for the foregoing third type of collection probe;

FIG. 246B is a view thereof showing the second type of collection probe mounted in the slot;

FIG. 247A is a perspective view of the coulter blade showing a radial slot for the foregoing fourth type of collection probe;

FIG. 247B is a view thereof showing the second type of collection probe mounted in the slot;

FIG. 248A is a perspective of the foregoing second type of collection probe;

FIG. 248B is a transverse cross sectional view thereof;

FIG. 249A is a perspective of the foregoing first type of collection probe;

FIG. 249B is a transverse cross sectional view thereof;

FIG. 250A is a perspective of the foregoing third type of collection probe;

FIG. 250B is a transverse cross sectional view thereof;

FIG. 251A is a perspective of the foregoing fourth type of collection probe;

FIG. 251B is a transverse cross sectional view thereof;

FIG. 252 is a top view of a first embodiment of an agricultural implement configured to perform soil sampling and analysis according to the present disclosure;

FIG. 253 is a side view of a second embodiment of an agricultural implement configured to perform soil sampling and analysis according to the present disclosure;

FIG. 254 is a side view of a third embodiment of an agricultural implement configured to perform soil sampling and analysis according to the present disclosure;

FIG. 255 is a top perspective view of a fourth embodiment of an agricultural implement configured to perform soil sampling and analysis according to the present disclosure;

FIG. 256 is an exploded perspective view of an on-disk pneumatically-actuated diaphragm micropump mountable in the microfluidic processing disk of FIG. 96;

FIG. 257 is a side cross-sectional view thereof showing the micropump in an unactuated position;

FIG. 258 is a view thereof showing the micropump in an actuated position;

FIG. 259 is a perspective view of a heated processing wedge of the microfluidic processing disk of FIG. 96;

FIG. 260 is an exploded view thereof;

FIG. 261 is a flow diagram showing a soil sample processing and analysis system with micro-porous filter in lieu of a centrifuge for separating supernatant from a prepared soil slurry and extractant mixture;

FIG. 262 is a perspective view of one of a porous inline type filter for separating supernatant from a soil slurry;

FIG. 263 is a flow diagram showing a soil sample processing and analysis system embodied in the microfluidic processing disk of FIG. 96 with an integrated micro-porous filter in lieu of a centrifuge for separating supernatant from a prepared soil slurry and extractant mixture;

FIG. 264 is schematic diagram of a first embodiment of a vehicle-mounted water filtration system usable with the soil analysis and processing systems disclosed herein;

FIG. 265 is schematic diagram of a second embodiment of a vehicle-mounted water filtration system usable with the soil analysis and processing systems disclosed herein;

FIG. 266 is schematic diagram of a third embodiment of a vehicle-mounted water filtration system usable with the soil analysis and processing systems disclosed herein;

FIG. 267 shows an example of a particulate filter unit which may with the water filtration systems of FIGS. 264-266;

FIG. 268 is a top perspective view of a rotary supernatant extraction apparatus for extracting supernatant from soil slurry using centrifugation;

FIG. 269 is a top exploded perspective view thereof;

FIG. 270 is a bottom exploded perspective view thereof;

FIG. 271 is a bottom view of the fluid plate thereof showing a plurality of supernatant separation devices formed in the plate;

FIG. 272 is a plan view of a first embodiment of a supernatant separation device of FIG. 271;

FIG. 273 is a plan view of a second embodiment of a supernatant separation device of FIG. 271;

FIG. 274 is a plan view of a third embodiment of a supernatant separation device of FIG. 271;

FIG. 275 is a plan view of a fourth embodiment of a supernatant separation device of FIG. 271;

FIG. 276 is a partial side cross-sectional of the supernatant extraction apparatus of FIG. 268;

FIG. 277 is a plan view showing sealing features of the supernatant separation devices;

FIG. 278 is a first enlarged perspective view thereof;

FIG. 279 is a second enlarged perspective view thereof;

FIG. 280 is a top perspective view of the lower clamping plate of the supernatant extraction apparatus of FIG. 268;

FIG. 281 is a graph depicting actual measured piston displacement vs. compressive force from testing performed on various soil types utilizing the compression soil testing apparatus shown in FIG. 282;

FIG. 282 is a schematic diagram of a compression soil testing apparatus;

FIG. 283 is schematic diagram of a weigh container for soil testing;

FIG. 284 is a schematic diagram of a volumetric and mass based analysis system for determining the moisture content of a collected "raw" soil plug or sample;

FIG. 285 is a schematic diagram of a slurry volume measurement device;

FIG. 286 is a side cross sectional view of an alternative embodiment of a centrifuge for preparing a soil slurry in a first operating position;

FIG. 287 is a view thereof showing a second operating position;

FIG. 288 is a perspective view of a soil weigh container with sliding gate;

FIG. 289 is a schematic diagram of a weighing device in the form of a weigh coil for measuring weight of a prepared soil slurry;

FIG. 290 is a schematic diagram of a tubular weigh container in a first operating mode;

FIG. 291 is a view thereof in a second operating mode;

FIG. 292 is a schematic diagram of a teapot shaped weigh container;

FIG. 293 is a schematic diagram showing a first embodiment of a vibration frequency response based weighing device for weighing slurry;

FIG. 294 is a schematic diagram showing a second embodiment of a vibration frequency response based weighing device for weighing slurry;

FIG. 295 is a schematic diagram of a slurry weigh coil having a moving magnet type weighing system;

FIG. 296 is a schematic diagram of a slurry weigh coil with quick disconnect tubing connectors for isolating the weigh coil from effects of interconnected flow conduits;

FIG. 297 is a schematic diagram of a slurry weigh coil including a custom load cell for weighing the slurry;

FIG. 298 is a schematic diagram of the custom load cell;

FIG. 299 is a side schematic diagram of a first embodiment of an isolation mounting apparatus for a slurry weighing device;

FIG. 300 is a side schematic diagram of a second embodiment of an isolation mounting apparatus for a slurry weighing device;

FIG. 301 is a schematic diagram showing a slurry weigh station; and

Figure 302:
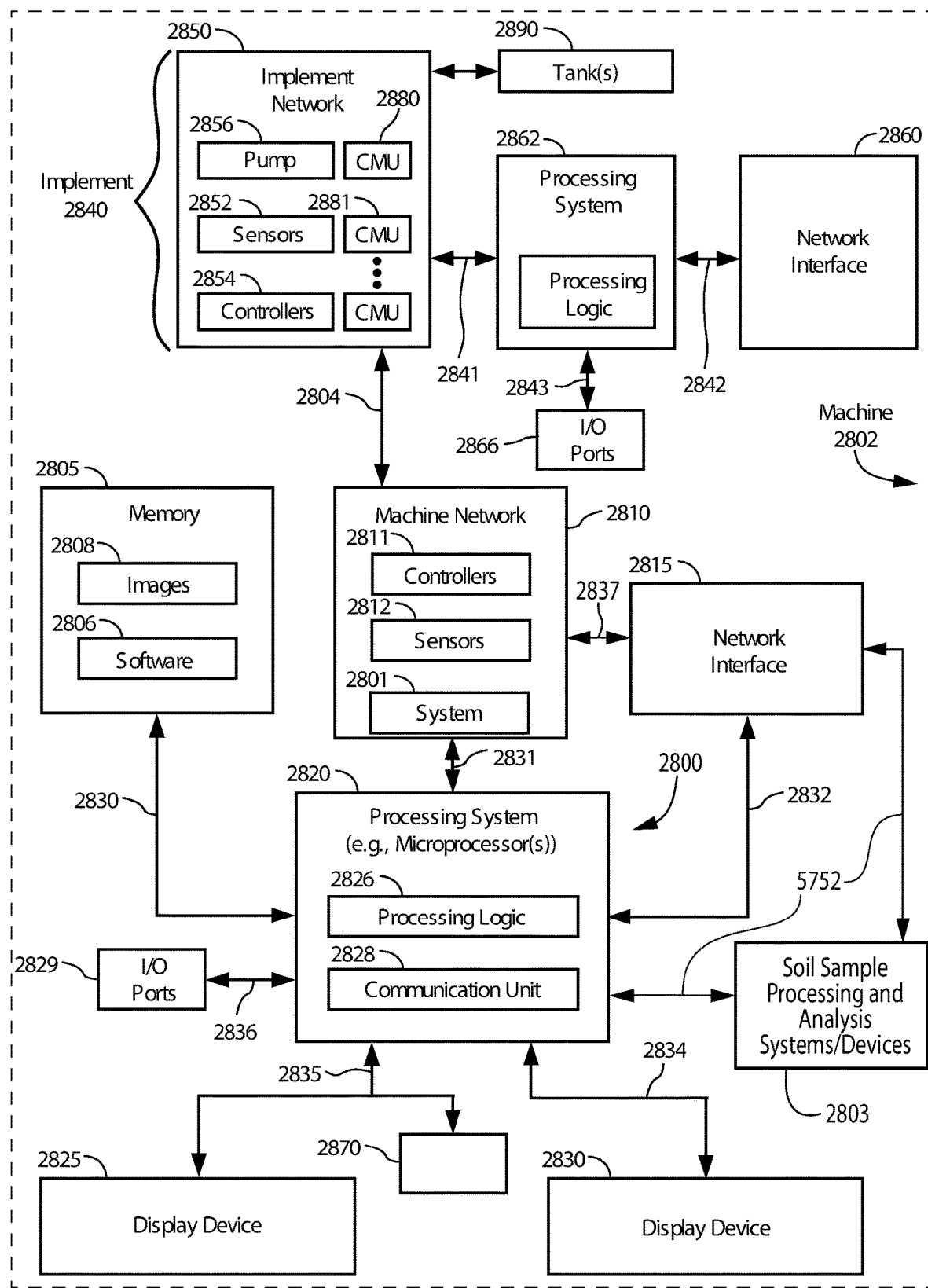

FIG. 302 is a schematic system diagram of a programmable processor-based central processing unit (CPU) or system controller for controlling the systems and apparatuses disclosed herein.

All drawings are not necessarily to scale. Components numbered and appearing in one figure but appearing unnumbered in other figures are the same unless expressly noted otherwise. A reference herein to a whole figure number which appears in multiple figures bearing the same whole number but with different alphabetical suffixes shall be constructed as a general refer to all of those figures unless expressly noted otherwise.

DETAILED DESCRIPTION

The features and benefits of the invention are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Chemical can be a solvent, an extractant, and/or a reagent. Solvent can be any fluid to make a slurry as described herein. In a preferred embodiment, the solvent is water because it is readily available, but any other solvent can be used. Solvent can be used as both a solvent and an extractant. Gas can be any gas. In a preferred embodiment, the gas is air because it is readily available, but any gas can be used.

Test material refers to supernatant, filtrate, or a combination of supernatant and filtrate. When used in this description in the specific form (supernatant or filtrate), the other forms of test material can also be used.

Fluid conveyor can be a pump, a pressure difference, or a combination of a pump and pressure difference.

Figure 1:
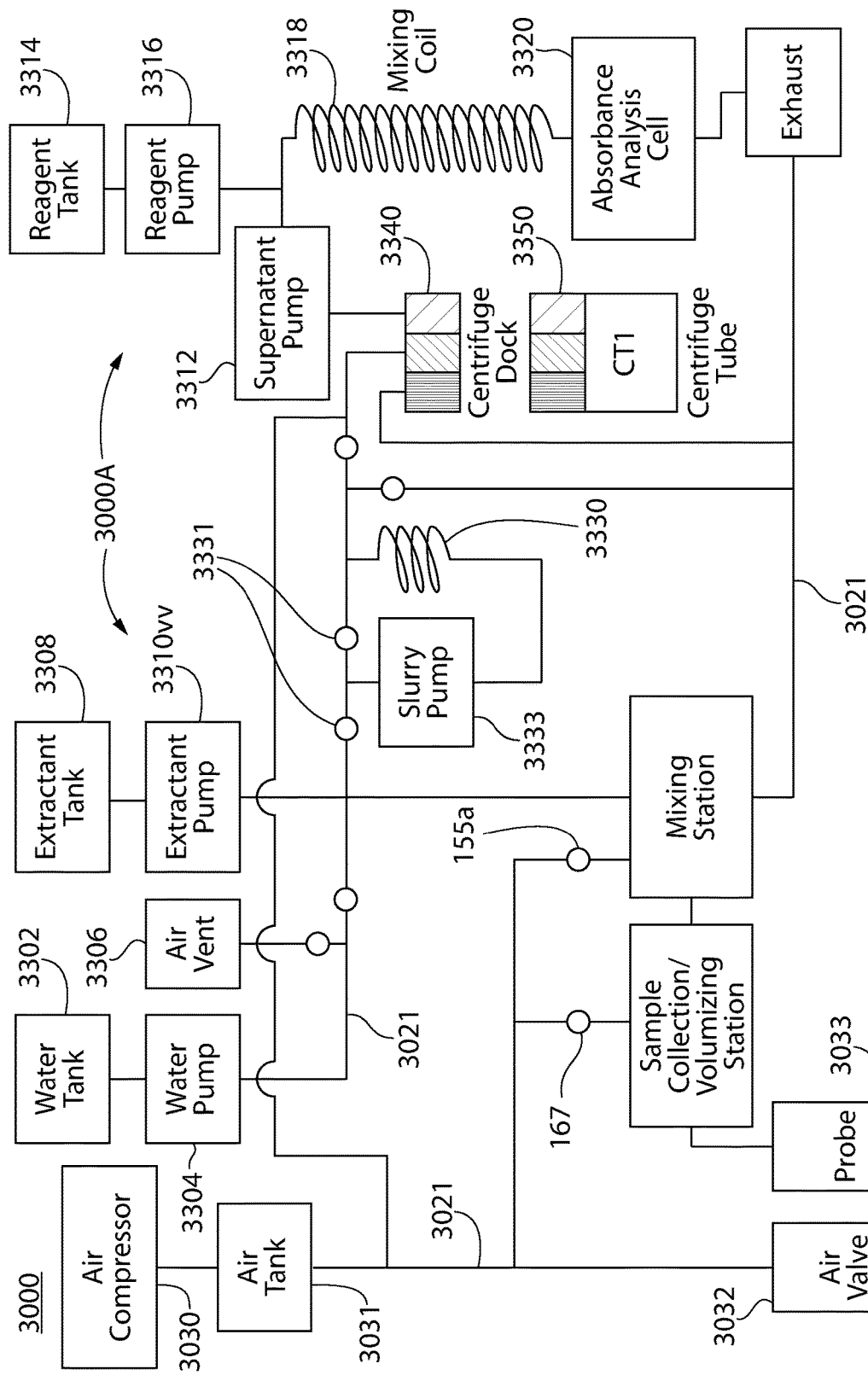
FIG. 1 is a schematic flow diagram of a soil sampling analysis system according to the present disclosure.
Figure 2:
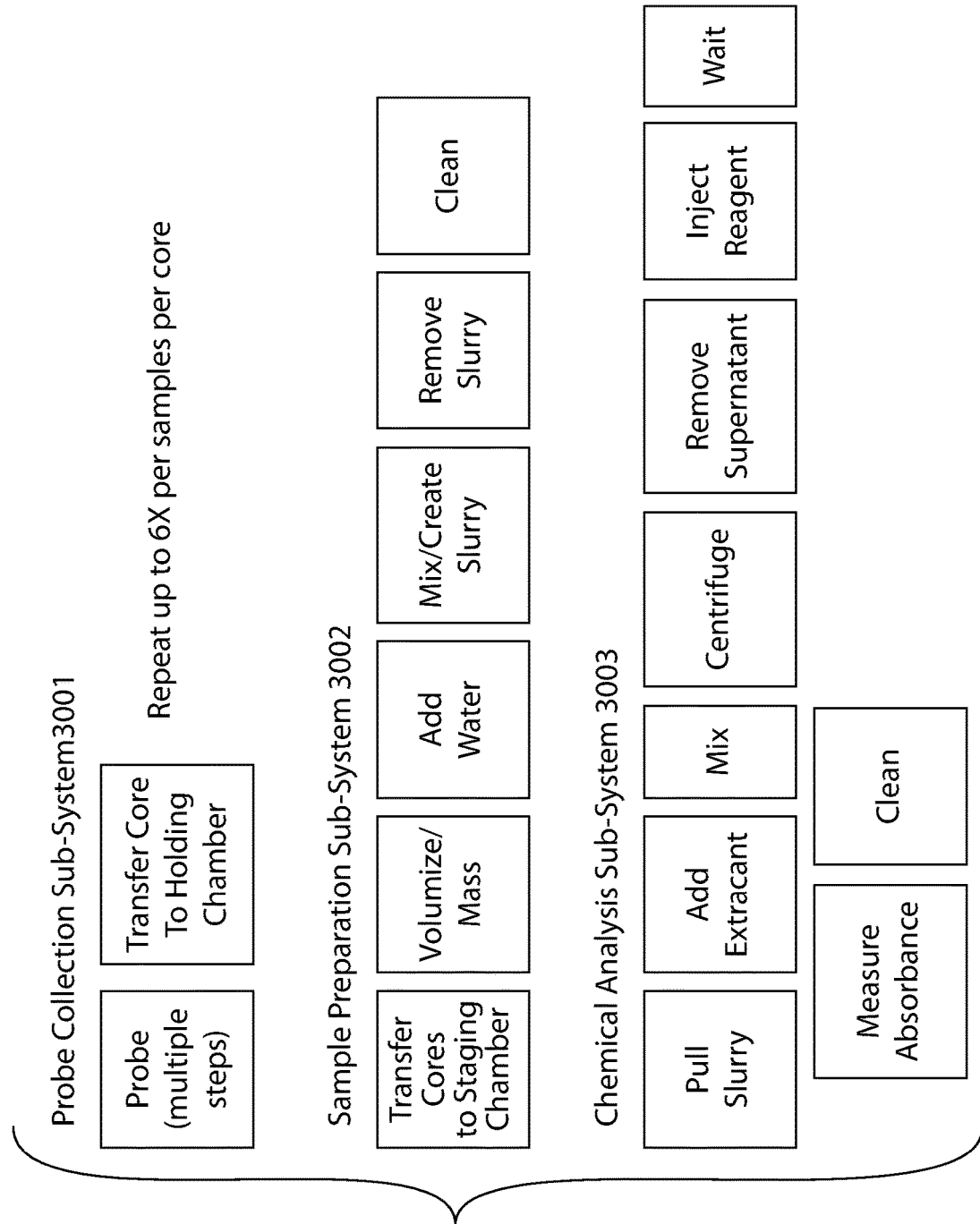
FIG. 2 is flow chart showing the functional aspects of each sub-system of the sampling analysis system.
Figure 3:
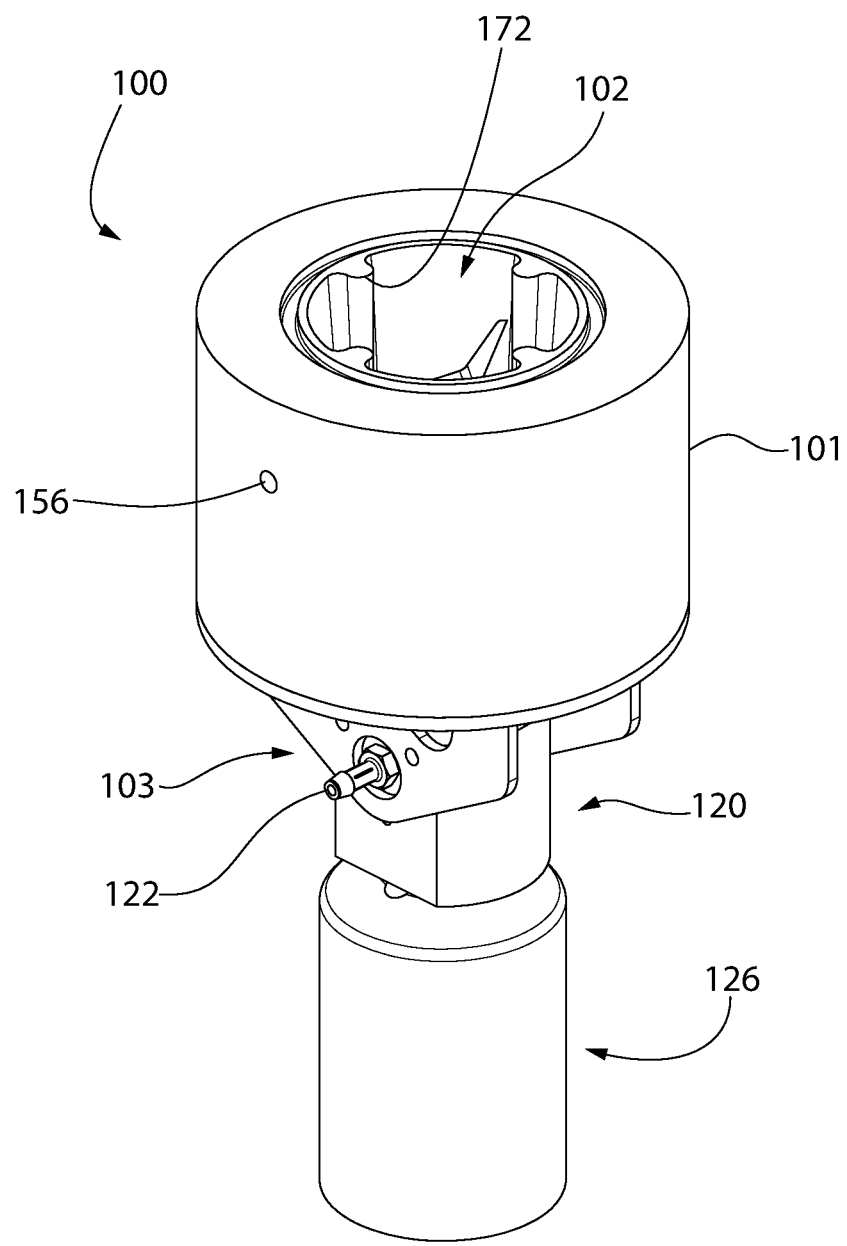
FIG. 3 is a top perspective view of a mixing device of the sample preparation sub-system.
Figure 4:
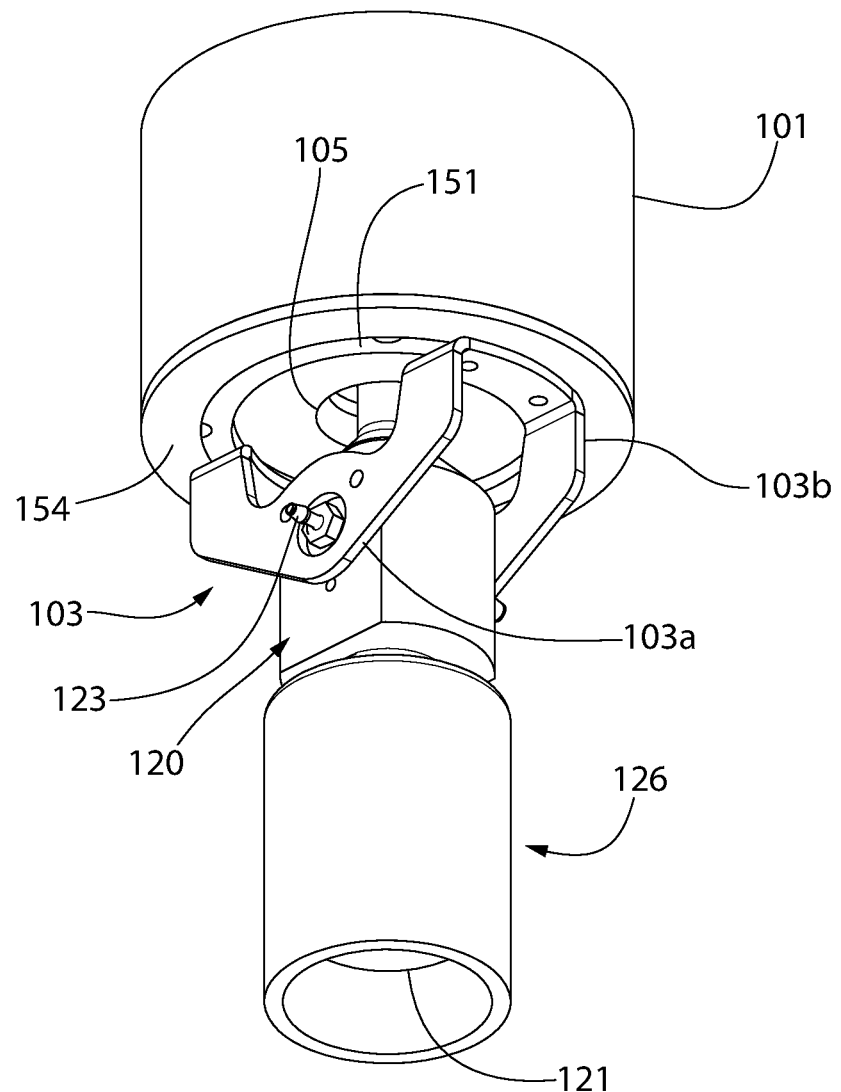
FIG. 4 is a bottom perspective view thereof.
Figure 5:
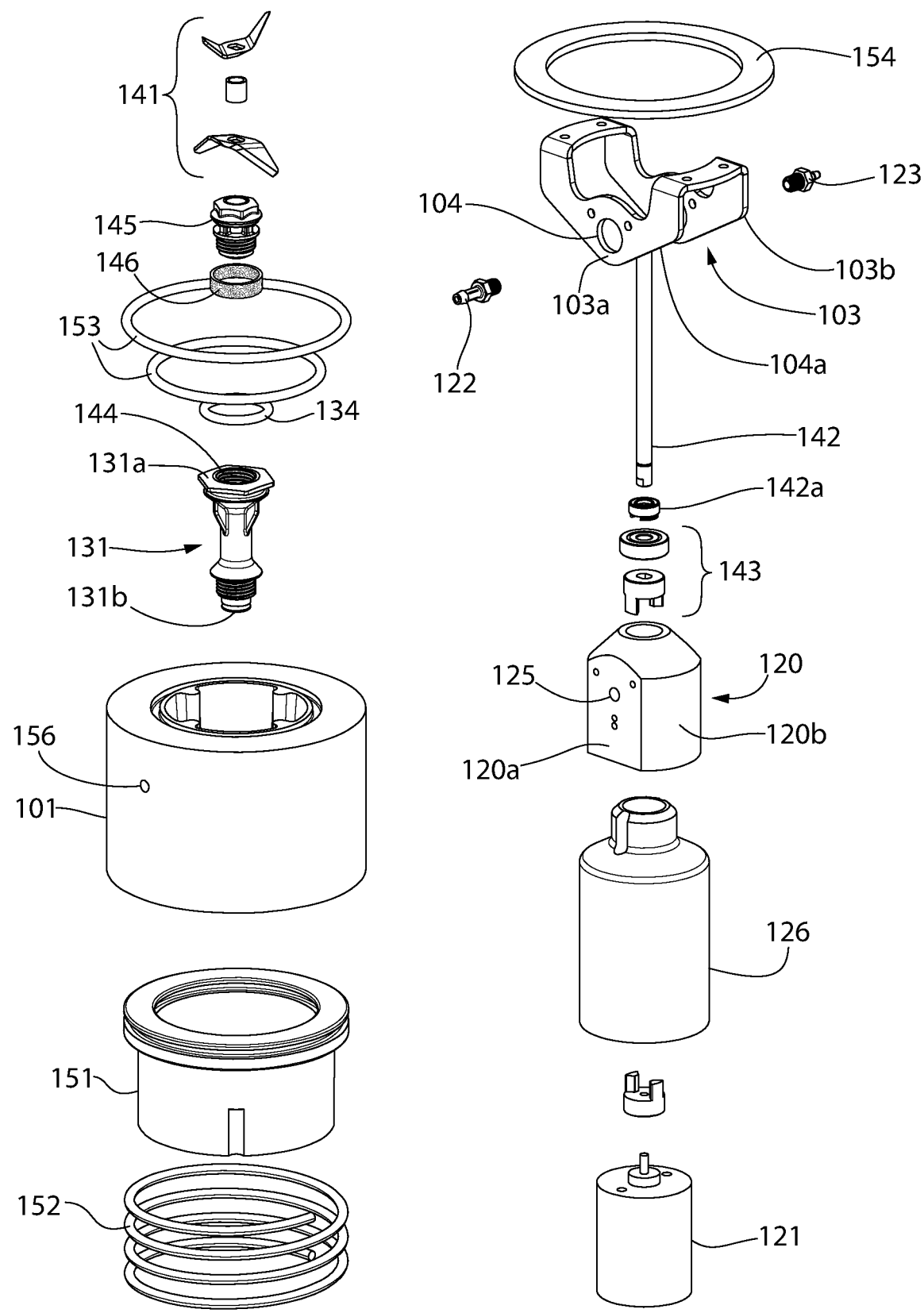
FIG. 5 is an exploded top perspective view thereof.
Figure 6:
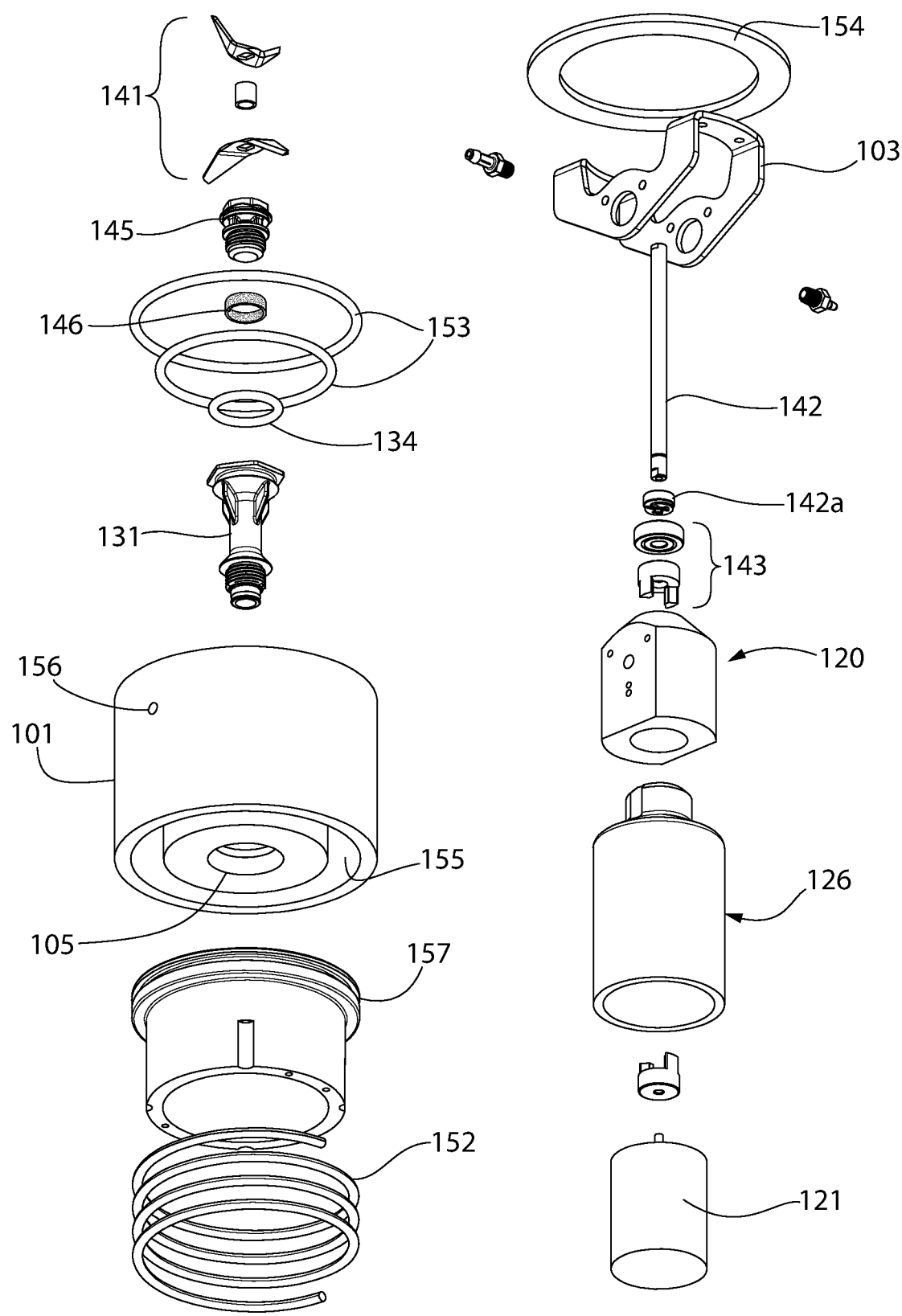
FIG. 6 is an exploded bottom perspective view thereof.
Figure 7:
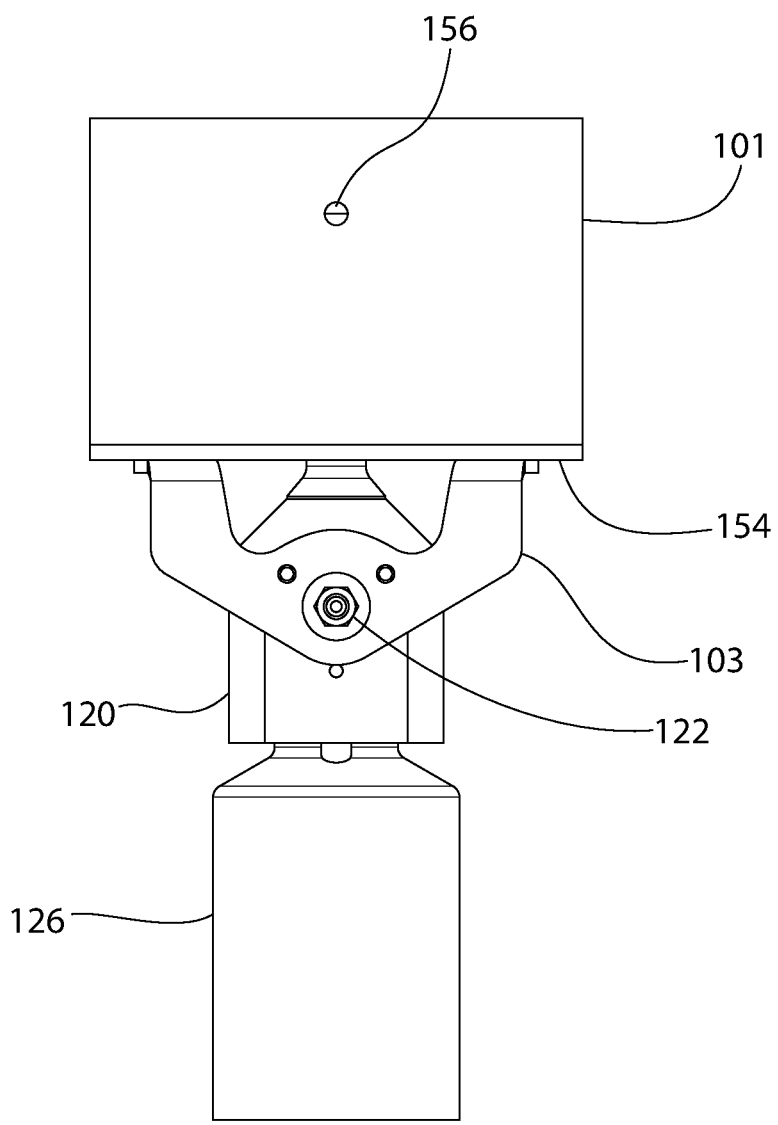
FIG. 7 is a front view thereof.
Figure 8:
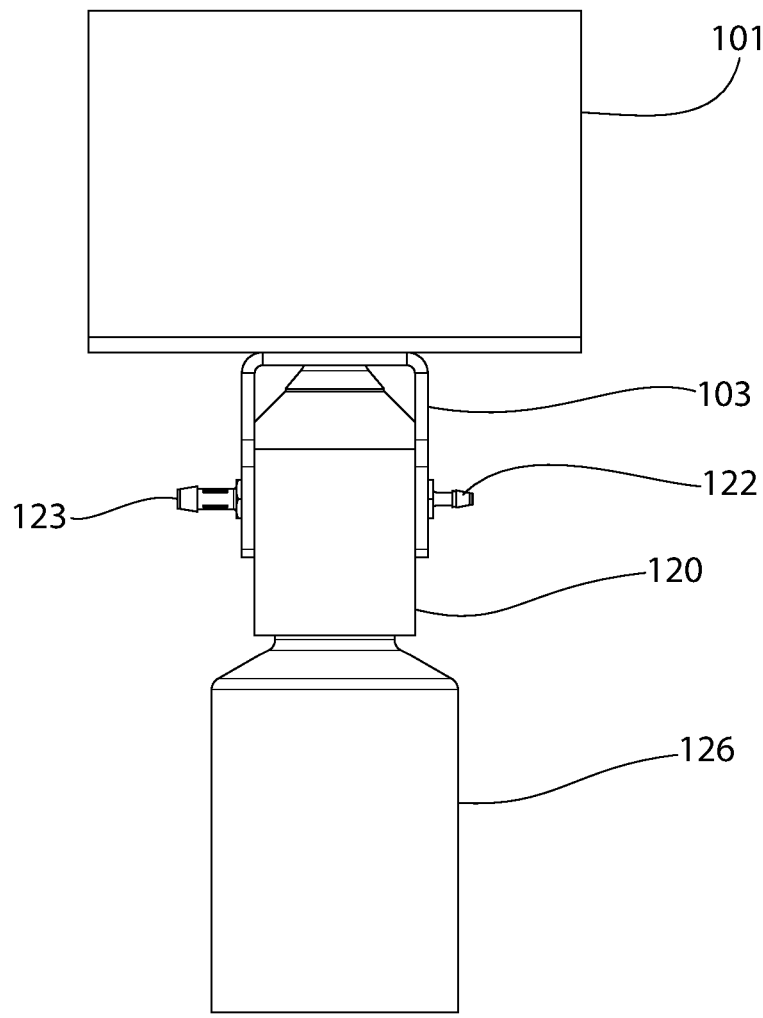
FIG. 8 is a first side view thereof.
Figure 9:
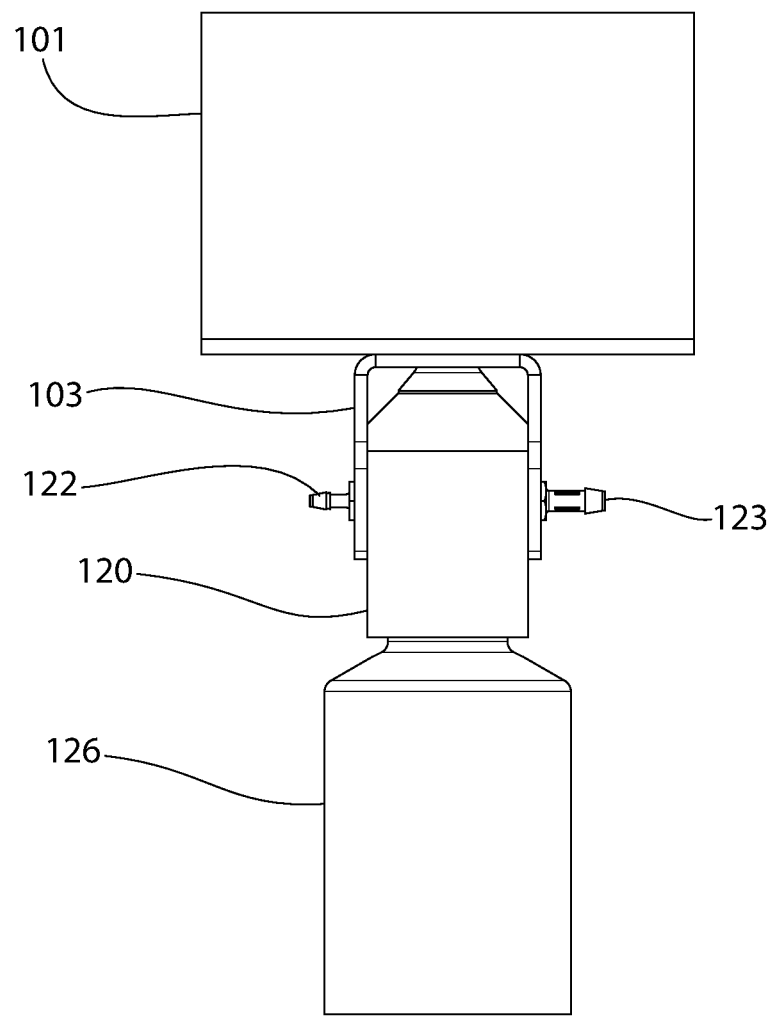
FIG. 9 is a second opposite side view thereof.
Figure 10:
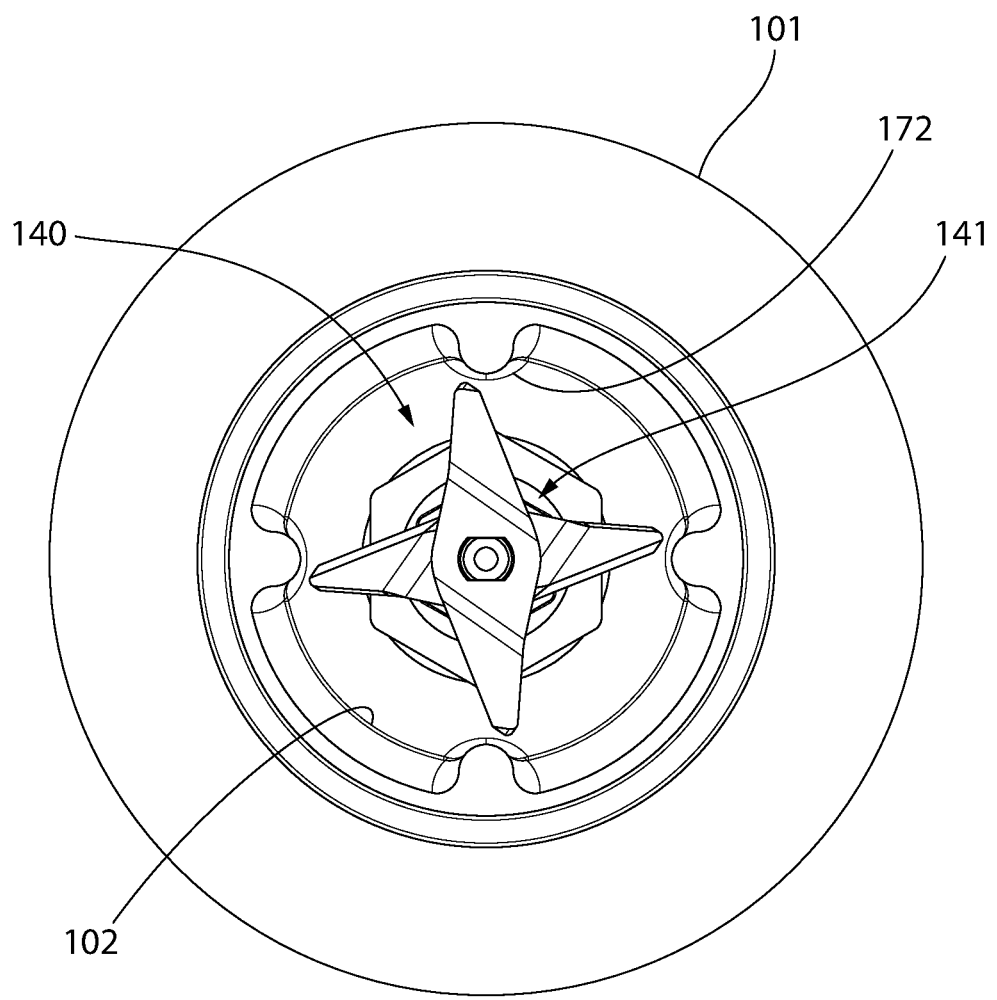
FIG. 10 is a top view thereof.
Figure 11:
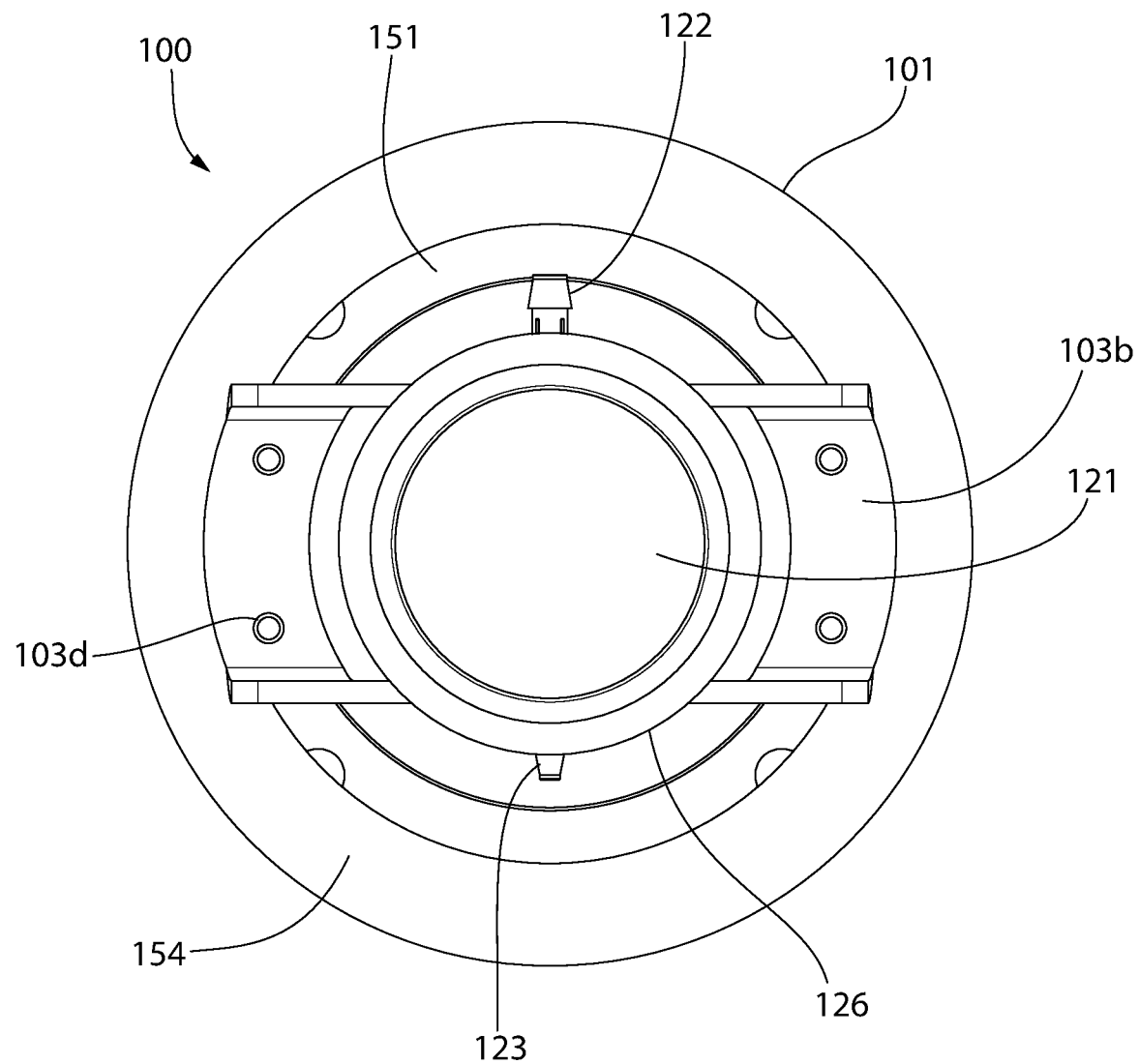
FIG. 11 is a bottom view thereof.

FIG. 1 is a schematic flow diagram of the soil sampling system 3000 according to the present disclosure. FIG. 2 is a flow chart describing the functional aspects of each sub-system of the sampling system. The sub-systems disclosed herein collectively provides complete processing and chemical analysis of soil samples from collection in the agricultural field, sample preparation, and final chemical analysis. In one embodiment, the system 3000 may be incorporated onboard a motorized sampling vehicle configured to traverse an agricultural field for collecting and processing soil samples from various zones of the field. This allows a comprehensive nutrient and chemical profile of the field to be accurately generated in order to quickly and conveniently identify the needed soil amendments and application amounts necessary for each zone based on quantification of the plant-available nutrient and/or chemical properties in the sample. The system 3000 advantageously allows multiple samples to be processed and chemically analyzed simultaneously for various plant-available nutrients.

The soil sampling system 3000 generally includes a sample probe collection sub-system 3001, a sample preparation sub-system 3002, and a chemical analysis sub-system 3003. The sample collection sub-system 3001 and motorized sampling vehicle are fully described in U.S. patent application Ser. No. 15/806,014 filed Nov. 7, 2017; which is incorporated herein by reference, thereby forming an integral part of the present disclosure. Sample collection sub-system 3001 generally performs the function of extracting and collecting soil samples from the field. The samples may be in the form of soil plugs or cores. The collected cores are transferred to a holding chamber or vessel for further processing by the sample preparation sub-system 3002.

The sample preparation sub-system 3002 generally performs the functions of receiving the soil sample cores in a mixer-filter apparatus 100, volumetric/mass quantification of the soil sample, adding a predetermined quantity or volume of filtered water based on the volume/mass of soil, and mixing the soil and water mixture to produce a soil sample slurry, removing or transferring the slurry from mixer-filter apparatus, and self-cleaning the mixer-filter apparatus for processing the next available soil sample.

The chemical analysis sub-system 3003 generally performs the functions of receiving the soil slurry from a mixer-filter apparatus 100 of sub-system 3002, adding extractant, mixing the extractant and slurry in a first chamber to pull out the analytes of interest (e.g. plant available nutrients), centrifuging the extractant-slurry mixture to produce a clear liquid or supernatant, removing or transferring the supernatant to a second chamber, injecting a reagent, holding the supernatant-reagent mixture for a period of hold time to allow complete chemical reaction with reagent, measure the absorbance such as via colorimetric analysis, and assist with cleaning the chemical analysis equipment.

The sample preparation and chemical analysis sub-systems 3002, 3003 and their equipment or components will now be described in further detail.

Mixer-Filter Apparatuses

FIGS. 3-18 depict a first embodiment of a mixer-filter apparatus 100 of the sample preparation sub-system 3002. Mixer-filter apparatus 100 has a substantially vertical structure and defines a corresponding vertical central axis VA1. The apparatus 100 generally includes a mixing container 101 defining an upwardly open internal mixing chamber 102 centered in the container, a fluid manifold chassis 120, an electric motor 121, and a movable piston-actuated stopper assembly 130. These components are arranged to define an inline sample processing unit. A mixing element 140 is mechanically coupled to motor 121 and disposed in mixing chamber 102 for producing a sample slurry. Motor 121 may be disposed inside and supported by a motor housing 126, which may be cylindrical in one non-limiting embodiment. Motor housing 126 may be fixedly mounted to the underside of manifold chassis 120, and in turn supports the motor 121 from the chassis. Motor 121 and housing 126 may be coaxially aligned with central axis VA1 in one embodiment.

In one embodiment, mixing container 101 may have a substantially cylindrical body. In addition to the upwardly open mixing chamber 102 which occupies the upper portion of the container 101, a downwardly open centered cleanout port 105 is formed in container body which is in fluid communication with the mixing chamber to allow the chamber to be cleaned out between samples processes through the container. Container cleanout port 105 may have a generally hourglass shape in one embodiment and defines an inwardly inclined or sloped annular seating surface 105a. An outwardly flared section 105b of cleanout port 105 below the seating surface 105a defines a diametrically narrower throat 105c between the flared section and seating surface (best shown in FIGS. 12 and 13). The mixing chamber 102 and cleanout port 105 collectively form a vertical fluid passage coaxially aligned with central axis VA1 passing completely through the mixing container 101 for flushing and dumping the contents of mixing chamber 102 between processing soil samples.

Fluid manifold chassis 120 may have a partial-cylindrical body in one configuration with a pair of opposing flat sides 120a and a pair arcuately curved sides 120b extending between the flat sides. The flat sides provide a convenient location for mounting the flow inlet and outlet nozzles 122, 123 and mounting bracket 103 thereto such as via threaded fasteners (not shown). In other possible configurations, however, the body of chassis 120 may have other shapes including completely cylindrical, rectilinear, polygonal, or have a variety of other shapes. The configuration of the chassis body is not limiting of the invention. The upper surfaces of chassis 120 may be sloped or angled to better shed water and debris when cleaning out the mixing chamber 102 of mixing container 101, as further described herein.

Fluid manifold chassis 120 includes a vertically-oriented central passageway 124, and opposing inlet and outlet flow conduits 125, 126 fluidly coupled to and in fluid communication with the central passage. Central passageway 124 may be coaxially aligned with central axis VA1. The flow conduits 125, 126 may be horizontally and perpendicularly oriented relative to the vertical central passageway 124 in one configuration. Inlet nozzle 122 is threadably and fluidly coupled to the inlet flow conduit 125. Similarly, outlet nozzle 123 is threadably and fluidly coupled to the outlet flow conduit 125. In one embodiment, the nozzles 122, 123 may have free ends configured for fluid connection to flow tubing. The central passageway 124 and inlet/outlet flow conduits 125, 126 may be formed in the body of fluid coupling chassis 120 by any suitable method, such as drilling or boring in some embodiments. Manifold chassis 120 may be formed of any suitable metallic or non-metallic material. In one embodiment, chassis 120 may be formed of metal such as steel or aluminum.

Referring to FIGS. 5-6 and 12-13, the piston-actuated stopper assembly 130 includes a vertically elongated stopper 131 including a top end 131a and bottom end 131b. Stopper 131 may have a generally cylindrical body configuration including a diametrically enlarged head 132 formed on the upper portion which is disposed in mixing chamber 102 of mixing container 101. In one embodiment, the stopper head 132 may be larger in diameter than the diameter of the container cleanout port 105 at throat 105c such that the stopper cannot be axially withdrawn in a vertical direction downwards from mixing chamber 102. Stopper head 132 is configured and operable to form a sealable engagement with the mixing chamber 102 of mixing container 101. More particularly, stopper head 132 defines an annular sealing surface 133 which sealingly engages mating annular seating surface 105a formed in mixing chamber 102 of mixing container 101. An annular seal 134, which may be an elastomeric or rubber O-ring in one embodiment, is mounted on stopper head 132 at sealing surface 133. The O-ring sealingly engages seating surface 105a of mixing container 101 to form a leak-resistant seal at the bottom of the mixing chamber 102 to close the mixing container cleanout port 105.

The cylindrical lower portion of stopper 131 beneath the enlarged head 132 may be diametrically narrower than throat 105c of the mixing container cleanout port 105, thereby allowing the lower portion to pass through the throat. In one embodiment, the bottom end 131b of stopper 131 may be externally threaded and threadably mounted to the top of fluid manifold chassis 120 at central passageway 124. The threaded bottom end 131b of stopper 131 threadably engages an internally threaded upper portion of the central passageway 124 (see, e.g. FIGS. 12-13).

Stopper 131 further includes a vertically oriented central bore 144 coaxially aligned with central axis VA1 and central passageway 124 of the fluid manifold chassis 120. Bore 144 extends completely through the stopper 131 from top end 131a to bottom end 131b. Central bore 144 is in fluid communication with mixing chamber 102 of container 101 at top and central passageway 124 of the fluid manifold chassis 120 at bottom of the bore.

Figure 12:
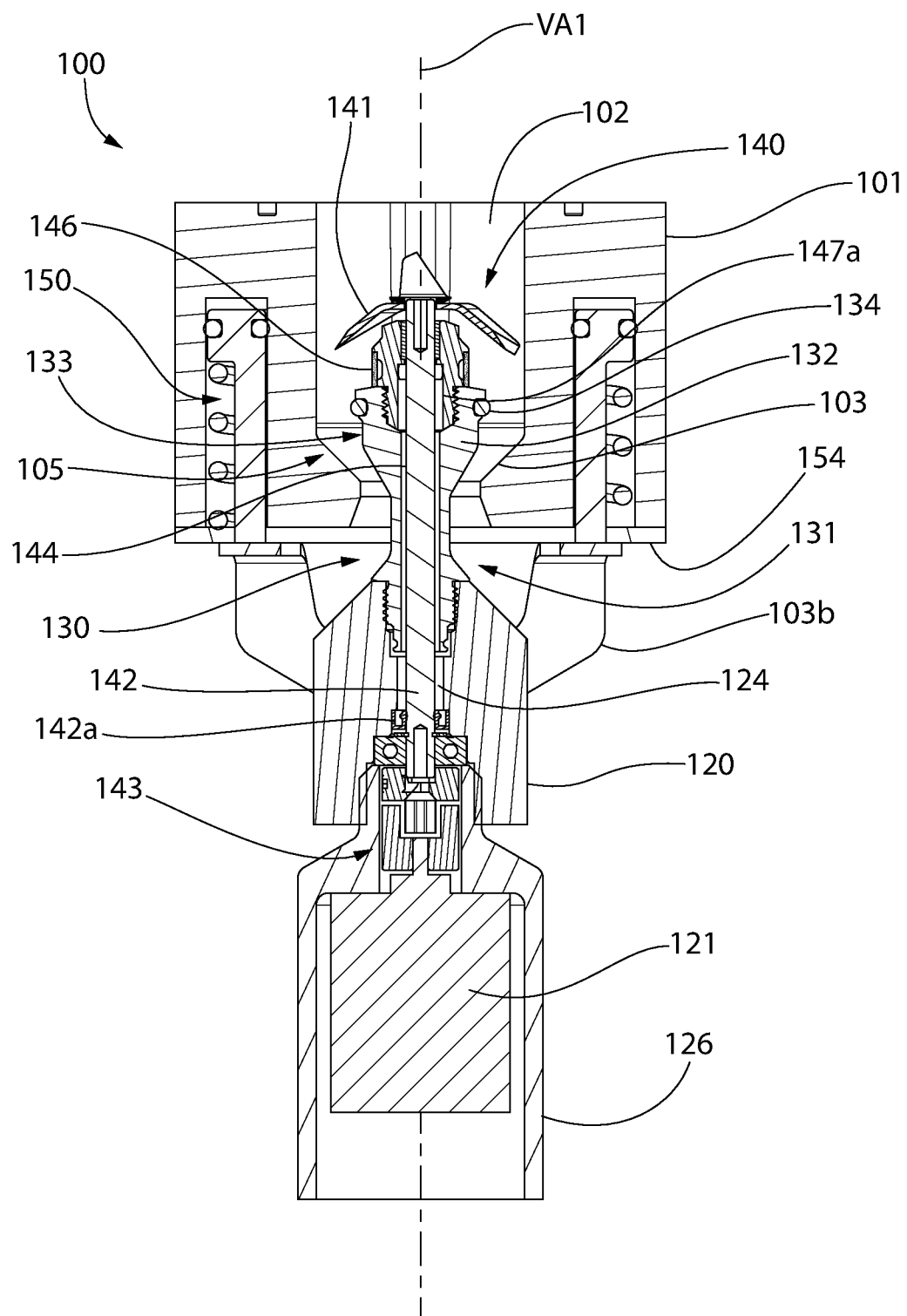
FIG. 12 is a front cross-sectional view thereof.
Figure 13:
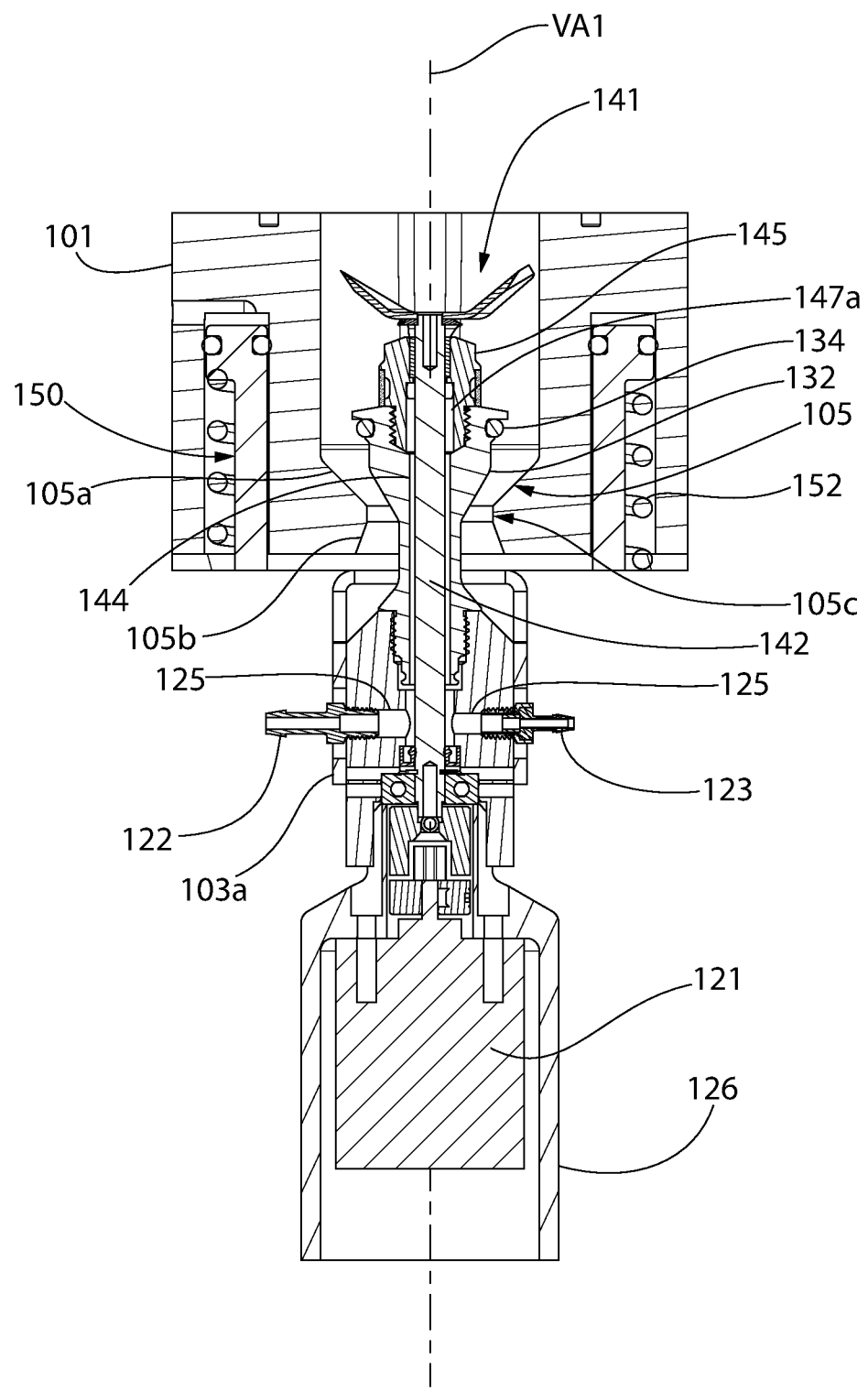
FIG. 13 is a side cross-sectional view thereof.

Motor drive shaft 142 extends through central bore 144 of stopper 131 and central passageway 124 of fluid manifold chassis 120 as shown in FIGS. 12 and 13. This forms an annular space or flow passage between the drive shaft 142 and the central bore 144 and passageway 124. The annular flow passage therefore provides a fluid path from adding water to mixing chamber 102 of mixing container 101, and extracting the fully mixed water and soil sample slurry from the mixing chamber 102 for further processing and chemical analysis.

Although stopper 131 and fluid manifold chassis 120 are depicted as separate discrete components, it will be appreciated that in other embodiments the stopper and chassis may be integral parts of a monolithic unitary structure cast, molded, and/or machined to provide the features disclosed.

Referring now to FIGS. 5-6 and 12-13, mixing element 140 generally comprises a blade assembly 141 fixedly mounted atop a vertical motor drive shaft 142 coupled to motor 121. Blade assembly 141 is therefor rotatable with the drive shaft 142. Drive shaft 142 may be coupled to motor 121 by a shaft seal 142a and flexible motor coupling assembly 143 in one embodiment. Seal 142a is configured to form a water-tight seal between the drive shaft 142 and manifold chassis 120. Drive shaft 142 is rotatably disposed in and extends completely through central bore 144 of stopper 131 and central passageway 124 of fluid manifold chassis 120.

Blade assembly 141 may be fixedly coupled to the top end of the drive shaft 142 by a threaded fastener in one embodiment. Blade assembly 141 is positioned in mixing chamber 102 and comprises a plurality of upwardly and downwardly angled blades to provide optimum mixing of the soil and water slurry in the mixing chamber. The blades may be formed of metal, and in one embodiment of a corrosion resistant metal such as stainless steel. Other materials may be used.

Blade assembly 141 is axially spaced apart from and positioned above top end 131a of stopper 131 exposing the top end of drive shaft 142 in the mixing chamber 102 of mixing container 101, as shown in FIGS. 12 and 13. This mounting position of the blade assembly also exposes the top of central bore 144 in stopper 131 to the mixing chamber 102 of mixing container 101 for two way fluid flow into/out of the mixing chamber.

In one embodiment, a filter assembly including a partially threaded filter retainer 145 and a detachable annular filter 146 is provided to filter the slurry extracted from the mixing chamber 102. FIGS. 38-42 show the retainer and filter in isolation. Filter retainer 145 includes a body having a vertical central bore 147a which communicates with a plurality of circumferentially arranged radial openings 147b for injecting water into mixing chamber 102 of container 101, and extracting slurry from the chamber. Bore 147a communicates with central bore 144 of stopper 131 to complete a fluid pathway between the manifold chassis 120 and mixing chamber 102. Motor drive shaft 142 is received through central bore 147a of the retainer. The annular filter 146 comprises an annular screen 146a disposed between the central bore 147a and mixing chamber 102. The screen includes a plurality of preselected size openings to filter out larger solids or particles from the soil slurry. Screen 146a may be in the form of screen mesh with rectilinear openings in one embodiment. The screen material may be metallic or non-metallic.

Retainer 145 includes a threaded bottom end or stem 148 which is threadably coupled to an internally threaded upper portion of the stopper central bore 144 (best shown in FIGS. 12-16, and in detail in FIGS. 38-42). The top end 149 of filter retainer is diametrically enlarged so as to trap the annular filter 146 between it and the top 131a of stopper 131 when the retainer is threaded into the stopper. Filter 146 is mounted to retainer 145 and the screen 146a covers the radial openings 147b to filter the slurry extracted from the mixing chamber 102. Top end 149 may include a tooling configuration such as a hex (shown) or other shape to facilitate threadably mounting the retainer 145 to the stopper 131. It bears noting that the central bore 147a of filter retainer 145 extends completely through the top and bottom ends 149, 148 to allow the drive shaft 142 to pass completely through the retainer, as shown.

Stopper 131 is fixedly coupled to a movable piston assembly 150 which operates to actuate and change position of the stopper in unison with the piston assembly movement. Referring to FIGS. 5-6 and 12-16, piston assembly 150 includes an annular piston 151, spring 152, spring retaining ring 154, and a pair of piston seal rings 153 which in one embodiment may be elastomeric or rubber O-rings. Piston 151 may have a sleeve-like construction and includes bottom and top ends. Piston 151 is slideably received in a downwardly open annular space 155 formed in the mixing container 101 between its cylindrical outer sidewalls 101a and bottom central cleanout port 105. The piston 151 is movable upward and downwards in annular space 155 between upper and lower positions.

The top of piston 151 may have a diametrically enlarged top rim 157 with outward facing annual grooves for mounting the pair of seal rings 153. Rim 157 protrudes radially outwards from the body of the piston 151 as shown. One seal ring 153 is an inner seal ring providing an inboard seal between the piston and container 101, and the other seal ring 153 is an outer seal ring providing an outboard seal.

The piston spring 152 is received and retained in the annular space 155 of mixing container 101 by retaining ring 154 fixedly attached to the bottom of the container. The top end of the spring 152 acts on the underside of the top rim 157 of piston 151 and the bottom end acts on the retaining ring 153. Spring 152 biases the piston 151 upwards inside annular space 155 of container 101 to the upper position. In one non-limiting embodiment, spring 152 may be a helically coiled compression spring. Other appropriate type springs may be used.

Piston 151 may be supported from and is mechanically coupled to fluid manifold chassis 120 by a generally U-shaped mounting bracket 103. Bracket 103 in one embodiment may comprise a lower portion formed by a pair of transversely spaced apart plate-like legs 103a fixedly attached to opposing sides of chassis 120, and a pair of plate-like upwardly extending arms 103b fixedly attached to the underside of the piston 151. Each leg 103a may include a transversely open hole 104 to accommodate inlet and outlet nozzles 122, 123 coupled to chassis 120 which extend through the holes. Mounting bracket 103 may be fixedly attached to the piston 151 and chassis 120 by threaded fasteners 103d in one embodiment (see, e.g. FIG. 11). Other configurations of mounting brackets and methods of attachment may of course be used.

The combination of the mounting bracket 103 and manifold chassis 120 collectively creates a generally rigid mechanical linkage that couples the stopper 131 to piston 151. The fluid manifold chassis 120, motor 121/motor housing 126, and stopper 131 thus move in unison with the piston 151 as a singular unit upwards and downwards when the piston 151 is actuated. The piston 151 thus acts as an actuator for stopper 131, and is operable to control and change the position of stopper.

In one embodiment, piston 151 may be pneumatically operated by pressurized air. Piston 151 is configured for spring return operation. The annular space 155 of container 101 may be considered to form an annular piston cylinder in which piston 151 moves upwards and downwards. An air exchange port 156 is formed through the circumferentially-extending outer sidewall 101a of the container 101 and fluidly connects to the top of annular space 155 (see, e.g. FIG. 14). Port 156 is in fluid communication with region of annular space 155 located above the piston 151.

Figure 16:
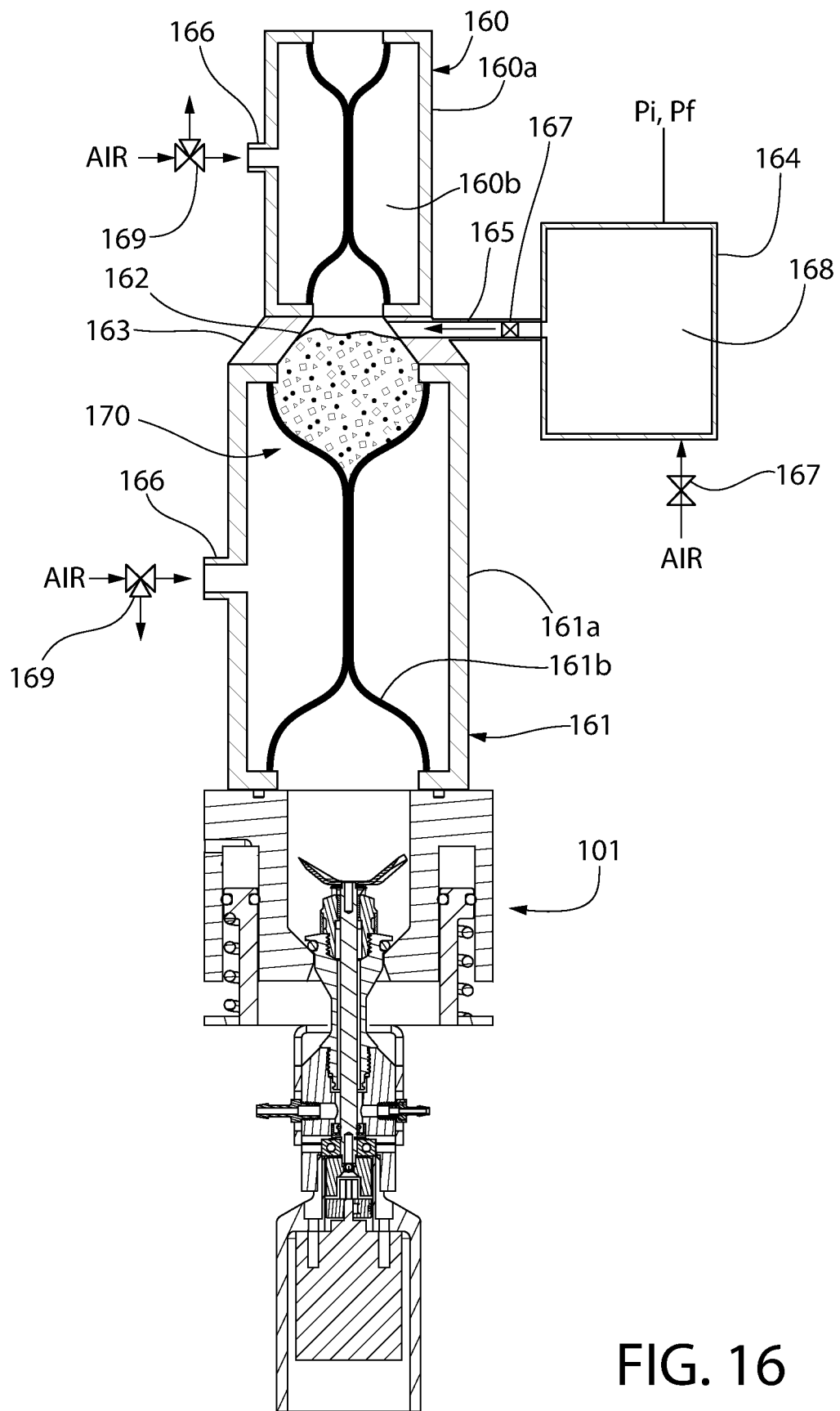
FIG. 16 is a second sequential view thereof showing the upper pinch valve closed.

In operation, piston 151 is normally biased upwards to the upper position shown in FIG. 16 by spring 152. To move the piston 151 to the lower position in annular space 155 of container 101, pressurized air is introduced into in the annular space and applied to the piston top rim 157 via the air exchange port 156 (see, e.g. FIG. 14 and directional air flow arrows). The air pressure forces the piston downwards, thereby compressing the spring. Air pressure must be continually applied to hold the piston 151 in the lower position against the biasing action of spring 152. To return the piston to its upper position, the pressurized air is bled off annular space 155 in container 101 outwards through the air exchange port 156 (see, e.g. directional flow arrows, FIG. 16). The spring 152 then urges the piston 151 back upwards to its upper spring-biased position in FIG. 14.

It bears noting that the air exchange port 156 is fluidly connected to a pressured source of compressed air such as compressor 3030 and air tank 3031 via air supply valve 3032 shown in FIG. 1 via a suitable flow conduit such as flexible and/or rigid hosing or tubing 3021. Tubing 3021 may be metallic or non-metallic. In some embodiments, fluoropolymer type slurry tubing may be used to transport slurry in various places in the system due to its inherent non-stick characteristics making it ideal for soil slurries. FEP (Fluorinated Ethylene Propylene) is a specific example of one fluoropolymer that may be used. FEP is similar to using teflon-based PTFE material due to its non-stick characteristics, but FEP is advantageously more transparent and moldable with standard tubing formation practices.

A three-way air valve 155a with an exhaust port may be fluidly coupled to and located upstream of port 156 (see, e.g. FIG. 19) to either pressurize the container annular space 155 or exhaust air to atmosphere from the annular space.

Figure 20:
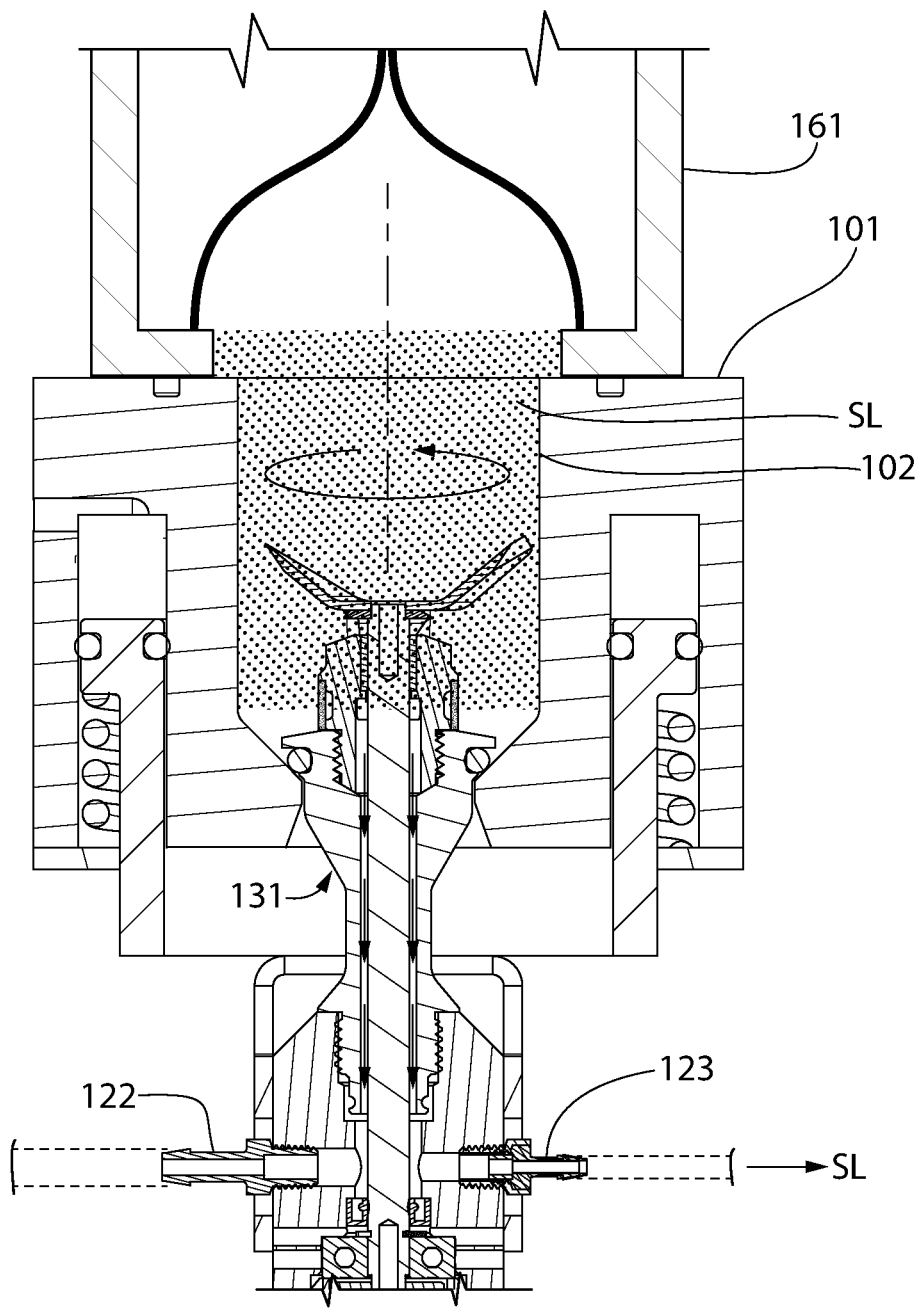
FIG. 20 is a sixth sequential view thereof showing the mixing device blending the soil sample and water to prepare a slurry.
Figure 21:
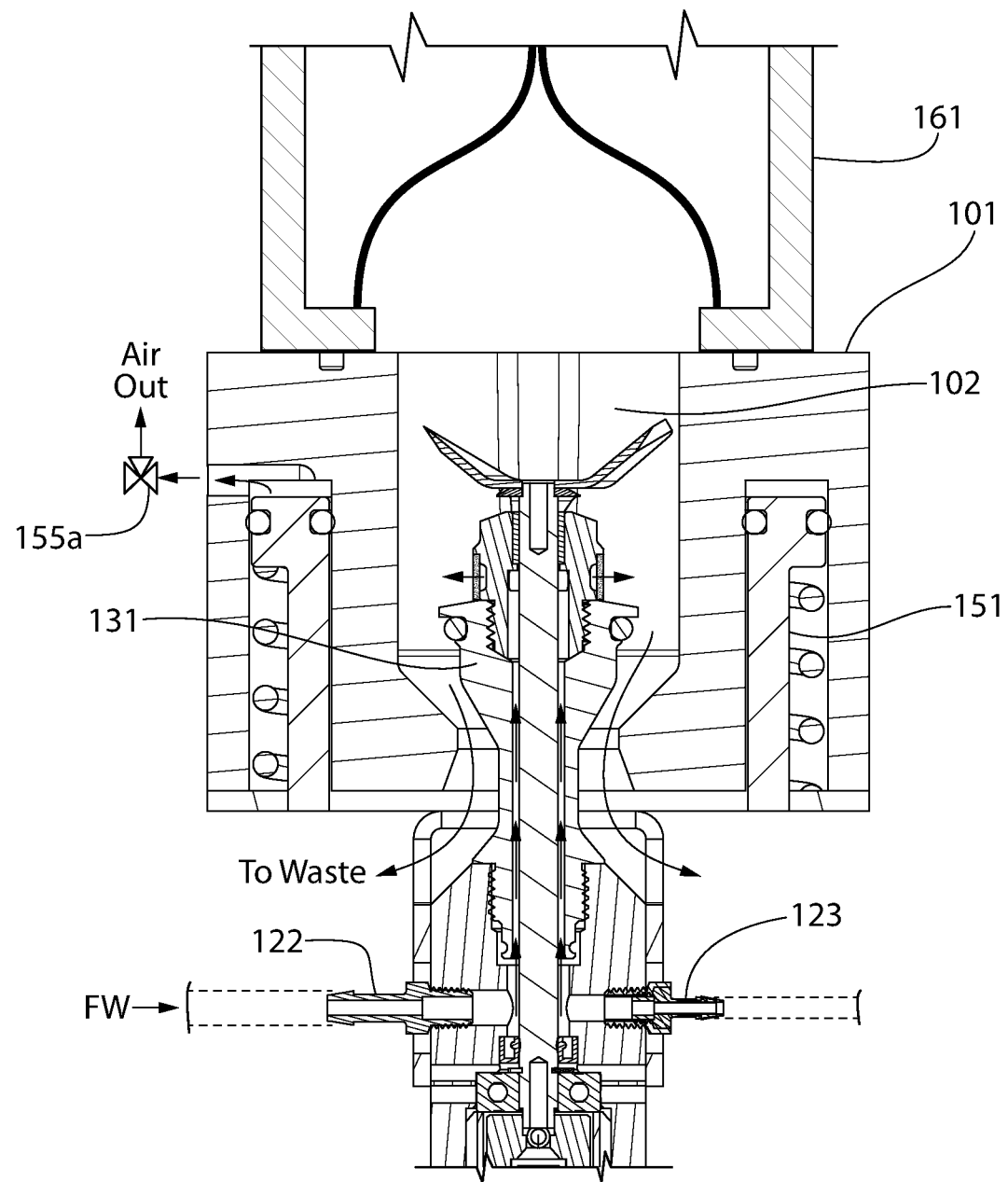
FIG. 21 is a seventh sequential view thereof showing the slurry removed from the mixing device and water injected into the mixing chamber for cleanout with the stopper of the mixing chamber in an open position.

By actuation of the piston assembly 150, the stopper 131 is axially movable in a vertical direction relative to mixing container 101 between a lower closed position (see, e.g. FIGS. 19-20) and an upper open position (see, e.g. FIG. 21). In the closed position, the stopper head 132 is sealingly engaged with annular seating surface 105a in container mixing chamber 102. This position closes and blocks the bottom container cleanout port 105. This position corresponds to the lower portion of piston 151 in the container 101 (see, e.g. FIGS. 18 and 19).

Conversely, in the open position, the stopper head 132 of stopper 131 disengages the seating surface 105a in container mixing chamber 102. This position corresponds to the upper position of piston 151 (see, e.g. FIG. 21). This position thus opens cleanout port 105 and establishes a cleanout flow path for rinsing and cleaning the mixing chamber 102 with filtered water after mixing and volumizing a soil sample in preparation for the next soil sample to be mixed and volumized. When the stopper head 132 is in the open position, an annular shaped cleanout path and zone is created between the stopper 131 and internal walls of the mixing chamber 102 that extends for a full 360 degrees around the stopper.

It bears noting that the fluid manifold chassis 120 attached to stopper 131, motor housing 126 (with motor 121 therein) attached to the chassis, and the blade assembly 141 with drive shaft 142 move in unison as a single unit with the stopper 131 between the lower closed position and upper open position when actuated.

In order to process, stage, and test multiple soil samples semi-concurrently, an assembly of inline valves and related components are provided as shown in FIGS. 14-18. The assembly is further configured and operable to volumize the soil sample, thereby representing and collectively forming a sample collection/volumizing station 160-1. Volumizing the sample is used to indirectly quantify the mass of the sample to determine the appropriate amount of water to add in the mixing chamber 102 (i.e. water/soil ratio) to prepare the sample slurry with the appropriate consistency or viscosity for further processing and chemical testing. In one embodiment, the assembly which defines a sample collection/volumization station comprises a pair of vertically stacked squeeze or pinch valves 160 and 161, an intermediate collar 163 defining an inner plenum 162 fluidly coupled between the valves, and a volumization vessel 164. Vessels 164 is a pressure vessel defining an initial volumization chamber 168 therein of known volume. Chamber 168 is fluidly coupled to a source of pressurized air such as compressor-tank assembly 30, 31 controlled by air valve 167 in tubing 21 at an inlet side of the vessel. Chamber 168 is further fluidly coupled to plenum 162 via an outlet tube 165 controlled by another air valve 167.

Pinch valves 160, 161 may be air actuated in one embodiment. Pinch valves are known in the art and commercially available for controlling the flow of solid materials such as soil. Each pinch valve 160/161 includes a valve body 160a/161a defining an internal space containing a flexible collapsible diaphragm or sleeve 160b/161b as shown. The sleeves may be made of any suitable elastomeric material, such as for example rubber, nitrile, butyl, silicon, or others. Each valve 160, 161 includes an air exchange port 166 controlled by a three-way air valve 169 including an exhaust port at one position. The lower valve 161 is sealingly and fluidly coupled to the mixing container 101 and in fluid communication with the mixing chamber 102.

Figure 14:
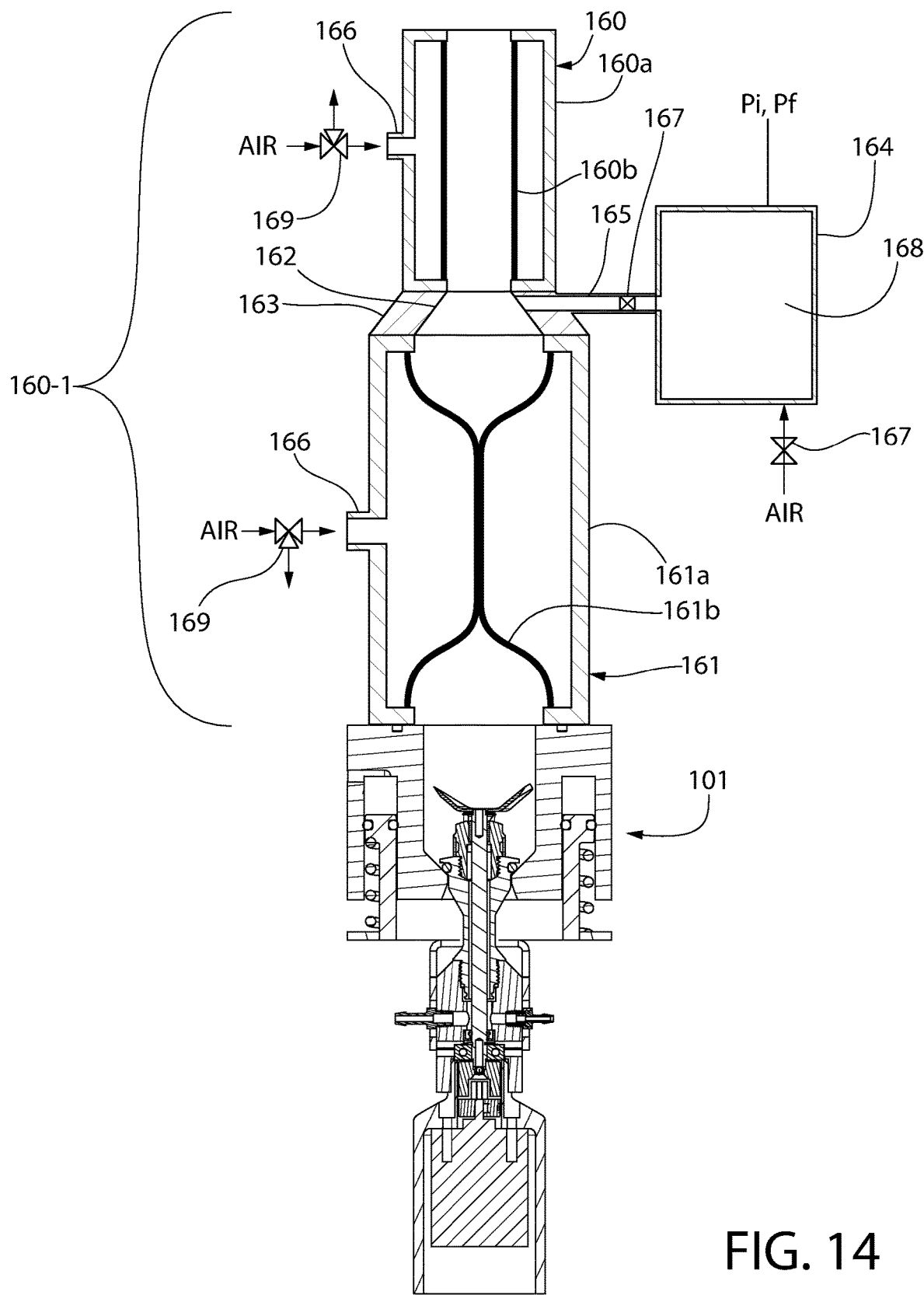
FIG. 14 is a side cross-sectional view of a sample collection/volumizing station mounted atop the mixing device and comprising an upper pinch valve in an open position and lower pinch valve in a closed position.

In the open position, the sleeves 160b, 161b of valves 160, 161 are spaced apart in generally parallel relationship to allow material to flow through the valves (see, e.g. FIG. 14, upper valve 160). To close the valves, air is injected into the internal space surrounding the sleeve which pressurizes the interior of the valves. This collapses the sleeve into a closed pinched position to seal against itself for blocking the flow of material (see, e.g. FIG. 14, lower valve 161). To return valve 160 for example to the open position, air is bled back off the internal space surrounding the sleeve 160b through air exchange port 166 and exhausted via the exhaust port of three-way valve 169 to atmosphere.

Staging of the soil samples and volumizing the sample (i.e. determining the mass or volume of the soil sample via a volume/pressure analysis technique) will now be briefly described with reference to FIGS. 14-18. This helps identify the proper amount of water to be added to the sample to produce the desired consistency (water/soil ratio). These preliminary processing steps are completed before preparing the slurry. Referring to FIG. 302, the process shown in FIGS. 14-18 and described below may be automatically controlled and monitored by a processor-based control system 2800 including a programmable central processing unit (CPU) (e.g. processing system) referred to herein as system controller 2820, such as disclosed in copending U.S. patent application Ser. No. 15/806,014 filed Nov. 7, 2017; which is incorporated herein by reference. As further described elsewhere below, system controller 2820 may include one or more processors, non-transitory tangible computer readable medium, programmable input/output peripherals, and all other necessary electronic appurtenances normally associated with a fully functional processor-based controller.

The processing system 2820 may further control operation of the mixer-filter apparatus 100 and other portions of sample preparation sub-system 3002, and the operation of chemical analysis sub-system 3003 described in detail elsewhere herein. This provides a unified control system for directing and coordinating all operations of the systems and components described herein.

Figure 15:
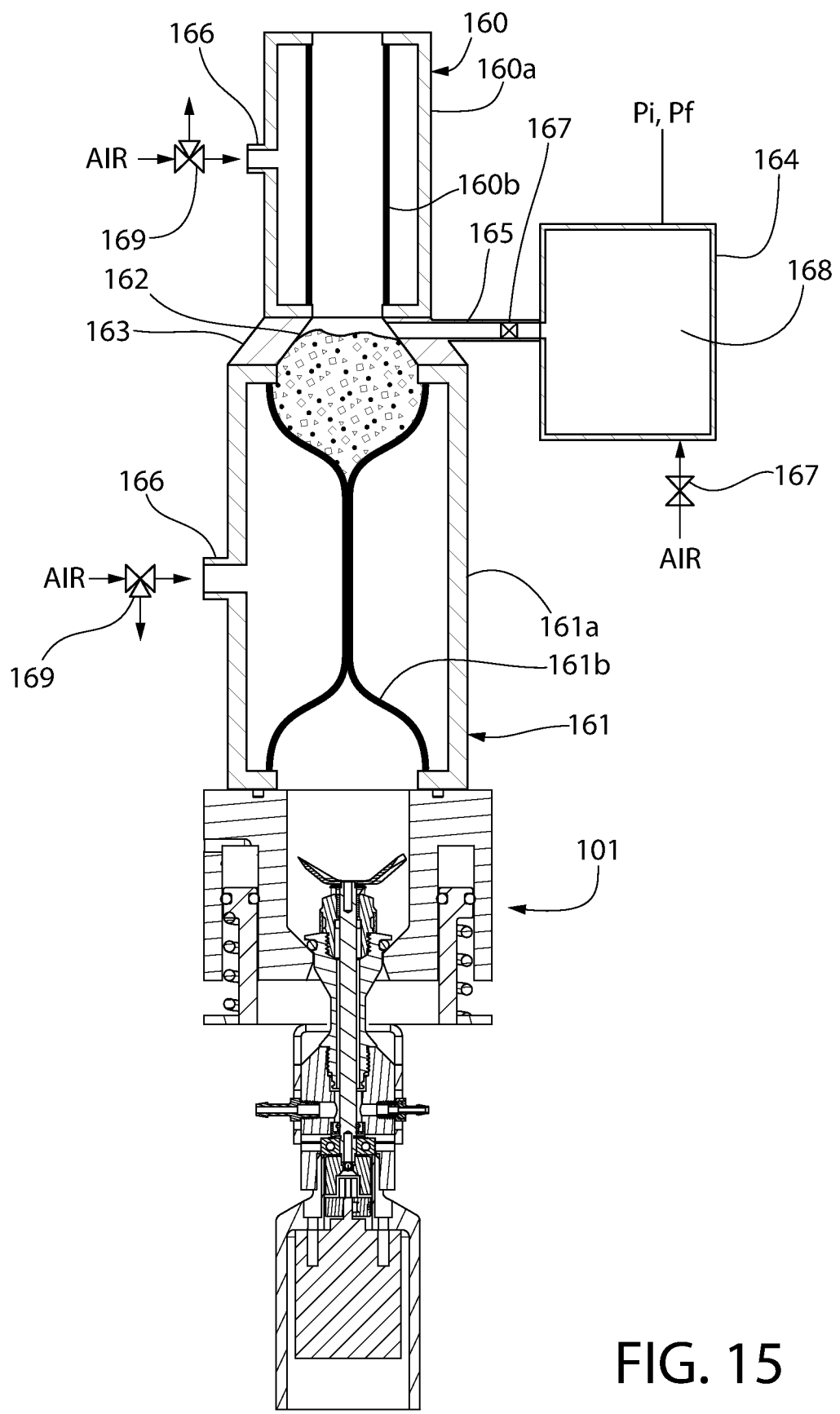
FIG. 15 is a first sequential view thereof showing a soil sample staged in lower pinch valve for mixing and stopper of the mixing chamber in a closed position.

Both pinch valves 160, 161 may initially be in an open position at the start of the process in some sequences. FIG. 14 next shows the pinch valves 160, 161 now in a position ready to receive a soil sample (which may comprise a blend of one or more cores) from the probe collection sub-system 3001 (see, e.g. FIG. 1). The lower valve 161 is first closed and the upper valve 160 remains open. If not already pressurized, the volumization chamber 168 may optionally be "charged" with air at this time as well to save processing time. The outlet valve 167 from volumization vessel 167 is closed during the charging step. The soil sample is next blown into valve 160 using pressurized air from the probe collection sub-system 3001 previously described herein, as shown in FIG. 15. The soil is deposited on top of sleeve 161b of the lower valve 161.

The upper valve 160 is next closed as shown in FIG. 16. This establishes a temporary sealed or trapped predetermined volume containing the soil which is referred to herein as a soil "staging chamber" 170 for convenience. Chamber 170 is fluidly isolated from the mixing chamber 101 by closed valve 161. The staging chamber 170 is collectively formed by the plenum 162 and internal space between the closed sleeves of the upper and lower valves 160, 161. An initial pressure reading Pi of the volumization chamber 168 is then measured and read by the processing system 2820. Pressure readings Pi may be averaged over a short period of time for accuracy. Next, the outlet valve 167 between the volumization chamber 168 and staging chamber 170 is opened to admit pressurized air from the volumization vessel 164 into the staging chamber. The pressure equalizes between the staging chamber 170 and volumization chamber 168 which are in fluid communication now that the outlet valve has been opened. A final pressure Pf, lower than Pi of the volumization chamber 168 alone when pressurized and previously isolated, is then measured and read by the system 2820. Pressure readings Pf may also be averaged over a short period of time for accuracy. Pressure reading Pf represents the collective pressure measured in the volumes that include the staging chamber 170, volumization chamber 168, and valving and tubing therebetween.

The processing system 2820 next automatically indirectly calculates the soil "mass" equated to a "volume" to determine the proper amount of water to add to the mixing chamber for achieving the desired water/soil ratio and consistency of the slurry. The volume of the soil may be calculated using Boyles Law: $Pi*Vp=Pf(Vp+Vc-Vs)$ where $Vc$=Volume of the staging chamber 170; $Vp$=Volume of initial volumization chamber 168; $Vs$=Volume of soil; $Pi$=Initial pressure of volumization chamber 168; and $Pf$=Final equilibrium pressure of connected volumes of the staging chamber 170 and volumization chamber 168 as noted above. The equation is solved for $Vs$ to identify the volume of soil in the staging chamber 170 to be dumped into the mixing container 101. The processing system 2820 then calculates the amount or volume of water to be added based on preprogrammed water/soil ratios to yield the proper consistency or viscosity of the sample slurry for chemical analysis. It will be appreciated that other possible volumizing methods of the soil sample may be used.

Figure 17:
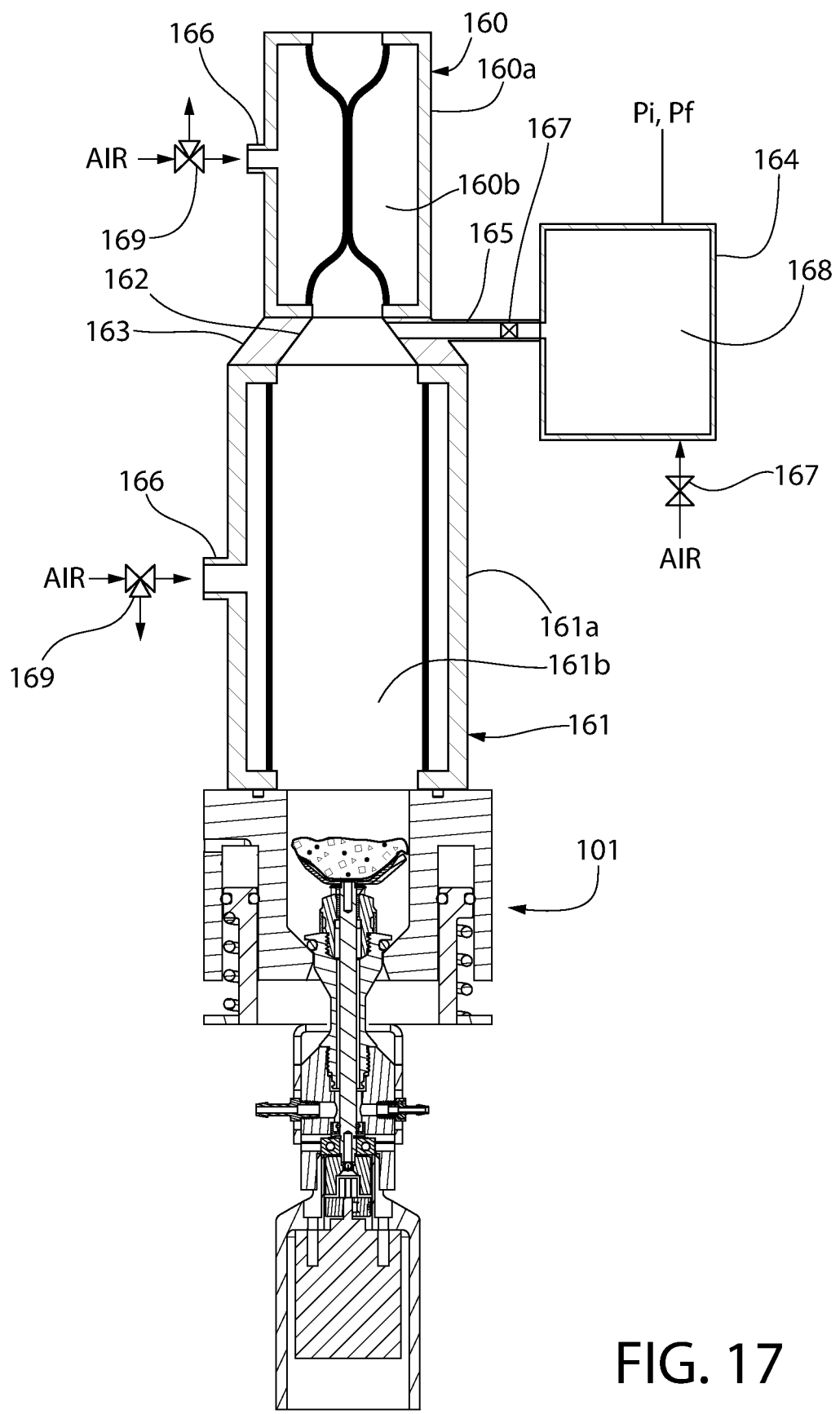
FIG. 17 is a third sequential view thereof showing the lower pinch valve open and the soil sample deposited in the mixing device.
Figure 18:
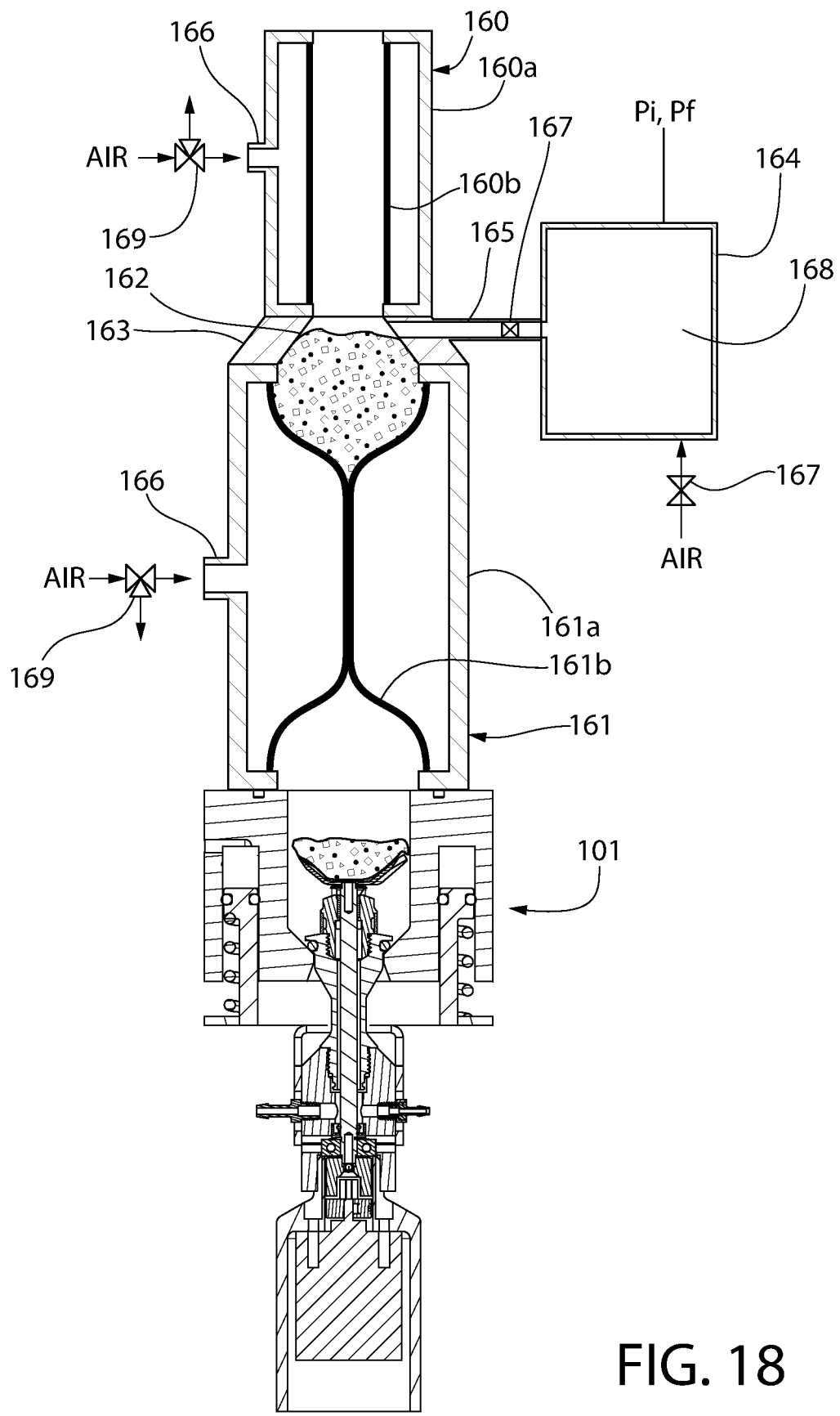
FIG. 18 is fourth sequential view thereof showing a second soil sample staged in the lower pinch valve in standby for mixing.

Once the sample has been volumized, slurry preparation may begin. As shown in FIG. 17, the lower valve 161 is opened to dump or add the soil sample into mixing chamber 101 of container 101. This eliminates the temporary staging chamber 170 until the next sample is processed and volumized. The upper valve 160 remains closed at this point. In order to stage the next waiting sample for slurry preparation, however, the lower valve 161 may be closed and the upper valve 160 opened to admit the next sample as shown in FIG. 18. This operation may occur semi-concurrently with processing of the first sample in the mixer-filter apparatus 100.

Figure 19:
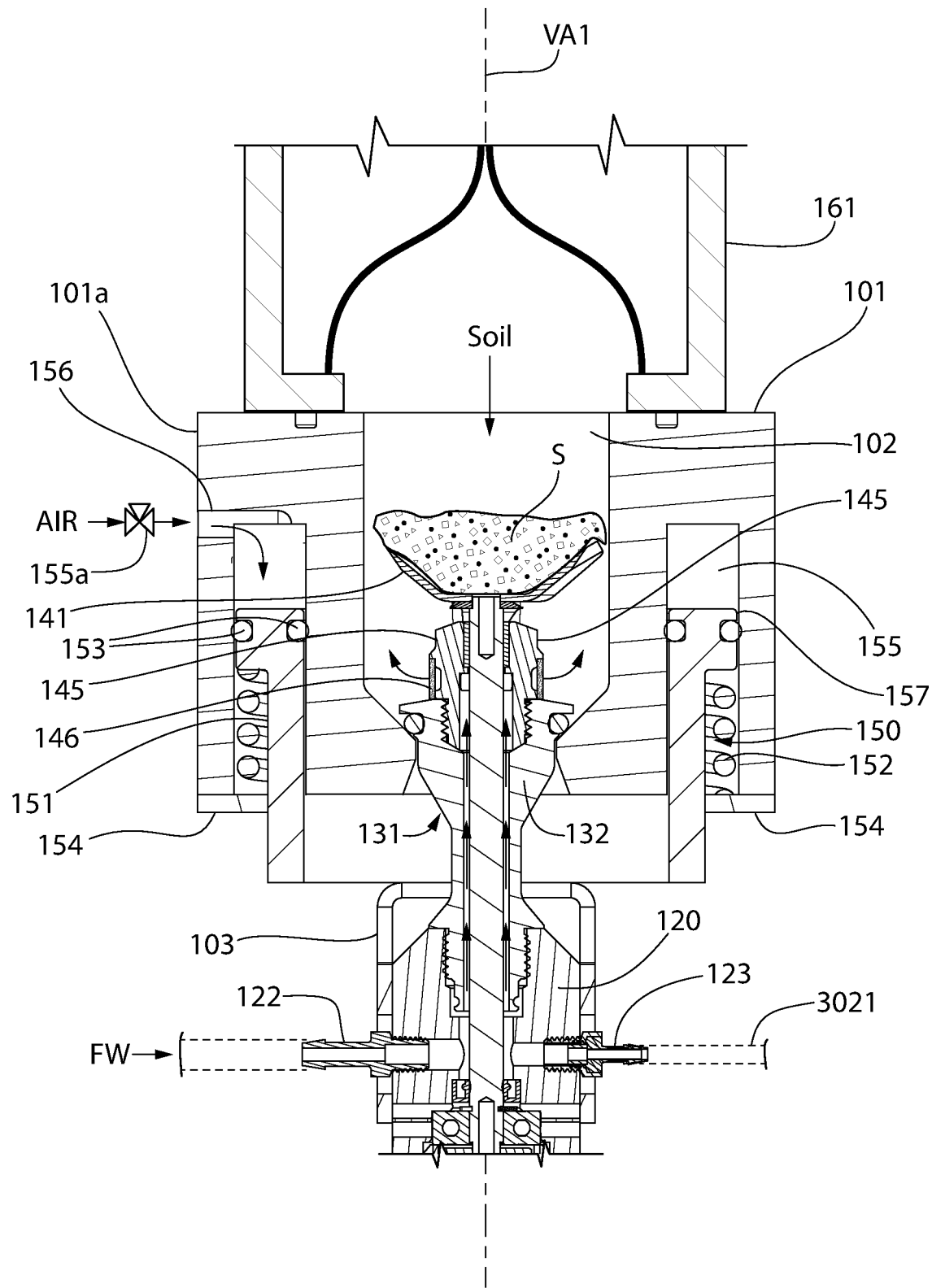
FIG. 19 is fifth sequential view thereof showing water added to the mixing device with the soil sample as indicated by directional flow arrows.

FIG. 19 shows the soil sample "S" in the "as collected" condition from the agricultural field which has first been loaded into mixing chamber 102 of mixing container 101. At this juncture, the stopper 131 is in lower closed position previously described herein to close the bottom container cleanout port 105. The sample may be comprised of several soil cores in some instances for generating blended sample chemical profile representing an averaged analysis.

Filtered water (FW) is pumped by water pump 3304 (FIG. 1) to the mixer-filter apparatus 100 and injected through inlet nozzle 122 (see directional arrow) into the fluid manifold chassis 120. The water flows radially into the central passageway 124, then axially upwards through the passageway and central bore 144 in stopper 131, and radially into the lower region of mixing chamber 102 through the annular filter 146. This fluid introduction location at the bottom of mixing chamber 101 helps fluidize soil in the bottom of the chamber (note that for clarity, the figures only show soil above the mixing blade assembly 141 recognizing that the soil will actually fill the entire lower portion of the chamber). In some implementations of the process, water may be added first to mixing chamber 101 and mixing blade assembly 141 run at a low idling speed (RPM) before the soil sample is added. The mixing chamber 101 is filled with a predetermined volume or amount of filtered water to achieve the desired water/soil ratio (e.g. 4:1, etc.) preprogrammed into processing system 2820 in to produce a slurry (SL) of proper consistency for processing and analysis. The amount of water needed is determined during the volumizing step at the volumization station previously described herein.

FIG. 20 next shows the mixing step. The water and soil mixture is being mixed by the blade assembly 141 which is rotated at a predetermined full mixing speed (RPM) to quickly and efficiently prepare the sample slurry (SL) of proper consistency. To help achieve thorough and rapid mixing, a plurality of circumferentially spaced apart mixing protrusions 172 may be provided in mixing chamber 101 which protrude radially inwards into chamber (best shown in FIG. 10). Protrusions 172 interact with mixing blade assembly 141 to promote thorough mixing. In one embodiment, two pairs of diametrically opposed mixing protrusions 172 may be provided; however, more or less protrusions and other arrangements may be used. Protrusions 172 may have a rounded profile in top plan view in one embodiment as shown.

Once the slurry has been fully mixed, the slurry is extracted from the mixing chamber 102 through outlet nozzle 123 under suction from the slurry pump 3333 of the chemical analysis sub-system 3003 (see directional flow arrow). Alternatively, a slurry forwarding pump may be added if required to forward slurry to the slurry pump depending on the flow dynamics of the system. It bears noting that the stopper 131 remains in the lower closed position to seal the cleanout port 105 of the mixing container 101 during the extraction step. In operation, the slurry generally flows inwards through the centrally-located annular screen 146 on filter housing 145 into the central bore 144 of stopper 131, and axially downwards through the bore and central passageway 124 in manifold chassis 120 to the outlet nozzle 123. The annular screen 146 has openings sized to preclude soil or other embedded particles from the field sample (e.g. small stones, etc.) of a predetermined size from entering the stopper 131 and manifold chassis 120. Because the slurry flows through the annular space or flow passage formed between the motor drive shaft 142 and the central bore and passageway 144, 124, the screen prevents this somewhat constricted flow space from plugging. The slurry extraction step may preferably be performed with the mixing blade assembly 141 speed reduced to the slower idling speed. Alternatively, the blade assembly may be fully stopped.

It should be noted that during the mixing step, waste sludge comprised of an agglomeration of fine soil particles primarily builds up against the vertical walls surrounding the mixing chamber 102 due to the centrifugal action of the mixing blades. Extracting the slurry from the lower central portion of the mixing chamber through the annular filter 146 advantageously minimizes plugging the filter in contrast to other possible slurry extraction locations that might be used along the walls of the mixing chamber.

FIG. 21 next shows the mixing chamber 102 flushing and cleanout step, which will be briefly described. The stopper 131 is initially still in the closed position from the slurry extraction step. In one implementation of the mixing chamber cleanout process, a two phase flush and rinse may be used to thoroughly clean the chamber. In the first initial phase, the mixing blade assembly 141 is run at slow idling speed while the stopper 131 is moved from the lower closed position upwards to the upper open position. This opens container cleanout port 105 at bottom of mixing chamber 102. The stopper 131 is moved via actuation of the piston assembly 150 in the manner previously described herein. Flushing water (e.g. filtered water FW) is injected and sprayed into the mixing chamber 102 of mixing container 101 through the inlet nozzle 122 and screened housing 145 while the cleanout port 105 remains open. The flushing water follows the flow path indicated by the directional flow arrows form the inlet nozzle 122 to the mixing chamber. A mixture of the flushing water and sludge from chamber 102 flows downwards and outwards through the cleanout port 105 and the 360 degree open cleanout zone formed by the cleanout port to waste (see directional waste flow arrows). This concludes the initial flushing and rinsing phase.

In the second final flushing and rinsing phase, the mixing chamber 102 is reclosed by moving the stopper 131 to the closed position to block cleanout port 105 while the flushing water continues to be injected into the mixing chamber. The mixing chamber 105 now begins to briefly fill with water. The mixing blade assembly 141 speed is increased to full speed for a few seconds to entrain any remaining sludge residue clinging to the mixing chamber walls in the water. The mixing chamber cleanout port 105 is opened again a second time by raising the stopper 131 to flush out the water and sludge mixture. This completes cleaning of the mixing chamber 102. It bears noting that both the initial and final flushing and rinsing phases are completed in rapid succession in a very short time within a matter of a few seconds.

Once the mixing chamber 102 has been thoroughly cleaned, stopper 131 is again returned to the lower closed position via operation of the piston assembly 150 in preparation to receive and process the next soil sample in line. The foregoing process steps of volumizing the soil sample, mixing the slurry, and cleaning the mixing chamber are summarized in FIG. 2.

Mixer-Filter Apparatus Alternative Embodiment

Figure 22:
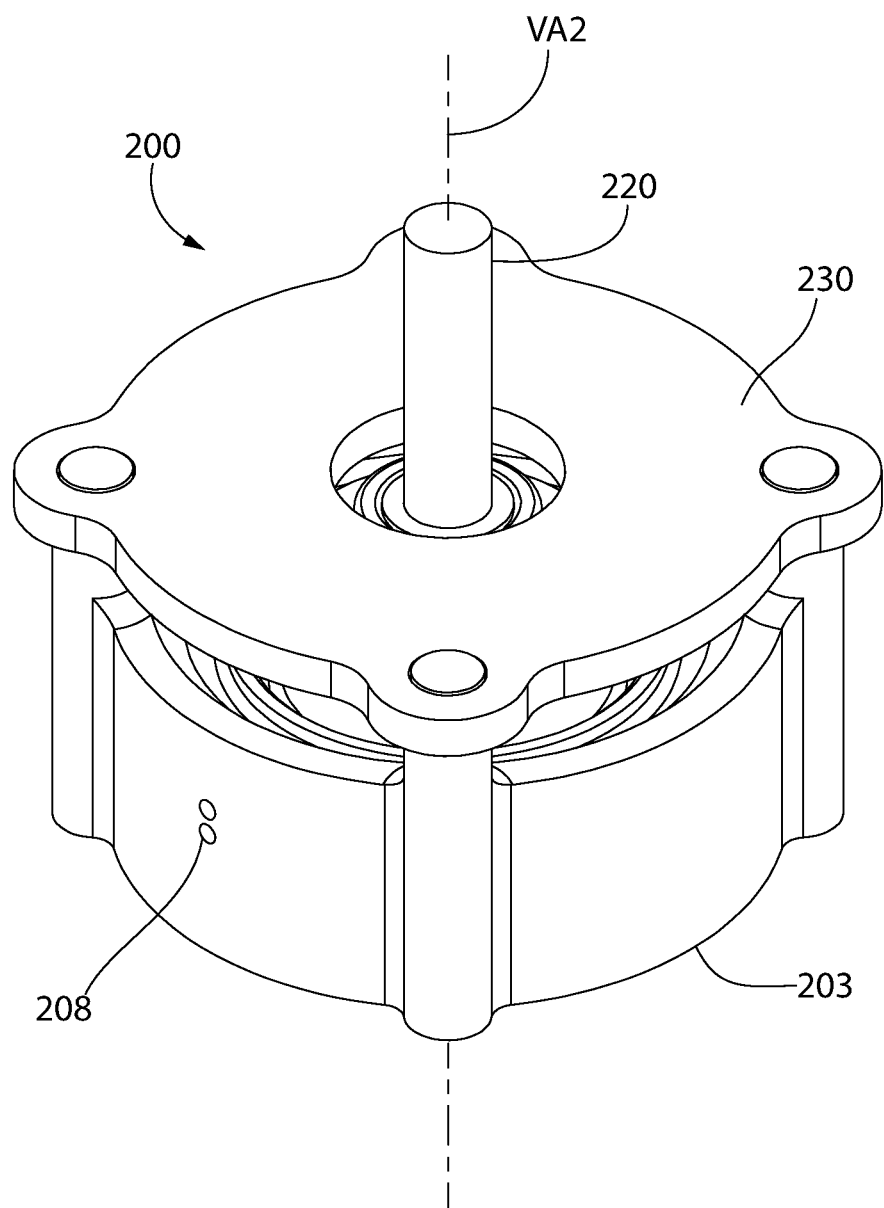
FIG. 22 is a top perspective view of a second embodiment of a mixing device.
Figure 23:
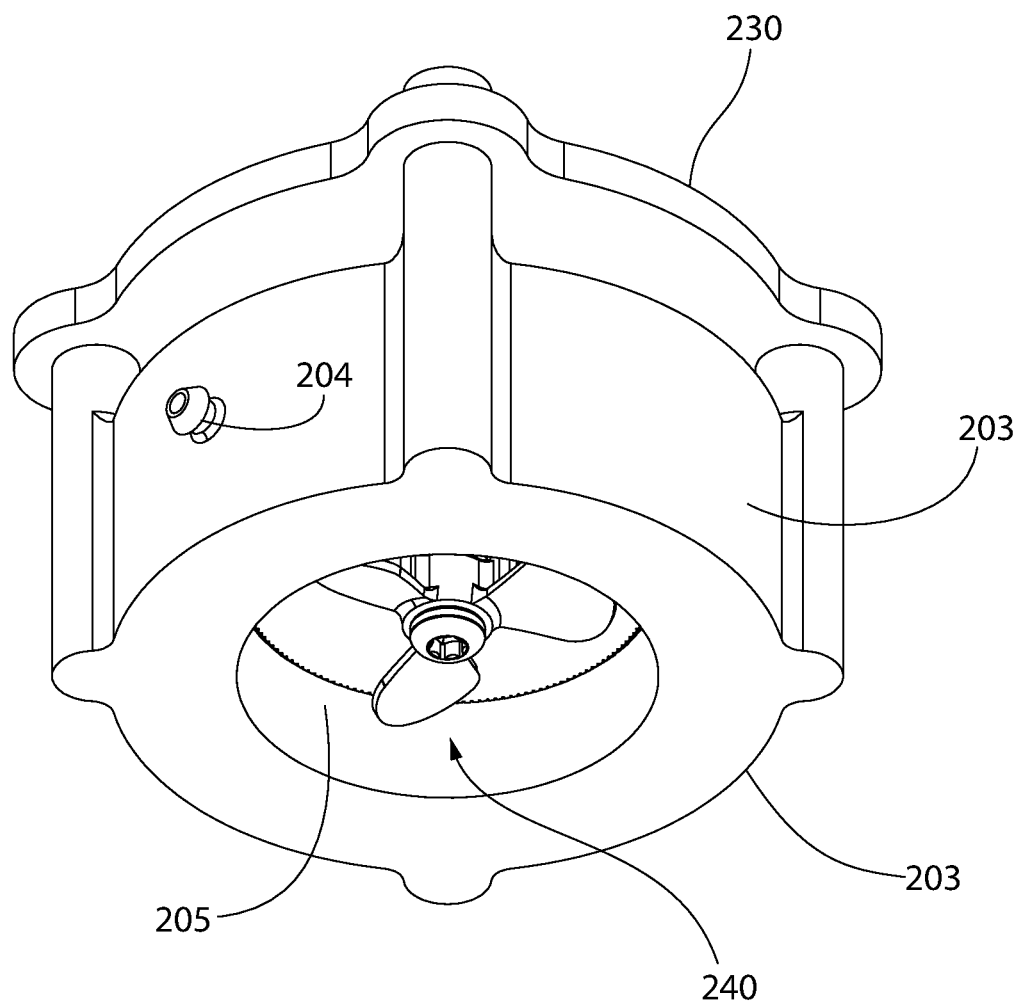
FIG. 23 is a bottom perspective view thereof.
Figure 25:
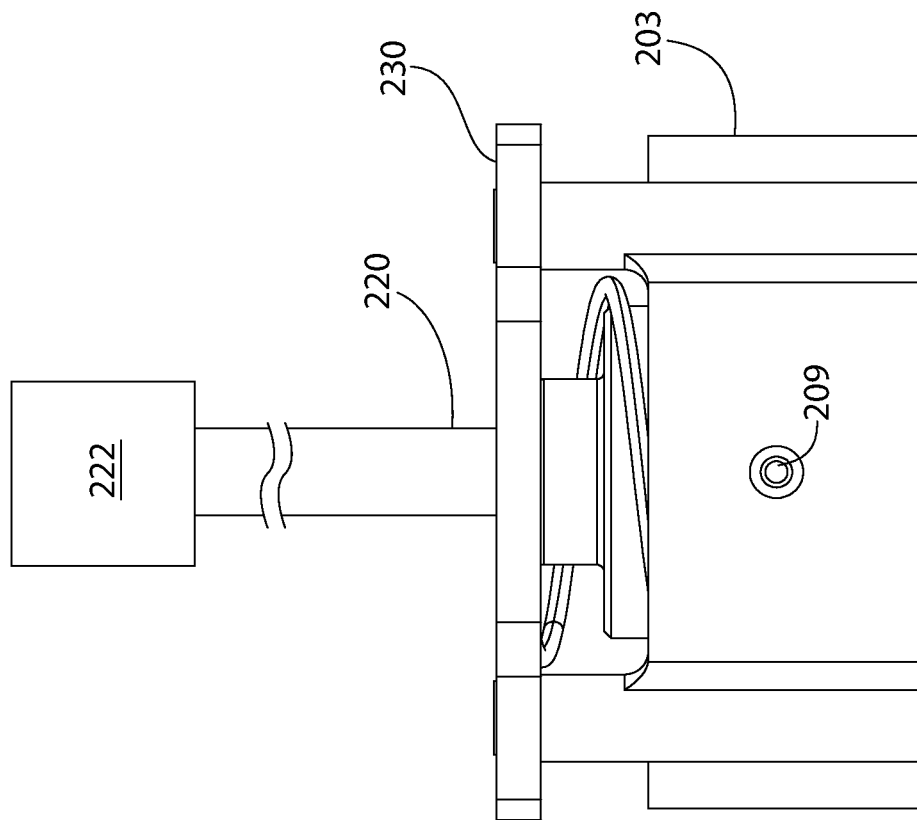
FIG. 25 is a top view thereof.
Figure 24:
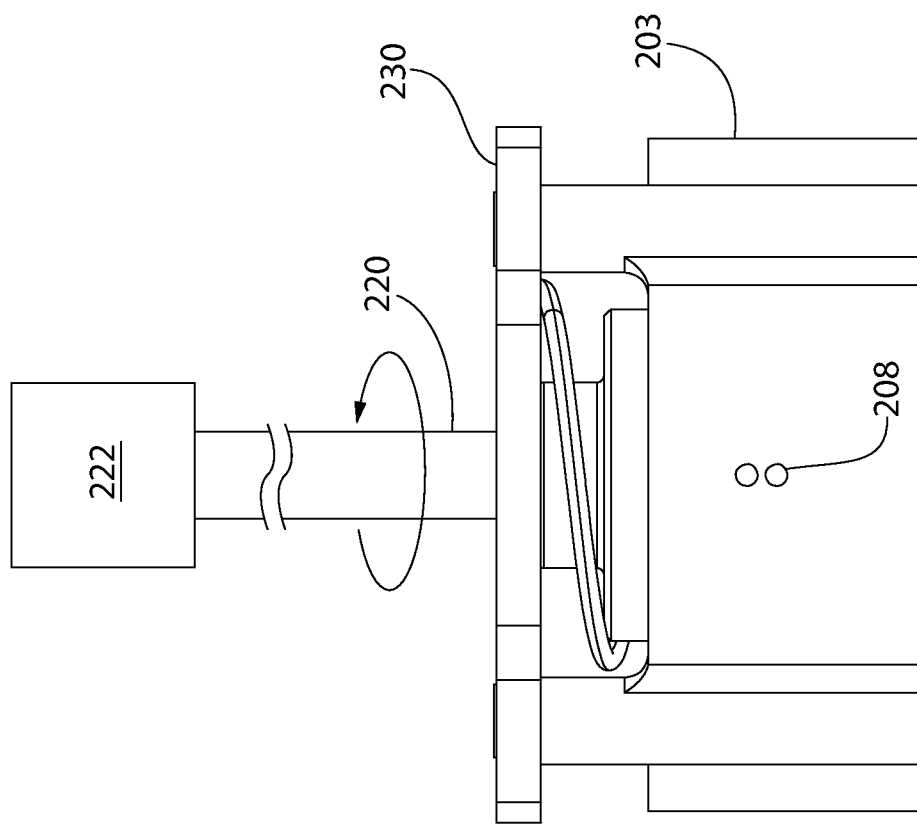
FIG. 24 is a rear view thereof.
Figure 27:
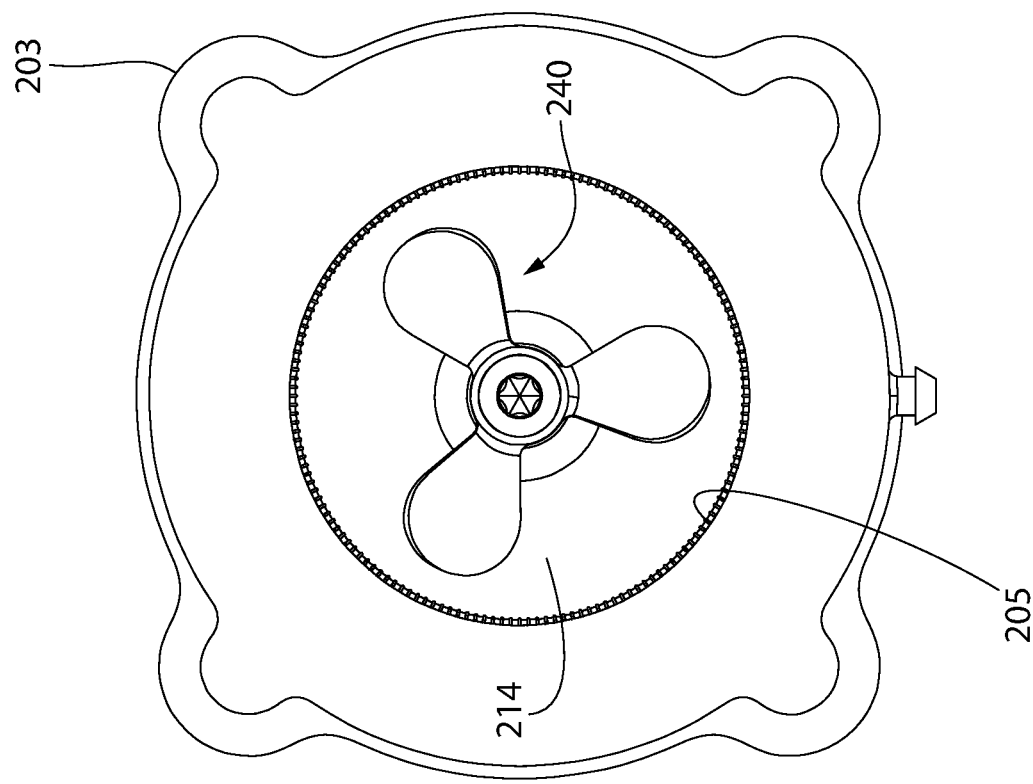
FIG. 27 is a top view thereof.
Figure 26:
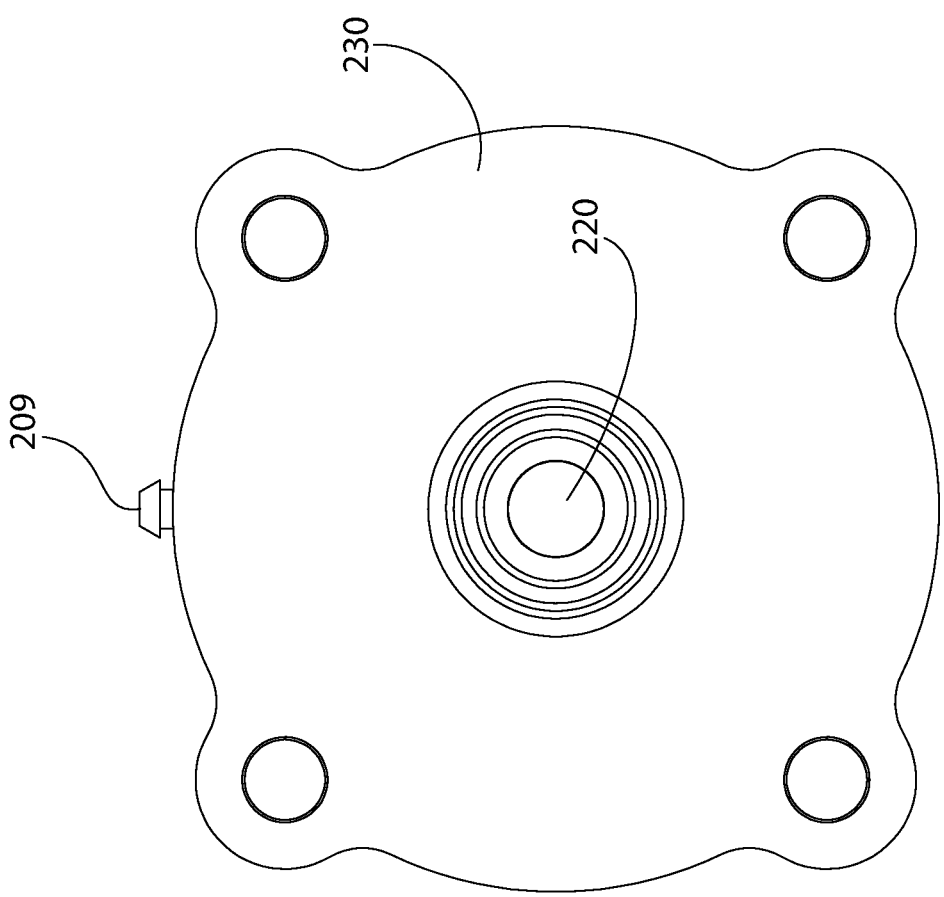
FIG. 26 is a bottom view thereof.

FIGS. 22-37 depict an alternative embodiment of a mixer-filter apparatus 200 which may be used with sample preparation sub-system 3002. Mixer-filter apparatus 200 generally includes a lower mixing container 201, an upper mixer housing 203, a vertically movable elastomeric stopper 210, and a mixing blade assembly 240 coupled to a motor drive shaft 220 such as via a threaded fastener or other means. Drive shaft 220 is coupled to an electric motor 222 for rotating the blade assembly 240. Motor 222 is shown only in FIG. 22 for simplicity. The drive shaft 220 is centered in the mixer housing 203 and defines a vertical central axis VA2 of the mixer-filter apparatus.

Container 201 defines a soil storage cavity 202 for holding a soil sample for mixing (see, e.g. FIGS. 28-29) to prepare the slurry for chemical analysis. Container 201 may be sealingly and detachably coupled to the bottom of mixer housing 203 such as via seals 204 which may be an O-ring in one embodiment to prevent leakage at the interface between the container and upper housing 203. In some embodiments, the floor 201-1 of container 201 may optionally be movable relative to the container walls 201-2 and mixer housing 203 and formed by a piston assembly 201-3 (shown in dashed lines). This allows the soil sample to be raised towards blade 420 for enhanced mixing.

The upper mixer housing 203 includes an axial central cavity 207 which penetrates and extends between the top and bottom of the housing as shown. Cavity 207 may be substantially circular in transverse cross section in one embodiment forming inner cylindrical sidewalls 205b bounding the cavity. In one embodiment, a portion of the sidewalls 205b may include flat portion 205a.

The lower portion of central opening 207 defines a downwardly open mixing cavity 207a formed below the elastomeric stopper 210 which contains the mixing blade assembly 240. Mixing cavity 207a and soil storage cavity 202 of soil container 201 collectively define a mixing chamber 205 when the container is coupled to the upper housing 203. The mixing chamber 205 for preparing the slurry mixture of soil and water. Chamber 205 may have a smaller diameter than the upper portion of central cavity 207 forming a stepped transition therebetween that defines an annular seating surface 206. The seating surface 206 may be chamfered in one embodiment producing an angled or inclined seating surface which is obliquely oriented to central axis VA2. Blade assembly 240 is rotatably disposed in the mixing chamber 205.

Housing 203 further includes an inlet port 208 for injecting filtered water into mixing chamber 205 and a diametrically opposite outlet port 209 for extracting slurry. An air vent 208a which optionally may comprise a valve is in fluid communication with the inlet port 208 and central cavity 207 of housing 203 for expelling air from the cavity prior to the mixing operation. In some embodiments, the entire housing and chamber may be angularly tilted via a rotary coupling 201-4 (see, e.g. FIG. 30) such that the air vent/valve 209 is at a high point in system and slurry extraction is below water level (to avoid extracting air with the slurry). Inlet port 208 and cleanout port 105 can be a single port with a three-way valve to control the flow material in and out.

Whereas the mixing blade assembly 41 and drive shaft 142 of mixer-filter apparatus 100 enters the mixing chamber 102 from the bottom, it bears noting that the present blade assembly 240 and drive shaft 22 enters mixing chamber 202 from the top. This arrangement advantageously decreases the complexity of shaft seals needed to prevent leakage of water from the chamber along the drive shaft.

Figure 28:
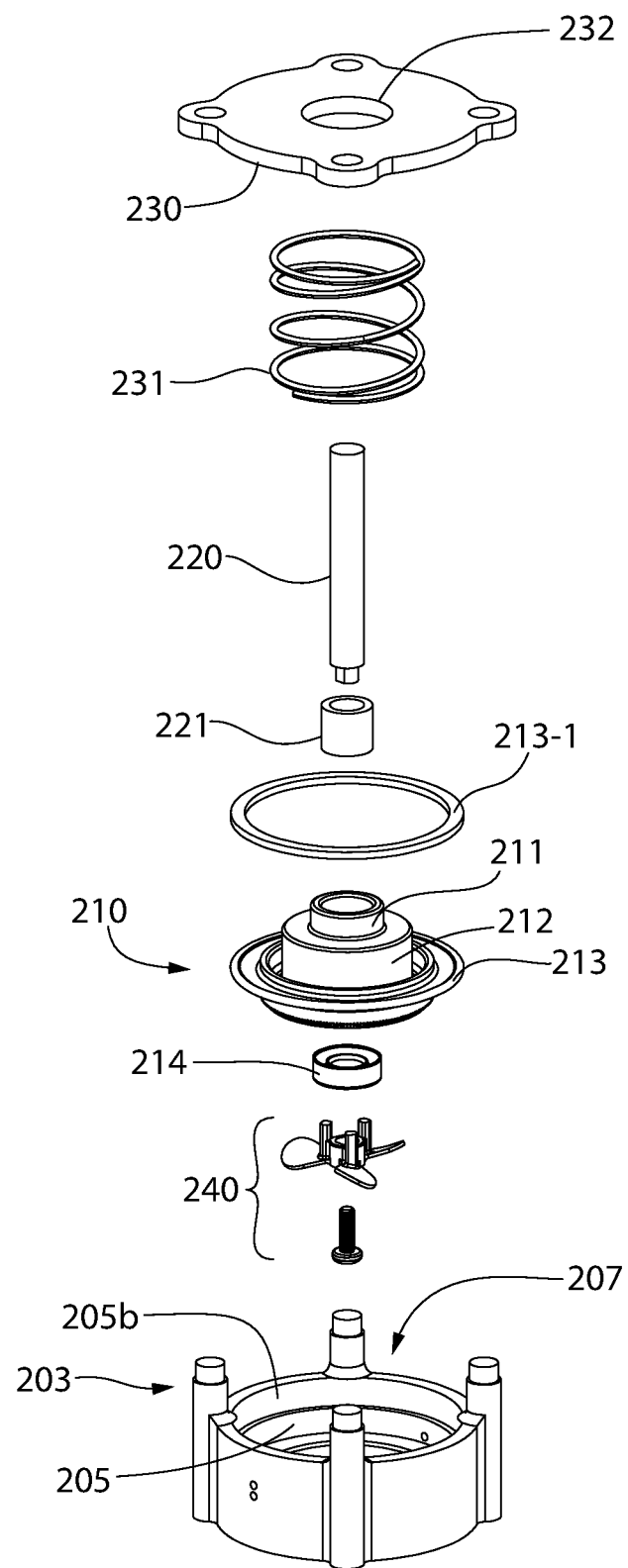
FIG. 28 is an exploded top view thereof.
Figure 29:
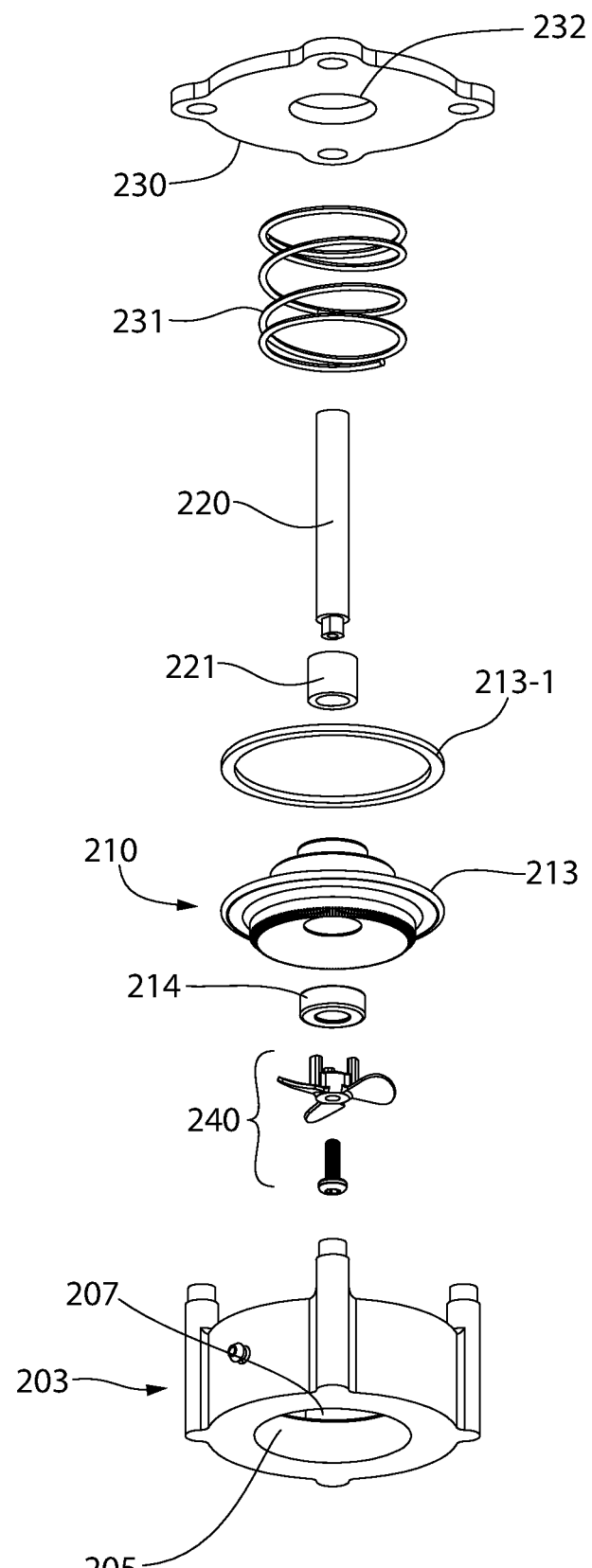
FIG. 29 is an exploded bottom view thereof.

The elastomeric stopper 210 is disposed at least partially in central cavity 207 of the mixer housing 203 as best shown in FIGS. 28 and 29. Referring additionally to FIGS. 21-23 and 30-32, mixing chamber 205 is formed beneath the stopper 210. Stopper 210 has a generally cylindrical main body including a top 215, bottom 214, and cylindrical sidewalls 216 extending therebetween. A circular central axial passageway 211 extends axially between and penetrates the top and bottom surfaces. The bottom 214 may be concavely shaped in one embodiment defining an arcuate profile in transverse cross section to further facilitate thorough mixing of the slurry. The stopper 210 assembly may also include a lower drive shaft ring seal 214 to prevent leakage of fluid from the mixing chamber 205 along the shaft, and an upper collar bearing 221 which supports the shaft within the axial central passageway 211 of the stopper.

A radially extending annular sealing flange 213 projects outwards from the main body of stopper 210 for forming a seal with sidewalls of the central cavity 207 in the mixer housing 203. Flange 213 is pliable and flexible being formed as an integral unitary structural part of the elastomeric stopper 210. In one embodiment, flange 213 may upwardly flared (upturned) when in an undeformed condition. A retaining ring 213-1 locks the flange 213 in place on mixer housing 203. The housing may include an annular shoulder 213-2 to facilitate engaging the flange (see, e.g. FIG. 37). The flange 213 engages and creates a seal with the sidewalls of the cavity 207. Water may be injected through inlet port 208 of housing 203 into the portion of mixing chamber 205 beneath the annular flange 213 of stopper 210 for preparing the slurry. An open air vent 208a in housing 203 is provided in for expelling air from the chamber beneath the flange 213 of stopper 210 during initial setup of the mixer-filter apparatus 200.

Stopper 210 is axially movable upwards and downwards in cavity 207 between a lower seated position and an upper unseated position. This creates an openable and closeable annular interface between the stopper and mixer housing 203 for both filtering the slurry and flushing the mixing chamber 205 between samples, as further described herein.

Figure 30:
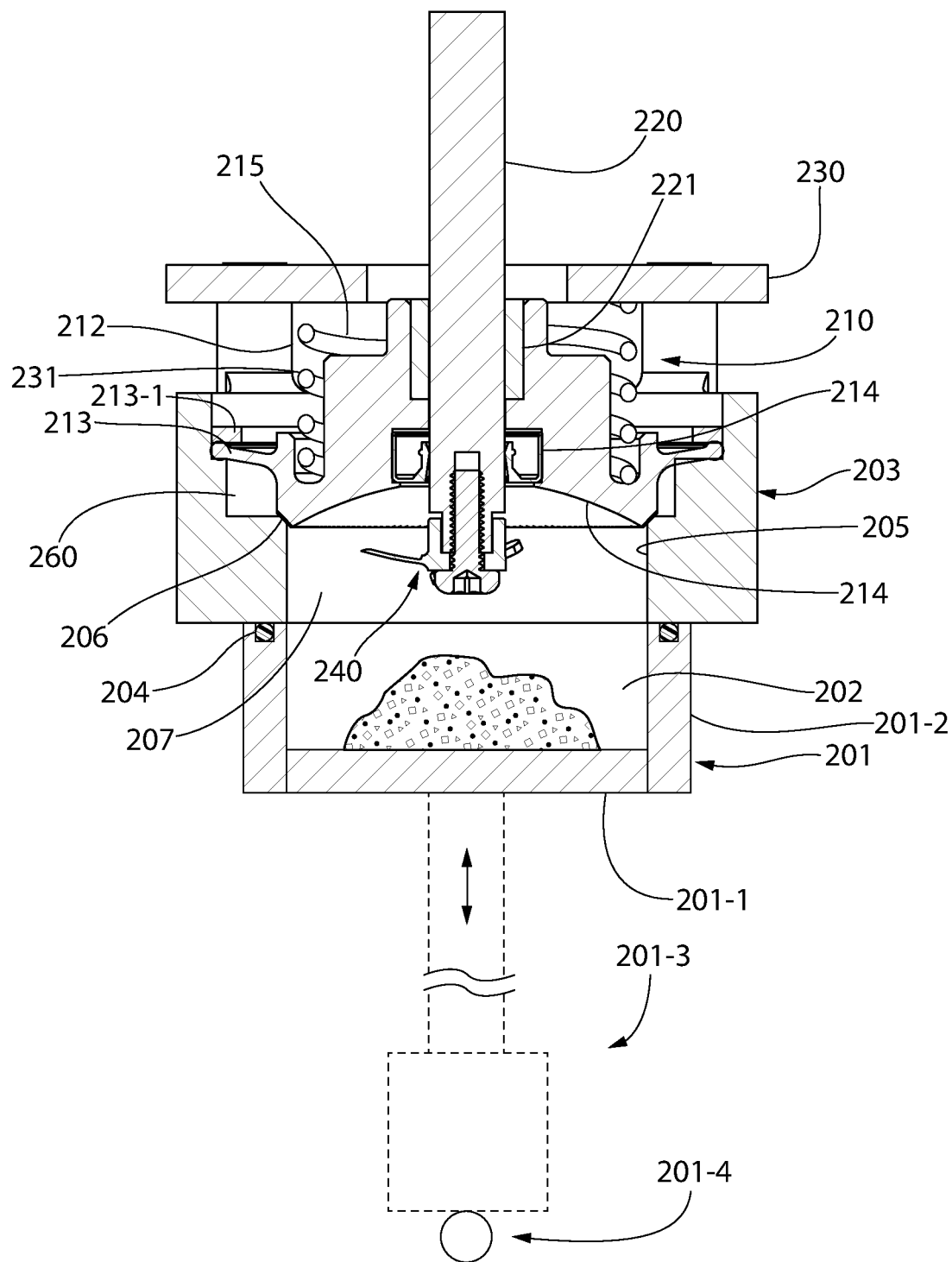
FIG. 30 is a first side cross-sectional view thereof showing the mixing device in a closed position.
Figure 31:
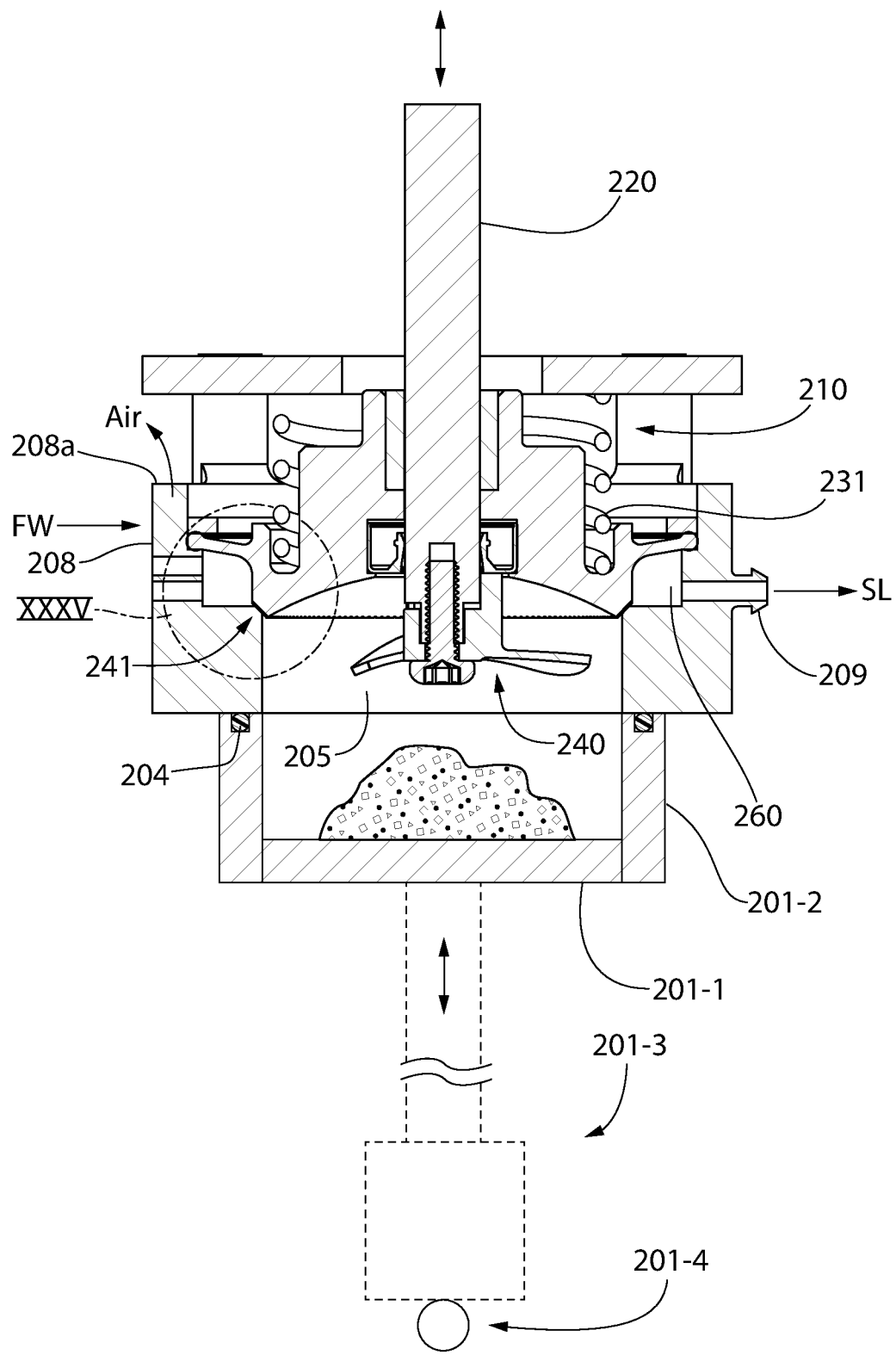
FIG. 31 is a second side cross sectional view thereof.
Figure 32:
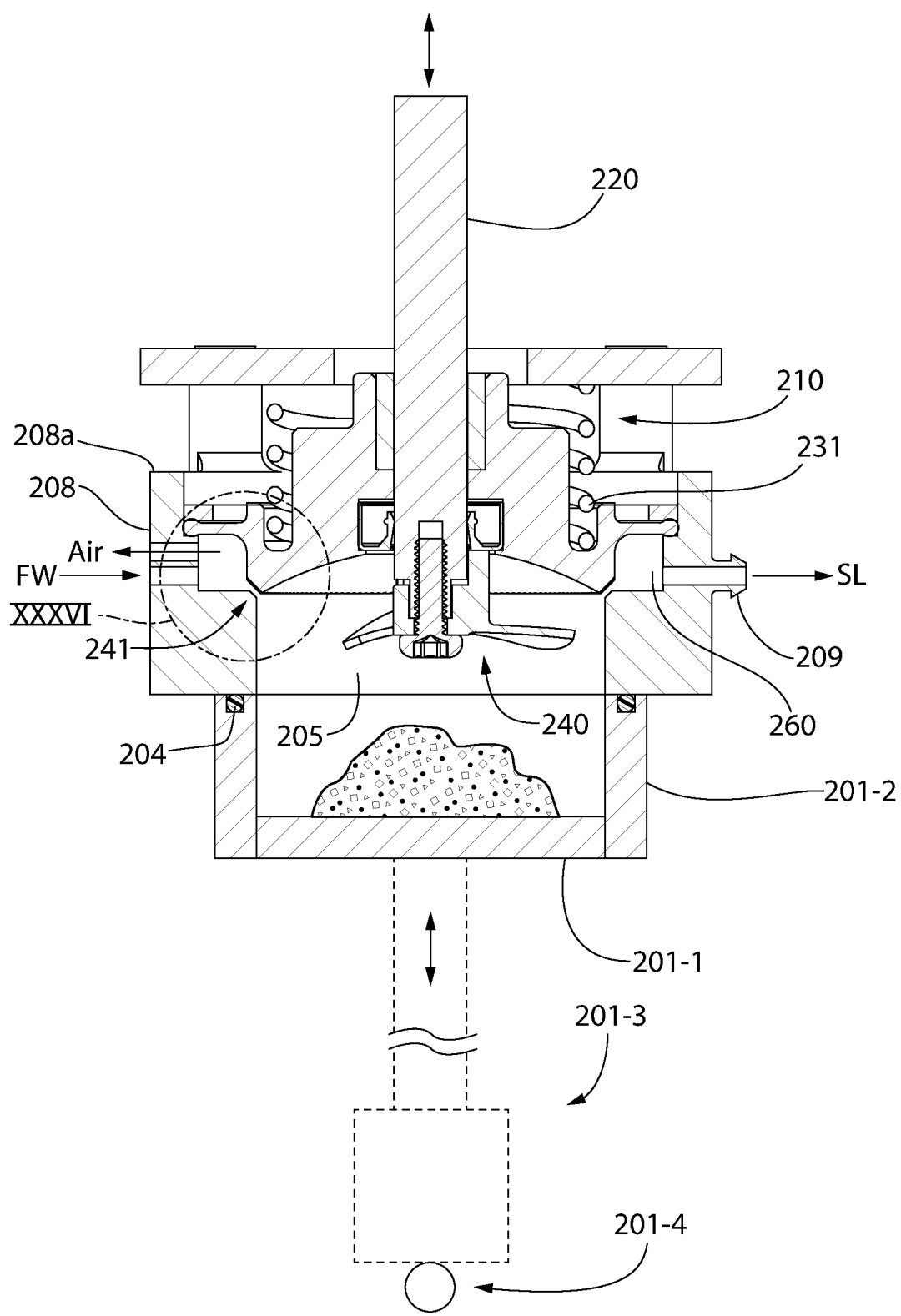
FIG. 32 is a third side cross-sectional view thereof showing the mixing device in an open position.
Figure 33:
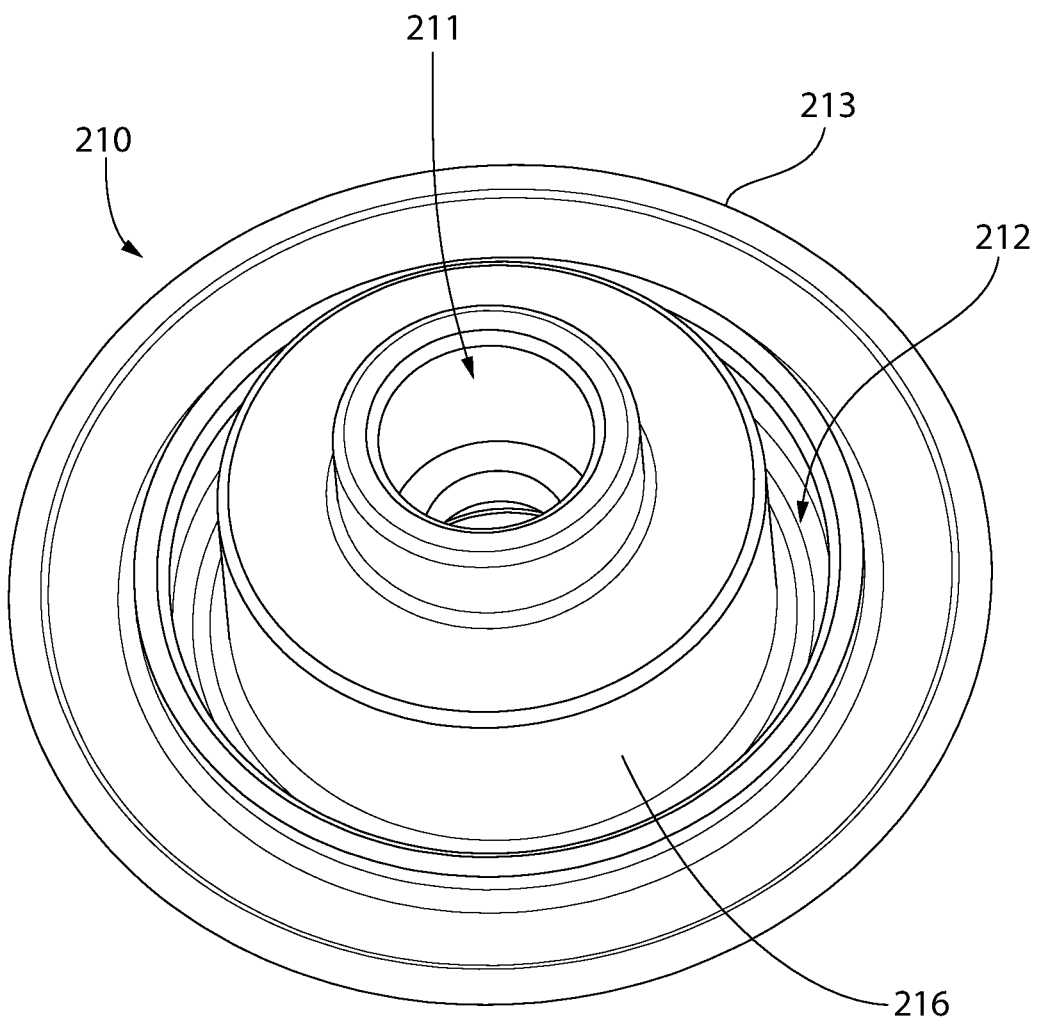
FIG. 33 is a top perspective view of a movable stopper of the mixing device of FIG. 22.

The stopper 210 further includes an upwardly open annular space 212 which receives a spring 231 therein (see, e.g. FIGS. 30-32). Spring 231 may be a helically coiled compression spring in one embodiment. Spring 231 is retained in the annular space by a cover plate 230 removably attached to mixer housing 203. The top end of spring 231 acts on the underside of the cover plate 230 and its bottom end acts on the stopper 210 to bias the stopper to the lower seated position.

The stopper 210 is fixedly coupled to the drive shaft 220 which is turned is rotatably coupled to motor 222 at one end and the mixing blade assembly 240 forming an inline movable assembly or unit. The stopper 210 may be moved between the lower and upper positions by lifting the movable unit such as via raising or lowering a motor mount (not shown). The blade assembly 240 engages the seal 214 embedded in the stopper body which pulls the stopper 210 upwards when the motor is raised. This action in turn compresses spring 231, which acts to force the stopper back downwards to the lower position when the motor is lowered.

According to one unique aspect of the alternate mixer-filter apparatus 200, the apparatus is configured to filter large soil particles or debris (e.g. stones) from the slurry extracted from the mixer without the use of conventional mesh filter screens which may be prone to plugging. Apparatus 200 further provides an openable/closeable filtering interface which allows the mixing chamber to be flushed and cleaned between processing samples.

To provide the filtering and flushing functions, an annular seating surface 217 is formed at the bottom of the cylindrical sidewall 216 of stopper 210. Seating surface 217 may be inclined or angled obliquely to central axis VA2. Seating surface 217 is selectably engageable with its mating seating surface 206 on the mixer housing 203 when the stopper 210 moves between the upper unseated and lower seated positions. Accordingly, seating surface 217 has a complementary angle to seating surface 206 to form a flat-to-flat interface thereby establishing an annular seating area.

Figure 34:
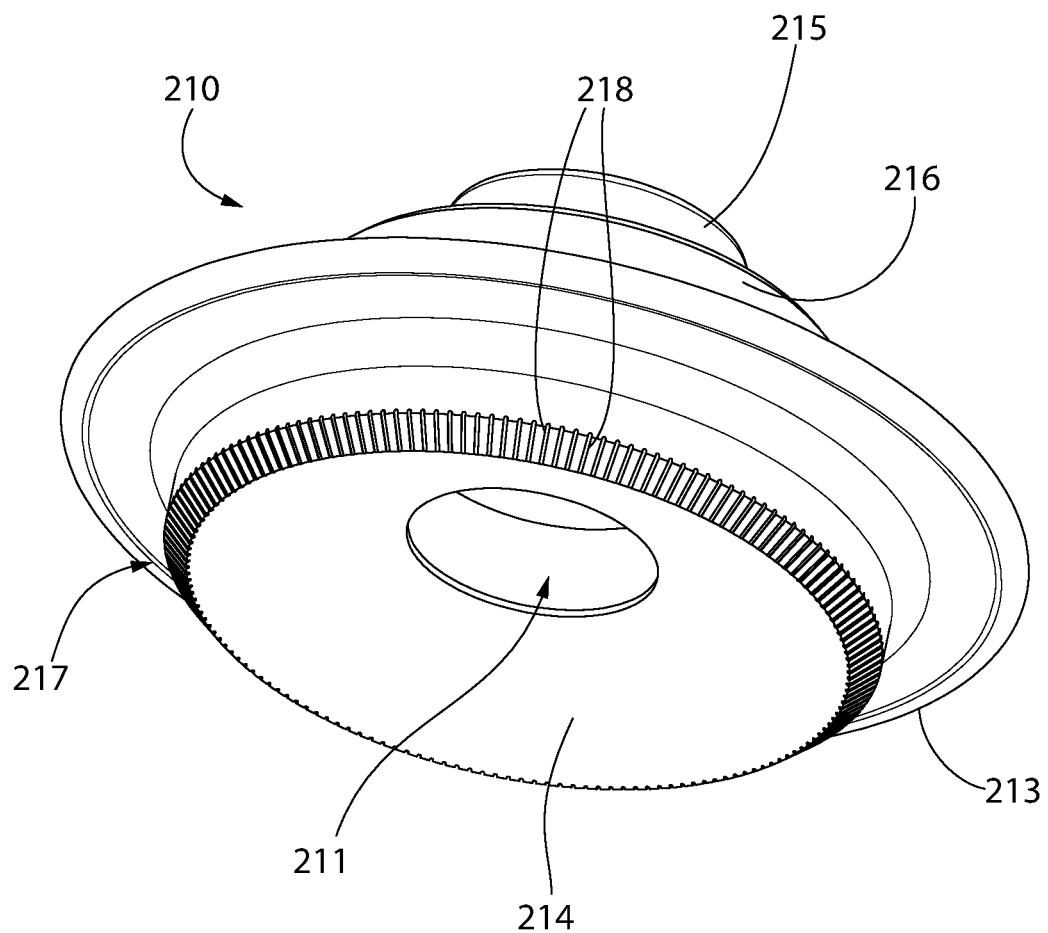
FIG. 34 is a bottom perspective view thereof.
Figure 35:
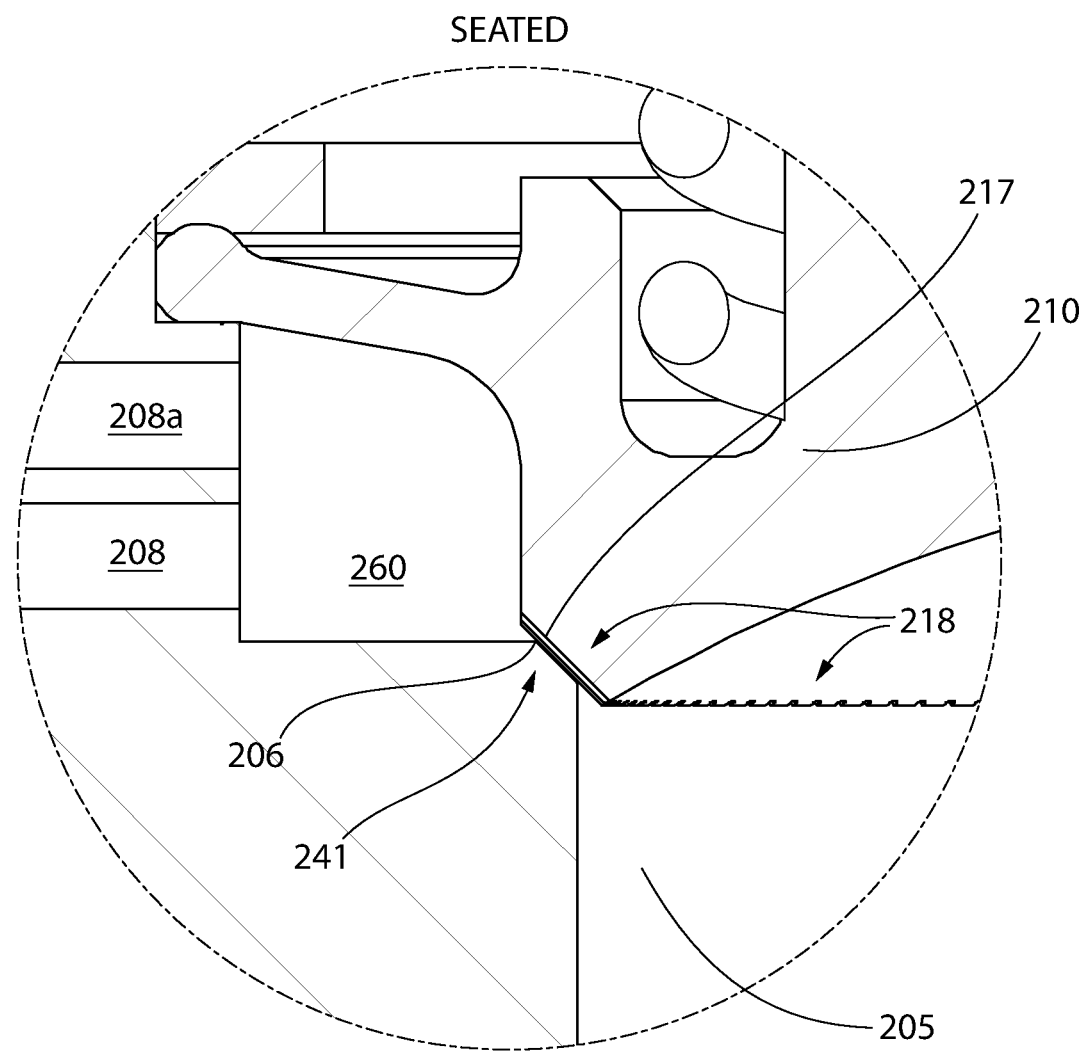
FIG. 35 is an enlarged detail taken from FIG. 31.
Figure 36:
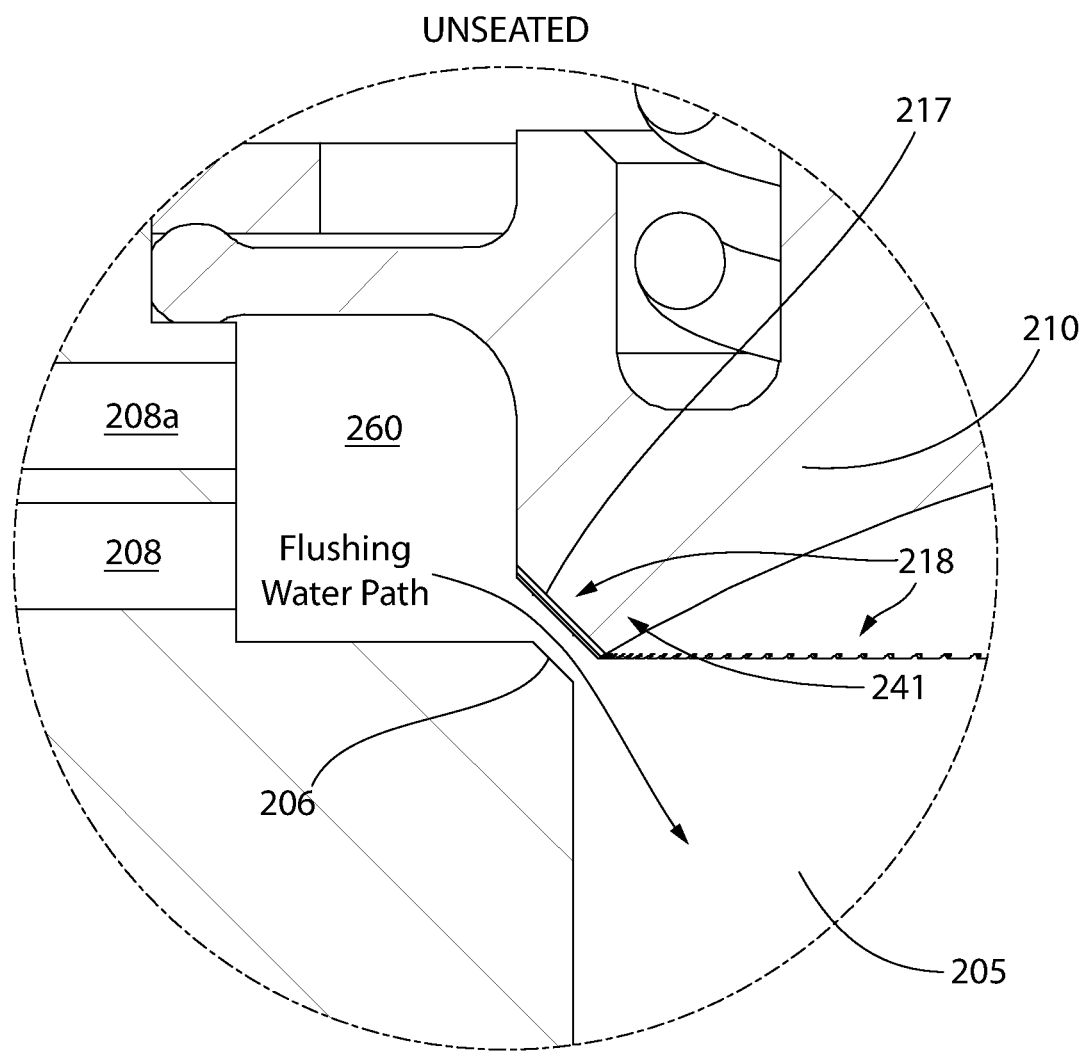
FIG. 36 is an enlarged detail taken from FIG. 32.
Figure 37:
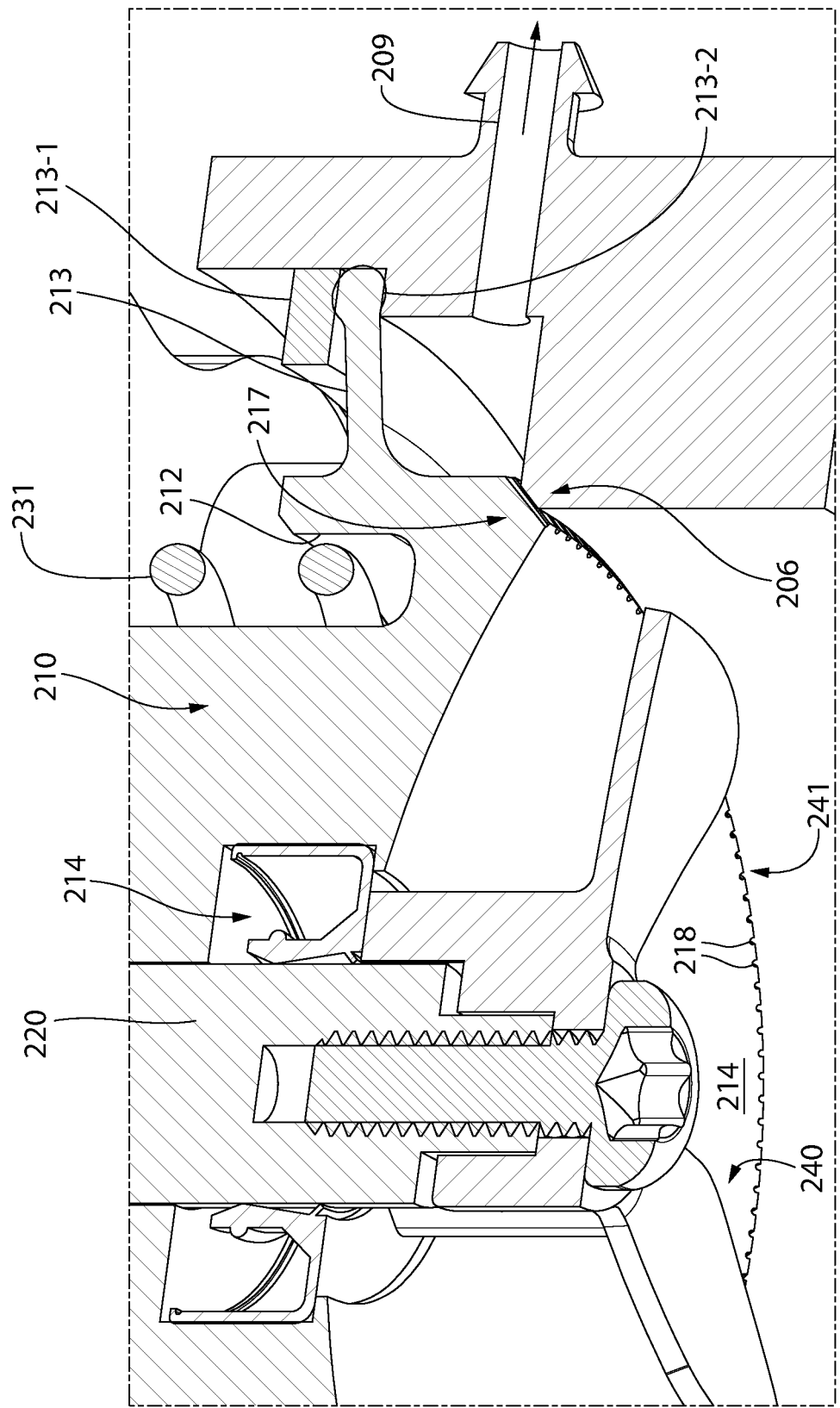
FIG. 37 is an enlarged detail of the stopper and mixing device housing interface.
Figure 38:
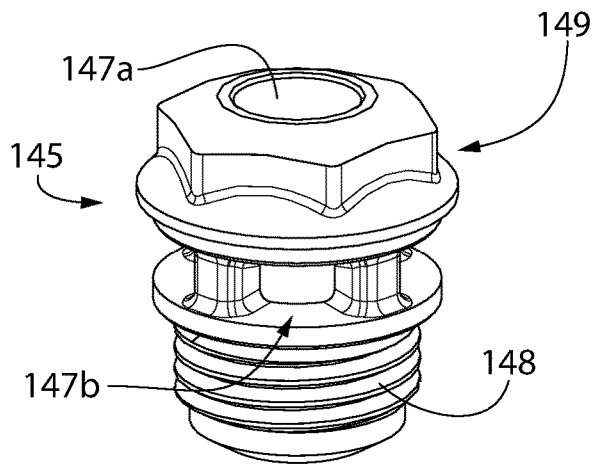
FIG. 38 is a top perspective view of a filter retainer usable in the first embodiment of the mixing device.
Figure 39:
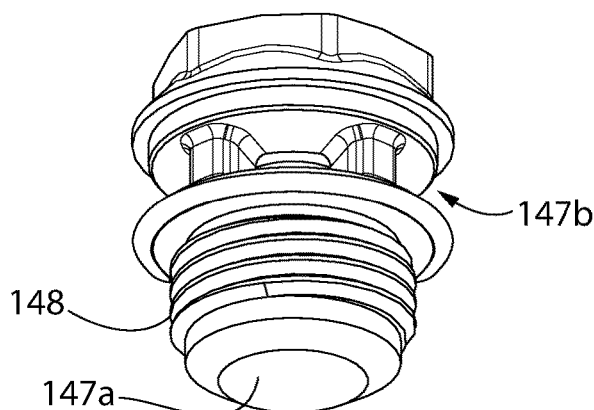
FIG. 39 is a bottom perspective view thereof.
Figure 40:
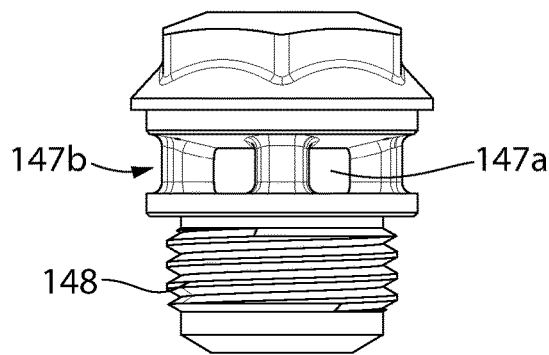
FIG. 40 is a side view thereof.
Figure 41:
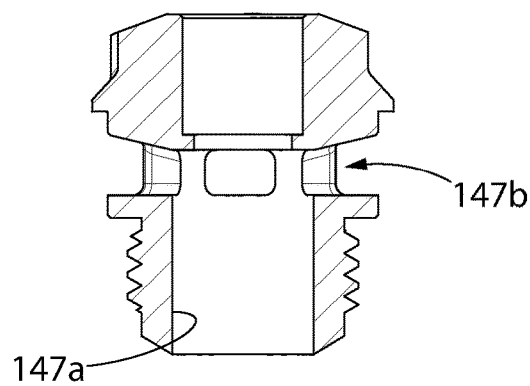
FIG. 41 is cross-sectional view thereof.
Figure 42:
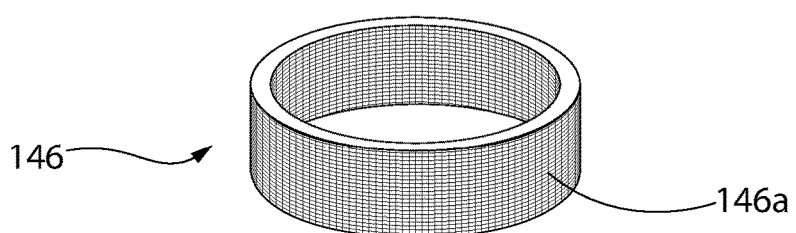
FIG. 42 is a perspective view of a filter coupleable to the retainer.

As best shown in FIG. 34, a plurality of radially oriented flow channels or grooves 218 are formed in seating surface 217 of stopper 210. The grooves 218 are circumferentially spaced apart and preferably extend 360 degrees around the seating surface 217. When the stopper is in its lower seated position, seating surfaces 217 and 206 are mutually engaged. The grooves 217, however, remain open to create an array of small diameter flow passages through which the slurry can be extracted from mixing chamber 205 via suction from a pump such as slurry pump 3333 (see, e.g. FIG. 1). The slurry flows in a radial direction outwards through the passages into an annular flow plenum 260 formed in the portion of housing central cavity 207 beneath annular flange 213 of stopper 210. From the plenum 260, the slurry flows through the outlet port 209 of the mixer housing 203 to the pump. Flow plenum 260 is also in fluid communication with the water inlet port 208 for receiving and injecting water into the mixing chamber 205 in addition to its role for extracting slurry. The diameter of the flow grooves 218 on stopper 210 is selected to act as a filter which precludes large particles and debris having a greater diameter than the grooves from being extracted with the slurry.

Operation of the stopper 210 for flushing and cleaning the mixing chamber 205 will now be briefly described. FIGS. 30-31, 35, and 37 show the stopper in the lower seated position. Seating surfaces 217 and 206 are mutually engaged forming a closed annular interface 241 between the stopper 210 and mixer housing 203. This seated position performs the filtering function since the flow grooves 218 remain the only open flow paths between flow plenum 260 and mixing chamber 205. Once the slurry is prepared and extracted from the mixer-filter apparatus through grooves 218, the stopper 210 is raised to the upper unseated position (see, e.g. FIGS. 32 and 36). This disengages seating surfaces 217 and 206, thereby fully opening the annular interface 241 for a full 360 degrees through which flow plenum 260 and mixing chamber 205 are fluid connected. The stopper 210 need only be raised far enough to form the circumferentially continuous opening between the seating surfaces 206 and 217. When the stopper 210 is raised to the unseated position, the peripheral edge of the annular flange 213 remains frictionally engaged with the sidewalls of the mixing chamber 205 and stationary via operation of the retaining ring 213-1. As such, the flange 213 will deform and deflect rather than simply slide upwards along the sidewalls. In the non-limiting illustrated embodiment, the flange 213 may be normally pre-angled in an upturned position (see, e.g. FIG. 31), and changed to a horizontal position when the flange deforms as the stopper 210 is raised (see, e.g. FIG. 32). In any case, the key point is that the annular interface 214 be fully opened for preferably its entire circumference. Cleaning water may then be injected, mixed, and flushed out of mixing chamber 205 for cleaning mixer-filter apparatus 100, thereby carrying the sludge outwards from the chamber to be discharged to waste. This flushing step also cleans any flow grooves 218 that might have been plugged by a larger particle or debris when filtering the slurry. Once complete, the stopper 210 is returned to the lower seated position for the next mixing cycle.

In other possible embodiments, the flow grooves 218 may alternatively be formed on annular seating surface 206 of mixer housing 203 and annular seating surface 217 on stopper 210 may have a flat face instead. Stopper may be formed of any natural or synthetic elastomeric material such as natural rubber, synthetic butyl rubber or neoprene, or other elastomeric materials. The remainder of the components of mixer-filter apparatus 200 described above may be made of any suitable metallic or non-metallic material.

In some embodiment, the mixer-filter apparatus 200 may be used in an angled position such as for example in a range from about and including 30-60 degrees to horizontal. In such a configuration, the inlet port 208 and air vent 208a preferably are positioned at the highest point of the mixer-filter apparatus at top.

In some implementations, the mixing container 201 may be raised and lowered into engagement with the mixer housing 203 after the soil sample is deposited in the container.

Chemical Analysis Sub-System

Referring to FIG. 1, the chemical analysis sub-system 3003 generally includes a slurry pump 3333 and mixing coil, a water supply system including a water tank 3302 and pump 3304, an air vent 3306, an extractant system including an extractant tank 3308 and pump 3310, a reagent system including a reagent tank 3314 and pump 3316, a supernatant pump 3312 and mixing coil 3318, a centrifuge 3400 including a dock 3340 and centrifuge tube 3350, and an absorbance analysis cell 3320. The foregoing components and system are fluidly coupled together via a suitable flow conduits such as without limitation tubing 3021 which may be metallic, non-metallic, or a combination thereof. Each component of the chemical analysis sub-system 3003 and operation of the sub-system will now be further described.

Slurry pump 3333 may be any suitable type pump which is fluidly coupled to either mixer-filter apparatus 100 or alternative mixer-filter apparatus 200. More specifically, pump 3333 may be fluidly coupled to the mixing chambers 102 or 205 of either mixer-filter apparatus 100 or 200 respectively via tubing 3021. Pump 3333 is configured and operable to extract the mixed soil sample slurry from the chamber for chemical analysis using sub-system 3003. In one embodiment, slurry pump 3333 may be a peristaltic positive displacement pump; however, other suitable type pumps may be used.

Slurry pump 3333 is fluidly coupled to water pump 3304, air vent 3306, and extractant pump 3310 via tubing 3021. Water pump 3304 takes suction from water tank 3302 which holds a reserve or supply of water such as filtered water in one embodiment for flushing and cleaning the slurry pump piping loop, as further described herein. Air vent 3306 allows pump 3333 to draw air into the slurry pump piping loop to aid in cleaning the loop. Extractant pump 3310 takes suction from extractant tank which holds a supply or reserve of an extractant.

Water pump 3304, extractant pump 3310, reagent pump 3316 and supernatant pump 3313 may also be positive displacement type pumps to regulate the flow of respective fluids provided to the sampling system components shown in FIG. 1.

It particularly bears noting at this juncture that FIG. 1 depicts merely a single chemical processing train 3000A of soil sampling system 3000 for convenience, which comprises the extractant system, reagent system, supernatant pump 3312, centrifuge tube 3350, mixing coil 3318, and analysis cell 3320. This processing train 3000A is configured and operable to extract and analyze the soil slurry for a single plant-available nutrient or analyte (e.g. potassium, nitrogen, phosphorus, etc.). When implemented, sampling system 3000 in fact actually may comprise multiple chemical processing trains (e.g. 3000B, 3000C, 3000D, etc.) which operate to extract and analyze multiple nutrients or analytes simultaneously in parallel rather than in a piecemeal series fashion. This advantageously saves processing time and provides a complete profile of the soil sample for all nutrients or analytes of interest. Each processing train is served by a single slurry pump 3333, water supply system, air vent 3306, and centrifuge 3400 which are fluidly coupled to each processing train in a parallel via separate parallel runs of tubing 3021.

Centrifuge 3400 is a central sample processing component of the chemical analysis sub-system 3003 of soil sampling system 3000, which provides a single unit configured for processing multiple slurry samples simultaneously in parallel for chemical analysis of different nutrients or analytes. The centrifuge and related appurtenances will now be described in further detail prior to discussing operation of the sampling system.

Referring initially to FIGS. 43-56, centrifuge 3400 includes a support housing 3401 generally comprising a vertical main support plate 3402, an upper support plate 3403, and a lower support plate 3405 oriented parallel to the upper support plate 3403. Lower support plate 3405 includes a relatively large central opening 3415 for receiving piston mechanism 3600 therethrough, as further described herein. Upper and lower support plates 3403, 3405 are vertically spaced apart and may be horizontally oriented as shown in the illustrated embodiment, thereby defining a partially or totally enclosed sample processing chamber 3501. Each support plate 3403, 3405 has one peripheral side or end attached to vertical support plate 3402 in a cantilevered manner via a suitable mechanical connection method, such as without limitation welding, soldering, threaded fasteners, adhesives, clips, interlocking features (e.g. tabs/slots), or other and combinations thereof. In one embodiment, support plates 3403 and 3405 may be oriented perpendicularly to the main support plate 3402 as shown.

Centrifuge housing 3401 further includes a safety shield assembly 3404 comprising a plurality of shields 3409. The shields enclose the rotary components of the centrifuge 3400 further described herein when spinning at high speeds and thus provide a safety function in the event of equipment failure. Shields 3409 may include arcuately curved shields, straight shields, or a combination thereof as depicted in the illustrated embodiment in which the front shields are curved. The straight shields 3409 may be affixed to housing 3401 by vertically-extending tabs on each top/bottom end which interlock with complementary configured slots formed in upper and lower support plates 3403, 3405.

Figure 51:
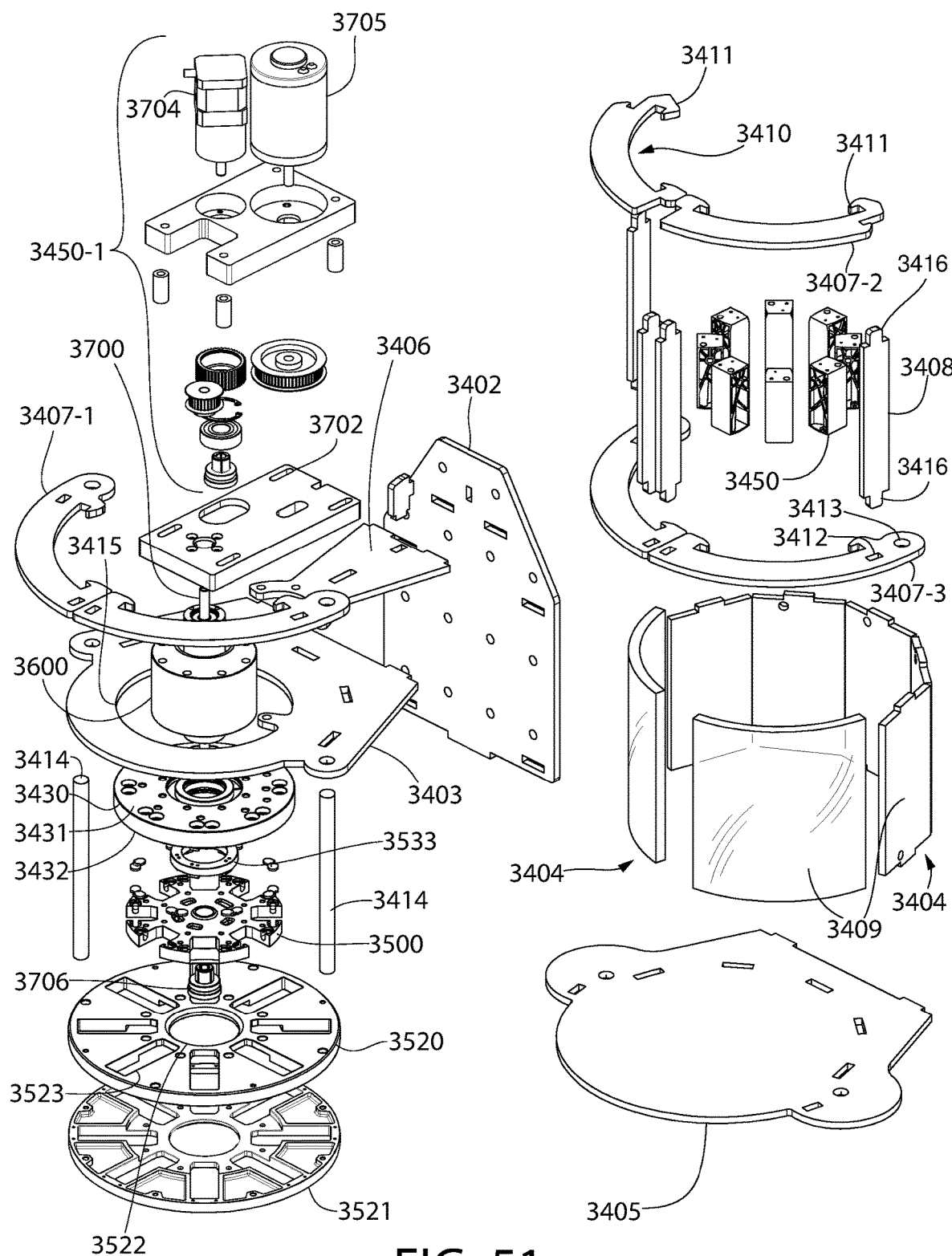
FIG. 51 is a top exploded perspective view thereof.
Figure 52:
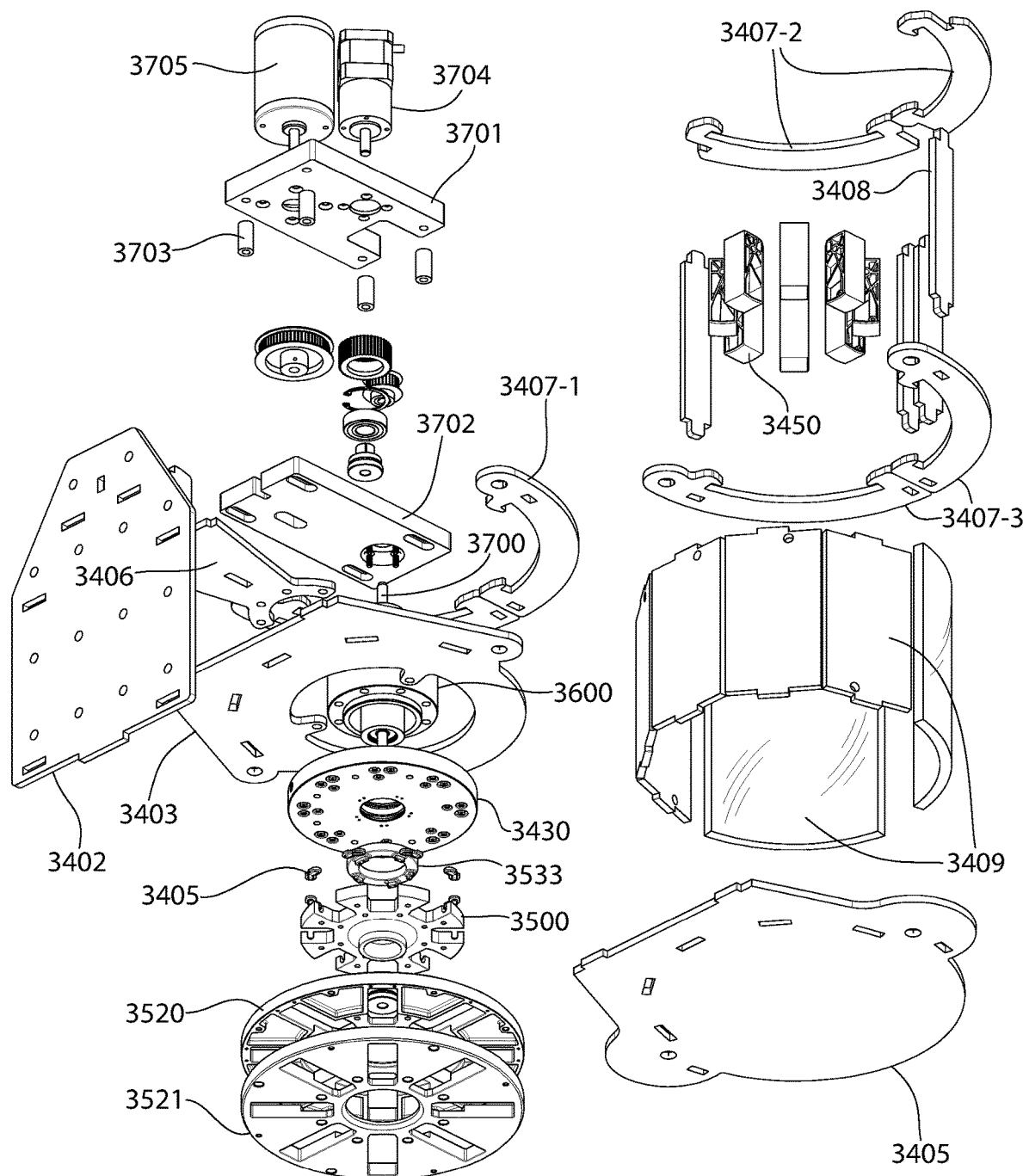
FIG. 52 is a bottom exploded perspective view thereof.
Figure 53:
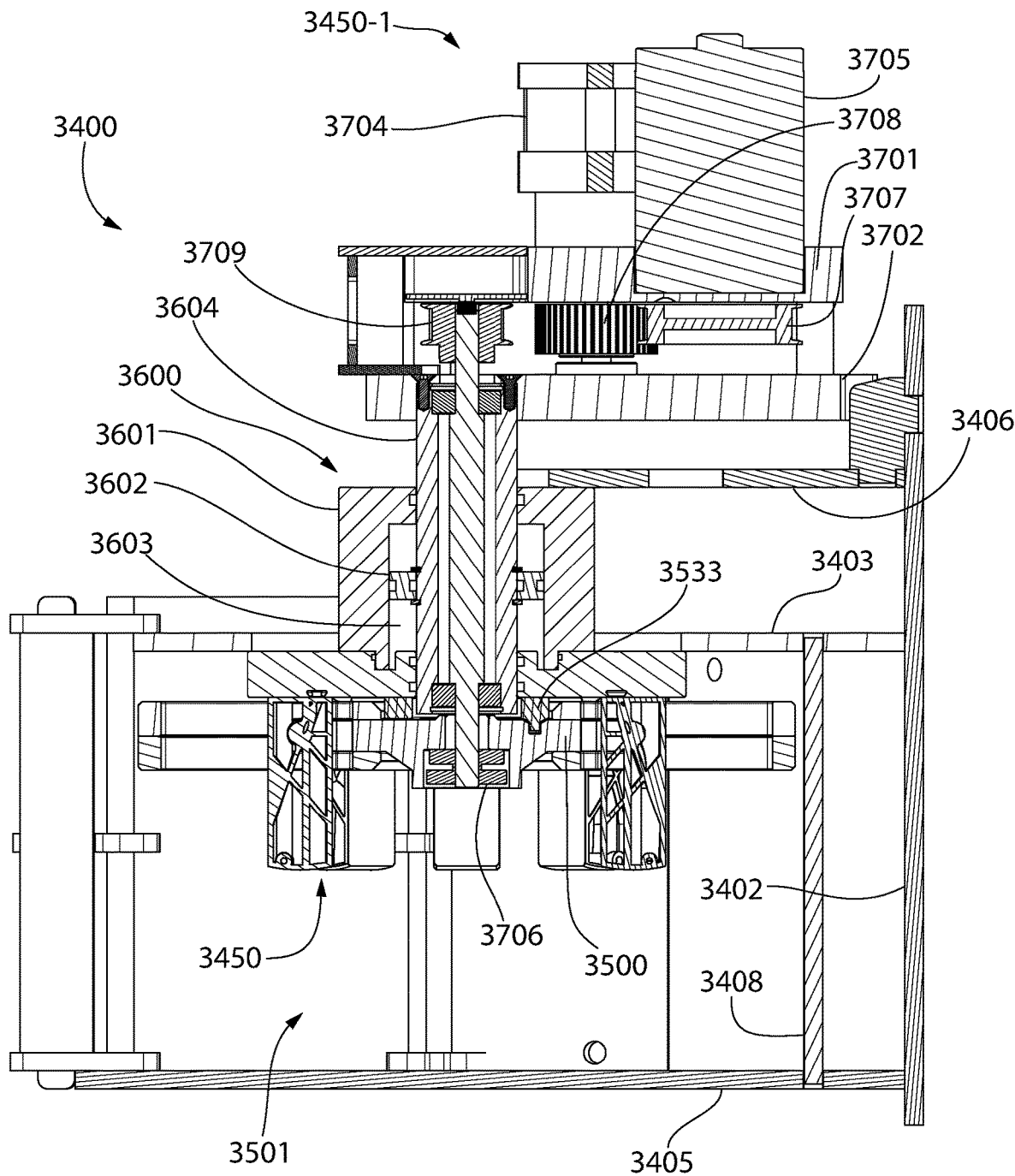
FIG. 53 is a front cross sectional view thereof.
Figure 54:
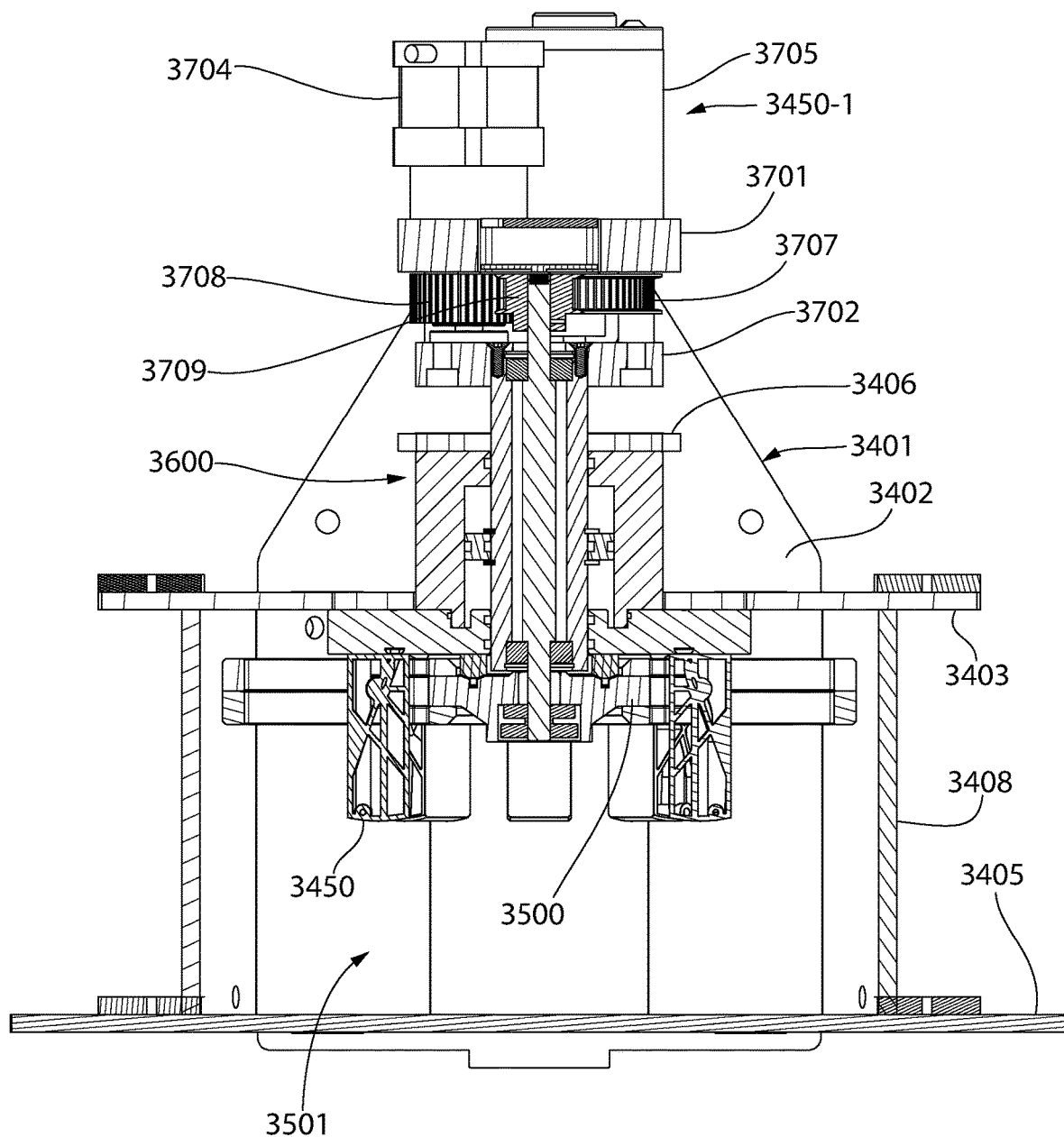
FIG. 54 is a side cross sectional view thereof.
Figure 55:
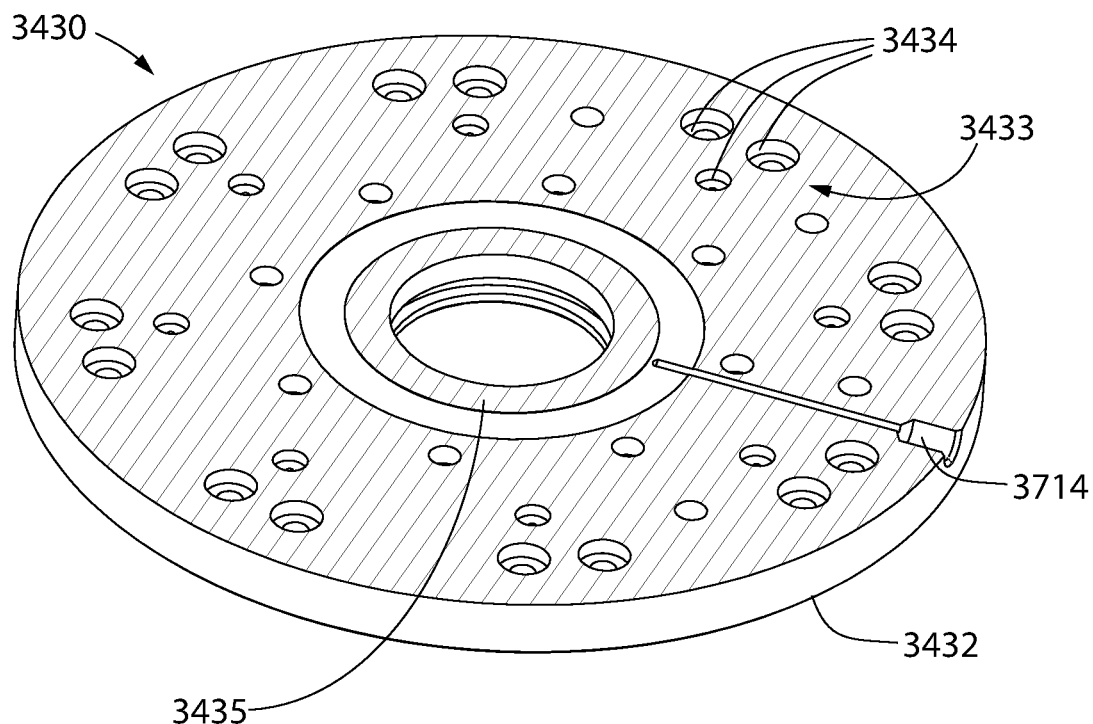
FIG. 55 is a top perspective view of a fluid exchange dock of the centrifuge.

Curved shields 3409 may be mounted to the upper and lower support plates 3403 and 3405 by pairs of arcuately curved upper shield supports 3407-1, intermediate shield supports 3407-2, and lower shield supports 3407-3. The shield supports may have a semi-circular shape and are vertically spaced apart as shown. In one embodiment, each shield support includes an inwardly open recess 3410 which receives the shields 3409 and an inwardly curved hook 3411 on each opposing end which traps the shield in the recess when installed. Shield supports 3407-1, 3407-2, and 3407-3 have a complementary radius to the radius of the shields 3409 to provide a relatively close and secure mount. A plurality of vertically-extending struts 3408 extend between the upper and lower shield supports 3407-1 and 3407-3, respectively. The top and bottom ends of each strut 3408 may be terminated with an elongate tab 3416 received in mating slots 3412 in the shield supports as best shown in FIG. 51. Other methods of coupling struts 3408 to the shield supports may be used. The struts 3408 maintain spacing between the upper shield supports 3407-1 and lower shield supports 3407-3 and add rigidity to the shield assembly 3404. Shield supports 3407-1, 3407-2, and 3407-3 may be welded or soldered to struts 3408 to complete the rigid structure.

Figure 43:
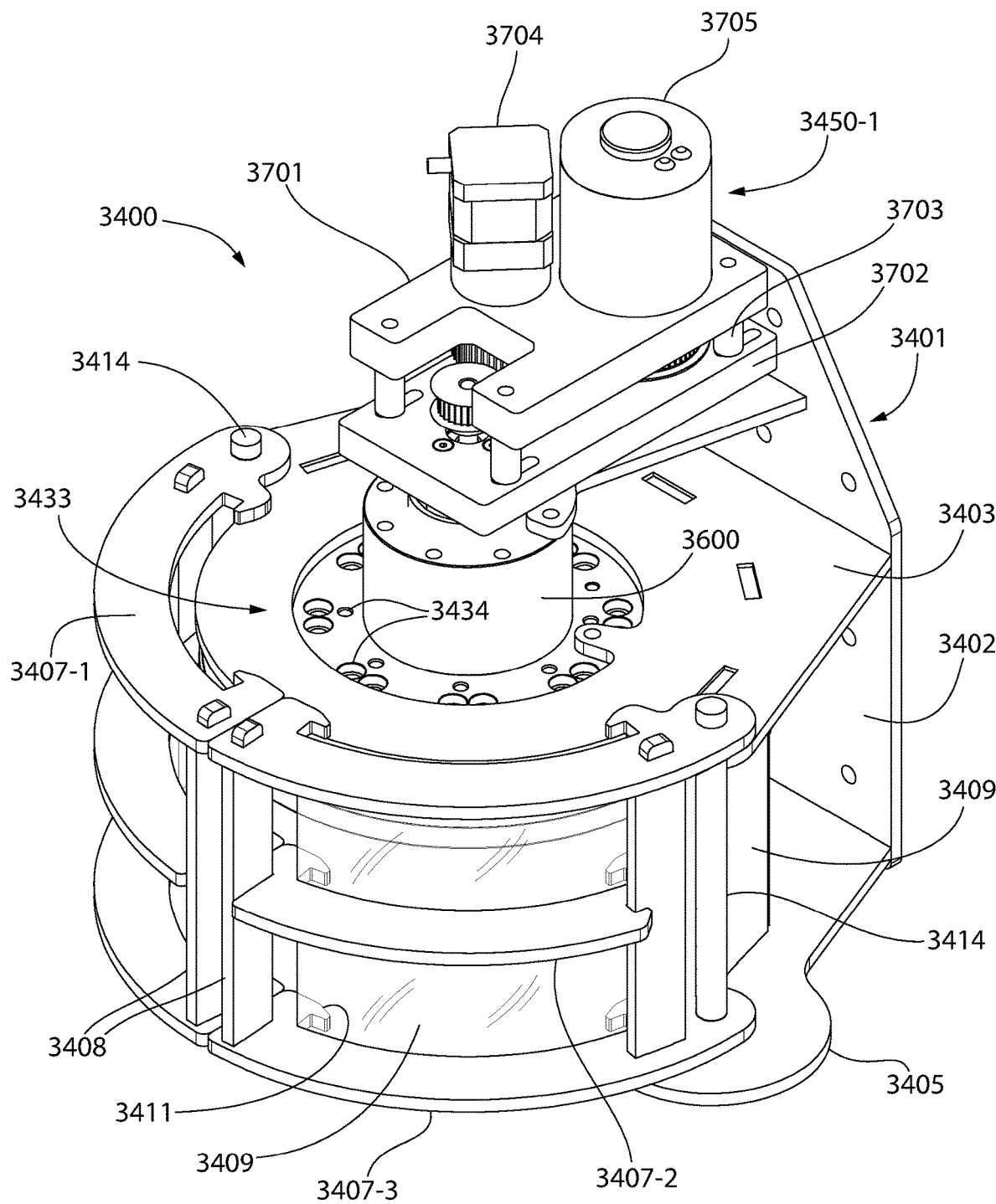
FIG. 43 is a top perspective view of a first embodiment of a centrifuge.
Figure 44:
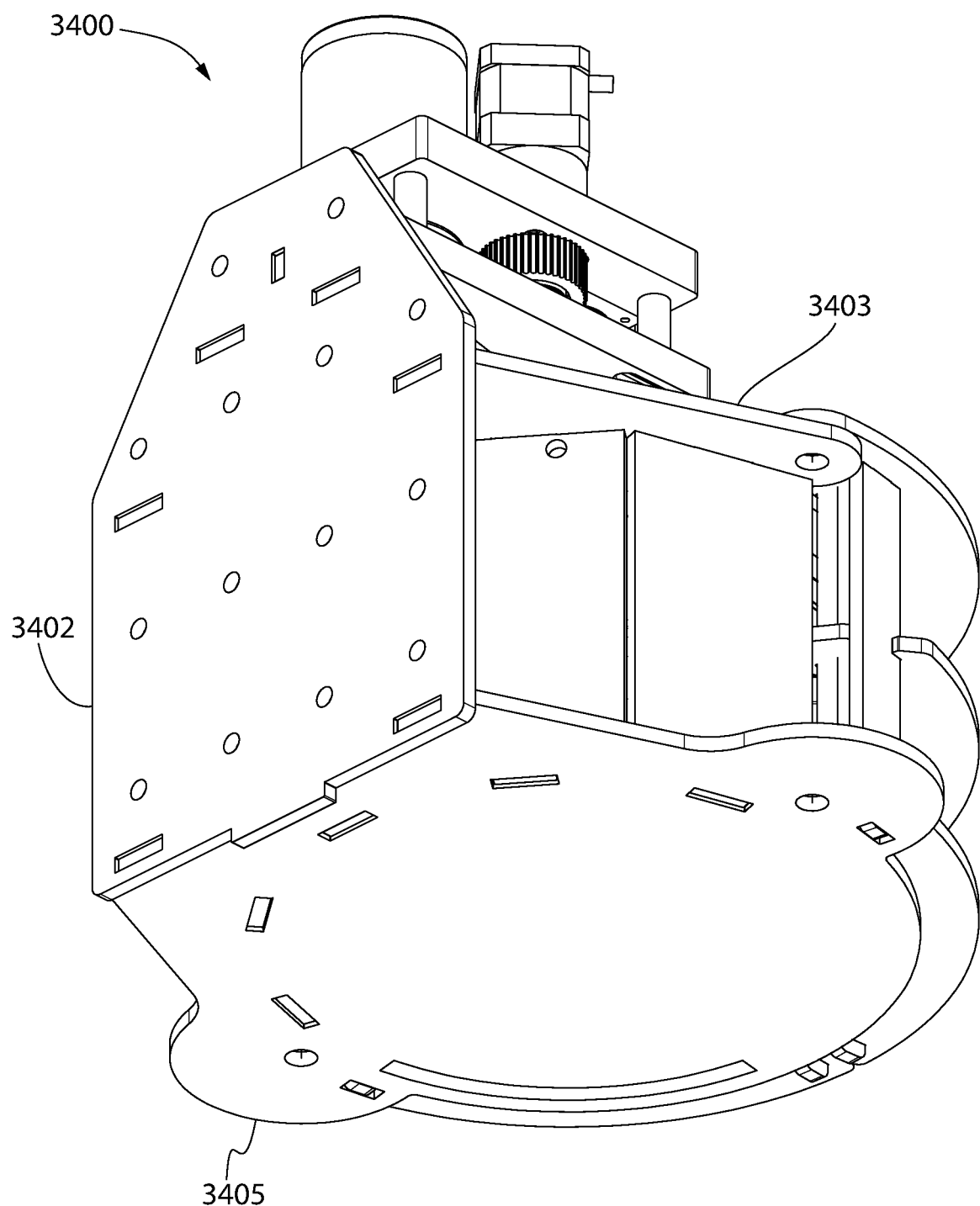
FIG. 44 is a bottom perspective view thereof.
Figure 45:
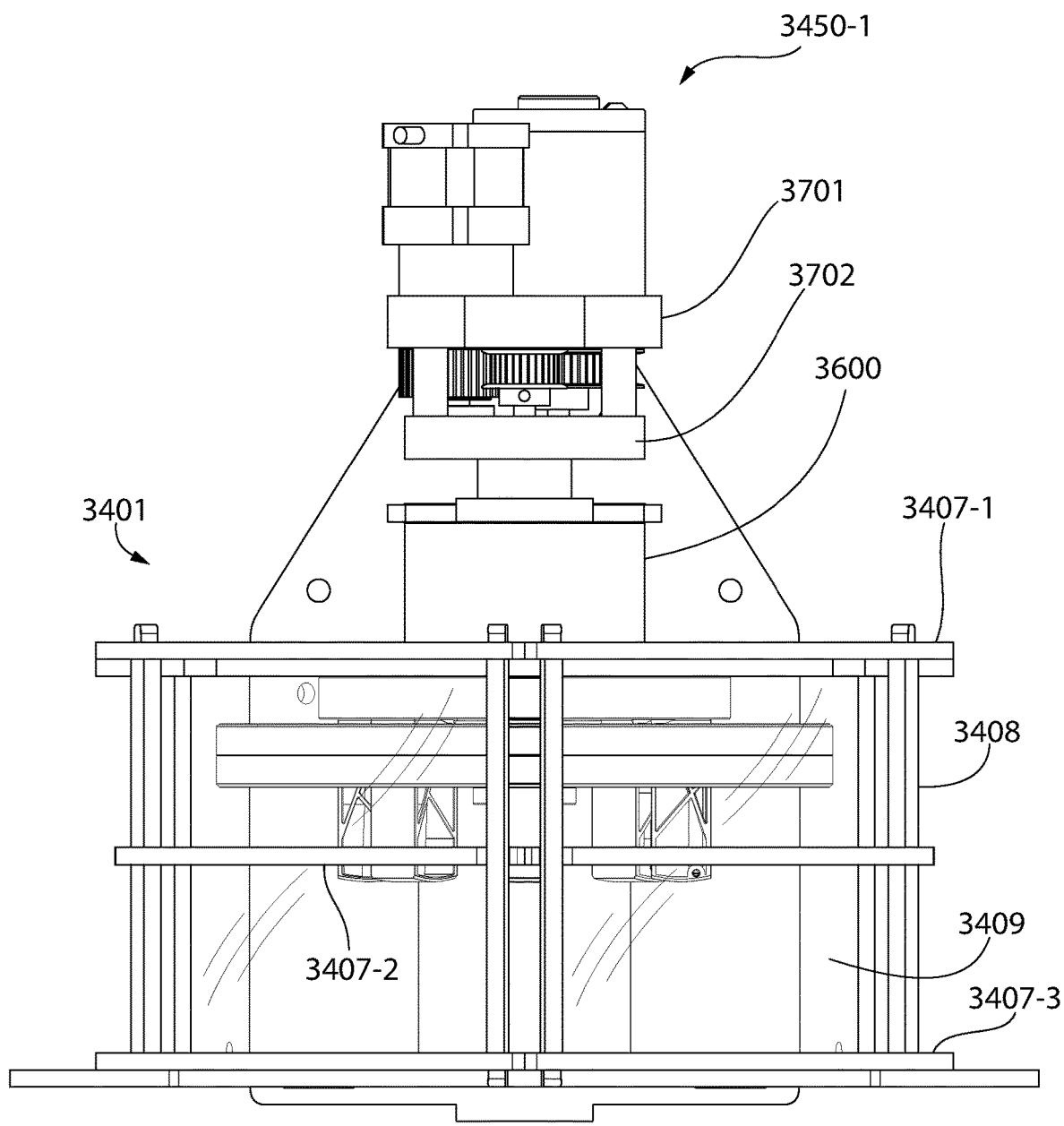
FIG. 45 is a front view thereof.
Figure 46:
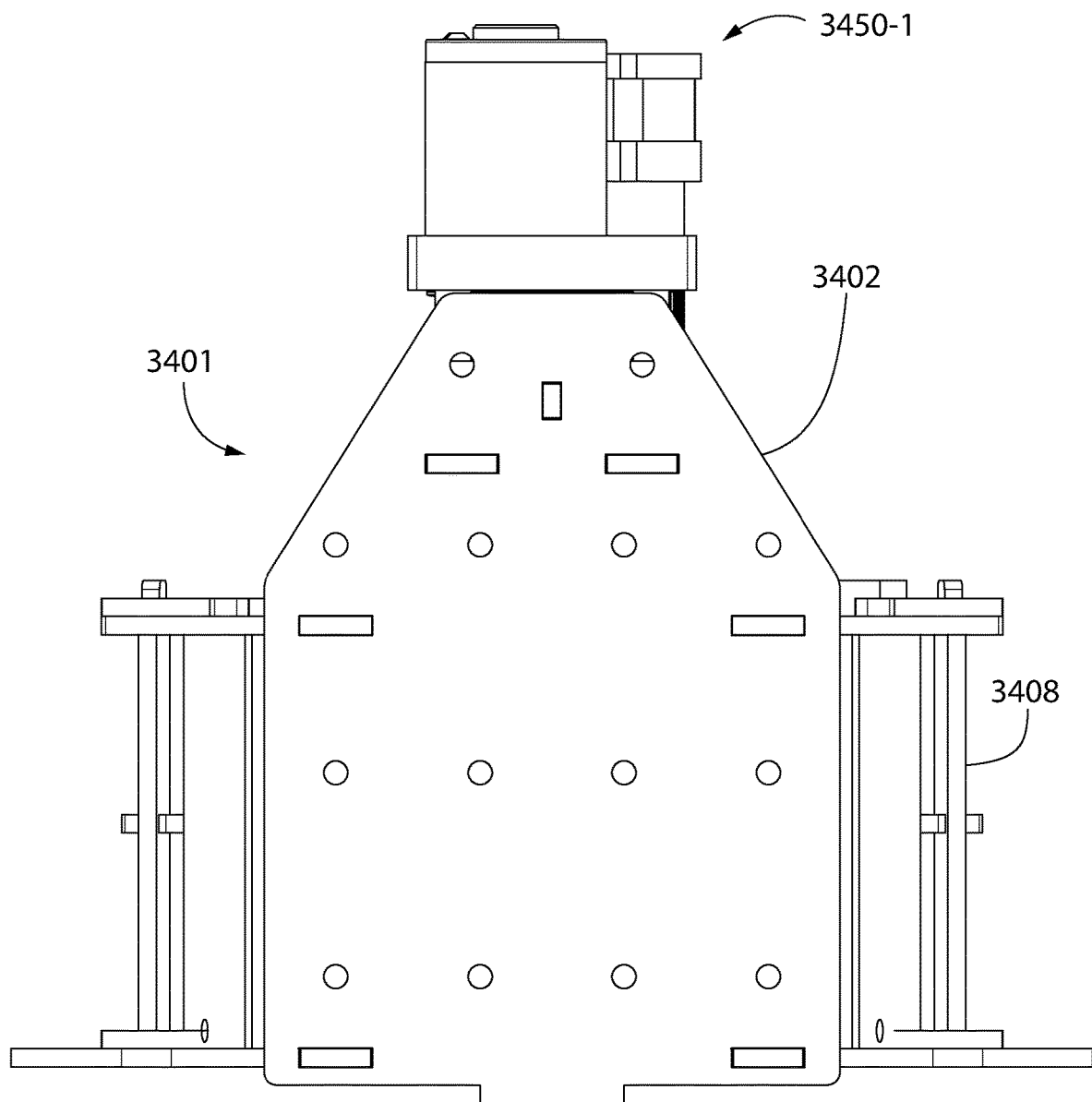
FIG. 46 is a rear view thereof.
Figure 47:
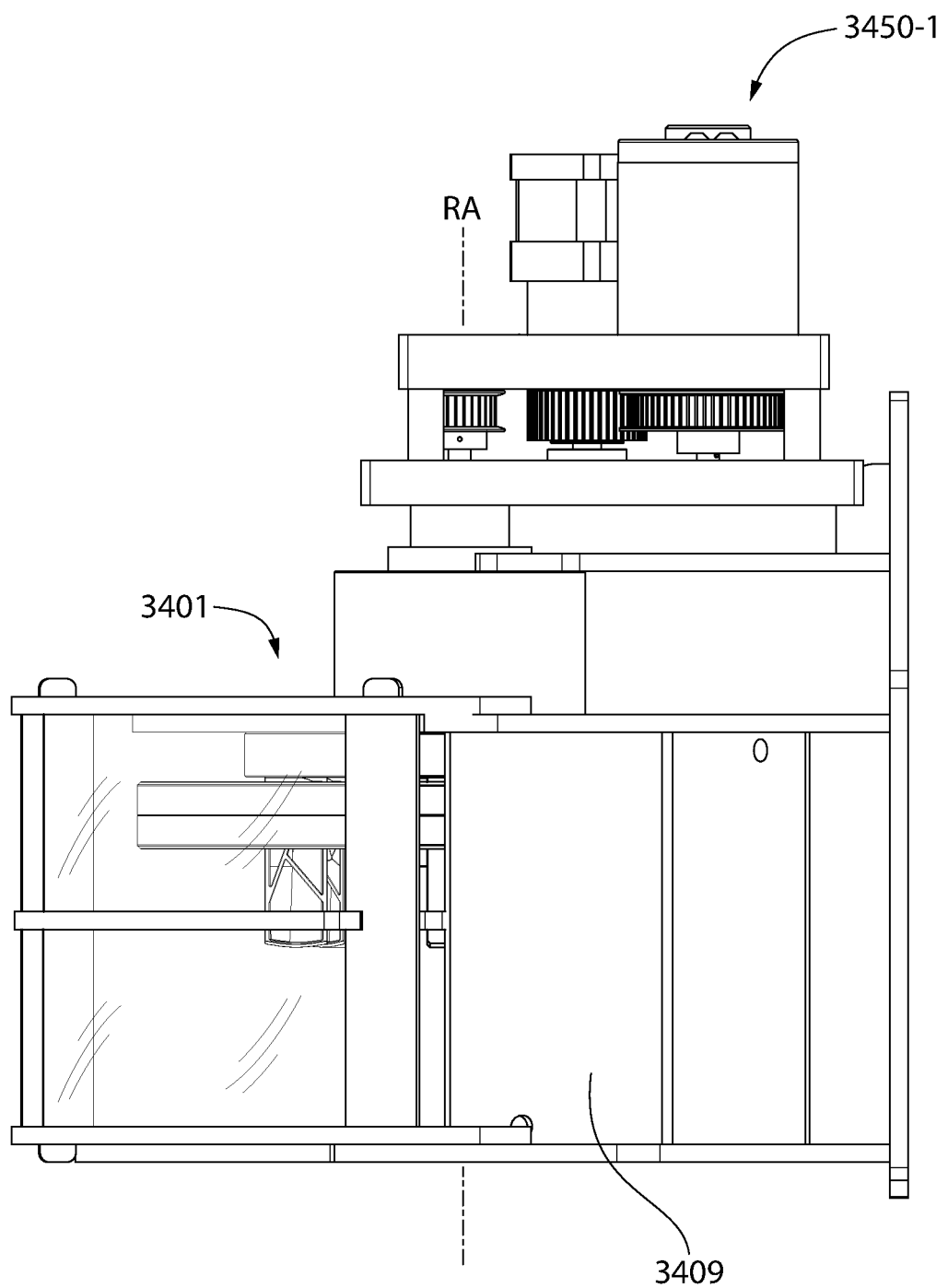
FIG. 47 is a first side view thereof.
Figure 48:
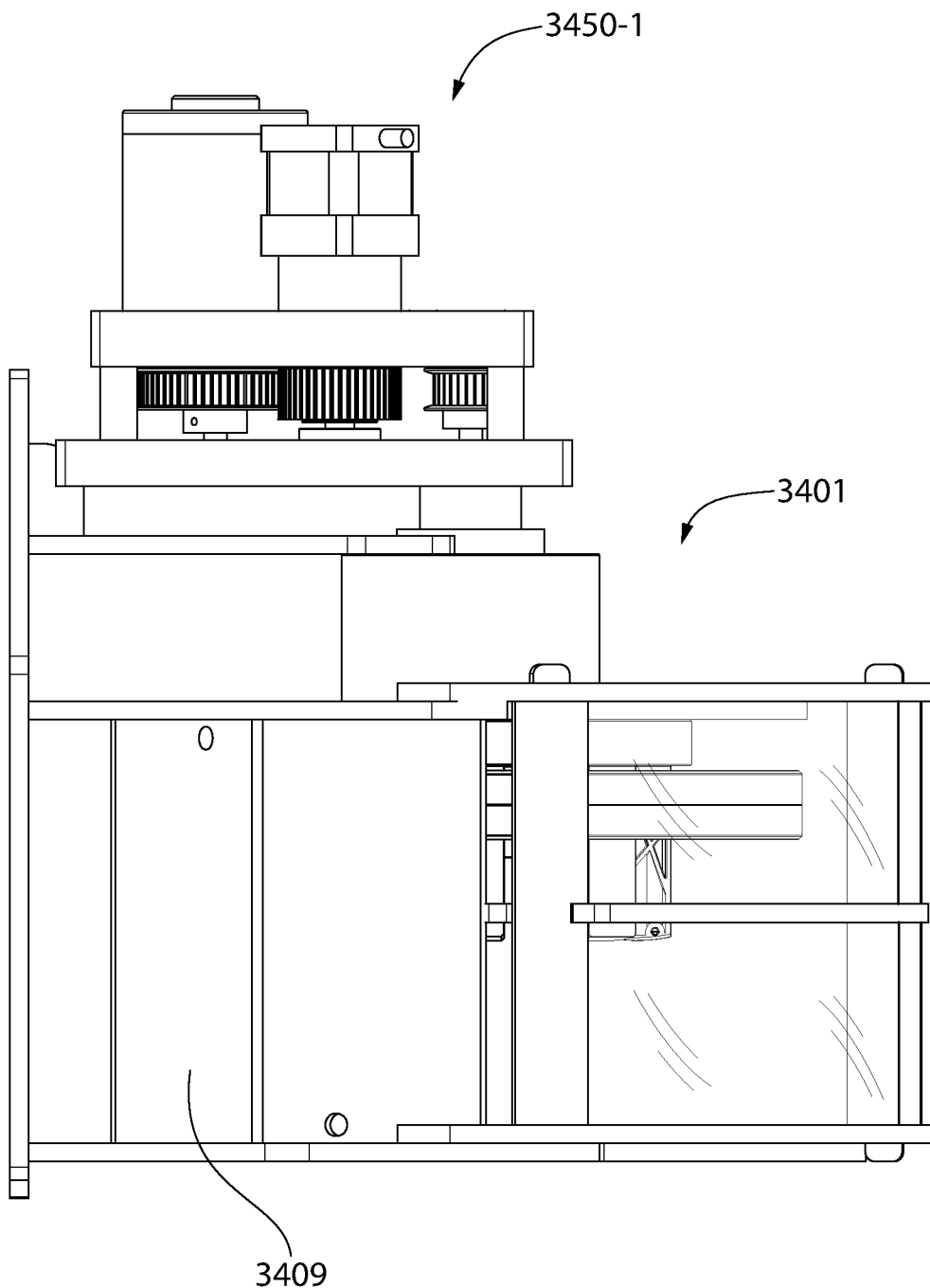
FIG. 48 is a second side view thereof.
Figure 49:
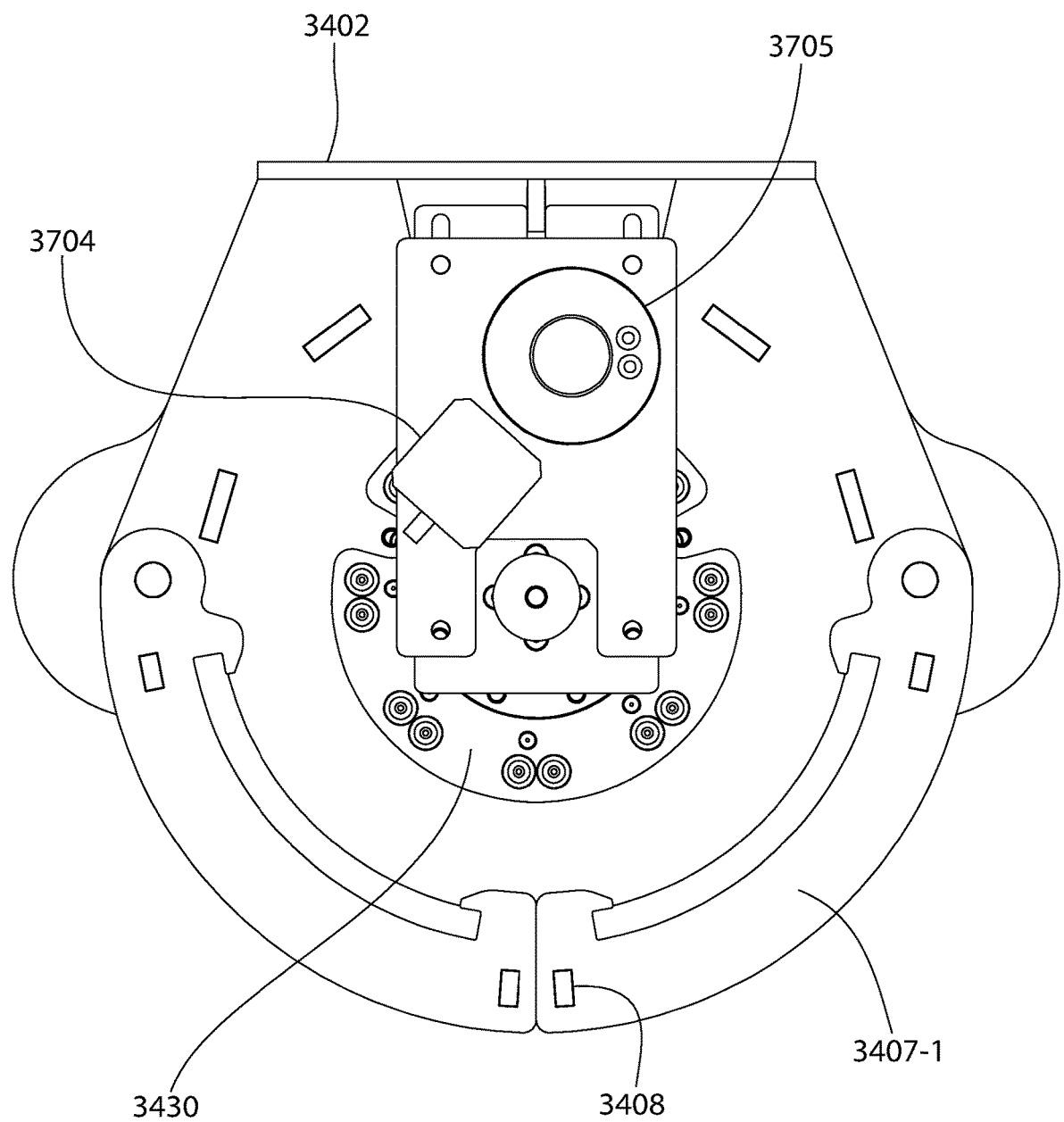
FIG. 49 is a top view thereof.
Figure 50:
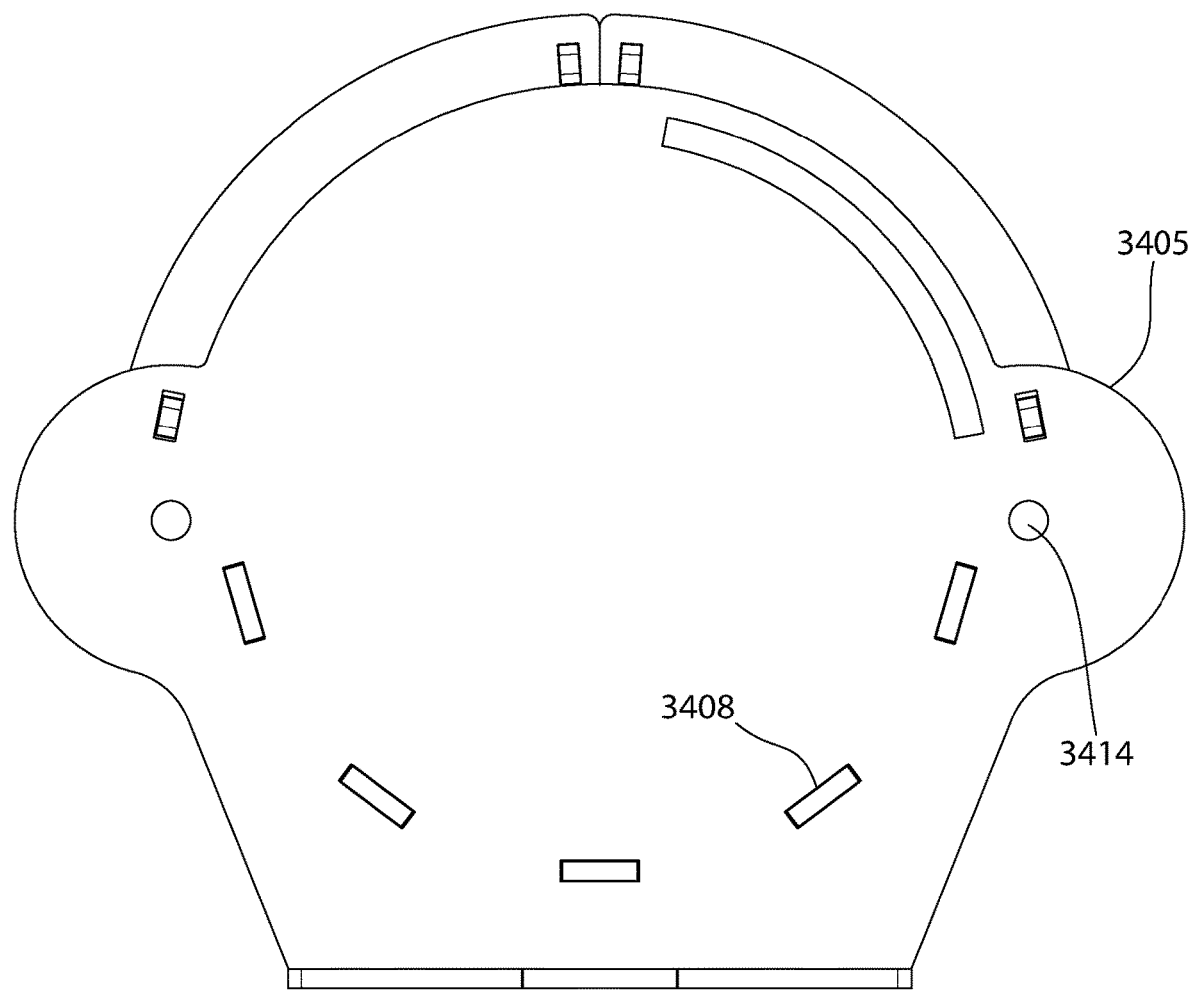
FIG. 50 is a bottom view thereof.

In one embodiment, the assembly of shield supports 3407-1, 3407-2, 3407-3 may be pivotably coupled to housing 3401 via vertically-extending pivot rods 3414 (see, e.g. FIGS. 43 and 51). This allows the shields 3409 to be pivotably opened to access the processing chamber 3501 inside the housing. Pivot rods 3414 extend through mounting holes 3413 on each of the opposing sides of support plates 3403, 3405. Mounting holes 3413 are positioned near the outboard ends of the supports 3407-1 and 3407-3 which are arranged to receive the rods 3414 therethrough. The outboard end portions of shield supports 3403 and 3405 may overlap portions of the upper and lower support plates 3403 and 3405 as shown in FIG. 43 thereby providing support for the ends of the shield supports.

Although pairs of upper, intermediate, and lower shield supports 3407-1, 3407-2, and 3407-3 are disclosed, in other embodiments a single unitary upper, intermediate, and lower shield support may instead be provided. In other embodiments, the intermediate shield support may be omitted. Other mechanisms or techniques instead of shield supports may be used for mounting shields 3409 to the centrifuge housing 3401 may of course be used and is not limiting of the invention.

The housing plates 3402, 3403, and 3405, shield supports 3407-1, 3407-2, and 3407-3, and struts 3408 may be formed of any suitable metallic or non-metallic material in various embodiments. In one non-limiting embodiment, aluminum may be used. Shields 3409 may be metallic, non-metallic, or combinations thereof. In one embodiment, the curved shields 3409 may be formed of a transparent impact-resistant plastic material to allow operation of the centrifuge to be observed. Straight shields 3409 may be formed of the same material, or metal in some embodiments.

Centrifuge 3400 further includes a motor drive mechanism 3450-1 including a vertically oriented and rotatable main drive shaft 3700 rotated by a drive mechanism, rotary tube hub 3500 coupled to the drive shaft 3700, and a stationary fluid exchange manifold or dock 3430. The rotary tube hub 3500 is configured for mounting and supporting a plurality of sample centrifuge tubes 3450 in a pivotable manner, as further described herein. The drive mechanism 3450-1 may be raised and lowered by a piston mechanism 3600 as a unit relative to centrifuge housing 3401 which may be fixedly attached to a support structure. Each of these components and their interaction is described below. As exemplified below, rotary tube hub 3500 is movable between the docked and undocked positions. Alternatively, the fluid exchange manifold or dock 3430 can be driven or both rotary tube hub 3500 and fluid exchange manifold or dock 3430 can be driven to dock or undock with each other.

Figure 76:
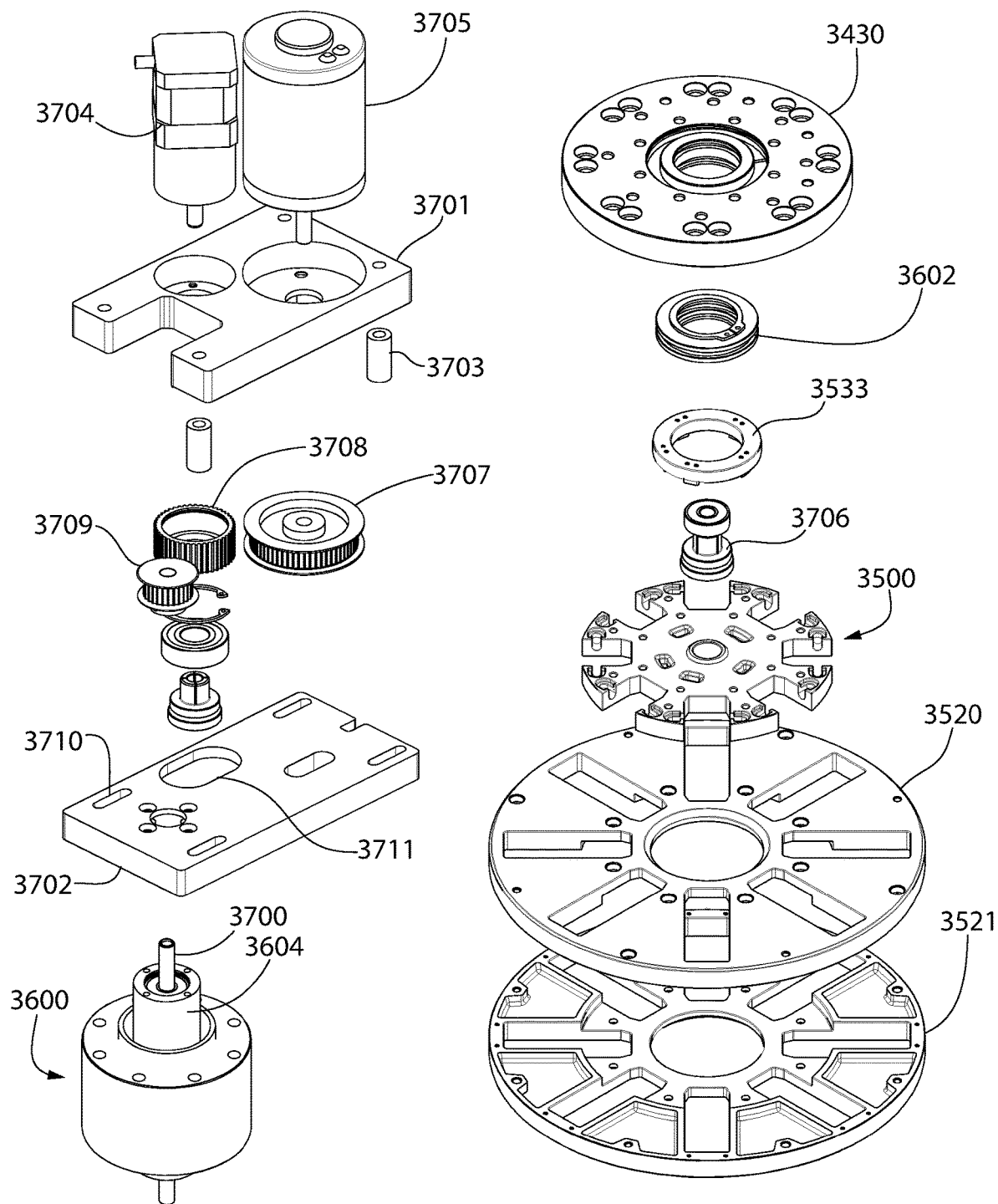
FIG. 76 is an top exploded perspective view of the drive mechanism.

The main drive shaft 3700 of motor drive mechanism 3450-1 is vertically oriented and defines a rotational axis RA (see, e.g. FIG. 47) creating a vertical centerline of centrifuge 3400 for reference purposes. Rotary tube hub 3500, fixedly coupled to the lower end of the drive shaft 3700 such as via tapered coupler 3706 (see, e.g. FIGS. 53 and 71), is rotated or spun by the shaft to process soil samples. In one embodiment, drive mechanism 3450-1 may comprise dual motors including a larger main motor 3705 and a smaller indexing motor 3704. The motors are supported by substantially planar upper and lower motor supports 3701, 3702, which may be made of rectangular metallic or non-metallic plates having a rectangular configuration in one embodiment. The motor supports are vertically spaced apart by a plurality of tubular spacers 3703 in one embodiment to maintain separation between the motor supports. Each spacer is fixed to the upper motor support 3701 and slideably connect to the lower motor support 3702 via horizontally elongated slots 3710 (see, e.g. FIG. 76). The upper motor support is thus slideably movable relative to the lower motor support. Four spacers 3703 may be provided in one embodiment with a spacer located near each of the four corners of the motor supports 3701, 3702. It bears noting that motor supports 3701, 3702 are free floating and not fixedly attached to centrifuge housing 3401 to allow the drive mechanism to be raised and lowered via operation of piston mechanism 3600, as further described herein.

Figure 95:
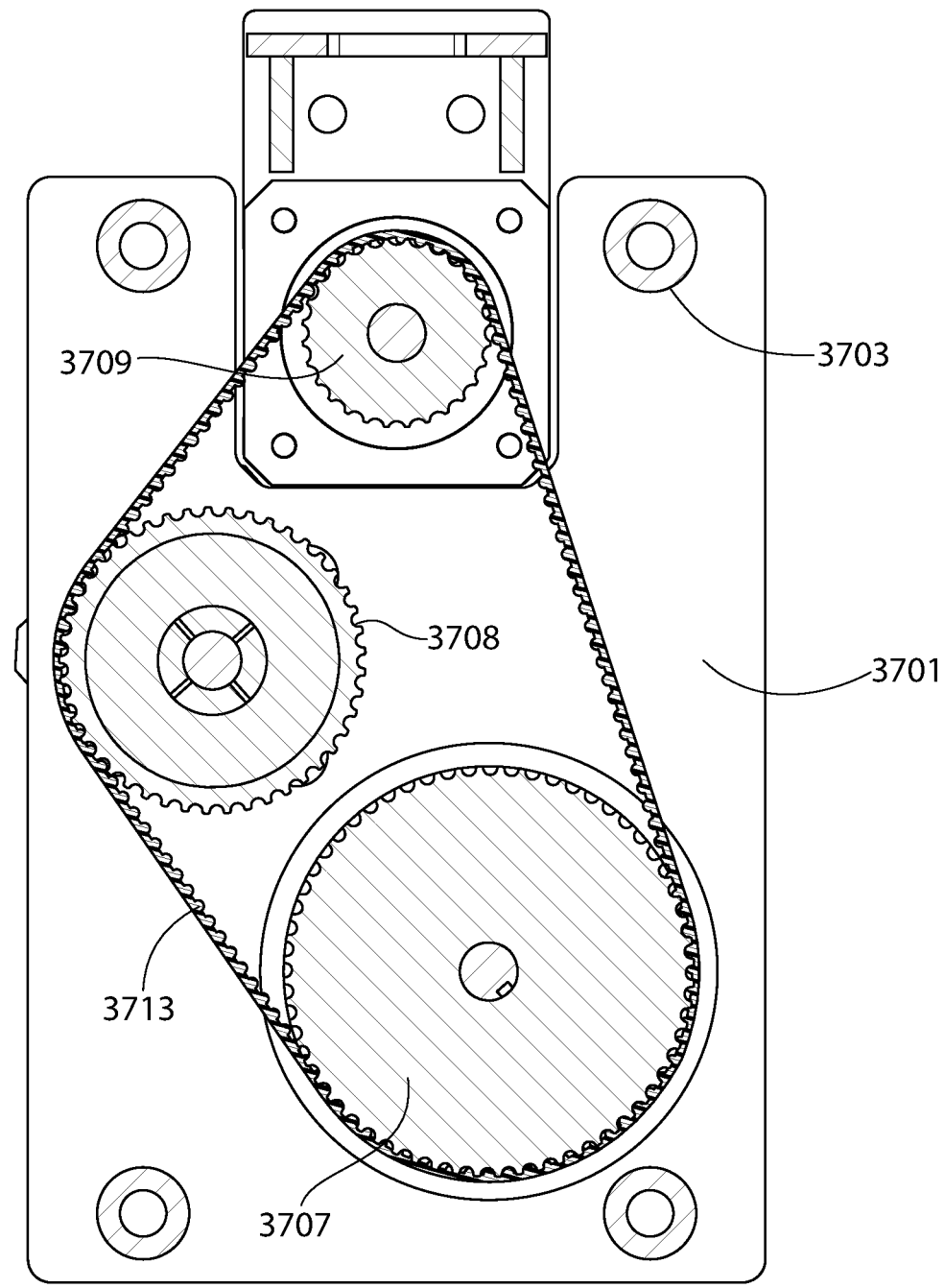
FIG. 95 is a top cross sectional view of the drive mechanism of the mixing device.

Main motor 3705 includes an associated main gear 3707 driven by the motor shaft of the main motor. Indexing motor 3704 similarly includes an associated indexing gear 3708 driven by the motor shaft of the indexing motor. Both gears 3707 and 3708 are selectively engageable with the main drive pulley gear 3709 which is fixedly attached to the top end of main drive shaft 3700 such as via set screws or other means. A toothed timing belt 3713 shown in FIG. 95 winds around and operably interconnects all three gears to provide a belt-drive system for rotating the main drive shaft 3700.

To adjust tension in the timing belt 3713, the upper motor support 3701 is slid in one of two opposing direction toward or away from the main drive shaft 3700, which is fixed in horizontal position in the lower motor support 3702 via a mounting hole. The main and indexing motors 3705, 3704 are fixed in horizontal position to the upper motor support 3701 via respective mounting holes. Sliding the upper motor support 3701 relative to the lower motor support 3702 back and forth allows the user to properly obtain the proper tension in the belt. The spacers 3703 will slide in their respective slots 3710 in the lower motor support when adjusting the belt tension.

The main motor 3705 is used to rotate the rotary tube hub 3500 at relatively high speeds for centrifugating the soil samples. The indexing motor 3704 is used to properly align and index the tube hub in rotational position relative to the fluid exchange dock 3430 for exchanging fluids between the centrifuge tubes 3450 carried by the hub and the dock. In one embodiment, indexing motor 3704 may be a stepper motor whose output is used to engage and incrementally rotate the main drive shaft 3700 in very small discrete steps to achieve proper rotational alignment between the dock and tube hub. This allows very precise speed control and positioning (i.e. motion control) of the main drive shaft which can be controlled by the system programmable controller. The stepper motor functions in cooperation with indexing features on the rotary tube hub 3500 and centrifuge housing 3401 to achieve proper rotational alignment between the dock 3430 and rotary tube hub 3500 when the hub is in a docked position. This ensures that the clusters 3433 of flow passages 3434 in the fluid exchange dock 3430 are concentrically aligned with flow ports 3451 formed in the top surface of centrifuge tubes 3450 for exchanging fluids when the rotary tube hub 3500 is in the upper docked position. In one embodiment, a rotational sensor (not shown) such as a Hall effect sensor may be provided which detects and communicates the rotational position of main drive shaft to the system controller, which in turn may control operation of the stepper motor and the rotational position of main drive shaft 3700.

Referring to FIGS. 43-56, dock 3430 includes a generally disk-shaped annular body having a central opening 3435, which may be coaxially aligned with rotational axis RA for passage of drive shaft 3700 therethrough. Dock 3430 is fixedly attached to upper support plate 3403, such as via threaded fasteners or other means and remains stationary with housing 3401. The dock body may have a generally solid metallic or non-metallic structure in one embodiment. In one embodiment, dock 3430 may be formed of plastic. A plurality of flow holes or passages 3434 extend vertically through the body between and through top and bottom surfaces 3431, 3432 of the fluid exchange dock 3430. The flow passages 3434 may be arranged in clusters 3433 having a number and pattern which matches and coincides with the number of centrifuge tubes 3450 and flow ports formed in the top surface of the tubes. When the centrifuge tubes 3450 are selectively mated to and engaged with the dock 3430, the flow ports 3451 and flow passages 3434 are concentrically aligned and in fluid communication. This allows sample slurry to be injected into and extracted from the centrifuge tubes 3450. In one configuration, clusters of three flow passages 3434 and flow ports 3451 may be provided. Other embodiments may have more or less holes/conduits in each cluster.

Figure 56:
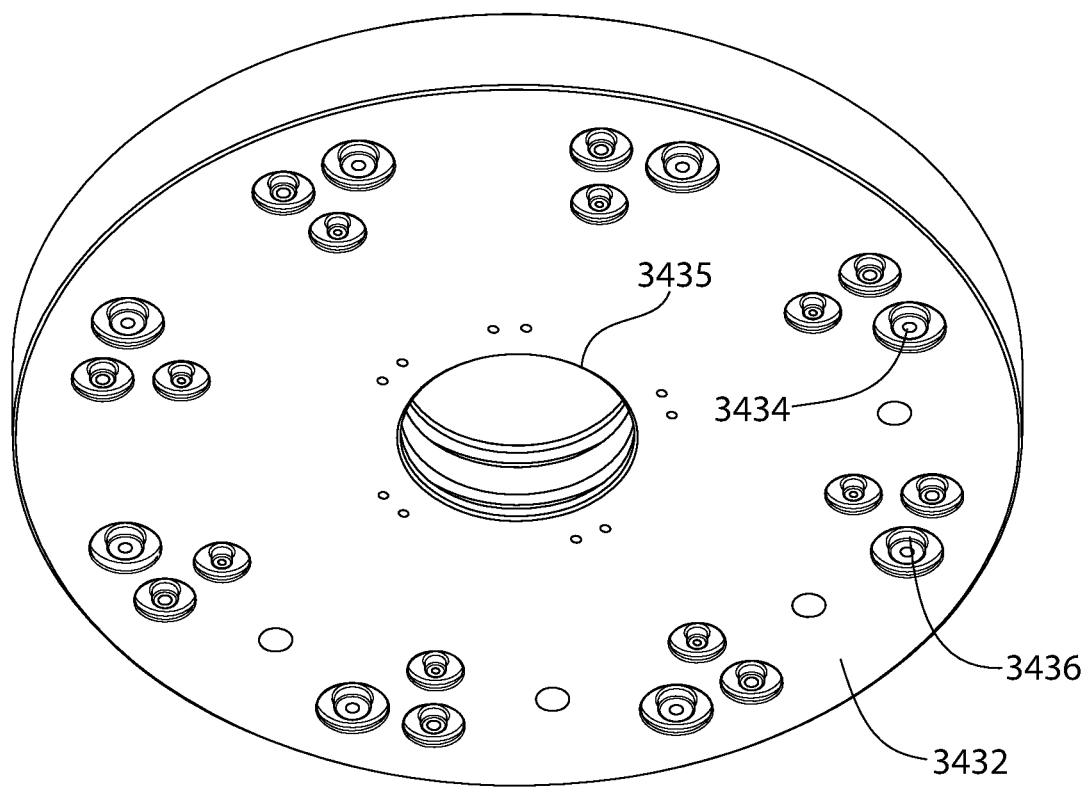
FIG. 56 is a bottom perspective view thereof.

The lower ends of each flow passages 3434 in dock 3430 may be terminated in a nozzle 3436 which is at least partially insertable into the open flow ports 3451 for forming a fluidic sealed connection therebetween (see, e.g. FIG. 56). Nozzles 3436 may be disposed inside downwardly open holes formed in the bottom surface 3432 of dock 3430 in one embodiment, thereby forming pin-like projections extending downwards from the dock.

Referring now to FIGS. 43-52 and 57-58, rotary tube hub 3500 has a generally disk-shaped body including a central opening 3515 coaxially aligned with rotational axis RA for passage of drive shaft 3700 therethrough. A tapered coupler 3706 is affixed to the bottom end of drive shaft 3700 which secures the rotary tube hub 3500 to the drive shaft. Bushing 3508 may be secured in turn to the drive shaft 3700 via a threaded fastener (not shown) in one example.

Rotary tube hub 3500 is configured for pivotably mounting centrifuge tubes 3450 to the hub for centrifuging the tubes with sample slurry therein. The rotary tube hub 3500 includes a top surface 3510, opposing bottom surface 3511, and a circumferentially-extending peripheral sidewall 3512 extending between the surfaces (best shown in FIG. 57). Rotary tube hub 3500 includes a plurality of radially and outwardly open peripheral recesses 3502 formed through the sidewall 3512; one recess for each centrifuge tube 3450. Recesses 3502 are further upwardly and downwardly open. This allows the centrifuge tubes 3450 to pivot radially outwards and upwards as the centrifuge is rotated to high speeds. The peripheral recesses 3502 may have a generally rectilinear shape in one embodiment and may be arranged in diametrically opposed pairs. In one construction, eight recesses may be provided; however, more or less recesses may be provided depending on the number of centrifuge tubes used and soil nutrients to be analyzed.

Figure 57:
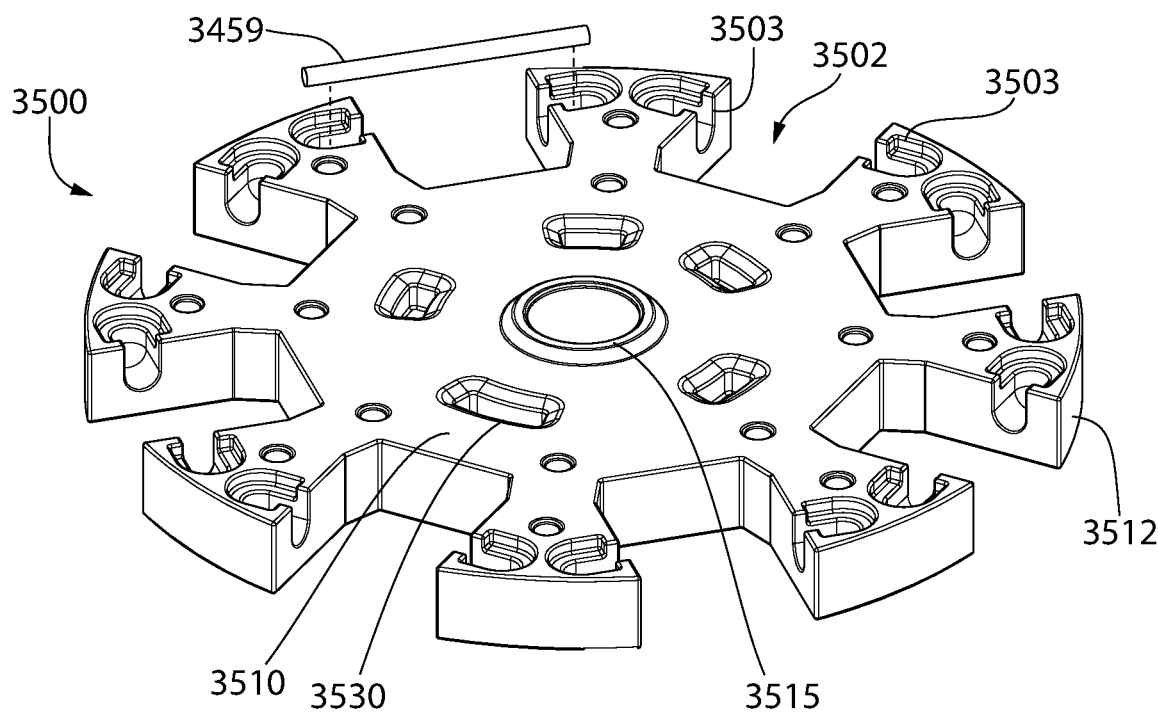
FIG. 57 is a top perspective view of a rotary tube hub of the centrifuge.
Figure 58:
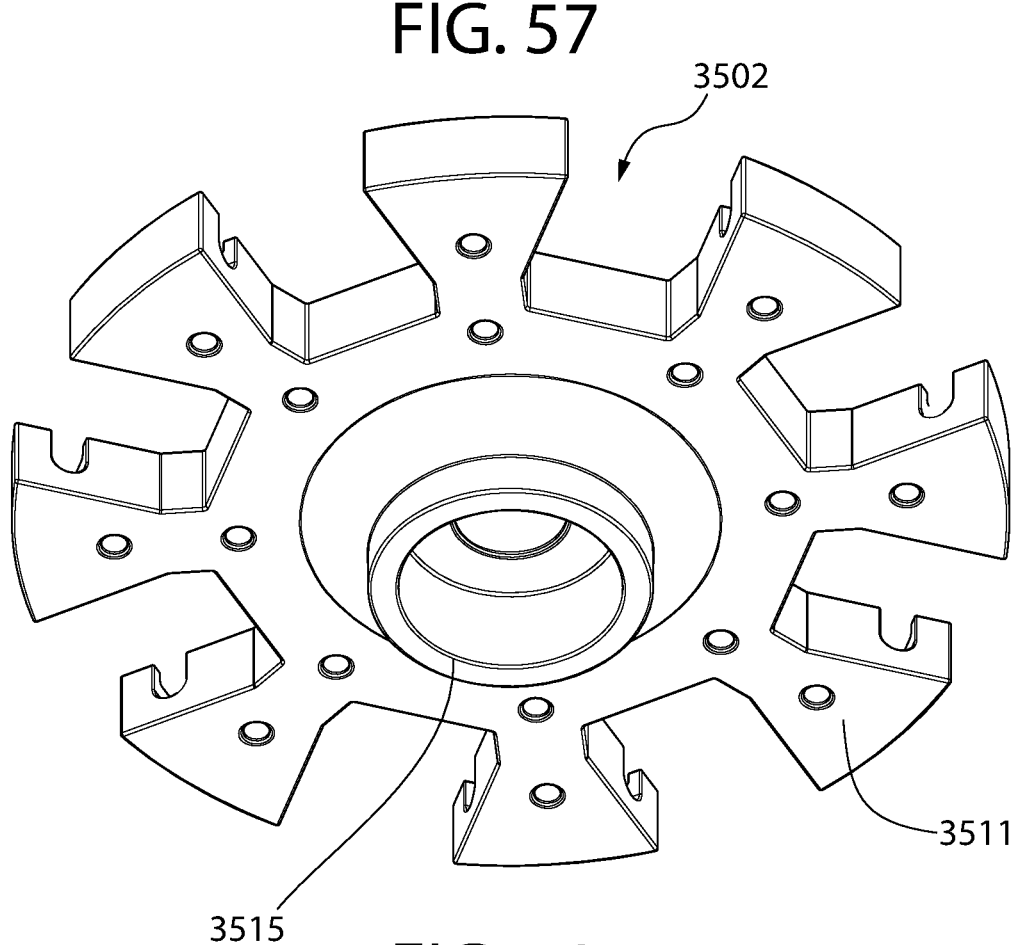
FIG. 58 is a bottom perspective view thereof.
Figure 59:
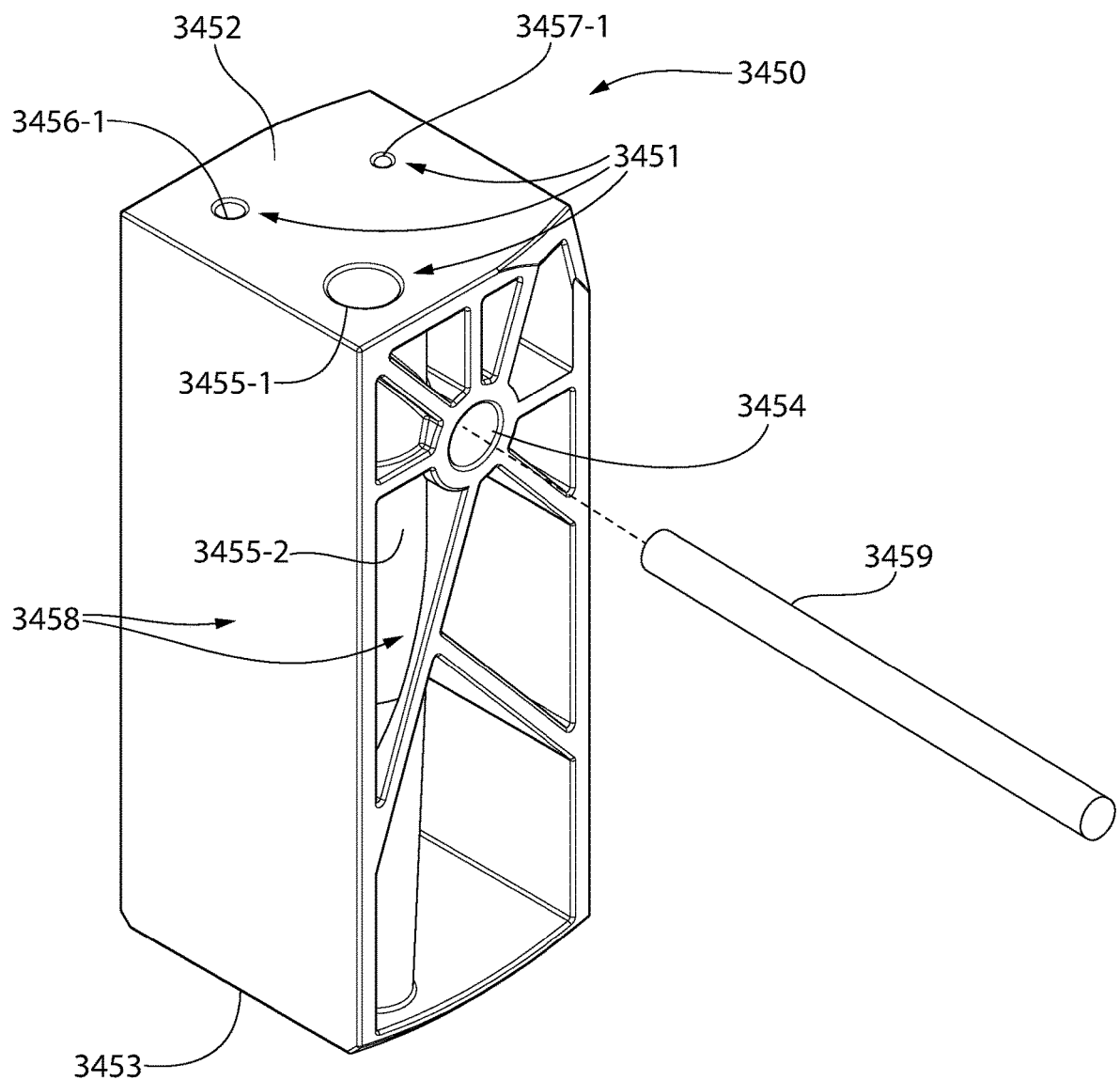
FIG. 59 is an exploded perspective view of a centrifuge tube of the centrifuge for mounting to the tube hub.
Figure 60:
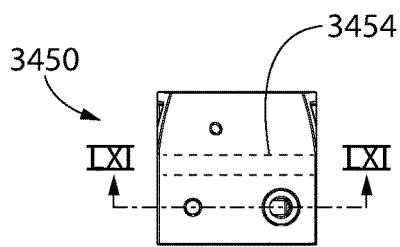
FIG. 60 is a first top view thereof.
Figure 62:
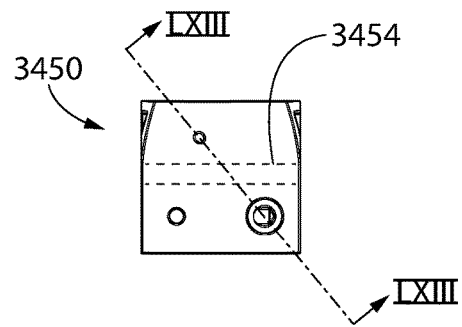
FIG. 62 is a second top view thereof.
Figure 61:
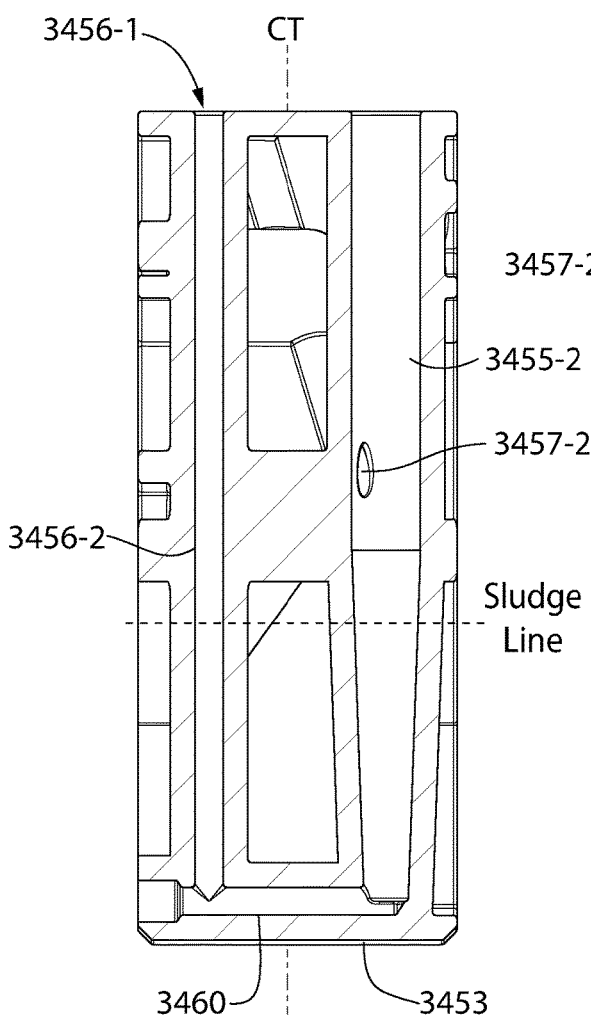
FIG. 61 is a cross-sectional view taken from FIG. 60.
Figure 63:
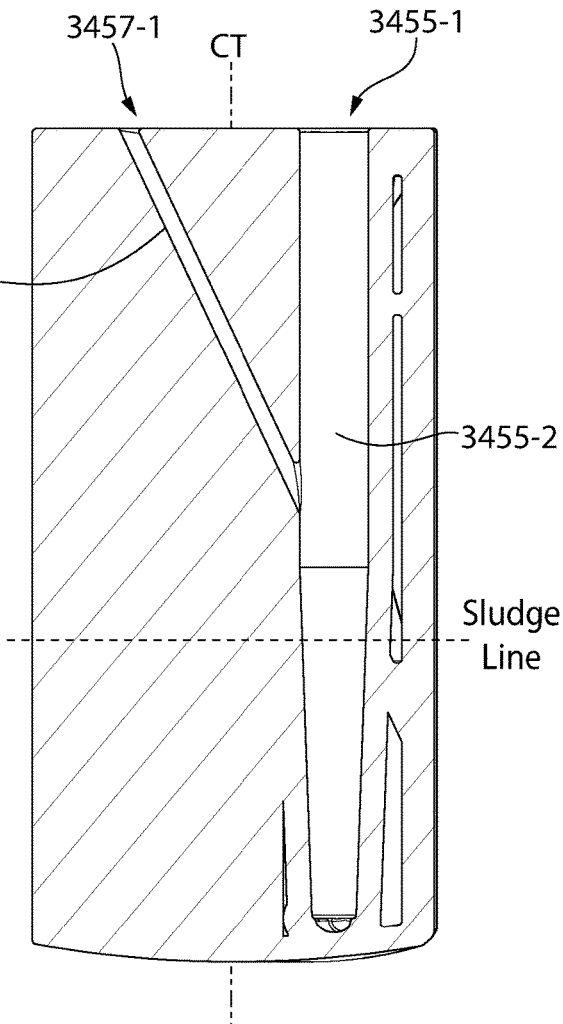
FIG. 63 is a cross sectional view taken from FIG. 62.

With additional reference to FIGS. 59-65, centrifuge tubes 3450 may each be pivotably mounted in a respective peripheral recess 3502 by a pivot pin 3459 (shown in FIGS. 57 and 59). The opposing ends of pivot pin 3459 are received in upwardly open pin slots 3503 formed on each side of the recess 3502 which also open inwardly towards the recess (see, e.g. FIG. 57). Slots 3503 have a depth that extends only partially through the thickness of the rotary tube hub 3500 (measured between the top and bottom surfaces 3510 and 3511) so that the slot does not penetrate the bottom surface. This forms a seating surface which can engage the pivot pin 3459. Pivot pins 3459 are inserted through a transversely oriented through-hole 3454 formed through centrifuge tube 3450 such that the ends of the pin remain exposed. Pivot pins 3459 thus preferably have a greater length than the transverse width of the centrifuge tubes measured in the direction of the through-hole 3454 for this purpose. When mounted, the pins 3459 bridge across the recesses 3502 within each tube 3450.

Figure 64:
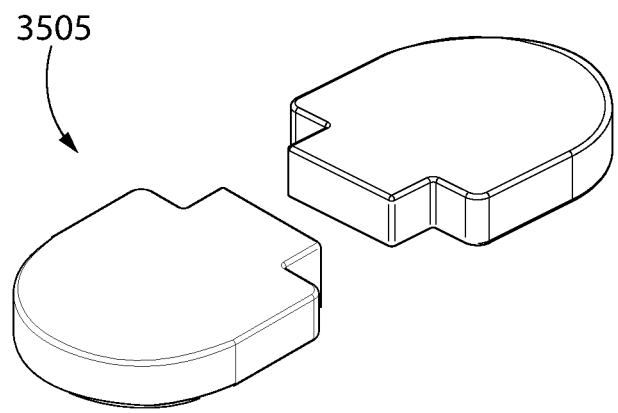
FIG. 64 is a top perspective view of a locking cap for the centrifuge tube.
Figure 65:
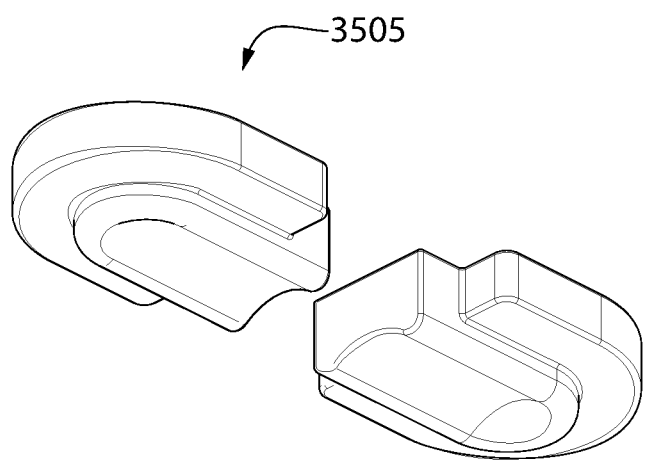
FIG. 65 is a bottom perspective view thereof.

To lock and trap the exposed ends of the pivot pins in slots 3503, locking caps 3505 are provided in one embodiment as best shown in FIGS. 64 and 65. To mount each centrifuge tube 3450 to the rotary tube hub 3500, one of the pivot pins 3459 is first inserted through the through-hole 3454 so that each end of the pin remains exposed. The tube 3450 is inserted into the peripheral recess 3502 with the pin 3459 positioned above the pin slots 3503 straddling the recess. The centrifuge tube 3450 is lowered downwards in the recess 3502 until the pivot pin 3459 ends enter and are fully seated inside the pair of pin slots 3503. One of the locking caps 3505 is then engaged with each of the slots 3503 to lock the pin in the slots. The locking caps 3505 may be configured to form a snap fit with the slots 3503 in one embodiment. In other embodiments, the locking caps 3505 may be retained in position on the pin slots 3503 by an aerodynamic cover assembly instead of or in addition to the snap lock fit.

The prime purpose of the aerodynamic cover assembly is to streamline the rotary tube hub 3500 assembly as it spins to reduce power input and noise due to aerodynamic losses since the tube hub with centrifuge tubes would act as an air impeller otherwise. The cover assembly comprises an upper cover 3520 and lower cover 3521 which are affixed to the hub such as via threaded fasteners in one embodiment or other mechanical fastening methods. FIGS. 51-54 show the covers. The rotary tube hub 3500 is thus sandwiched and compressed between the covers, as further shown in FIGS. 66 and 67 which depict the completed hub assembly. The cover assembly advantageously also serves to trap the locking caps 3505 beneath the upper cover 3520 as noted.

Figure 66:
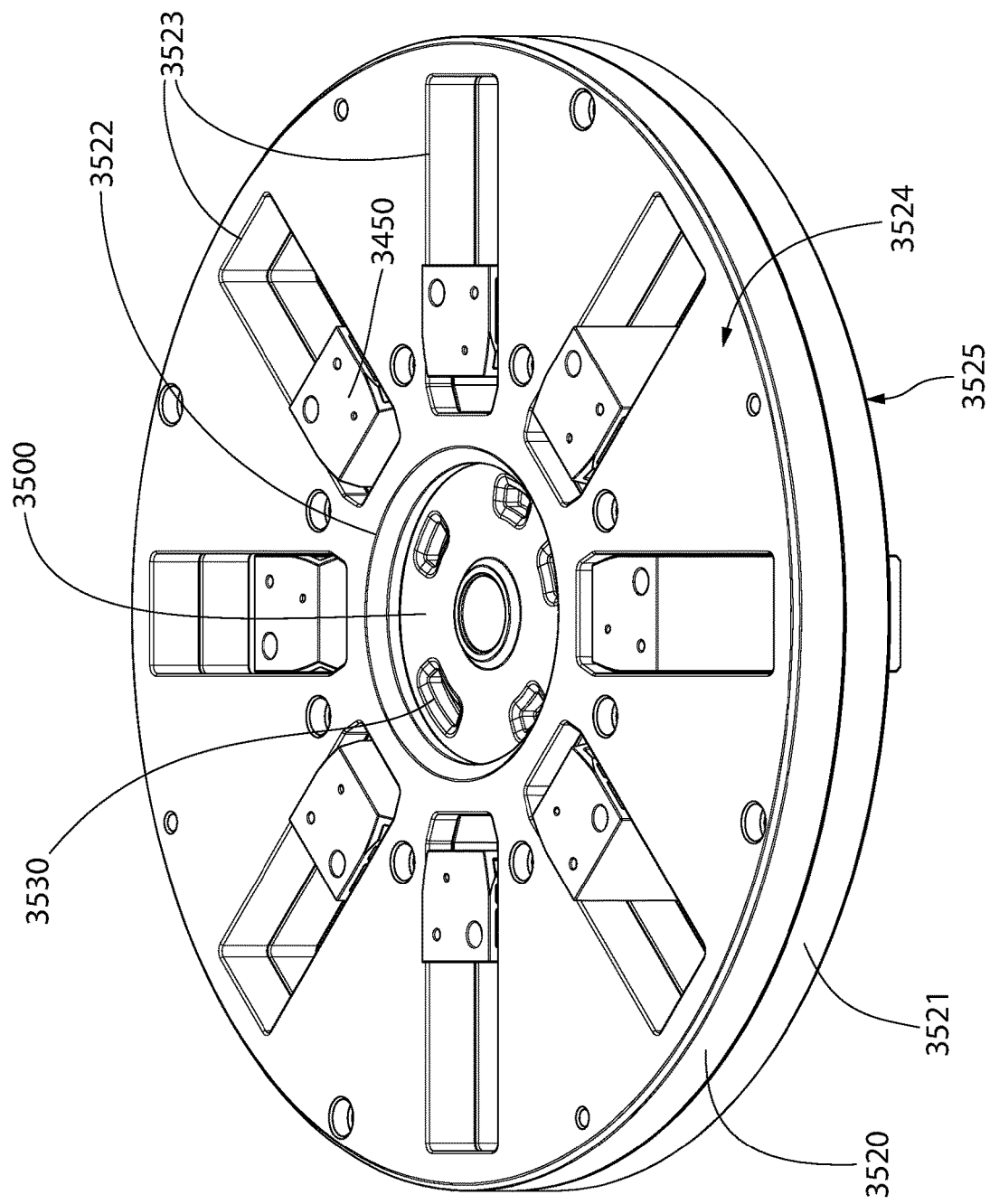
FIG. 66 is a top perspective view of a cover assembly for the tube hub showing the centrifuge tubes in a non-centrifugated vertical position.
Figure 67:
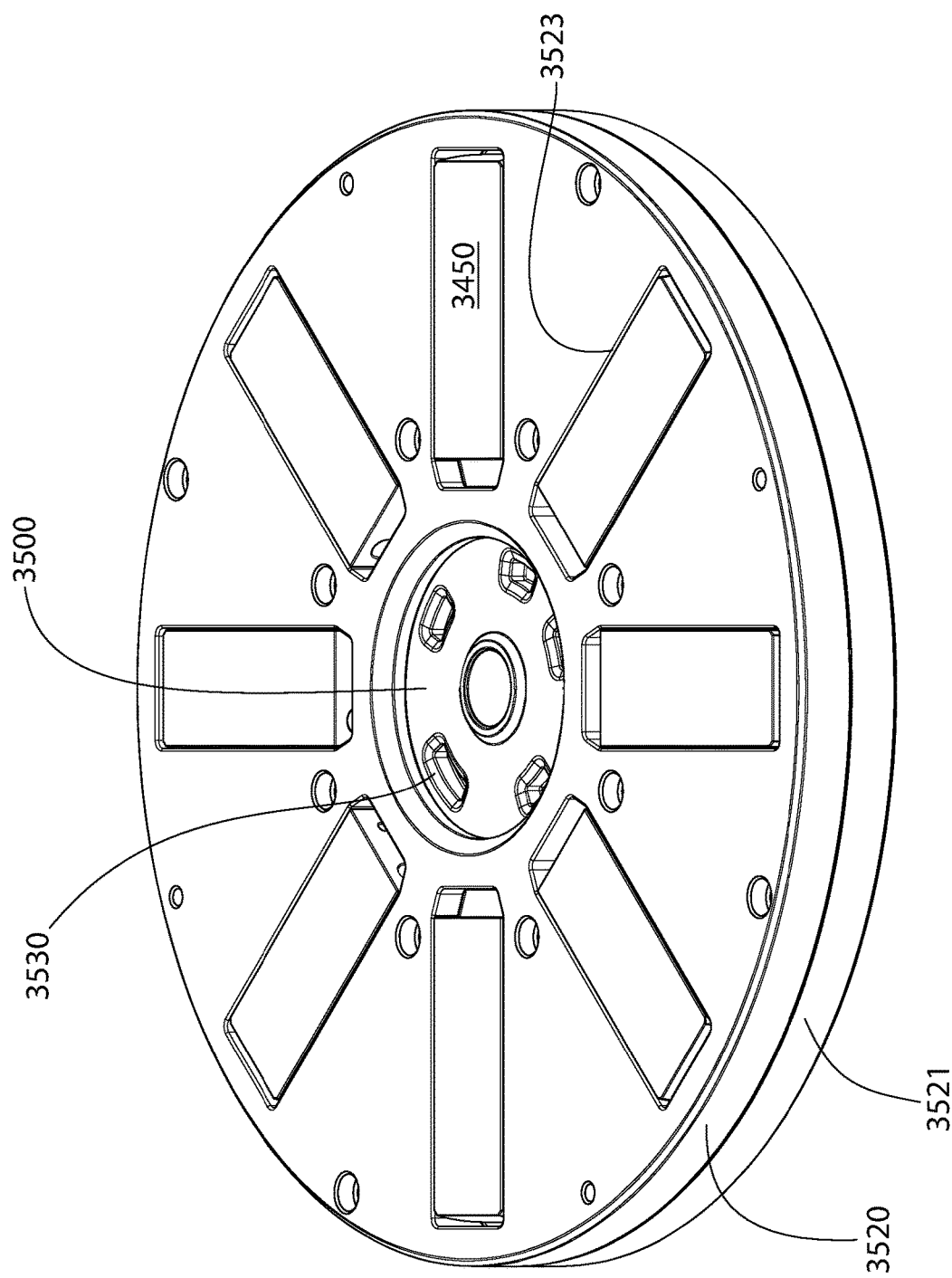
FIG. 67 is a view thereof showing the centrifuge tubes in a pivoted centrifugated horizontal position.

With continuing reference to FIGS. 51-54 and 66-67, each of the upper and lower covers 3520, 3521 may have a disk-shaped body including a central opening 3522 and plurality of rectangular tube openings 3523 formed completely through the cover between their top and bottom surfaces. Tube openings 3523 may be arranged in a circumferential pattern around central opening and are radially elongated as shown. The tube openings 3523 are arranged to coincide with the layout and arrangement of the peripheral recesses 3502 formed in rotary tube hub 3500 such that the mounted centrifuge tubes 3450 are exposed within the covers (see, e.g. FIGS. 66-67). Tube openings 3523 preferably have a radial length sized to allow the mounted centrifuge tube to fully swing outwards and upwards within the opening when rotated by the centrifuge 3400 (see FIG. 67). Centrifuge tubes 3452 are each angularly movable between a vertical position shown in FIG. 66 when the rotary tube hub 3500 is stationary, and a horizontal position shown in FIG. 67 when the hub is rotated at full speed by the drive mechanism. This ensures that the acceleration experienced by the sample due to gravity or rotational acceleration is always away from the tube ports. The tubes 3450 are preferably configured with the through-hole 3454 located more proximately to the top surface 3452 of the tube such that the top surface is substantially flush with the top surface 3524 of the upper cover 3520, or preferably slightly raised and protruding above the top surface as seen in FIG. 66 to be engaged by the bottom surface 3432 of the dock 3430 to form a sealed connection between the flow ports 3451 of the tube and flow passages 3434 of the rotary tube hub 3500 as previously described herein. In the vertical position, the centrifuge tubes 3450 project downwards below the bottom surface 3525 of the lower cover 3521 such that a majority of the height of the tube extends beneath the bottom surface 3525 (see, e.g. FIGS. 53-54).

Figure 68:
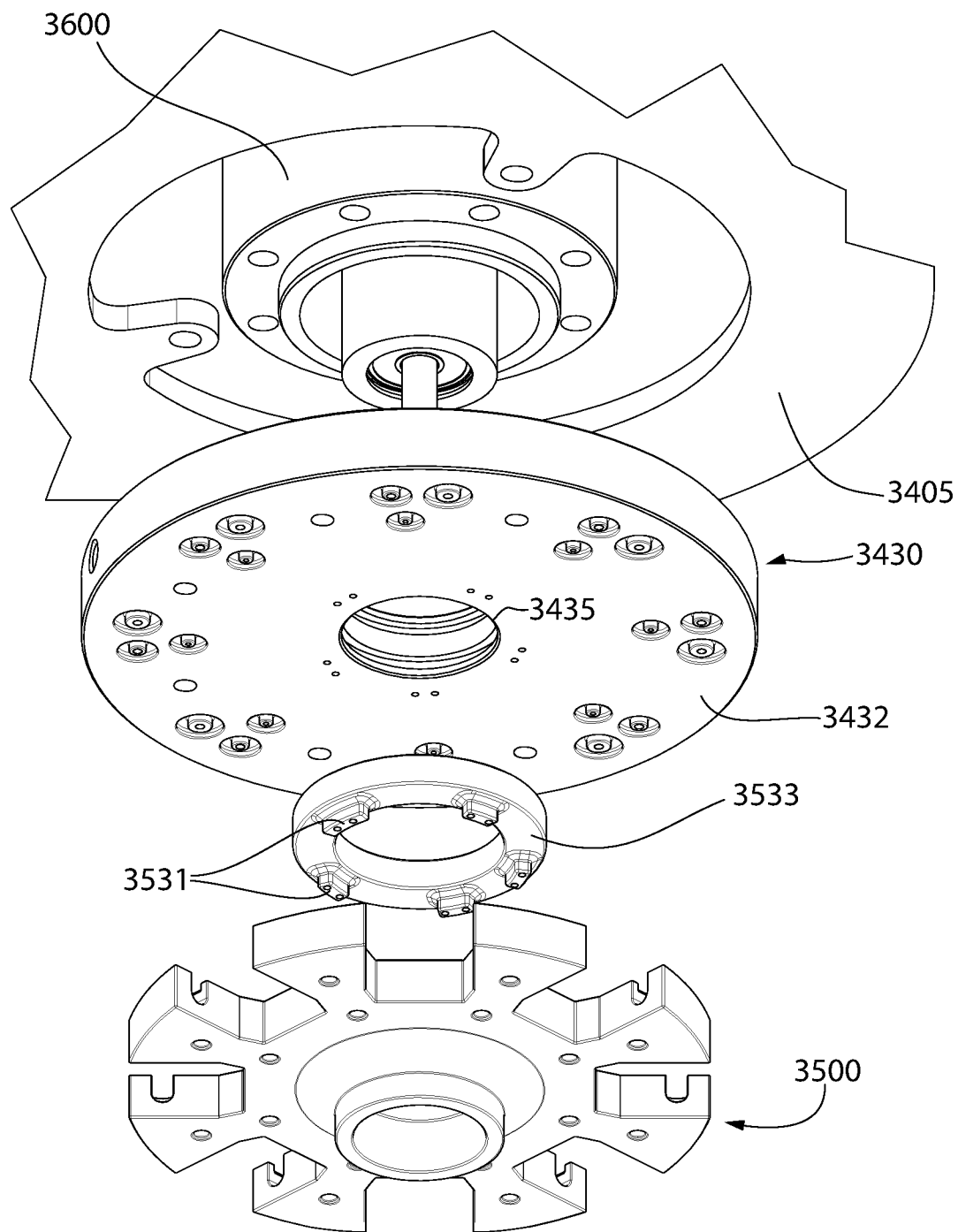
FIG. 68 is a bottom exploded perspective view of the tube hub and fluid exchange dock.
Figure 69:
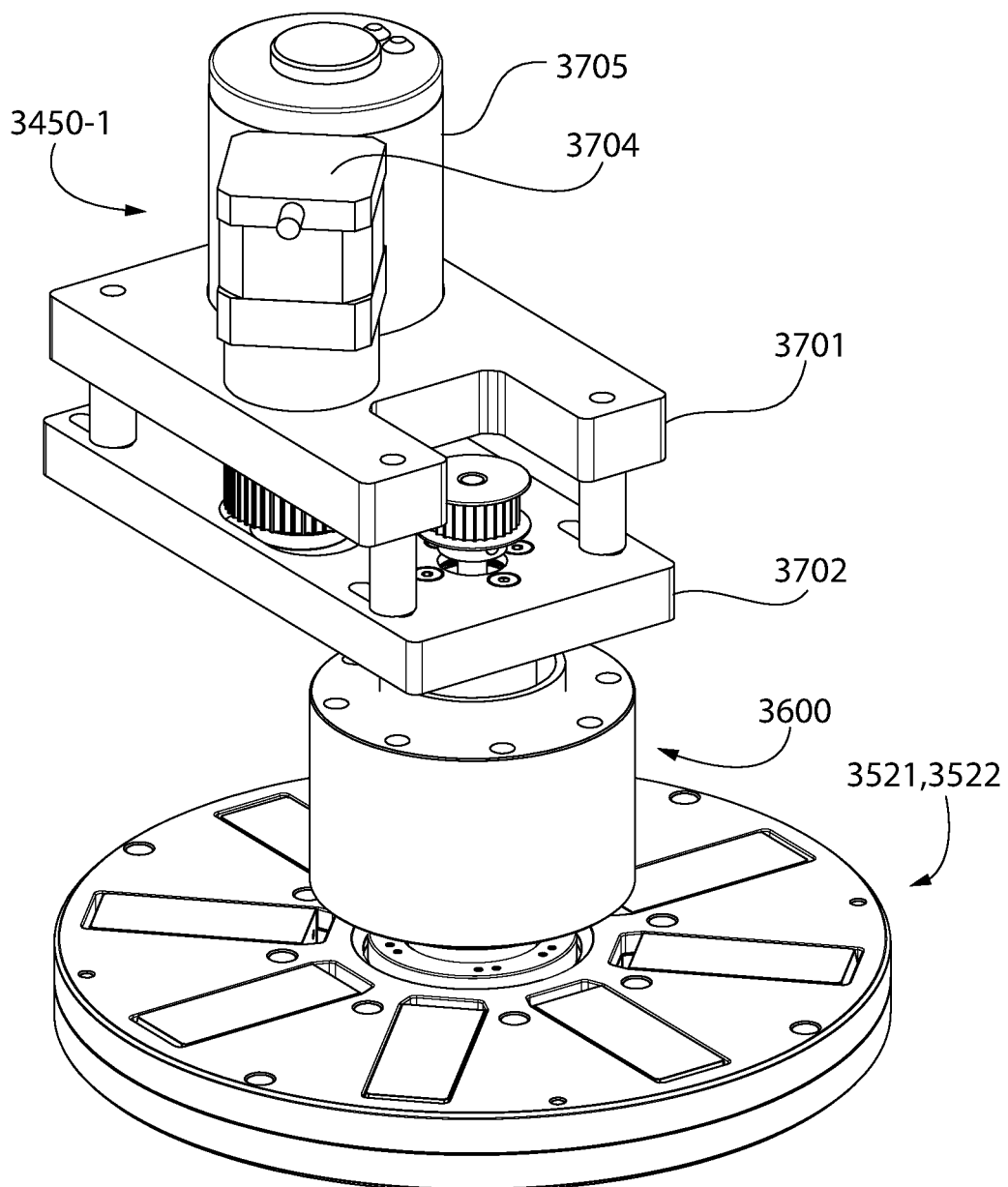
FIG. 69 is a first front perspective view of a piston-movable drive system of the centrifuge.

To ensure proper angular alignment between the clusters of flow ports 3451 of the centrifuge tubes 3450 and flow passages 3434 of the fluid exchange rotary tube hub 3500, centrifuge 3400 further includes an indexing mechanism comprising mating index features disposed in/on the rotary tube hub 3500 and centrifuge housing 3401. In one embodiment, the index features on rotary tube hub 3500 comprise a plurality of circumferentially spaced apart and upwardly open index depressions 3530 formed on the hub's top surface 3510 encircling central opening 3515 (see, e.g. FIG. 57). Depressions 3530 mate with a plurality of complementary configured and downwardly protruding index protrusions 3531 disposed in centrifuge housing 3401, which are arranged in the same circumferential pattern as the index depressions. In one embodiment, index protrusions 3531 may be formed on an annular shaped index ring 3533 fixedly attached to the bottom surface 3432 of fluid exchange dock 3430 by any suitable means (see, e.g. FIG. 68). Ring 3533 with index protrusions 3531 represents the fixed component of the indexing system whereas the rotary tube hub 3500 with index depressions 3530 is the movable component. In other embodiments, the index depressions 3530 may be on the ring 3533 and protrusions 3531 located on hub instead. Ring 3533 further includes a central opening 3534 for passage of main drive shaft 3700 and piston support tube 3604 therethrough. The foregoing mating indexing features are used in conjunction with the indexing motor 3704 to achieve rotational alignment between the index depressions and protrusions, thereby allowing insertion of the protrusions into the depressions when the rotary tube hub 3500 is in the upper docked position.

Reference is made now to FIGS. 59-63 and a vertical orientation of centrifuge tubes 3450 in these figures for convenience of description, recognizing that the tube changes between the vertical and horizontal positions previously described herein when pivotably rotated by centrifugal forces when the centrifuge is operated. The centrifuge tubes 3450 generally function to separate a clear supernatant from the soil sample slurry and extractant mixture for chemical analysis. Centrifuge tubes 3450 may each have a rectangular cuboid body in one non-limiting embodiment including top surface 3452, opposing bottom surface 3453, and four lateral sides 3458 extending vertically between the top and bottom surfaces. The body of each tube 3450 may be completely or partially solid in construction. In one embodiment, centrifuge tubes 3450 may be formed of injection molded plastic. Top surface 3452 is penetrated by flow ports 3451 for introducing the slurry-extractant mixture and extracting the clear supernatant after centrifugating the slurry-extractant mixture. The ports include a slurry port 3455-1, supernatant extraction port 3457-1, and cleanout port 3456-1. Each port fluidly connects to its respective fluid conduit 3455-2, 3456-2, and 3457-2 which extend vertically downwards from the ports inside tube 3450. Slurry and cleanout conduits 3455-2 and 3456-2 respectively may be vertically oriented and are fluidly connected via a cross flow conduit 3460 (see, e.g. FIG. 61). Supernatant extracting conduit 3457-2 is obliquely angled to centerline CT of centrifuge tube 3450 and fluid conduits 3455-2 and 3456-2. Conduit 3457-2 is fluidly connected to slurry conduit 3455-2 (see, e.g. FIG. 63). None of the conduits penetrate the bottom surface 3453 of tube 3450. In some embodiments, the slurry conduit 3455-2, cleanout conduit 3456-2, and supernatant extracting conduit 3457-2 may have a high length to diameter ratio (L/D) to create high velocity flow during the centrifuge tube 3450 water flushing and cleaning procedure to thoroughly clean the tubes. In some embodiments, each conduit may have an L/D greater than 10.

Figure 70:
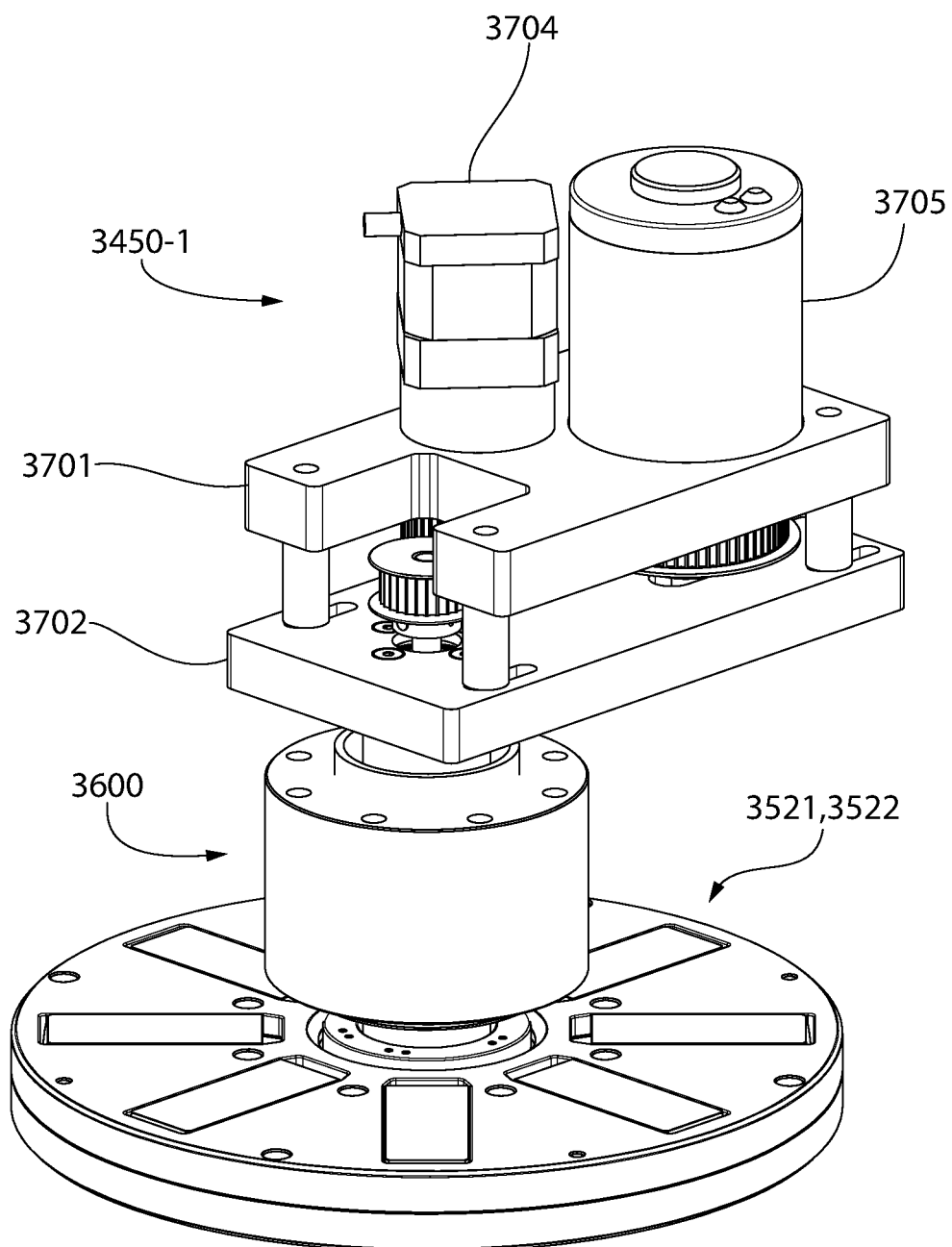
FIG. 70 is a second front perspective view thereof.
Figure 71:
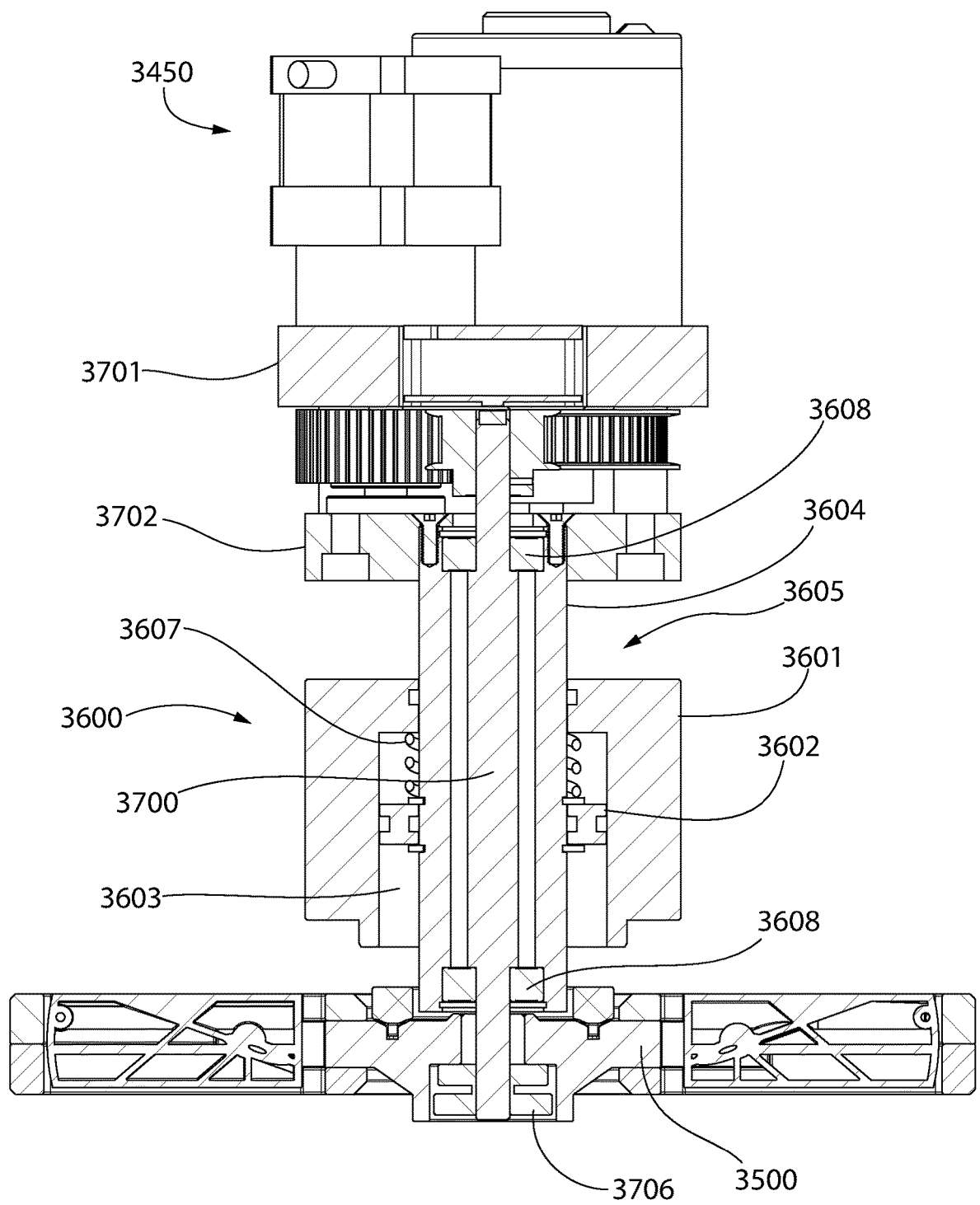
FIG. 71 is a side cross-sectional view showing the centrifuge with centrifuge tubes in a horizontal position.

According to another aspect, the centrifuge 3400 includes a piston mechanism 3600 operable to raise and lower the motor drive mechanism 3450-1 and rotary tube hub 3500 operably coupled thereto relative to the stationary housing 3401. Referring initially to FIGS. 70 and 71, piston mechanism 3600 includes a cylinder 3601 defining an internal chamber 3603, a piston 3605 comprising an annular piston head 3602, and an elongated drive support tube 3604 extending through the sleeve and chamber 3603. A return spring 3607 inside cylinder 3601 biases piston ring downwards. Motor drive shaft 3700 extends vertically through support tube 3604 and is rotatable relative to the tube which does not rotate via operation of the motor drive mechanism 3450-1. Axially spaced apart annular bearings 3608 support the drive shaft 3700 at each end of the tube for rotational movement (FIG. 71). The support tube 3604 and bottom of piston cylinder 3601 are fluidly sealed to the fluid exchange dock 3430 by an annular seal 3609 (see, e.g. FIG. 72) which is configured to allow the tube to slide up or down through the dock.

Cylinder 3601 is fixedly attached to housing 3401 via cylinder support member 3406 (see, e.g. FIGS. 53-54) and thus remains stationary during operation of the piston.

Support member 3406 may have a plate-like body and be affixed to housing main support plate 3402 via interlocking tabs and slots. Other modes of attaching support member 3406 to plate 3402 may be used including welding or fasteners as examples. In one embodiment, cylinder 3601 may be coupled to support member 3406 via threaded fasteners.

With additional general reference to FIGS. 43-54 and FIGS. 70-71, piston 3605 is slideably disposed inside the internal cylinder chamber 3603 for upwards/downwards movement therein. Piston head 3602 is provided with annular seals (e.g. O-rings) on both the inside and outside circumferential surfaces of the head. This forms leak resistant fluid seals between the piston head 3602 and the support tube 3604 and cylinder 3601 within chamber 3603 to maintain air or hydraulic fluid therein used to operate the piston.

Piston head 3602 is fixedly attached to support tube 3604 at a position between the ends of the tube. The top end of support tube 3604 is in turn fixedly attached to the lower motor support 3702. Accordingly, moving piston 3605 upwards and downwards in piston cylinder 3601 therefore moves the support tube 3604 with the motor drive and tube hub attached thereto upwards/downwards when the piston is actuated (compare FIGS. 72 and 73). This axially moves the tube hub 3500 between its upper docked and lower undocked positions for exchanging fluids with the centrifuge tubes 3450 (e.g. slurry-extractant, supernatant, or tube flushing water-air stream) in the upper position, or alternatively centrifugating the soil samples in the tubes in the lower position.

Figure 72:
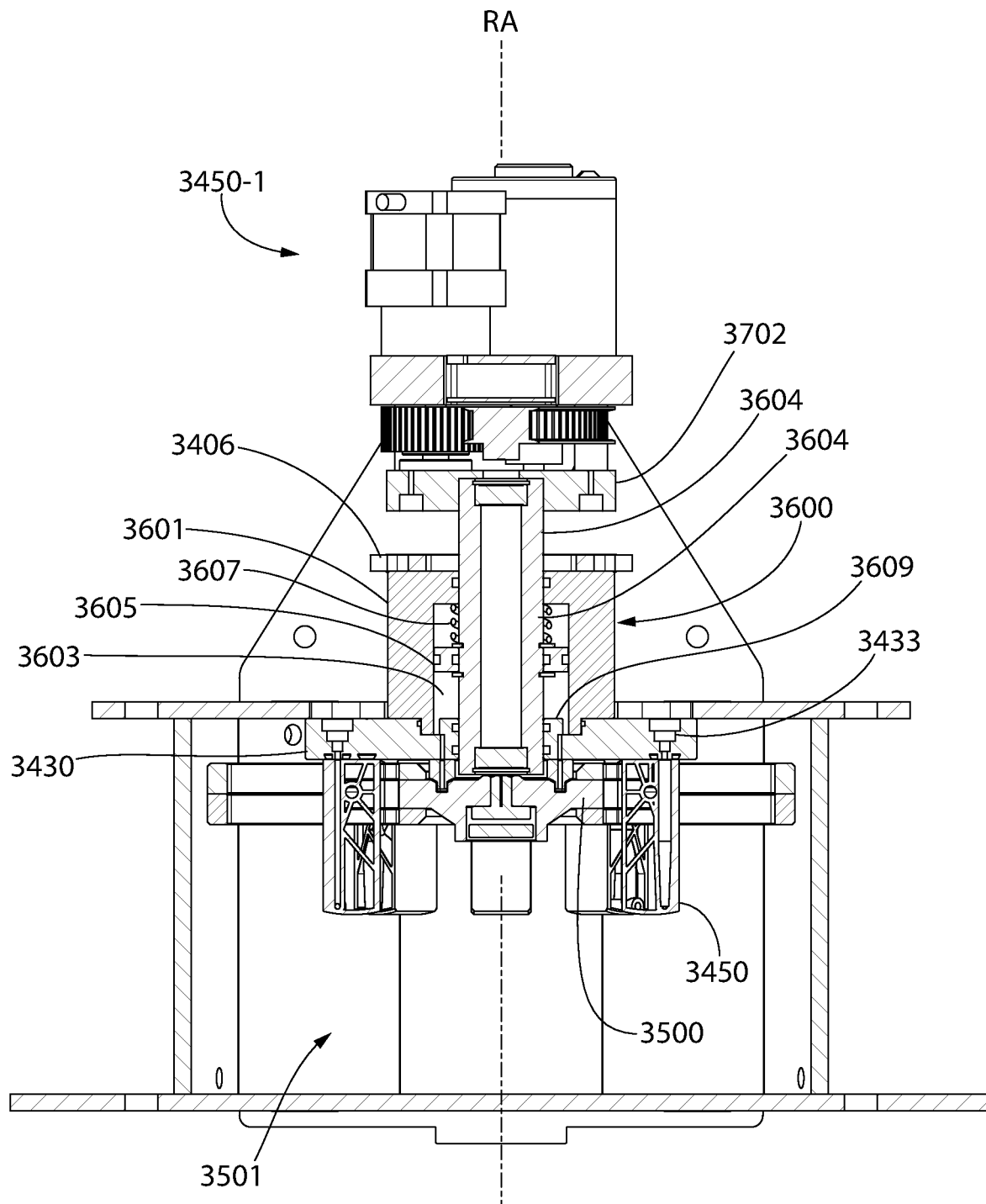
FIG. 72 is a first cross sectional sequential view thereof showing the centrifuge and drive mechanism in a non-rotating first upper docked position.
Figure 73:
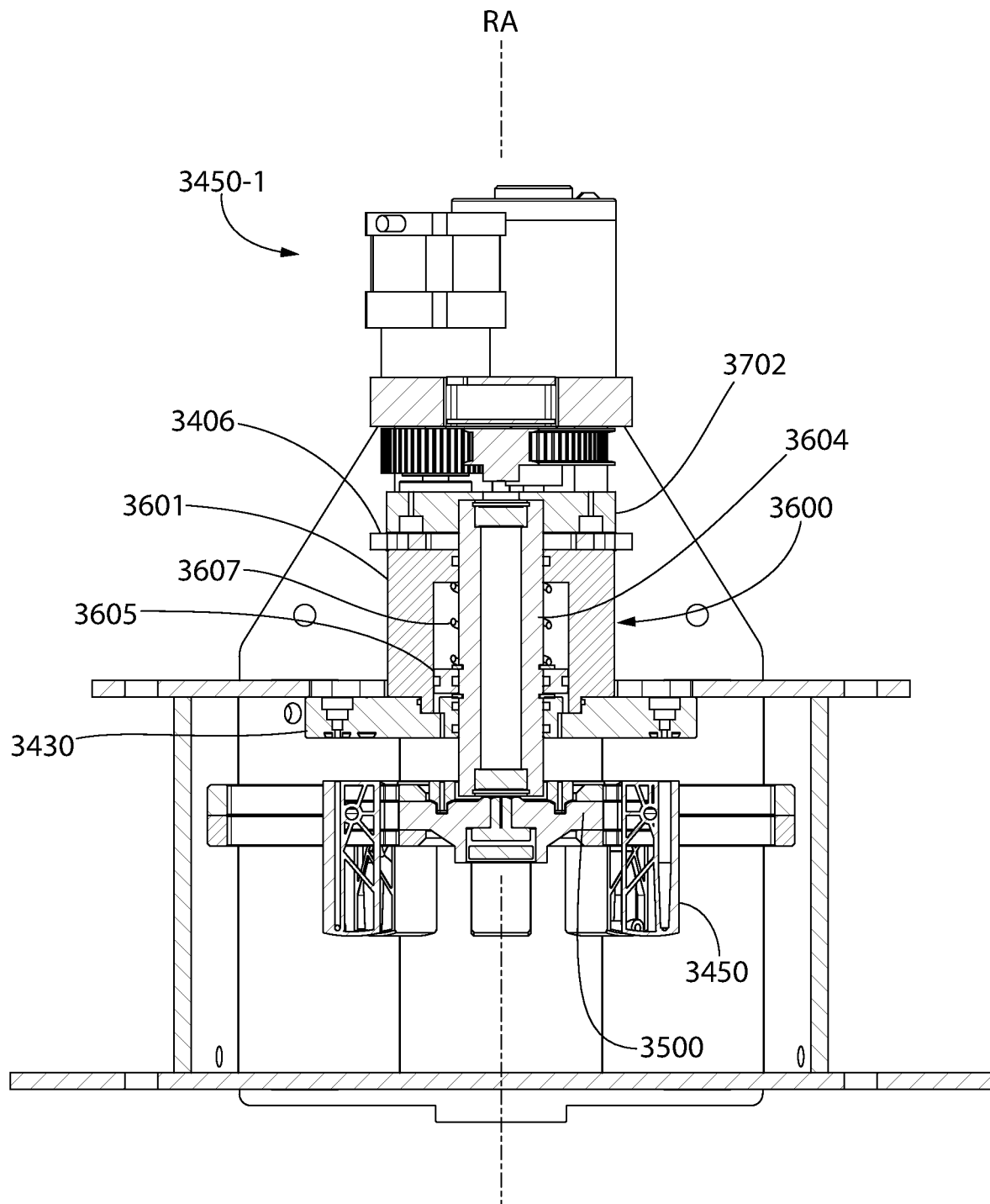
FIG. 73 is a second cross-sectional sequential view showing the centrifuge and drive mechanism in a non-rotating second lower undocked position.
Figure 74:
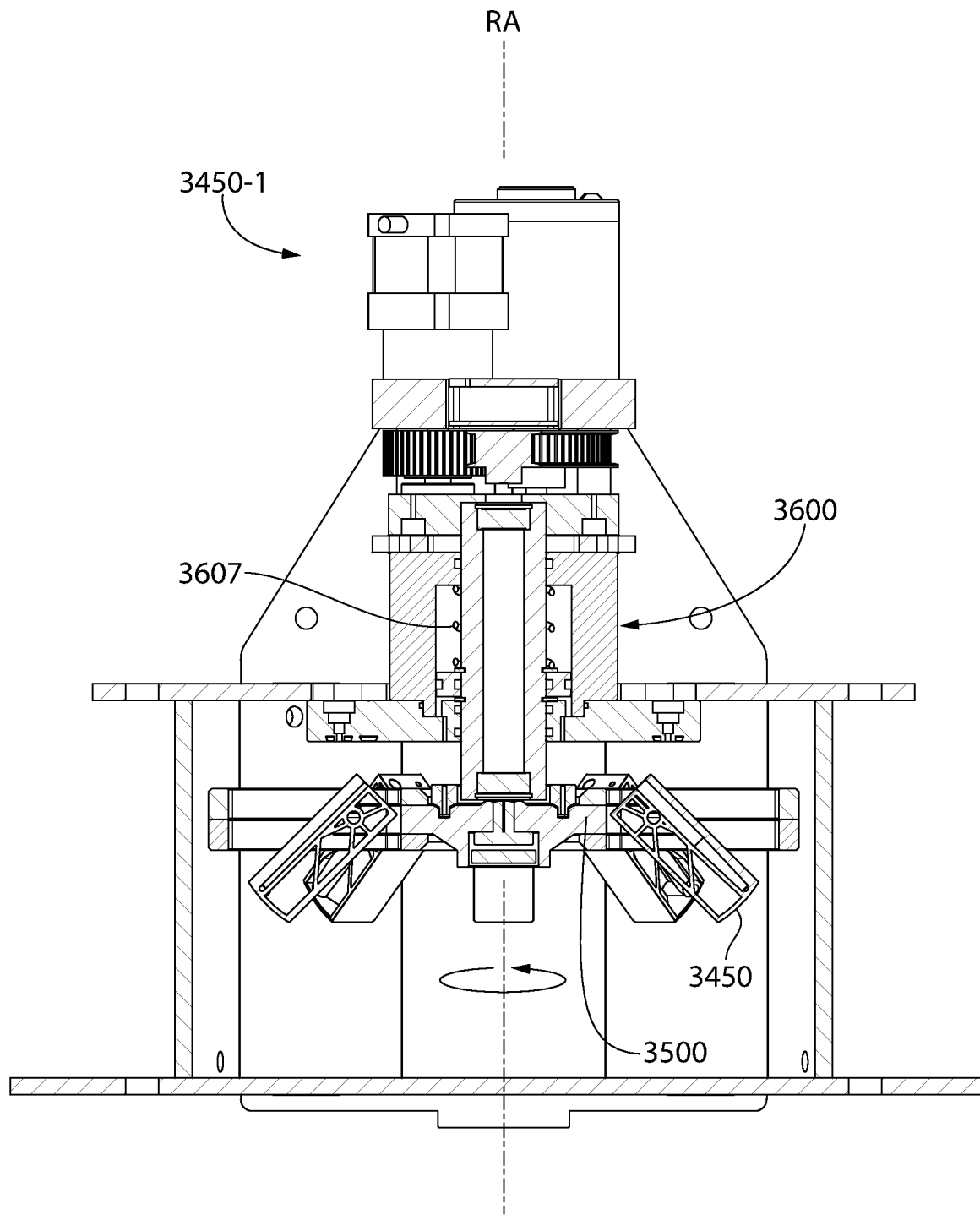
FIG. 74 is a third cross-sectional sequential view showing the centrifuge and drive mechanism in a low speed rotating second lower undocked position.
Figure 75:
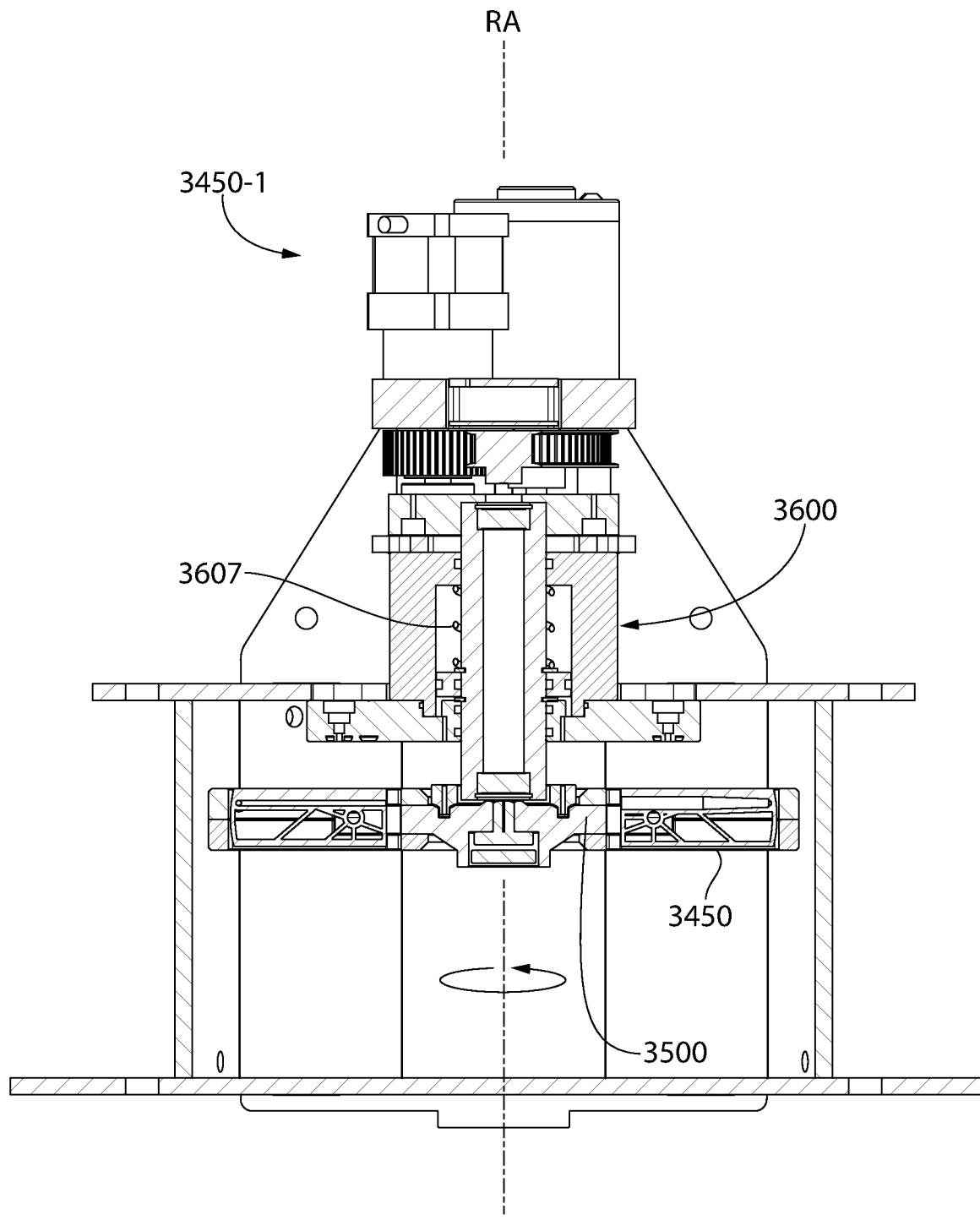
FIG. 75 is a fourth cross-sectional sequential view showing the centrifuge and drive mechanism in a high speed rotating second lower undocked position for centrifugating a slurry sample.

Operation of the piston mechanism 3600 will now be briefly described with reference to FIGS. 72-73. In one embodiment, piston 3605 may be air operated and fluidly connected to a source of operating air such as air tank 3031 (see, e.g. FIG. 1 air lines to centrifuge). In one embodiment, an air conduit 3714 formed in the fluid exchange dock 3430 (see, e.g. FIG. 55) is provided to introduce operating air into chamber 3603 of cylinder 3601. This allows operating air to be introduced into or removed from the cylinder chamber 3603 for raising or lowering the piston 3605 and support tube 3604 assembly (along with motor drive and rotary tube hub 3500 coupled thereto) which collectively form a movable unit actuated by the piston. Rotary tube hub 3500 is normally in the default lower position when operating air is not supplied to piston cylinder 3601 as seen in FIG. 73. Rotary tube hub 3500 is disengaged and spaced vertically apart form fluid exchange dock 3430 being in an "undocked" position. To "dock" the rotary tube hub 3500 with dock 3430, air is supplied to chamber 3603 of cylinder 3601 beneath the piston head 3605. This raises the piston head 3605, which in turn raises the rotary tube hub 3500 to its upper position via support tube 3604 and the motor drive mechanism 3450-1 as seen in FIG. 72 until the hub engages the dock 3430. To return the rotary tube hub 3500 to the lower position, air is simply released from the cylinder 3601 such as via a three-way air valve similar to those already described herein in relation to the mixers. Piston return spring 3607 automatically returns the piston, drive mechanism, and tube hub downwards. The centrifuge 3400 is now ready to rotate the tube hub 3400 and centrifugate the soil slurry samples as seen in FIGS. 74 and 75 with hub in the lower position.

Figure 77:
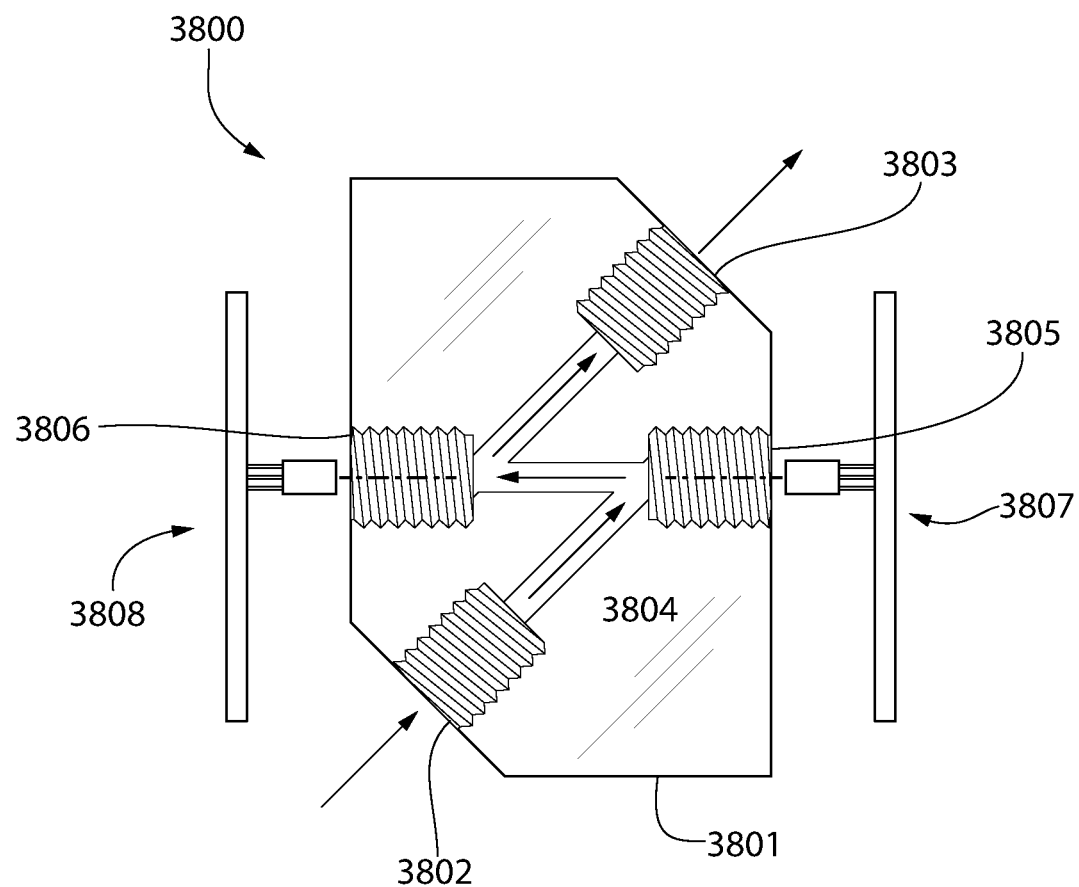
FIG. 77 is a side view of an absorbance analysis cell for performing colorimetric analysis of a supernatant.

The chemical analysis sub-system 3003 further includes an absorbance analysis cell 3800 for performing colorimetric analysis of the supernatant after addition of a color-changing chemical reagent. Analysis cells of some sort are commonly used in absorbance measurement systems, but not embodiments such as those disclosed herein. Referring to FIG. 77, the cell 3800 may comprise a generally rectangular cuboid body 3801 which may be molded of a transparent or translucent plastic material. A pair of diagonally opposing top and bottom corners may be angled at a diagonal and define a threaded inlet and outlet ports 3802 and 3803 as shown. Inlet port 3802 is fluidly coupled to mixing coil 3318 which receives an influent from supernatant pump 3312 and reagent pump 3316 (see, e.g. FIG. 1). Outlet port 3803 discharges the effluent to waste/exhaust. The inlet and outlet ports 3802 and 3803 may fluidly coupled to flow tubing 3021 via threaded tube connectors. The inlet and outlet ports are fluidly coupled together by a Z-shaped internal flow conduit 3804 in cell 3800 comprising two obliquely angled diagonal sections extending diagonally and a horizontal straight section therebetween. A threaded LED emitting port 3805 and receiving port 3806 are each disposed on opposite lateral sides of the cell body at the ends of the straight horizontal section of flow conduit 3804 as shown. Ports 3805 and 3806 are linearly aligned. Emitting port 3805 is coupled to an emitting diode circuit board 3807 including an LED emitting diode. Receiving port 3806 is coupled to a receiving diode circuit board 3808 including an LED receiving diode. In operation, supernatant extracted from the centrifuge tubes 3450 to which a reagent is added and mixed is received at the inlet port 3802 (see directional flow arrows). The mixture flows upwards through the first diagonal section of flow conduit 3804 to the straight section of the conduit at the emitting diode port end. The mixture then horizontal transverses the straight section in a linear flow path aligned with both the emitting and receiving diodes to the second diagonal section of the flow conduit at the receiving diode port end. Colorimetric analysis of the sample is performed by the system within the horizontal straight section of the flow conduit 3804 to quantify the nutrient or analyte being analyzed in the soil sample at this time. The supernatant and reagent mixture then flows upwards through the second diagonal section of the flow conduit and is discharged from the outlet port 3803. Advantageously, mixture flows inline and parallel with the direction of light emitted by the emitting diode in the straight section of the flow conduit 3804 as shown. This increases and maximizes the time for colorimetric analysis of the sample, thereby improving accuracy yet quickly processing the sample.

In one embodiment, a plurality of analysis cells 3800 may be provided to allow multiple samples to be processed simultaneously in parallel for different nutrients or analytes, thereby decreasing the time required to fully analyze a given soil sample for levels of multiple nutrients or analytes.

FIGS. 78-94 are schematic flow diagrams showing chemical processing train 3000A of the chemical analysis subsystem 3003 of FIG. 1 depicting sequential views of a method or process for processing and analyzing a soil sample. These diagrams therefore represent the processing sequence which occurs in a single chemical processing train 3000A of FIG. 1. It will be appreciated that in some implementations of the method, the same sequential process shown is performed simultaneously in parallel in all of the processing trains of the soil sampling system 3000 to analyze the soil sample slurry for all chemical parameters of interest (analytes), thereby resulting in a significant reduction in sample processing time. Each processing train may therefore process and analyze the sample for a different analyte to complete the full chemical analysis profile of the soil sample.

The process described below and in the flow diagrams may be automatically controlled and executed by the system programmable controller, such as for example processing system 2820 disclosed in copending U.S. patent application Ser. No. 15/806,014 filed Nov. 7, 2017. The controller is operably coupled to the components shown in FIGS. 78-94 (e.g. pumps, valves, centrifuge, compressor, etc.) for controlling the process sequence and flow of fluids through the system to fully process and analyze the soil sample.

In the flow diagrams, it bears noting that the emboldened and thicker dark lines represent the active fluid flow paths during each of the process sequences shown and described. Valve position of the pneumatically or electrically actuated fluid valves 3331 and air valves 155a, 167 are schematically represented by solid or open circles (solid circle=closed; open circle=open). Attention is drawn to the open and closed valves in the flow diagrams which create the active portions of the flow network. Valves 3331 may be pneumatically operated pinch valves in one non-limiting example.

Figure 78:
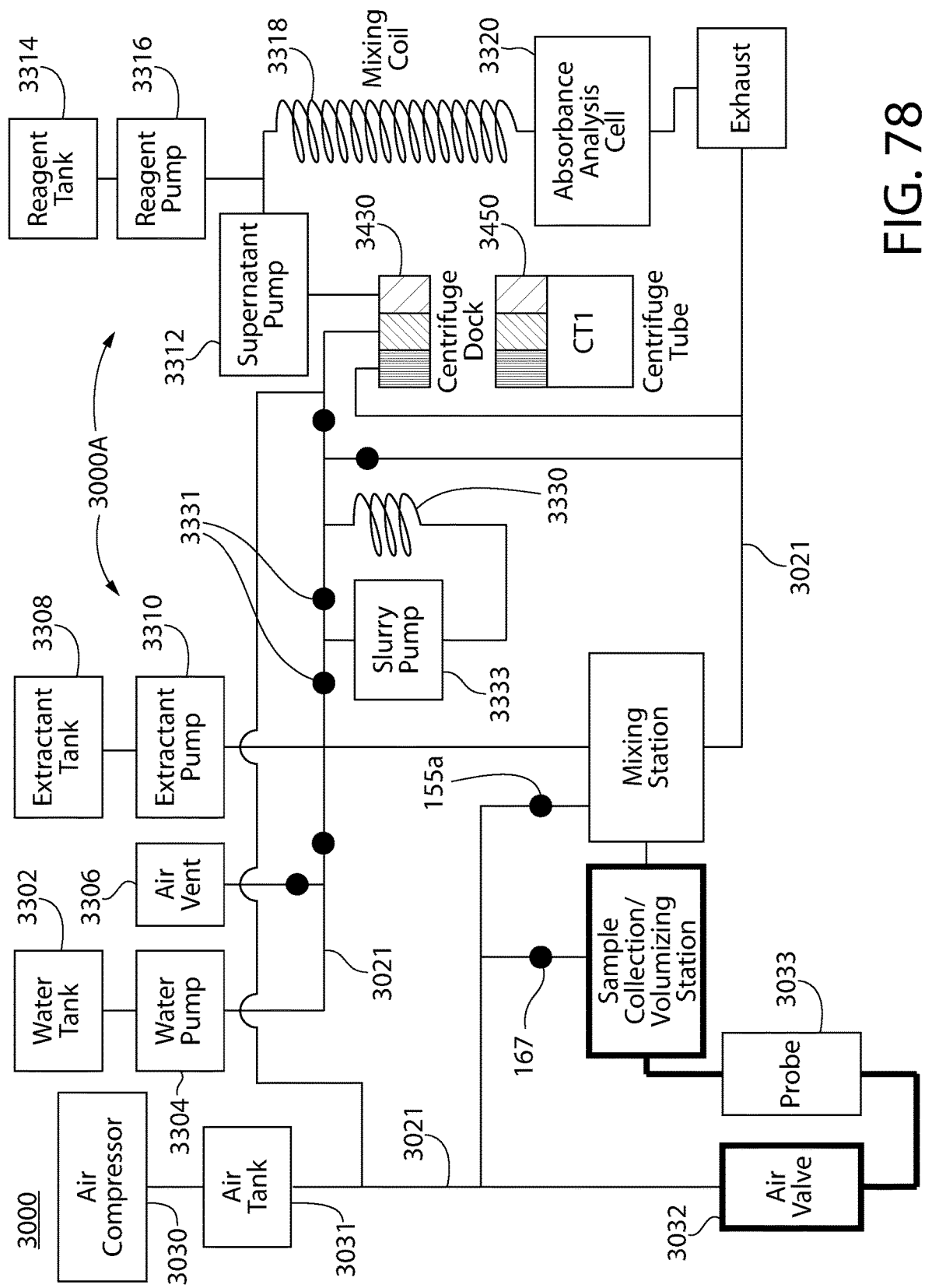
FIG. 78 is a schematic flow diagram of a soil sampling and processing system in a first operating mode configuration.
Figure 79:
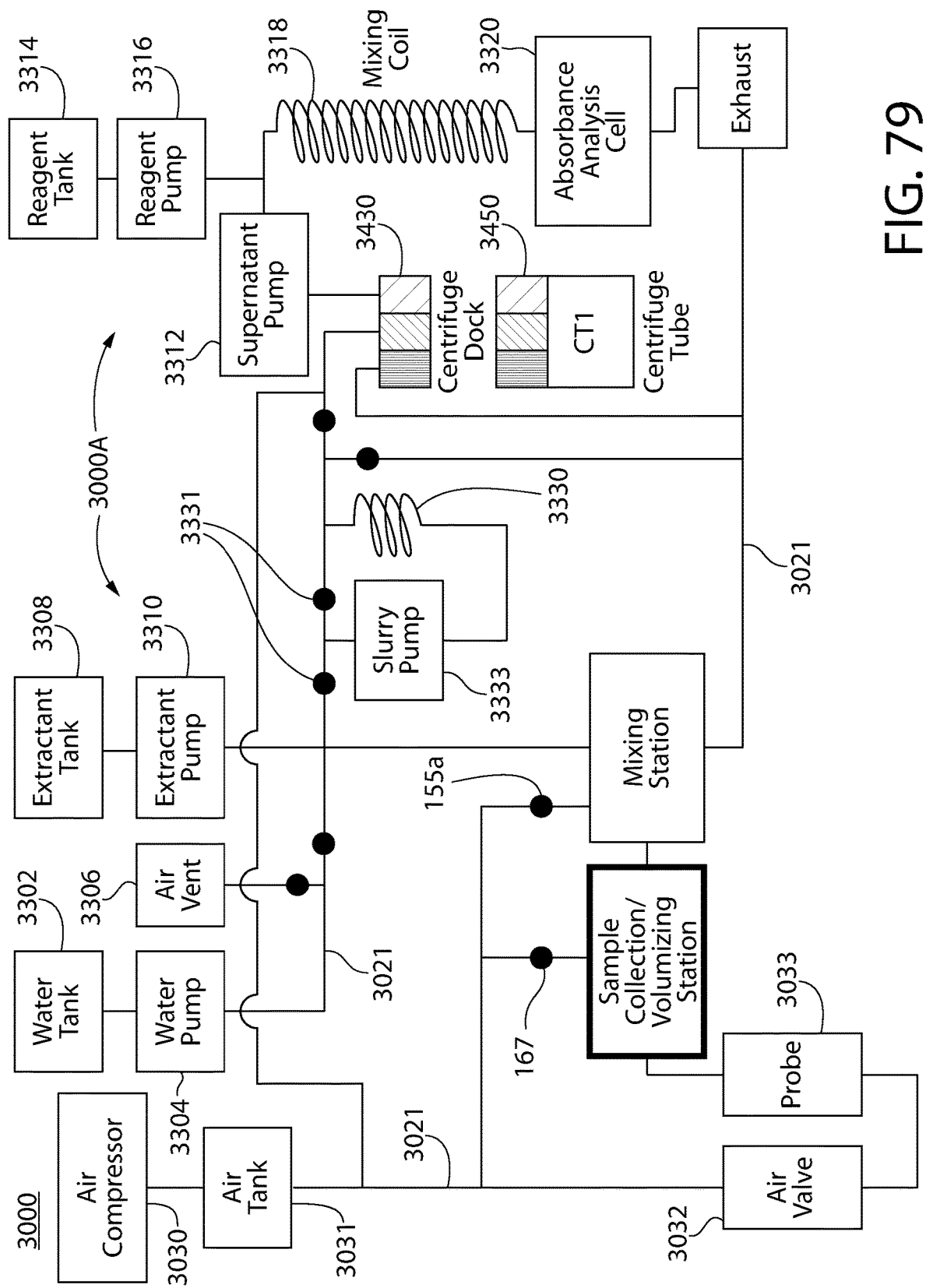
FIG. 79 is a schematic flow diagram of a soil sampling and processing system in a second operating mode configuration.

FIG. 78 shows the provision of the soil sampling system 3000 at the start and readied for processing and chemically analyzing a soil sample. In FIG. 78, after collection of the "dry" sample soil "cores" directly from the agricultural field by a sample collector (e.g., collection probe) 3033 of the probe collection sub-system 3001, the cores are pneumatically transferred (i.e. blown) via process tubing 3021 of suitable size to the sample collection/volumizing station 160-1 disposed above mixer 100 or 200 (previously described herein) by delivering a pulse of air via air valve 3032. The sample cores from multiple sampling locations (i.e. different depths and/or areas) collected by the soil collection probe 3033 may be aggregated together in the collection/volumizing station to create a combined "sample." Pressurized air provided via air valve 3032 provides the motive force for transferring the soil core to station 160-1. In FIG. 79, this aggregated "sample" is then volumized in the manner previously described herein (i.e. mass is estimated to determine proper amount of water to add to the mixing chamber of the mixer to form a soil sample slurry of proper viscosity/consistency).

Figure 80:
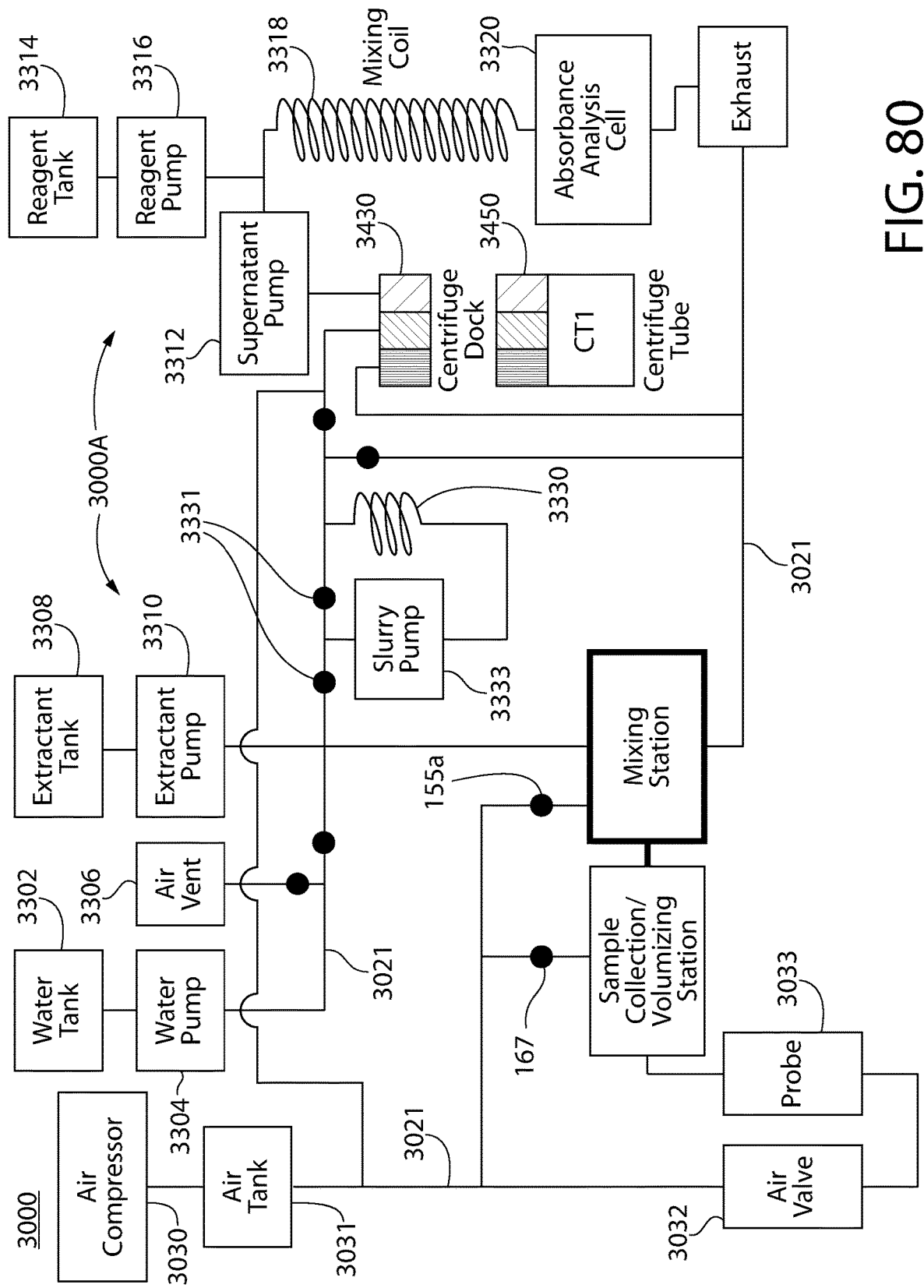
FIG. 80 is a schematic flow diagram of a soil sampling and processing system in a third operating mode configuration.
Figure 81:
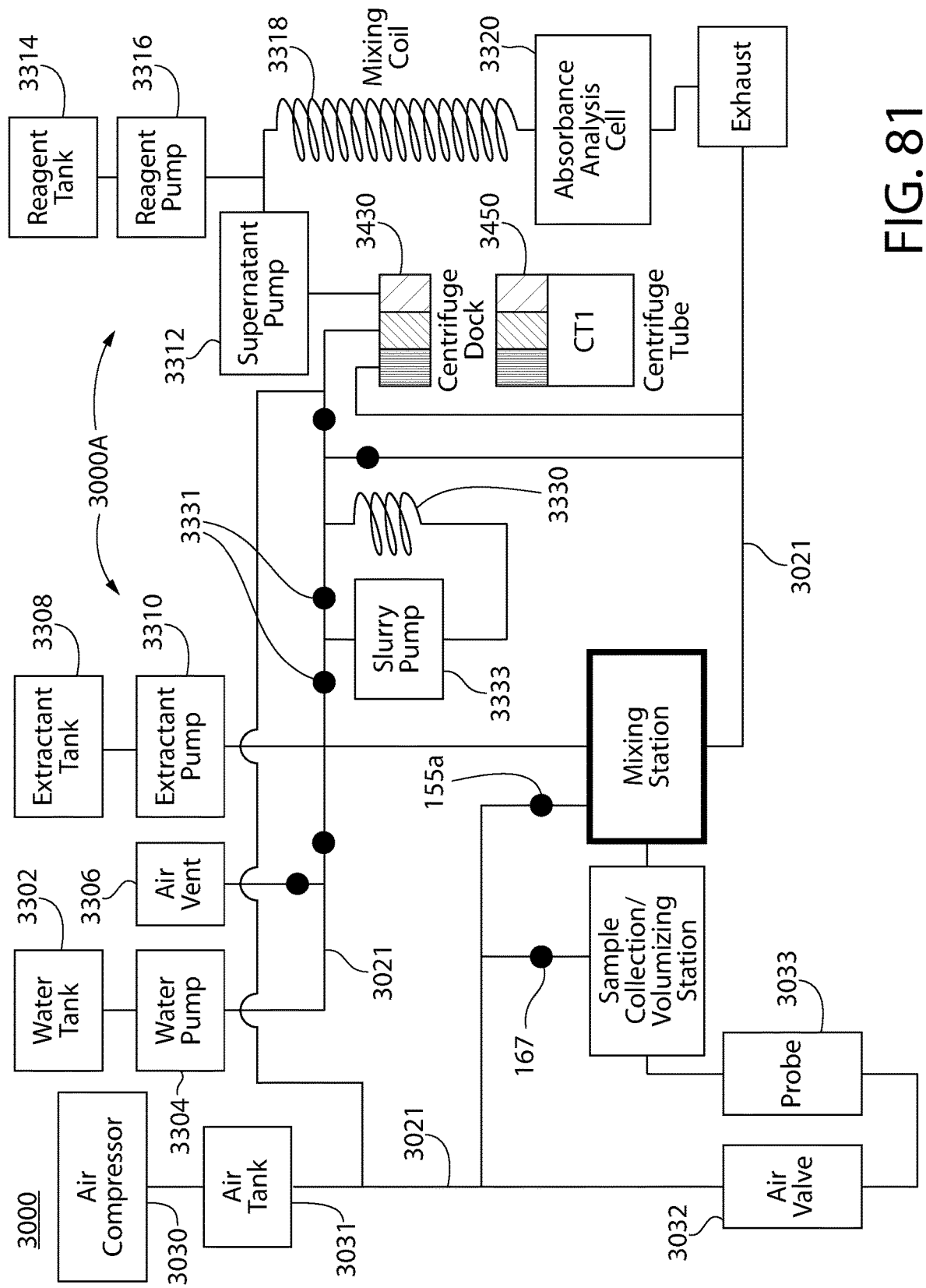
FIG. 81 is a schematic flow diagram of a soil sampling and processing system in a fourth operating mode configuration.
Figure 82:
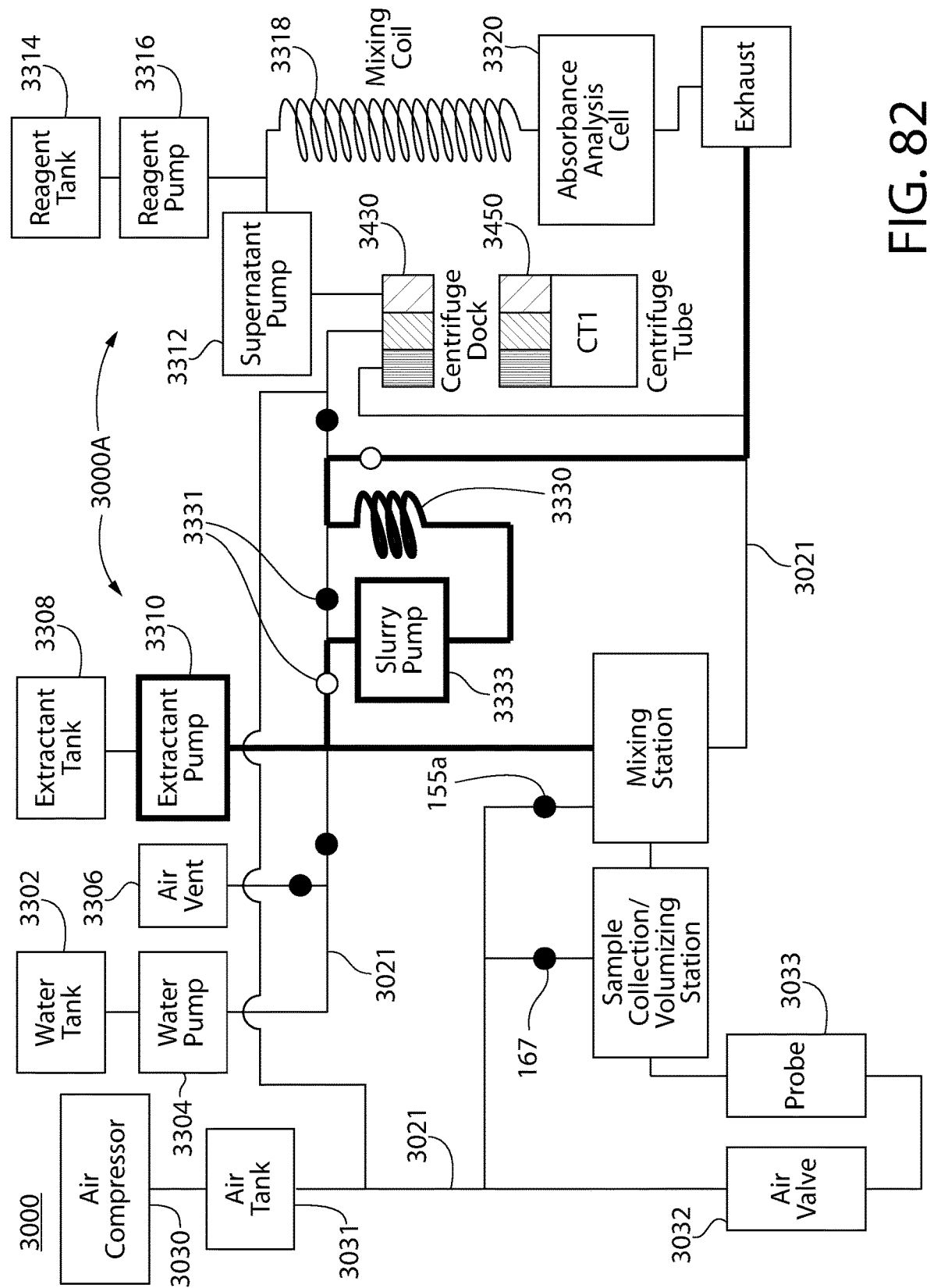
FIG. 82 is a schematic flow diagram of a soil sampling and processing system in a fifth operating mode configuration.

In FIG. 80, the aggregated sample is transferred (e.g. dropped into) to the mixing station (e.g. mixer-filter apparatus 100 or 200). In FIG. 81, water has been added to the sample via water pump 3304 in a predetermined water/soil ratio and mixed to form a soil sample slurry. All valving connected to the mixer is closed as shown during the mixing operation. In FIG. 82, slurry pump 3333 draws a known ratio of slurry and pumped extractant into the mixing loop or coil 3330 and past the second open valve 3331 to exhaust/waste to establish stable flow before the next stages in sample processing occurs. The extractant pump 3310 rate compared to the slurry pump rate determines the slurry to extractant ratio. For example, if slurry pump draws total flow of 4 mL/sec, and extractant pump runs at 1 mL/sec, then the ratio will be 3:1 (Total rate (sample pump) minus extractant rate=raw slurry rate). Note the open position of the two slurry pump isolation valves 3331.

Figure 83:
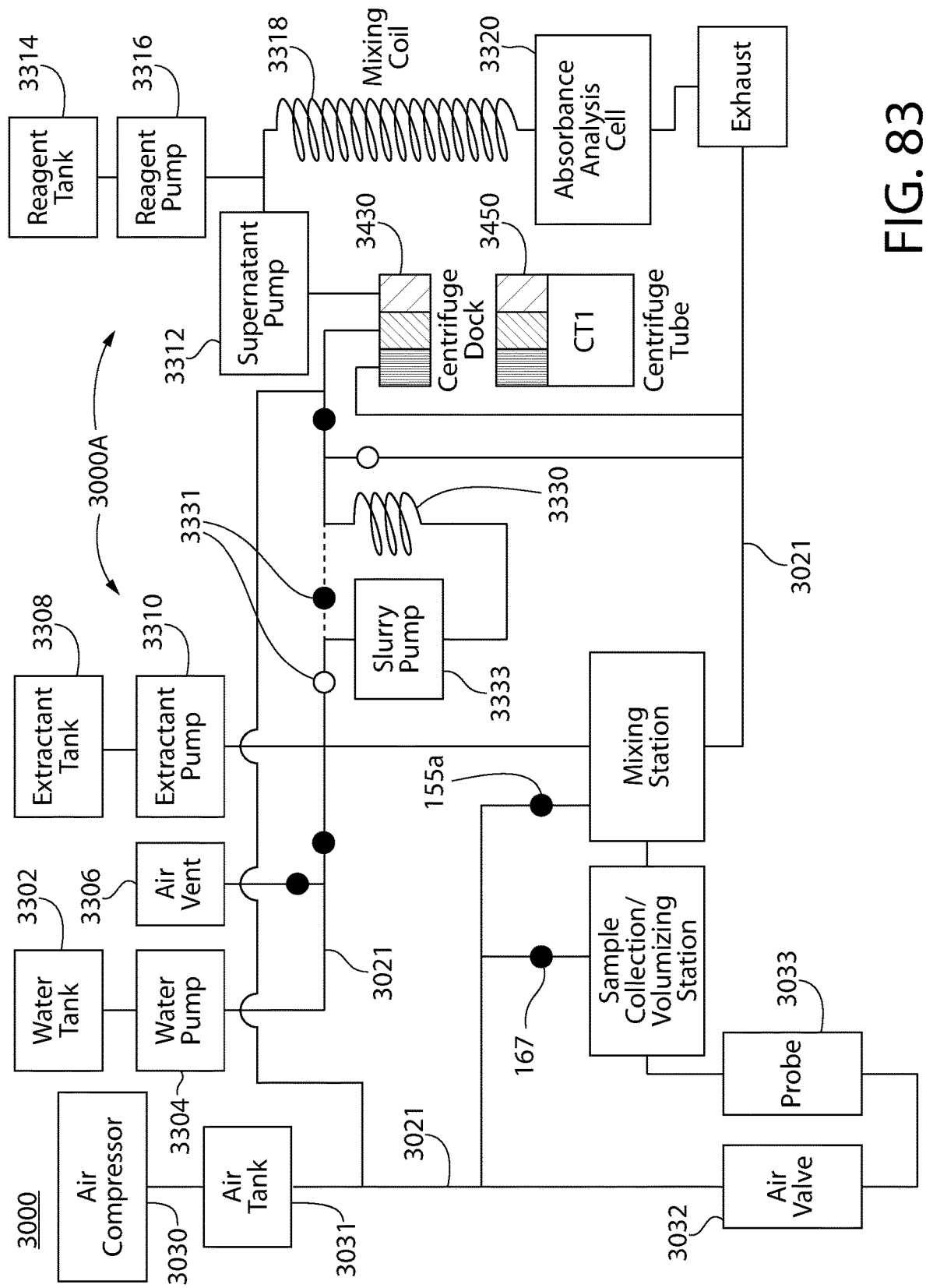
FIG. 83 is a schematic flow diagram of a soil sampling and processing system in a sixth operating mode configuration.
Figure 84:
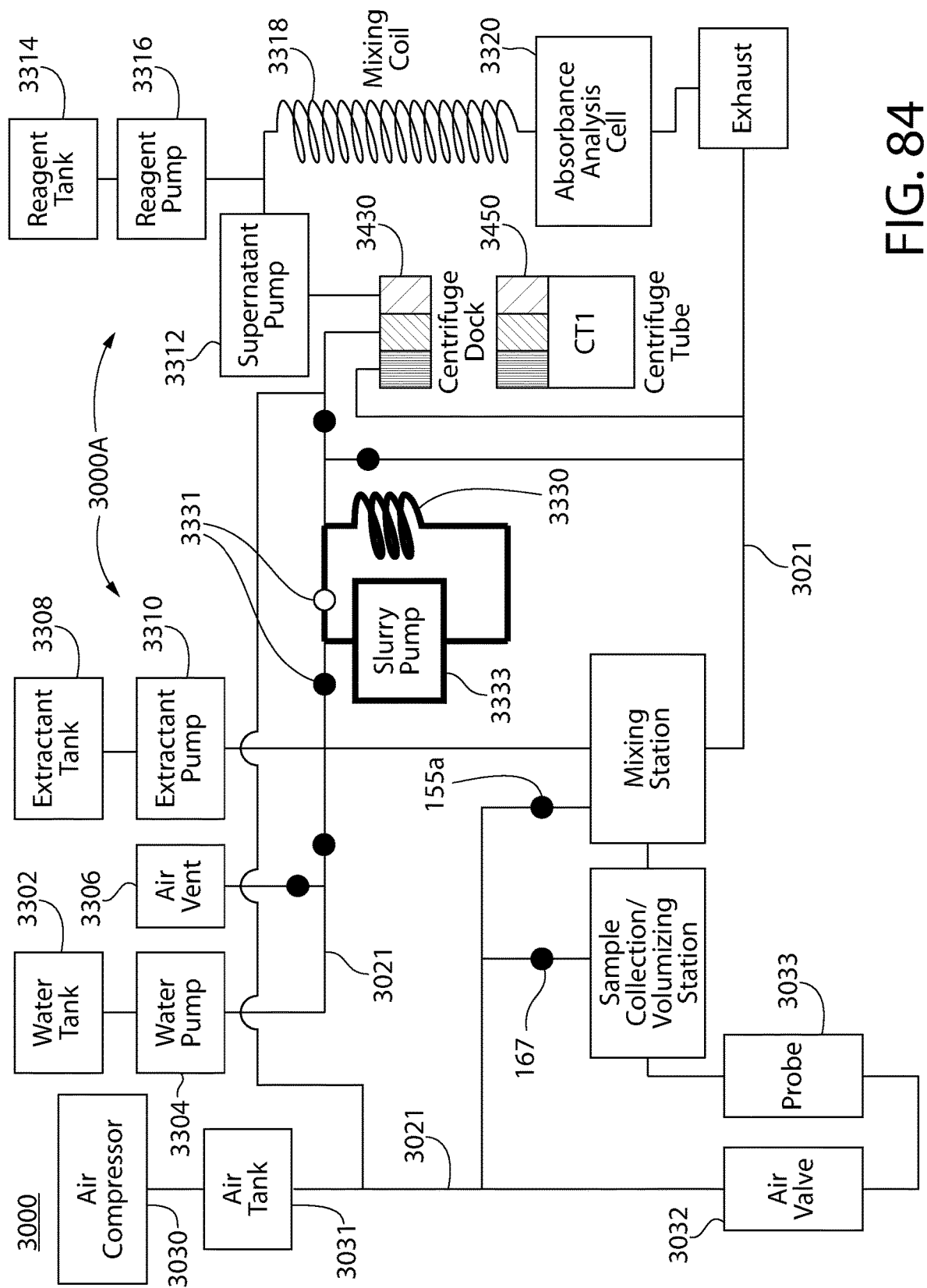
FIG. 84 is a schematic flow diagram of a soil sampling and processing system in a seventh operating mode configuration.

In FIG. 83, at this point in the process, there is a stagnant fluid pocket (represented by a dashed line) in tubing 3021 between the two junctions on either side of the stagnant fluid pocket that has not been filled yet with soil sample slurry. The pocket may contain air and/or liquid. To remedy this situation, the two previously open slurry pump isolation valves 3331 upstream and downstream of slurry pump 3333 are closed and the flow conduits are changed from the once-through load/unload configuration to a recirculation closed pump loop configuration which includes the stagnant section of tubing 3021 and mixing loop or coil 3330. Slurry pump 3333 pumps slurry fluid backwards a small amount through the closed pump loop to relocate the stagnant fluid pocket into position so it can be exhausted in the following steps and fills the previously empty and stagnant tubing section with slurry as shown in FIG. 84.

Figure 85:
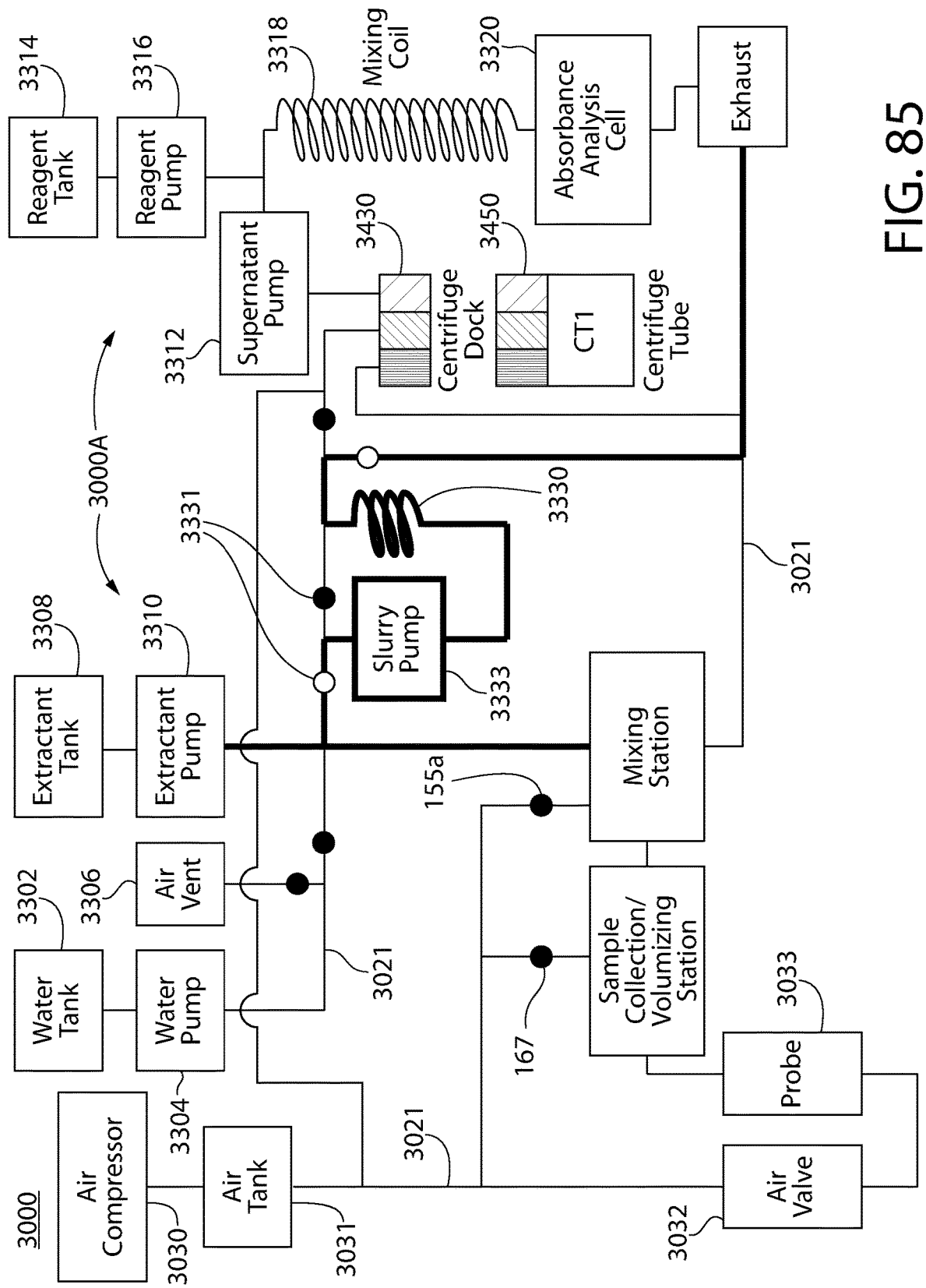
FIG. 85 is a schematic flow diagram of a soil sampling and processing system in a eighth operating mode configuration.

In FIG. 85, the flow conduits are reconfigured again by opening the slurry pump isolation valves 3331 to change the conduits from the closed pump loop configuration back to load/unload configuration. More sample slurry and extractant are pumped by slurry pump 3333 through the tubing 3021 to purge the stagnant pocket to exhaust.

Figure 86:
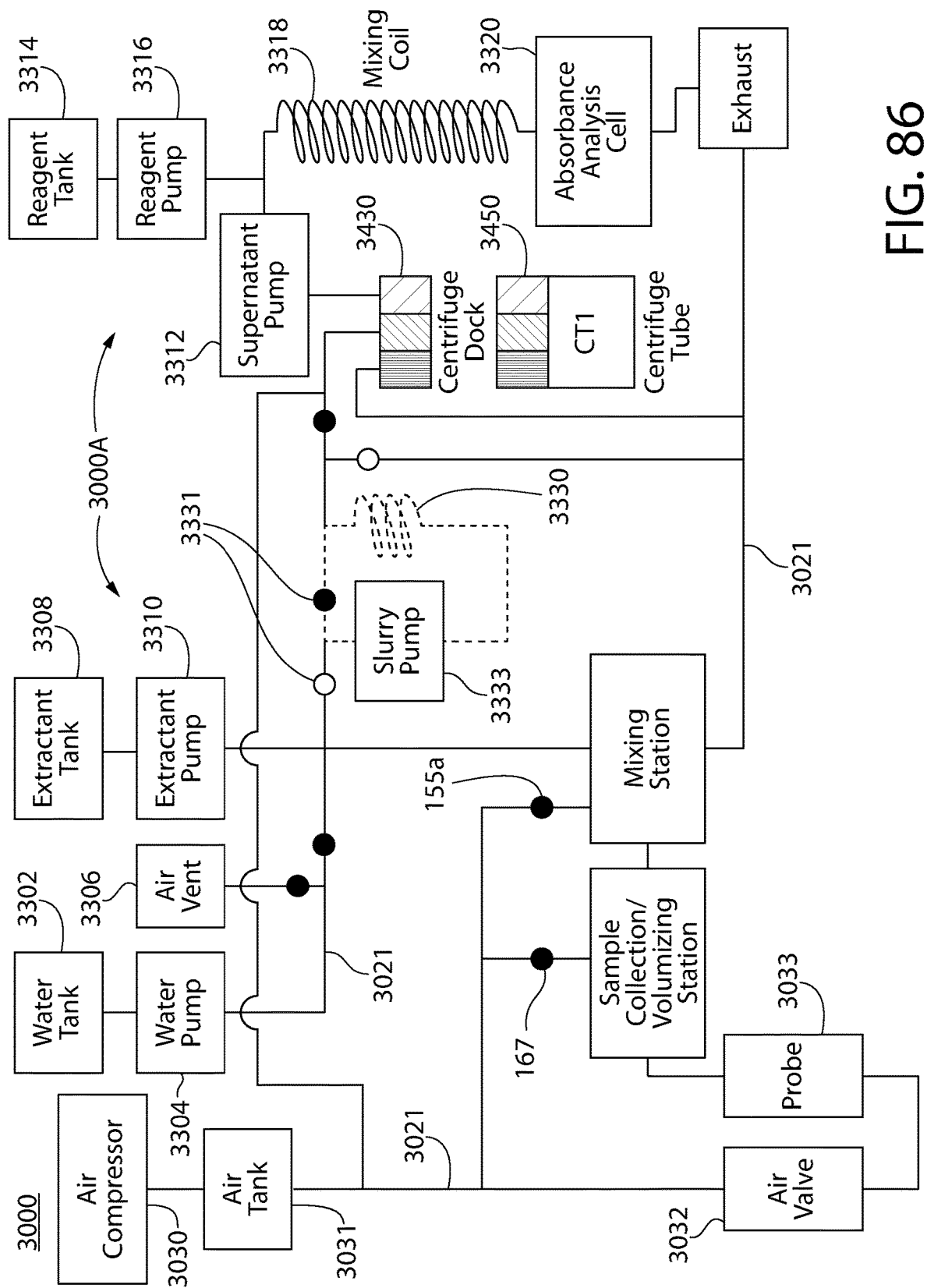
FIG. 86 is a schematic flow diagram of a soil sampling and processing system in a ninth operating mode configuration.
Figure 87:
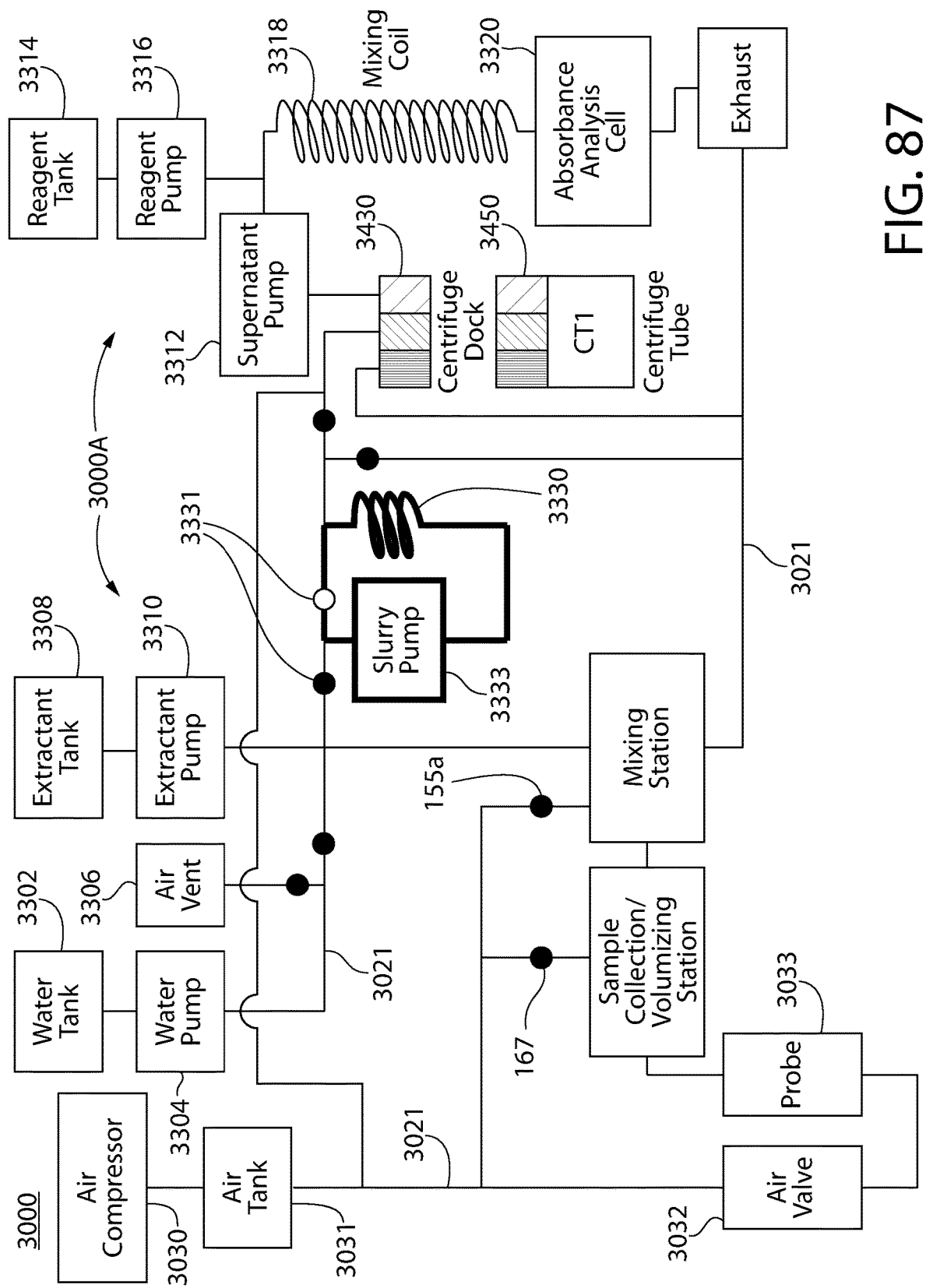
FIG. 87 is a schematic flow diagram of a soil sampling and processing system in a tenth operating mode configuration.
Figure 88:
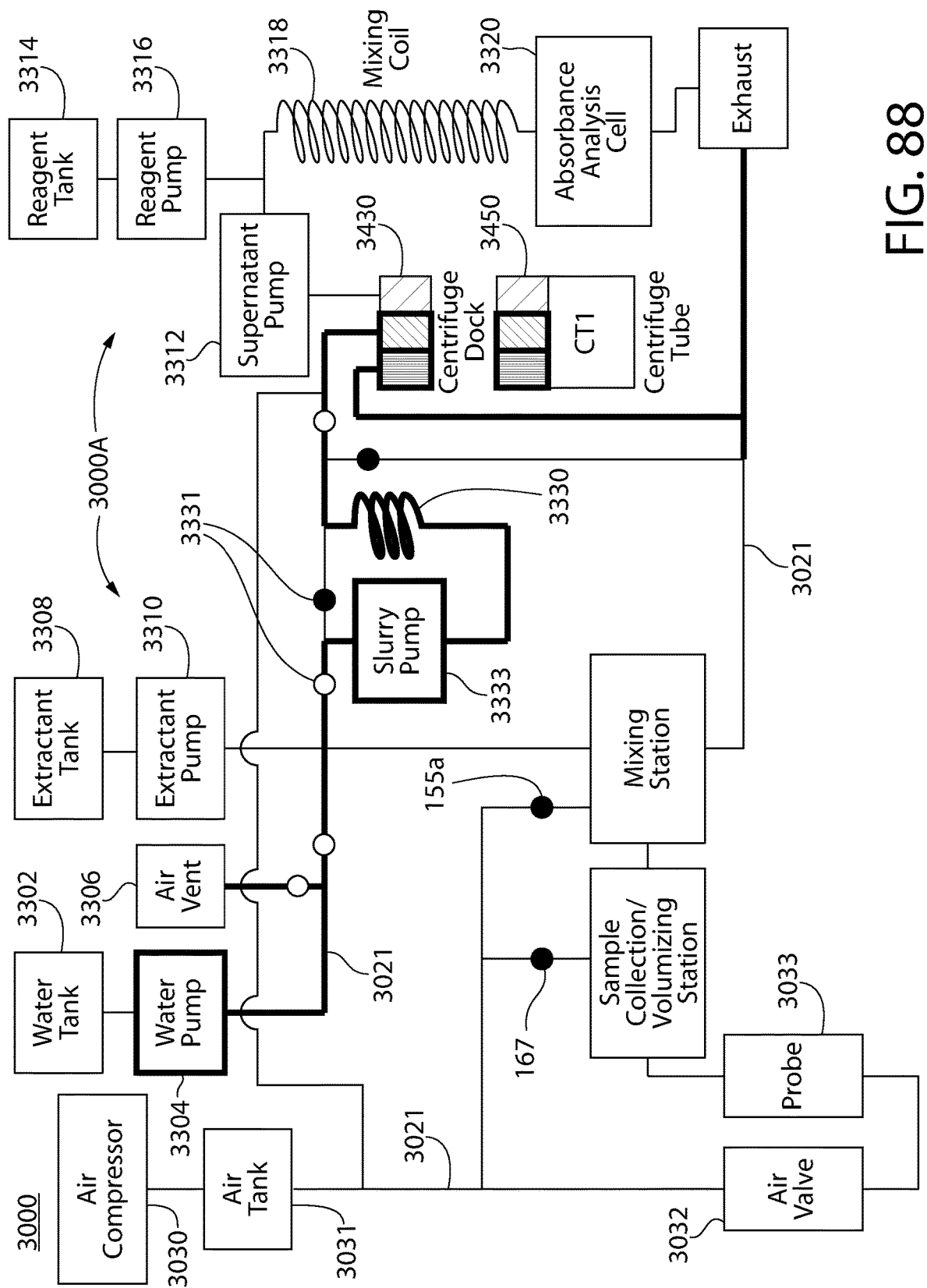
FIG. 88 is a schematic flow diagram of a soil sampling and processing system in a eleventh operating mode configuration.

In FIG. 86, at this point in the process, the entire slurry loop (represented by dashed lines) is full of slurry and extractant in a precisely known ratio. In FIG. 87, slurry pump 3333 can be operated to mix in the closed pump loop shown if necessary to speed up extraction of the analyte from the slurry. The closed pump loop is forming by closing the two slurry pump isolation valves 3331 and opening the intermediate valve between the pump inlet and the mixing coil 3330 as shown. In FIG. 88, the now thoroughly mixed soil sample slurry is ready to be pumped to the centrifuge to separate the liquid from the soil particles in the slurry which produces the clear supernatant for colorimetric analysis. The valves 3331 are changed in position as shown (i.e. open/closed) to reconfigure the flow conduit configuration again from the recirculation closed pump loop configuration to once-through load/unload configuration. Previously closed cleaning valve 3331 fluidly coupled to water pump 3304 and the air vent valve 3331 fluidly coupled to air vent 3306 are opened as shown to allow a cleaning air/water mixture to be drawn into the slurry flow tubing by slurry pump 3333 in order to flush the tubing out. Entrainment of air bubbles in the aerated water improves the effectiveness of cleaning the tubing. This step also pushes the sample slurry to the centrifuge 3400, and into and through centrifuge tube 3450 which then flows to exhaust/waste. Slurry pump is operated 2× the rate as water pump 3304 in order to draw air bubbles into tubing conduits for more effective cleaning later.

Figure 89:
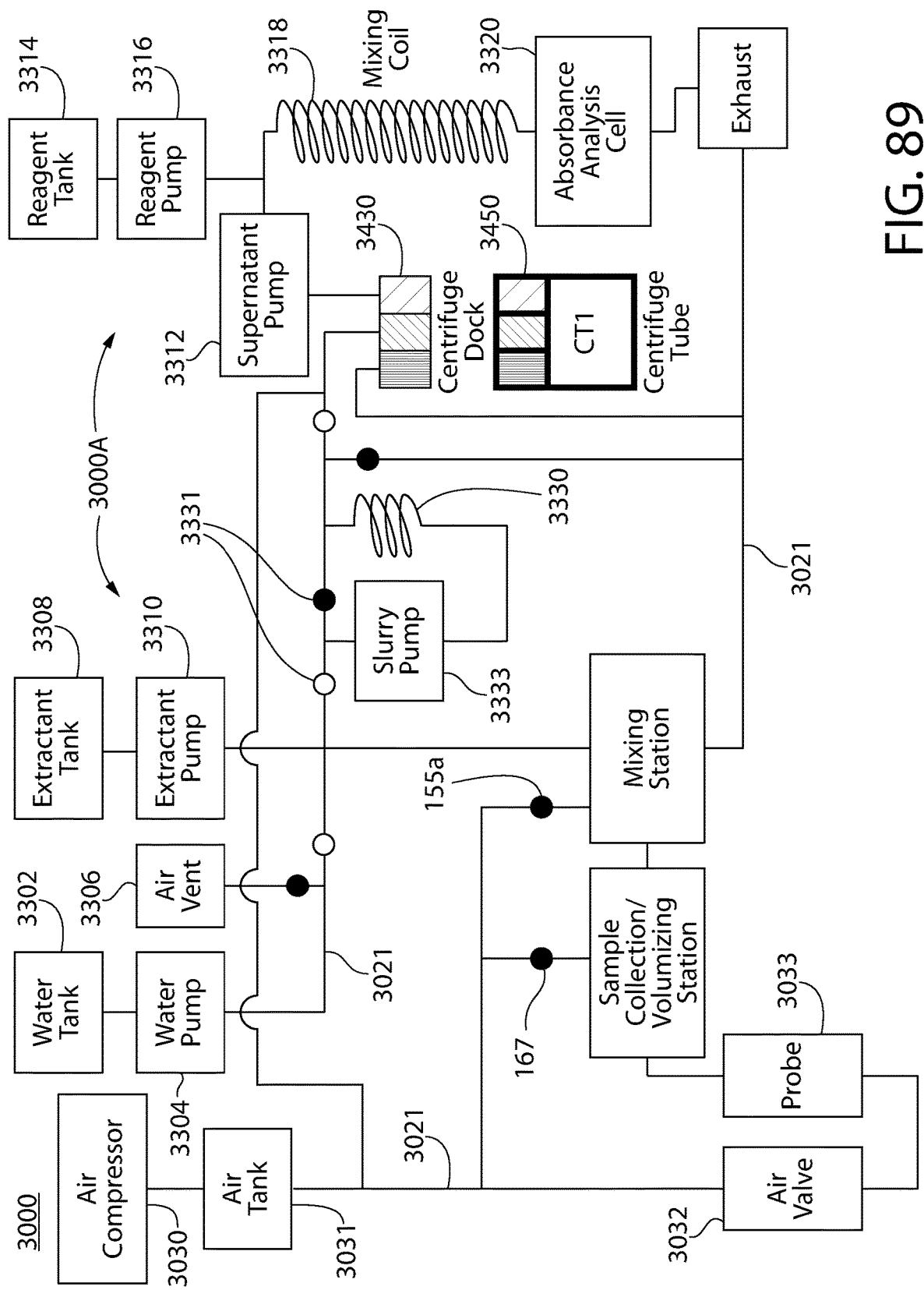
FIG. 89 is a schematic flow diagram of a soil sampling and processing system in a twelfth operating mode configuration.
Figure 90:
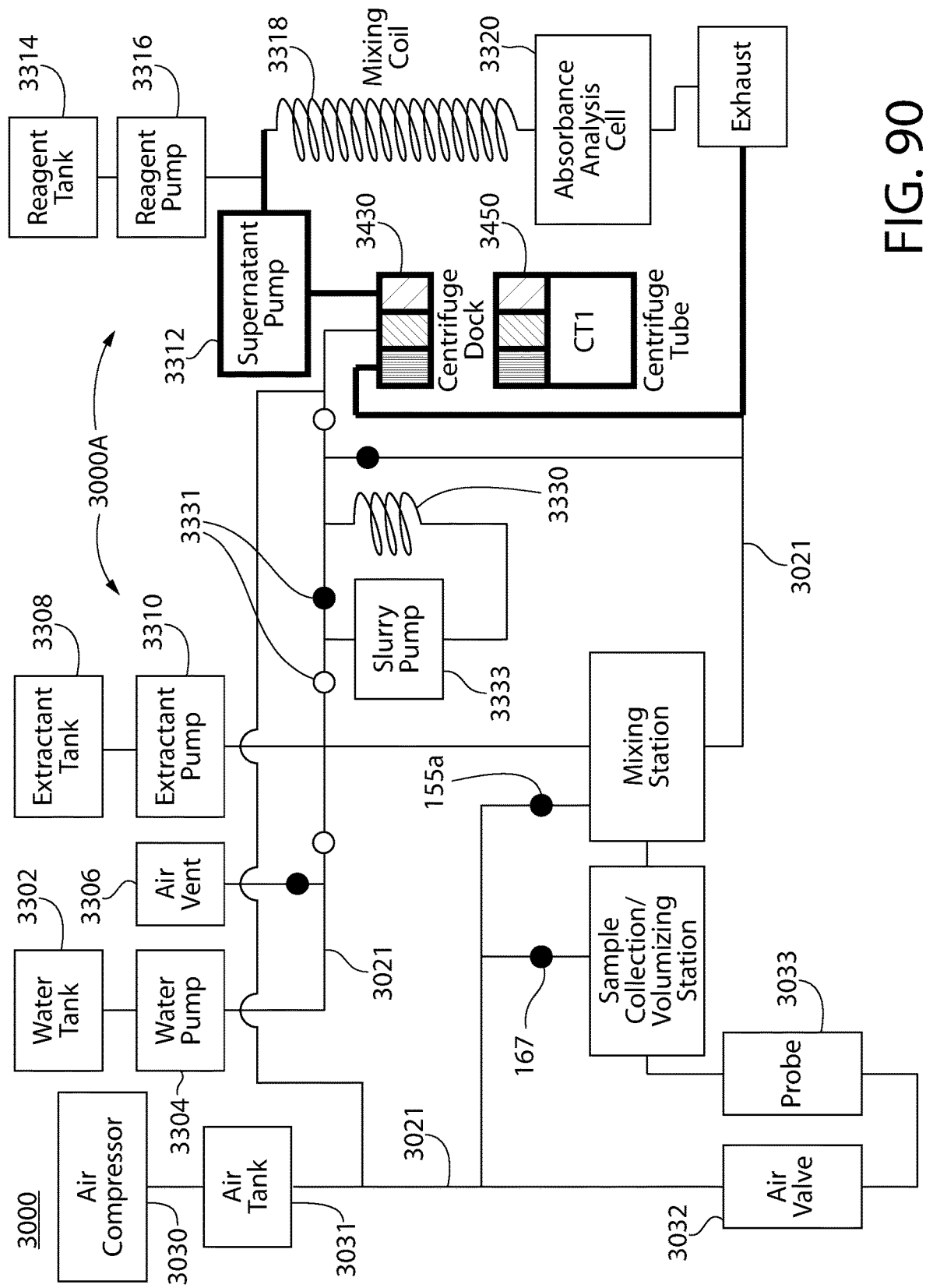
FIG. 90 is a schematic flow diagram of a soil sampling and processing system in a thirteenth operating mode configuration.

In FIG. 89, centrifuge 3400 undocks from fluid exchange dock 3430, and centrifugates the slurry sample in the manner previously described herein to create the transparent supernatant containing the analyte (i.e. chemical constituent of interest). In FIG. 90, centrifuge 3400 re-docks, then supernatant pump 3312 draws or pulls a small amount of supernatant from centrifuge tube 3450 through fluid exchange dock 3430 and past the reagent injection junction in the tubing 3021 as shown. This column of supernatant contains: (1) any debris that was in the connection point, and (2) a raw sample of supernatant to use as a "zero point" for absorbance before the reagent indicator is added. The slurry port 3455-1 in centrifuge tube 3450 (see, e.g. FIG. 59 et seq.) is used as a vent to atmosphere so air can replace supernatant in the centrifuge tube as the supernatant is drawn out by supernatant pump 3312 to prevent forming a vacuum which would impede the removal of supernatant from the centrifuge tube.

Figure 91:
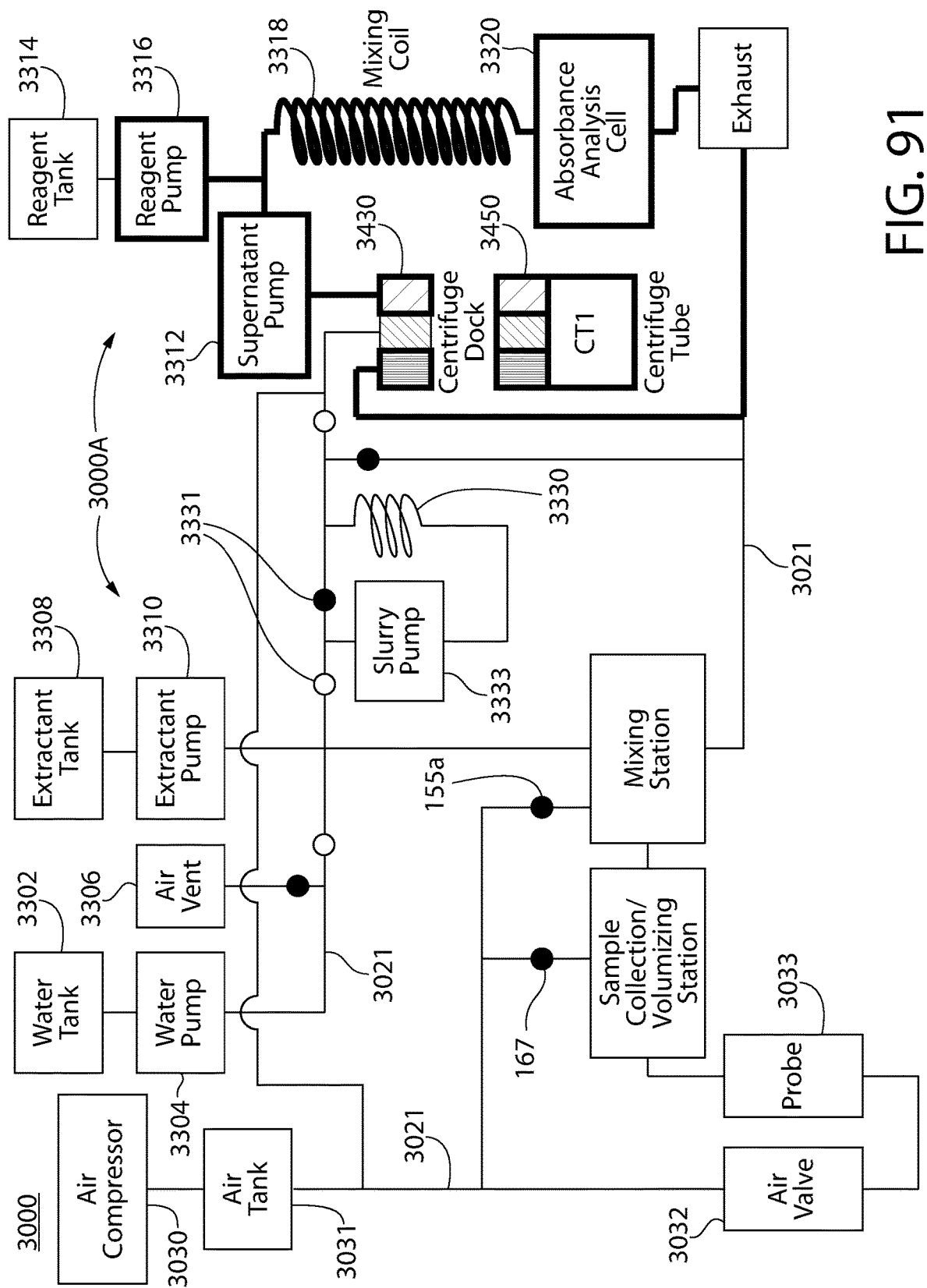
FIG. 91 is a schematic flow diagram of a soil sampling and processing system in a fourteenth operating mode configuration.

In FIG. 91, reagent pump 3316 and supernatant pump 3312 operate at desired ratio to pump the mixture through the mixing coil 3318 and through the flow cell 3800 to exhaust/waste. The initial (potentially dirty) sample is ignored, then the middle portion of the sample is used as the control, and the final portion is the portion that indicates the desired value representative of the initial soil sample.

Figure 92:
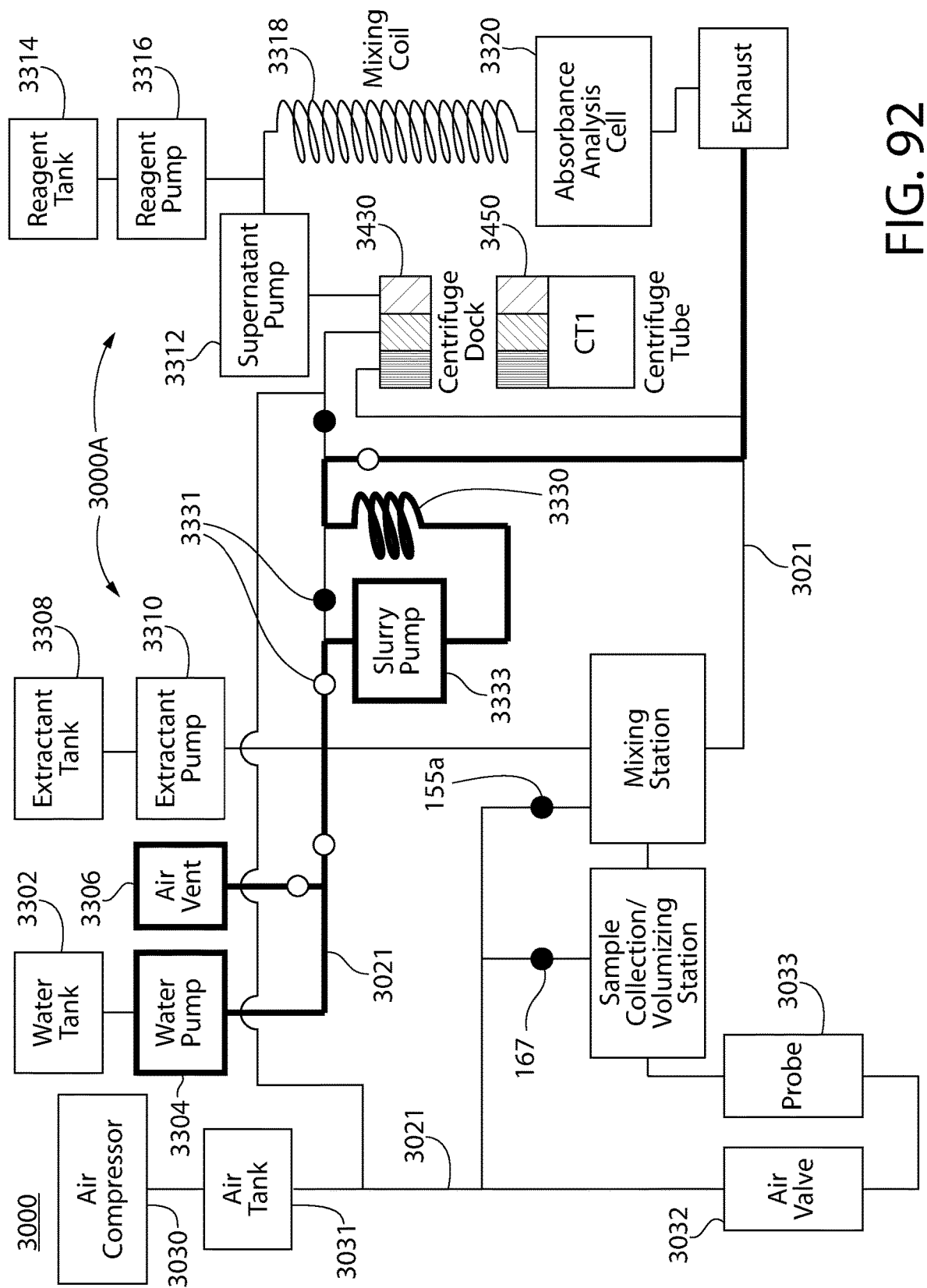
FIG. 92 is a schematic flow diagram of a soil sampling and processing system in a fifteenth operating mode configuration.

The flow conduits are next cleaned and flushed for processing the next sample. In FIG. 92, the water/air mixture pumps via slurry pump 3333 through the slurry loop portion of the flow conduits to clean slurry loop. The centrifuge

Figure 93:
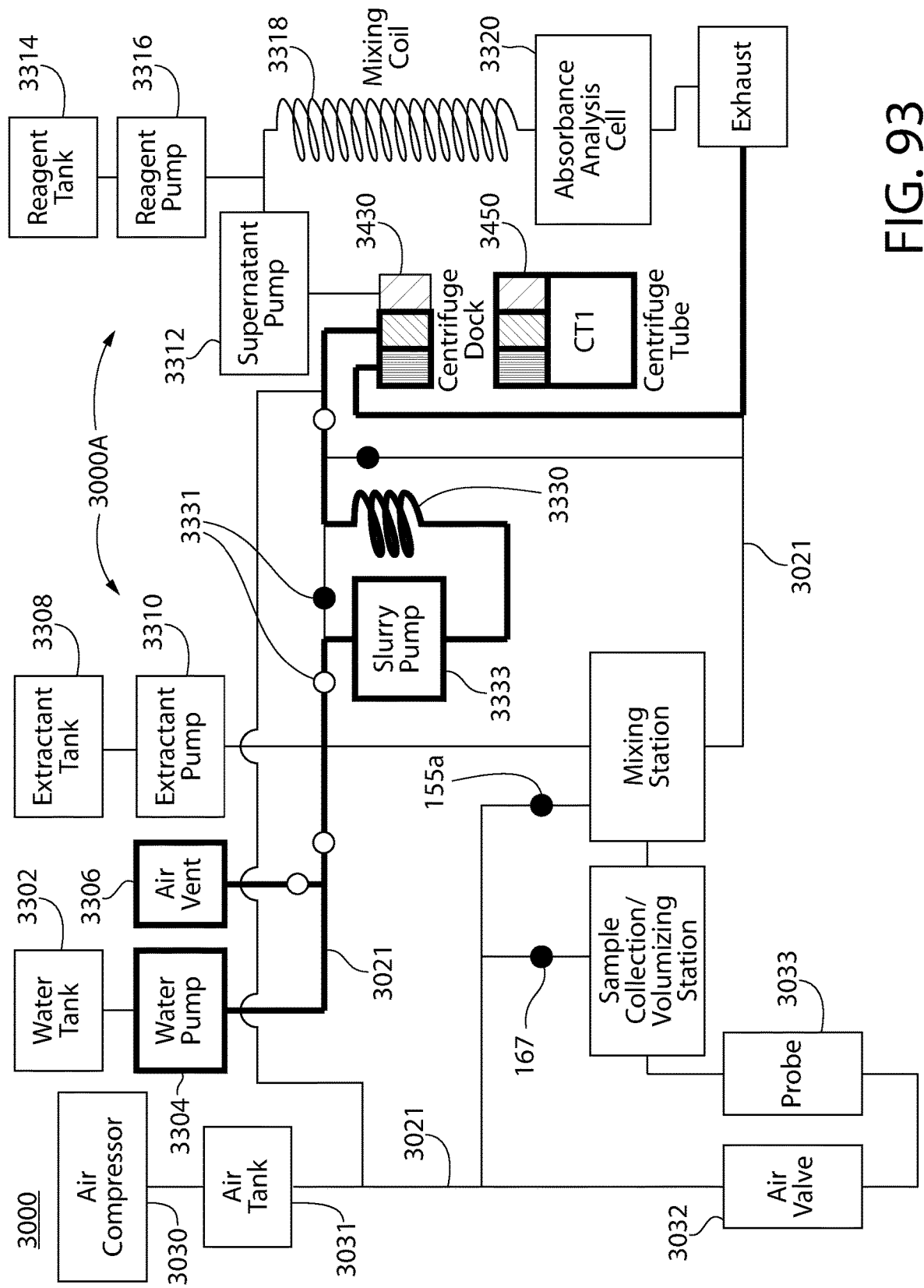
FIG. 93 is a schematic flow diagram of a soil sampling and processing system in a sixteenth operating mode configuration.
Figure 94:
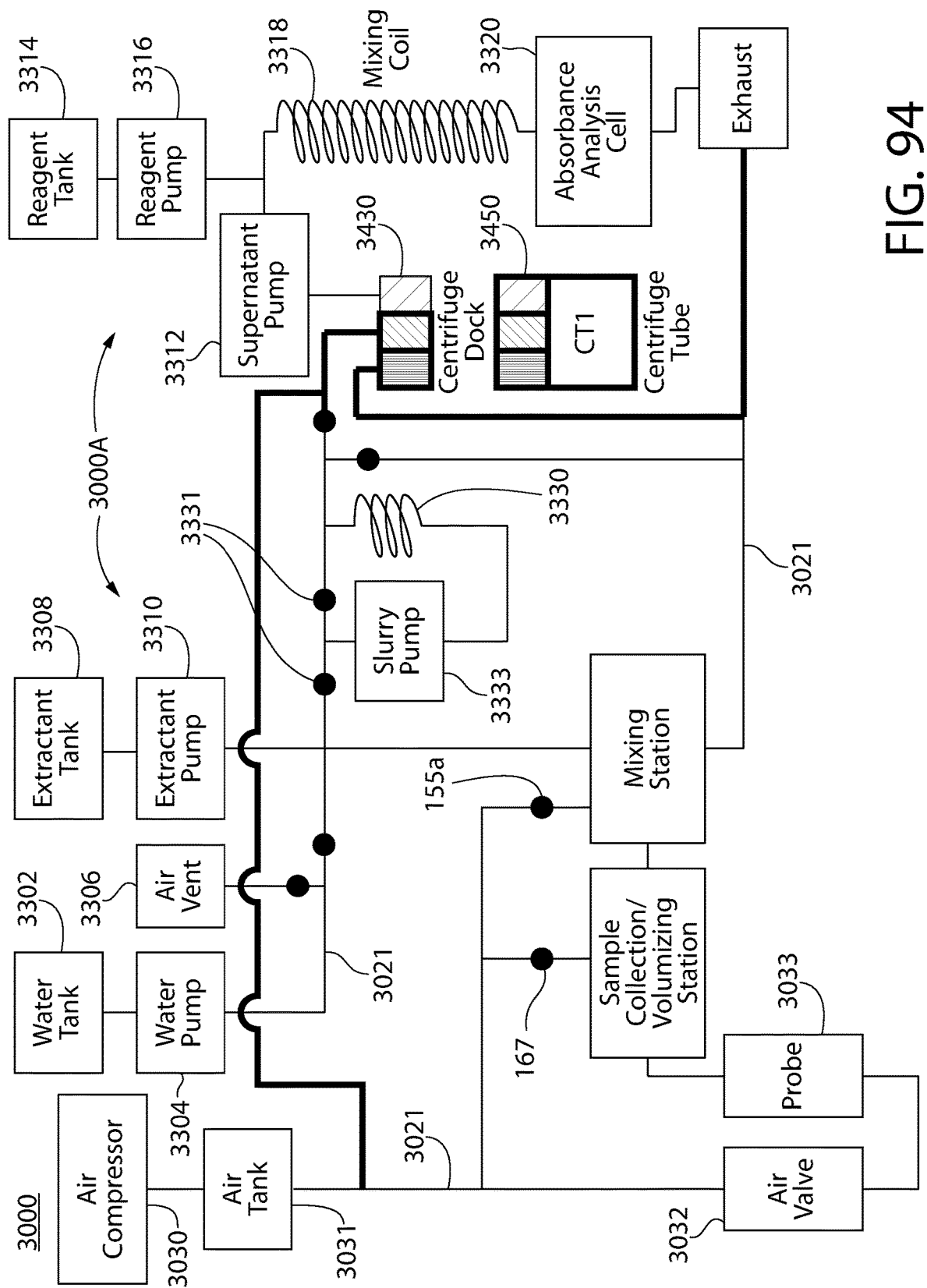
FIG. 94 is a schematic flow diagram of a soil sampling and processing system in a seventeenth operating mode configuration.

3400 is fluidly isolated from the slurry loop as shown (note valving positions). In FIG. 93, the water/air mixture pumps to centrifuge 3400 and through the centrifuge tube 3450 for cleaning. Note that the air vent 3306 is open and active to draw and entrain ambient air into the form of bubbles into the water which acts to scrub the exposed surfaces in the components to be cleaned. Alternatively or in addition, chemicals, and/or abrasive particles may be introduced into the cleaning water stream to further facilitate more aggressive cleaning measures if required. In FIG. 94, high pressure air from compressor 3030 is used to aggressively push the water/air mixture through centrifuge tube for final cleaning. The system is now prepared to process the next sample in a similar manner to that described above.

It will be appreciated that variations and different ordering of the foregoing process steps for chemically processing a soil sample may be used in other embodiments. The process is therefore not limited to number and types of operations presented herein, which represent one possible and non-limiting operating scenario.

Alternative Supernatant Separators

In some alternative embodiments, liquid may be separated from the soil sample to produce clear supernatant for chemical analysis using suitable filter media in lieu of the centrifuge 3400 and its centrifuge tubes 3450 described elsewhere herein.

FIG. 261 is a flow chart showing the same centrifuge-based soil sample processing and analysis system of FIGS. 78-94, but with the centrifuge 3400 replaced by a suitable micro-porous filter 5757 configured and constructed to produce the clear supernatant from the soil slurry and extractant mixture. The slurry/extractant mixture is pumped under relatively high pressure by slurry pump 333 in a flow path established via flow tubing 3021 and select opening/closing certain valves 3331 through the preferably back-washable porous filter 5757. The filter 5757 is configured and constructed to withstand the high pressure. The filter is shown schematically. In operation, the supernatant exits the filter 5757 and flows to supernatant pump 3312, and then is pumped through the remainder of the sample analysis loop where the supernatant is mixed with reagent and analyzed in the same manner already previously described herein and shown in FIGS. 78-94.

Once the supernatant is separated from the soil slurry, the filter may be back-flushed with clean high pressure liquid (e.g. filtered water) using water pump 3304 to clean the filter media for reuse during the next soil sample run. To accomplish a backwash cycle, the flow paths formed by flow tubing 3021 in the system may be reconfigured by selectively opening/closing certain valves 3331 in combination to reverse filtered water flow through the filter media of filter 5757. Additional filter backwash flow tubing 3021-1 and valving 3331 may be provided as shown in FIG. 261 to reverse the flow. The filter backwash is exhausted from the system.

In some embodiments, a porous sintered metal filter media of suitable shape and structure may be used for filter 5757. FIG. 262 shows one non-limiting example of an inline type filter 5757 with tubular cylindrical shaped metal filter media encased in a complementary configured housing 5757-1 which includes an inlet fitting 5757-2 and outlet fitting 5757 each configured for connection to external flow tubing or piping (e.g. threaded or tubing connector). Of course, numerous other suitable types and configurations of filters may be used to suit the apparatus used to mount and retain the filter (e.g. disk shaped, cone shaped, solid cylinder shape, etc.). Other types of porous filter media may be used which are suitable for pressure requirements of the system (e.g. polymeric, etc.). Preferably, the filter media material and shape selected are suitable for backwashing.

FIG. 263 is a flow chart showing the same centrifuge-based soil sample processing and analysis system of FIGS. 104-119 described elsewhere herein comprising a microfluidic processing or disk 4000 in a carousel assembly with analysis processing manifolds (e.g., wedges) 4002, but with the centrifuge 3400 replaced by a suitable micro-porous filter 5757 in the process to produce the clear supernatant from the soil slurry and extractant mixture. In this case, filter 5757 may be configured and constructed for mounting onboard within each of the processing wedges 4002 as shown (dashed lines connoting the boundary of the wedge). The filter operates in the same manner and flow sequence already described elsewhere herein with respect to use of the centrifuge instead. A suitable external off-disk high pressure filtered water source may be used for the filter backwash operation, which is conducted in a similar manner to that already described herein by reversing flow through the filter media.

Chemical Analysis Sub-System Alternative Embodiment

FIGS. 96-136 generally depict various aspects of an alternative embodiment of chemical analysis sub-system 3003 based on centrifuge 3400 previously described herein. In this embodiment, however, a microfluidic processing disk 4000 is added which mounts above and is in fluid communication with the fluid exchange dock 3430 which is detachably fluidly coupled to centrifuge tubes 3450 carried by rotary tube hub 3500. Advantageously, the microfluidic processing disk 4000 is a microfluidic device (e.g. M2D2) which is configured and operable to integrate and incorporate the entire slurry analysis system including substantially all aspects of fluid pumping, mixing, valving, and flow distribution and control previously shown in FIG. 1 associated with handling the slurry, extractant, reagent, and supernatant fluids. The pumps, valving, mixing, and flow distribution functions for example are thus integrated into microfluidic processing disk 4000 in a known manner of constructing microfluidic devices with active micro-components (e.g. pumps, valves, mixing chambers, etc.). This eliminates the need for the multiplicity of physically discrete and separate flow control devices (e.g. pumps, valves, mixing chambers, etc.) which need to be fluidly interconnected via tubing, thereby allowing for improved compactness of the centrifuge 3400 and its ancillary components associated with the chemical processing and analysis portion of the system. The microfluidic processing disk 4000 advantageously provides single unified platform or device for processing and controlling flow of all the foregoing fluids in addition to chemical analysis and quantification of the analytes of interest extracted from the soil sample. The microfluidic processing disk 4000 further provides parallelization of the soil sample processing to reduce analysis time and quantification of all chemical parameters associated with the sample. Pressurized air provided by air compressor 3000 (shown in FIG. 1) or another compressor provides the motive force for flowing and processing the foregoing fluids through the microfluidic processing disk 4000 in accordance with the flow charts of FIGS. 104-119, as further described herein.

Referring initially to FIGS. 96-103, the microfluidic processing disk 4000 may have a generally disk-shaped composite body in one embodiment formed from multiple layers of material bonded or laminated together by any suitable means used in the art (e.g. adhesives, heat fusion, etc.). Each layer may be substantially planar or flat in the sandwiched construction, typical of microfluidic devices (e.g. M2D2). One or more of the layers are configured and patterned to create micro-sized channels, chambers/reservoirs, and diaphragm-operated valves and pumps embedded in the microfluidic devices in a known manner. The materials used to construct the layers of the microfluidic processing disk 4000 may include a combination of rigid thermoplastics and flexible elastomeric material sheets. Transparent materials may be used in one embodiment to permit visual observation of the fluids being processed in the microfluidic processing disk 4000. The rigid plastics may be used to form the overall rigid substrate or body of microfluidic processing disk 4000 which defines its exposed exterior surfaces and includes an interior patterned to create a plurality of internal microchannels 4012 and chambers for creating the active microfluidic flow control devices (e.g. diaphragm-operated pumps, valves, mixing chambers, etc.). Examples of thermoplastics which may be used include for example without limitation PMMA (polymethyl methacrylate commonly known as acrylic), PC (polycarbonate), PS (polystyrene), and others. Examples of suitable elastomeric materials which may used include for example without limitation silicone, PDMS (polydimethylsiloxane), neoprene, and others. The elastomeric materials may be used to form the flexible and deformable active portions of the microfluidic flow control devices such as the movable diaphragms of the micropumps and microvalves which are acted upon by air pressure (alternatively water pressure) to operate these pumps and valves for controlling fluid flow within the microfluidic processing disk 4000. This is typically achieved by forming a thin flexible elastomeric layer (e.g. silicon, PDMS, etc.) above a layer of the more rigid thermoplastic layer in disk 4000 which is patterned with the microchannels and microchambers associated with the pumps, valves, or mixing chambers, thereby forming a flexible roof portion thereof. Applying air pressure to the top of the normally flat elastomeric deforms and deflects the elastomeric material downwards to seal off and close the microchannel/microchamber. Removing air pressure causes the elastomeric material to return its original flat condition via its elastic memory to reopen the microchannel/microchamber. This type action is well known in the art without undue further elaboration. In some embodiments, a vacuum may optionally be applied to return the elastomeric material to its original condition if removal of air pressure alone does not suffice.

In one embodiment, the disk-shaped microfluidic processing disk 4000 comprises a plurality of generally interchangeable and separable triangular or "pie-shaped" chemical processing wedges 4002. The wedges 4002 may be detachably interlocked together such as via suitable mechanical interlock features (e.g. snap-fit tabs/slots, etc.) and/or fasteners to collectively form the body of the processing disk 4000. In other embodiments, the wedges 4002 may be permanently joined together such as via adhesives or ultrasonic welding as some examples Each processing wedge 4002 of microfluidic processing disk 4000 is a discrete microfluidic device which may be fluidly isolated from every other processing wedge in one embodiment within the confines of the processing disk structure (i.e. no cross flow through the disk). Beyond the microfluidic processing disk physical boundary, however, individual processing wedges may fluidly share common inlet manifolds connected to a source flow (e.g. water, slurry, air) or outlet manifolds (e.g. waste/exhaust manifold) for convenience of construction. Each processing wedge 4002 is a complete chemical processing device or train operable to process and analyze a soil sample initially provided in slurry form (from one of the mixing stations previously described herein) for a different analyte. Advantageously, this provides a plurality of chemical processing trains (i.e. wedges 4002) capable of processing and analyzing soil samples simultaneously in parallel for different analytes (e.g. plant-available nutrients or other chemical constituents/properties) in conjunction with the centrifuge 3400. This parallelization reduces the time required for completely processing and analyzing a soil sample for multiple analytes. Microfluidic processing disk 4000 is configured and operable to form a detachable fluid coupling to centrifuge tubes 3350 carried by the rotary tube hub 3500 through intermediary fluid exchange dock 3430 previously described herein. Fluid exchange dock 3430 is fluidly coupled and interposed between the microfluidic processing disk 4000 and centrifuge tubes 3350.

Each processing wedge 4002 may have a truncated wedge shape including a top major surface 4003, an opposing bottom major surface 4004, opposing arcuately curved inner and outer surfaces 4005, 4006, and a pair of converging radial side surfaces 4007. Side surfaces 4007 each define radial reference lines R1 which intersect at a geometric vertical centerline C1 of the processing wedge 4002. When the processing wedges 4002 are assembled together in microfluidic processing disk 4000, they collectively define a circular central opening 4014 (for purposes similar to central opening 3435 of dock 3430). Processing wedge 4002 defines an outer peripheral portion or region 4008 defined as proximate to outer surface 4006, and an inner hub portion or region 4009 defined as proximate to inner surface 4005. Although the non-limiting illustrated embodiment includes eight processing wedges 4002, other embodiments may use more or less wedges.

A plurality of fluid exchange ports are formed in each processing wedge 4002. The ports may include a plurality of outer ports 4010 arranged in an array in peripheral region 4008 of the processing wedge, and a plurality of inner ports 4011 arranged in an array in the inner hub region 4009. In one embodiment, the outer ports 4010 may penetrate only the top major surface 4003 of the processing wedge 4002 and the inner ports 4010 may penetrate only the bottom major surface 4004. In one non-limiting implementation, eight outer ports 4010 and three inner ports 4011 may be provided as illustrated. Other numbers of ports may be used in other embodiments and is not limiting of the invention. The inner ports 4011 correspond in number and arrangement to the clusters 3433 of flow passages 3434 in the fluid exchange dock 3430 (see, e.g. FIGS. 55-56), which in turn match the flow ports 3451 formed in the top surface of centrifuge tubes 3450 for exchanging fluids when the rotary tube hub 3500 is in the upper docked position. Inner ports 4011 may be mutually configured with the top inlets to the flow passages 3434 in the fluid exchange dock 3430 to form a detachable leak-resistant sealed joint therebetween. For example, inner ports 4011 may thus be configured with the same type nozzles 3436 shown in FIG. 56 on the bottom of fluid exchange dock 3430 to form a detachable sealed therewith in a similar manner.

Outer ports 4010 are configured for fluid connection to external process tubing 3021 (see, e.g. FIG. 1). In one embodiment, outer ports 4010 may optionally include upwardly protruding tubing barbs 4013 to facilitate the coupling (see, e.g. FIG. 103). Alternatively, outer ports 4010 may instead include recessed nozzles 3436 configured similarly to the inner ports 4011 which can also facilitate fluid connection to process tubing 3021 without having a protruding tubing barb.

Referring to the flow diagrams of FIGS. 104-119, the inner and outer ports 4010, 4011 are fluidly coupled together by a branched microchannel network 4015 of microchannels 4012 formed internally within the microfluidic processing disk 4000. On the liquid side, the microchannel network forms flow paths between the inner and outer ports, and fluidly couples the flow control microfluidic devices together embedded in microfluidic processing disk 4000. The flow network 4015 also includes air microchannels 4012 which forms air connections to the liquid microchannels and microfluidic flow control devices by the pneumatic system which may include sources of high pressure and low pressure air as shown. Pressurized air provided by air compressor 3000 (example shown in FIG. 1) or another compressor/compressors provides the motive force for flowing and processing the foregoing fluids through the microfluidic processing disk 4000 in accordance with the flow diagrams and as described herein.

The microchannels 4012 (air and liquid) of each processing wedge 4002 are configured and patterned to form the functional layout and fluid connections represented in the flow diagrams of FIGS. 104-119 (recognizing that the physical layout may differ to create the functional connections shown). The blocks on the left of this figure represent the outer ports 4010 and those on the right represent the inner ports 4011 of each processing wedge 4002. It is well within the ambit of a microfluidic device manufacturer to create the depicted flow network (and flow control microfluidic devices shown) using computer-aided fabrication methods without undue further elaboration here. The microchannels 4012 may be formed in one or more of the layers of the microfluidic processing disk by any suitable process or combination of processes commonly used to construct microfluidic devices, such as for example without limitation micro-machining, laser milling, laser or chemical etching, lithography, hot embossing, injection molding, or other.

The microchannel network 4015 further includes a plurality of microfluidic valves, pumps, mixing chambers shown in FIGS. 104-119. In one embodiment, these microfluidic devices may be diaphragm operated and created using a flexible elastomeric flow control layer embedded within the microfluidic processing disk 4000 which is in communication with the microchannels and chambers created within the microfluidic processing disk 4000, as described elsewhere herein. The microfluidic devices may further include pneumatically-actuated diaphragm micropumps including extractant pump 4020, slurry pump 4021, reagent pump 4022, and transfer pump 4023. The microchannels 4012 are opened/closed by a plurality of pneumatically-actuated diaphragm microvalves 4018 schematically represented by circles (solid circle=closed; open circle=open). Pneumatically-actuated micro-mixing chambers 4024 may optionally be provided as required for mixing soil sample slurry with extractant, and/or upstream of the flow analysis cell 4027 and flow cell window 4025 each integrated into the processing wedge 4002 to ensure complete mixing of the color changing reagent (also sometimes referred to as "indicator") and supernatant if required. In some embodiments, the micro-mixing chambers 4024 may be formed by two closely fluidly coupled cells connected via a narrow short microchannel which is well known construction in the microfluidic arts. The cells are alternatingly pressurized by air to cyclically transfer the liquid back and forth multiple times between the cells, thereby providing thorough mixing. They mixers may or may not be diaphragm operated. It will be appreciated that other types of microfluidic mixers, pumps, and valves however may be used and the invention is not limited to the disclosed non-limiting examples.

FIGS. 256 and 257-258 are exploded and side cross-sectional views respectively of an on-disk pneumatically-actuated diaphragm micropump 5760, which may be used for the extractant pump 4020, slurry pump 4021, reagent pump 4022, transfer pump 4023, or other pumps that may be required. These pumps are incorporated into the microchannel network 4015 of each disk processing wedge 4002 and apply the motive force to the fluid to drive it through the microchannel network and various flow-related features of the disk. The micropumps and features shown are each integrally formed or molded within two adjacent layers of each wedge 4002 as unitary structural portions thereof. The illustration in FIG. 256 depicts a portion of the disk which includes the micropump recognizing that in actuality the micropumps are only defined by boundaries of the openings and/or concave structures formed directly in the disk layers.

Each micropump 5760 is a sandwiched structure including an upper layer 5761 of the microfluidic processing disk 4000, adjacent lower layer 5762 of the disk, and a thin resiliently deformable diaphragm 5763 having an elastic memory and defining a top surface 5763-1 and opposing bottom surface 5763-2. It bears particular note that the upper and lower layers 5761, 5762 are not necessary the uppermost (i.e. top) and lowermost (i.e. bottom) layers of the multi-layered microfluidic processing disk 4000, but instead may be two adjacent intermediate layers therebetween. In one non-limiting embodiments, the upper and lower layers 5761, 5762 are intermediate layers in a 5-layer processing disk 4000.

The diaphragm 5763 may be made of a suitable elastomeric material or polymer, such as silicone in some embodiments, and may have thicknesses less than 1 mm (0.04 inches). Diaphragm 5763 is resiliently movable between a normally flat standby condition when no pneumatic air pressure signal is applied and a deformed downwardly projecting convex actuated condition when air is applied to the top surface of the diaphragm. The diaphragm 5763 may be oval in one configuration; however, other shapes may be used.

The micropump 5760 further includes an upper pump chamber 5764 recessed into the bottom surface of the upper layer 5761 of microfluidic processing disk 4000, and a concavely shaped lower pump chamber 5765 directly opposing and vertically aligned with the upper chamber formed in the lower layer 5762. The upper chamber 5764 may have straight sidewall surfaces 5764-1 and a flat top surface 5764-2 in some embodiments. Lower chamber 5765 is recessed into the top surface of lower layer 5762 and may include arcuately curved sidewall surfaces 5765-1 which extend perimetrically around the chamber. A flat bottom surface 5765-2 adjoins the sidewall surfaces around the perimeter of the lower chamber as shown. The curved sidewall surfaces ensure that the diaphragm 5763 does not tear or crack when actuated over multiple operating cycles. It bears noting that the lower chamber 5765 defines the volumetric pumping capacity of the micropump which is expelled with each actuation of the micropump.

The micropump 5760 further includes a pneumatic air pressure signal port 5768 formed in upper layer 5761 which in fluid communication with the upper chamber 5764. Port 5768 is preferably centered in the top surface of the upper chamber 5764 and in fluid communication with a pneumatic or air microchannel network 4015-1 formed in the disk layer immediately above the upper layer 5761 and fluidly coupled to an air source such as those described herein. The lower layer 5762 includes a fluid inlet port 5766 for introducing fluid into the lower chamber 5765, and a fluid outlet port 5767 for discharging fluid from the lower chamber causes by operation of the micropump 5760. Each port 5766, 5767 is thus in fluid communication with the lower chamber 5765. The fluid inlet port 5766 preferably penetrates the lower chamber 5765 at an opposite end of the chamber than its outlet port 5767 at the other end. Each of the fluid inlet and outlet ports is in fluid communication with the fluid microchannel network 4015 formed in the disk layer immediately below the lower layer 5762. In one embodiment, the upper and lower chambers 5761, 5762 may be oval shaped; however, other shapes may be used.

Operation of micropump 5760 will be briefly described. Each micropump has an associated fluid inlet diaphragm microvalve 4018 and fluid outlet diaphragm microvalves 4018 fluidly coupled to the fluid inlet and outlet ports 5766, 5767 respectively which are necessary for operation of the micropump. The diaphragm valves have the same general construction and operation as the micropumps including a diaphragm, air pressure signal port, and fluid inlet and outlet ports. Operation of the valves between an open and closed position is performed in the same manner as described below for the micropumps which are thus analogous in structure and function to the valves. The valves however are generally smaller in size due to the multitude of valves arranged in the microfluidic processing disk 4000 to conserved space, and typically utilize circular diaphragms and upper and lower chambers in contrast to the elongated features of the micropumps intended to hold a predetermined volume of fluid necessary for the chemical processes and soil analysis. A single control signal can command simultaneous actuation of a pump(s), a valve(s), or a pump (s) and valve(s) in a plurality of manifolds. A single control signal can command simultaneous actuation of a plurality of pumps, a plurality of valves, or a plurality of pumps and valves in a manifold.

FIG. 257 shows the pump in the initial flat unactuated or standby condition. Diaphragm 5763 is fully nested inside upper pump chamber 5764 and does not project downwards into lower pump chamber 5765. The diaphragm is trapped in the upper chamber 5764 between the upper and lower disk layers 5761, 5762. No air is applied to the diaphragm at this stage. The fluid outlet diaphragm microvalve 4018 is first closed and the fluid inlet diaphragm valve is opened to fill the lower chamber 5765 beneath the diaphragm with the fluid to be pumped from the microchannel network 4015 (e.g. soil slurry, extractant, reagent, supernatant, or other fluid). The fluid inlet diaphragm microvalve 4018 is then closed and the fluid outlet diaphragm microvalve 4018 is opened.

To pump the fluid volume contained in the lower pump chamber 5765, air is supplied to the top of the diaphragm 5763 via the air pressure signal port 5768 from the air source which is controlled by an air valve. The air pressure drives the diaphragm downward, which deforms and generally conforms to the shape of the lower chamber 5765, thereby expelling the fluid through the fluid outlet port 5767 and its associated outlet microvalve 4018. The diaphragm 5763 is now in the deformed convex actuated condition shown in FIG. 258. After pumping is completed, the air pressure is relieved from the air pressure signal port 5768 and the diaphragm 5763 returns to its original undeformed flat standby condition ready for the next pumping cycle.

In testing, it was discovered that if smooth surfaces are provided within the lower pump chamber 5765 (left screenshots), the flexible diaphragm 5763 tends on occasion to get sucked into the fluid outlet port 5767 for either the pneumatic signal or fluid liquid-side communication prematurely. This unfortunately blocks fluid flow and pumping before the diaphragm is fully displaced/deformed and prevents the liquid volume in the lower chamber from being fully expelled. This causes inconsistency in the volume of fluid pumped per actuation, which can adversely affect proper slurry processing and analysis since the volumetric capacity for each pumping chamber is carefully predetermined and exacting to ensure the proper ratio of chemicals (e.g. reagent, extractant, etc.) are mixed with the slurry.

To combat the foregoing diaphragm and pumping problems, the concave lower pump chamber 5765 preferably is provided with a plurality of "anti-stall" grooves 5769 which act to keep the flexible diaphragm 5763 from getting sucked into the fluid outlet port 5767 and blocking flow. This also prevents the diaphragm from attaching via formation of suction to but not fully releasing from the generally flat bottom surface 5765-2 of the lower pump chamber. The anti-stall grooves 5769 are therefore configured to prevent adherence of the diaphragm 5763 to the lower pump chamber 5765, thereby advantageously allowing the diaphragm 5763 to fully and reliably displace substantially the entire volumetric fluid contents of the lower chamber with each pumping cycle, thereby ensuring accuracy of the amount of fluid dispensed and ultimate soil slurry analysis. The recessed anti-stall grooves 5769 are cut or otherwise formed into preferably all surfaces within the lower chamber 5765 (e.g. sidewall surfaces 5765-1 and flat bottom surface 5765-2), as shown in FIG. 256. In one embodiment, the grooves 5769 may be arranged in a two-directional perpendicularly intersecting grid array of grooves as shown forming a somewhat checkerboard pattern. In other embodiments, the grooves may be unidirectional and formed by a plurality of non-intersecting and spaced apart parallel grooves arranged either along the major axis or minor axis of the lower chamber 5765, or diagonally to the axes. In some embodiments, the upper pump chamber 5764 formed in the upper disk layer 5761 may include anti-stall grooves similar to or different in configuration than the grooves in the lower chamber 5765. Any suitable pattern and number of grooves may be provided.

The microchannel network 4015 may further include a plurality of microreservoirs of predetermined volume for holding and staging the extractant, reagent, slurry, etc. for processing. In one embodiment, this may include an extractant microreservoir 4030, soil slurry microreservoir 4031, reagent microreservoir 4032, and supernatant microreservoir 4033. The microreservoirs 4030-4033 may be formed by a series of closely spaced, undulating loops of microchannels as shown. Sample non-limiting volumetric capacities of each microreservoir are shown in FIGS. 104-119. Other volumetric capacities, however, may of course be used.

FIGS. 104-119 are schematic flow diagrams depicting sequential views of a method or process for processing and analyzing a soil sample. These diagrams represent the processing sequence which occurs in a single processing wedge 4002 of microfluidic processing disk 4000. It will be appreciated that in some implementations of the method, the same sequential process shown is performed simultaneously in parallel in all of the processing wedges 4002 of processing disk 4000 to analyze the soil sample slurry for all chemical parameters of interest (analytes), thereby resulting in a significant reduction in sample processing time. Accordingly, the same corresponding pneumatically-actuated micropumps, microvalves, and micro-mixing chambers in each processing wedge 4002 may be actuated simultaneously via a common control air header or channel and air valves. Each processing wedge 4002 may therefore process and analyze the sample for a different analyte to complete the full chemical analysis profile of the soil sample.

The process described below and in the flow diagrams may be automatically controlled and executed by the system programmable controller, such as for example processing system 2820 disclosed in copending U.S. patent application Ser. No. 15/806,014 filed Nov. 7, 2017. The controller is operably coupled to the low and high pressure air supply, such as air compressor 3030 and air tank 3031 (see, e.g. FIG. 1). The low pressure air may be created in any suitable known manner such as by employing a pressure reducing valve station taking suction from the air tank 3031, which may contain high pressure air produced by the compressor 3030. All air supply related components (compressor, tank (s), and valves) may therefore be controlled by the system programmable controller (e.g. processing system 2820). Other sources of low and high pressure air for pneumatically controlling operation of the microfluidic processing disk 4000 such as separate compressors may of course be used.

In the flow diagrams, it bears noting that the emboldened and thicker dark lines represent the active fluid flow paths during each of the process sequences shown and described. Valve position of the pneumatically-actuated diaphragm microvalves 4018 are schematically represented by solid or open circles (solid circle=closed; open circle=open).

To reiterate, as previously noted, the blocks on the left of the flow diagrams represent the outer ports 4010 of the respective processing wedge 4002 and blocks on the right represent the inner ports of the wedge. In one implementation, the outer ports 4010 may include a high pressure air inlet 4010-1, low pressure air inlet 4010-2 also configured to operate as an air vent when required, extractant inlet 4010-3, cleaning solution 4010-4, slurry sample inlet 4010-5, reagent (indicator) inlet 4010-6, low pressure exhaust outlet 4010-7, and high pressure exhaust outlet 4010-8. The cleaning solution provided to inlet 4010-4 may be any suitable solution including deionized water or other. The inner ports 4011 may include a slurry sample outlet 4011-1 from processing wedge 4002 to centrifuge 3400 (i.e. centrifuge tube 3450), supernatant inlet 4011-2 from centrifuge 3400, and centrifuge waste inlet 4011-3 from the centrifuge. Other types and numbers of outer and inner ports 4010, 4011 may of course be provided.

Figure 104:
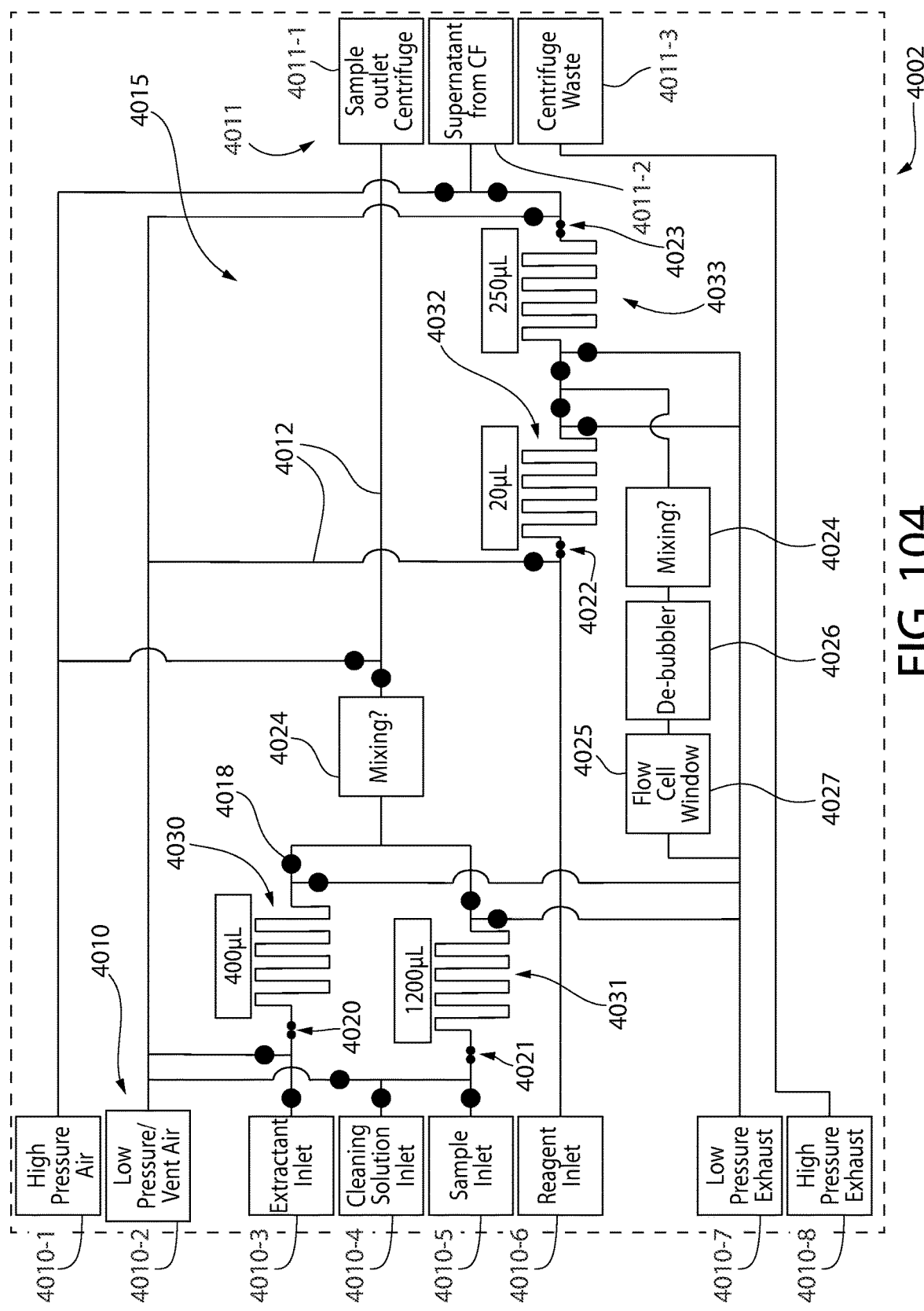
FIG. 104 is a schematic flow diagram showing the arrangement of the microfluidic flow distribution network and its fluidic micro-components of a single chemical processing wedge of the microfluidic processing disk in a first operating mode configuration.
Figure 105:
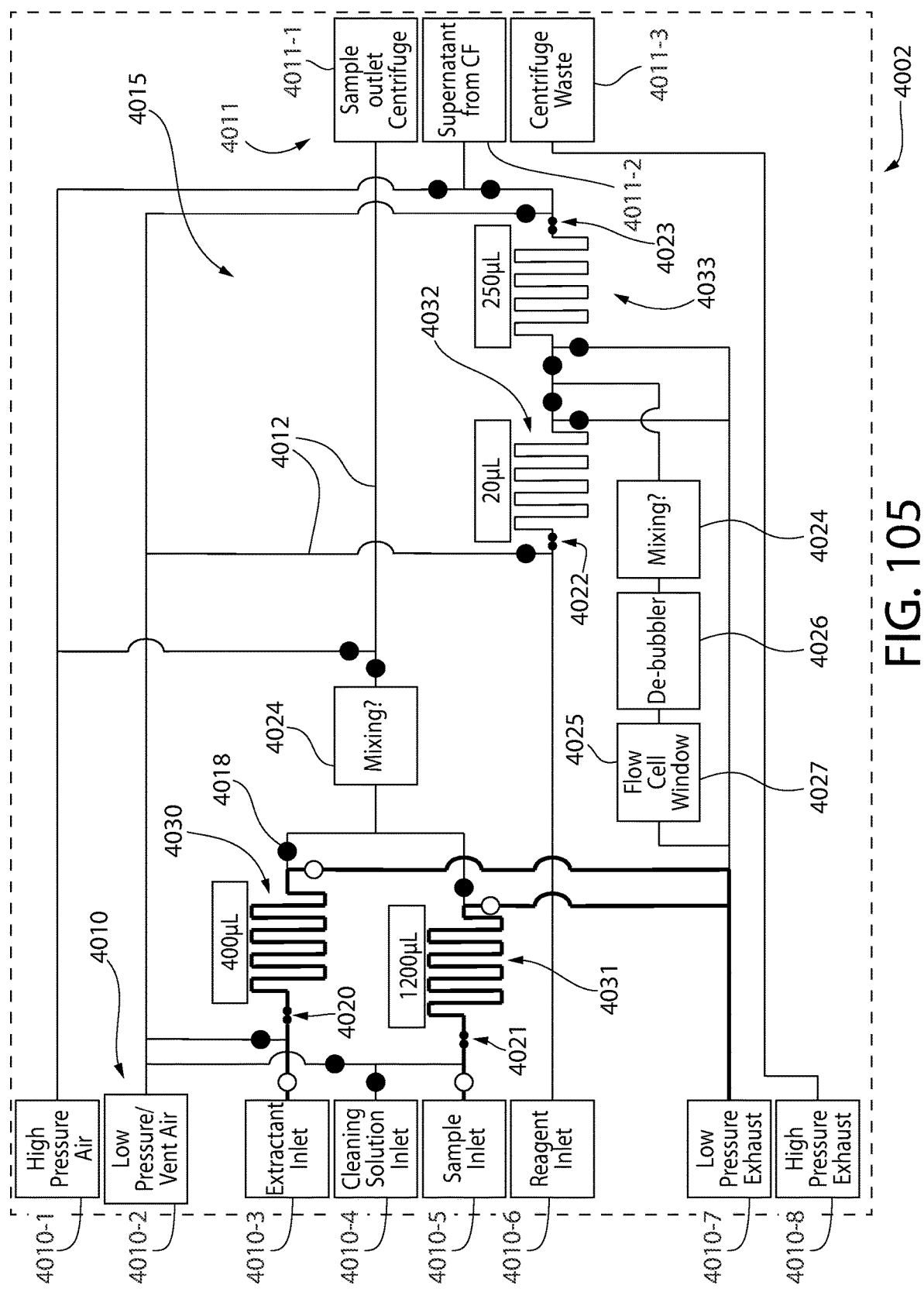
FIG. 105 is a schematic flow diagram thereof in a second operating mode configuration.

FIG. 104 shows the provision of the microfluidic processing disk 4000 and processing wedge 4002 with microchannel network 4015 at the start and readied for processing and chemically analyzing a soil sample. In FIG. 105, the soil slurry sample from the mixing station previously described herein (e.g. mixer-filter apparatus 100 or 200) and extractant from extractant tank 3308 (see, e.g. FIG. 1) are pumped into the sample/extractant measurement loops (reservoirs) to fill microreservoirs 4030 and 4031 at a precise predetermined ratio of slurry to extractant. It bears noting that the low pressure exhaust path to outlet 4010-7 is opened briefly to not only drive any air from the active microchannels 4012, but to also very briefly discharge some of the slurry and extractant to waste to ensure the microreservoirs 4030, 4031 are completely filled before shutting off the slurry and extractant sources. Also noteworthy are closed/open valving 4018 positions in these and the remaining flow diagrams which open and close various flow paths in the microchannels 4012 of microchannel network 4015.

Figure 106:
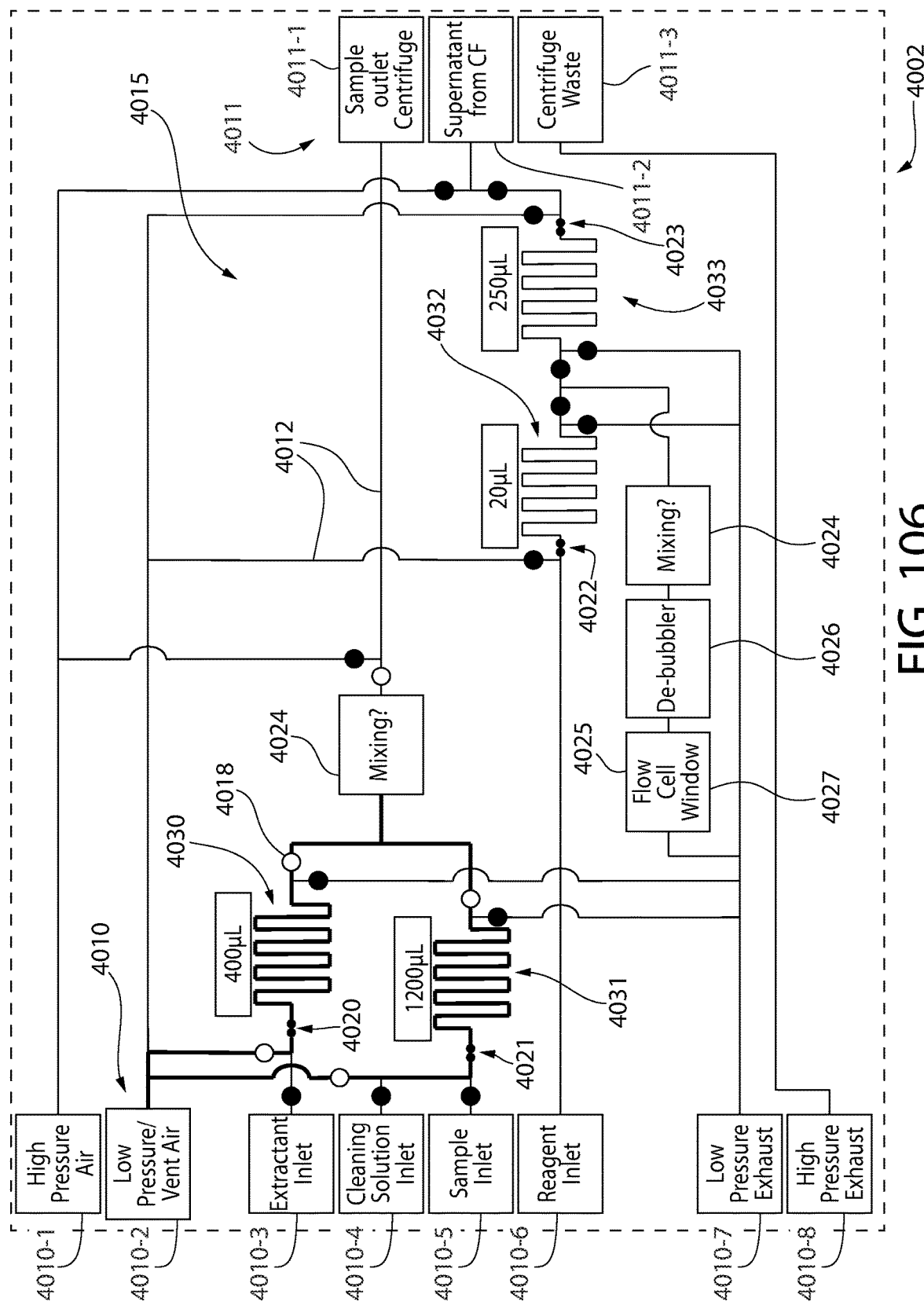
FIG. 106 is a schematic flow diagram thereof in a third operating mode configuration.
Figure 107:
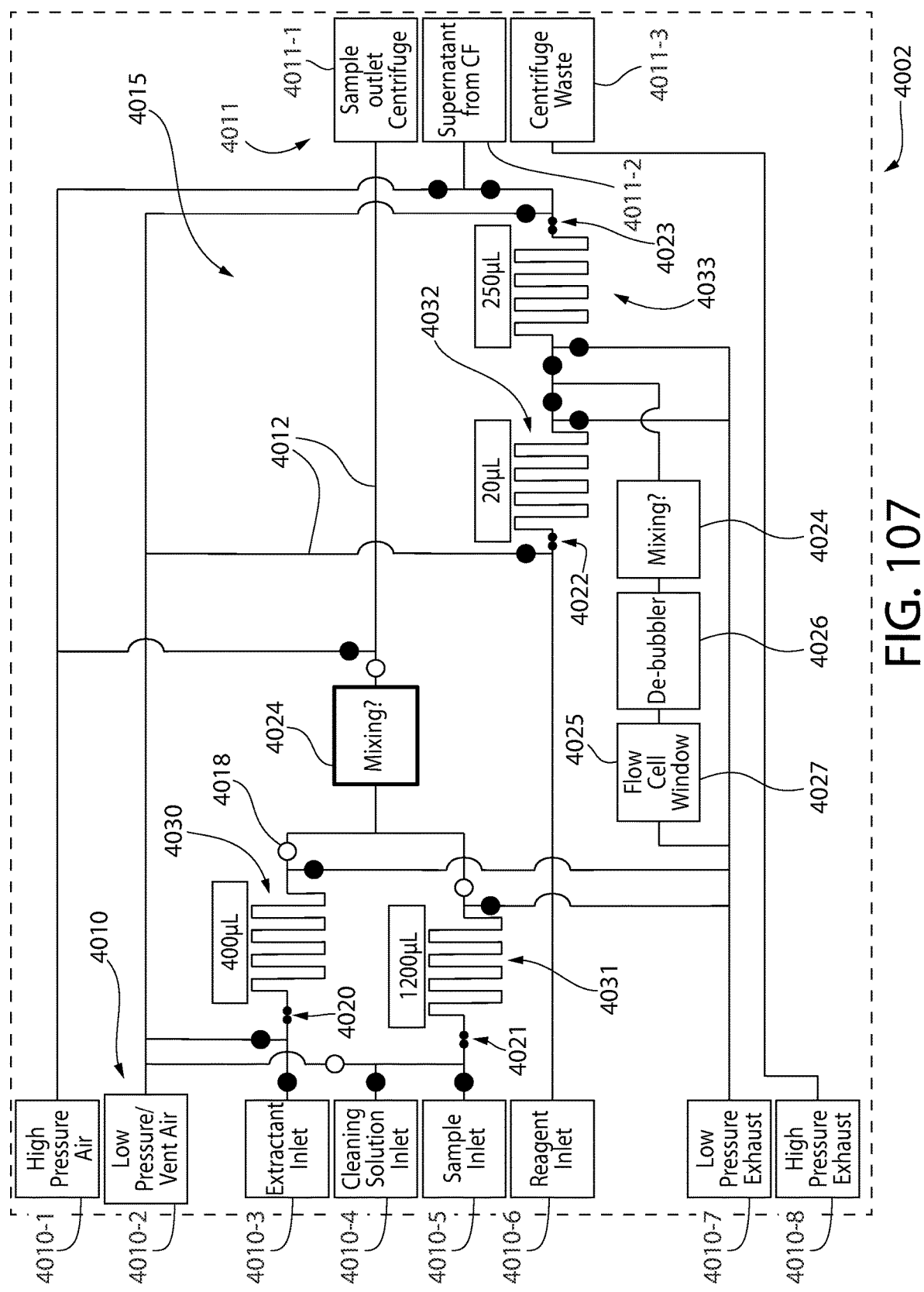
FIG. 107 is a schematic flow diagram thereof in a fourth operating mode configuration.
Figure 108:
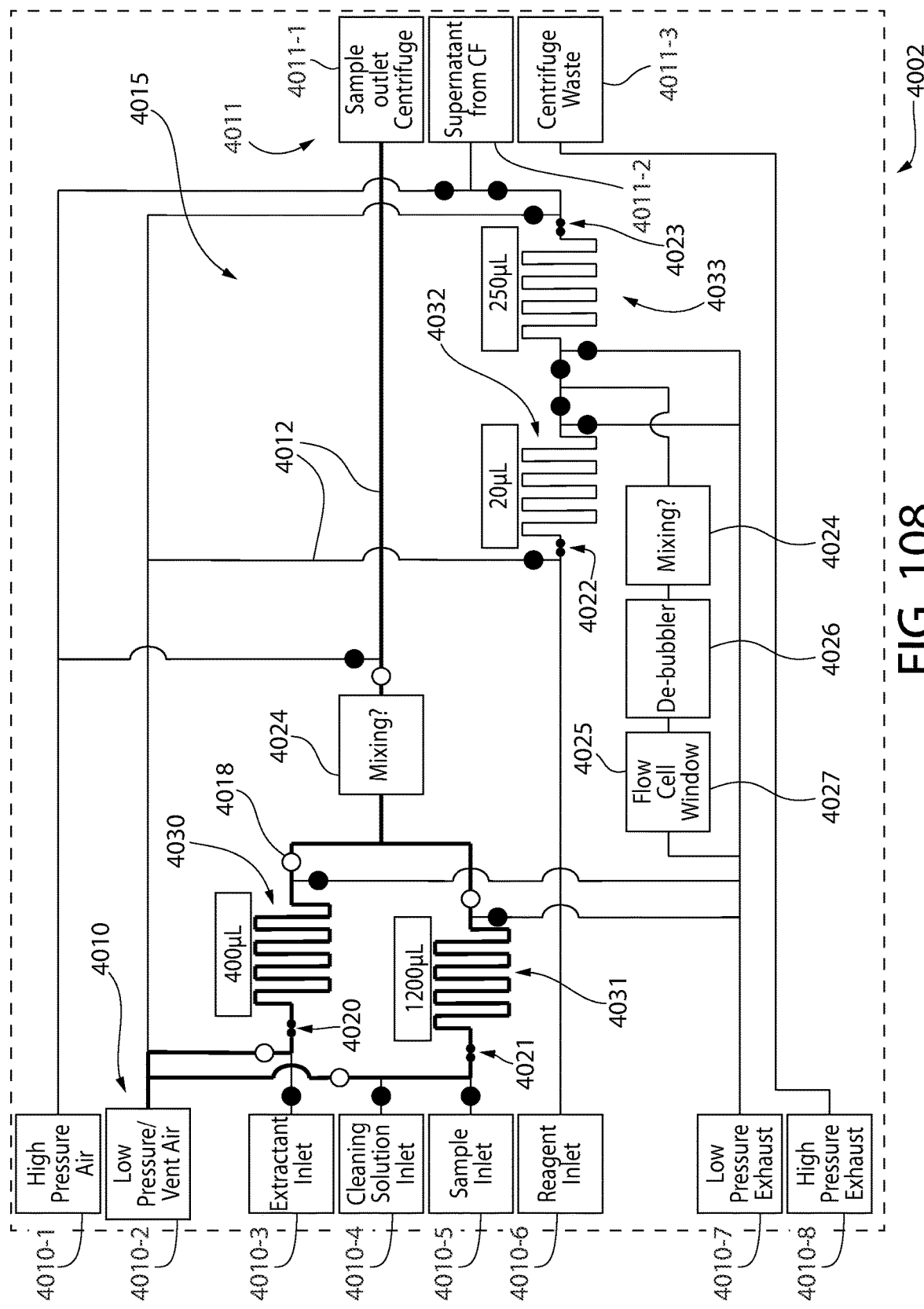
FIG. 108 is a schematic flow diagram thereof in a fifth operating mode configuration.
Figure 109:
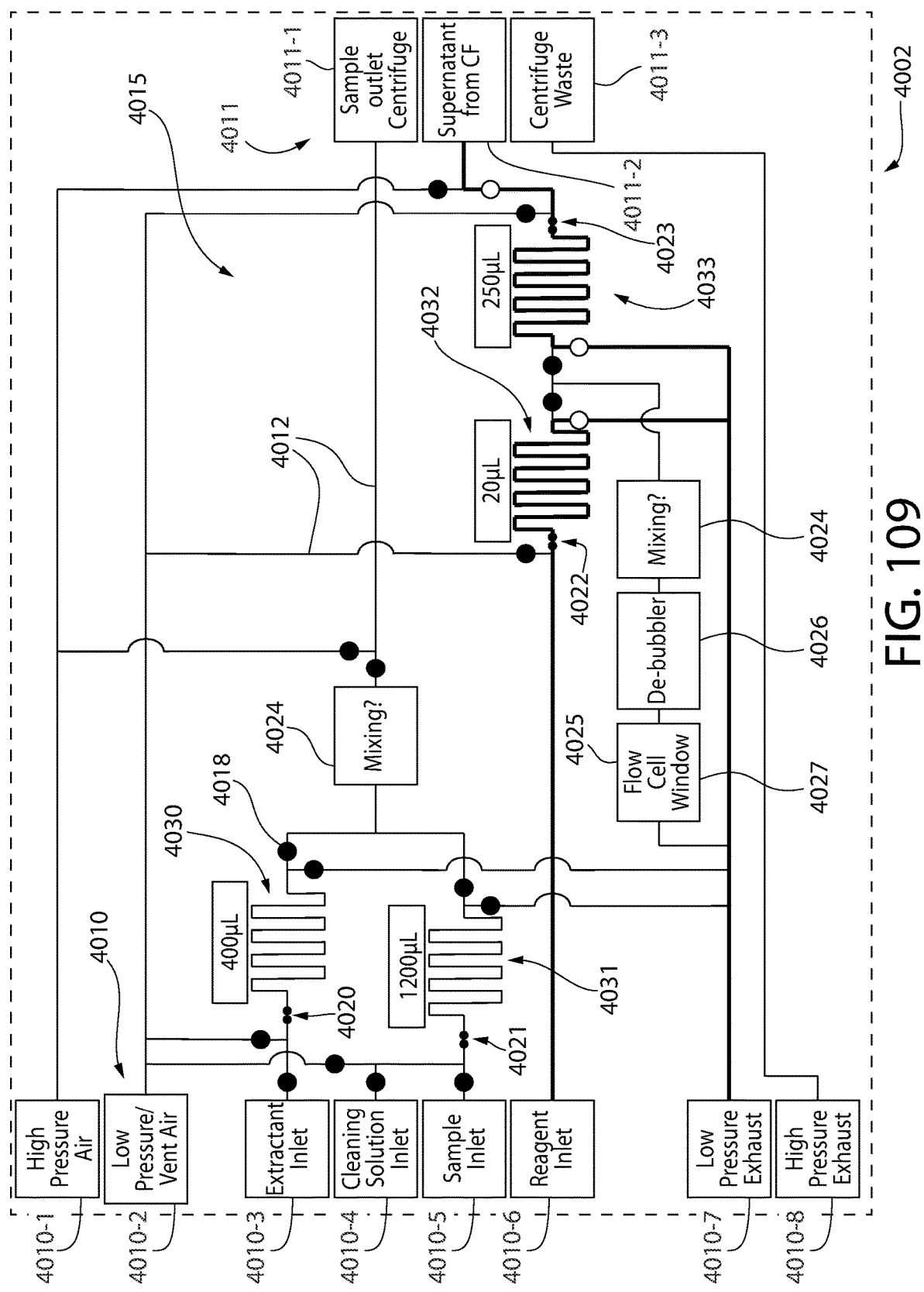
FIG. 109 is a schematic flow diagram thereof in a sixth operating mode configuration.
Figure 110:
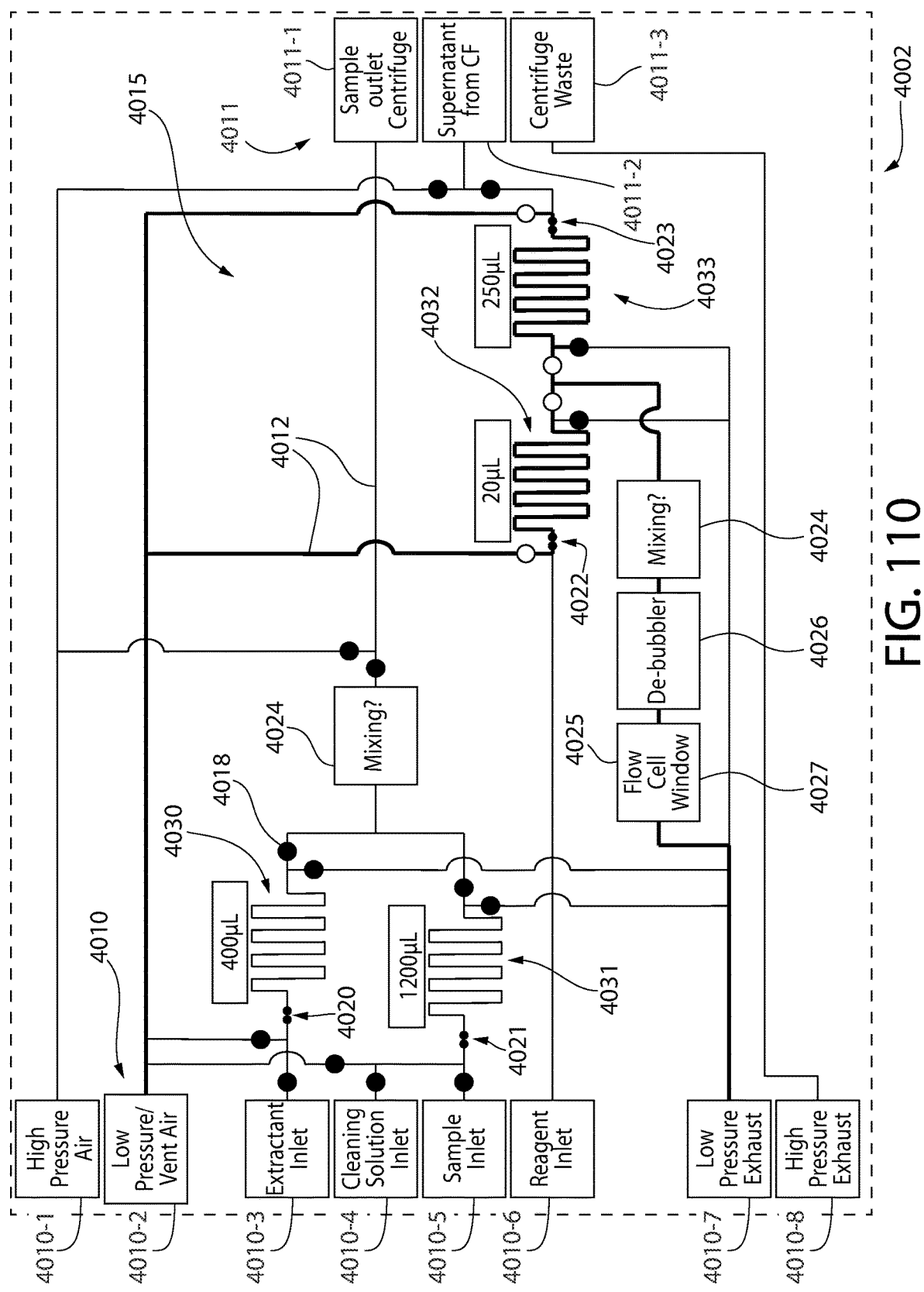
FIG. 110 is a schematic flow diagram thereof in a seventh operating mode configuration.
Figure 111:
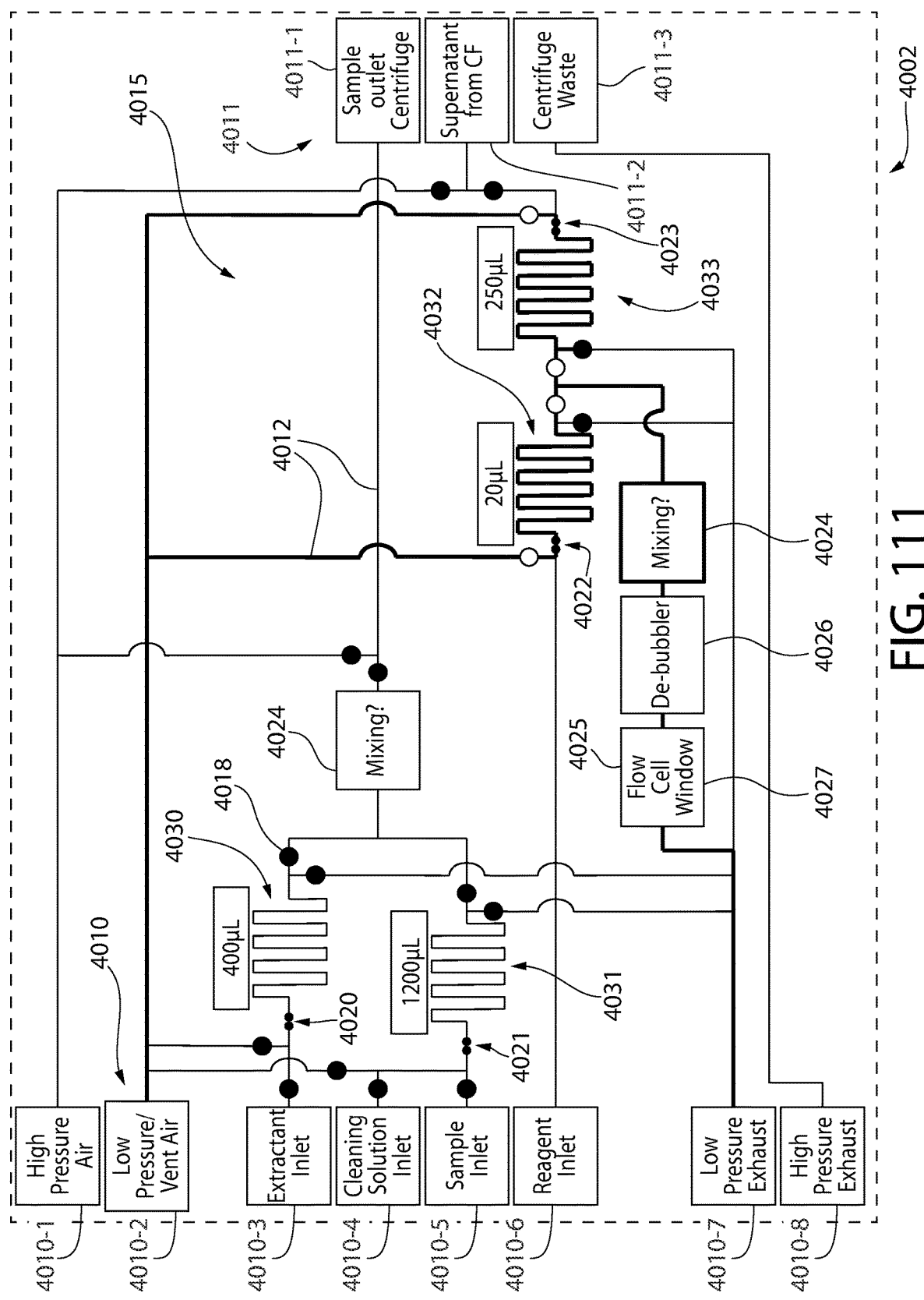
FIG. 111 is a schematic flow diagram thereof in a eighth operating mode configuration.
Figure 112:
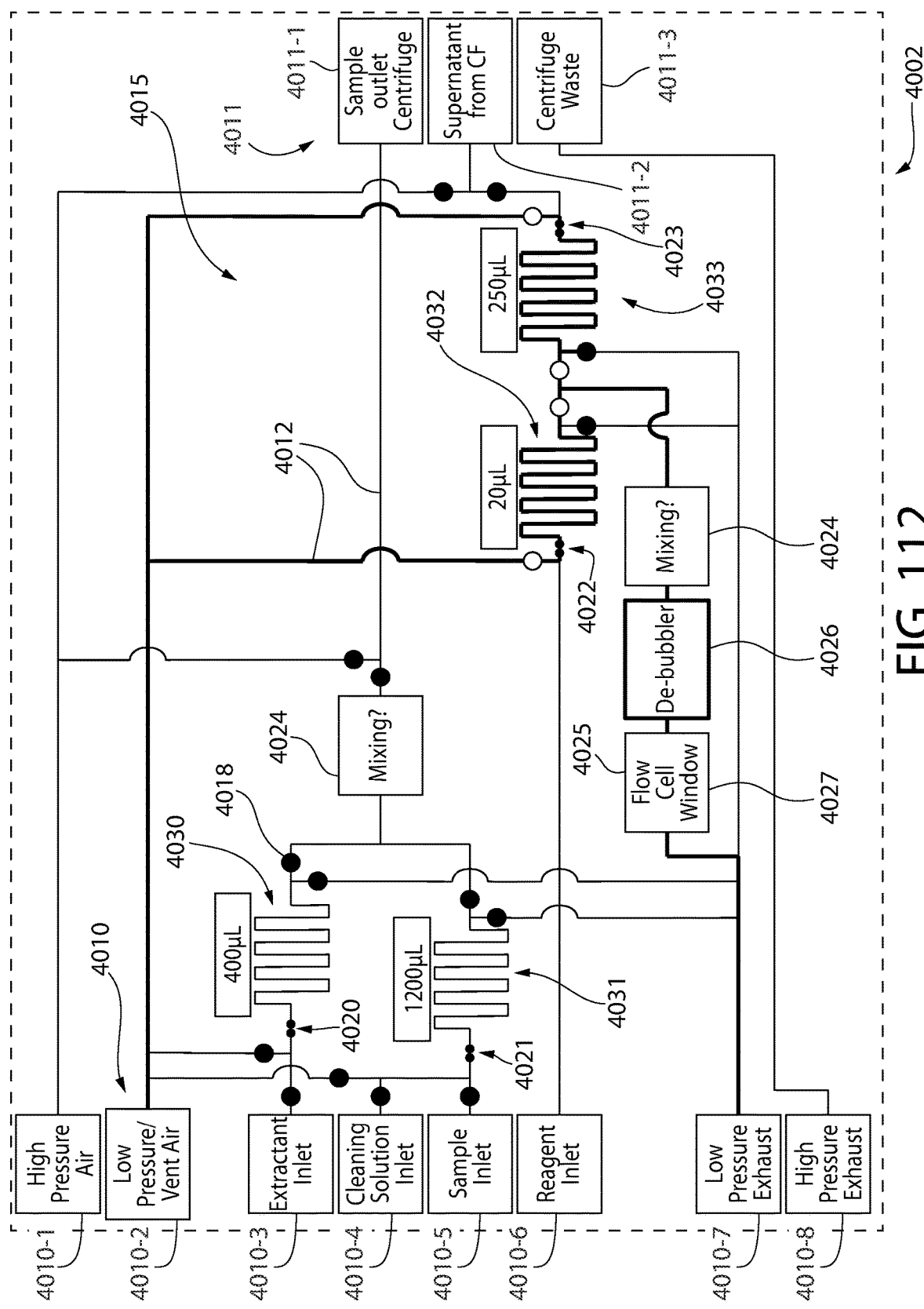
FIG. 112 is a schematic flow diagram thereof in a ninth operating mode configuration.

In FIG. 106, the slurry sample and extractant measurement loops (reservoirs) are pumped together into an optional first micro-mixing chamber 4024 where they are mixed. In some situations, adequate mixing of the sample and extractant may be achieved within the microchannels 4012 to obviate the need to a separate micro-mixing chamber (hence designation of the same with a "?" in the figure). Diaphragm-operated micropumps 4020, 4021 are pressurized with low pressure air as shown to achieve pumping of the fluids. In FIG. 107, complete mixing of the slurry sample and extractant is performed. In FIG. 108, the extractant/sample mixture is pumped from first micro-mixing chamber 4024 to the centrifuge 3400 for processing. In FIG. 109, supernatant and reagent are staged and pumped into their respective measurement loops (i.e. microreservoirs 4033 and 4032 at a precise predetermined ratio of supernatant to reagent. Some supernatant and reagent are very briefly dumped to waste via the flow path to lower pressure exhaust outlet 4010-7 to ensure these microreservoirs are completely filled. In FIG. 110, the supernatant and reagent are pumped to a second micro-mixing chamber 4024. Note that the microchannel flow path comprising the micro-mixing chamber 4024, de-bubbler 4026, and flow cell window 4025 are active and fluidly connected to low pressure exhaust outlet 4010-7. In FIG. 111, complete mixing of the supernatant and reagent is performed in the second micro-mixing chamber 4024, thereby causing a color change in the solution for detection by the absorbance analysis flow cell 4027 via downstream flow cell window 4025. In FIG. 112, the supernatant and reagent mixture incorporating the analyte therein is pumped through the de-bubbler 4026 in the de-bubbling station which removes any residual air bubbles entrained in the mixture. Bubbles in the liquid stream may cause volume anomalies in the downstream flow analysis cell 427 and adversely affect analytical accuracy. De-bubblers are well known devices in the art without further undue elaboration.

Figure 113:
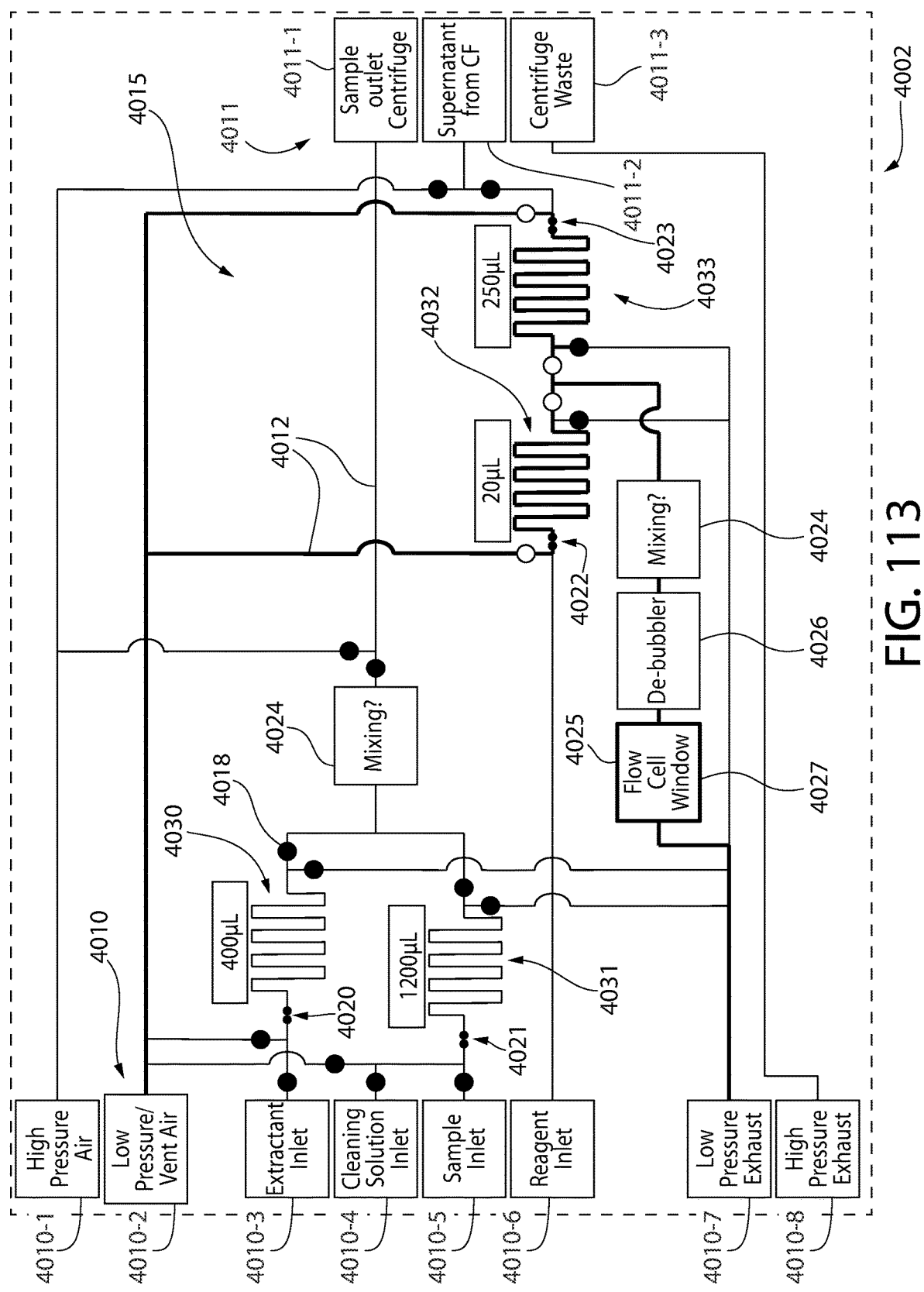
FIG. 113 is a schematic flow diagram thereof in a tenth operating mode configuration.
Figure 114:
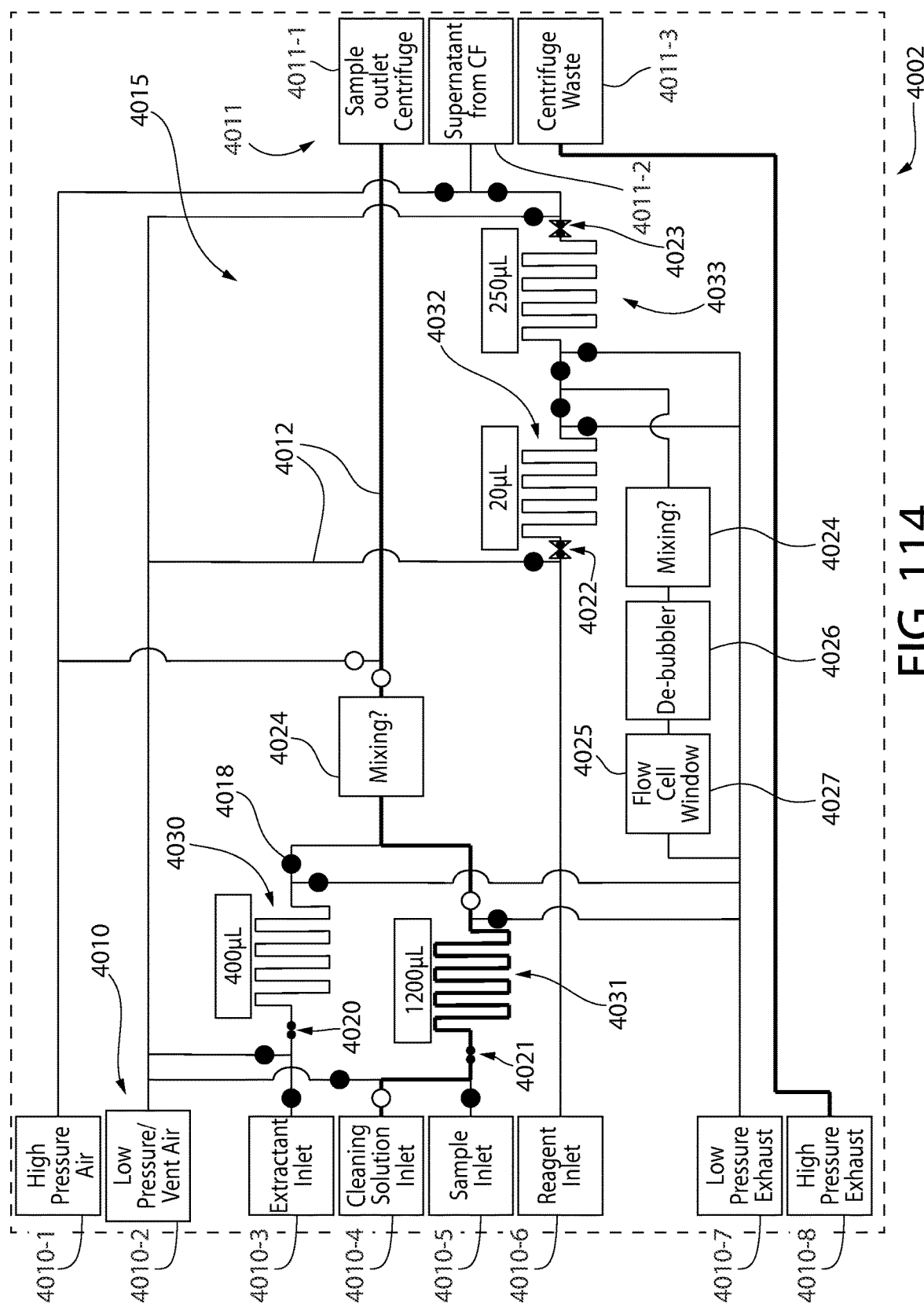
FIG. 114 is a schematic flow diagram thereof in a eleventh operating mode configuration.
Figure 115:
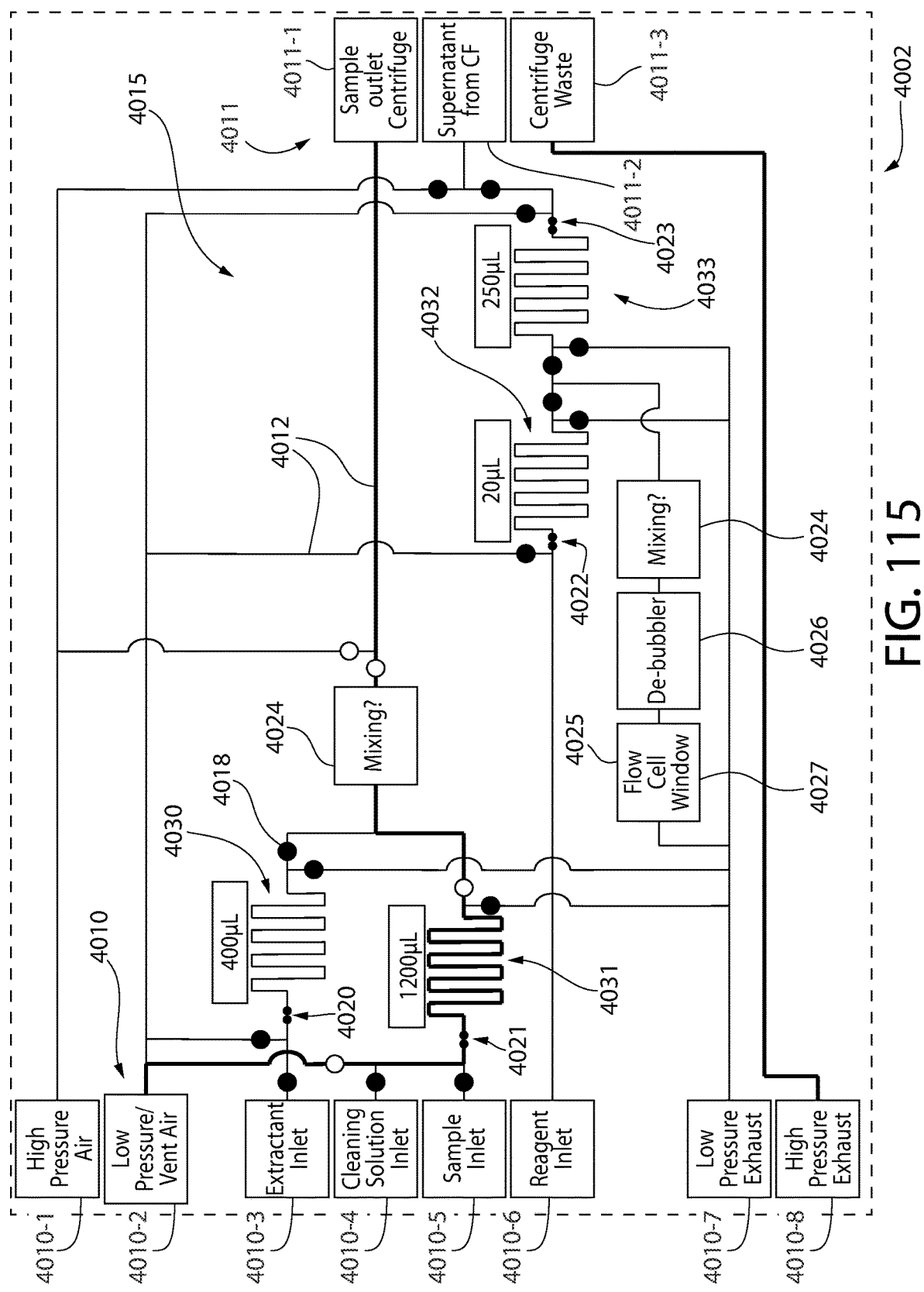
FIG. 115 is a schematic flow diagram thereof in a twelfth operating mode configuration.
Figure 116:
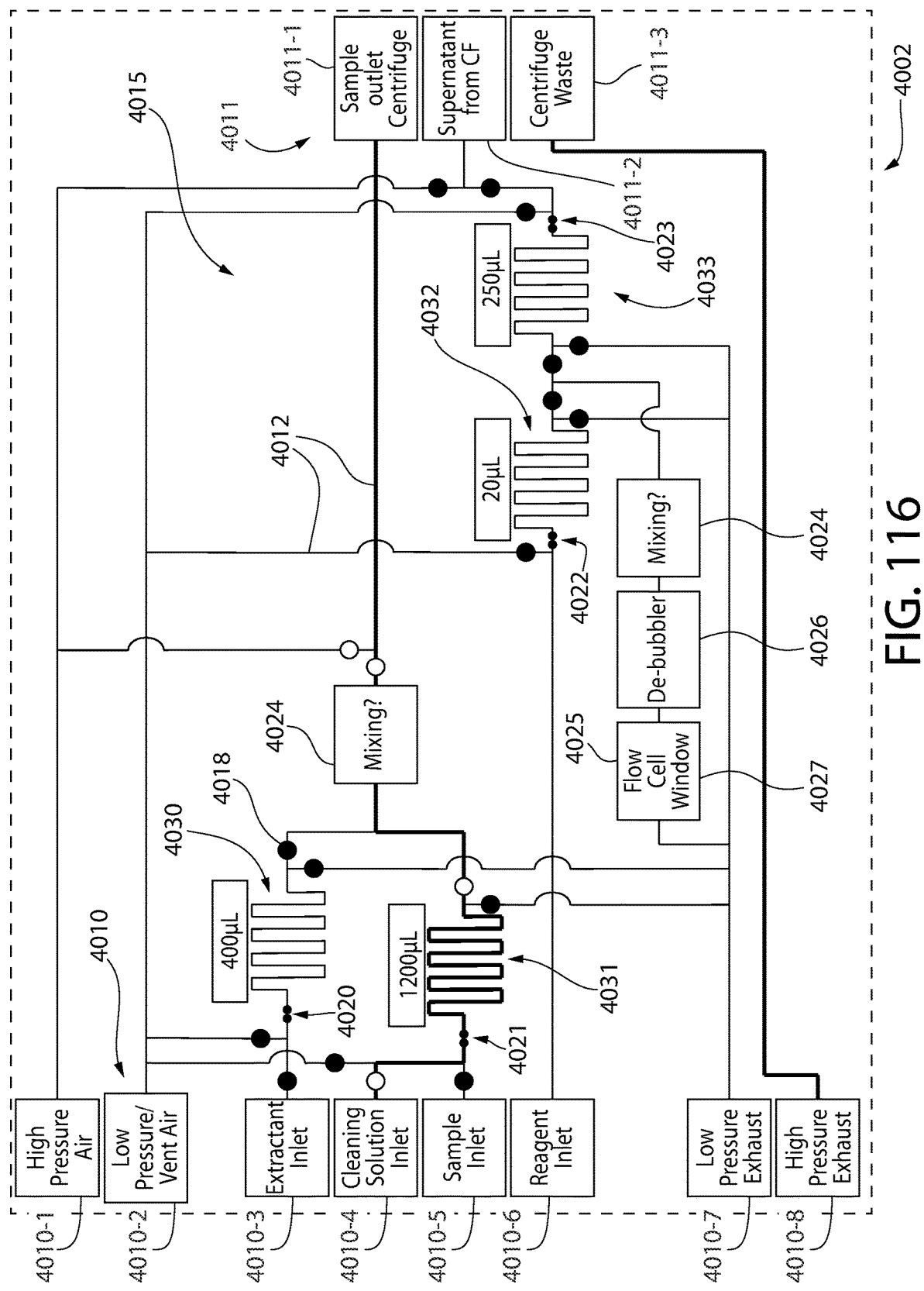
FIG. 116 is a schematic flow diagram thereof in a thirteenth operating mode configuration.
Figure 117:
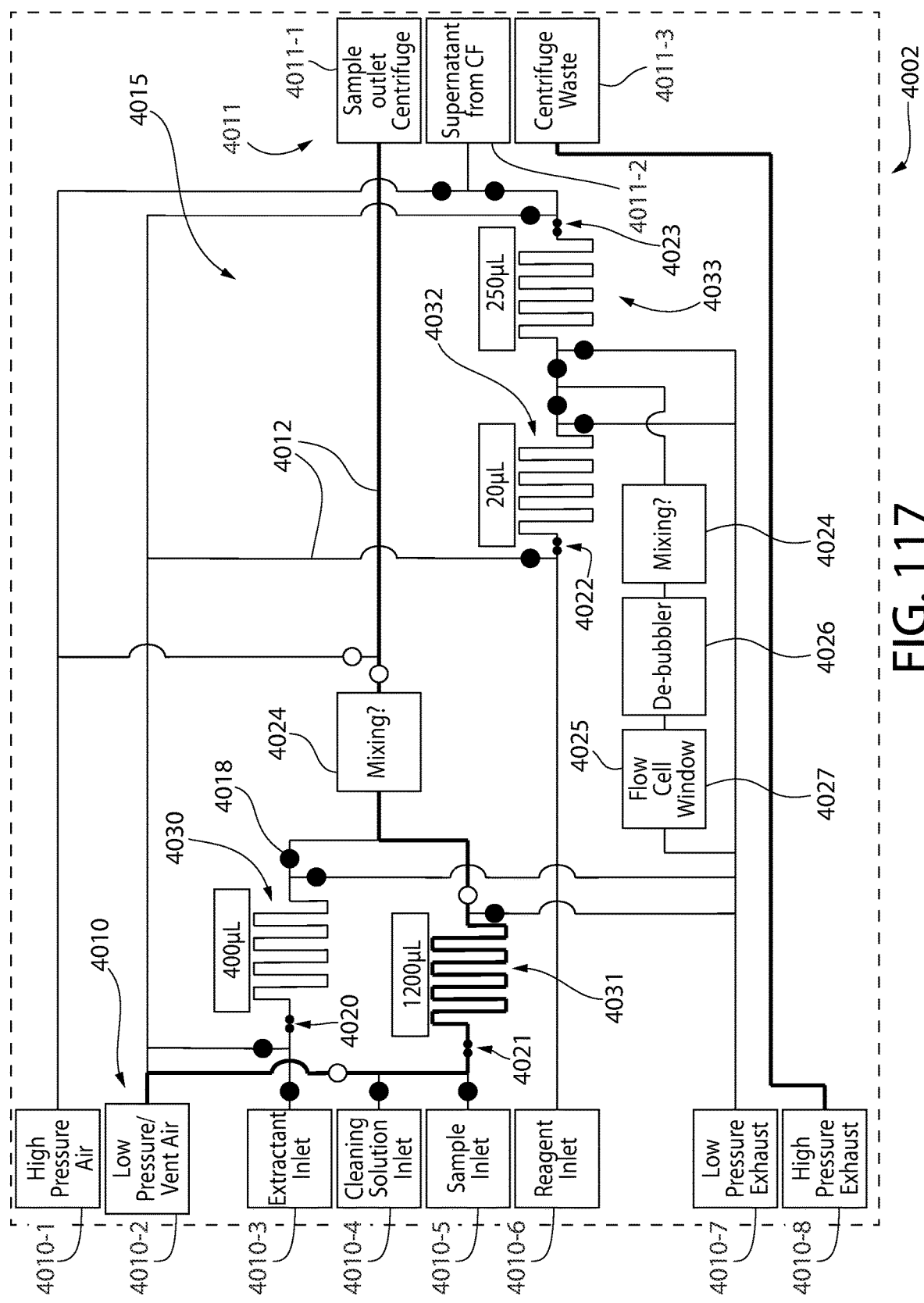
FIG. 117 is a schematic flow diagram thereof in a fourteenth operating mode configuration.
Figure 120:
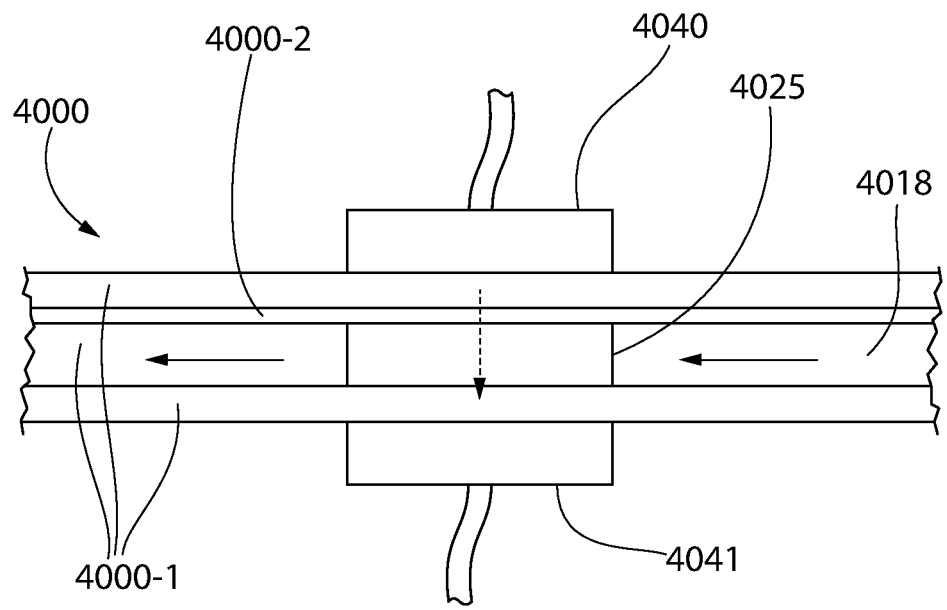
Figure 121:
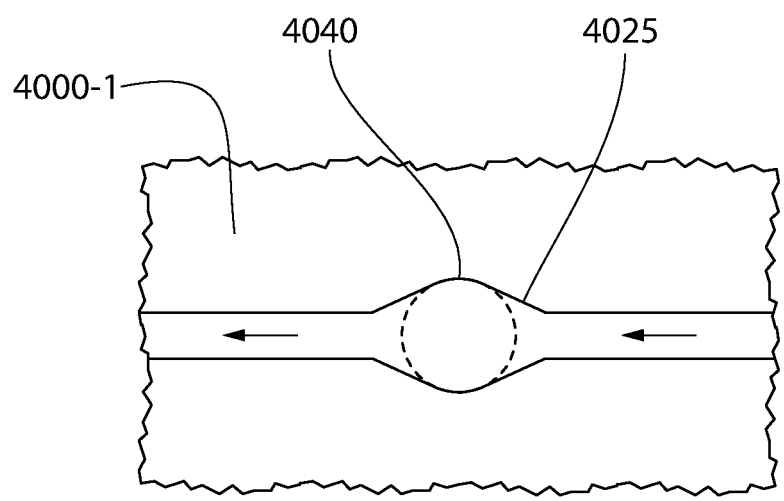
Figure 122:
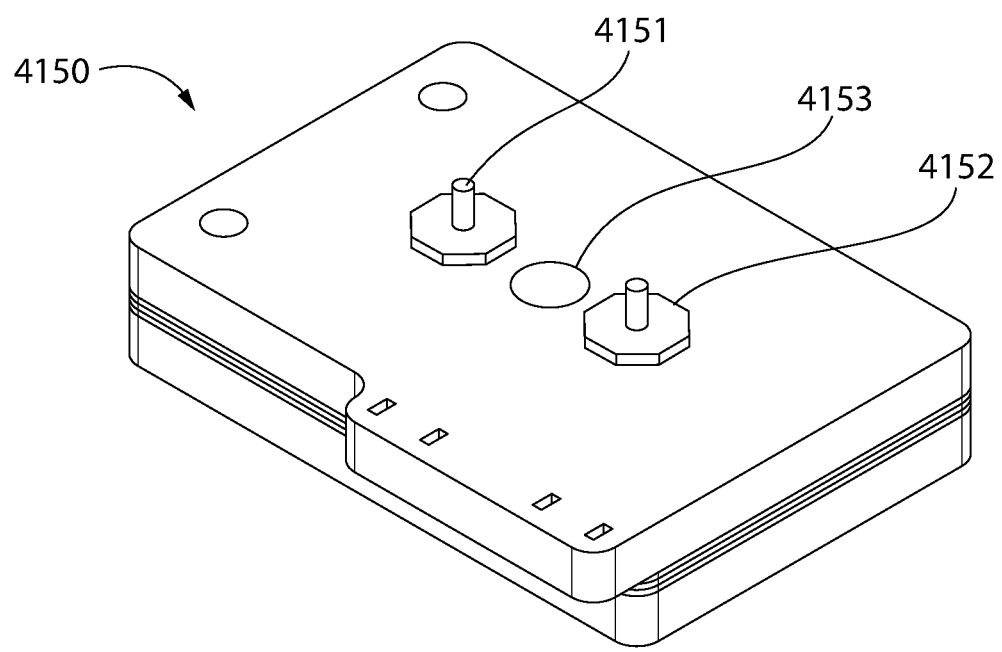
Figure 123:
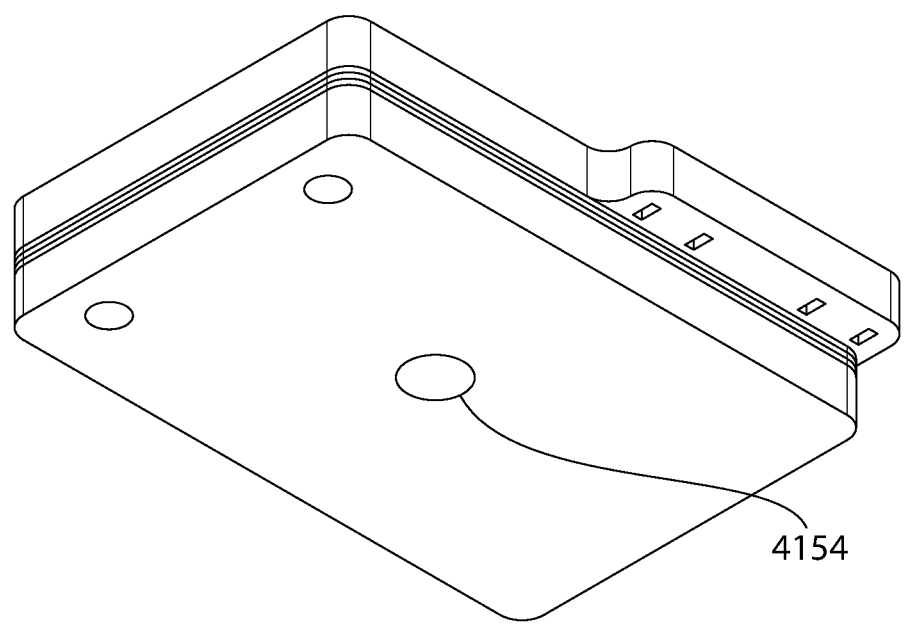

In FIG. 113, the supernatant/reagent mixture incorporating the analyte is pumped into flow cell window 4025 of absorbance flow analysis cell 4027 for colorimetric measurement by the absorbance flow analysis cell 4027 in a similar manner to that previously discussed herein in relation to absorbance flow analysis cell 3800 (see, e.g. FIG. 77). In contrast to flow analysis cell 3800, the present flow analysis cell 4027 is formed integrally with and incorporated directly into a portion of processing wedge 4002. FIGS. 120 and 121 schematically depict the portion of wedge 4002 containing absorbance flow analysis cell 4027 and flow cells window 4025 formed within the bonded layer structure of the processing wedge. In the exemplary non-limiting construction shown, the layers comprises three hard plastic layers 4000-1 (e.g. PC, etc.) forming a top layer, bottom layer, and intermediate patterned with the foregoing microchannels and other fluid control devices such as the micropumps, microvalves, and micro-mixing chambers. The thin flexible elastomeric layer 4000-2 (e.g. silicon, etc.) is formed immediately on top of the intermediate hard layer 4000-1 for functioning as a diaphragm of the fluid control devices. In one embodiment, flow analysis window 4025 may be a laterally widened diamond-shaped chamber (see, e.g. FIG. 121). An LED emitting diode assembly 4040 and LED receiving diode assembly 4041 are mounted above and below the flow analysis window 4025 respectively. LED emitting diode assemblies 4040, 4041 are attached to the outmost top and bottom surfaces of processing wedge 4002 above and below window 4025 as shown, but fluidly isolated from the window and liquid flow stream in the processing wedge 4002. Layer 4000-2 may have a cutout formed directly above flow analysis window 4025 corresponding in size and shape to the LED emitting diode assembly 4040 to avoid possible reflective/refractive interference with the emitted analysis light beam.

In operation, the liquid reagent and supernatant mixture flows through flow analysis window 4025 (see, e.g. solid liquid flow arrows). As the flow passes through the window 4025, the LED emitting diode assembly 4040 transmits and shines light through the window and liquid therein to the LED receiving diode assembly 4041 for colorimetric measurement in a known manner. The measurement of the analyte in the sample mixture liquid stream is transmitted to the system programmable controller for analysis and quantification. During the analysis, it bears noting that the sample mixture flows continuously through the flow cell window 4025 to the low pressure exhaust outlet 41010-7 where it is then dumped to waste.

It bears noting that the micro-mixing chambers 4024 described above may be omitted in some instances if complete mixing can be achieved within the microchannels themselves. The micro-mixing chambers 4024 are therefore optional for use when required.

Figure 118:
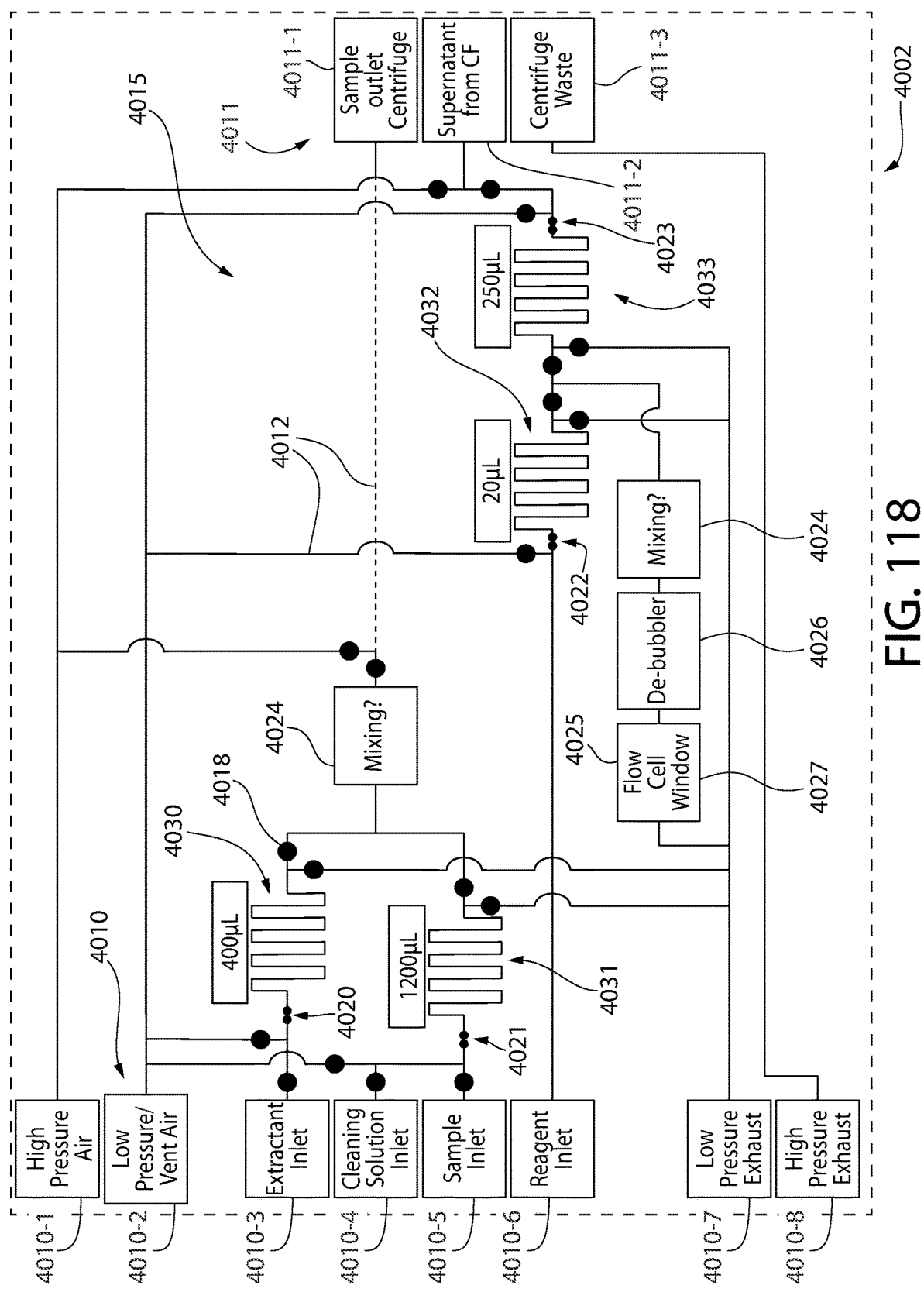
FIG. 118 is a schematic flow diagram thereof in a fifteenth operating mode configuration.
Figure 119:
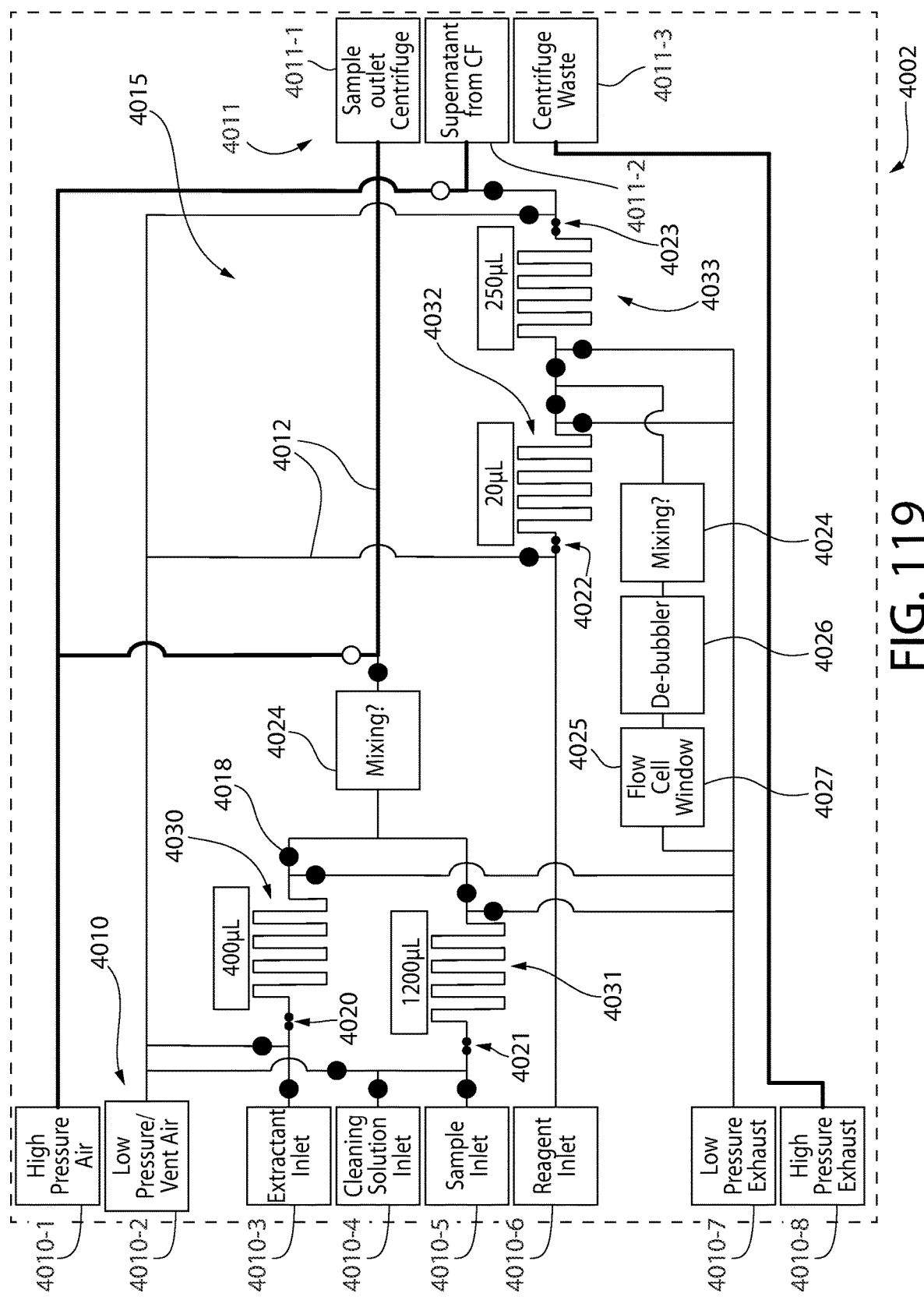

After the soil sample has been fully processed in the above manner, the system programmable controller is configured to initiate a cleaning cycle to prepare the microfluidic processing disk 4000 for processing a new soil sample. In FIGS. 114-117, cleaning solution and low pressure air are each selectively and alternately pumped into and through the emboldened active sample loop microchannels 4012 and through the centrifuge 3400 to the high pressure exhaust outlet 4010-8 as shown. This clears residual soil slurry and chemicals from these components and microchannels. After several cycles of alternating cleaning solution and purge air is processed through the microchannels and centrifuge, FIG. 118 shows that at this point, the sample loop and flow paths upstream of the emboldened segment of the sample loop microchannels has only air in it. There is a column containing a mixture of air and cleaning solution remaining in the emboldened section of flow path. In FIG. 119, the microvalves 4018 shown open to allow high pressure air from high pressure air inlet 4010-1 to force the air/cleaning solution mixture column (emboldened) through the centrifuge 3400. The high pressure air then purges the centrifuge and flows to the high pressure exhaust outlet 4010-8, which completes the cleaning cycle.

In other embodiments, it will be appreciated that separate and discrete absorbance analysis cells such as standalone absorbance flow analysis cell 3800 or other configurations may be used in lieu of the integral absorbance flow analysis cell 4027 incorporated into the chemical processing wedge of microfluidic processing disk 4000. Advantageously, the integral absorbance flow analysis cell 4027 results in a greater compactness of the centrifuge 3400 by eliminating spatial requirements necessary to accommodate discrete flow analysis cells.

Referring to FIGS. 259-260, in some embodiments the microfluidic processing disk 4000 may be heated to better process the soil sample slurry, chemicals, and water by maintaining viscosity and fluidity particularly during cooler weather and in cooler climate zones. A single processing wedge 4002 with its multi-layered construction described herein is shown. Outer ports 4010, inner ports 4011 (previously described herein), and some intermediate ports 4010-1 are shown as examples. Chemicals and soil sample slurry are heated prior to processing and mixing within the slice as described above via electric resistance heating pads 4050 which heat each slice or wedge 4002 to preferably maintain constant temperature in the wedge. Pads 4050 are complementary configured to the wedge as shown. Preferably, a heating pad 4050 is affixed to both the top and bottom surfaces 4051, 4052 of each wedge to maintain even heat distribution between the surfaces. Each heating pad 4050 includes ports 4010, 4010-1, and 4011 which are concentrically aligned with those same ports formed in the body of the processing wedge 4002. The heating pads 4050 are wired to a suitable main electric power source provided for the soil sampling and analysis system process equipment.

Temp sensor(s) 4054 monitor the wedge temperature and communicate via wired or wireless communication links 4055 with the heater control circuitry 4053, which may be local and mounted on one of the heating pads 4050 in one embodiment. In other embodiments, the heater control circuitry may not be onboard and remotely located in the soil sampling and analysis system relative to the microfluidic processing disk 4000. The heater control circuitry 4053 may be communicably linked to the main system programmable controller, such as for example central processing unit (CPU) 2820 via suitable wired or wireless communication links 4055 to exchange real-time temperature data measured by sensors 4054 with the controller.

In addition to heating pads 4050 or instead of, other suitable upstream pre-slice heat exchanger(s) not attached to each processing wedge 4002 could be used in certain other embodiments to preheat the slurry sample, chemicals and/or process water upstream of and before entering the individual processing wedges 4002. As one example, the process purified/filtered water tank 5741 shown schematically in FIGS. 264-266 which supplies process water to the microfluidic processing disk 4000 or other chemical processing systems described herein could optionally be heated by one or more separate electric resistance external and/or immersion elements or heaters 5742 for use during cooler weather.

FIGS. 122-129 depict an alternative embodiment of a standalone absorbance flow analysis cell 4150 usable as a substitute for cell 3800 in FIG. 1. Either cell 4150 or 3800 may be substituted for the integral flow analysis cell 4027 incorporated into processing wedge 4002 shown in FIG. 104. Cell 4150 has a multi-layered composite construction comprising a top outer layer 4155-1, bottom outer layer 4155-5, and three inner layers 4155-2, 4155-3, and 4155-4 arranged in vertically stacked relationship. The layers may be bonded or laminated together in the order shown via any suitable method, including for example via adhesives, heat fusion, ultrasonic welding, etc. Any suitable thermoplastic such as those previously described herein to construct microfluidic processing disk 4000 may be used. In one embodiment, each layer may be formed of clear acrylic.

An inlet tubing connector 4151 and outlet tubing connector 4152 provides fluid communication via flow tubing 3021 to the supernatant and reagent mixture flow tubing in FIG. 1. If used with processing wedge 4002 in lieu of integral flow analysis cell 4027 which would therefore be omitted from the wedge, the inlet tubing connector 4151 may be fluidly connected to a mating tubing connector on the wedge immediately downstream of de-bubbler 4026. The supernatant and reagent mixture fluid would then flow directly from the de-bubbler outlet to flow analysis cell 4150 for colorimetric analysis. In one embodiment, the tubing connectors may be configured as tubing barbs; however, other type tubing flow connectors may be used.

Figure 124:
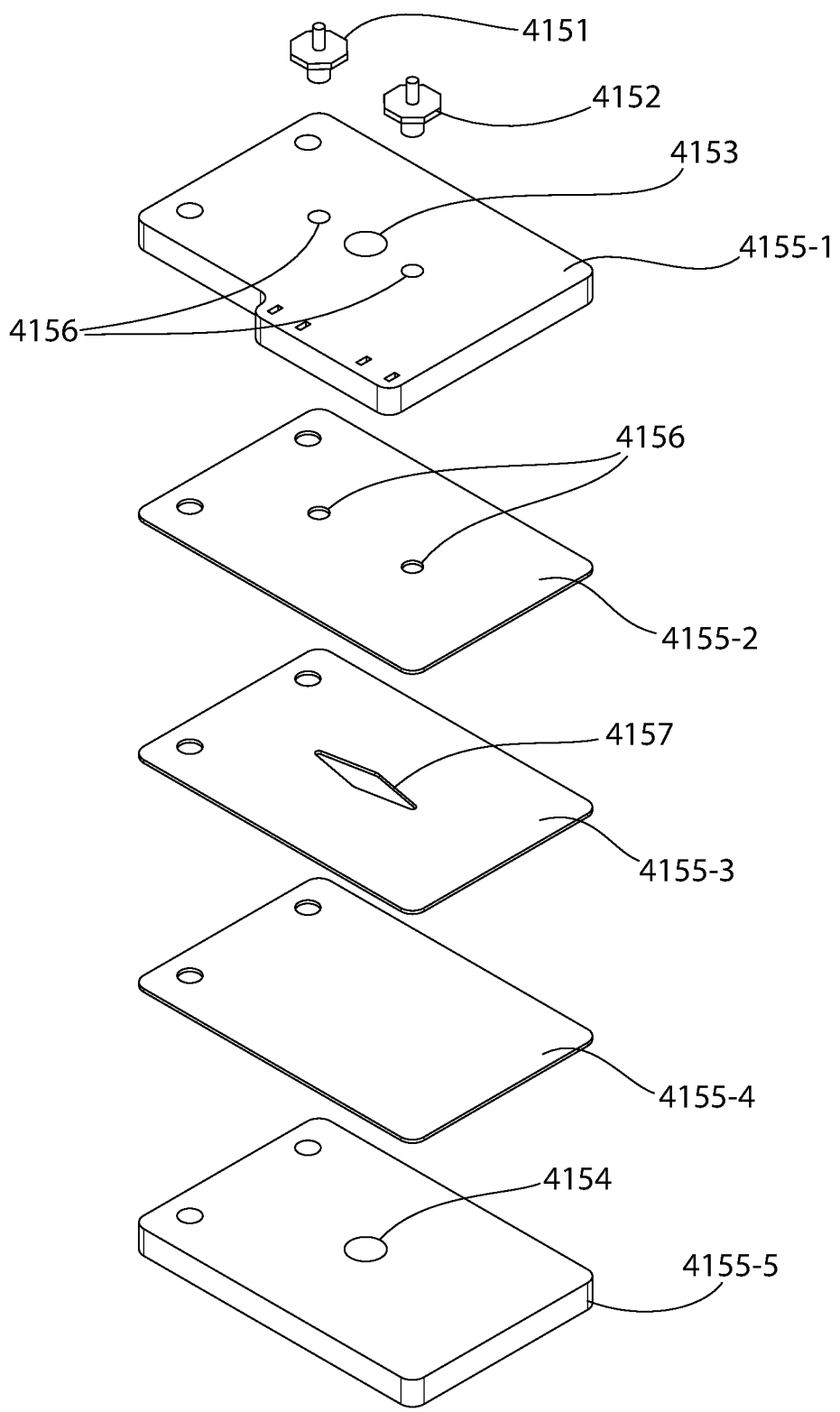
Figure 125:
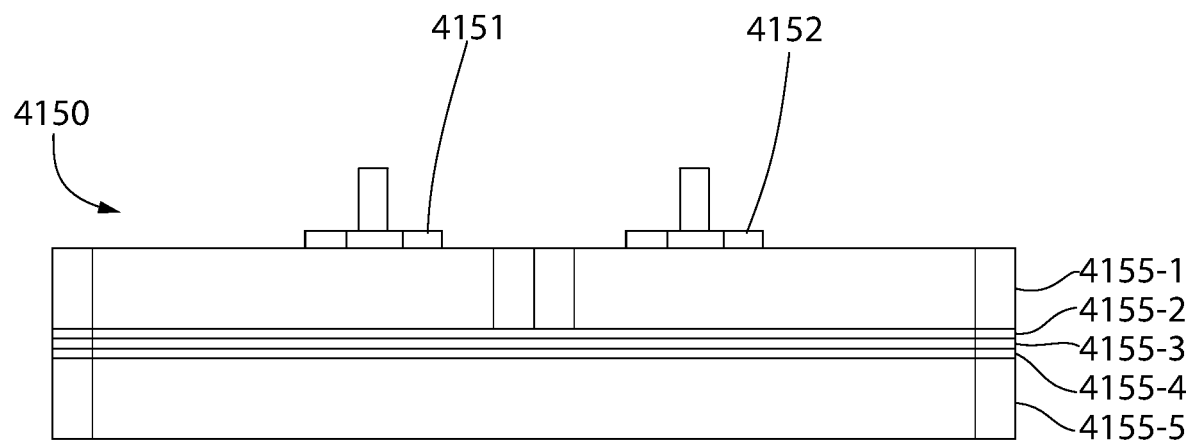
Figure 126:
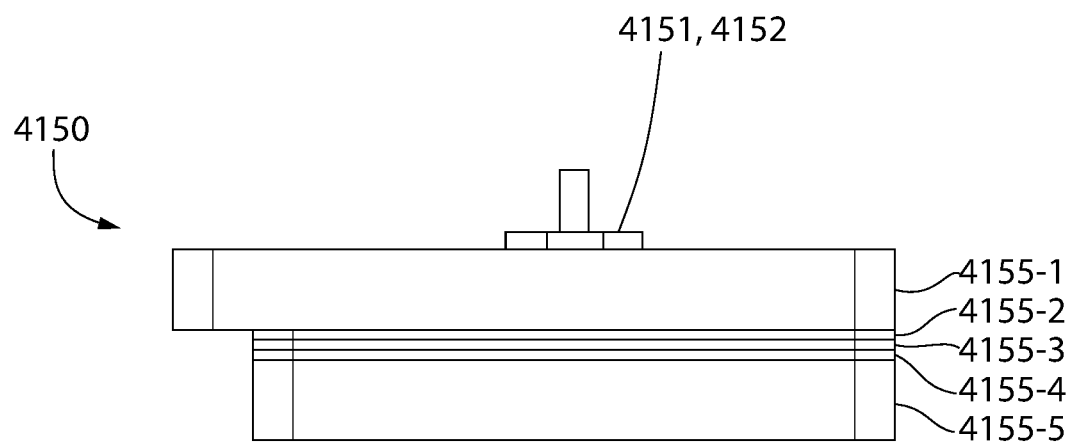
Figure 127:
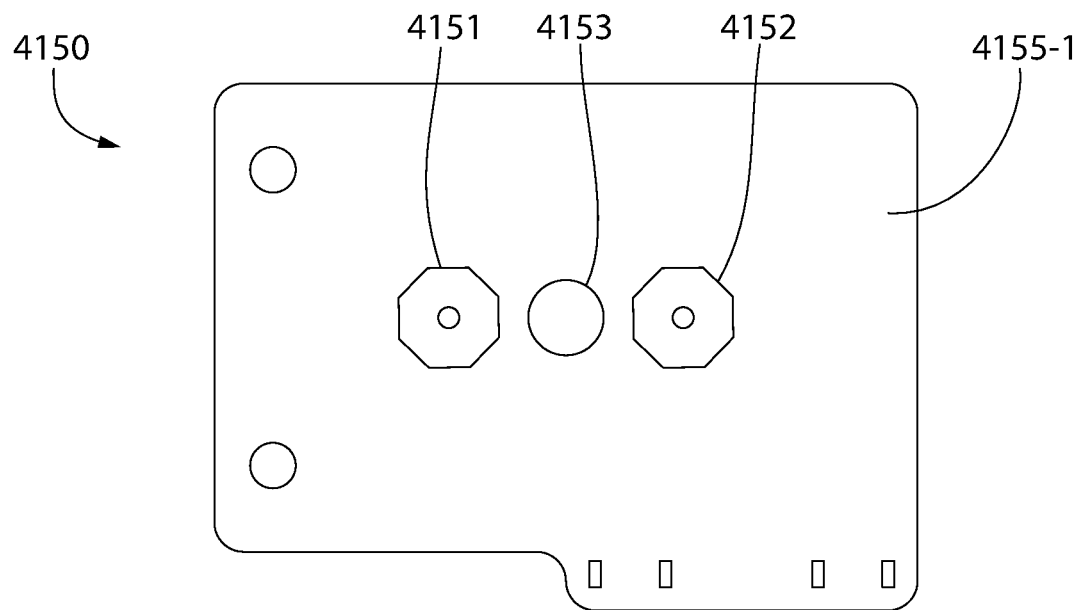
Figure 128:
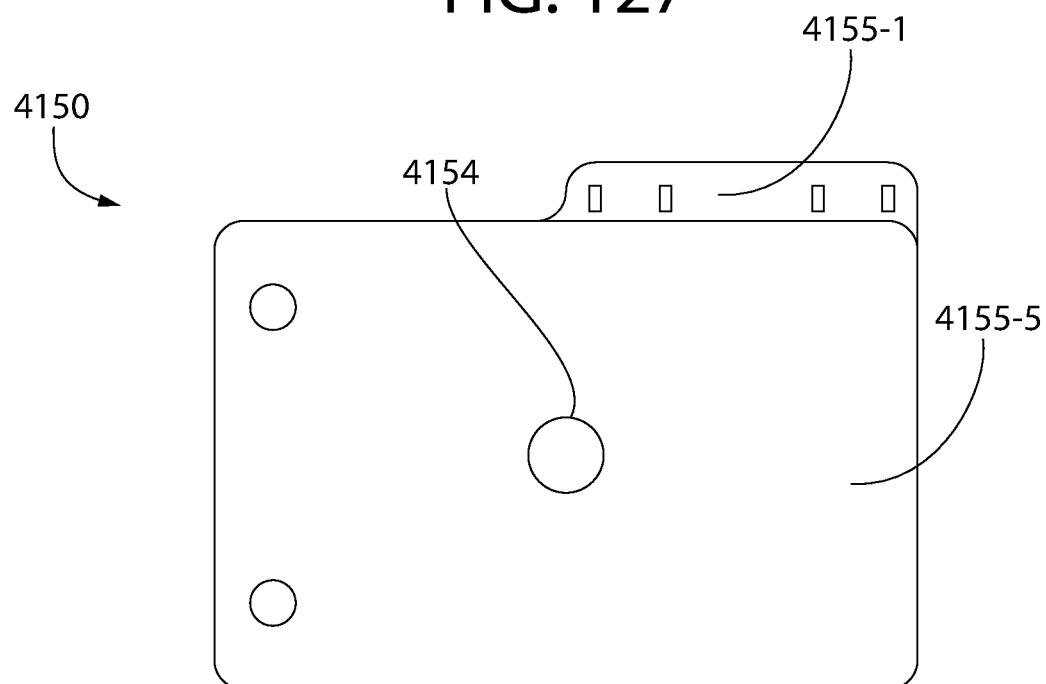

The supernatant and reagent mixture flows through flow ports 4156 formed in top outer layer 4155-1 and uppermost inner layer 4155-2 (see, e.g. FIG. 124). An elongated, slot-shaped flow cell 4157 is formed in the middle inner layer 4155-3. Flow enters the inlet tubing connector 4151 to one end of the flow cell 4157, traverses the window, and leaves the outlet tubing connector 4152.

Figure 129:
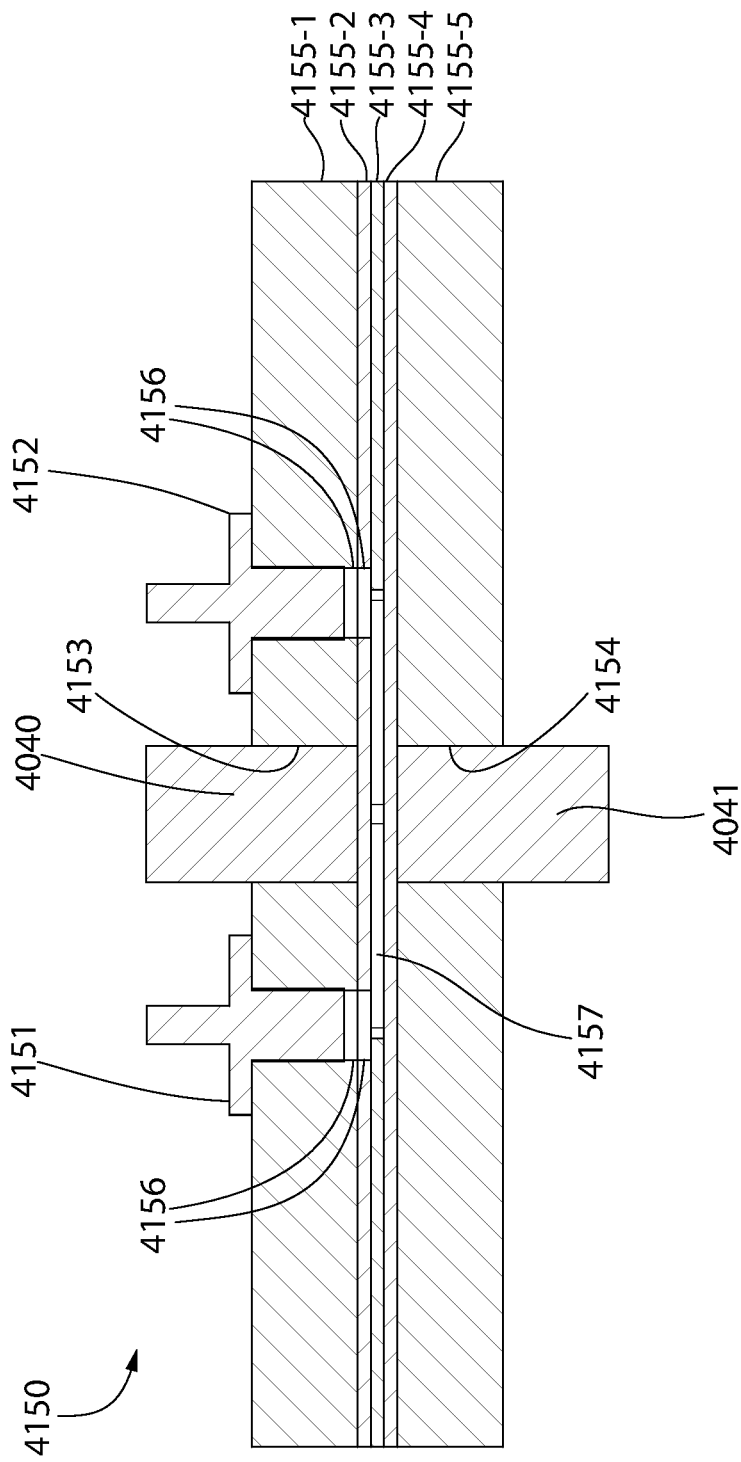
Figure 130:
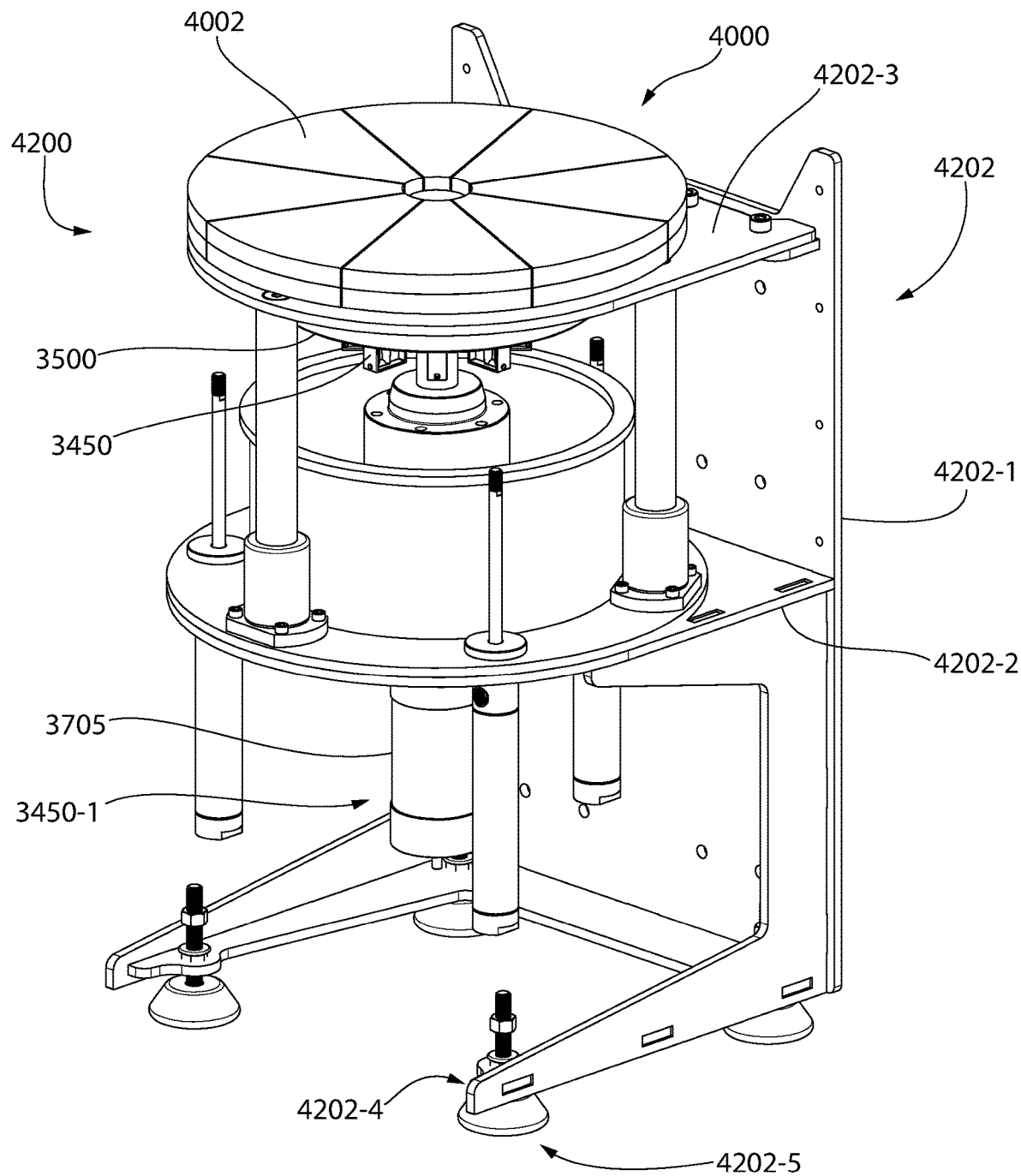

LED emitting diode assembly 4040 and LED receiving diode assembly 4041 from FIG. 120 would be mounted above and below the flow analysis cell 4150 at transmission openings 4153 and 4154 in the outer layers, respectively (see, e.g. FIG. 129). Openings 4153, 4154 are complementary sized to the diode probe bodies and completely penetrate the top and bottom outer layers to efficiently transmit the analysis light through the liquid sample flowing through the flow analysis cell. The LED assemblies 4040, 4041 and openings 4153, 4154 are vertically aligned with the center of flow cell 4157. The flow cell 4157 may be laterally broadened creating a somewhat diamond shape in one embodiment having a width commensurate with the diameter of the LED probes. As flow traverses the flow cell 4157, the analysis light passed transversely through the flow cell window from the LED emitting diode assembly 4040 to receiving LED diode assembly 4041 to perform a colorimetric of the reagent and supernatant mixture to quantify the concentration of the analyte contained therein in a known manner.

It bears noting that the uppermost and lowermost inner layers 4155-2 and 4155-4 present a solid surface to transmission openings 4153, 4154 associated with the diode probes to fluidly isolate the probes from supernatant and reagent mixture in the flow analysis cell 4150.

In order to accommodate the microfluidic processing disk 4000, centrifuge 3400 previously described herein is modified to permit mounting the disk 4000 on top of the motor drive mechanism 3450-1 which is relocated to the bottom of the centrifuge beneath the rotary tube hub 3500 which is coupled to the drive shaft 3700 the drive mechanism. FIGS. 130-136 depict a modified centrifuge 4200 which may include a majority of the primary centrifuge components previously described herein with respect to centrifuge 3400; albeit some being rearranged in location as shown. Note that the shields are omitted from these figures to better show the operating components of centrifuge 4200.

Referring to FIGS. 130-136, centrifuge 4200 generally includes motor drive mechanism 3450-1, plurality of centrifuge tubes 3450 pivotably mounted to rotary tube hub 3500 which is mechanically coupled to the drive shaft 3700 of the drive mechanism, stationary fluid exchange dock 3430, air-operated piston mechanism 3600 for raising and lowering the tube hub, and microfluidic processing disk 4000. Motor drive mechanism 3450-1 may comprise at least the main motor 3705, and in some embodiments may have the same drive assembly previously described which further includes the indexing motor 3704 and the assembly of gears 3707-3709 and timing belt 3713 (see, e.g. FIGS. 43-54, 76, and 95). The drive mechanism 3450-1 is mounted below the rotary tube hub 3500, piston mechanism 3600, fluid exchange dock 3430, and microfluidic processing disk 4000. Main drive shaft 3700 defines the rotational axis RA creating a vertical centerline of centrifuge 4200 for reference purposes.

A slightly modified main support housing 4202 is provided which supports the foregoing components of centrifuge 4200. Housing 4202 may have the same general configuration and members as support housing 3401 previously described. Housing 4202 generally comprise a vertical main support plate 4202-1, an upper support plate 4202-3, a lower support plate 4202-2 oriented parallel to the upper support plate, and optionally base 4202-4 for mounting on a horizontal support surface either fixedly or via a plurality of vertically adjustable legs 4202-5. In some embodiments, particularly when centrifuge 4200 is mounted to a separate support frame such as that provided with a wheeled collection vehicle with an internal combustion engine drive that can be operated to collect soil samples from the field, base 4202-4 may be modified or omitted including the adjustable legs.

Upper and lower support plates 4202-3, 4202-2 of housing 4202 are vertically spaced apart and may be horizontally oriented as shown in the illustrated embodiment, thereby defining a partially or totally enclosed sample processing chamber 3501. Each support plate 4202-3, 4202-2 may have one peripheral side or end attached to vertical support plate 4202-1 in a cantilevered manner via a suitable mechanical connection method, such as without limitation welding, soldering, threaded fasteners, adhesives, clips, interlocking features (e.g. tabs/slots), or other and combinations thereof. In one embodiment, support plates 4202-3, 4202-2 may be oriented perpendicularly to the main support plate 3402 as shown.

Upper support plate 4202-3 of support housing 4202 includes a relatively large circular central opening 4202-6 for mounting and receiving a lower diametrically narrower portion of fluid exchange dock 3430 therein and therethrough which is supported by the upper support plate (see, e.g. FIGS. 135-136). Microfluidic processing disk 4000 is mounted directly on top of fluid exchange dock 3430 as previously described herein. The rotary tube hub 3500 assembly (including covers 3520, 3521) is mounted below upper support plate 4202-3. This allows the rotary tube hub 3500 to be axially raised and lowered by the piston mechanism 3600 in the sample processing chamber 3501 of centrifuge 4200 between its upper docked and lower undocked positions for exchanging fluids with the centrifuge tubes 3450 (e.g. slurry-extractant, supernatant, or tube flushing water-air stream) in the upper position, or alternatively centrifugating the soil samples in the tubes in the lower position.

Fluid exchange dock 3430 may include a plurality of circumferentially spaced apart tube travel stops 4203 projecting downwards from the bottom surface of the dock. Travel stops 4203 are selectably insertable into the plurality of rectangular tube openings 3523 formed in upper and lower covers 3520, 3521 of the rotary tube hub assembly when the rotary tube hub 3500 is lowered and raised via operation of the piston mechanism 3600. With additional reference to FIG. 66, travel stops 4203 are received in the outer vacant portions of tube openings 3523 as best shown in FIG. 136 when the centrifuge tubes 3450 are in a vertical position when the rotary tube hub 3500 is in the upper docked position engaged with fluid exchange dock 3430. This advantageously maintains and snuggly holds the centrifuge tubes in the vertical upright position when fluids are exchanged between the fluid exchange dock and tubes from or to the microfluidic processing disk 4000, which ensures a tight leak-resistance seal between dock and tubes to prevent leakage.

The operation of centrifuge 4200 is substantially the same as previously described herein for centrifuge 3400, and will not be repeated in its entirety for sake of brevity. In sum, rotary tube hub 3500 is axially raised and lowered by the piston mechanism 3600 in the sample processing chamber 3501 of centrifuge 4200 between its upper docked and lower undocked positions for exchanging fluids with the centrifuge tubes 3450 (see, e.g. FIGS. 72-75). The centrifuge 4200 is rotated by motor drive mechanism 3450-1 in the same manner when rotary tube hub 3500 is in the lower undocked position to centrifugate the soil samples. The drive shaft 3700 and motor drive mechanism 3450-1 is suspended from and raised and lowered with the rotary tube hub 3500 by the piston mechanism.

As already noted herein, the agricultural sampling system, sub-systems, and related processes/methods disclosed herein may be used for processing and testing soil, vegetation/plants, manure, feed, milk, or other agricultural related parameters of interest. Particularly, embodiments of the chemical analysis portion of the system (chemical analysis sub-system 3003) disclosed herein can be used to test for multitude of chemical-related parameters and analytes (e.g. nutrients/chemicals of interest) in other areas beyond soil and plant/vegetation sampling. Some non-limiting examples (including soil and plants) are as follows.

Soil Analysis: Nitrate, Nitrite, Total Nitrogen, Ammonium, Phosphate, Orthophosphate, Polyphosphate, Total Phosphate, Potassium, Magnesium, Calcium, Sodium, Cation Exchange Capacity, pH, Percent Base Saturation of Cations, Sulfur, Zinc, Manganese, Iron, Copper, Boron, Soluble Salts, Organic Matter, Excess Lime, Active Carbon, Aluminum, Amino Sugar Nitrate, Ammoniacal Nitrogen, Chloride, C:N Ratio, Electrical Conductivity, Molybdenum, Texture (Sand, Silt, Clay), Cyst nematode egg counts, Mineralizable Nitrogen, and Soil pore space.

Plants/Vegetation: Nitrogen, Nitrate, Phosphorus, Potassium, Magnesium, Calcium, Sodium, Percent Base Saturation of Cations, Sulfur, Zinc, Manganese, Iron, Copper, Boron, Ammoniacal Nitrogen, Carbon, Chloride, Cobalt, Molybdenum, Selenium, Total Nitrogen, and Live plant parasitic nematode.

Manure: Moisture/Total Solids, Total Nitrogen, Organic Nitrogen, Phosphate, Potash, Sulfur, Calcium, Magnesium, Sodium, Iron, Manganese, Copper, Zinc, pH, Total Carbon, Soluble Salts, C/N Ratio, Ammoniacal Nitrogen, Nitrate Nitrogen, Chloride, Organic Matter, Ash, Conductance, Kjeldahl Nitrogen, *E. coli*, Fecal Coliform, *Salmonella*, Total Kjeldahl Nitrogen, Total Phosphate, Potash, Nitrate Nitrogen, Water Soluble Nitrogen, Water Insoluble Nitrogen, Ammoniacal Nitrogen, Humic Acid, pH, Total Organic Carbon, Bulk Density (packed), Moisture, Sulfur, Calcium, Boron, Cobalt, Copper, Iron, Manganese, Arsenic, Chloride, Lead, Selenium, Cadmium, Chromium, Mercury, Nickel, Sodium, Molybdenum, and Zinc Feeds: Alanine, Histidine, Proline, Arginine, Isoleucine, Serine, Aspartic Acid, Leucine, Threonine, Cystine, Lysine, Tryptophan, Glutamic Acid, Methionine, Tyrosine, Glycine, Phenylalanine, Valine (Requires Crude Protein), Arsenic, Lead, Cadmium, Antimony, Mercury Vitamin E (beta-tocopherol), Vitamin E (alpha-tocopherol), Vitamin E (delta-tocopherol), Vitamin E (gamma-tocopherol), Vitamin E (total), Moisture, Crude Protein, Calcium, Phosphorus, ADF, Ash, TDN, Energy (Digestible and Metabolizable), Net Energy (Gain, Lactation, Maintenance), Sulfur, Calcium, Magnesium, Sodium, Manganese, Zinc, Potassium, Phosphorus, Iron, Copper (not applicable to premixes), Saturated Fat, Monounsaturated Fat, Omega 3 Fatty Acids, Polyunsaturated Fat, Trans Fatty Acid, Omega 6 Fatty Acids (Requires Crude or Acid Fat), Glucose, Fructose, Sucrose, Maltose, Lactose, Aflatoxin (B1, B2, G1, G2), DON, Fumonisin, Ochratoxin, T2-Toxin, Zearalenone, Vitamin B2, B3, B5, B6, B7, B9, and B12, Calories, Chloride, Crude fiber, Lignin, Neutral Detergent Fiber, Non Protein Nitrogen, Selenium U.S. Patent, Total Iodine, Total Starch, Vitamin A, Vitamin D3, and Free Fatty Acids.

Forages: Moisture, Crude Protein, Acid Detergent Fiber ADF, NDF, TDN, Net Energy (Gain, Lactation, Maintenance), Relative Feed Value, Nitrate, Sulfur, Copper, Sodium, Magnesium, Potassium, Zinc, Iron, Calcium, Manganese, Sodium, Phosphorus, Chloride, Fiber, Lignin, Molybdenum, Prussic Acid, and Selenium USP.

Milk: Butterfat, True Protein, Somatic Cell Count, Lactose, Other Solids, Total Solids, Added Water, Milk Urea Nitrogen, Acidity, pH, Antibiotic tests, and Micro-organisms.

Sample Collection Probes

Piston-Operated Sample Collection Probe

FIGS. 137-152 depict an embodiment of a ground-engaging coulter assembly 5000 with a sample collection apparatus or probe mounted thereto comprising a piston-operated soil sample collection probe. Coulter assembly 5000 includes an onboard cam-operated sample collection probe in the form of a piston mechanism 5020 configured and operable for collecting soil core samples (surface and subterranean) at selected depths as the coulter or blade 5001 rolls and cuts through the ground, and then ejecting the cores to a collection receptacle. Coulter assembly 5000 may be mounted to the frame of towed agricultural implement pulled by an engine-powered wheeled/tracked sample collection vehicle which traverses an agricultural field (e.g. tractor, etc.) to collect soil samples.

Coulter assembly 5000 generally comprises a disk-shaped sample collection coulter or blade 5001 configured to engage and cut/penetrate through the soil 5002 to a depth DP1 below its surface 5003, a blade hub 5004 for mounting the blade thereto, an outer hub collar 5007 fixedly attached to the hub and rotatable therewith, and an annular bearing 5008. A camming mechanism is provided including an annular cam ring 5006 and a follower 5021 defined by the piston mechanism 5020, as further described herein. The coulter assembly is assembled in the manner shown in the figures and further described below.

Blade 5001 is preferably formed of a suitable flat metal plate of circular shape, and may have a sharpened annular peripheral edge to penetrate the soil more easily. Any suitable diameter blade may be used depending in part on the depth at which soil samples are to be collected.

Hub 5004 may be a flanged tube including a radial flanged portion 5004-3 and a tubular portion 5004-2 projecting from the flanged portion. Tubular portion 5004-3 is insertable through a central opening 5005 in the blade 5001 as shown for mounting the blade thereto. The flanged portion 5004-3 engages a first side surface 5001-2 of the blade when the blade is mounted to the hub. The tubular portion 5004-2 projects outwards from the opposite second side surface 5001-1 of the blade 5001 and is coaxially aligned with a rotational axis RA1 of the blade defined by the central opening 5005 of the blade perpendicular to the side surfaces 5001-1, 5001-2. The flange portion 5004-3 of hub 5004 may be fixedly attached to the blade 5001 via a plurality of threaded fasteners 5001-3 (see, e.g. FIG. 139) in one embodiment insertable through mating pairs of the mounting holes 5001-4. This locks the blade 5001 to the hub 5004. Hub 5004 defines an outwardly open bore 5004-1 which receives an end of an axle 5009 therein as shown in FIGS. 143 and 144. Hub 5004 may be secured to axle 5009 via any suitable mechanical means, including set screws, shrink fitting, or other as some non-limiting examples. One end of bore 5004-1 may be closed as shown to limit the insertion depth of axle 5009 in the hub.

Hub collar 5007 may similarly be a flanged tube including a radial flanged portion 5007-1 and tubular portion 5007-2 projecting axially therefrom. The tubular portion 5004-2 of hub 5004 is insertable through the tubular portion 5007-2 of collar 5007 as shown. Collar 5007 may be fixed to the hub 5004 by any suitable manner such as via set screws inserted through tubular portion 5007-2 of the collar into tubular portion 5004-2 of the hub. This ensures that the collar rotates in unison with the hub.

The annular bearing 5008 may be a spherical roller bearing, deep groove ball bearing, or set of tapered roller bearings in one non-limiting embodiment comprising an inner race or ring 5008-1 and outer race or ring 5008-2 each rotatable relative to each other in conventional operation. Inner ring 5008-1 is fixedly coupled (e.g. screwed/bolted) to flanged portion 5007-1 of collar 5007 (not fastener holes) and rotates with the collar and blade hub 5004. The tubular portion 5007-2 of the collar is inserted through central opening 5008-3 of bearing 5008. The inner ring 5008-1 represents the rotating part of the bearing. The outer ring 5008-2 is fixed coupled to cam ring 5006 and represents the stationary part of the bearing. The inner and outer rings 5008-1, 5008-2 are mutually and slideably engaged in a typical manner via an annular bearing surface interface therebetween.

Cam ring 5006 is configured for fixed attachment to the frame of the wheeled collection vehicle such as via mounting bracket 5010. Cam ring 5006 and bearing outer ring 5008-1 therefore remain stationary and fixed in position relative to the frame, inner ring 5008-2, and the blade-hub-collar assembly as the blade 5001 is pulled through the soil. Bracket 5010 may have any suitable configuration including a T-shape as shown. The bracket 5010 may be bolted to the cam ring 5006 and the frame of the collection vehicle in one embodiment (note fastener holes).

Cam ring 5006 has a generally planar annular body comprising a central opening 5006-4, first major surface 5006-1, opposing second major surface 5006-2 parallel to the first major surface, and a peripheral sides 5006-3 extending between the surfaces. First major surface 5006-1 may be plain in one embodiment. The second major surface 5006-2 faces the blade 5001 when assembled and defines a circumferentially-extending annular cam track 5006-5 recessed into the surface. Cam track 5006-5 extends a full continuous 360 degrees around the central opening 5006-4 of the cam ring and is spaced between the central opening and peripheral sides 5006-3.

Referring particularly to FIGS. 145-146, the cam track 5006-5 generally defines pear-shaped cam lobe profile of asymmetrical configuration including a base curve portion 5006-6 (extent represented by dashed line) uniformly spaced radially apart from the central opening 5006-4 by a first radial distance D1, and a nose or lobe portion 5006-7 (extent represented by dashed line) defining an arcuately curved apex 5006-8. The part of lobe portion 5006-7 containing the apex is spaced radially outwards from the base curve portion and farther from the central opening by a second radial distance D2 larger than distance D1. D2 may represent a maximum distance and D1 may represent a minimum distance. In one embodiment, a transition portion 5006-9 of cam track 5006-5 may be provided between the base curve and lobe portions 5006-6, 5006-7 in which the radial distance varies between the first and second distances D1, D2. The lobe portion 5006-7 may be located in one quadrant of the cam ring 5006 while the base curve and transition portions may occupy the majority of the remaining three quadrants as shown.

Cam ring 5006 may have a monolithic unitary construction in one embodiment with cam track 5006-5 recessed into one side of the ring as previously described herein. In other embodiments, the cam ring 5006 may be an assembly of discrete annular outer and inner ring members affixed in a rigid manner to a common annular backing plate (see, e.g. cam ring 5506, FIGS. 208-210). The ring members are spaced radially apart to define the cam track 5006-5. Reference is made to description of cam ring 5506 herein for further details of a cam ring assembly.

The cam track 5006-5 actuates the piston mechanism 5020 in the collection and ejection of soil sample cores captured by the blade 5001. Piston mechanism 5020 includes an elongated soil sample collection sleeve or cylinder 5022 with open internal through passage extending between its ends and an elongated piston rod 5023 which slideably moves in a linear and radially reciprocating manner back and forth inside the cylinder when actuated by the cam track in cam ring 5006. Collection cylinder 5022 is fixedly mounted to blade 5001 in an elongated radial slot 5024 formed in the blade. Cylinder 5022 may be welded to the blade in one construction. Thus the piston mechanism 5020 rotates with the blade 5001 for capturing soil sample cores. Slot 5024 may be a through slot in one embodiment penetrating both major surfaces 5001-1, 5001-2 of the blade. The slot 5024 defines a radial actuation axis AA along which piston rod 5023 reciprocates within the cylinder 5022. Axis AA intersects the center of the blade central opening 5005 and is perpendicular to rotational axis RA1. The collection cylinder 5022 may protrude above the major surfaces 5001-1, 5001-2 of blade 5001 to facilitate capturing a soil plug or core (see, e.g. FIG. 143).

Cam follower 5021 is fixedly disposed on the inside end 5023-1 of piston rod 5023 and operably engages the cam track 5006-5. Follower 5021 may be T-shaped in one embodiment having opposite ends that similarly protrude above the major surfaces 5001-1, 5001-2 of blade 5001; one of the ends being inserted the cam track (see, e.g. FIG. 148). The cam follower 5021 may be cylindrical and oriented perpendicularly to piston rod 5023. A tubular bushing 5025 may be rotatably disposed on the cam follower to interface with the cam track 5006-5. Bushing 5025 thus provides smooth rolling/sliding engagement with the cam track 5006-5 as the follower moves around and through the track as the blade 5001 rotates, thereby causing the piston rod 5023 to reciprocate linearly back and forth in position based on the shape of the cam track (noting cam ring 5006 remaining stationary as previously described herein). The follower and cam track transform rotary motion of the blade 5001 into linear motion of the piston rod 5023 for capturing and ejecting the soil core from the collection cylinder 5022.

The outside end 5023-2 of piston rod 5023 may be diametrically enlarged relative to adjoining portions of the rod. During operation of the rod 5023 as the blade 5001 rotates, the outside end 5023-2 selectively opens or closes the outside soil collection end 5022-2 of the collection cylinder 5022 and a pair of transverse holes 5022-1 therein. The cylinder outside end is spaced inward from the outer end 5024-2 of radial slot 5024 to form an open gap or recess 5024-3 in blade 5001 to allow soil to enter or be ejected from the outside end 5023-2 of cylinder 5022. The inside end 5024-1 of the slot may intersect the central opening 5005 of blade 5001 in one embodiment. A tubular rod retaining end cap 5026 may be mounted to the inside end 5022-3 of cylinder 5022 to retain the rod 5023 therein. End cap 5026 has a through bore than the enlarged outside end 5023-2 of the piston rod 50223 for that purpose. The remaining portions of the rod are thus diametrically smaller than the through bore to allow the rod to slide back and forth through the end cap 5026.

Operation of the coulter assembly 5000 for capturing and ejecting a soil sample will now be described with reference to FIGS. 149-152. FIG. 149A shows the sample collection piston mechanism 5020 in a first operating position. The collection cylinder 5022 of the piston mechanism is located above the surface 5003 of the ground or soil 5002 at this point as the blade 5001 rotates through the soil (see rotational direction arrows in these figures). The cam follower 5021 is shown just leaving the transition portion 5006-9 of cam track 5006-5 in the cam ring 5006. As shown in FIG. 149B, the piston rod 5023 is in a flush position via operation of the follower 5021 such that the outside end 5023-2 of piston rod is flush with outside end 5022-2 of the cylinder 5022. This closes the otherwise end 5022-2 of cylinder 5020 to prevent soil from entering the cylinder.

FIG. 150A shows the blade 5001 rotated further with the sample collection piston mechanism 5020 in a second operating position. In this position, the collection cylinder 5022 is below the surface 5003 of the soil. The cam follower 5021 is shown now in the base curve portion 5006-6 of cam track 5006-5. Because the base curve portion 5006-6 is closer to central opening 5005 of blade 5001, this pulls the piston rod 5023 radially inwards within the cylinder 5022. As shown in FIG. 150B, the piston rod 5023 is now in a retracted position via operation of the follower 5021 such that the outside end 5023-2 of piston rod is no longer flush with and instead recessed within the outside end 5022-2 of the cylinder 5022 (note rear transverse hole 5022-1 is now visible due to absence of the piston rod end). A void is therefore created in the terminal outside end 5022-2 of cylinder 5022 which defines a collection port so that soil will enter the cylinder to fill the void, thereby capturing a soil plug or core as the piston mechanism is driven into the ground (see soil directional arrow). The timing of when exactly this happens (i.e. piston rod 5023 retracts to open the end 5022-2 of cylinder 5022) can be adjusted by changing the shape and length of the various portion of cam track 5006-5 in order to change the soil sample collection depth. Collection depth could also be varied by providing multiple piston mechanisms circumferentially spaced around the blade 5001 with cylinders of different radial lengths. This would change where the collection end of the cylinders each fall relative to a radial distance from the central opening of the blade 5001. In some embodiments, a plurality of sample collection piston mechanisms 5020 with cylinders 5022 of different lengths may be provided.

FIG. 151A shows the blade 5001 rotated further with the sample collection piston mechanism 5020 in a third operating position. In this position, the collection cylinder 5022 is again above the surface 5003 of the soil. The cam follower 5021 however remains within the base curve portion 5006-6 of cam track 5006-5. As shown in FIG. 151B, the piston rod 5023 remains in the retracted position with the soil core remaining stuck in the outside end 5022-2 of the cylinder 5022 (note rear transverse hole 5022-1 is now visible due to absence of the piston rod end). A void is created in the end 5022-2 of cylinder 5022 so that soil will enter the cylinder to fill the void and is captured as the piston mechanism is driven into the ground (see soil directional arrow). The timing of when exactly this happens (i.e. piston rod 5023 retracts to open the end 5022-2 of cylinder 5022) can be adjusted by changing the shape and length of the various portion of cam track 5006-5 in order to change the soil sample collection depth.

FIG. 152A shows the blade 5001 rotated further with the sample collection piston mechanism 5020 in a fourth operating position. In this position, the collection cylinder 5022 is still below the surface 5003 of the soil. The cam follower 5021 is shown now in the lobe portion 5006-7 of cam track 5006-5. Because the lobe portion 5006-7 is farthest from central opening 5005 of blade 5001, this pushes the piston rod 5023 radially outwards within the cylinder 5022. As shown in FIG. 152B, the piston rod 5023 is now in a projected position via operation of the follower 5021 such that the outside end 5023-2 of piston rod is extends beyond the outside end 5022-2 of the cylinder 5022, thereby effectively ejecting the captured soil plug or core (see soil directional arrow) which in turn is collected by a collection receptacle for further processing and analysis using other portions of the mixing and chemical analysis systems described herein.

Rotatable Shaft Sample Collection Probe

FIGS. 153-178B depict an embodiment of a ground-engaging coulter assembly 5100 for collecting soil samples with an onboard sample collection apparatus or probe in the form of a rotatable collection shaft 5101. A plurality of angularly spaced apart collection shafts may be provided. Each collection shaft 5101 rotates about a radial axis of rotation relative to the coulter or blade 5001 of the assembly, and includes one or more openable/closeable collection ports 5102 actuated by a sprocket mechanism 5103 to alternatingly open and close the collection ports, as further described herein. The ports 5102 are arranged to retrieve soil sample plugs or cores at different preselected depths as the coulter blade rolls and cuts through the ground. The cores are then ejected/extracted from the collection shaft 5101 and transferred to a collection receptacle. Coulter assembly 5100 may be mounted to the frame of or trailer pulled by an engine-powered wheeled sample collection vehicle which traverses an agricultural field (e.g. tractor, etc.) for collecting soil samples.

Coulter assembly 5100 generally comprises many of the same components as coulter assembly 5000 previously described herein. This includes the disc-shaped body or blade 5001, blade hub 5004 for mounting the blade thereto, outer hub collar 5007 fixedly attached to the hub and rotatable therewith, and annular bearing 5008. These components will not be described again here for sake of brevity. The present coulter assembly is assembled in the manner shown in the figures and further described below.

Collection shaft 5101 may have an elongated solid cylindrical body including a plurality of laterally open collection ports 5102 spaced axially apart along its length. Collection ports 5102 may be through ports open from two opposing sides of the collection shaft 5101 as shown. The remaining two sides of the shaft are solid and closed. Ports 5102 may be in the form of radially elongated slots in the illustrated embodiment; however other shaped ports including round ports may be provided. Any number of collection ports 5102 may be provided depending on the number and depths of soil samples desired.

Collection shaft 5101 is mounted to blade 5001 and rotatable independently relative to the blade in an elongated radial slot 5107. Thus the collection shaft 5101 is supported by and angularly rotates with the blade 5001 as it moves through the soil for capturing soil sample cores. However, the collection shaft 5101 also rotates independently of the blade 5001 about its own rotational axis Rc for selectively collecting soil samples depending on the shaft's rotational position. Slot 5107 may be a through slot in one embodiment penetrating both major surfaces 5001-1, 5001-2 of the blade. The slot may be generally T-shaped in one embodiment having a contiguous wider lateral portion 5107-1 at the inside end of the slot than the longer straight radial portion 5107-2.

The radial centerline of the slot 5107 defines radially-oriented axis of rotation Rc of the collection shaft 5101, which is perpendicular to the axis of rotation RA1 of the blade 5001 defined by axle 5009 attached to blade hub 5004. Axis Rc intersects the center of the blade central opening 5005.

Collection shaft 5101 is rotatably supported on blade 5001 in slot 5107 by an inboard and outboard bearing 5106 disposed at each end of the shaft. Any suitable type bearing including cylindrical bushings may be used to support the shaft. A pair of radially elongated guide shields 5108 may be provided; one each of which is mounted on opposite sides of the slot 5107 (either within the slot or adjacent thereto). Shields 5108 may mounted substantially flush with the major surfaces 5001-1, 5001-2 of blade 5001, or protrude slightly above the major surfaces as shown in the illustrated embodiment. The shields 5108 may be formed by flat metal strips spot welded or otherwise fixedly attached to the blade 5001 on each side of the slot. The collection shaft 5101 is rotatable disposed between the shields 5108. Bearings 5106 may in turn be fixedly mounted to the shields 5108, and the collection shaft 5101 is rotatably supported by the bearings as noted before. The shields 5108 help properly position and locate the collection shaft 5101 and/or the bearings (e.g. bushings) on blade 5001 within the slot 5107. Notably, the guide shields also advantageously help shield and block the collection ports 5102 in collection shaft 5101 when rotated to a closed position to prevent soil from entering the ports when not wanted for collection.

Collection shaft 5101 is rotatable between an open position in which the collection ports 5102 are open for capturing soil, and a closed position in which the collection ports are closed to preclude soil from entering the collection ports. In the open position, the collection ports 5102 of collection shaft 5101 may protrude at least slightly above the guide shields 5108 to facilitate entry of the soil sample into the collection ports 5102. Further, in the open position, the collection ports 5102 of collection shaft 5101 face outwards away from the slot 5107 and are exposed for capturing soil for either side of the dually open ports. In the closed position when a soil sample is not desired, the collection ports of collection shaft 5101 face inwards towards the opposing sides of slot 5107 and the plane of the blade 5001. This exposes the solid sides of the collection shaft to the soil which precludes soil from entering the collection ports 5102. Further, in the closed position, the collection shaft 5101 may be configured with a non-circular transverse cross section at least at the port locations so its outer profile is partially or substantially flush with the guide shields 5108 to further prevent soil from working its way into the collection ports 5102 beneath the shields 5108. Accordingly, in one non-limiting embodiment the opposing solid sides of the collection shaft 5101 may be planar or flat, and the open sides of the shaft with collection ports 5102 may be arcuately curved and convex to enhance the foregoing functionality of capturing soil samples.

To actuate and rotate the collection shaft 5101 between its open and closed positions, a rotary mechanism such as sprocket mechanism 5103 is provided to rotate the collection shaft 5101 for selectively collecting soil samples at predetermined depths. Sprocket mechanism 5103 in one embodiment includes an annular cam timing or indexing ring 5104 and a sprocket 5105 fixedly attached to the inside end of the collection shaft 5110 at the inboard bearing 5106 which engages the ring. Indexing ring 5104 is fixedly mounted to the frame of the engine-powered wheeled sampling vehicle via bracket 5101 as previously described herein (similarly to cam ring 5006). The indexing ring 5104 thus remains stationary as the blade 5001 and collection shaft 5101 rotate about the axle 5009.

Referring to FIGS. 165-172, sprocket 5105 may be any type of geared or toothed sprocket, gear, cogwheel, lever(s), or other geometry (hereafter simply "sprocket") mounted on the inside end of the collection shaft 5101 having a configuration designed to operably engage one or more mating indexing segments 5104-5 having a camming profile arranged on the indexing ring 5104. In one embodiment, a plurality of indexing segments 5104-5 is provided. Indexing segments 5104-5 each may have an undulating camming configuration or profile in side view which operably engages and rotates the sprocket 5105. The indexing segments may each comprise a series of alternating raised protrusions or teeth, ramps, and recesses selected in sequence and dimension to engage and actuate/rotate the sprocket arms or lugs 5105-1, thereby in turn rotating the collection shaft 5101 as it rotates with the coulter 5100. The indexing segments 5104-5 are circumferentially spaced at predetermined intervals separated by flat areas in between on the indexing ring 5104 which do not actuate or rotate the sprocket 5105. The camming profile segments 5104-5 may have an arcuately curved shape in plan view on the annular-shaped indexing ring.

Indexing ring 5104 has a generally planar annular body comprising a central opening 5104-4, first major surface 5104-1, opposing second major surface 5104-2 parallel to the first major surface, and a peripheral sides 5104-3 extending between the surfaces. First major surface 5104-1 may be plain in one embodiment. The second major surface 5104-2 faces the blade 5001 when assembled and includes the indexing segments 5104-5. In some embodiments, two or more indexing segments 5104-5 may be provided. Four may be provided in the non-limiting illustrated embodiment which may be spaced circumferentially apart at uniform arc lengths. The indexing segments 5104-5 are circumferentially spaced apart around the indexing ring at specific discrete intervals or locations selected to time actuation (i.e. rotation) of the collection shaft 5101 at predetermined intervals in conjunction with rotation of blade 5001 to collect soil samples to either open or close the sample collection ports 5102 in the shaft. The indexing segments 5104-5 are therefore used to precisely time and rotationally position the sprocket 5105 in cooperation with the rotational position of blade 5001 to capture or not capture soil samples based on the rotational positions of the blade and collection shaft 5101 (e.g. above or in soil and depth) by opening or closing the collection ports 5102, as further described herein.

FIG. 164 depicts a side perspective view showing the profile of one example of an indexing segment 5104-5. FIG. 163 is cross section of the indexing segment taken from FIG. 162. In on non-limiting embodiment illustrated, the indexing segment may include a pair of arcuately spaced apart raised protrusions or teeth 5110, 5114. A recess or valley 5113 is formed between the teeth having a depth which defines a thickness T2 of the indexing ring 5104 (measuring between the top and bottom major surfaces 5104-1, 5104-2) which is less than the baseline thickness T1 of the flat portions of the ring without an indexing see, e.g. In one embodiment, the valley 5113 may be separated from the leading tooth 5110 by a short flat portion 5115 of the indexing ring 5104 having an arc length less than the arc length between the leading and trailing teeth 5110, 5114. This defines a flat ledge or shelf 5112 at the trailing side of leading tooth 5110 forward of the valley 5113. Valley 5113 may be disposed on the leading side of the trailing tooth 5114 and adjoins this tooth. The trailing/leading teeth or sides are defined herein by directional rotation of the coulter 5100 and sprocket 5105 as the sprocket initially engages and rotates through each indexing segment 5104-5. In one embodiment, the leading tooth 5110 may include an inclined ramp 5111 on the leading side to more gradually engage and rotate the lugs 5105-1 of sprocket 5105. The thickness T3 of the indexing ring 5104 at each tooth 5110, 5114 measured between the apex of the teeth and bottom surface 5104-2 of the ring is greater than the baseline thickness T1 of the flat portions 5115 of the ring. Other numbers and configurations of the indexing segments 5104-5 and teeth/valleys are possible in other embodiments.

Sprocket 5105 in one non-limiting embodiment may include a plurality of radially protruding arms or lugs 5105-1 arranged to engage the indexing segments 5104-5 of indexing ring 5104. In this example, four lugs 5105-1 are provided; however, other embodiments may have more or less lugs. The lugs 5105-1 may be arranged in two diagonal pairs as shown which are uniformly spaced apart on the sprocket.

It will be appreciated that in other possible embodiments contemplated, the sprocket 5105 may be a convention geared sprocket with uniform teeth extending a full 360 degrees and each mating indexing segment 5104-5 may a geared or tooth rack having convention teeth selected to engage the teeth of the sprocket. Other arrangement of mutually configured and engaging sprockets and indexing segments may be used in other embodiments.

Operation of the coulter assembly 5100 for capturing and ejecting a soil sample will now be briefly described with reference to FIGS. 173A-178B. By changing the geometry of the indexer (i.e. the location and number of the indexing segments 5104-5 on indexing ring 5104 and their configuration), the coulter assembly 5100 can be used to close or open the collection ports 5102 on the collection shaft 5101 at any point in the coulter blade's rotation.

FIGS. 173A-B shows the coulter assembly in a first operating position with the collection shaft 5101 in about the 8 o'clock position (lower left quadrant of blade profile). Sample collection shaft 5101 is in the fully closed position rotated so that the collection ports 5102 are closed to the ingress of soil. The blade 5001 and shaft assembly are rotating counter-clockwise (arcuately left to right in the figure), and the sprocket 5105 is about to contact the indexing ring 5104. The collection shaft 5101 is located above the surface 5003 of the ground or soil 5002 at this point as the blade 5001 rotates through the soil (see blade and shaft rotational direction arrows in these figures). It will be remembered that the blade and shaft rotate relative to the indexing ring 5104 which remains stationary being affixed to the frame of the wheeled sample collection vehicle.

FIGS. 174A-B show the coulter assembly in a second operating position rotated farther downward closer to the 6 o'clock position. Sample collection shaft 5101 is still in the closed position rotated with collection ports 5102 closed. The collection shaft 5101, however, has now penetrated the surface 5003 of the ground or soil 5002 at this point as the blade 5001 rotates through the soil. The sprocket 5105 has made initial engagement with one of the indexing segments 5104-5 (i.e. leading tooth 5110) to initiate rotation of collection shaft 5101.

FIGS. 175A-B show the coulter assembly in a third operating position rotated farther downwards closer to the 6 o'clock position than before. The sprocket 5105 is further engaged with the indexing segment which continues to rotate the collection shaft 5101 and further opens the sample collection ports 5102 which are still not quite open enough to collect soil. The indexing segment 5104-5 kicks off the trailing lug of the sprocket in order to nose down the leading lug of the sprocket. The collection shaft 5101 is in a partially open position, but approximately less than halfway opened at this juncture.

FIGS. 176A-B show the coulter assembly in a fourth operating position rotated farther downwards almost at the 6 o'clock position. The sprocket 5105 is more fully engaged now with the indexing segment 5104-5. The leading lug of the sprocket is pulled back by the indexing segment, which continues to rotate the collection shaft 5101 and further opens the sample collection ports 5102 so that they are about halfway opened. This is the mid-way point of the collection shaft 5101 between its fully closed position and fully open position.

FIGS. 177A-B show the coulter assembly in a fifth operating position with collection shaft 5101 rotated farther downwards to the vertical 6 o'clock position in the soil. The sprocket 5105 is further engaged with the indexing segment 5104-5 which continues to rotate the collection shaft 5101 to its fully open position with the outward facing collection ports 5102 now fully open to retrieve a soil sample plug or core. The position at which the ports open and the length of time that the vessels remain open can be varied at any rotational position of the coulter blade 5001 and collection shaft 5101 by changing the configuration and design of the indexing ring 5104 with respect to the indexing features (i.e. teeth, valleys, etc.) of the index segments 5104-5, their number, and placement along the ring. It is well within the ambit of those skilled in the art to make such adjustment to achieve the desired opening and closing timing of the collection ports without further undue elaboration.

FIGS. 178A-B show the coulter assembly in a sixth operating with collection shaft 5101 now rotated upward past the 6 o'clock position closer towards the 3 o'clock position. The first indexing segment 5104-5 has been disengaged by the sprocket 5105 as blade 5001 and collection shaft 5101 rotates beyond the first indexing second. A second indexing segment 5104-5 has now engaged and disengaged the sprocket 5105 causing it to further rotate such that the collection shaft 5101 is returned to its fully closed position as shown with collection ports 5102 fully closed again as the coulter assembly continues to roll; the process being very similar to the one just described to expose the collection ports. Sprocket 5105 is shown disengaged with the second indexing segment 5104-5 and is traveling over one of the flat portions 5115 of the indexing ring 5104 which do not operably engage and rotate the collection shaft 5101 to maintain its closed position.

Once the coulter assembly (e.g. blade 5001 and collection shaft 5101) has rotated to the point where the collection shaft 5101 is above the surface of the surface of the ground or soil, the next succeeding indexing segment 5104-5 may then engage and rotate the sprocket 5105 to again turn the collection shaft to its fully open position so the collected soil samples (e.g. plugs or cores) can be removed by any suitable means (e.g. via a blast of pressurized air directed at the collection ports or insertion of a mechanical ejector such as a rod or lever through the ports as some non-limiting examples).

Slider Sample Collection Probes

FIGS. 179-185 depict an embodiment of a ground-engaging coulter assembly 5200 for collecting soil samples with an onboard sample collection probe in the form of linearly moveable collection sliders 5201. The collection sliders 5201 are radially movable along an actuation axis AA perpendicular to the axis of rotation RA1 of the coulter blade 5001. Each slider operates to selectively open/close a corresponding collection recess or port 5202 formed within a radial slot 5203 in the blade. Collection ports 5202 may extend completely through the blade 5001 between its major surfaces. The sliders 5201 are actuated by a stationary cam ring 5204 (e.g. analogous to cam ring 5006 previously described herein) to alternatingly open and close the collection ports as the coulter blade 5001 rotates. The ports 5102 are arranged and may be configured to retrieve soil sample plugs or cores at the same or different preselected depths as the coulter blade rolls and cuts through the ground. The collected cores are then ejected/extracted from the collection ports 5202 and transferred to a collection receptacle. Coulter assembly 5200 may be mounted to the frame of or trailer pulled by an engine-powered wheeled sample collection vehicle which traverses an agricultural field (e.g. tractor, etc.) for collecting soil samples.

Coulter assembly 5200 generally comprises many of the same components as coulter assembly 5000 previously described herein. This includes the disc-shaped coulter blade 5001, blade hub 5004 for mounting the blade thereto, outer hub collar 5007 fixedly attached to the hub and rotatable therewith, and annular bearing 5008. These components will not be described here again and are not shown in FIGS. 179-185 for sake of brevity and clarity. For simplicity, the blade hub 5004, hub collar 5007, and bearing 5008 are represented by dashed shaft. The present coulter assembly is assembled in the manner shown in the figures and further described below.

Collection sliders 5201 may have an elongated solid rectangular body with a rigid bar-like construction (best shown in FIG. 181). The sliders 5201 occupy a majority, and preferably more than ¾ of the length of each radial slot 5203 but not the entire slot to allow formation of the openable/closeable collection ports 5202 in the outboard ends of each radial slot. Sliders 5201 are slideably retained in each radial slot 5203 by a plurality of mounting straps 5205 affixed to opposite sides (i.e. blade major surfaces 5001-1 and 5001-2) of the blade 5001. The straps 5205 span or bridge across and over the collection sliders 5201 trapping the sliders therebetween within the radial slot 5203. Straps 5205 may be fixedly attached to the coulter blade 5001 by any suitable means, such as without limitation tack welding, adhesives, fasteners, or other. The straps 5205 may be arranged in mating pairs directly opposite each other on the blade major surfaces 5001-1 and 5001-2.

The collection sliders 5201 are selectively and automatically actuated via a camming mechanism provided by annular cam ring 5204 and a follower 5206 mounted to the inside ends of the collection sliders 5201. Each slider 5201 is linearly and radially movable independently of each other via configuration of the cam ring 5204. Cam ring 5204 is configured for fixed attachment to the frame of the wheeled collection vehicle such as via mounting bracket 5010 shown in FIGS. 137 and 139. Cam ring 5204 therefore remains stationary and fixed in position relative to the coulter blade 5001 with collection sliders 5201 which rotates as the blade is pulled or pushed through the soil.

Cam ring 5204 may be similar in construction and configuration to cam ring 5006 and includes the same constituent portions/parts previously described herein in detail, which will not be repeated here again for the sake of brevity. The cam track 5006-5 may be shaped similarly to cam ring 5006, or cam ring 5204 may have a 360 degree cam track with different configuration in some embodiments. In either case, portions of the cam track 5006-5 are spaced by varying radial distances D1 (minimum) and D2 (maximum) from central opening 5006-4 of the cam ring 5204 to selectively slide the collection sliders 5201 radially outwards and inwards. Other locations within cam track 5006-5 may vary between distances D1 and D2.

In one embodiment, the follower 5206 may be formed by an annular bearing 5207 mounted to the inside end of each collection sliders 5201 by any suitable means. Bearing 5207 may be a ball bearing in one example. In one embodiment, the follower bearing 5207 may be mounted to the slide 5201 via a fastener such as a nut and bolt 5208 assembly; the latter of which is passed through the bearing and a hole in the slider as shown. This allows the follower 5206 to rotate about the bolt defining a follower axis as the follower moves along the annular track in the cam ring 5204. The followers 5206 associated with each collection sliders 5201 will travel through and circulate around the cam track 5006-5 to selectively actuate the sliders and open/close the collection ports 5202.

In operation, as the coulter blade 5001 rotates, the cam track 5006-5 is configured to selectively open and close the collection ports 5202 at different rotational positions of the blade for either collection of or preventing collection of soil samples (this is similar to the operation of cam ring 5006 previously described herein). Each slider 5201 is independently actuated to be fully radially extended within its radial slot 5203 as it rotates into the soil to close its collection port 5202, not allowing collection of a sample. After the blade 5001 enters the soil, the slider 5201 embedded in the soil is drawn fully and radially inwards at the desired depth by interaction between the cam track 5006-5 and follower 5206 (representing the portion of the track associated with distance D1). This fully opens the collection port 5202 at the outboard end of radial slot 5203 to retrieve a soil sample. Before the collection port 5202 rotates out of the desired depth, the slider begins to close to retain the sample in the port. The cam ring 5204 continues to apply pressure on the collection slider 5201 via the cam follower 5206 keeping the collection soil sample packed and retained in the collection port 5202. After the sample leaves the soil, the cam ring 5204 begins to open the slider 5201 to release pressure on the sample allowing for extraction of the sample. At some point above the soil surface, the soil sample is removed pneumatically or mechanically in similar fashion to that already described herein with respect to the piston-operated coulter assembly 5000. After extraction, the now empty collection port 5202 is then fully re-closed by the slider 5201 via the cam ring 5204 before it enters the soil again as the blade 5001 continues to rotate. When the slider 5201 again enters the soil and reaches the desired collection depth, the collection port 5202 will again open in the same manner previously described to retrieve a second soil sample. It bears noting that this process occurs for each of the plurality of sample collection sliders 5201 and collection ports 5202 disposed on the coulter blade. Accordingly, a sample may be collected concurrently or semi-concurrently by one below-grade slider 5201 and extracted from another above-grade slider. Any desired number of sliders may be provided.

It will be appreciated that soil samples may be collected at varying depths by timing the opening/closing of the collection ports 5202 through configuring the shape of the cam track 5006-5 of cam ring 5204. It is well within of those skilled in the art to provide an appropriate cam ring configuration for collecting samples at the desired depths.

The outside terminal ends 5201-1 of the collection sliders 5201 and the outside terminal ends 5203-1 of the radial slot 5203 (collection ports 5202 defines therebetween) may have a variety of configurations which define the shape of the collection ports 5202. FIGS. 179-185 show straight terminal ends of the sliders and slots forming a rectilinear geometry of the collection pockets (best shown in FIG. 182). FIG. 186 shows an alternative non-rectilinear and undulating terminal end shape of the sliders and slots having a variable geometry. This geometry creating multiple arcuately curved and concave sub-pockets 5203-2 which are ideally suited for collection and retention of variable soils. Sub-pockets 5203-2 may have the same or different sizes as illustrated. Other geometries may be used for collection ports 5202.

FIG. 187 shows a non-limiting example of how cam ring 5204 with cam track 5006-5 can be configured to open or close the collection port 5202 via operation of the slider 5201 in a timed manner for collecting, retaining, and removing a soil sample using coulter blade assembly 5200. This figure shows the rotational progression of a single collection slider 5201 and port 5202 as the blade 5001 rotates through the soil and is self-explanatory. It will be appreciated that the blade 5001 will include a plurality of angularly/circumferentially spaced apart collection slides as shown for example in FIG. 179.

FIG. 188 shows an alternative variation of the sample collection coulter assembly 5200 for collecting soil samples at different depths using a single coulter blade 5001. Whereas the collection sliders 5201 and radial slots 5203 in FIGS. 179-187 each have the same length, the sliders and radial slots in coulter assembly 5230 have different lengths. This places the collection ports 5202 at different radial distances from the center of the coulter blade. This design thus allows collection of samples at different depths in the soil using a single blade 5001.

Slider Sample Collection Probe With Shielded Ports

FIGS. 189-196 depict an alternative embodiment of a ground-engaging coulter assembly 5300 for collecting soil samples with an onboard sample collection probe in the form of linearly moveable collection sliders 5301. The coulter assembly 5300, including elongated collection sliders 5301, is essentially identical to coulter assembly 5200 previously described herein above and functions in the same manner. The collection sliders 5301 are selectively and automatically actuated via the same camming mechanism provided by annular cam ring 5204 and followers 5206 mounted to the inside ends of the collection sliders 5301. These same components and their operation for collecting soil samples will not be repeated here for sake of brevity.

By contrast, a difference in the present design variation embodied in coulter assembly 5300 is that each slider 5301 further includes a plurality of outwards facing collection ports 5302 spaced radially apart along the length of the slider for capturing soil samples at different depths. Collection ports 5302 may preferably be through openings penetrating both opposing sides (e.g. front and back) of the slider to allow the extracted soil samples to be ejected mechanically or pneumatically from ports for chemical processing/analysis. Collection ports 5302 may be round holes or apertures in one embodiment.

Each collection port 5302 in slider 5301 has an associated pair of mounting straps 5205 affixed to opposite sides (i.e. blade major surfaces 5001-1 and 5001-2) of the blade 5001; the same as coulter assembly 5200. As previously described herein, the straps 5205 span or bridge across and over the collection sliders 5201 trapping the sliders therebetween within the radial slots 5203. The straps 5201 rotate with coulter blade 5001 and remains fixed relative thereto. The sliders 5301 operate in the same manner as sliders 5201 previously described herein, and therefore reciprocate in a radial linear direction beneath the straps.

The straps 5205 in coulter assembly 5300 however act as shields which alternatingly expose or conceal the collection ports 5302 beneath them as the blade 5001 rotates through the soil. As shown in FIGS. 190-192, the sliders 5301 are moveable between a first radial position in which the collection ports 5302 are retracted and covered by the straps 5205 to prevent collection of soil samples/cores (see, e.g. slider at 3 o'clock position), and a second radial position in which the collection ports emerge from beneath the straps and are exposed (see, e.g. slider at 6 o'clock position) for either capturing a soil sample if exposed below grade, or extracting a collected sample if exposed above grade.

In operation, as the coulter blade 5001 rotates, each slider 5301 linearly reciprocates within its radial slot 5203 cause by interaction with the stationary camming mechanism (i.e. cam ring 5204 and followers 5206 on each slider). This linear motion alternatingly exposes or conceals the collection ports 5302 as shown in FIG. 190 while the blade rotates (note open ports at 6 o'clock position and closed ports at 9 and 10 o'clock positions). FIGS. 195 and 196 also shows ports 5302 in the closed and open positions, respectively.

Coulter assembly 5300 generally comprises many of the same components as coulter assembly 5000 previously described herein. This includes the disc-shaped coulter blade 5001, blade hub 5004 for mounting the blade thereto, outer hub collar 5007 fixedly attached to the hub and rotatable therewith, and annular bearing 5008. These components will not be described again here again and are not shown in FIGS. 189-196 for sake of brevity and clarity. For simplicity, the blade hub 5004, hub collar 5007, and bearing 5008 are represented by dashed shaft. The present coulter assembly is assembled in the manner shown in the figures.

Rotatable Spindle Collection Probe

FIGS. 197-206 depict an embodiment of a ground-engaging coulter assembly 5400 for collecting soil samples with an onboard sample collection probe. The collection probe may comprise a tubular assembly comprising a rotatable inner collection spindle 5401 enclosed inside a hollow outer shield tube 5403 fixedly mounted to the coulter blade 5001 and rotatable therewith. A plurality of angularly spaced apart pairs of collection spindles and shield tubes may be provided on coulter blade 5001. Each collection spindle 5401 rotates about a radial axis of rotation Rc relative to the coulter blade 5001 of the assembly, and includes one or more openable/closeable collection ports 5402 actuated by sprocket mechanism 5103 cam ring 5104 previously described herein to alternatingly open and close the collection ports, as further described herein. The ports 5402 are arranged to retrieve soil sample plugs or cores at different preselected depths as the coulter blade rolls and cuts through the ground. The cores are then ejected/extracted from the collection spindle 5401 and transferred to a collection receptacle. Coulter assembly 5400 may be mounted to the frame of or implement pulled by an engine-powered wheeled sample collection vehicle which traverses an agricultural field (e.g. tractor, etc.) for collecting soil samples.

Coulter assembly 5400 generally comprises many of the same components as coulter assembly 5000 previously described herein. This includes the disc-shaped body or blade 5001, blade hub 5004 for mounting the blade thereto, outer hub collar 5007 fixedly attached to the hub and rotatable therewith, and annular bearing 5008. These components will not be described again here for sake of brevity.

The present coulter assembly is assembled in the manner shown in the figures and further described below.

Collection spindle 5401 may have an elongated solid cylindrical body including a plurality of laterally open collection ports 5402 spaced axially apart along its length. Collection ports 5402 may be through ports open from two opposing sides of the spindle 5401 as shown. The remaining two sides of the shaft are solid and closed. Ports 5402 may be in the form of round through holes extending transversely to rotational axis Rc in the illustrated embodiment; however other shaped ports including elongated ports in the form of slots may be provided. Any number of collection ports 5402 may be provided depending on the number and depths of soil samples desired.

The outer shield tubes 5403 each comprise a plurality of spaced apart windows 5404 formed along the length of the tubes to provide access to the collection ports 5402 in spindle 5401. Each window is therefore located on shield tube 5403 for alignment with a mating collection port 5402 in spindle 5401 inside the tube. The collection ports and windows 5404 therefore have the same spacing along the lengths of the shield tubes 5403 and spindles 5401. This forms pairs of collection ports and windows which are concentrically aligned. Windows 5404 may be complementary configured to collection ports 5402. In the non-limiting illustrated embodiment, the windows 5404 and collection ports 5402 each have a round shape. In other embodiments, the windows 5404 and collection ports 5402 may have other shapes such as mating pairs of elongated slots. Shield tube windows 5404 preferably are through openings extending through two opposing exposed sides of the shield tube 5403 as shown. The remaining two sides of the shaft are solid and closed.

The shield tubes 5403 are disposed in each elongated radial slot 5203 in blade 5001. The opposing arcuately shaped circumferential walls of the tubes 5403 protrude outwards above each of the major surfaces 5001-1, 5001-2 of the blade to better capture soil. Each shield tube 5403 is rigidly affixed or mounted to blade 5001 in the slots 5203 such as via welding or other suitable fixation means. The shield tubes 5403 therefore remain stationary relative to the blade 5001 as it rotates. The collection spindles 5401 mounted inside the shield tubes 5403, however, are rotatable relative to its tube about each spindle's radially-oriented axis of rotation Rc defined by the radial centerline of the an axis blade 5001. The spindles 5401 thus rotate independently relative to the blade inside the shield tubes 5403.

Collection spindles 5401 are rotatably supported inside shield tubes 5403 by a plurality of radially spaced apart bearings 5405, as best shown in FIGS. 204-206. Bearings 5405 may have an annular circular shape and may be formed by diametrically enlarged portions of the spindle relative to other portions of the spindle between the bearings as shown. The bearings 5405 may be formed as integral unitary structural parts of a monolithic spindle body in one embodiment. In one arrangement, the collection ports 5402 are formed through the bearings to provide a maximum volume in each port for capturing a soil sample. In other embodiments contemplated, collection ports 5402 may be formed in the diametrically narrower portions of spindle 5401 between bearings 5405. Each collection port 5402 may be sealed off within shield tube 5403 by a pair of annular seals such as an O-ring mounted in circumferential grooves of the bearings 5405 on each side of the ports.

Collection spindle 5401 is rotatable between an open rotational position in which the collection ports 5102 are each concentrically aligned with its mating shield tube window 5404 and open for capturing soil (see, e.g. FIGS. 204 and 206), and a closed rotational position in which the collection ports are each rotated away from and misaligned with its mating tube window and closed to preclude soil from entering the collection ports (see, e.g. FIG. 205) In the open position, the protrusion of the open windows of the shield tubes 5403 above the major surfaces 5001-2, 5001-2 facilitate entry of the soil sample into the collection ports 5102. Further, in the open position, the collection ports 5402 of spindle 5401 and shield tube windows 5404 both face outwards away from the slot 5203 and are exposed for capturing soil for either side of the dually open ports and windows. In the closed position when a soil sample is not desired, the collection ports of spindle 5401 face inwards and laterally towards the opposing sides of slot 5203 and the plane of the blade 5001. This exposes the solid sides of the collection spindle to the shield tube windows 5404 which precludes soil from entering the collection ports 5402.

To actuate and rotate the collection spindle 5401 between its open and closed positions, a rotary mechanism such as without limitation sprocket mechanism 5103 may be used to rotate the collection spindle for selectively collecting soil samples at predetermined depths. Sprocket mechanism 5103 already described above with respect to coulter probe assembly 5100 includes the annular timing or indexing ring 5104 and sprocket 5105. In the present design, sprocket 5105 may instead be fixedly attached to the inside end of the collection spindle 5401 in a similar manner to mounting the sprocket to collection shaft 5101 previously described herein. Indexing ring 5104 is fixedly mounted to the frame of the engine-powered wheeled sampling vehicle via bracket 5110 as previously described herein (similarly to cam ring 5006). The indexing ring 5104 thus remains stationary as the blade 5001 and collection shaft 5101 rotate about the axle 5009.

As the coulter blade 5400 rotates, the collection ports 5402 alternatingly open and close to collect or preclude collection of soil samples in the same general manner previously described herein with respect to coulter blade assembly 5100.

Piston-Operated Sample Collection Probe with Flexible Cam Ring

FIGS. 207-216 depict a variation of the piston-operated coulter assembly 5000 of FIGS. 137-152 for collecting soil samples. The same piston mechanism 5020 comprising cam follower 5021 fixedly disposed on the inside end 5023-1 of piston rod 5023 which operably engages the cam track 5006-5A is provided in the present embodiment. However, the rigidly structured annular cam ring 5006 of coulter assembly 5000 is modified and replaced in the present coulter assembly 5500 by a resiliently deformable cam ring 5506. At least a part of cam ring 5506, or in some embodiments the entire cam ring 5506 may be formed of an elastically deformable and resilient material having an elastic memory.

One potential shortcoming of a rigidly structured coulter cam ring is that, in certain situations, it may be structurally unforgiving of any substantial mechanical resistance or temporary jams in the piston mechanism as it reciprocates when plowing through the soil to collect a sample. Debris or rocks/stones in the soil may create such resistance or jams. In some circumstances if the jam is severe enough, this could lead to potential failure in the piston mechanism of the coulter assembly. For example, if a jam would occur, the cam ring could exert enough force on the cam follower 5021 to damage some part of the jammed mechanism (e.g. piston rod 5023, collection cylinder 5022, bushing 5025, etc.), thereby compromising the coulter's ability to collect soil samples.

To prevent such an overstressing event on the piston mechanism, a deformable cam ring 5506 is provided in the present embodiment. The cam ring 5506 may be made of a durable, semi-rigid yet elastic material or combination of materials, that would enable the cam ring to partially compress and yield in the event of any mechanical issue or external forces that prevents the cam follower 5021 from properly rolling/sliding and changing position in the cam track 5006-5 as the coulter blade 5001 rotates. Optimally, the widest or thickest areas of the cam ring 5506 adjoining the cam track preferably should be structured to be especially compliant/flexible as those portions of the track would be the areas used to displace the cam follower roller the largest radial distances resulting in generation of the greatest radially-acting forces.

FIG. 207 depicts a force-resistant coulter assembly 5500 having a camming mechanism with elastically deformable cam ring 5506. Coulter assembly 5500 may be mounted to the frame of or implement pulled by an engine-powered wheeled sample collection vehicle which traverses an agricultural field (e.g. tractor, etc.) for collecting soil samples in a similar manner to the prior coulter assemblies.

Referring to FIGS. 207-216, coulter assembly 5500 generally comprises many of the same components as coulter assembly 5000 previously described herein. This includes the disc-shaped body or blade 5001, blade hub 5004 for mounting the blade thereto, outer hub collar 5007 fixedly attached to the hub and rotatable therewith, and annular bearing 5008. These components will not be described again here for sake of brevity. The present coulter assembly is assembled in the manner shown in the figures and further described below. Piston mechanism 5020 may be same as previously described herein and operates for collecting soil samples in the same manner. During the radially reciprocating operation of the piston rod 5023 as the blade 5001 rotates, the outside end 5023-2 of the piston rod selectively opens or closes the outside soil collection end 5022-2 of the collection cylinder 5022 and a pair of transverse holes 5022-1 therein. The cylinder outside end is spaced inward from the outer end 5024-2 of radial slot 5024 to form an open gap or recess 5024-3 in blade 5001 to allow soil to enter or be ejected from the outside end 5023-2 of cylinder 5022 as previously described herein.

Deformable cam ring 5506 may be configured similarly to rigid cam ring 5006 previously described herein. Cam ring 5506 has an annular body defining a central opening 5525 for receiving the blade hub assembly and circumferentially continuous cam track 5006-5 which extends a full 360 degrees around the ring. Similar to cam ring 5006, the deformable cam ring 5506 is configured for fixed attachment to the frame of the wheeled collection vehicle such as via mounting bracket 5010. Cam ring 5506 therefore remains stationary and fixed in position relative to the frame and the blade-hub-collar assembly as the coulter blade 5001 is pulled through the soil and rotates.

The deformable cam ring 5506 may be an assembly of discrete annular outer and inner guide ring members 5506-1 and 5506-2 affixed in a rigid manner to a common annular backing plate 5501 for support. The backing plate 5501 may have a substantially planar body and may have a rigid structure in one embodiment. The ring members 5506-1, 5506-2 are fixedly mounted to and spaced radially apart on backing plate 5501 to define the annular opening for the cam track 5006-5. Backing plate 5501 forms a closed bottom wall of the cam track 5006-5 opposite the outwardly open top end of the cam track which receives the cam follower 5021 therein to engage the track. In some embodiments, each ring member 5506-1, 5506-2 may be mounted on its own circular annular mounting flange 5521 and 5522, which in turn are each mounted to the common backing plate 5501. The mounting flanges may each have a generally L-shaped transverse cross section in one embodiment. Flanges 5521, 5522 each define a first mounting section 5521-2, 5522-2 configured for mounting to backing plate 5501 and a second guide ring support section 5521-1, 5522-1 for securing the outer and inner guide ring members 5506-1, 5506-2 thereto. The guide ring support sections may be oriented perpendicularly to the mounting sections in one embodiment. The mounting sections 5521-2, 5522-2 may include a plurality of mounting holes for fixedly attaching the mounting flanges 5521, 5522 to the backing plate 5501 in radially spaced apart relationship. Other mounting arrangements and methods of mounting are possible, such as for example industrial adhesives, welding, riveting, etc. The backing plate 5501 and mounting flanges 5521, 5522 can be formed of any suitable rigid metallic or non-metallic material. In one embodiment, these components are preferably made of a suitable metal such as steel or aluminum as some non-limiting examples.

The outer and inner guide ring members 5506-1, 5506-2 are each fixedly mounted in a cantilevered manner to the guide ring support sections 5521-1, 5522-1 of the mounting flanges 5521, 5522. In one embodiment, the guide ring members are overmolded onto the mounting flanges; however, other methods may be used for fixedly securing the guide ring members thereto such as industrial adhesives. The guide ring members 5506-1, 5506-2 are each spaced apart from the mounting sections 5521-2, 5522-2 of the mounting flanges. This forms annular air gaps 5510, 5511 therebetween which communicate with the open cam track 5006-5. Advantageously, the air gaps provide freedom of movement and impart maximum flexibility to the outer and inner guide ring members 5506-1, 5506-2 which are unencumbered by the rigid attachment of the mounting flanges 5521, 5522 to the backing plate 5501.

It bears noting that although the annular mounting flanges 5521, 5222 may be circular in shape (e.g. in top plan view) with a generally uniform measured between the inner and outer circumferential peripheral edges of the mounting sections 5521-2, 5522-2 of each flange, the guide ring members 5506-1, 5506-2 will have corresponding variable widths at different portions and therefore are not perfectly circularly in shape (in top plan view). This is seen for example in FIG. 214 noting inner peripheral edges of mounting section 5522-2 (extending beyond portions of guide ring member 5506-2) and 5521-2 (visible through slots 5505 in guide ring member 5506-1). The primary reason for this difference is that the portions of the guide ring members 5506-1, 5506-2 width will change depending on the desired variable configuration of the cam track 5006-5 necessary to actuate the piston mechanism 5020 at the desired rotational timing interval of the coulter blade assembly 5500 for collecting soil sample.

Backing plate 5501 of the cam ring 5506 assembly is configured for rigid mounting to mounting bracket 5010 (FIG. 140) of the coulter assembly 5500, such as via a plurality of mounting holes as shown which receive threaded fasteners. Other methods of fixedly mounting the cam ring base 5501 to mounting bracket 5010 may be used, such as riveting, welding, or industrial adhesives as some non-limiting examples. The cam track 5006-5 may have the same or different shape/configuration as cam ring 5006 depending on the type of action to be imparted to piston mechanism 5020 and timing of the opening/closing of the sample collection cylinder 5022 for capturing or extracting a soil sample.

The outer and inner guide ring members 5506-1, 5506-2 may be formed of the same or different materials. In certain embodiments, one or both of the ring members may be formed at least in part or completely of a resiliently deformable material with elastic memory. In some embodiments, one of the guide ring members 5506-1, 5506-2 may be formed of a rigid material and the other one may be formed of a deformable material. Accordingly, numerous variations are possible to accommodate different situations or design goals.

Guide ring members 5506-1, 5506-2 of cam ring 5506 may be made of any suitable material. For example, one or both of the guide ring members may formed of a semi-rigid or semi-stiff (i.e. relatively hard), yet deformable polymeric material such as polyurethane, or a combination of materials to achieve the desired mechanical/structural properties. The polyurethane ring members are structured to be at least partially deformable for engaging cam follower 5021 and deforming under radially acting forces generated along axis AA by the piston mechanism 5020 when encountering a jammed or other abnormal operating condition of the coulter blade when collecting a sample.

The deformable base material such as polyurethane or another material used to form outer and inner guide ring members 5506-1, 5506-2 may each having the same or different hardnesses. A suitable durometer hardness material may be used. It is well within the ambit of those skilled in the art to select suitable durometer hardnesses for the ring member material.

In some embodiment, the deformable outer and inner guide ring members 5506-1, 5506-2 may be configured to include one or more arrays of deformation-enabling openings 5520 designed to facilitate the flexibility and deformability of the cam ring 5506 under applied radial loads produced by the piston mechanism 5020. In some embodiments, these openings 5520 may transversely extend at least partially through the ring members between one major side and the opposite parallel major side. In a preferred but non-limiting embodiment, the openings 5520 extending completely through the guide ring members 5506-1, 5506-2 parallel to rotational axis RA1 of the coulter blade assembly 5500 to maximize flexibility and deformability under applied compressive loading/forces.

The outer circumferential sidewall 5504 of the outer guide ring member 5506-1 and inner circumferential sidewall 5509 of inner guide ring member 5506-2 may be solid in some embodiments, and they may be rigid or flexible. The opposite inner circumferential sidewall 5512 of outer guide ring member 5506-1 and outer circumferential sidewall 5513 of inner guide ring member 5506-2 may similarly be solid in some embodiments, and they may be rigid or flexible.

The material removed by the forgoing deformation-enabling openings 5520 provide controlled weakening of the guide ring members 5506-1, 5506-2 in the radial direction parallel to radial actuation axis AA. The material reduction in the guide ring members increase flexibility in the radial direction, thereby allowing the ring member material to compress more easily under radial acting forces imparted by the piston mechanism 5020 during a jam or other abnormal operating condition. These through openings 5520 (or other topographical features such as blind slots, dimples, etc.) may have any suitable shape or geometry, such as round holes, obround holes, polygonal or non-polygonal holes or slots (e.g. honeycombs), or other shapes. Some non-limiting examples of suitable openings 5520 are described below.

In one embodiment, one or both of the outer and inner guide ring members 5506-1, 5506-2 may include a plurality of elongated and obliquely angled radial through slots 5505. In the illustrated embodiment, slots 5505 are provided in only the outer ring member 5506-1 but they can be used in both or just the inner guide ring member 5506-2 may have the slots. Slots 5505 may be arcuately curved in one embodiment and extend completely through the opposing major sides 5502 and 5503 of the outer ring guide member 5506-1 in the axial direction of rotational axis RA1. Slots 5505 are radially oriented and arrayed at least partially around the circumference and the central opening 5506-4 of the cam ring 5506. The slots 5505 allow outer ring member 5506-1 to deform and compress more easily when radially engaged by the cam follower 5021. The through slots 5505 extend transversely and obliquely with respect to the outer ring member 5506-1 and the rotational direction vector Vd of the coulter blade 5001 (albeit the cam ring 5506 remains stationary relative to the coulter blade 5001). Accordingly, the leading edge of each slot 5505 with respect to the rotational direction vector Vd of the wheel is proximate to the inside annular edge of the ring member 5506-1 whereas the trailing edge is proximate to the outside annular edge.

In one embodiment, the through slots 5505 may be provided primarily in only the widest/thickest portions of outer ring member 5505-1 to increase flexibility and facilitate deformation of these areas where greater deformation may be needed than adjoining narrower/thinner portions. In other possible embodiments, the entire outer ring member may include one or more slots 5505. The slots 5505 may have the same or different shape and/or size.

In some embodiments the deformation-enabling openings 5520 may comprise an array of round bore holes 5526 each having a circular cross-sectional shape. Bore holes 5526 are shown for example formed in the inner guide ring member 5506-2, recognizing that in other embodiments holes 5526 may be formed in the outer ring member 5506-1 or both. The bore holes 5526 may extend completely through the ring member between the opposing major sides 5507 and 5508. Bore holes 5526 in the array may have any suitable diameter and pitch spacing between the holes. In one embodiment, the holes 5526 may be closely spaced apart with a pitch spacing measured between the centerlines of the adjacent holes being less than 5 hole diameters, or preferably less than 3 hole diameters. Any suitable pattern of holes 5526 may be provided. In one embodiment, the holes 5526 may be arranged in concentric rings of holes extending at least partially around the circumference of the inner guide ring member 5506-2. The bore holes 5526 may be disposed substantially in only the thickest/widest portions of the inner guide ring member to add flexibility to those areas where more deformation may be needed. The narrower portions of the guide ring member 5506-2 may have fewer or no holes to increase rigidity.

It bears noting that a large variety of possible geometries and patterns of arrays of the deformation-enabling openings 5520 may be used. Such patterns could take the shape of isotropic patterns (i.e. same in all orientations/directions such as bore holes 5526), or directionally biased patterns (e.g. swept slots 5505). The opening geometries and patterns may be used to create a linear or non-linear compression force response profile. The opening geometries/patterns may be varied around the guide ring members 5506-1, 5506-2 to create customized areas of specific stiffness or flexibility.

Accordingly, a guide ring member may be rigidly structured in some areas (e.g. narrow areas), yet more deformable in other areas (e.g. wide areas). Whatever the specific geometry and patterns selected for deformation-enabling openings 5520, the openings are preferably designed to provide the necessary rigidity to properly actuation and position the piston mechanism 5020 mechanism and the flexibility to prevent overstressing the parts of the piston mechanism in the event of jams to avoid permanent damage to the mechanism.

Accordingly, it is important to note here that different geometries and patterns of deformation-enabling openings 5520 will have different responses to compression. Therefore, round holes (e.g. bore hole 5526 arrays might be used in one region or area of the guide ring members 5506-1, 5506-2 while elongated slots (e.g. through slots 5505) may be used in another region or area of each guide ring member to achieve a different "spring" response from the material. Some geometries may act differently to different external loading scenarios or directions of applied force by the cam follower 5021. For such foregoing constructions, the collective whole structure of the guide ring members 5506-1, 5506-2 would then be considered to exhibit a "non-linear effective spring rate."

In operation, the piston mechanism 5020 of the coulter assembly 5500 will operate in the same manner as embodied in coulter assembly 5000 for collecting soil sample. Reference is made to FIG. 148 showing the piston mechanism 5020 which is the same in the coulter blade assembly 5500. However, if the piston rod 5023 becomes jammed for some reason in coulter blade assembly 5500 with the deformable cam ring 5506, the cam follower 5021 will impart a radially acting force on either the outer or inner guide ring members 5506-1, 5506-2 as the follower circulates through the cam track 5006-5. The ring member acted upon by the cam follower will depend on which portion of the cam track 5006-5 that the cam follower happens to be moving through at the time of the jam. The cam follower 5021 will therefore engage and compress the inner or outer guide ring member in a radial direction. The deformation-enabling openings 5520 will allow the ring members to elastically deform more readily to absorb the impact forces without damaging the piston mechanism. This allows time for the jam to clear itself if possible.

It will be appreciated that numerous variations of the coulter assembly 5500 with deformable cam ring 5506 are possible within the scope of the present disclosure. Furthermore, the deformable cam ring may be used with any of the coulter assemblies discloses herein which utilize a cam ring to actuate the collection sliders or similar collection devices.

Slider Sample Collection Probe with Laminated Blade Assembly

FIGS. 217-251B depict an embodiment of a ground-engaging coulter assembly 5600 with laminated blade assembly 5601 for collecting soil samples. Blade assembly 5601 has a disk shape like all other coulter blades discloses herein and comprises one or more internally mounted sample collection probe in the form of linearly and radially moveable collection sliders 5620. Sliders 5620 may be similar in general design principle and basic operation to sliders 5201 previously described herein (see, e.g. FIG. 179). By contrast to sliders 5201, however, no external mounting hardware such as straps 5205 are used in the present laminated blade embodiment to attach the sliders to the blade. Instead, each of the present sliders 5630 are captively mounted and at least partially embedded inside laminated blade assembly 5601 between first and second half-sections 5601-1, 5601-2 of the blade in a sandwich-type composite construction. Advantageously, this eliminates external mounting hardware to retain the sliders 5620 in the blade assembly, which may be susceptible to damage by rocks or debris when the blade assembly plows through the soil to collect samples.

Each half-section 5601-1 of blade assembly 5601 may be a configured as a mirror image of the other half-section 5601-2 having identical features, as further described herein. In other possible embodiment, there may be differences. The two half-sections may be permanently laminated or joined together by any suitable method, including for example welding, industrial adhesives, rivets, or other permanent type mechanical joining methods. In one embodiment, the annular outer peripheral edges of the disk half-sections 5601-1, 5601-2 may be welded together and then machined to form an acutely angled wedge-shaped edge profile to improve penetration through the soil. In yet other embodiments, the two-half-sections may be detachably joined together via a suitable non-permanent type joining method such as fasteners or others.

The collection sliders 5630 are radially movable along an actuation axis AA perpendicular to the axis of rotation RA1 of the coulter blade 5001. Each slider operates to selectively open/close a corresponding collection recess or port 5602 formed within a radial slot 5603 in the blade. Slots 5603 and collection ports 5602 may extend completely through the laminated blade assembly 5601 between its exterior major surfaces. The sliders 5630 are actuated by a stationary cam ring which may be any of the cam rings 5006, 5204, or 5506 (previously described herein) to alternatingly open and close the collection ports 5602 as the coulter blade assembly 5601 rotates. The ports 5602 are arranged and may be configured to retrieve soil sample plugs or cores at the same or different preselected depths as the coulter blade rolls and cuts through the ground. The collected cores are then ejected/extracted from the collection ports 5602 and transferred to a collection receptacle. Coulter assembly 5600 may be mounted to the frame of or trailer pulled by an engine-powered wheeled sample collection vehicle which traverses an agricultural field (e.g. tractor, etc.) for collecting soil samples.

Coulter assembly 5600 generally comprises many of the same components as coulter assembly 5000 previously described herein. This includes the disc-shaped coulter blade 5001, blade hub 5004 for mounting the blade thereto, outer hub collar 5007 fixedly attached to the hub and rotatable therewith, and annular bearing 5008. These components will not be described here again and are not shown in FIGS. 217-251B for sake of brevity and clarity. The present coulter assembly is assembled in the manner shown in the figures and further described below.

Laminated blade assembly 5601 and mounting of the sliders 5630 will now be further described. Half-section 5601-1 of laminated blade assembly 5601 has a disk-shaped body including an interior major surface 5610 and opposing parallel exterior major surface 5611 facing outwards. Similarly, half-section 5601-2 has a disk-shaped body including interior major surface 5612 and opposing parallel exterior major surface 5613 facing outwards in an opposite direction to exterior major surface 5611 (see, e.g. exploded views of FIGS. 219 and 220). When joined together, the sliders 5630 are trapped between the two half-sections 5601-1, 5601-2.

Four possible examples of collection sliders 5630 are disclosed herein which may be used with the laminated blade assembly 5601. This includes sliders 5630-1, 5630-2, 5630-3, and 5630-4 each having a different configuration. One common feature is that each of the collection sliders 5630 is slideably mounted in a complementary configured radial slot 5603 formed in the laminated blade assembly 5601 such that only portions of each slider are exposed and visible, as described below.

Referring generally to FIGS. 226-251B, each of the collection sliders 5630-1 to 5630-4 may have an elongated solid body with a generally rigid bar-like or rod-like overall construction. The sliders occupy a majority, and preferably more than ¾ of the length of each respective radial slot 5603 but not the entire slot to allow formation of the openable/closeable collection ports 5602 in the outboard ends of each radial slot. Each slider has common features including a cylindrically shaped cam follower 5021 (previously described herein) on an inside end which engages cam track 5006-5 of the cam ring to selectively actuate at predetermined time intervals based on rotation of the laminated blade assembly 5601. Each slider 5630-1 to 5630-4 is further generally T-shaped at its inside end which includes the cam follower 5021. The opposite outside ends of the sliders may have different shapes. The sliders and their corresponding radial slots 5603 are mutually configured to cooperate and form an interlocked arrangement which retains each slider internally within in the laminated blade assembly 5601 in a captive manner without reliance on externally mounted hardware. Portions of the sliders however may be exposed after mounting to the blade assembly as seen in the figures. Since each collection slider 5630-1 to 5630-4 and its corresponding radial slots are shaped differently, they are described separately below.

FIGS. 227, 230, 236, 237, 242, 246A-B, and 250A-B show collection slider 5630-1. Slider 5630-1 includes cylindrical cam follower 5021 at its inside end, a cylindrical soil collection boss 5631 at its outside end, and an elongated operating rod 5636 with extending therebetween. Operating rod 5636 may be cylindrical having a circular transverse cross section in one embodiment; however, other embodiments may utilize a rectilinear cross-sectional shape (e.g. square or rectangular) or other polygonal shape (e.g. hexagonal). The cam follower 5021 and collection boss 5631 are enlarged structures each having larger diameters than operating rod 5636. The follower and boss are perpendicularly oriented to the length of the operating rod as shown. A central portion of radial slot 5603 has a circular cross-sectional shape and is disposed entirely between the exterior major surfaces 5610, 5613 of the laminated blade assembly 5601. This forms a concealed radially-extending circular bore 5633 which slideably receives the operating rod 5636 therethrough. Elongated bore 5633 extends between and is in communication with a pair of open oblong windows 5632 formed through the blade assembly at each end of the bore. Each half-section 5601-1, 5601-2 of the laminated blade assembly 5601 has a semi-circular concave recess which forms one-half of the complete circular bore 5633 when the two half-sections 5601-1, 5602-2 of the blade assembly are joined together (see, e.g. FIG. 242). The cam follower 5021 and collection boss 5631 are each received in one of the windows 5632 and slideable therein between the ends of the window when actuated by the cam ring. The windows 5632 may be oval shaped in one embodiment and oriented with their lengths arranged parallel to actuation axis AA defined by the radial slot. The cam follower 5021 has a length (measured between its flat ends) that is greater than the thickness of the laminated blade assembly 5601 (measured between its exterior major surfaces 5610 and 5613) such that the follower protrudes above the exterior surfaces as shown. Conversely, the cylindrical collection boss 5631 may have a length (measured between its flat ends) which is equal to or less than thickness of the laminated blade assembly 5601 such that the boss does not protrude above the exterior major surfaces. In other possible embodiments, the boss may protrude above the blade exterior major surfaces to help guide soil samples into the collection ports 5602. It bears noting that the relatively slender rod 5636 in comparison to the cam follower and collection boss advantageously reduces weight, friction with soil, and allows the rod to be easily concealed and protected beneath the exterior of the laminated blade assembly 5601.

FIGS. 227, 231, 238, 239, 243, and 2476A-B, and 251A-B show collection slider 5630-2. Slider 5630-1 similarly includes cylindrical cam follower 5021 at its inside end, a cylindrical soil collection boss 5631 at its outside end, and an elongated operating strap 5634 with rectangular transverse cross section extending therebetween. A central portion of radial slot 5603 has a rectangular cross-sectional shape and is disposed entirely between the exterior major surfaces 5610, 5613 of the laminated blade assembly 5601. This forms a concealed radially-extending rectangular passage 5635 which slideably receives the operating strap 5634 therethrough. Elongated radial passage 5635 extends between and is in communication with a pair of open oblong windows 5632 formed through the blade assembly at each end of the passage. Each half-section 5601-1, 5601-2 of the laminated blade assembly 5601 has a partial rectangular recess which forms one-half of the complete rectangular passage 5635 when the two half-sections 5601-1, 5602-2 of the blade assembly are joined together (see, e.g. FIG. 243). The cam follower 5021 and collection boss 5631 are each received in one of the windows 5632 and slideable therein between the ends of the window when actuated by the cam ring. The windows 5632 may be oval shaped in one embodiment and are oriented with their length parallel to actuation axis AA defined by the radial slot. It bears noting that the relatively slender/thin operating strap 5634 in comparison to the cam follower and collection boss advantageously reduces weight and allows the strap to be easily concealed and protected beneath the exterior of the laminated blade assembly 5601.

FIGS. 226, 228, 234, 235, 241, 245A-B, and 249A-B show collection slider 5630-3. Slider 5630-3 has a generally rectangular body in transverse cross section with cylindrical cam follower 5021 at its inside end. The outside soil collection end creates the openable/closeable soil collection port 5602 at the peripheral portion of the blade assembly 5601. Slider 5630-3 includes a pair of radially-extending and opposing guide flanges 5637 protruding outwards from each side of the slider body in opposite directions. Guide flanges 5637 are each slideably received in a mating complementary configured and radially-extending guide channel 5638 formed in opposing sides of radial slot 5603 (see, e.g. FIG. 241). Channels 5638 are inwardly open towards radial slot 5603. The opposing outer major surfaces of the rectangular collection slider 5630-3 are exposed and visible in radial slot 5603 when mounted to the blade assembly 5601. This contrasts to the concealed portions of sliders 5630-1 and 5630-2 described above. Each half-section 5601-1, 5601-2 of the laminated blade assembly 5601 has a perpendicular stepped shoulder which forms one-half of the complete guide channel 5638 when the two half-sections 5601-1, 5602-2 of the blade assembly are joined together (see, e.g. FIG. 241). The guide flanges 5637 are trapped within the channels 5638 when the half-sections 5601-1 and 5601-2 are joined together, thereby captively retaining the slider 5630-3 in the laminated blade assembly without the need for external mounting hardware.

FIGS. 226, 229, 232, 233, 240, 244A-B, and 248A-B show collection slider 5630-4. Slider 5630-4 has a generally rectangular body in transverse cross section with cylindrical cam follower 5021 at its inside end. The outside soil collection end creates the openable/closeable soil collection port 5602 at the peripheral portion of the blade assembly 5601. Slider 5630-4 includes a pair of radially-extending and opposing V-shaped guide protrusions 5639 extending outwards from each side of the slider body in opposite directions. The guide protrusions 5639 define upper and lower opposing angled guide surfaces which form an acute angle therebetween. Guide protrusions 5639 are each slideably received in a mating complementary configured and radially-extending V-shaped guide recess 5640 formed in opposing sides of radial slot 5603 (see, e.g. FIG. 240). Recesses 5640 are inwardly open towards radial slot 5603. The opposing outer major surfaces of the rectangular collection slider 5630-3 are exposed and visible in radial slot 5603 when mounted to the blade assembly 5601. This contrasts to the concealed portions of sliders 5630-1 and 5630-2 described above. Each half-section 5601-1, 5601-2 of the laminated blade assembly 5601 has an angled chamfered surface which forms one-half of the complete guide recess 5640 when the two half-sections 5601-1, 5602-2 of the blade assembly are joined together (see, e.g. FIG. 240). The guide protrusions 5639 are trapped within the recesses 5640 when the half-sections 5601-1 and 5601-2 are joined together, thereby captively retaining the slider 5630-4 in the laminated blade assembly without the need for external mounting hardware.

Soil Sampling Implements and Equipment

FIGS. 252-255 illustrate non-limiting examples of various implements configured to perform soil sampling and analysis, and the placement of the sample preparation sub-system 3002 and the chemical analysis sub-system 3003. FIG. 252 illustrates a planter 10 having a drawbar 15, a toolbar 14, and one or more row units 11 pulled by a motorized self-propelled wheeled tractor 5. For ease of access, the sample preparation sub-system 3002 and the chemical analysis sub-system 3003 can be placed at either end of toolbar 14 or on drawbar 15 (each possible position illustrated in the figure). This allows a user to access the sample preparation sub-system 3002 and the chemical analysis sub-system 3003 for maintenance or to replenish any materials.

FIG. 253 illustrates a combine harvester 20 having a collection area 21, a grain tank 23, a cross auger 22, a fountain auger 25, and a clean grain elevator housing 24. Sample system 3001 can be disposed to pull samples from collection area 21 or grain tank 23 and send grain to the sample preparation sub-system 3002 and the chemical analysis sub-system 3003, which can be disposed on combine harvester 20 such as on one or more available walls 26.

FIG. 254 illustrates a center pivot irrigation system 30 having a central pivot 31 one or more movable wheeled supports 16 (16-A, 16-B, 16-C, 16-D) with wheels 32 which rotate about central pivot 31, a common longitudinally-extending transport line conduit 34, one or more connection line conduits 35 (35-A, 35-B, 35-C, 35-D) fluidly coupled to the transport line conduit 34, one or more valves 36 (36-A, 36-B, 36-C, 36-D) (e.g. three-way valves shown or two-way valves) to selectively place transport line conduit 34 into selectable fluid communication with one of connection line conduits 35 (35-A, 35-B, 35-C, 35-D), one or more soil collection systems 3001 (3001-A, 3001-B, 3001-C, 3001-D) in communication with connection line conduits 35 (35-A, 35-B, 35-C, 35-D), a vacuum source 37 fluidly connecting transport line conduit 34 to a sample preparation sub-system 3002 and the chemical analysis sub-system 3003. Optionally, a pressure source 38 (e.g. air pump) can be disposed at an end opposite the central pivot 31 to provide a motive pressure force to move or convey samples through transport line 34 to the sample preparation sub-system 3002 and the chemical analysis sub-system 3003. Pressure source 38 may be used in conjunction with or instead of vacuum source 38. Valves 36-A, 36-B, 36-C, 36-D are in signal communication with CPU 2820 to provide selective opening from one soil collection system 3001-A, 3001-B, 3001-C, 3001-D for processing and testing of soil at a given time. As illustrated, there are four sections in this non-limiting embodiment, but center pivot irrigation system 30 can have fewer or more sections depending on the length of the transport line conduit 34 desired.

FIG. 255 illustrates a bailing system 40 having an accumulation frame 41, a conveyor 42, a pickup 43, housing 45, and baler 44. A sample system 3001 can be disposed to pull a sample from conveyor 42 and transport the sample via flow conduit 46 to the sample preparation sub-system 3002 and the chemical analysis sub-system 3003, which can be disposed on housing 45 or any other convenient mounting location on the bailer that does not interfere with the operation of bailing system 40.

Mass Determination of Collected Soil Samples

In order to analyze the collected soil sample and determine the desired chemical levels and characteristics such as nutrient content (i.e. ppm), and prepare the slurry with the desired water to soil ratio for processing, the amount (mass) of the raw soil sample processed through the systems and processes disclosed herein must be properly quantified and understood. Ideally, soil that does not have any moisture (e.g. sample which has been fully dried down) would be added to a known amount of water to create a slurry ratio used for downstream procedures/calculations. For example, adding 20 grams of dry soil to 40 mL of water would generate a 2:1 water to soil ratio. The amount of water added to generate this ratio is dependent on both the amount of soil collected as well as its initial moisture content (which pre-dilutes the slurry). Field collected soil samples however will very likely not be completely dry. In order to understand the collected soil makeup, mass and volume of the soil must measured to correctly and accurately calculate and prepare the finalized slurry water to soil ratio.

Some methods for "volumizing" and/or "massing" collected soil (or other agricultural related samples that might be processed in the present systems such as stalk mass, manure, etc.) will now be described. One assembly and method for volumizing the soil sample using sample collection/volumizing station 160-1 shown in FIGS. 14-18 has already been described elsewhere herein. Following are some additional examples and approaches for volumizing and/or massing the soil sample which includes both various indirect and direct methodologies.

Indirect Volume/Mass:

A pneumatic/hydraulic piston or electric linear actuator may be used to press the collected soil into a cylindrical "plug." This soil plug can be made using a consistent force from sample to sample, such that the density is better understood. By using feedback such as pressure and/or speed and/or electrical current and/or position of the piston or actuator, one can draw conclusions about the makeup of the soil. For example, if the soil compresses very little and then the measured pressure/force climbs rapidly, it can be concluded that the soil likely does not have a lot of moisture present. If the soil continues to compress as force slowly climbs, we may also make a conclusion about its texture (i.e.: sand, high organic matter) based on the response—in this case that the soil has a high organic matter content and is not dry. FIG. 281 is a graph depicting actual measured piston displacement vs. compressive force (psi) from testing performed on various soil types utilizing the compression apparatus shown in FIG. 282 as further described below. Each line in the graph represents a different soil sample, which were of different types and composition such as organic matter (OM), moisture content, particle size, etc. The graph demonstrates the effect that soil type and composition have on piston displacement and force required to compress the soil sample using the device of FIG. 282.

FIG. 282 depicts a compression apparatus 5900 which includes a compressing member 5902 coupled to an actuator be a hydraulic or pneumatic piston type or electric linear actuator 5907. The apparatus is configured and operable to compress a soil sample plug in conjunction with determining its "as collected" moisture content. By compressing the soil into a plug, it is possible to calculate the soil's volume based on piston or actuator position. This result can be used to calculate other required measurements (i.e. how much soil was collected, how much water will need to be added to make a slurry, etc.).

The apparatus 5900 includes an elongated hollow cylinder 5904 defining an internal cylinder bore or chamber 5905 which receives and holds the collected soil plug. Cylinder 5904 may be cylindrical with an annular circular cross-sectional shape that defines the chamber in one embodiment as illustrated. In one representative non-limiting example, a ¾ inch bore was used for processing soil samples. The apparatus includes an inlet 5903 for adding the soil sample to the chamber and an outlet 5906. The inlet may be adjacent to the top of the cylinder and the outlet may be at the bottom. The outlet may be controlled by an openable/closeable gate 5901 such as provided by a gate valve 5911 (represented schematically) which selectively closes or opens the outlet 5906. The gate 5901 is preferably flat and defines a top surface against which the soil is compressed by compressing member 5902 for compaction. The inlet 5903 may be a tube or piping segment which may be controlled by a gate valve 5911 or other type valve for adding soil to the cylinder at selected times. The compressing member 5902 is slideably movable vertically within chamber 5905 from an upper position to a lower position for compressing the soil sample. Other orientations of the apparatus and cylinder may be used in other embodiments including horizontal and a plurality of angular positions therebetween. Compressing member 5902 may have a cylindrical solid body and be coupled to actuator 5907 by an operating rod 5910 which may be cylindrical in one embodiment. FIG. 282 shows an example of actuator 5907 in the form of a hydraulic or pneumatic cylinder including an inlet 5908 for introducing a working fluid to activate the compressing member 5902 and an outlet 5909 for discharging the working fluid. The working fluid may be oil or air. The actuator may also be an electric linear actuator in some embodiments.

In operation of apparatus 5900, a soil sample plug is first added to chamber 5905 via inlet 5903 with compressing member 5902 being in an upper position. Actuator 5907 is then actuated either hydraulically, pneumatically, or electrically depending on the type provided. The soil sample is compressed as the compressing member moves downward towards the outlet of the cylinder 5904 into a lower position. As the compressing member moves to the lower position while compressing the soil sample, the compression force applied by the actuator is measured using a sensor 5912 which may be a force-type sensor or a position/displacement type sensor either of which are commercially available and known in the art. Sensor 5912 may be operably and communicably coupled via a wired or wireless communication link 5752 to transmit the measured force or displacement to the system controller 2820 which may control operation of the apparatus 5900. The measured force or displacement is then used by the controller to calculate the moisture content of the soil sample in its "as collected" condition to then determine the amount of water required to be added to the soil to achieve the desired predetermined soil to moisture ratio for creation of the soil slurry to be further analyzed by the systems disclosed herein.

Direct Volume:

Once the soil is in a closed container, the volume of the soil can be calculated using a derivation of the Ideal Gas Law. Using assumptions, the equation can thus be reduced to: $V1*P1/T1=V2*P2/T2$ where V1 is the volume of an independent reference container 5923 of fixed known volume, and V2 is the mixing chamber volume of the mixing container with blade assembly 141 minus the input soil and/or water plus the V1 chamber and any valves and passages. The mixing chamber may be provided by mixing container 101 of mixer-filter apparatus 100 in some embodiments, which has internal mixing chamber 102 that defines V2 (see, e.g. FIGS. 3-12) or variations thereof.

FIG. 284 is schematic diagram of one non-limiting embodiment of a volumetric and mass based analysis system 5999 for determining the mass and moisture content of a collected "raw" soil plug or sample utilizing mixing container 101 of the mixer-filter apparatus 100 previously described herein. The system shown includes equipment and provisions for volumizing the soil sample, adding water to form the slurry for further processing and analysis in the systems disclosed herein, and weighing the slurry using a weighing device. These foregoing basic steps are used and followed for preparing the water and soil slurry mixture in all instances described herein. Although the weighing device shown for convenience is a weigh coil 5960 described further below, it will be appreciated that the other weighing devices enumerated below may alternatively be used and substituted for the coil shown in the system of FIG. 284. Reference is also made to FIGS. 286 and 287 which shows an alternative arrangement of the mixing container 101 further described below and labeled with reference numeral 101A.

Referring now to FIGS. 284 and 286-287, the process for "volumizing" the soil sample using the "direct volume" method may be performed as follows in some embodiments. The process and system components/equipment which follow may be automatically controlled by programmable system controller 2820. Accordingly, the components/equipment are all operably and communicably linked to the controller 2820 via wired and/or wireless communication links 5752 described and shown elsewhere. Representative links 5752 are only shown in FIG. 284 to prevent obscuring the image. The fluid components and containers shown are fluidly coupled together in the manner shown by a suitable enclosed flow conduit 6006, which may be piping or tubing. Flow conduit 6006 in this portion of the system is an air conduit. Different flow conduits 6006 in system 5999 are used for different purposes defined by their location and uses in the system as shown in FIG. 284 and described herein. Accordingly, such flow conduits 6006 are designated with the common reference number 6006 for convenience whose purpose varies with the particular type of fluid handled.

Before the cycle begins, isolation valve 5921 between containers 101 and 5923 opens (via controller 2820) and a atmospheric/zero pressure reading may be optionally taken of volume V1 in container 5923 such as via a pressure sensor 5925. To record the pressure, the bottom drain valve 5927 associated with mixing container 101, which may be formed by vertically movable and sealable stopper 131 previously described herein in detail, is first placed in an open position thereby allowing the mixing chamber 102 (volume V2 of container 101) to reach ambient atmospheric pressure. With isolation valve 5921 open, the pressures between volumes V2 and V1 equalize thereby bringing the pressure measured inside volume V1 of container 5923 to the same atmospheric pressure which is measured by sensor 5925. After the pressure reading is taken by the sensor and received by programmable controller 2820 which closes the mixing container drain valve 5927 thereby sealing mixing chamber 102 inside mixing container 101. Isolation valve 5921 is also closed by controller 2820.

Next, the soil sample is then added to the closed mixing container 101 of known empty volume V2 (i.e. of mixing chamber 102) via a soil loading valve 5926 fluidly coupled to the soil inlet of the container, which may be a pinch valve 160 in some non-limiting embodiment as previously described herein. Other type valves of course may be used. An optional volumization step (similar to the Ideal Gas Law calibration and described further below) may occur here to determine the "bulk" density of the soil (soil with entrapped air). Either based on this volumization step or using sample collection assumptions, a known volume of water is then added to the soil via water pump 6100 through the water inlet of the container 101, which may be a positive displacement pump in some embodiments (e.g. micropump 5760 in FIGS. 256-258 or water pump 3304 in FIG. 261 previously described herein). Other type water pumps may of course be used, which could include a timed pressure over orifice pump. In some variations of the present process, the water may instead be added to mixing container 101 before the soil.

The soil loading valve 5926 is next closed after the water and soil are in mixing container 101. The soil/water mixture is blended via motor driven blade assembly 141 in the manner previously described herein to homogenize the sample and remove entrapped air. A vacuum may optionally be applied via a vacuum pump 5928 connected to mixing chamber 102 (shown in dashed lines) to further remove air and also reduce error in the P1/P2 measurement. With isolation valve 5921 still in the closed position, air inlet valve 5929 opens to "charge" the reference container 5923 (defining volume V1). After a few seconds, inlet valve 5929 is closed by programmable controller 2820 and the pressurized air is trapped in container 5923 (V1). The pressure sensor 5925 takes a reading P1 and temperature sensor 5930 records temperature T1 in container 5923 which are each recorded by the sensors and transmitted to controller 2820.

If not already done, controller 2820 closes all valves fluidly connecting to mixing container 101 (e.g. isolation valve 5921, soil loading valve 5926, drain valve 5927, etc.) which forms a pressure seal of mixing chamber 102 therein. Next, isolation valve 5921 opens and after equalization of pressures between containers 101 and 5923, a new pressure reading P2 is recorded by pressure sensor 5925 and temperature reading T2 is taken by temperature sensor 5920 operably coupled to mixing container 101. The temperature could alternately be read by temperature sensor 5930 in reference container 5923, such that only one temperature sensor is needed. It bears noting that any suitable commercially available mechanical and/or electronic temperature and pressure sensors may be used for this process, which are well known in the art without undue elaboration.

Using the actual readings recorded by the sensors, the slurry volume is next solved using equation: Vsoil+Vwater=V1+V2−(P1/P2)*(T2/T1)*V1 which may be executed and calculated by programmable controller 2820 via a suitable preprogrammed algorithm. It should be appreciated that the relationship of soil sample volume to sensor readings will likely not follow the Ideal Gas Law completely, and thus an alternative calculation that can be determined empirically through regression can model the system behavior. In this case, values such as P1/P2, $P2^2$, P1*P2, T2, et cetera may be used to determine the sample volume by applying factors and offsets.

For improved accuracy, the system can be made "robust" against changes in container volume and other disturbances that occur over time by means of a volume calibration. On an as-needed basis, a calibration procedure may be used which will add a known amount of water to the mixing chamber 102 of mixing container 101. The above steps can be followed to determine volume. This could be repeated with multiple volume levels to establish a relationship between pressure ratios and volume and used in the volume determination of soil slurry. Alternatively, the calibration could be done with an empty mixing chamber 102 or even by opening the chamber to another reference chamber similar to V1.

After the volumizing step is completed, a small reference portion (i.e. "representative sample") of the filtered slurry is extracted from mixing chamber 102 of mixer-filter apparatus 100 and directed to flow downstream to the weighing device (e.g. weigh coil 5960 as shown or other weighing device described herein) via slurry sample drain flow conduit 6006 controlled by openable/closeable reference slurry valve 6011. This small extracted portion or sample of slurry is representative of the water to soil ratio for the majority of slurry remaining in the mixing chamber 102 which will be used to determine the chemical characteristic/properties of the slurry (e.g. nitrogen, calcium, phosphorus, etc.). The weigh coil and other weighing devices allow determination of the weight of the slurry needed to determine the present water to soil ratio so that the amount of water needed to be added to the mixing chamber 102 (if any) to achieve the desired target water to soil ratio preprogrammed into controller 2820 may be achieved. The slurry weight determination methods and weigh devices are further described below under the discussion related to Direct Mass approaches.

FIG. 285 shows an alternative apparatus for the purpose of volumization. Volume can be measured by means of a level sensor 5941 in reference container 5940 of known dimensions and volume. A known amount of water is added to the soil which is placed in container 5940. The soil/water mixture is blended to homogenize the sample and remove entrapped air. A vacuum may then be applied to further remove air (e.g. vacuum pump 5928). The level of slurry mixture inside container 5940 is then measured using either (a) a continuous level sensor 5943 (e.g. ultrasonic, laser or capacitance), or by continually adding water to the container until a level switch 5944 is tripped in a sensing standpipe 5941 fluidly coupled to the bottom of the chamber in the container to indicate a known volume.

Referring to FIGS. 286 and 287, the alternative mixing container 101A noted above differs primarily from the previous apparatus 101 shown in FIGS. 3-21 in the rearrangement of the motor 126 to instead be mounted above. This avoids wetting the motor each time the slurry contents of the container are dumped out of the bottom of the mixing container 101A by opening the stopper 131 which serves as the container drain valve. The alternate mixing container 101A is similar in other respects which will not be repeated again here for sake of brevity. The soil loading valve 5926 and reference container 5923 previously described herein are also shown. FIG. 286 shows mixing container 101A in a closed position—stopper 131 engaged with and sealing the bottom container cleanout port 105. FIG. 287 shows the open position—stopper 131 displaced downwards and disengaging cleanout port 105 to dump the contents of the mixing chamber 102. The stopper assembly may be moved vertically and linearly between upper sealed and lower unsealed positions via a suitable pneumatic, hydraulic, or electric actuator 5945 (shown schematically) coupled to operating shaft 5946, or a plurality of actuators.

Direct Mass:

A first approach using a direct mass method for "massing" the soil sample utilizes the soil sample in a "field collected" condition which may be referred to a "dry" mass method (albeit the sample may have some initial moisture content in the condition extracted from the agricultural field). The term "dry" is used to connote that no additional water is added to the sample for processing at this point in process in order to determine its mass, in contrast to a "wet" direct mass method described below. Referring to FIG. 283, the soil sample can be transferred to a weigh container 5950 from the soil collection apparatus (which may be any of those disclosed herein or others). The container may be any suitable type of metallic or non-metallic container (e.g. polymeric) and shape. A cylindrical container may be used in one embodiment. The container 5950 is equipped with an openable/closeable gate 5951 at its base or bottom. Any suitable type of manual or automatically actuated (e.g. pneumatic, hydraulic, or electric) gate actuation mechanism 5953 may be used. The gate is initially closed while soil is loaded into the volumetric container such as via a soil loading pinch valve 160 of the type previously described herein, or another apparatus. After the soil is loaded, its mass can be determined by several methods. For example, a strain gauge 5952 may be attached to a rigid sidewall or bottom of the container 5950 at one end and to a rigid support structure S at an opposite end, thereby supporting the container in a cantilevered manner as shown. An initial strain gauge reading may be obtained with an empty or water filled container 5950. After loading the soil into the container, the added weight will cause the strain gauge to deform which can provide a second loaded reading which can be measured via the programmable controller 2820 operably coupled to the strain gauge. The differential in strain gauge readings can be used by the controller to quantify the mass and weight of the soil. For better sensitivity, the container 5950 could be lighter weight if the gate actuation mechanism 5953 were not rigidly attached to and supported by the weigh container, but instead supported separately via a suitable support structure. An example of this arrangement is shown in FIG. 288.

A "wet" direct mass method for "massing" the soil sample includes first adding water (moisture) to the collected sample and thoroughly mixing the mixture to produce slurry which can then be weighed. The method or process may include the following steps. Optionally estimate volume initially using the Ideal Gas Law method above with system shown in FIG. 284. Add a predetermined amount of water that ensures that the ratio is less than the final desired ratio (for example, add water to make a water to soil ratio of about 1.6 if targeting a ratio of 2.0). Mix the water and soil to prepare a slurry by blending using mixing container 101 or 101A. Pump (e.g. peristaltic or pressure) the slurry into a weighing device of known volume to obtain the weight of the slurry. The weighing device used may be any of the following examples of type devices described in further detail below.

A first example of a weighing device for weighing the slurry is a coiled weigh tube or "weigh coil" 5960 shown in system diagram of FIG. 284, and in isolation in FIG. 289. The weigh coil is preferably constructed with as few interruptions as possible and of similar diameter throughout, so as to avoid getting air pockets, and to improve clog-free flow and also cleanout. The weigh coil should also preferably be as thin walled as possible to keep weight to a minimum. A feature of the weight coil is having a fixed volume in order to calculate the density of the slurry. The coil 5960 may be valved at both inlet and outlet ends by inlet and exit/outlet valves 5961, 5962, as shown, or alternatively open to atmosphere in other embodiments (not shown). The weigh coil 5960 may be supported by a support structure, such as a tubing manifold block 5963 or simply a support structure without tube connection provisions. Strain gauge 5952 is coupled between the manifold block and coils of weigh coil 5960 for measuring the change in strain created by the downward deflection of the coils when loaded with slurry versus empty or water filled to determine the weight of the slurry. Any suitable commercially available strain gauge may be used for this or any of the strain gauges described herein.

FIG. 301 is a schematic diagram showing a slurry weigh station 6000 configured for weighing a small sample portion of the already mixed and prepared soil slurry with provisions for additionally volumizing the slurry mixture sample. This weigh station is located downstream of the volumizing and mixing system shown in FIG. 284, and thus receives the slurry sample from the mixer-filter apparatus 100. Station 6000 includes an example of a weighing device in the form of a slurry weigh container 6005 having an associated weigh scale 6004 for obtaining a direct weight of the slurry in the container. The design and arrangement of the weigh station 6000 with volumizing provisions is similar to that shown in FIG. 284 including many of the same fluid components. However, the mixer-filter apparatus 100 is replaced by simply the slurry weigh container 6005 of known volume V2 which is used in conjunction with reference container 5923. Since slurry weigh container 6005 contains no moving parts, blades, piston actuators, filters, etc. like the mixer-filter apparatus 100, it is easier to accurately measure the weight of the slurry by weighing the container once filled and comparing that to the tare weight of the container.

The weigh system 6000 further includes a slurry inlet valve 6001 fluidly coupled to the container inlet port 6007 at top via flow conduit 6006 and which receives the prepared slurry from mixer-filter apparatus 100, and waste valve 6002 fluidly coupled to the container outlet port 6008 at bottom. The reference container 5929 and other valving shown is the same as described for FIG. 284. In operation, a small representative sample of the mixed slurry is transferred from mixer-filter apparatus 100 shown in FIG. 284 through slurry valve 6011 and flows into internal chamber 6009 of a slurry weigh container 6005 after. The slurry sample volume is determined using the same Ideal Gas Law equations and methodology already described above with respect to FIG. 284. Accordingly, the entire "volumizing" step will not be described here for brevity. After the volumizing process of the slurry sample is completed, all valving to the container 6005 is closed and the slurry weight is measured by a scale 6004 coupled to the container (shown schematically in figure). The difference between the empty container (tare weight) and filled container 6005 allows determination of the actual slurry weight. Any suitable commercially-available scale may be used.

In yet another example of a weighing device, slurry fluid fills a known volume provided by a tubular container 5964 from the bottom and pushes air out the top as it fills. Container 5964 may have an elongated tubular body of relatively uniform diameter and includes a top outlet port 5966, bottom inlet port 5967, and an internal chamber 5965 extending between the ports along an axis. A three-way inlet valve 5968 may be fluidly coupled to inlet port 5967 via an enclosed flow conduit 5970 which may be tubing or piping. A three-way outlet valve 5969 is fluidly coupled to outlet port 5966 via a similar flow conduit. The remaining ports of the valves may be coupled to flow conduits as shown. FIG. 290 shows the valving position for filling container 5964 with slurry. FIG. 291 shows the valving positions for cleaning by introducing water in a reverse direction downwards through the container from above. The container 5964 is supported by a strain gauge (not shown) that measures the strain induced by deflection of the container under the weight of the slurry.

In yet another example, a "teapot" shaped container 5971 of known volume shown in FIG. 292 may be used as the weighing device and filled with slurry to the point of overflowing. The container includes upper slurry inlet port 5972, lower waste outlet port 5973 normally closed by waste valve 5976, and vent/overfill port 5974 at the uppermost portion or top of the container which fluidly communicates with atmosphere or an exhaust line connected to atmosphere. Each port is fluidly connected to internal chamber 5975 for receiving and weighing the slurry. Chamber 5975 may have a polygonal cross-sectional shape in some embodiments; however, other shaped chambers may be used. The slurry inlet port is controlled by isolation valve 5977. For cleaning, valve 5976 at the base opens for draining. The container 5971 is supported in a cantilevered manner by strain gauge 5952 which measures the strain induced by deflection of the container under the weight of the slurry.

In yet another example of a weighing device, the microfluidic pumping chamber 5765 shown in FIGS. 257-258 may be used.

After any of the foregoing weighing devices, the weight may next be determined such as via the strain gauge 5952 associated with each device. It bears noting that the slurry weight preferably should be a large part of the overall mass of any of the foregoing weighing devices to reduce noise when measuring dynamically. The weight measurement could be done on a continuous slurry flow basis (for better averaging) or by stopping the pump and taking a static weight measurement. The slurry inlet for the weigh chamber may be through a separate filter than the downstream filtered slurry for more volume or to allow larger particles into the weigh chamber of the devices. Accordingly, the inlet filter to the weighing device containers may have larger sized openings than the downstream filters.

Accordingly, the slurry weight measurement may be done by attaching the weighed portion of the weighing devices or containers (i.e. load cell) to a support structure by using a strain gauge according to any of the approaches described above.

Accordingly, the slurry could be recirculated back into the mixing chamber instead of being wasted in order to preserve the most sample according to any of the approaches described above.

Alternatively, other embodiments, the slurry weight measurement may be done by measuring sinusoidal response to sinusoidal or random system dynamic input. The slurry mass can thus be estimated by using the relationship between output frequency or natural frequency and mass in which the weight measurement is obtained by measuring frequency response of the weigh coil 5960 to a predetermined or random external excitation. For example, in the embodiment shown FIG. 293, the slurry may be loaded into the weigh coil 5960 and the coil is then excited by means of electromechanical plunger which strikes the coil with a constant fixed force. This frequency response weigh device assembly includes weigh coil 5960 supported in cantilevered manner from support structure 5963, a linearly movable excitation plunger 5978 which acts on a target surface defined by a vibration measurement protrusion 5980 integrally formed with or rigidly attached to the coil, and an electronic vibration sensor 5979. Sensor 5979 is positioned either proximate to but no contacting the vibration measurement protrusion 5980 for a non-contact type vibration sensor, or in contact with protrusion 5980 for contact-type vibration sensor. The sensor is configured and operable to measure the frequency response of the coil due to excitation by the plunger. The vibration measurement protrusion 5980 is located within the striking range of the plunger 5978. Any suitable type of contact or non-contact vibration sensor 5979 may be used, such as for example without limitation contact-type strain gauge based transducers, piezoelectric ("piezo") sensors, accelerometers, non-contact type capacitive or eddy-current displacement sensors, or others. The sensor 5979 is operable to transmit the measured vibration frequency of the weigh coil 5960 to system controller 2820.

The equation which describes natural frequency is:

$$fn = \frac{1}{2\pi}\sqrt{K/M} \text{ (cycles/second)}.$$

In operation, the plunger 5978 strikes the vibration measurement protrusion 5980 which induces vibration of the coil; the frequency of the vibrating coil being detected and measured by the sensor 5979. Because the natural frequency of the vibrating coil will change between an empty state and a weighted state filled with the slurry, the change in frequency response attributable to the weight of the slurry between these states can be measured by the frequency sensor and used by system controller 2820 to calculate the weight of the slurry. This change in frequency is thus correlated to the slurry mass/weight. When the massing/volumizing system is mounted on vehicle in motion traversing the agricultural field during soil sample collection, the material stiffness of the weigh coil 5960 will be chosen such that frequency of oscillation will be above disturbance frequency encountered by a vehicle moving over terrain thereby avoiding interference. It bears noting that the slurry may be weighed in either batch mode (i.e. fill and empty the coil between weight measurements) or by a continuous flow through the coil either of which is compared to a preprogrammed baseline "empty" frequency value stored in controller 2820.

In an alternative vibration frequency based weighing device shown in FIG. 294, an emitting piezo transducer 5982 excited at a specified predetermined frequency is mounted on one end of the weigh coil 5960 to excite the coil (i.e. induce vibration), and a separate receiving piezo transducer 5981 which may be used as a receiver may be mounted on the opposite end of the weigh coil. Each transducer is operably and communicable linked to the programmable system controller 2820 and their operation is controlled by the controller. The amplitude, frequency, or phase shift will be measured and then correlated to soil mass or weight by the programmable system controller 2820.

To isolate the tubing connections from affecting the weighing device or load cell and weight measurement accuracy, the strain in the weigh coil 5960 may be applied to a custom load cell 5983 that has the tube passage 5984 running through it with inlet and outlet fittings 5985, 5986 on each end for tubing connections as shown in FIGS. 297 and 298. Load cell 5983 may have a solid rectangular cuboid body in one embodiment; however, other shapes may be used.

In some embodiments, the fluid tubing connections themselves may be used as the strain gauge as shown in FIG. 295. Each straight end of the weigh coil is rigidly mounted to a support structure 5954 in a cantilevered manner as shown. A magnet 5988 is mounted to the coiled portion of the weigh coil at a side opposite the tubing ends which are on the same side of the coil. Loading the weigh coil with slurry causes the cantilevered coil to deflect downwards under the weight of the added slurry. This in turn changes the position of the magnet 5988 relative to a located proximity sensor 5989 such as a Hall effect sensor, which measures the change in magnitude of a magnetic field. The output voltage is directly proportional to the magnetic field strength and is transmitted to the system controller 2820. The controller compares an "empty coil" baseline voltage corresponding to the magnet field with the measured "full coil" voltage to correlate a weight of the slurry.

In yet other embodiments, the weigh coil 5960 tubing connections may be isolated for measuring the weight of slurry in the coil by docking and undocking the tube inlet and outlet end connections. This is shown in FIG. 296. Quick-connect type tubing connectors 5990 may be used which are commercially available. The weigh coil 5960 is supported in a cantilevered manner by the strain gauge 5952 having one end rigidly coupled to the coil and the opposite end rigidly mounted to a support structure 5954. Either the weigh coil or the tubing connections may be movable to dock and undock the weigh coil. Preferably, the docking connection is at least the highest point in the system to avoid any fluid loss (not shown). The weigh coil is first docked to fill the coil with slurry. The weigh coil is then undocked and the strain gauge measures the strain of the cantilevered coil which is transmitted to the programmable system controller 2820 for determining the weight of the slurry by comparing the measured strain to a preprogrammed baseline strain.

It bears noting that isolation mounting of the weighing device or load cell is important when determining mass to reduce some of the dynamic interference. Two possible methods for isolation are shown in FIGS. 299 and 300 for mounting certain configurations of weighing device other than a coil such as a container or other device with a frame or support member. In FIG. 299, isolation of the supported member 5991 of the weighing device is through a compliant material (such as rubber, NBR, SBR, etc.) of the vibration dampener 5992. In FIG. 300, isolation is achieved by the unique compliant structure and shape of the dampener 5992 which may include a central opening or multiple openings.

Returning now to the process of volumizing and massing the soil sample, once the small extracted slurry sample is weighed via any of the foregoing weighing devices, the water and slurry mixture can now be understood and characterized using the following equation to determine the percentage of water and soil content of the slurry: Volume soil=(Weight total−Volume Total*density water)/(density soil−density water). Assuming water density=1 and soil density=2.55 g/mL, if total volume is 10 mL and the total slurry weight is 13 g, then Volume soil=1.935 mL and therefore water volume is 8.065 mL and soil mass is 4.934 g. That gives a slurry ratio of 8.065/4.934=1.634. This value tells us the makeup of the homogenous slurry ratio remaining in the mixer-filter apparatus 100 since the small extracted portion of slurry which was weighed is representative of the slurry in the mixer-filter apparatus. To get the precise ratio output needed (i.e.: 2:1), the slurry volume left in the mixer can be re-volumized (using Ideal Gas Law). The appropriate amount of additional water needed to achieve the target desired water to soil ratio is then added to the slurry and remixed.

For making an accurate water to soil slurry ratio, it is important to be able to add the correct amount of water to the mixing chamber 102 of mixing container 101 or other device to which water will be added to the soil or slurry. One possible method for this is using multiple pumping chambers of varying volume. In one embodiment, to be able to get the correct amount of water, a selection of different size water pumps having different volumetric capacity pumping chambers can be utilized. For example, a 10 mL, 5 mL, 1 mL and 0.1 mL pump could be used in the following way: To add 44.2 mL of water, use 4×10 mL, 4×1 mL, 2×0.1 mL; or To add 37.6 mL of water, use 3×10 mL, 1×5 mL, 2×1 mL, 6×0.1 mL. Any suitable type water pumps may be used. In one embodiment, multiple different size stand-alone water diaphragm pumps 5760 having a configuration similar to that shown in FIGS. 256-258 may be provided for metering the proper amount of water for the slurry. Diaphragm pump can be a separate pump from diaphragm valves described below, or the diaphragm pump can be both a diaphragm pump and a diaphragm valve. When used throughout, a recitation to a diaphragm pump and a diaphragm valve refers to each individually or to a diaphragm pump that performs as both a pump and a valve.

In order to transport soil and/or slurry, it is important to not allow buildup or friction on various components. To reduce the possibility of this, portions of components which come into contact with the soil or slurry could be coated with a hydrophobic, super hydrophobic, omniphobic or fluoropolymer coating. Other components could be made from UHMW or HDPE or other low surface energy base material, such as fluoropolymers. Tubing could be made of a fluoropolymer, such as FEP (Fluorinated Ethylene Propylene) or other materials.

End users may want the option to use the device without the soil collection mechanism which automatically transfers the collected soil to the slurry mixing chamber 102 of the mixer such as mixing container 101. This would allow the device to be used on a lab bench or would allow the user to input soil using a different collection techniques (such as deeper cores). The mixing chamber could thus be outfitted with a funnel or container to allow the user to manually load the chamber in an alternate fashion.

Following is a high level summary of a method for preparing a soil slurry with desired target water to soil ratio for chemical analysis of the soil sample using the foregoing volumizing and massing techniques and apparatuses. The process to be described uses illustrative but non-limiting numerical values {in brackets} to more clearly demonstrate the process and parameters involved by example. It will be recognized, however, that the illustrative values do not limit the method or invention. The steps below may be all performed automatically by system controller 2820, manually, or a combination thereof.

The following assumptions may be made: There is a somewhat consistent volume of soil coming in, which has a somewhat consistent density across all samples; "Particle" density of soil is constant (same across all soils); Effects of atmospheric temperature, pressure, etc. are limited or are empirically calibrated out; Temperature effects from pressurizing/depressuring are negligible; Final slurry target output ratio is 3:1 (water mass to soil mass); and Water density is constant (1 g/mL).

With these assumptions, the method or process includes the following basic steps with initial reference to FIG. 284 showing the volumetric and mass based analysis system 5999 previously described herein for determining the moisture content of a collected "raw" soil plug or sample utilizing mixing container 101 of the mixer-filter apparatus 100.

Mixing chamber 102 (V2) of mixer-filter apparatus 100 is prepared to receive the raw soil by closing the drain valve 1131 and closing the main and reference slurry outlet valves 6010, 6011 (filtered slurry to downstream and filtered slurry to weigh coil). The water pump 6100 accurately dispenses a preprogrammed predetermined volume of water {100 mL} into the mixer and the motor is turned on slow speed {1,000 rpm}.

A preprogrammed predetermined amount of soil is then blown from the collection device via a pulse of pressurized air from the air compressor associated with the soil collection system or air compressor 3030 (see, e.g. FIG. 1) into mixing chamber 102 via soil loading valve 5926 (e.g. pinch valve 160) {-38.5 mL of 5% gravimetric water content soil—47 g soil and 2.474 g water}. The soil loading (pinch) valve 5926 is then closed. Alternatively, the soil may be added first to mixing chamber 102 and followed by adding the predetermined volume of water.

The water/soil mixture is blended into a homogeneous slurry by pulsing the mixer at high speed {15,000 rpm}, then slowed to stirring {600 rpm}. Slurry ratio is set {(100+2.474)/47=2.18}.

The filtered slurry to weigh coil 5960 reference slurry drain valve 6011 is opened and begins to waste out. The soil is then "pumped" by pressuring the V2 volume mixing chamber 102 {15 psi} via air compressor 3030 or another air source into weigh coil 5960. During this time, continuous weight (e.g. via strain gauge or other coil weighing techniques described above) readings {13 g} are taken on the weigh loop. Slurry ratio is calculated, either manually or via system controller 2820.

Volume soil=(Weight total−Volume Total*density water)/(density soil−density water) Assuming water density=1 and soil density=2.55 g/mL, then Volume soil={1.524 mL} and therefore water volume is {8.476 mL} and soil mass is {3.887 g}. That yields a slurry ratio of 8.476/3.887={2.18}.

The filtered slurry to weigh coil reference slurry valve 6011 closes and air pumping pressure is removed.

Since the current slurry's water-to-soil ratio is now known, the proper adjustment can be made to move to an example target ratio of 3:1 water to soil once we know the volume of slurry remaining. The controller 2820 may compare the now known initial water to soil ratio to a target water to soil ratio preprogrammed into the controller. Alternatively, this comparison can be performed manually. Next, air supply pressure air inlet valve 5929 opens to "charge" the V1 volume chamber defined by reference container 5923 with air. After a few seconds, valve 5929 closes and the pressurized air is trapped in volume V1 of the reference container. The pressure sensor 5925 takes a reading (P1).

All valves fluidly connected to volume V2 of the mixer-filter apparatus mixing chamber 102 are closed to create a sealed chamber or volume. This includes stopper 131 (outlet valve 5927, and slurry valves 6010, 6011 fluidly coupled to mixing chamber 102 through the stopper assembly. Next, isolation valve 5921 opens and after pressure equalization with the reference container 5923 now in fluid communication through the valve with mixing chamber 102, a pressure reading (P2) is taken.

The slurry volume is next solved: V slurry=V1+V2−(P1/P2)*V1*calibration factor. V1={150 mL} and V2={150 mL} in one embodiment. V slurry=150+150−(45 psia/33 psia)*150*1.1={105 mL}. Slurry ratio=Water Mass/Soil Mass=Vol water*1/Vol soil*2.55={2.18}. Vol water+Vol soil={105 mL} therefore Vol water={2.18*2.55*105/(2.18*2.55+1)=88.99 mL} and Vol soil={105−88.99=16.01 mL=40.826 g}.

To produce the desired target 3:1 water to soil ratio: {40.826 g*3=122.48 g} of additional water is needed. Since we already have {88.99 mL} of that amount of water, need to add {33.49 mL} more water to the existing slurry mixture. The water pump 5924 accurately dispenses the additional water {33.49 mL} into the mixer 100 and the motor 126 is turned on {15,000 rpm} to re-homogenize the slurry mixture with the added amount of water. The target 3:1 water to soil ratio is thus achieved.

With the fully prepared soil slurry now having the final water to soil ratio of 3:1, the motor is idled and the filtered slurry is then pumped to any of the downstream processes previously described herein for chemical analysis via first opening the main slurry outlet valve 6010 with the main bottom drain valve 5927 (e.g. vertically movable stopper 131) of mixing container 101 remaining in the sealed closed position to seal the mixing chamber 102 of mixer-filter apparatus 100. Air pressure is again applied to mixing chamber 102 by air compressor 3030 or another air source as before which drives the soil slurry to the next downstream station via slurry outlet valve 6010 for chemical processing and analysis as indicated in FIG. 284. After removing the slurry for chamber analysis, the main the bottom drain valve 5927 associated with mixer-filter apparatus 100 (e.g. stopper 131) is opened to purge and dump the excess slurry remnants in the mixing chamber 102. A cleaning cycle follows to prepare for the next sample by rinsing the mixing chamber 102 with filtered water.

Variations in the foregoing sequence/steps and components of the method or process are possible.

Utilizing the system of FIG. 284, basic steps which may be automatically controlled and operated by the programmable controller 2820 may be as follows via suitable preprogrammed computer instructions or control logic. The controller may be configured to: open the soil inlet loading valve 5926 to add the soil sample to the mixing chamber; operate the water pump to add water to the mixing chamber 102; operate the mixer blade assembly to prepare the slurry; open the reference slurry outlet valve 6011, whereby a portion of the slurry flows into the weighing device 5960; and obtain a weight of the slurry from the weighing device. The controller may be further configured to add additional water to the slurry in the mixing chamber in accordance with a preprogrammed target water to soil ratio, operate the blade assembly again to remix the additional water and slurry, open the main slurry outlet valve 6010 to transfer the remixed slurry to any of chemical analysis systems and/or devices previously described herein to measure an analyte in the remixed slurry.

Process Water Filtration System

FIGS. 264-266 show a system and select components for filtering process water for use in the soil sample analysis processing systems disclosed herein. The process water is used for creating the soil slurry and/or cleaning portions of the sample processing system between different sample runs. These figures show one non-limiting embodiment in which the water filtration system 5751 which may be mounted on the soil sample collection/processing vehicle in one embodiment. In essence, the vehicle is a portable and mobile sample collection/processing lab on wheels. In other embodiments, the water filtration system may be mounted on a stationary support or apparatus. One possible embodiment of a wheeled and self-propelled sample collection/processing vehicle 5750 is shown which may include an electric or internal combustion engine coupled to a conventional drive train which drives the wheels to power the vehicle through the agricultural field. The vehicle has an on-board power supply. Other types of vehicles, some of which are disclosed herein, may of course be used. The type of self-propelled vehicles or agricultural equipment, or pulled vehicles or equipment may be used and is not limiting of the invention in any respect.

As shown, the water filtration system 5751 is mounted on vehicle 5750 along with the sample processing "factory" 5747 which includes the sample preparation sub-system 3002 and chemical analysis sub-system 3003 and its components, the sample probe collection apparatus 5748 which includes sample probe collection sub-system 3001, and processor-based programmable controller, such as for example central processing unit (CPU) 2820. The programmable controller may be operably and communicably coupled via communication wired and/or wireless communication links 5752 to the water filtration system 5751 components and sub-systems 3001-3003 components to control part of or the entire soil sample collection and chemical processing/analysis from start to finish. An interactive user interface touch screen display device or a processor-based personal electronic device such as an electronic pad (e.g. iPad, etc.), laptop/notebook, cell phone, or other may be provided which is operably and communicably coupled to the system controller 2820 via communication link 5752. Such user interface devices are collectively represented and designated by reference numeral 5749 in the figures.

Referring to FIGS. 264-266, water filtration system 5751 may include in fluid communication and flow order an onboard raw water tank 5740, at least one filter unit 5743, or optionally two filter units 5743 and 5744, and a purified or filtered water tank 5741. These components may be fluidly coupled together in a serial flow path as shown via suitable enclosed flow conduit 5746 which may be piping or tubing. Raw water tank 5740 includes an inlet water fill port 5756 for filling the tank with water from an available water source, and an outlet port fluidly coupled to the first filter unit 5743. The inlet port of filtered water tank 5741 is fluidly coupled to second filter unit 5744 and the outlet port is fluidly coupled to the factory 5747 via flow conduit 5746. This section of flow conduit may include an openable/closeable valve 5745 to control the supply and timing of filtered water to the factory. Similarly, another valve 5745 may be provided to regulate flow of raw water to the train of filters 5743, 5744. The valves may be configured for an open position, closed position, and partially open or throttle positions therebetween. Operation of the valving and the control of raw and filtered water may be automatically controlled by system controller 2820 via communication links 5752 in some embodiments. One or both of the valves may be manually controlled in other implementations. A level sensor 5753 operably and communicably coupled to the controller 2820 may be mounted to filtered water tank 5741 which is operable to measure the liquid level in the tank in real time. Sensor 5753 controls the supply and level of filtered water in tank 5741 available for the process. When the level drops to a preprogrammed setpoint value, the controller may open the raw water valve 5745 to process and filter additional water from raw water tank 5740 to replenish the support of filtered water in the filtered water tank 5741.

Various other types of filtered water system sensors 5754 may be provided which are linked to programmable system controller 2820 such as for example without limitation unprocessed and processed water quality sensors (e.g. resistivity/conductivity, temperature, etc.). These sensors may be located anywhere in the filtration system, including in the tanks or flow conduits.

In some embodiments, the two-stage water filtration process shown may be used to produce highly purified water for the soil analysis system. For example, filter unit 5743 may be a particulate filter to remove sediment and particulate matter suspended in the raw water. The second filter unit 5744 may be used to further refine water quality, and may be an ion exchange filter, or other filtration device such as without limitation a reverse osmosis unit, UV purification unit, carbon filtration unit, etc. FIG. 267 shows an example of a particulate filter unit such as the type which may be used for filter unit 5743. Filter unit 5743 may include a housing 5743-1 defining an internal cavity 5743-2 which contains a porous filter media 5743-3. The filter media may be cylindrical and tubular in shape in some embodiments. Any suitable filter media may be used, including paper, fabric, polymer, sintered metal, etc. Any suitable flow path may be used internally within the filter housing.

In operation and flow sequence, water from raw water tank 5751 flows through filters 5743 and 5744, and into the filtered/purified water tank 5741. The filtered water is held in tank 5741 until demanded by the factory 5747, at which time the system controller 2820 opens the normally closed filtered water valve 5745 to provide filtered water (see directional water flow arrows).

In some embodiments as shown in FIG. 265, certain factory operations (e.g. component flushing/cleaning) may not require fully processed (filtered/purified) water and minimally filtered water may suffice. In this case, some water may bypass a portion of filtration train via a bypass flow conduit 5755 and flow directly to the factory 5747 and bypass filter unit 5744. The bypass conduit may be automatically controlled by controller 2820 which may be operably and communicably coupled to bypass valve 5745 via communication link 5752. All other aspects of the filtered water system 5751 shown in the present embodiment with filtered water bypass are the same.

In some cases, the capacity of the filtered water tank 5741 may be sufficient to meet the needs of an entire soil sampling and processing run through the agricultural field. Accordingly, FIG. 266 shows an example of a filtered water system without raw water tank 5740. In this case, raw water from an available source is provided to water fill port 5746 via a suitable flow coupling and fluidly coupled via flow conduit 5746 and raw water supply valve 5745 directly to filter unit 5743. Raw water is immediately processed and filtered to fill filtered water tank 5741 to capacity, which may have a larger volumetric capacity than the filtered water tank used in the raw water batch processing mode embodiments previously described herein. All other aspects of the filtered water system 5751 shown in the present embodiment without a raw water tank are the same.

Alternative Centrifugation Apparatus for Supernatant Separation

In lieu of using pivotably movable or swinging centrifuge tubes 3450 in the centrifuge 3400 assembly for separating the supernatant from the soil slurry as previously described herein, FIGS. 268-280 depict an alternative embodiment of a rotary supernatant extraction apparatus 5800 for extracting the supernatant from the slurry using centrifugation. In the present embodiment, a disk-shaped fluid plate 5801 is provided which is specially configured with a plurality of fluid passageways and chambers designed to perform the supernatant extraction with no movable parts (unlike tubes 3450) that move relative to the body of the plate itself, as further described below.

The rotary supernatant extraction apparatus 5800 has a generally disk-shaped or "saucer-like" body and includes including an upper or top fluid plate 5801, lower or bottom clamping plate 5802, and an intermediate or inner gasket 5803 interspersed between the plates. The plates and gasket may have a generally annular disk-shaped circular configuration for centrifugation with central openings 5801-3, 5802-3, and 5803-3 which may be coaxially aligned with rotational axis RA for passage of the centrifuge drive shaft 3700 therethrough. This present alternative assembly replaces the top and bottom covers 3520, 3521 that hold centrifuge tubes 3450 (see, e.g. FIGS. 67 and 76) and is mounted below and in selective fluid communication with the stationary fluid exchange manifold or dock 3430 at the same relative position in the centrifuge 3400 as further shown in FIG. 53. The rotary tube hub 3500 coupled to the drive shaft 3700 is disposed between the fluid plate 5801 and clamping plate 5802, and passes completely through the gasket 5803 in a complementary configured central through opening 5805. The spoke-shaped rotary tube hub 3500 with multiple radial projecting arms is interlockingly engaged with the plate and gasket assembly to rotate the assembly via the centrifuge for separating the supernatant from the soil slurry. To accomplish this, bottom surface 5801-2 of upper fluid plate 5801 and top surface 5802-2 of the lower clamping plate 5802 each include a locking recess 5806, 5804 respectively which are complementary configured to and receive the rotary tube hub 3500 and its radial spokes/arms as shown. Accordingly, locking recesses 5806, 5804, which extend partially through the thickness of the fluid and clamping plates 5801, 5802, may have a spoke shape and dimensions which generally corresponds to the shape and dimensions of the hub in the illustrated embodiment. When the plates are coupled together, the rotary tube hub 3500 is thus locking into and trapped between the plates in the recesses. The inner gasket 5803 in turn is trapped as well between the plates. The rotary supernatant extraction apparatus 5800 is fixedly mounted to the main drive shaft 3700 and piston support tube 3604 in a similar manner to top and bottom covers 3520, 3521 of the centrifuge tube 3450 assembly, and movable upwards and downwards with the shaft to dock and undock the extraction apparatus for centrifugation of the soil slurry sample.

The fluid plate 5801 and clamping plate 5802 preferably may be made of a polymeric or plastic material in one embodiment for weight reduction, which may be injection molded or cast. The fluid plate 5801 may be transparent or translucent in some embodiments to allow visual inspection of the fluid and flow features in the plate further described below for slurry sediment residue. In other possible embodiments, one or both of the plates may be made of a preferably lightweight metallic material.

Clamping plate 5802 has a disk shaped circular body including planar major top surface 5802-1 and opposing planar major bottom surface 5802-2. The outer peripheral side 5802-4 of the plate may be vertical and planar as shown, or have a non-planar side profile. The top surface may be parallel to the bottom surface. The clamping plate 5802 has a circular central opening 5802-3 for receiving the centrifuge shaft therethrough.

Microfluidic processing disk 4000 is configured and operable to form a detachable fluid coupling to the fluid plate 8501 carried by the rotary tube hub 3500 through the intermediary stationary fluid exchange dock 3430 of the centrifuge 3400, as previously described and shown herein. Fluid exchange dock 3430 is fluidly coupled and interposed between the microfluidic processing disk 4000 mounted on top of the dock and fluid plate 8501.

With continuing general reference to FIGS. 268-280, fluid plate 5801 has a disk shaped circular body including planar major top surface 5801-1 and opposing planar major bottom surface 5801-2. The outer peripheral side 5801-4 of the plate may be vertical and planar as shown, or have a non-planar side profile. The top surface may be parallel to the bottom surface. The bottom surface 5801-2 includes a plurality of specially designed fluid passageways and enlarged reservoirs or chambers recessed into the surface which extend partially through the top-to-bottom thickness of the fluid plate's body, but not penetrating its top surface 5801-1 (best shown in FIGS. 270 and 276). The fluid passageways and chambers are grouped or clustered into a plurality of discrete supernatant separation features or devices 5807 configured to separate and extract the supernatant from the soil slurry via rotary centrifugal action. Unlike the swinging centrifuge tubes 3450 which provide a similar function, the rotational acceleration of the present rotary supernatant extraction apparatus 5800 causes the fluid to flow both radially and tangentially within the fluid passageways when centrifugated whereas the centrifuge tubes produce primary inside to outside radial fluid motion alone.

The supernatant separation devices 5807 are spaced circumferentially apart around the fluid plate 5801 and arranged symmetrically in different sectors of the fluid plate. This allows multiple soil samples to be processed simultaneously in each device for different chemical properties/constituents in a single centrifugation cycle. Each separate device 5807 comprises a plurality of fluidly interconnected fluid passageways 5808 and a sediment chamber 5809 configured and arranged to provide the functions of separating and extracting the supernatant from the soil slurry fluid, and then flushing accumulated residual sediment from the passageways and chamber after separation using preferably filtered water.

It bears particular noting that each chemical processing wedges 4002 of microfluidic processing disk 4000 has its own dedicated and corresponding supernatant separation device 5807 which is fluidly isolated in fluid plate 8501 and the rotary supernatant extraction apparatus 5800 from every other flow element. When the processing disk 4000 and supernatant extraction disk assembly are mounted in the centrifuge 3400, the supernatant separation device 5807 associated with each processing wedge 4002 is located directly beneath it and in fluid communication through the fluid ports in the stationary fluid exchange dock 3430 interposed between processing disk 4000 and rotary supernatant extraction apparatus 5800.

FIG. 271 shows the bottom surface of fluid plate 5801 with plural supernatant separation devices 5807 arranged in different sectors of the disk-shaped plate. This figure shows four different examples and configurations of supernatant separation devices 5807A-D for convenience, bearing in mind that the fluid plate 5801 may typically contain a plurality of supernatant separation devices of a single configuration, or alternatively may include a combination of two or more different device configurations. Each supernatant separation device however has fluid elements in common albeit the specific configuration of those common elements may be different as seen.

Each supernatant separation device 5807A-D formed in the bottom of the top fluid plate 5801 includes a fluidly interconnected cluster of fluid passageways 5808 including a fluid inlet passageway 5808-1, fluid outlet passageway 5808-2, supernatant extraction passageway 5808-3, and sediment chamber 5809. Each passageway is fluidly connected separately to the sediment chamber and now to each other forming three discrete flow passages only fluidly interconnected via the sediment chamber, as shown. The passageways 5808 and sediment chamber 5809 are recessed into the bottom surface 5801-2 of fluid plate 5801 and downwardly open before the fluid plate 5801 is assembled to gasket 5803 and bottom clamping plate 5802 (see, e.g. FIGS. 270 and 271). The passageways and sediment chamber may be formed integrally with injection molding or casting of the fluid plate 5801, machining, or combinations thereof.

The fluid passageways 5808-1, 5808-2, and 5808-3 are elongated structures which may be in the form of channels or grooves in the fluid plate 5801. The passageways may each have a substantially uniform polygonal or non-polygonal cross-sectional flow area in some embodiments with corresponding generally uniform lateral width for a majority or substantially the entirety of their lengths. Other embodiments may vary in cross-section and/or width. The passageways are oriented and extend horizontally along the bottom surface 5801-2 of fluid plate 5801. Preferably, the supernatant extraction passageway 5808-3 preferably has a smaller width and/or cross-sectional flow area than the fluid inlet passageway 5808-1 and fluid outlet passageway 5808-2 to reduce the likelihood of pulling sludge from sediment chamber 5809 when the supernatant is extracted therefrom. The passageways each may have a non-linear Each fluid passageway 5808-1, 5808-2, and 5808-3 of each supernatant separation device 5807A-D in fluid plate 5801 has one end fluidly connected separately to sludge or sediment chamber 5809, and an opposite end terminated with a vertical fluid port 5810-1, 5810-2, 5810-3 which extends upwards through the fluid plate 5801 and penetrates its top surface 5801-1 (see, e.g. FIG. 276) for fluid connection to mating ports formed in the stationary fluid exchange dock 3430 of centrifuge 3400. The layout or pattern of the ports in the fluid plate 5801 and dock 3430 therefore match so each may become concentrically aligned when the fluid plate 5801 docks with the dock to exchange fluids (analogous in function to that shown in FIG. 72 for covers 3520, 3521 in the pivoting centrifuge tubes 3450 embodiment). The fluid passageways 5808-1, 5808-2, and 5808-3 each may have a non-linear circuitous configuration such that there is no straight line of sight between the ends connected to the sediment chamber 5809 and its respective vertical fluid port 5810-1, 5810-2, 5810-3. However, it bears noting that each fluid passageway may include linear/straight sections and angled or arcuately curved sections as shown in FIGS. 271-275. The fluid passageways are configured and arranged with respect to the sediment chamber 3809 to minimize entry of the remaining soil sludge or sediment into the passageways when the centrifuge 3400 slows down and stops, thereby preferably retaining a majority of the sediment in its chamber.

The location of the vertical fluid ports 5810-1, 5810-2, 5810-3 of the fluid passageways 5808-1, 5808-2, and 5808-3 are predetermined and designed to optimize the performance and function of each port for extracting the supernatant from soil slurry sediment, exchanging fluids with the fluid exchange dock 3430, and rinsing/cleaning the passageways and sediment chamber 5809 after each centrifugation cycle when the rotary supernatant extraction apparatus 5800 is stationary and docket in the centrifuge 3400. The port layout is therefore not random. In one embodiment, each supernatant extraction fluid port 5810-3 is preferably positioned closest to the center or axis of rotation RA of the rotary supernatant extraction apparatus 5800 than the other vertical fluid ports so that (1) it would be the least likely to get contaminated with "sloshing" sludge solution during centrifugation, and (2) because matching the longest flow path of the supernatant extraction fluid passageway with the cleanest fluid (i.e. clear supernatant) helps reduce the passageways that need rinsing and cleaning after each centrifugation cycle.

As the inverse of the supernatant extraction port 5810-3 being the radially innermost port, the outlet of high-density soil sediment waste from the sediment chamber 5809 of the centrifuge should preferably have the shortest path length possible to minimize or prevent blockage. Accordingly, the fluid outlet port 5810-2 from the sediment chamber 5809 may be the radially outermost port. The fluid inlet port 5810-1 may therefore be the radial middle port between ports 5810-2 and 5810-3. Thought of one way, the vertical fluid ports are organized radially inward-to outward from cleanest to dirtiest or densest fluids handled. In other possible embodiments, however, the vertical fluid ports 5810-1, 5810-2, 5810-3 may be at the same radial distance from the center or axis of rotation RA of the rotary supernatant extraction apparatus 5800 (which coincides with axis RA of the centrifuge 3400). In yet other possible embodiments, some or all of the fluid ports may be on the bottom or outer radial sides of the fluid plate 5801.

In some embodiments, each of the fluid ports 5810-1, 5810-2, 5810-3 may be axially aligned with a radial centerline RC of each supernatant separation device 5807A-D. This facilitates and simplifies the fluid exchange arrangement with mating clusters 3433 of flow passages 3434 in the fluid exchange dock 3430 (see, e.g. FIGS. 55-56) for transferring fluid to and from the fluid plate 5801.

The sediment chamber 5809 is dimensionally larger than the passageways at least in maximum lateral width (measured transversely to the rotational axis RA of the centrifuge 3400 in the plane of the rotary supernatant extraction disk 5800, and greater in volumetric capacity to accumulate sludge or sediment solids for separating the supernatant liquid out. Sediment chambers 5809 may have symmetric or asymmetric configurations selected to optimize the separation of supernatant from the soil slurry or fluid and deposition of the remaining sludge or sediment in the chamber. In some embodiments, as shown in FIGS. 272 to 275, each sediment chamber 5809 may be located generally between supernatant extraction passageway 5808-3 and fluid inlet passageway 5803-1 which have a generally radial orientation (allowing for portions which extend circumferentially).

The sediment chambers 5809 may be located preferably in the peripheral regions of the annular disk-shaped fluid plate 5801 beyond central locking recess 5806 nearer the peripheral sides 5801-4 than the central opening 5801-3 (see, e.g. FIG. 271). The fluid ports 5810-1 to 5810-3 are preferably located radially inside the sediment chambers as shown. When the fluid plate 5801 is centrifugated, the soil slurry will be driven radially outward by centrifugal force such that the denser/heavier sludge or sediment accumulates in the outward region of each sediment chamber 5809 while the less dense/lighter clear supernatant accumulates in regions more inwards thereof.

A brief description of the layouts/designs of fluid passageways and sediment chambers of the different example supernatant separation device 5807 configurations disclosed herein will now be provided. FIG. 272 shows a first embodiment of supernatant separation device 5807A also seen in FIG. 271. The layout provides long gentle arcuate curves for easy rinsing and cleaning of the fluid passageways 5808-1 to 5808-3. During spin up of the centrifuge 3400, this layout provides a low-volume spillway (left of the radial centerline RC) for sloshing the soil slurry-supernatant mixture. During spin down, this design more aggressively cradles the compacted sediment solids (left of "X") from moving and thus preventing fluid re-agitation of the sediment.

FIG. 273 shows a second embodiment of supernatant separation device 5807B also seen in FIG. 271. During spin up, the slurry-supernatant mixture is cradled into the area of the sediment chamber 5809 marked "X") and hold clear supernatant liquid to the right of and left of radial centerline RC to prevent back flowing the supernatant out of the passageways and ports.

FIG. 274 shows a third embodiment of supernatant separation device 5807C also seen in FIG. 271. This layout is intended to: (1) be easy to fill the passageways and sediment chamber with slurry and rinse/cleanout after centrifugation (note minimal number of corners or large spaces); (2) keep most of the clear supernatant fluid as close to the ports 5810-1 to 5810-3 as possible (i.e. minimal pumping needed to extract supernatant); and (3) during spin up, bias the slurry-supernatant mixture or solution from pushing radially inwards into the supernatant extraction passageway 5808-3.

FIG. 275 shows a fourth embodiment of supernatant separation device 5807D also seen in FIG. 271. This layout is intended to: (1) during spin up of centrifuge 3400, bias the slurry-supernatant mixture/solution to the left of the radial centerline RC to prevent pushing the slurry solution out of fluid passageways and ports 5810-1 to 5810-3; (2) during spin down, cradle the compacted sediment solids to the left of "X" to prevent remixing with the supernatant in supernatant extraction passageway 5808-3; (3) provide plenty of relief spaced around the area of compacted soil sediment particularly in sediment chamber 5809 for easy rinsing/cleaning of the chamber and passageways.

In all of the embodiments of supernatant separation devices 5807A to 5807D, it bears noting that supernatant extraction passageway 5808-3 and all ports 5810-1 to 5810-3 are radially inwards of the outermost portion of the sediment chambers 5809 to minimize chances of drawing the residual sludge or sediment in the chambers out with the clear supernatant.

To improve sealing of the fluid passageways 5808-1, 5808-2, and 5808-3 and sediment chambers 5809 in the underside of fluid plate 5801 with the gasket 5803 when the plate assembly is coupled together, each passageway and chamber may include a complementary configured raised sealing lip 5811. Referring to FIGS. 277-279 which show the bottom surface 5801-2 of fluid plate 5801, sealing lips 5811 outline and extend for the entire perimeter of the fluid passageways and chambers on all sides to completely seal them in a fluid tight manner when the gasket 5803 is compressed against the fluid plate by the lower clamping plate 5802. In one, the fluid plate 5801, clamping plate 5802, and gasket 5803 may be coupled and clamped together by a plurality of threaded fasteners 5812 which are inserted through mounting holes 5813 formed in the plates and gasket (see, e.g. FIGS. 269-270). Holes 5813 in clamping plate 5802 may be tapped and threaded to engage the fasteners. Other types of fasteners or mechanical coupling devices may be used, such as rivets, adhesives, ultrasonic welding, etc. The mounting holes 5813 may be arranged in relatively close proximity to the fluid passageways and sediment chambers to provide tight sealing thereof by the gasket.

In yet other embodiments, the lower clamping plate 5802 and gasket 5803 may be eliminated the fluid passageways 5808 and sediment chambers 5809 be may formed entirely internally within the fluid plate 5801 having a suitable thickness. This can be readily visualized with reference to FIG. 276 without need for further illustration by picturing the fluid passageways and chambers disposed between, but not penetrating the top or bottom surfaces 5801-1, 5801-2 of fluid plate 5801 except for the fluid ports 5810-1, 5810-2, 5810-3.

Operation of the rotary supernatant extraction apparatus 5800 with supernatant separation devices 5807 will now be briefly described. The apparatus may include any of the supernatant separation device 5807A-D designs described herein. The process or method for separating supernatant from a soil slurry mixture starts with apparatus 5800 in an upper position docked and fluidly coupled to fluid exchange dock 3430 to exchange fluids (analogously similar to that shown in FIG. 72 but substituting the rotary apparatus 5800 of the centrifuge tubes 3450). The supernatant and slurry mixture may be pumped by and transferred simultaneously from the analysis processing wedges 4002 of microfluidic processing disk 4000 to the fluid inlet ports 5810-1 and fluid inlet passageways 5808-1 of each supernatant separation device 5807 in fluid plate 5801. The slurry mixture flows through each passageway 5808-1 into its respective sediment chamber 5809. It bears noting that some slurry mixture may occupy portions of the various fluid passageways as well. In systems which do not utilize the compact microfluidic processing disk 4000, the slurry pump 3333 such as shown in FIG. 78 may pump the slurry and supernatant mixture to the rotary supernatant extraction apparatus 5800. In this figure, it bears noting that the apparatus replaces the centrifuge tubes 3450 of the centrifuge 3400.

Once the slurry mixture is transferred, the supernatant extraction apparatus 5800 is then lowered and undocked from the fluid exchange dock 3430 of centrifuge 3400 (analogously similar to that shown in FIG. 73). The supernatant extraction apparatus 5800 is then rotated to separate the clear supernatant from the slurry leaving behind concentrated solids (sludge or sediment) primarily in the sediment chamber 5809 (analogously similar to that shown in FIGS. 74-75). During centrifugation, the solids will be driven radially outwards into and accumulate in the outermost portions of the sediment chamber by centrifugal force. The clear supernatant will accumulate radially inwards in the chamber.

The centrifuge 3400 is then stopped and the supernatant extraction apparatus 5800 is raised from its lower position upwards until it re-docks with fluid exchange dock 3430 in the first upper position (analogously similar to that shown in FIG. 72). The supernatant is then extracted from the sediment chamber 5809 via the supernatant extraction passageway 5808-3 and port 5810-3, then finally through the fluid exchange dock 3430 back to the sample processing system for chemical analysis of the supernatant. The supernatant pump 3312 in FIG. 78 for that system or the transfer ump 4023 in FIG. 104 of the microfluidic processing disk 4000 based processing system may be used to draw the supernatant out of the supernatant extraction apparatus 5800.

After the supernatant is withdrawn from the supernatant extraction apparatus 5800, the sediment chamber 5809 and fluid passageways 5808-1, 5808-2, and 5808-3 are rinsed by injecting preferably filtered water therethrough to remove the sludge/sediment and exhausted to waste. The supernatant extraction apparatus 5800 is now readied for the next slurry sample run.

It bears noting that the enclosed flow conduits shown and described herein which interconnect the fluid system components may be rigid or flexible tubing or piping of suitable material including metallic or non-metallic materials such as polymers. Some specific examples are mentioned elsewhere herein.

According to another aspect of the invention, a vision system 6200 may be provided to identify previous crop rows in the agricultural field and to quantify how much of soil sampled for soil testing comes from what area in the field. The system may further be employed to determine where to collect soil samples based on any number of soil parameters such as organic matter or other.

The vision system 6200 in one embodiment can comprise one or more digital cameras 6201 that captures real-time images of the agricultural field during the soil sampling or other farming operations to determine where crop rows from prior plantings are located. The cameras 6201 may be mounted on a self-propelled agricultural vehicle which may be a tractor or sampling vehicle 5750 (see, e.g. FIG. 264), or an implement or device pulled or pushed through the field by an agricultural vehicle to capture real-time images of the field.

Digital images captured by the cameras 6201 may be relayed via suitable wired or wireless communication links 5752 to a central system controller 2820 described herein for analysis as shown in FIG. 264, or another CPU-based controller or monitor such as disclosed in commonly-owned U.S. Pat. No. 9,943,027, which is incorporated herein by reference. Such systems as disclosed in that patent are configured to generate a soil map of the agricultural field which may be used to determine where soil samples should be collected from in the field for chemical analysis according to the present disclosure. Such systems are commercially available such as SmartFirmer™ from Precision Planting, LLC. The system can be used to keep increasing sampling density until variation between zones in the field is at "X" level setpoint which may be preprogrammed into the controller or processor.

In some embodiments, soil sampling locations for chemical analysis can be determined and selected based on measured organic matter amounts in the field. An example of an implement that measures organic matter in the field such as planting furrows and other soil parameters (e.g. temperature, moisture content, etc.) is the SmartFirmer™ which is mountable on the seed firmer or other agricultural implement or device pulled through the soil as disclosed in the foregoing patent. The firmer is an angled device which travels through the furrow to ensure contact of the dispensed seed with the soil during planting (see, e.g. U.S. Pat. No. 9,943,027). It bears noting that the actual measured initial raw soil moisture data associated with each soil sampling location may be utilized by the system controller 2820 to perform the volumizing and massing operations previously described herein with respect to FIG. 284 for determining the amount of water which needs to be added to the collected soil for preparing a slurry meeting the preprogrammed desired target water to soil ratio for chemical analysis.

Using the above technology, an initial soil sampling zone grid for a field can be planned. The grid can be adjusted to smaller zones until the differences between the zones is less than a selected amount (i.e. "X" level setpoint). This allows for zones to be changed actively during the soil sampling process to a resolution that minimizes differences.

Control System

FIG. 302 is a schematic system diagram showing the control or processing system 2800 including programmable processor-based central processing unit (CPU) or system controller 2820 as referenced to herein. System controller 2820 may include one or more processors, non-transitory tangible computer readable medium, programmable input/output peripherals, and all other necessary electronic appurtenances normally associated with a fully functional processor-based controller. Control system 2800, including controller 2820, is operably and communicably linked to the different soil sample processing and analysis systems and devices described elsewhere herein via suitable communication links to control operation of those systems and device in a fully integrated and sequenced manner.

Referring to FIG. 302, the control system 2800 including programmable controller 2820 may be mounted on a translatable self-propelled or pulled machine 2802 (e.g., vehicle, tractor, combine harvester, etc.) which may include an agricultural implement 2840 (e.g., planter, cultivator, plough, sprayer, spreader, irrigation implement, etc.) in accordance with one embodiment. In one example, the machine 2802 performs operations of a tractor or vehicle that is coupled to an implement 2840 for agricultural operations. In other embodiments, the controller may be part of a stationary station or facility. The machine 2802 and its boundaries are designated by dashed lines in the figure. Control system 2800, whether onboard or off-board machine 2802, generally includes the controller 2820, non-transitory tangible computer or machine accessible and readable medium such as memory 2805, and a network interface 2815. Computer or machine accessible and readable medium may include any suitable volatile memory and non-volatile memory or devices operably and communicably coupled to the processor(s). Any suitable combination and types of volatile or non-volatile memory may be used including as examples, without limitation, random access memory (RAM) and various types thereof, read-only memory (ROM) and various types thereof, hard disks, solid-state drives, flash memory, or other memory and devices which may be written to and/or read by the processor operably connected to the medium. Both the volatile memory and the non-volatile memory may be used for storing the program instructions or software. In one embodiment, the computer or machine accessible and readable non-transitory medium (e.g., memory 2805) contains executable computer program instructions which when executed by the system controller 2820 cause the system to perform operations or methods of the present disclosure including measuring properties and testing of soil and vegetative samples. While the machine accessible and readable non-transitory medium (e.g., memory 2805) is shown in an exemplary embodiment to be a single medium, the term should be taken to include a single medium or multiple media (e.g., a centralized or distributed database, and/or associated caches and servers) that store the one or more sets of control logic or instructions. The term "machine accessible and readable non-transitory medium" shall also be taken to include any medium that is capable of storing, encoding or carrying a set of instructions for execution by the machine and that cause the machine to perform any one or more of the methodologies of the present disclosure. The term "machine accessible and readable non-transitory medium" shall accordingly also be taken to include, but not be limited to, solid-state memories, optical and magnetic media, and carrier wave signals.

Network interface 2815 communicates with the soil sample processing and analysis systems and devices described elsewhere (collectively designated 2803 in FIG. 302), and other systems or devices which may include without limitation implement 2840 having its own controllers and devices, and the machine network 2810 of the machine 2802 (e.g., a controller area network (CAN) serial bus protocol network, an ISOBUS network, etc.).

The machine network 2810 can include sensors 2812 (e.g., sensors for measuring properties of soil and vegetative samples, speed sensors, etc.), controllers 2811 (e.g., GPS receiver, radar unit) for controlling and monitoring operations of the machine or implement, and soil sample collection system 2801. The network interface 2815 can be configured for wired and/or wireless bidirectional communications which may include at least one of a GPS transceiver, a WLAN transceiver (e.g., WiFi), an infrared transceiver, a Bluetooth transceiver, Ethernet, Near Field Communications, or other suitable communication interfaces and protocols for communications with the other devices and systems including the implement 2840. The network interface 2815 may be integrated with the control system 2800 as illustrated in FIG. 302, the machine network 2810, implement 2840, or elsewhere. The I/O (input/output) ports 2829 of control system 2800 (e.g., diagnostic/on board diagnostic (OBD) port) enable communication with another data processing system or device (e.g., display devices, sensors, etc.).

The programmable controller 2820 may include one or more microprocessors, processors, a system on a chip (integrated circuit), one or more microcontrollers, or combinations thereof. The processing system includes processing logic 2826 for executing software instructions of one or more programs and a communication module or unit 2828 (e.g., transmitter, transceiver) for transmitting and receiving communications from the machine 2802 via machine network 2810, or network interface 2815, or implement 2840 via implement network 2850. The communication unit 2828 may be integrated with the control system 2800 (e.g. controller 2820) or separate from the processing system. In one embodiment, the communication unit 2828 may be in operable data communication with the machine network 2810 and implement network 2850 via a diagnostic/OBD port of the I/O ports 2829.

Programmable processing logic 2826 of the control system 2800 which directs the operation of system controller 2820 including one or more processors may process the communications received from the communication unit 2828 or network interface 2815 including agricultural data (e.g., test data, testing results, GPS data, liquid application data, flow rates, etc.), and soil sample processing and analysis systems and devices 2803 data. The memory 2805 of control system 2800 is configured for preprogrammed variable or setpoint/baseline values, storing collected data, and computer instructions or programs for execution (e.g. software 2806) used to control operation of the controller 2820. The memory 2805 can store, for example, software components such as testing software for analysis of soil and vegetation samples for performing operations of the present disclosure, or any other software application or module, images 2808 (e.g., captured images of crops), alerts, maps, etc. The system 2800 can also include an audio input/output subsystem (not shown) which may include a microphone and a speaker for, for example, receiving and sending voice commands or for user authentication or authorization (e.g., biometrics).

In the embodiments with sampling system 2801 (e.g., processing system 2801), vehicle 2802 (e.g., machine 2802) can further include a sensing system 2812 or be coupled to an implement 2840 that includes a sensing system 2852. The sensing systems (e.g., sensing system 2812, sensing system 2852) are in data communication with system controller 2820. Additional data at each point sampled can be tested by the sensing system. Sensing systems can include one or more of the following: spectrographic measurement, electrical conductivity, apparent electrical conductivity, LIDAR, radar, ground penetrating radar, sonar, optical height, camera, time of flight camera. Examples of spectrographic measurement include, but are not limited to, visible light, laser, near-infrared, infrared, transient infrared spectroscopy, RAMAN spectroscopy, ultraviolet, and x-ray. The combination of soil and/or vegetation sampling along with sensing can provide a more detailed analysis of the conditions in the field.

The system controller 2820 communicates bi-directionally with memory 2805 via communication link 2830, machine network 2810 via communication link 2831 and or alternatively via communication link 2837, network interface 2815 via communication link 2832, display devices 2830 and optionally a second display device 2825 via communication links 2834, 2835, and I/O ports 2829 via communication links 2836. System controller 2820 further communicates with the soil sample processing and analysis systems and devices 2803 via the wired/wireless communication links 5752 previously described herein via the network interface 2815 and/or directly as shown.

Display devices 2825 and 2830 can provide visual user interfaces for a user or operator. The display devices may include display controllers. In one embodiment, the display device 2825 is a portable tablet device or computing device with a touchscreen that displays data (e.g., test results of soil, test results of vegetation, liquid application data, captured images, localized view map layer, high definition field maps of as-applied liquid application data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 2830 may be a display (e.g., display provided by an original equipment manufacturer (OEM)) that displays images and data for a localized view map layer, as-applied liquid application data, as-planted or as-harvested data, yield data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

The implement 2840 (e.g., planter, cultivator, plough, sprayer, spreader, irrigation implement, etc.) may include its own implement network 2850, a processing system 2862, a network interface 2860, and optional input/output ports 2866 for communicating with other systems or devices including the machine 2802. In one example, the implement network 2850 (e.g., a controller area network (CAN) serial bus protocol network, an ISOBUS network, etc.) includes a pump 2856 for pumping liquid from a storage tank(s) 2890 to control monitoring units (CMUs) 2880, 2881, . . . N of the implement, sensors or sensing system 2852 (e.g., soil sensors, vegetation sensors, soil probe, speed sensors, seed sensors for detecting passage of seed, downforce sensors, actuator valves, OEM sensors, flow sensors, etc.), controllers 2854 (e.g., GPS receiver), and the processing system 2862 for controlling and monitoring operations of the machine. The CMUs control and monitor the application of the liquid to crops or soil as applied by the implement. The liquid application can be applied at any stage of crop development including within a planting trench upon planting of seeds, adjacent to a planting trench in a separate trench, or in a region that is nearby to the planting region (e.g., between rows of corn or soybeans) having seeds or crop growth. Alternatively, solids can be applied via the spreader.

The implement processing system 2862 communicates bi-directionally with the implement network 2850, network interface 2860, and I/O ports 2866 via communication links 2841-2843, respectively. The implement 2840 communicates with the machine network 2810 via wired and/or wireless bi-directional communications 2804. The implement network 2850 may communicate directly with the machine network 2810 or via the networks interfaces 2815 and 2860. The implement 2840 may also be physically coupled to the machine 2802 as indicated in FIG. 302 for agricultural operations (e.g., planting, harvesting, spraying, etc.).

While the foregoing description and drawings represent some example systems, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention.

The invention claimed is:

1. A coulter assembly for collecting soil samples from an agricultural field, the assembly comprising:
   an annular collection blade configured for penetrating soil to capture a sample;
   an annular indexing ring configured for stationary mounting to a frame of an agricultural vehicle or implement, the annular indexing ring comprising at least one indexing segment;
   a blade hub coupled to the annular collection blade for rotatably supporting the annular collection blade from the annular indexing ring, the annular collection blade rotatable relative to the annular indexing ring;
   a sample collection shaft rotatably supported by the annular collection blade and defining a radial axis of rotation, the sample collection shaft comprising an operating end configured to engage the at least one indexing segment of the annular indexing ring as the collection blade rotates;
   the at least one indexing segment of the indexing ring being configured to cause rotation of the sample collection shaft about its radial axis of rotation;
   wherein the sample collection shaft is configured and operable for extracting a soil sample as the annular collection blade is rotated through the soil.

2. The assembly according to claim 1, wherein the sample collection shaft comprises at least one laterally open sample collection port which alternatingly opens and closes for capturing and retaining the soil sample as the sample collection shaft rotates about its radial axis of rotation.

3. The assembly according to claim 2, wherein the sample collection shaft comprises a plurality of laterally open sample collection ports which comprise elongated slots spaced apart along a length of the sample collection shaft.

4. The assembly according to claim 3, wherein the sample collection ports are through ports open from two opposing longitudinal sides of the shaft.

5. The assembly according to claim 3, wherein the sample collection shaft is rotatable about its radial axis or rotation between an open position in which the collection ports face outwards from the annular collection blade for capturing soil, and a closed position in which the collection ports do not face outwards to preclude soil from entering the collection ports.

6. The assembly according to claim 5, wherein the sample collection shaft is rotatably disposed in a radial slot extending through opposite first and second major surfaces of the annular collection blade.

7. The assembly according to claim 6, further comprising a pair of radially elongated guide shields at the radial slot, one each of the guide shields being affixed to the annular collection blade on each side of the radial slot.

8. The assembly according to claim 1, wherein the operating end of the sample collection shaft comprises a sprocket which operable engages the at least one indexing segment of the annular indexing ring.

9. The assembly according to claim 8, wherein the at least one indexing segment comprises an undulating configuration comprising spaced apart raised portions which engage the sprocket to rotate the sample collection shaft relative to the annular collection blade as the annular collection blade rotates through the soil.

10. The assembly according to claim 9, wherein the sprocket comprises a plurality of radial lugs which engage the at least one indexing segment to impart rotation to the sample collection shaft about its radial axis of rotation.

11. The assembly according to claim 10, wherein the lugs are oriented perpendicularly to an elongated body of the sample collection shaft.

12. The assembly according to claim 11, wherein the sample collection shaft and sprocket are rotatably disposed in a T-shaped slot extending through opposite first and second major surfaces of the annular collection blade.

13. The assembly according to claim 12, wherein the lugs each have a length which protrudes above opposing major surfaces of the annular collection blade as the sample collection rotates in the T-shaped slot.

14. The assembly according to claim 9, wherein the at least one indexing segment further comprises an inclined ramp located adjacent to a first one of the raised portions, and a recess having a flat floor formed between the first one of the raised portions and a second one of the raised portion.

15. The assembly according to claim 9, wherein the annular indexing ring comprises a plurality of circumferentially spaced apart indexing segments, each of the indexing segments alternatingly engaging the sprocket in turn as the annular collection blade rotates relative to the stationary indexing ring.

16. The assembly according to claim 9, wherein the at least one indexing ring comprises a first major surface facing the annular collection blade, an opposing second major surface parallel to the first major surface, and a circumferentially-extending peripheral sides extending between the surfaces, the at least one indexing segment being formed on the first major surface.

17. The assembly according to claim 1, wherein the annular indexing ring is coaxially aligned with the annular collection blade.

18. The assembly according to claim 17, wherein the annular collection blade is rotatable relative to the indexing ring about an axis of rotation which is different than the radial axis of rotation of the sample collection shaft.

19. The assembly according to claim 18, wherein the sample collection shaft is rotatable with the annular collection blade about the axis of rotation of the annular collection blade such that the sample collection shaft remains in a radial orientation relative to the annular collection blade at all times.

20. A coulter assembly for collecting soil samples from an agricultural field, the assembly comprising:
- an annular collection blade configured for penetrating soil to capture a sample;
- an annular indexing ring configured for stationary mounting to a frame of an agricultural vehicle or implement, the annular indexing ring comprising a first major surface facing the annular collection blade and an opposite second major surface;
- the annular indexing ring comprising at least one indexing segment disposed on the first major surface, the at least one indexing segment comprising an undulating configuration comprising raised portions and recessed portions;
- a blade hub coupled to the annular collection blade for rotatably supporting the annular collection blade from the annular indexing ring, the annular collection blade rotatable about a blade axis of rotation relative to the annular indexing ring;
- an elongated sample collection shaft rotatably supported by the annular collection blade and defining a radial axis of rotation perpendicular to the blade axis of rotation;
- the sample collection shaft comprising a sprocket configured to engage the at least one indexing segment of the annular indexing ring as the annular collection blade rotates, the at least one indexing segment of the indexing ring operable to cause rotation of the sample collection shaft about its radial axis of rotation;
- the sample collection shaft comprising at least one laterally open sample collection port which alternatingly opens and closes for capturing and retaining a soil sample as the sample collection shaft rotates when the annular collection blade is rotated through the soil.

\* \* \* \* \*